(12) United States Patent
George et al.

(10) Patent No.: US 9,115,151 B2
(45) Date of Patent: Aug. 25, 2015

(54) SUBSTITUTED 2,10-DIHYDRO-9-OXA-1,2,4A-TRIAZAPHENANTHREN-3-ONES AND USES THEREOF

(71) Applicants: Dawn M. George, Charlton, MA (US); Maria A. Argiriadi, Wayland, MA (US); Martine Barth, Asnières les Dijon (FR); Dominique Bonafoux, Winthrop, MA (US); Eric C. Breinlinger, Charlton, MA (US); Linlin Dai, Shanghai (CN); Jeremy Edmunds, Acton, MA (US); Michael M. Friedman, Newton, MA (US); Fabrice Guillier, Belleneuve (FR); Adrian D. Hobson, Shrewsbury, MA (US); Dominique Potin, Talant (FR); Didier Thomas, Saint Apollinaire (FR); Jianfei Wang, Shanghai (CN); Wentao Wu, Shanghai (CN); Yang Zhang, Shanghai (CN)

(72) Inventors: Dawn M. George, Charlton, MA (US); Maria A. Argiriadi, Wayland, MA (US); Martine Barth, Asnières les Dijon (FR); Dominique Bonafoux, Winthrop, MA (US); Eric C. Breinlinger, Charlton, MA (US); Linlin Dai, Shanghai (CN); Jeremy Edmunds, Acton, MA (US); Michael M. Friedman, Newton, MA (US); Fabrice Guillier, Belleneuve (FR); Adrian D. Hobson, Shrewsbury, MA (US); Dominique Potin, Talant (FR); Didier Thomas, Saint Apollinaire (FR); Jianfei Wang, Shanghai (CN); Wentao Wu, Shanghai (CN); Yang Zhang, Shanghai (CN)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/219,233

(22) Filed: Mar. 19, 2014

(65) Prior Publication Data
US 2014/0206663 A1    Jul. 24, 2014

Related U.S. Application Data

(63) Continuation of application No. PCT/CN2013/001480, filed on Nov. 29, 2013, which is a continuation-in-part of application No. PCT/CN2012/086292, filed on Dec. 10, 2012, application No. 14/219,233, which is a continuation-in-part of application No. PCT/CN2012/086292, filed on Dec. 10, 2012.

(51) Int. Cl.
| | | |
|---|---|---|
| *A61K 31/53* | (2006.01) | |
| *C07D 253/10* | (2006.01) | |
| *C07D 513/04* | (2006.01) | |
| *C07D 413/04* | (2006.01) | |
| *C07D 417/04* | (2006.01) | |
| *C07D 471/06* | (2006.01) | |
| *C07D 498/06* | (2006.01) | |
| *C07D 513/06* | (2006.01) | |
| *C07D 498/04* | (2006.01) | |
| *C07D 498/14* | (2006.01) | |
| *C07D 471/04* | (2006.01) | |
| *C07D 519/00* | (2006.01) | |

(52) U.S. Cl.
CPC ............ *C07D 513/04* (2013.01); *C07D 413/04* (2013.01); *C07D 417/04* (2013.01); *C07D 471/04* (2013.01); *C07D 471/06* (2013.01); *C07D 498/04* (2013.01); *C07D 498/06* (2013.01); *C07D 498/14* (2013.01); *C07D 513/06* (2013.01); *C07D 519/00* (2013.01)

(58) Field of Classification Search
CPC .............................. A61K 31/53; C07D 253/10
USPC ................ 514/230.2; 544/184, 375; 546/199, 546/282.7; 548/159, 525, 950; 549/356
See application file for complete search history.

(56) References Cited

U.S. PATENT DOCUMENTS

| | | | |
|---|---|---|---|
| 4,080,192 | A | 3/1978 | Wolf |
| 4,134,974 | A | 1/1979 | Melloni et al. |
| 4,254,118 | A | 3/1981 | Gauthier et al. |
| 4,254,121 | A | 3/1981 | Gauthier et al. |

FOREIGN PATENT DOCUMENTS

| | | |
|---|---|---|
| EP | 0046267 A1 | 2/1982 |
| EP | 0073060 A1 | 3/1983 |
| EP | 0272868 A1 | 6/1988 |
| WO | WO-2006/017822 A2 | 2/2006 |
| WO | WO-2008/025821 A1 | 3/2008 |
| WO | WO-2008/051808 A2 | 5/2008 |
| WO | WO-2008/141975 A1 | 11/2008 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — McCarter & English, LLP; Wei Song; Yu Lu

(57) ABSTRACT

The invention provides a compound of Formula (I)

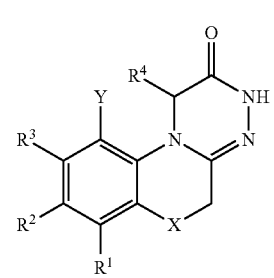

Formula (I)

pharmaceutically acceptable salts, pro-drugs, biologically active metabolites, stereoisomers and isomers thereof wherein the variable are defined herein. The compounds of the invention are useful for treating immunological and oncological conditions.

19 Claims, No Drawings

(56) References Cited

FOREIGN PATENT DOCUMENTS

| WO | WO-2012/100135 A1 | | 7/2012 |
|----|----|----|----|
| WO | WO 2014/089904 | * | 6/2014 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Wolff, Manfred E., Ed. Burger's Medicinal Chemistry and Drug Discovery—Fifth Edition, New York: John Wiley & Sons, 1996, 1, 975-976.*

Deshmukh, M.B., "Synthesis and study of biological activity of some new 1,4-benzothiazines." Indian Journal of Chemistry, vol. 46B, May 2007, pp. 852-859.

Deshmukh, M.B., "Synthesis of some new tricyclic 1,4-benzothiazinones." Journal of Indian Chemistry Society., vol. 79, May 2002, pp. 472-474.

Hogale, M.B., "Synthesis of some 2(H), 4(H)-1,2,4 Triazino [3,4-c]-1,4-benzoxazin-5-ones." Journal of Indian Chemistry Society., vol. LXV, Oct. 1988, pp. 735-737.

Periolo, Luana , Studies on Annelated 1,4-Benzothiazines and 1,5-Benzothiazepines VIII-synthesis and inhibition of benzodiazepine receptor binding of some derivatives of triazino[3,4-c]-1,4-benzothiazine and triazino[3,4-d]-1,5-benzothiazepine, two new heterocyclic ring systems. *IL Farmaco*, 49 (4), 1994, pp. 245-251.

Reddy, Sastry, C.V., et al., "Synthesis and biological activity of some substituted 4H-[1,2,4]-triazino[3,4-c][1,4]-benzoxazin-5-ones and 4H[1,2,4]-triazino-[3,4-c][1,4]-benzothiazin-5-ones", Indian Journal of Pharmaceutical Sciences, 1991, vol. 53, No. 4, pp. 180-183.

* cited by examiner

SUBSTITUTED 2,10-DIHYDRO-9-OXA-1,2,4A-TRIAZAPHENANTHREN-3-ONES AND USES THEREOF

REFERENCE TO RELATED APPLICATION

This application is a continuation application of International Patent Application No. PCT/CN2013/001480, filed on Nov. 29, 2013, which claims, under 35 U.S.C. §365(b), priority to and the benefit of the filing date of International Patent Application No. PCT/CN2012/086292, filed on Dec. 10, 2012; this application is also a continuation-in-part application of International Patent Application No. PCT/CN2012/086292, filed on Dec. 10, 2012; the entire contents of each of the two International Applications are incorporated herein by reference.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the PKC, Jak1, Jak2, Jak3, Tyk2, KDR, Flt-3, ROCK, CDK2, CDK4, TANK, Trk, FAK, Abl, Bcr-Abl, cMet, b-RAF, FGFR3, c-kit, PDGF-R, Syk, or Aurora kinases.

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 25-300 amino acid catalytic domain. The kinases may be categorized into families by the substrate that they phosphorylate (e.g., protein-tyrosine, protein-serine/threonine, lipids etc.). Sequence motifs have been identified that generally correspond to each of these families (see e.g., Hanks and Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

The protein kinase C family is a group of serine/threonine kinases including at least ten related isoenzymes, including alpha, beta 1, beta 2, gamma, delta, epsilon, eta, lambda, iota, theta and zeta. The isoenzymes have been divided into three groups based on their different expression patterns and co-factor requirements. The classical PKC enzymes (cPKC), including alpha, beta 1, beta 2 and gamma isozymes require diacylglycerol (DAG), phosphatidylserine (PS) and calcium for activation. The novel PKC's (nPKC), including delta, epsilon, theta and eta isozymes, require DAG and PS but are calcium independent. The atypical PKC's (aPKC), including zeta, lambda/iota do not require calcium or DAG.

PKC isoforms have been shown to play key roles in cellular signaling, proliferation, differentiation, migration, survival, and death. In resting cells, PKCs are predominantly localized in the cytosol and are catalytically inactive due to autoinhibition by their pseudosubstrate domain. Upon cell activation, PKC isotype-specific signals trigger translocation from the cytosol to the membrane and induce conformational changes, which displace the pseudosubstrate moiety from the catalytic domain and enable PKC isotypes to phosphorylate specific protein substrates (*Biochem. J.* 370:361-371, 2003). Most isoforms are ubiquitously expressed, except PKCγ and PKCθ. While PKCγ is exclusively found in the brain, high protein levels of PKCθ are seen predominantly in hematopoietic cells and skeletal muscle. PKCα and PKCθ as well as PKCβ and PKCδ are functionally important for T and B cell signaling, respectively (*Nat. Immunol.* 5:785-790, 2004. *Curr. Opin. Immunol.* 16:367-373, 204. *Nature.* 416:860-865, 2002). PKCθ plays an essential role in T cell activation because it is the only isoform that is selectively translocated to the T cell/antigen-presenting cell contact site immediately after cell-cell interaction (*Nature.* 385:83-86, 1997). Furthermore, PKCθ is crucial for IL-2 production, a prerequisite for the proliferation of T cells (*Eur. J. Immunol.* 30:3645-3654, 2000). PKCθ-deficient mice are defective in NF-κB (*Cell Mol. Immunol.* 3:263-270, 2006), NFAT and AP-1 activation (*Nature,* 404 (96776), 402-407, 2000. *Journal of Immunology* 176:6004-6011, 2006) and are resistant to experimental autoimmune encephalomyelitis (*J. Immunol.* 176:2872-2879, 2006), collagen-induced arthritis (*Journal of Immunology* 177 (3), 1886-1893, 2006) and asthma (*Journal of Immunology* 173 (10), 6440-6447, 2004). PKCα in T cells is required for proliferation and IFN-γ production (*J. Immunol.* 176:6004-6011, 2006). B cells require PKCβ for proper antigen receptor function and PKCδ for the induction of tolerance (*Nature.* 416:860-865, 2002). Thus, PKC isoforms in T and B cells are considered attractive therapeutic targets for autoimmune diseases and transplantation (*Curr. Opin. Investig. Drugs.* 7:432-437, 2006).

Further, PKCε and PKCγ have been suggested to play a role in nociception and inflammatory pain (*J. Pharm. Exp. Ther. Pain* 110, 281-289, 2004) and PKCζ has been proposed as an intermediary in the activation of the NF-κB and IL-4/Stat6 pathway (*Cell Death Differ.* 13: 702, 2006). The NF-κB pathway is important for inflammatory and immune diseases, therefore a PKCζ inhibition may serve to reduce the severity of these type of diseases (*Allergol. Int.* 55: 245, 2006. *J. Biol. Chem.* 281: 24124, 2006. *Arthritis Rheum.* 56: 4074, 2007. *J. Interferon Cytokine Res.* 27: 622, 2007).

The novel compounds of this invention inhibit the activity of one or more protein kinases and are, therefore, expected to be useful in the treatment of kinase-mediated diseases.

SUMMARY OF THE INVENTION

In a first embodiment the invention provides a compound of Formula (I):

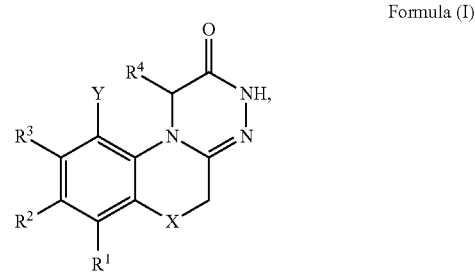

Formula (I)

a pharmaceutically acceptable salt, an isomer, a stereoisomer, a tautomer, a pro-drug, or a biologically active metabolite thereof, wherein $R^1$ is —H, deuterium, —CF$_3$, halo, optionally substituted $(C_1$-$C_3)$alkyl, or optionally substituted $(C_3$-$C_6)$cycloalkyl;

$R^2$ is —H, deuterium, halo, —CF$_3$, —CHF$_2$, —CH$_2$F, —C(H)(CH$_3$)CF$_3$, cyano, —NR$^a$R$^b$, —OR$^c$, optionally substituted ($C_1$-$C_6$)alkyl, optionally substituted ($C_3$-$C_6$) cycloalkyl, optionally substituted ($C_5$-$C_7$)cycloalkenyl, optionally substituted bridged ($C_3$-$C_8$)cycloalkyl, optionally substituted ($C_1$-$C_3$)alkoxy, optionally substituted aryl, optionally substituted 5-10 membered heteroaryl, optionally substituted aryloxy, optionally substituted 5-10 membered bridged carbocyclyl or heterocyclyl, or optionally substituted 4-10 membered heterocyclyl;

$R^3$ is —H, deuterium, halo, —$CF_3$, —$CH_2F$, —$CHF_2$, —$NR^aR^b$, —$OR^c$, —$SR^c$, —$SCH_3$, —$S(O)R^c$, —$S(O)_2R^c$, —$S(O)CH_3$, optionally substituted ($C_1$-$C_3$)alkyl, optionally substituted heterocyclic spirocyclyl, optionally substituted 5-10 membered bridged heterocyclyl, optionally substituted aromatic, nonaromatic, or partially aromatic ring system, which may be heterocyclic or carbocyclic, or —$C(R^d)(R^e)$-optionally substituted 4-10 membered heterocyclyl; or $R^2$ and $R^3$, together with the carbon atoms to which they are attached, form an optionally substituted 5-7 membered heterocyclyl or an optionally substituted 5-6 membered heteroaryl ring;

$R^4$ is —$CF_3$, —$CHF_2$, —$CH_2F$, or optionally substituted ($C_1$-$C_6$)alkyl;

$R^a$ is independently —H or optionally substituted ($C_1$-$C_3$) alkyl;

$R^b$ is independently —H, —($C_1$-$C_3$)alkyl, optionally substituted aryl, optionally substituted 4-10 membered heterocyclyl, optionally substituted aralkyl, optionally substituted 4-8 membered bridged heterocyclyl, or —C(O)-optionally substituted 4-10 membered heterocyclyl; and $R^c$ is independently —H, optionally substituted aralkyl, optionally substituted phenyl, or optionally substituted 4-10 membered heterocyclyl;

$R^d$ and $R^e$, together with the carbon atom to which they are attached, form an optionally substituted ($C_3$-$C_4$)cycloalkyl or optionally substituted 4-10 membered heterocyclyl, or, $R^d$ and $R^e$ are independently —H or —($C_1$-$C_3$)alkyl;

X is O or S, or is —$CH_2$— optionally substituted by —($C_1$-$C_4$)alkyl, phenyl, —CN, —OH, or —($C_1$-$C_4$)alkoxy; and Y is —H, deuterium, or —F;

provided that $R^1$, $R^2$, $R^3$ and Y are not all —H, when X is O or S.

In a second embodiment the invention provides a compound according to the first embodiment, wherein:

$R^2$ is —H; halo; —$CF_3$; cyano; —$NR^aR^b$; —$OR^c$; optionally substituted ($C_1$-$C_6$)alkyl; optionally substituted ($C_3$-$C_6$)cycloalkyl; optionally substituted ($C_5$-$C_7$)cycloalkenyl; optionally substituted bridged ($C_3$-$C_8$)cycloalkyl; optionally substituted ($C_1$-$C_3$)alkoxy; optionally substituted aryl; optionally substituted 5-10 membered heteroaryl; optionally substituted 5-10 membered bridged carbocyclyl; or optionally substituted 4-10 membered heterocyclyl;

wherein ($C_1$-$C_3$)alkoxy is optionally substituted with aryl;

wherein ($C_1$-$C_6$)alkyl is optionally substituted with one or more halo; and, wherein in $R^2$, ($C_3$-$C_6$)cycloalkyl, ($C_5$-$C_7$)cycloalkenyl, bridged ($C_3$-$C_8$)cycloalkyl, aryl, 5-10 membered heteroaryl, and 4-10 membered heterocyclyl are each independently optionally substituted with one or more groups selected from halo, —$CF_3$, cyano, —($C_1$-$C_4$) alkyl, -hydroxy($C_1$-$C_4$)alkyl, -halo($C_1$-$C_3$)alkyl, -halo ($C_1$-$C_3$)alkoxy, —$S(O)(C_1$-$C_3)$alkyl, —$S(O)_2(C_1$-$C_3)$ alkyl, —$NR^aR^b$, —($C_1$-$C_3$)alkoxy, —($C_1$-$C_4$)alkoxy ($C_1$-$C_3$)alkyl or piperazinyl.

In a third embodiment the invention provides a compound according to any of the foregoing embodiments, wherein:

$R^3$ is —$CF_3$; —$CH_2F$; —$CHF_2$; —F; —$NR^aR^b$; —$OR^c$; optionally substituted ($C_1$-$C_3$)alkyl; —$CH_2$-(4-10 membered)heterocyclyl; —$CH((C_1$-$C_3)$alkyl)-(4-10 membered)heterocyclyl; —$C((C_1$-$C_3)$alkyl)$_2$-(4-10 membered)heterocyclyl; optionally substituted heterocyclic spirocyclyl; optionally substituted 4-10 membered heterocyclyl; or —$C(R^d)(R^e)$-(4-10 membered)heterocyclyl;

wherein the ($C_1$-$C_3$)alkyl is optionally substituted with one or more halo or —OH;

wherein the heterocyclic spirocyclyl is optionally substituted with 1-3 groups selected from halo, —$CH_3$, or —OH;

wherein the 4-10 membered heterocyclyl is optionally substituted with 1-3 groups selected from —H, halo, —$CF_3$, —OH, —($C_1$-$C_3$)alkyl, -hydroxy($C_1$-$C_4$)alkyl, -halo ($C_1$-$C_3$)alkyl, —($C_1$-$C_4$)alkoxy($C_1$-$C_3$)alkyl, —C(O) ($C_1$-$C_3$)alkyl, —C(O)halo($C_1$-$C_3$)alkyl, —C(O)hydroxy($C_1$-$C_4$)alkyl, —C(O)—($C_1$-$C_3$)alkylene-N($CH_3$)$_2$, —($C_1$-$C_3$)aralkyl, oxetanyl, —$CH_2$-oxetanyl, tetrahydropyranyl, —$CH_2$-tetrahydropyranyl, or —$NR^aR^b$; and, wherein —$C(R^d)(R^e)$ forms cyclopropyl, oxetanyl, or cyclobutyl, and wherein the cyclopropyl, oxetanyl, and cyclobutyl are each independently optionally substituted with 1 or 2 groups selected from halo, —$CH_3$, or —OH.

In a fourth embodiment the invention provides a compound according to any of the foregoing embodiments, wherein $R^2$ is —H; halo; —$CF_3$; cyano; —$NR^aR^b$; —$OR^c$; optionally substituted ($C_3$-$C_6$)cycloalkyl; optionally substituted ($C_5$-$C_6$)cycloalkenyl, optionally substituted furanyl; optionally substituted benzothiazolyl; optionally substituted tetrahydropyran; optionally substituted piperidinyl; optionally substituted 1,4-diazabicyclo[2.2.1] heptanyl, optionally substituted bicyclo[1.1.1]pentyl, optionally substituted bicyclo[2.1.0]pentyl, optionally substituted pyrrolidinyl; optionally substituted pyridinyl; optionally substituted phenyl, optionally substituted naphthyl; or —($C_1$-$C_6$)alkyl optionally substituted with one or more halo, wherein the —($C_3$-$C_6$)cycloalkyl, —($C_5$-$C_6$)cycloalkenyl, furanyl, benzothiazolyl, tetrahydropyran, piperidinyl, 1,4-diazabicyclo[2.2.1]heptanyl, bicyclo[1.1.1]pentyl, bicyclo[2.1.0]pentyl, pyrrolidinyl, pyridinyl, phenyl, and naphthyl are each optionally substituted with 1-3 groups independently selected from halo, —$CF_3$, cyano, —($C_1$-$C_4$)alkyl, -hydroxy($C_1$-$C_4$)alkyl, -halo($C_1$-$C_3$) alkyl, -halo($C_1$-$C_3$)alkoxy, —($C_1$-$C_3$)alkoxy, —S(O) ($C_1$-$C_3$)alkyl, —$S(O)_2(C_1$-$C_3)$alkyl, —$NR^aR^b$, —($C_1$-$C_4$)alkoxy($C_1$-$C_3$)alkyl or piperazinyl.

In a fifth embodiment the invention provides a compound according to any of the foregoing embodiments, wherein:

$R^3$ is —$NR^aR^b$, —$OR^c$, —$CH_2$-(4-10 membered)heterocyclyl, —$CH((C_1$-$C_3)$alkyl)-(4-10 membered)heterocyclyl, —$C((C_1$-$C_3)$alkyl)$_2$-(4-10 membered)heterocyclyl, or 4-10 membered heterocyclyl;

wherein each 4-10 membered heterocyclyl is independently selected from the group consisting of azetidinyl, oxetanyl, tetrahydrofuranyl, pyrrolidinyl, imidazolidinyl, pyrazolidinyl, tetrahydropyranyl, piperidinyl, piperazinyl, morpholinyl, 1,4-dioxanyl, 1,3-dioxanyl, azepanyl, octahydroindolizinyl, octahydropyrrolo[1,2-a]pyrazinyl; and, wherein each 4-10 membered heterocyclyl is optionally substituted with 1-3 groups independently selected from —$CF_3$, —($C_1$-$C_3$)aralkyl, —($C_1$-$C_3$)alkyl, halo($C_1$-$C_3$) alkyl, hydroxy($C_1$-$C_3$)alkyl, or amino($C_1$-$C_3$)alkyl.

In a sixth embodiment the invention provides a compound according to any of the foregoing embodiments, wherein:

$R^1$ is —H, deuterium, halo, —$CF_3$, —$(C_1$-$C_3)$alkyl, or —$(C_3$-$C_6)$cycloalkyl, wherein —$(C_1$-$C_3)$alkyl is optionally substituted with 1-3 groups selected from halo, hydroxyl, or —$(C_1$-$C_3)$alkoxy; and wherein —$(C_3$-$C_6)$cycloalkyl is optionally substituted with 1-3 groups selected from halo, hydroxyl, —$(C_1$-$C_3)$alkyl, or —$(C_1$-$C_3)$alkoxy;

$R^4$ is —$CF_3$, —$CHF_2$, —$CH_2F$, or —$(C_1$-$C_6)$alkyl optionally substituted with 1-3 groups selected from halo, hydroxyl, or —$(C_1$-$C_3)$alkoxy;

$R^a$ is independently —H or —$(C_1$-$C_3)$alkyl;

$R^b$ is independently —H, phenyl optionally substituted with hydroxyl or —$(C_1$-$C_3)$alkyl, or 4-10 membered heterocyclyl; wherein the 4-10 membered heterocyclyl is optionally substituted with 1-3 groups independently selected from: halo, —$(C_1$-$C_3)$alkyl, -hydroxy$(C_1$-$C_4)$ alkyl, -halo$(C_1$-$C_3)$alkyl, —$(C_1$-$C_4)$alkoxy$(C_1$-$C_3)$ alkyl, —$(C_1$-$C_3)$alkoxy, -halo$(C_1$-$C_3)$alkoxy, —$C(O)$ $(C_1$-$C_3)$alkyl, —$C(O)$halo$(C_1$-$C_3)$alkyl, —$C(O)$ hydroxy$(C_1$-$C_4)$alkyl, —$C(O)(C_1$-$C_3)$alkyleneN$(CH_3)_2$, —$(C_1$-$C_3)$aralkyl, oxetanyl, —$CH_2$-oxetanyl, tetrahydropyran, or —$CH_2$-tetrahydropyran; and, $R^c$ is independently —$CH_2$-optionally substituted phenyl, optionally substituted phenyl, or 4-10 membered heterocyclyl optionally substituted with one or more $(C_1$-$C_3)$ alkyl; wherein each phenyl is independently optionally substituted with —$(C_1$-$C_3)$alkyl.

In a seventh embodiment the invention provides a compound according to any of the foregoing embodiments, having the Formula (II):

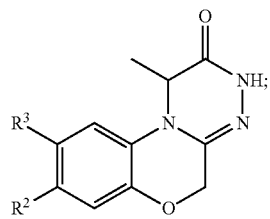

(II)

a pharmaceutically acceptable salt, an isomer, a stereoisomer, a tautomer, a pro-drug, or a biologically active metabolite thereof.

In an eighth embodiment the invention provides a compound according to any of the foregoing embodiments, wherein $R^3$ is represented by structural formula (i):

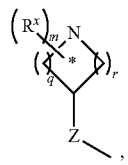

(i)

wherein:
m is 1, 2, 3, or 4;
q is 1, 2, or 3;
r is 1 or 2; and,
Z is absent, $NR^7$, O, or $C(H)R^7$; wherein $R^7$ is —H or —$(C_1$-$C_3)$alkyl;

when Z is $NR^7$ or $C(H)R^7$, each $R^x$ is independently —H, halo, —$(C_1$-$C_3)$alkyl, -hydroxy$(C_1$-$C_4)$alkyl, -halo$(C_1$-$C_3)$alkyl, —$(C_1$-$C_4)$alkoxy$(C_1$-$C_3)$alkyl, —$C(O)(C_1$-$C_3)$alkyl, —$C(O)$halo$(C_1$-$C_3)$alkyl, —$C(O)$hydroxy$(C_1$-$C_4)$alkyl, —$C(O)$—$(C_1$-$C_3)$alkylene-N$(CH_3)_2$, —$(C_1$-$C_3)$aralkyl, oxetanyl, —$CH_2$-oxetanyl, tetrahydropyranyl, or —$CH_2$-tetrahydropyranyl;

when Z is O, each $R^x$ is independently H or —$(C_1$-$C_3)$alkyl; and, when Z is absent, each $R^x$ is independently H, —$CF_3$, —$(C_1$-$C_3)$alkyl, -hydroxy$(C_1$-$C_4)$alkyl, or —$(C_1$-$C_3)$ aralkyl; or when Z is absent, two $R^x$, together with the atoms to which they are attached, form a ring fused to the heterocyclic ring to form an optionally substituted bicyclic ring.

In a ninth embodiment the invention provides a compound according to any of the foregoing embodiments, wherein the compound is of Formula (III) or (IV):

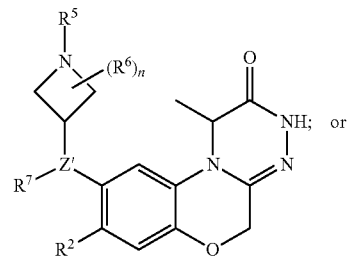

(III)

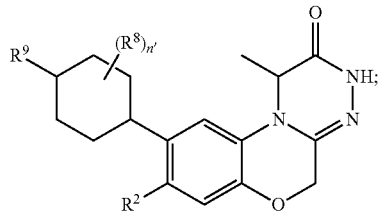

(IV)

a pharmaceutically acceptable salt, an isomer, a stereoisomer, a tautomer, a pro-drug, or a biologically active metabolite thereof, wherein:

$R^5$, $R^6$, $R^8$ and $R^9$ are each independently an $R^x$; wherein $R^5$ and $R^9$ are independently —H, —$(C_1$-$C_3)$alkyl, -hydroxy$(C_2$-$C_4)$alkyl, -halo$(C_1$-$C_3)$alkyl, —$(C_2$-$C_4)$ alkoxy$(C_1$-$C_3)$alkyl, —$C(O)(C_1$-$C_3)$alkyl, —$C(O)$ halo$(C_1$-$C_3)$alkyl, —$C(O)$hydroxy$(C_1$-$C_4)$alkyl, —$C(O)(C_1$-$C_3)$alkyleneN$(CH_3)_2$, —$(C_1$-$C_3)$aralkyl, oxetanyl, —$CH_2$-oxetanyl, tetrahydropyranyl, or —$CH_2$-tetrahydropyranyl;

$R^6$ is independently —H or —$(C_1$-$C_3)$alkyl;

$R^8$ is —H, —$CF_3$, —$(C_1$-$C_3)$alkyl or $(C_1$-$C_3)$aralkyl; or two $R^8$, together with the atoms to which they are attached, form a ring fused to a piperidine ring to form an optionally substituted bicyclic ring;

$R^7$ is —H or —$(C_1$-$C_3)$alkyl;

n is 0, 1, 2, or 3;

n' is 0, 1, 2, or 3; and

Z' is N or CH, or Z' is O and $R^7$ is absent.

In a tenth embodiment the invention provides a compound according to any of the foregoing embodiments, wherein the compound is of Formula (IV), (V), or (VI):

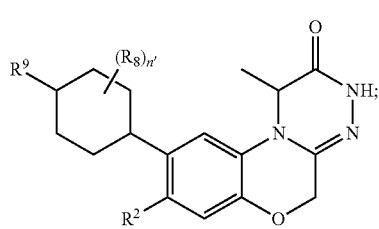

(IV)

-continued (V)
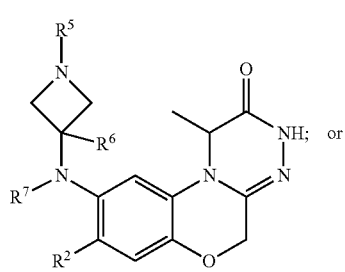

(VI)
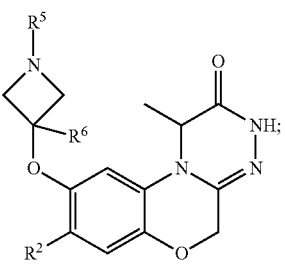

wherein R⁸ is —H, —CF₃, —CH₃, or —CH₂-aryl.

In an eleventh embodiment the invention provides a compound according to any of the foregoing embodiments 10, wherein $R^5$ and $R^7$ are each independently —H or —(C₁-C₃)alkyl; $R^6$ is —(C₁-C₃)alkyl; and $R^8$ is —H, —CH₃, or —CH₂-aryl.

In a twelfth embodiment the invention provides a compound according to any of the foregoing embodiments, wherein $R^3$ is represented by structural formula (II):

(ii)

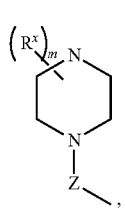

wherein:

m is 1, 2, 3, or 4;

Z is absent or —CH₂- optionally substituted with —(C₁-C₃)alkyl; and each substitutable ring atom of $R^3$ is optionally substituted by $R^x$, and each $R^x$ is independently —H, halo, —CF₃, —(C₁-C₃)alkyl, -hydroxy(C₁-C₄)alkyl, -halo(C₁-C₃)alkyl, —(C₁-C₄)alkoxy(C₁-C₃)alkyl, —C(O)(C₁-C₃)alkyl, —C(O)halo(C₁-C₃)alkyl, —C(O)hydroxy(C₁-C₄)alkyl, —C(O)—(C₁-C₃)alkylene-N(CH₃)₂, —(C₁-C₃)aralkyl, oxetanyl, —CH₂-oxetanyl, tetrahydropyranyl, or —CH₂-tetrahydropyranyl; or when Z is absent, two $R^x$, together with the atoms to which they are attached, form a ring fused to the heterocyclic ring to form an optionally substituted bicyclic ring.

In a thirteenth embodiment the invention provides a compound according to any of the foregoing embodiments, wherein the compound is of Formula (IV-1), (IV-2), (IV-3), or (IV-4):

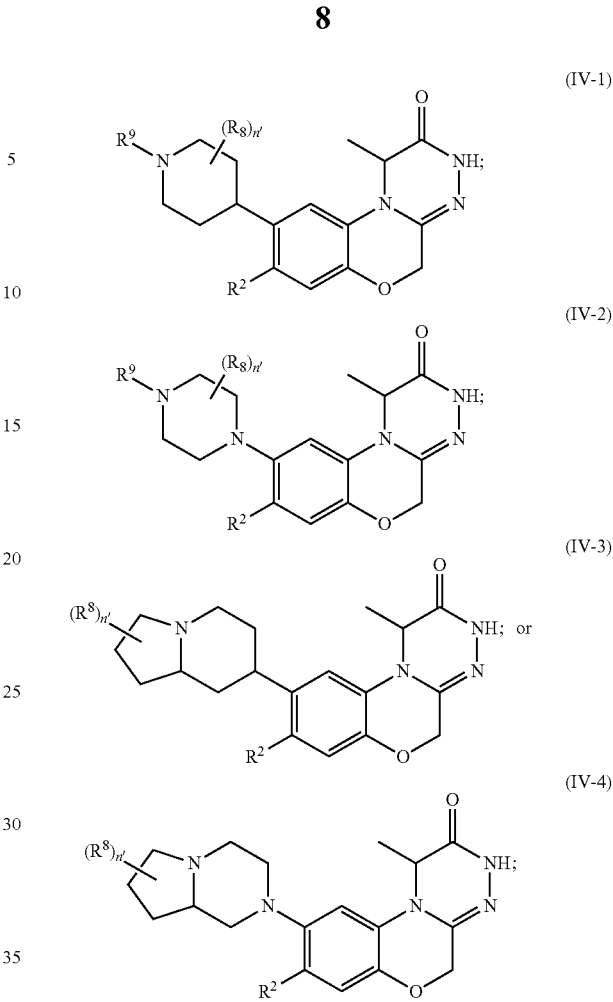

a pharmaceutically acceptable salt, an isomer, a stereoisomer, a tautomer, a pro-drug, or a biologically active metabolite thereof, wherein:

$R^8$ and $R^9$ are each independently an $R^x$;

n' is 0, 1, 2 or 3;

$R^8$ is —CF₃, —(C₁-C₃)alkyl or —CH₂-aryl; and $R^9$ is independently —H, —(C₁-C₃)alkyl, -hydroxy(C₂-C₄)alkyl, -halo(C₁-C₃)alkyl, —(C₂-C₄)alkoxy(C₁-C₃)alkyl, —C(O)(C₁-C₃)alkyl, —C(O)halo(C₁-C₃)alkyl, —C(O)hydroxy(C₁-C₄)alkyl, —C(O)(C₁-C₃)alkylene-N(CH₃)₂, —(C₁-C₃)aralkyl, oxetanyl, —CH₂-oxetanyl, tetrahydropyranyl, or —CH₂-tetrahydropyranyl.

In a fourteenth embodiment the invention provides a compound according to any of the foregoing embodiments, wherein $R^2$ is selected from —H; halo; —CF₃; —CH₃; ethyl; isopropyl; —CH(CH₃)CF₃; furanyl; cyclopentyl; cyclopropyl; bicyclo[1.1.1]pentyl, bicyclo[2.1.0]pentyl, benzothiazolyl; optionally substituted cyclohexenyl; optionally substituted naphthyl; optionally substituted tetrahydropyranyl, optionally substituted pyridinyl; or optionally substituted phenyl;

wherein the cyclohexenyl is optionally substituted with halo;

wherein the naphthyl is optionally substituted with one or more groups selected from halo, —(C₁-C₃)alkyl, or —(C₁-C₃)alkoxy; and, wherein the phenyl is optionally substituted with one or more groups independently selected from halo, —CF₃, —CH₃, —CN, —(C₁-C₄)alkyl, —(C₁-C₃)alkoxy, -halo(C₁-C₃)alkoxy, —(C₁-C₄)alkoxy(C₁-C₃)alkyl, -halo(C₁-C₃)alkyl, —N((C₁-C₃)alkyl)₂, —S(O)CH₃, and —S(O)₂CH₃.

In a fifteenth embodiment the invention provides a compound according to any of the foregoing embodiments, wherein R² and R³, together with the carbon atoms to which they are attached, form a 5-7 membered heterocyclyl or a 5-6 membered heteroaryl, wherein each substitutable nitrogen atom in the heterocyclyl and heteroaryl is optionally substituted with: optionally substituted (C₁-C₄)alkyl, —C(O)— optionally substituted (C₁-C₃)alkyl, optionally substituted 4-10 membered heterocyclyl, —(C₁-C₃)alkyl-(4-10 membered) heterocyclyl, or —(C₁-C₃)aralkyl, or 5-6 membered heteroaryl, and wherein each substitutable carbon atom in the heterocyclyl and heteroaryl is optionally substituted with one or more substituents independently selected from deuterium, halo, —CN, —OH, —NRᵃRᵇ, —ORᶜ, optionally substituted —(C₁-C₄)alkyl, —C(O)-optionally substituted (C₁-C₃)alkyl, —C(O)hydroxy, optionally substituted 4-10 membered heterocyclyl, —(C₁-C₃)alkyl-(4-10 membered) heterocyclyl, or —(C₁-C₃)aralkyl.

In a sixteenth embodiment the invention provides a compound according to any of the foregoing embodiments, wherein R² and R³, together with the carbon atoms to which they are attached, form a 5-6 membered heterocyclyl or 5-6 membered heteroaryl, wherein each substitutable nitrogen atom in the heterocyclyl and heteroaryl is optionally substituted with —(C₁-C₃)alkyl, -hydroxy(C₂-C₄)alkyl, -halo(C₁-C₃)alkyl, —(C₂-C₄)alkoxy(C₁-C₃)alkyl, —C(O)(C₁-C₃)alkyl, —C(O)halo(C₁-C₃)alkyl, —C(O)hydroxy(C₁-C₄)alkyl, —C(O)(C₁-C₃)alkylene-N(CH₃)₂, optionally substituted azetidinyl, oxetanyl, optionally substituted piperidinyl, optionally substituted pyrrolidinyl, —CH₂-oxetanyl, -tetrahydropyranyl, —CH₂-tetrahydropyranyl, or —(C₁-C₃)aralkyl; and wherein each substitutable carbon atom in the heterocyclyl and heteroaryl is optionally substituted with one or more substituents independently selected from deuterium, halo, —(C₁-C₄)alkyl, -hydroxy(C₁-C₄)alkyl, -halo(C₁-C₄)alkyl, —(C₁-C₄)alkoxy(C₁-C₄)alkyl, —C(O)(C₁-C₃)alkyl, —C(O)halo(C₁-C₃)alkyl, —C(O)hydroxy, —C(O)(C₁-C₃)alkylene-N(CH₃)₂, oxetanyl, —(C₁-C₃)alkyl-oxetanyl, -tetrahydropyranyl, —(C₁-C₃)alkyl-tetrahydropyranyl, or —(C₁-C₃)aralkyl.

In a seventeenth embodiment the invention provides a compound according to any of the foregoing embodiments, wherein the compound is of Formula (VIII-1) or (VIII-2):

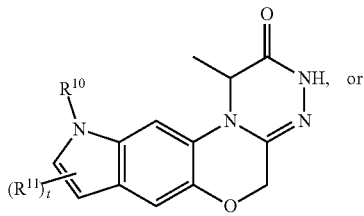

(VIII-1)

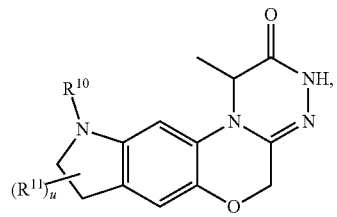

(VIII-2)

wherein
t is 0, 1, or 2;
u is 0, 1, 2, 3, or 4;
R¹⁰ is independently —H, —(C₁-C₃)alkyl, azetidinyl, pyrrolidinyl, or piperidinyl, wherein the azetidinyl, pyrrolidinyl, and piperidinyl are each independently optionally substituted with —(C₁-C₃)alkyl or —C(O)(C₁-C₃)alkyl; and,
R¹¹ is independently deuterium, halo, —(C₁-C₃)alkyl, or hydroxy(C₁-C₃)alkyl.

In an eighteenth embodiment the invention provides a compound according to any of the foregoing embodiments, wherein:
R¹ is —H or —F;
R² is —H, —Br, —F, —CF₃, —NRᵃRᵇ, —CH₃, ethyl, isopropyl, isobutyl, —C(H)(CH₃)CF₃, cyclopropyl, cyclopentyl, cyclohexyl, methoxy, optionally substituted naphthyl, optionally substituted phenyl, optionally substituted tetrahydropyran, benzothiazolyl, optionally substituted pyridinyl, or phenoxyl;
R³ is —NRᵃRᵇ, —ORᶜ, —CH₂-azetidinyl, 3,7-diazaspiro[3.5]nonanyl, optionally substituted piperidinyl, optionally substituted piperazinyl, or optionally substituted pyrrolidinyl; or
R² and R³, together with the carbon atoms to which they are attached, form optionally substituted 2,3-dihydro-1H-pyrrolyl or optionally substituted pyrrolyl;
R⁴ is —CH₃;
Rᵃ is —H or —CH₃;
Rᵇ is —H, phenyl, optionally substituted azetidinyl, azabicyclo[3.2.1]octanyl, or optionally substituted piperidinyl; and
Rᶜ is —H, or optionally substituted azetidinyl; and
X is O.

In a nineteenth embodiment the invention provides a compound according to the first embodiment, wherein the compound is selected from:
6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
(R)-6-(1-Cyclobutyl-ethylamino)-4,7-dimethyl-2,10-dihydro-9-oxa-1,2,4a-triaza-phenanthren-3-one;
6-(Azetidin-3-ylamino)-4-(R)-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;

(R)-6-(Azetidin-3-ylamino)-4-methyl-7-o-tolyl-2,10-dihydro-9-oxa-1,2,4a-triaza-phenanthren-3-one;
(R)-6-(Azetidin-3-ylamino)-7-(3-fluoro-phenyl)-4-methyl-2,10-dihydro-9-oxa-1,2,4a-triaza-phenanthren-3-one;
(R)-6-(Azetidin-3-ylamino)-7-(4-chloro-phenyl)-4-methyl-2,10-dihydro-9-oxa-1,2,4a-triaza-phenanthren-3-one;
(R)-6-(Azetidin-3-ylamino)-7-(2,4-dichloro-phenyl)-4-methyl-2,10-dihydro-9-oxa-1,2,4a-triaza-phenanthren-3-one;
(R)-6-(Azetidin-3-ylamino)-7-(4-fluoro-phenyl)-4-methyl-2,10-dihydro-9-oxa-1,2,4a-triaza-phenanthren-3-one;
(R)-6-(Azetidin-3-ylamino)-4-methyl-7-naphthalen-1-yl-2,10-dihydro-9-oxa-1,2,4a-triaza-phenanthren-3-one;
(R)-6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(azetidin-3-ylamino)-4(R)-methyl-7-trifluoromethyl-2,10-dihydro-9-oxa-1,2,4a-triaza-phenanthren-3-one;
6-(Azetidin-3-ylamino)-4(R),7-dimethyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-(azetidin-3-ylamino)-7-fluoro-4(R)-methyl-2,10-dihydro-9-oxa-1,2,4a-triaza-phenanthren-3-one;
6-(Azetidin-3-ylamino)-7-isopropyl-4(R)-methyl-2,10-dihydro-9-oxa-1,2,4a-triaza-phenanthren-3-one;
6-(Azetidin-3-ylamino)-7-cyclopropyl-4(R)-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
6-Azetidin-3-ylmethyl-4-methyl-2,10-dihydro-9-oxa-1,2,4a-triaza-phenanthren-3-one;
4-Methyl-6-(3-methyl-azetidin-3-ylamino)-7-phenyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4-Methyl-6-(3-methyl-azetidin-3-ylamino)-7-trifluoromethyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-yloxy)-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(2-Benzyl-piperidin-4-yl)-4-methyl-2,10-dihydro-9-oxa-1,2,4a-triaza-phenanthren-3-one;

6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4-methyl-7-o-tolyl-2,10-dihydro-9-oxa-1,2,4a-triaza-phenanthren-3-one;
6-[(1,3-Dimethyl-azetidin-3-yl)-methyl-amino]-7-(2-fluoro-phenyl)-4-methyl-2,10-dihydro-9-oxa-1,2,4a-triaza-phenanthren-3-one;
4-Methyl-6-[methyl-(3-methyl-azetidin-3-yl)-amino]-7-phenyl-2,10-dihydro-9-oxa-1,2,4a-triaza-phenanthren-3-one;
6-[(1-Isopropyl-3-methyl-azetidin-3-yl)-methyl-amino]-4-methyl-7-phenyl-2,10-dihydro-9-oxa-1,2,4a-triaza-phenanthren-3-one;
6-[(1-Ethyl-3-methyl-azetidin-3-yl)-methyl-amino]-4-methyl-7-phenyl-2,10-dihydro-9-oxa-1,2,4a-triaza-phenanthren-3-one;
(R)-6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-ylamino)-2,10-dihydro-9-oxa-1,2,4a-triaza-phenanthren-3-one;
6-Azetidin-3-ylmethyl-4-methyl-7-trifluoromethyl-2,10-dihydro-9-oxa-1,2,4a-triaza-phenanthren-3-one;
(R)-4-Methyl-6-(3-methyl-azetidin-3-ylamino)-7-trifluoromethyl-2,10-dihydro-9-oxa-1,2,4a-triaza-phenanthren-3-one;
(R)-6-(1,3-dimethyl-azetidin-3-ylamino)-4-methyl-7-trifluoromethyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
6-[(1,3-dimethyl-azetidin-3-yl)-methyl-amino]-4(S)-methyl-7-phenyl-2,10-dihydro-9-oxa-1,2,4a-triaza-phenanthren-3-one;
6-(1,3-Dimethyl-azetidin-3-ylamino)-4-methyl-7-phenyl-2,10-dihydro-9-oxa-1,2,4a-triaza-phenanthren-3-one;
(R)-6-((2S,4S)-2-Benzyl-piperidin-4-yl)-4-methyl-2,10-dihydro-9-oxa-1,2,4a-triaza-phenanthren-3-one;
(R)-6-((2S,4R)-2-benzyl-piperidin-4-yl)-4-methyl-2,10-dihydro-9-oxa-1,2,4a-triaza-phenanthren-3-one;
(R)-6-(Azetidin-3-ylamino)-4-methyl-7-(2,2,2-trifluoro-1-methyl-ethyl)-2,10-dihydro-9-oxa-1,2,4a-triaza-phenanthren-3-one;
6-(3-Isopropyl-azetidin-3-ylamino)-4-methyl-2,10-dihydro-9-oxa-1,2,4a-triaza-phenanthren-3-one;
6-(2-Benzyl-piperidin-4-yl)-4-methyl-7-trifluoromethyl-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(1-Isopropyl-3-methyl-azetidin-3-ylamino)-4-methyl-7-(tetrahydro-pyran-4-yl)-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
(R)-6-(Azetidin-3-ylamino)-4-methyl-7-((R)-2,2,2-trifluoro-1-methyl-ethyl)-2,10-dihydro-9-oxa-1,2,4a-triaza-phenanthren-3-one;
(R)-6-(Azetidin-3-ylamino)-4-methyl-7-((S)-2,2,2-trifluoro-1-methyl-ethyl)-2,10-dihydro-9-oxa-1,2,4a-triaza-phenanthren-3-one;
4-Methyl-6-(3-methyl-azetidin-3-ylamino)-7-(2,2,2-trifluoro-1-methyl-ethyl)-2,10-dihydro-9-oxa-1,2,4a-triaza-phenanthren-3-one;
6-(Azetidin-3-yloxy)-4,7-dimethyl-2,10-dihydro-9-oxa-1,2,4a-triaza-phenanthren-3-one;
7-Fluoro-4-methyl-6-piperidin-4-yl-2,10-dihydro-9-oxa-1,2,4a-triaza-phenanthren-3-one;
4-Methyl-6-(3-methyl-piperidin-4-yl)-2,10-dihydro-9-oxa-1,2,4a-triaza-phenanthren-3-one;
6-(3,3-Dimethyl-piperidin-4-yl)-4-methyl-2,10-dihydro-9-oxa-1,2,4a-triaza-phenanthren-3-one;
6-[(1-Benzyl-3-methyl-azetidin-3-yl)-methyl-amino]-4-methyl-7-phenyl-2,10-dihydro-9-oxa-1,2,4a-triaza-phenanthren-3-one;
4-Methyl-6-{methyl-[3-methyl-1-(tetrahydro-pyran-4-yl)-azetidin-3-yl]-amino}-7-phenyl-2,10-dihydro-9-oxa-1,2,4a-triaza-phenanthren-3-one;
4-Methyl-6-{methyl-[3-methyl-1-(tetrahydro-pyran-4-ylmethyl)-azetidin-3-yl]-amino}-7-phenyl-2,10-dihydro-9-oxa-1,2,4a-triaza-phenanthren-3-one;
6-(Azetidin-3-ylamino)-4-methyl-2,10-dihydro-9-thia-1,2,4a-triaza-phenanthren-3-one;
(S)-4-methyl-6-(3-methyl-azetidin-3-ylamino)-7-trifluoromethyl-2,10-dihydro-9-oxa-1,2,4a-triaza-phenanthren-3-one;
(S)-6-(1,3-Dimethyl-azetidin-3-ylamino)-4-methyl-7-trifluoromethyl-2,10-dihydro-9-oxa-1,2,4a-triaza-phenanthren-3-one;
(R)-4-Methyl-6-[methyl-(3-methyl-azetidin-3-yl)-amino]-7-trifluoromethyl-2,10-dihydro-9-oxa-1,2,4a-triaza-phenanthren-3-one;
10-Azetidin-3-yl-1-methyl-3,5-dihydro-10H-6-oxa-3,4,10,11b-tetraaza-cyclopenta[b]phenanthren-2-one;

6-(Azetidin-3-ylamino)-4-methyl-7-phenoxy-2,10-dihydro-9-oxa-1,2,4a-triaza-phenanthren-3-one;
4-Methyl-6-(3-methyl-azetidin-3-yloxy)-7-trifluoromethyl-2,10-dihydro-9-oxa-1,2,4a-triaza-phenanthren-3-one;
6-(Azetidin-3-ylamino)-4-methyl-9,10-dihydro-2H-1,2,4a-triaza-phenanthren-3-one;
(R)-6-((S)-1-Azetidin-3-yl-ethyl)-4-methyl-2,10-dihydro-9-oxa-1,2,4a-triaza-phenanthren-3-one;
(R)-6-((R)-1-Azetidin-3-yl-ethyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
4-Methyl-6-(2-methyl-azetidin-3-ylamino)-2,10-dihydro-9-oxa-1,2,4a-triaza-phenanthren-3-one;
4-Methyl-6-piperidin-4-yl-7-trifluoromethyl-2,10-dihydro-9-oxa-1,2,4a-triaza-phenanthren-3-one;
(R)-7-Isopropyl-4-methyl-6-(3-methyl-azetidin-3-yloxy)-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
(R)-6-(Azetidin-3-yloxy)-7-fluoro-4-methyl-2,10-dihydro-9-oxa-1,2,4a-triaza-phenanthren-3-one;
4,7-Dimethyl-6-(1-methyl-azetidin-3-ylamino)-2,10-dihydro-9-oxa-1,2,4a-triaza-phenanthren-3-one;
6-(Azetidin-3-ylamino)-7-benzyloxy-4-methyl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
4-Methyl-6-[1-(3-methyl-azetidin-3-yl)-ethyl]-2,10-dihydro-9-oxa-1,2,4a-triaza-phenanthren-3-one;
6-(azetidin-3-ylamino)-4-(S)-methyl-7-phenyl-2,10-dihydro-9-oxa-1,2,4a-triaza-phenanthren-3-one;
6-(Azetidin-3-ylamino)-4(S)-methyl-7-trifluoromethyl-2,10-dihydro-9-oxa-1,2,4a-triaza-phenanthren-3-one;
6-(azetidin-3-ylamino)-4(S),7-dimethyl-2,10-dihydro-9-oxa-1,2,4a-triaza-phenanthren-3-one;
6-(Azetidin-3-ylamino)-7-fluoro-4(S)-methyl-2,10-dihydro-9-oxa-1,2,4a-triaza-phenanthren-3-one;
6-(azetidin-3-ylamino)-7-isopropyl-4(S)-methyl-2,10-dihydro-9-oxa-1,2,4a-triaza-phenanthren-3-one;
6-(azetidin-3-ylamino)-7-cyclopropyl-4(S)-methyl-2,10-dihydro-9-oxa-1,2,4a-triaza-phenanthren-3-one;
(S)-7-isopropyl-4-methyl-6-(3-methyl-azetidin-3-yloxy)-2,10-dihydro-9-oxa-1,2,4a-triaza-phenanthren-3-one;
3-((R)-7-Fluoro-4-methyl-3-oxo-2,3,4,10-tetrahydro-9-oxa-1,2,4a-triaza-phenanthren-6-ylamino)-azetidine-1-carboxylic acid 1-acetoxy-ethyl;
(S)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(S)-6-(Azetidin-3-ylamino)-4-methyl-7-o-tolyl-2,10-dihydro-9-oxa-1,2,4a-triaza-phenanthren-3-one;
(S)-6-(Azetidin-3-ylamino)-7-cyclopropyl-4-methyl-2,10-dihydro-9-oxa-1,2,4a-triaza-phenanthren-3-one;
(S)-6-(Azetidin-3-ylamino)-7-(3-fluoro-phenyl)-4-methyl-2,10-dihydro-9-oxa-1,2,4a-triaza-phenanthren-3-one;
(S)-6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
(S)-6-(Azetidin-3-ylamino)-7-(4-fluoro-phenyl)-4-methyl-2,10-dihydro-9-oxa-1,2,4a-triaza-phenanthren-3-one;
(S)-6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
(S)-6-(Azetidin-3-ylamino)-4-methyl-7-phenyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-isopropyl-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-isopropyl-4-methyl-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
(S)-6-(Azetidin-3-ylamino)-4-methyl-7-trifluoromethyl-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
(S)-6-(Azetidin-3-ylamino)-4-methyl-7-(4-trifluoromethoxy-phenyl)-2,10-dihydro-9-oxa-1,2,4a-triaza-phenanthren-3-one;
(S)-6-(Azetidin-3-ylamino)-4,7-dimethyl-2,10-dihydro-9-oxa-1,2,4a-triaza-phenanthren-3-one;
(S)-6-(Azetidin-3-ylamino)-7-fluoro-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;

6-(Azetidin-3-ylamino)-7-(3-methoxy-phenyl)-4-methyl-2,
10-dihydro-9-oxa-1,2,4a-triaza-phenanthren-3-one;
6-(Azetidin-3-ylamino)-7-(4-fluoro-phenyl)-4-methyl-2,10-
dihydro-9-oxa-1,2,4a-triaza-phenanthren-3-one;
6-(Azetidin-3-yloxy)-7-isopropyl-4-methyl-2,10-dihydro-9-
oxa-1,2,4a-triaza-phenanthren-3-one;
6-(Azetidin-3-ylamino)-4-methyl-7-(4-trifluoromethoxy-
phenyl)-2,10-dihydro-9-oxa-1,2,4a-triaza-phenanthren-3-
one;
6-(Azetidin-3-ylamino)-4-methyl-7-m-tolyl-2,10-dihydro-
9-oxa-1,2,4a-triaza-phenanthren-3-one;
10-Methyl-6-(3-methyl-azetidin-3-ylamino)-7-phenyl-2,10-
dihydro-9-oxa-1,2,4a-triaza-phenanthren-3-one;
6-(Azetidin-3-ylamino)-7-(3,4-difluoro-phenyl)-4-methyl-
2,10-dihydro-9-oxa-1,2,4a-triaza-phenanthren-3-one;
6-(Azetidin-3-ylamino)-4-methyl-7-(3-trifluoromethyl-phe-
nyl)-2,10-dihydro-9-oxa-1,2,4a-triaza-phenanthren-3-
one;
6-(Azetidin-3-ylamino)-4-methyl-7-trifluoromethyl-2,10-
dihydro-9-oxa-1,2,4a-triaza-phenanthren-3-one;
7-Fluoro-4-methyl-6-(3-methyl-azetidin-3-yloxy)-2,10-di-
hydro-9-oxa-1,2,4a-triaza-phenanthren-3-one;
4,7-Dimethyl-6-piperidin-4-yl-2,10-dihydro-9-oxa-1,2,4a-
triaza-phenanthren-3-one;
4-Methyl-6-(3-methyl-azetidin-3-yloxy)-2,10-dihydro-9-
oxa-1,2,4a-triaza-phenanthren-3-one;
6-(1,3-Dimethyl-azetidin-3-ylamino)-4-methyl-7-trifluo-
romethyl-2,10-dihydro-9-oxa-1,2,4a-triaza-phenanthren-
3-one;
4-Methyl-6-piperidin-4-yl-2,10-dihydro-9-oxa-1,2,4a-
triaza-phenanthren-3-one;
6-(Azetidin-3-ylamino)-7-(3,4-dichloro-phenyl)-4-methyl-
2,10-dihydro-9-oxa-1,2,4a-triaza-phenanthren-3-one;
6-(Azetidin-3-ylamino)-7-(4-tert-butyl-phenyl)-4-methyl-2,
10-dihydro-9-oxa-1,2,4a-triaza-phenanthren-3-one;
6-(Azetidin-3-ylamino)-4-methyl-7-(2-trifluoromethoxy-
phenyl)-2,10-dihydro-9-oxa-1,2,4a-triaza-phenanthren-3-
one;
6-(Azetidin-3-ylamino)-4-methyl-7-(2-trifluoromethyl-phe-
nyl)-2,10-dihydro-9-oxa-1,2,4a-triaza-phenanthren-3-
one;
(1R,3S)-3-Amino-cyclopentanecarboxylic acid ((R)-4-me-
thyl-3-oxo-2,3,4,10-tetrahydro-9-oxa-1,2,4a-triaza-
phenanthren-6-yl)-amide;
7-Isopropyl-4-methyl-6-piperidin-4-yl-2,10-dihydro-9-oxa-
1,2,4a-triaza-phenanthren-3-one;
7-Cyclopropyl-4-methyl-6-piperidin-4-yl-2,10-dihydro-9-
oxa-1,2,4a-triaza-phenanthren-3-one;
(1R,3S)-3-Amino-cyclopentanecarboxylic acid ((S)-4-me-
thyl-3-oxo-2,3,4,10-tetrahydro-9-oxa-1,2,4a-triaza-
phenanthren-6-yl)-amide;
6-(Azetidin-3-ylamino)-2,10-dihydro-9-oxa-1,2,4a-triaza-
phenanthrene-3,4-dione;
6-Azetidin-3-ylmethyl-4-methyl-2,10-dihydro-9-oxa-1,2,
4a-triaza-phenanthren-3-one;
(S)-6-(Azetidin-3-yloxy)-7-fluoro-4-methyl-2,10-dihydro-
9-oxa-1,2,4a-triaza-phenanthren-3-one;
6-(Azetidin-3-ylamino)-4-methyl-7-p-tolyl-2,10-dihydro-9-
oxa-1,2,4a-triaza-phenanthren-3-one;
7-Fluoro-4-methyl-6-(3-methyl-azetidin-3-ylamino)-2,10-
dihydro-9-oxa-1,2,4a-triaza-phenanthren-3-one;
6-(Azetidin-3-ylamino)-4-methyl-7-phenyl-2,10-dihydro-9-
oxa-1,2,4a-triaza-phenanthren-3-one;
6-(Azetidin-3-ylamino)-7-(4-methoxy-phenyl)-4-methyl-2,
10-dihydro-9-oxa-1,2,4a-triaza-phenanthren-3-one;
6-(Azetidin-3-ylamino)-7-isobutyl-4-methyl-2,10-dihydro-
9-oxa-1,2,4a-triaza-phenanthren-3-one;
6-(Azetidin-3-ylamino)-7-cyclopentyl-4-methyl-2,10-dihy-
dro-9-oxa-1,2,4a-triaza-phenanthren-3-one;
6-(Azetidin-3-ylamino)-7-ethyl-4-methyl-2,10-dihydro-9-
oxa-1,2,4a-triaza-phenanthren-3-one;
6-(Azetidin-3-ylamino)-7-(2-fluoro-5-methyl-phenyl)-4-
methyl-2,10-dihydro-9-oxa-1,2,4a-triaza-phenanthren-3-
one;
6-(Azetidin-3-ylamino)-7-(4-fluoro-3-methyl-phenyl)-4-
methyl-2,10-dihydro-9-oxa-1,2,4a-triaza-phenanthren-3-
one;
6-(Azetidin-3-ylamino)-7-fluoro-4-methyl-2,10-dihydro-9-
oxa-1,2,4a-triaza-phenanthren-3-one;
6-(Azetidin-3-ylamino)-4-methyl-7-naphthalen-1-yl-2,10-
dihydro-9-oxa-1,2,4a-triaza-phenanthren-3-one;
6-(Azetidin-3-ylamino)-4-methyl-7-phenylamino-2,10-di-
hydro-9-oxa-1,2,4a-triaza-phenanthren-3-one;
6-(Azetidin-3-ylamino)-7-(3-fluoro-5-methyl-phenyl)-4-
methyl-2,10-dihydro-9-oxa-1,2,4a-triaza-phenanthren-3-
one;
6-(Azetidin-3-ylamino)-7,8-difluoro-4-methyl-2,10-dihy-
dro-9-oxa-1,2,4a-triaza-phenanthren-3-one;
6-(Azetidin-3-ylamino)-4,7-dimethyl-2,10-dihydro-9-oxa-
1,2,4a-triaza-phenanthren-3-one;
6-(Azetidin-3-yloxy)-4,7-dimethyl-2,10-dihydro-9-oxa-1,2,
4a-triaza-phenanthren-3-one;
6-(Azetidin-3-ylamino)-7-(2-methoxy-phenyl)-4-methyl-2,
10-dihydro-9-oxa-1,2,4a-triaza-phenanthren-3-one; 2
6-(Azetidin-3-yloxy)-7-fluoro-4-methyl-2,10-dihydro-9-
oxa-1,2,4a-triaza-phenanthren-3-one;
4-Methyl-6-(3-methyl-azetidin-3-ylamino)-2,10-dihydro-9-
oxa-1,2,4a-triaza-phenanthren-3-one;
4,7-Dimethyl-6-(1-methyl-azetidin-3-ylamino)-2,10-dihy-
dro-9-oxa-1,2,4a-triaza-phenanthren-3-one;
6-(2-Aminomethyl-pyrrolidin-1-yl)-4-methyl-2,10-dihydro-
9-oxa-1,2,4a-triaza-phenanthren-3-one;
6-(Azetidin-3-yl-methyl-amino)-4,7-dimethyl-2,10-dihy-
dro-9-oxa-1,2,4a-triaza-phenanthren-3-one;
6-[(1S,5R)-(8-Aza-bicyclo[3.2.1]oct-3-yl)amino]-7-fluoro-
4-methyl-2,10-dihydro-9-oxa-1,2,4a-triaza-phenanthren-
3-one;
6-(Azetidin-3-yl-benzyl-amino)-4-methyl-2,10-dihydro-9-
oxa-1,2,4a-triaza-phenanthren-3-one;
6-(Azetidin-3-ylamino)-7-(6-methoxy-naphthalen-2-yl)-4-
methyl-2,10-dihydro-9-oxa-1,2,4a-triaza-phenanthren-3-
one;
6-(Azetidin-3-ylamino)-4-methyl-7-naphthalen-2-yl-2,10-
dihydro-9-oxa-1,2,4a-triaza-phenanthren-3-one;
6-(Azetidin-3-ylamino)-7-benzothiazol-5-yl-4-methyl-2,10-
dihydro-9-oxa-1,2,4a-triaza-phenanthren-3-one;
6-(Azetidin-3-ylamino)-7-benzothiazol-6-yl-4-methyl-2,10-
dihydro-9-oxa-1,2,4a-triaza-phenanthren-3-one;
7-Fluoro-4-methyl-6-piperidin-4-yl-2,10-dihydro-9-oxa-1,
2,4a-triaza-phenanthren-3-one;
6-(1,7-Diaza-spiro[3.5]non-1-yl)-4,7-dimethyl-2,10-dihy-
dro-9-oxa-1,2,4a-triaza-phenanthren-3-one;
(3S,4S)-3-Methyl-piperidine-4-carboxylic acid (4-methyl-3-
oxo-2,3,4,10-tetrahydro-9-oxa-1,2,4a-triaza-phenan-
thren-6-yl)-amide;
7-Fluoro-4-methyl-6-(1-methyl-azetidin-3-ylamino)-2,10-
dihydro-9-oxa-1,2,4a-triaza-phenanthren-3-one;
4-Methyl-7-phenyl-6-piperidin-4-yl-2,10-dihydro-9-oxa-1,
2,4a-triaza-phenanthren-3-one;
6-(Azetidin-3-ylamino)-7-cyclohexyl-4-methyl-2,10-dihy-
dro-9-oxa-1,2,4a-triaza-phenanthren-3-one;
6-(Azetidin-3-ylamino)-7-(6-cyclopropylmethoxy-pyridin-
3-yl)-4-methyl-2,10-dihydro-9-oxa-1,2,4a-triaza-phenan-
thren-3-one;

3-[6-(Azetidin-3-ylamino)-4-methyl-3-oxo-2,3,4,10-tetrahydro-9-oxa-1,2,4a-triaza-phenanthren-7-yl]-benzonitrile;
(R)-6-(Azetidin-3-ylamino)-4-methyl-7-trifluoromethyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-chloro-4-methyl-2,10-dihydro-9-oxa-1,2,4a-triaza-phenanthren-3-one;
4,7-Dimethyl-6-(1,2,3,6-tetrahydro-pyridin-4-yl)-2,10-dihydro-9-oxa-1,2,4a-triaza-phenanthren-3-one;
6-(Azetidin-3-ylamino)-4-methyl-7-(tetrahydro-pyran-4-yl)-2,10-dihydro-9-oxa-1,2,4a-triaza-phenanthren-3-one;
4-Methyl-6-(1-methyl-azetidin-3-ylamino)-2,10-dihydro-9-oxa-1,2,4a-triaza-phenanthren-3-one;
(R)-6-(Azetidin-3-ylamino)-7-isopropyl-4-methyl-2,10-dihydro-9-oxa-1,2,4a-triaza-phenanthren-3-one;
6-(Azetidin-3-yl-methyl-amino)-7-fluoro-4-methyl-2,10-dihydro-9-oxa-1,2,4a-triaza-phenanthren-3-one;
6-(Azetidin-3-ylamino)-7-methoxy-4-methyl-2,10-dihydro-9-oxa-1,2,4a-triaza-phenanthren-3-one;
4-Methyl-6-(1-methyl-piperidin-4-yl)-2,10-dihydro-9-oxa-1,2,4a-triaza-phenanthren-3-one;
4-Methyl-6-pyrrolidin-3-yl-2,10-dihydro-9-oxa-1,2,4a-triaza-phenanthren-3-one;
6-(Azetidin-3-yl-cyclopropyl-amino)-2,10-dihydro-9-oxa-1,2,4a-triaza-phenanthren-3-one;
(1R,8r)-8-(2,6-difluorophenyl)-9-((3R,4R)-1,3-dimethylpiperidin-4-yl)-1-methyl-3,5-dihydrobenzo[5,6][1,4]oxazino[3,4-c][1,2,4]triazin-2(1H)-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-6-(3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(S)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-7-(3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-7-(2,6-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((2R,5S)-2,5-Dimethyl-piperazin-1-yl)-7-(2-fluoro-phenyl)-4-methyl-2,10-dihydro-9-oxa-1,2,4a-triaza-phenanthren-3-one hydrochloride;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one; or
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one.

In a twentieth embodiment the invention provides a method of treating a disease or condition, comprising administering a therapeutically effective amount of a compound of any one of the foregoing embodiments.

In a twenty-first embodiment the invention provides a method according to the twentieth embodiment, wherein the disease or condition is selected from the group consisting of an ocular condition, a cancer, rheumatoid arthritis, ankylosing spondilitis, psoriasis, psoriatic athritis, ulcerative colitis, Crohn's disease, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, juvenile idiopathic athritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization, diabetic retinopathy, retinopathy of prematurity, choroidal neovascularization due to age-related macular degeneration, infantile hemangiomas in human beings, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration, hyperproliferative disorders, thyroid hyperplasia, Grave's disease, cysts, hypervascularity of ovarian stroma characteristic of polycystic ovarian syndrome, Stein-Leventhal syndrome, or polycystic kidney disease.

In a twenty-second embodiment the invention provides a method according to the twentieth or twenty-first embodiment wherein the disease or condition is an autoimmune disease.

In a twenty-third embodiment the invention provides a method according to the twentieth, twenty-first or twenty-second embodiment, wherein the autoimmune disease is rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy or systemic lupus erythematosus.

In a twenty-fourth embodiment the invention provides a pharmaceutical composition comprising a compound according to any of the foregoing embodiments and a pharmaceutically acceptable carrier or diluent.

In a twenty-fifth embodiment the invention provides a pharmaceutical composition compound according to any of the foregoing embodiments wherein the compound is:

6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
(R)-6-(1-Cyclobutyl-ethylamino)-4,7-dimethyl-2,10-dihydro-9-oxa-1,2,4a-triaza-phenanthren-3-one;
6-(Azetidin-3-ylamino)-4-(R)-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(R)-6-(Azetidin-3-ylamino)-4-methyl-7-o-tolyl-2,10-dihydro-9-oxa-1,2,4a-triaza-phenanthren-3-one;
(R)-6-(Azetidin-3-ylamino)-7-(3-fluoro-phenyl)-4-methyl-2,10-dihydro-9-oxa-1,2,4a-triaza-phenanthren-3-one;
(R)-6-(Azetidin-3-ylamino)-7-(4-chloro-phenyl)-4-methyl-2,10-dihydro-9-oxa-1,2,4a-triaza-phenanthren-3-one;
(R)-6-(Azetidin-3-ylamino)-7-(2,4-dichloro-phenyl)-4-methyl-2,10-dihydro-9-oxa-1,2,4a-triaza-phenanthren-3-one;
(R)-6-(Azetidin-3-ylamino)-7-(4-fluoro-phenyl)-4-methyl-2,10-dihydro-9-oxa-1,2,4a-triaza-phenanthren-3-one;
(R)-6-(Azetidin-3-ylamino)-4-methyl-7-naphthalen-1-yl-2,10-dihydro-9-oxa-1,2,4a-triaza-phenanthren-3-one;
(R)-6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(azetidin-3-ylamino)-4(R)-methyl-7-trifluoromethyl-2,10-dihydro-9-oxa-1,2,4a-triaza-phenanthren-3-one;
6-(Azetidin-3-ylamino)-4(R),7-dimethyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-(azetidin-3-ylamino)-7-fluoro-4(R)-methyl-2,10-dihydro-9-oxa-1,2,4a-triaza-phenanthren-3-one;
6-(Azetidin-3-ylamino)-7-isopropyl-4(R)-methyl-2,10-dihydro-9-oxa-1,2,4a-triaza-phenanthren-3-one;
6-(Azetidin-3-ylamino)-7-cyclopropyl-4(R)-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;

6-(Azetidin-3-yloxy)-7-isopropyl-4-methyl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
6-Azetidin-3-ylmethyl-4-methyl-2,10-dihydro-9-oxa-1,2,4a-triaza-phenanthren-3-one;
4-Methyl-6-(3-methyl-azetidin-3-ylamino)-7-phenyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4-Methyl-6-(3-methyl-azetidin-3-ylamino)-7-trifluoromethyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-yloxy)-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(2-Benzyl-piperidin-4-yl)-4-methyl-2,10-dihydro-9-oxa-1,2,4a-triaza-phenanthren-3-one;
6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4-methyl-7-o-tolyl-2,10-dihydro-9-oxa-1,2,4a-triaza-phenanthren-3-one;
6-[(1,3-Dimethyl-azetidin-3-yl)-methyl-amino]-7-(2-fluoro-phenyl)-4-methyl-2,10-dihydro-9-oxa-1,2,4a-triaza-phenanthren-3-one;
4-Methyl-6-[methyl-(3-methyl-azetidin-3-yl)-amino]-7-phenyl-2,10-dihydro-9-oxa-1,2,4a-triaza-phenanthren-3-one;
6-[(1-Isopropyl-3-methyl-azetidin-3-yl)-methyl-amino]-4-methyl-7-phenyl-2,10-dihydro-9-oxa-1,2,4a-triaza-phenanthren-3-one;
6-[(1-Ethyl-3-methyl-azetidin-3-yl)-methyl-amino]-4-methyl-7-phenyl-2,10-dihydro-9-oxa-1,2,4a-triaza-phenanthren-3-one;
(R)-6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-ylamino)-2,10-dihydro-9-oxa-1,2,4a-triaza-phenanthren-3-one;
6-Azetidin-3-ylmethyl-4-methyl-7-trifluoromethyl-2,10-dihydro-9-oxa-1,2,4a-triaza-phenanthren-3-one;
(R)-4-Methyl-6-(3-methyl-azetidin-3-ylamino)-7-trifluoromethyl-2,10-dihydro-9-oxa-1,2,4a-triaza-phenanthren-3-one;
(R)-6-(1,3-dimethyl-azetidin-3-ylamino)-4-methyl-7-trifluoromethyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
6-[(1,3-dimethyl-azetidin-3-yl)-methyl-amino]-4(S)-methyl-7-phenyl-2,10-dihydro-9-oxa-1,2,4a-triaza-phenanthren-3-one;
6-(1,3-Dimethyl-azetidin-3-ylamino)-4-methyl-7-phenyl-2,10-dihydro-9-oxa-1,2,4a-triaza-phenanthren-3-one;
(R)-6-((2S,4S)-2-Benzyl-piperidin-4-yl)-4-methyl-2,10-dihydro-9-oxa-1,2,4a-triaza-phenanthren-3-one;
(R)-6-((2S,4R)-2-benzyl-piperidin-4-yl)-4-methyl-2,10-dihydro-9-oxa-1,2,4a-triaza-phenanthren-3-one;
(R)-6-(Azetidin-3-ylamino)-4-methyl-7-(2,2,2-trifluoro-1-methyl-ethyl)-2,10-dihydro-9-oxa-1,2,4a-triaza-phenanthren-3-one;
6-(3-Isopropyl-azetidin-3-ylamino)-4-methyl-2,10-dihydro-9-oxa-1,2,4a-triaza-phenanthren-3-one;
6-(2-Benzyl-piperidin-4-yl)-4-methyl-7-trifluoromethyl-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(1-Isopropyl-3-methyl-azetidin-3-ylamino)-4-methyl-7-(tetrahydro-pyran-4-yl)-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
(R)-6-(Azetidin-3-ylamino)-4-methyl-7-((R)-2,2,2-trifluoro-1-methyl-ethyl)-2,10-dihydro-9-oxa-1,2,4a-triaza-phenanthren-3-one;

(R)-6-(Azetidin-3-ylamino)-4-methyl-7-((S)-2,2,2-trifluoro-1-methyl-ethyl)-2,10-dihydro-9-oxa-1,2,4a-triaza-phenanthren-3-one;

4-Methyl-6-(3-methyl-azetidin-3-ylamino)-7-(2,2,2-trifluoro-1-methyl-ethyl)-2,10-dihydro-9-oxa-1,2,4a-triaza-phenanthren-3-one;

6-(Azetidin-3-yloxy)-4,7-dimethyl-2,10-dihydro-9-oxa-1,2,4a-triaza-phenanthren-3-one;

7-Fluoro-4-methyl-6-piperidin-4-yl-2,10-dihydro-9-oxa-1,2,4a-triaza-phenanthren-3-one;

4-Methyl-6-(3-methyl-piperidin-4-yl)-2,10-dihydro-9-oxa-1,2,4a-triaza-phenanthren-3-one;

6-(3,3-Dimethyl-piperidin-4-yl)-4-methyl-2,10-dihydro-9-oxa-1,2,4a-triaza-phenanthren-3-one;

6-[(1-Benzyl-3-methyl-azetidin-3-yl)-methyl-amino]-4-methyl-7-phenyl-2,10-dihydro-9-oxa-1,2,4a-triaza-phenanthren-3-one;

4-Methyl-6-{methyl-[3-methyl-1-(tetrahydro-pyran-4-yl)-azetidin-3-yl]-amino}-7-phenyl-2,10-dihydro-9-oxa-1,2,4a-triaza-phenanthren-3-one;

4-Methyl-6-{methyl-[3-methyl-1-(tetrahydro-pyran-4-ylmethyl)-azetidin-3-yl]-amino}-7-phenyl-2,10-dihydro-9-oxa-1,2,4a-triaza-phenanthren-3-one;

6-(Azetidin-3-ylamino)-4-methyl-2,10-dihydro-9-thia-1,2,4a-triaza-phenanthren-3-one;

(S)-4-methyl-6-(3-methyl-azetidin-3-ylamino)-7-trifluoromethyl-2,10-dihydro-9-oxa-1,2,4a-triaza-phenanthren-3-one;

(S)-6-(1,3-Dimethyl-azetidin-3-ylamino)-4-methyl-7-trifluoromethyl-2,10-dihydro-9-oxa-1,2,4a-triaza-phenanthren-3-one;

(R)-4-Methyl-6-[methyl-(3-methyl-azetidin-3-yl)-amino]-7-trifluoromethyl-2,10-dihydro-9-oxa-1,2,4a-triaza-phenanthren-3-one;

10-Azetidin-3-yl-1-methyl-3,5-dihydro-10H-6-oxa-3,4,10,11b-tetraaza-cyclopenta[b]phenanthren-2-one;

6-(Azetidin-3-ylamino)-4-methyl-7-phenoxy-2,10-dihydro-9-oxa-1,2,4a-triaza-phenanthren-3-one;

4-Methyl-6-(3-methyl-azetidin-3-yloxy)-7-trifluoromethyl-2,10-dihydro-9-oxa-1,2,4a-triaza-phenanthren-3-one;

6-(Azetidin-3-ylamino)-4-methyl-9,10-dihydro-2H-1,2,4a-triaza-phenanthren-3-one;

(R)-6-((S)-1-Azetidin-3-yl-ethyl)-4-methyl-2,10-dihydro-9-oxa-1,2,4a-triaza-phenanthren-3-one;

(R)-6-((R)-1-Azetidin-3-yl-ethyl)-4-methyl-2,10-dihydro-9-oxa-1,2,4a-triaza-phenanthren-3-one;

6-(Azetidin-3-ylamino)-7,8-difluoro-4-methyl-2,10-dihydro-9-oxa-1,2,4a-triaza-phenanthren-3-one;

6-(1,7-Diaza-spiro[3.5]non-1-yl)-4,7-dimethyl-2,10-dihydro-9-oxa-1,2,4a-triaza-phenanthren-3-one;

6-(2-Aminomethyl-pyrrolidin-1-yl)-4-methyl-2,10-dihydro-9-oxa-1,2,4a-triaza-phenanthren-3-one;

4-Methyl-6-(2-methyl-azetidin-3-ylamino)-2,10-dihydro-9-oxa-1,2,4a-triaza-phenanthren-3-one;

4-Methyl-6-piperidin-4-yl-7-trifluoromethyl-2,10-dihydro-9-oxa-1,2,4a-triaza-phenanthren-3-one;

(R)-7-Isopropyl-4-methyl-6-(3-methyl-azetidin-3-yloxy)-2,10-dihydro-9-oxa-1,2,4a-triaza-phenanthren-3-one;

6-(Azetidin-3-ylamino)-4,7-dimethyl-2,10-dihydro-9-oxa-1,2,4a-triaza-phenanthren-3-one;

6-(Azetidin-3-yloxy)-7-fluoro-4-methyl-2,10-dihydro-9-oxa-1,2,4a-triaza-phenanthren-3-one;

(R)-6-(Azetidin-3-yloxy)-7-fluoro-4-methyl-2,10-dihydro-9-oxa-1,2,4a-triaza-phenanthren-3-one;

4,7-Dimethyl-6-(1-methyl-azetidin-3-ylamino)-2,10-dihydro-9-oxa-1,2,4a-triaza-phenanthren-3-one;

6-(Azetidin-3-ylamino)-7-benzyloxy-4-methyl-2,10-dihydro-9-oxa-1,2,4a-triaza-phenanthren-3-one;

6-(Azetidin-3-ylamino)-4-methyl-7-phenylamino-2,10-dihydro-9-oxa-1,2,4a-triaza-phenanthren-3-one;

4-Methyl-6-[1-(3-methyl-azetidin-3-yl)-ethyl]-2,10-dihydro-9-oxa-1,2,4a-triaza-phenanthren-3-one;

6-(azetidin-3-ylamino)-4-(S)-methyl-7-phenyl-2,10-dihydro-9-oxa-1,2,4a-triaza-phenanthren-3-one;

6-(Azetidin-3-ylamino)-4(S)-methyl-7-trifluoromethyl-2,10-dihydro-9-oxa-1,2,4a-triaza-phenanthren-3-one;

6-(azetidin-3-ylamino)-4(S),7-dimethyl-2,10-dihydro-9-oxa-1,2,4a-triaza-phenanthren-3-one;

6-(Azetidin-3-ylamino)-7-fluoro-4(S)-methyl-2,10-dihydro-9-oxa-1,2,4a-triaza-phenanthren-3-one;

6-(azetidin-3-ylamino)-7-isopropyl-4(S)-methyl-2,10-dihydro-9-oxa-1,2,4a-triaza-phenanthren-3-one;

6-(azetidin-3-ylamino)-7-cyclopropyl-4(S)-methyl-2,10-dihydro-9-oxa-1,2,4a-triaza-phenanthren-3-one;

(S)-7-isopropyl-4-methyl-6-(3-methyl-azetidin-3-yloxy)-2,10-dihydro-9-oxa-1,2,4a-triaza-phenanthren-3-one;

3-((R)-7-Fluoro-4-methyl-3-oxo-2,3,4,10-tetrahydro-9-oxa-1,2,4a-triaza-phenanthren-6-ylamino)-azetidine-1-carboxylic acid 1-acetoxy-ethyl;

(S)-6-(Azetidin-3-ylamino)-7-(2-fluoro-phenyl)-4-methyl-2,10-dihydro-9-oxa-1,2,4a-triaza-phenanthren-3-one;

6-(Azetidin-3-ylamino)-7-(2-fluoro-phenyl)-4-methyl-2,10-dihydro-9-oxa-1,2,4a-triaza-phenanthren-3-one;

(R)-6-(Azetidin-3-ylamino)-7-(2,4-difluoro-phenyl)-4-methyl-2,10-dihydro-9-oxa-1,2,4a-triaza-phenanthren-3-one;

(S)-6-(Azetidin-3-ylamino)-4-methyl-7-o-tolyl-2,10-dihydro-9-oxa-1,2,4a-triaza-phenanthren-3-one;

(S)-6-(Azetidin-3-ylamino)-7-cyclopropyl-4-methyl-2,10-dihydro-9-oxa-1,2,4a-triaza-phenanthren-3-one;

(S)-6-(Azetidin-3-ylamino)-7-(3-fluoro-phenyl)-4-methyl-2,10-dihydro-9-oxa-1,2,4a-triaza-phenanthren-3-one;

(S)-6-(Azetidin-3-ylamino)-7-(4-chloro-phenyl)-4-methyl-2,10-dihydro-9-oxa-1,2,4a-triaza-phenanthren-3-one;

(S)-6-(Azetidin-3-ylamino)-7-(2,4-dichloro-phenyl)-4-methyl-2,10-dihydro-9-oxa-1,2,4a-triaza-phenanthren-3-one;

6-(Azetidin-3-ylamino)-7-(2,4-dichloro-phenyl)-4-methyl-2,10-dihydro-9-oxa-1,2,4a-triaza-phenanthren-3-one;

(S)-6-(Azetidin-3-ylamino)-7-(4-fluoro-phenyl)-4-methyl-2,10-dihydro-9-oxa-1,2,4a-triaza-phenanthren-3-one;

(S)-6-(Azetidin-3-ylamino)-4-methyl-7-naphthalen-1-yl-2,10-dihydro-9-oxa-1,2,4a-triaza-phenanthren-3-one;

6-(Azetidin-3-ylamino)-7-(2-fluoro-4-methyl-phenyl)-4-methyl-2,10-dihydro-9-oxa-1,2,4a-triaza-phenanthren-3-one;

6-(Azetidin-3-ylamino)-7-(4-fluoro-2-methyl-phenyl)-4-methyl-2,10-dihydro-9-oxa-1,2,4a-triaza-phenanthren-3-one;

6-(Azetidin-3-ylamino)-7-(2-chloro-phenyl)-4-methyl-2,10-dihydro-9-oxa-1,2,4a-triaza-phenanthren-3-one;

(S)-6-(Azetidin-3-ylamino)-4-methyl-7-phenyl-2,10-dihydro-9-oxa-1,2,4a-triaza-phenanthren-3-one;

6-(Azetidin-3-ylamino)-7-(4-chloro-phenyl)-4-methyl-2,10-dihydro-9-oxa-1,2,4a-triaza-phenanthren-3-one;

(S)-6-(Azetidin-3-ylamino)-7-isopropyl-4-methyl-2,10-dihydro-9-oxa-1,2,4a-triaza-phenanthren-3-one;

6-(Azetidin-3-ylamino)-7-(3-fluoro-phenyl)-4-methyl-2,10-dihydro-9-oxa-1,2,4a-triaza-phenanthren-3-one;

6-(Azetidin-3-ylamino)-7-(2,4-difluoro-phenyl)-4-methyl-2,10-dihydro-9-oxa-1,2,4a-triaza-phenanthren-3-one;

6-(Azetidin-3-ylamino)-4-methyl-7-o-tolyl-2,10-dihydro-9-oxa-1,2,4a-triaza-phenanthren-3-one;

6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-isopropyl-4-methyl-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
S)-6-(Azetidin-3-ylamino)-4-methyl-7-trifluoromethyl-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
(S)-6-(Azetidin-3-ylamino)-4-methyl-7-(4-trifluoromethoxy-phenyl)-2,10-dihydro-9-oxa-1,2,4a-triaza-phenanthren-3-one;
(S)-6-(Azetidin-3-ylamino)-4,7-dimethyl-2,10-dihydro-9-oxa-1,2,4a-triaza-phenanthren-3-one;
(S)-6-(Azetidin-3-ylamino)-7-fluoro-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
10-Methyl-6-(3-methyl-azetidin-3-ylamino)-7-phenyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-4-methyl-7-trifluoromethyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
(1R,3S)-3-Amino-cyclopentanecarboxylic acid ((R)-4-methyl-3-oxo-2,3,4,10-tetrahydro-9-oxa-1,2,4a-triaza-phenanthren-6-yl)-amide;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
(1R,3S)-3-Amino-cyclopentanecarboxylic acid ((S)-4-methyl-3-oxo-2,3,4,10-tetrahydro-9-oxa-1,2,4a-triaza-phenanthren-6-yl)-amide;
6-(Azetidin-3-ylamino)-2,10-dihydro-9-oxa-1,2,4a-triaza-phenanthrene-3,4-dione;
6-Azetidin-3-ylmethyl-4-methyl-2,10-dihydro-9-oxa-1,2,4a-triaza-phenanthren-3-one;
(S)-6-(Azetidin-3-yloxy)-7-fluoro-4-methyl-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-4,7-dimethyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
4-Methyl-6-(3-methyl-azetidin-3-ylamino)-2,10-dihydro-9-oxa-1,2,4a-triaza-phenanthren-3-one;

4,7-Dimethyl-6-(1-methyl-azetidin-3-ylamino)-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-[(1S,5R)-(8-Aza-bicyclo[3.2.1]oct-3-yl)amino]-7-fluoro-4-methyl-2,10-dihydro-9-oxa-1,2,4a-triaza-phenanthren-3-one;
6-(Azetidin-3-yl-benzyl-amino)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;
7-Fluoro-4-methyl-6-piperidin-4-yl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
(3S,4S)-3-Methyl-piperidine-4-carboxylic acid (4-methyl-3-oxo-2,3,4,10-tetrahydro-9-oxa-1,2,4a-triaza-phenanthren-6-yl)-amide;
7-Fluoro-4-methyl-6-(1-methyl-azetidin-3-ylamino)-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(Azetidin-3-ylamino)-7-cyclohexyl-4-methyl-2,10-dihydro-9-oxa-1,2,4a-triaza-phenanthren-3-one;
6-(Azetidin-3-ylamino)-7-(6-cyclopropylmethoxy-pyridin-3-yl)-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
(R)-6-(Azetidin-3-ylamino)-4-methyl-7-trifluoromethyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-chloro-4-methyl-2,10-dihydro-9-oxa-1,2,4a-triaza-phenanthren-3-one;
4,7-Dimethyl-6-(1,2,3,6-tetrahydro-pyridin-4-yl)-2,10-dihydro-9-oxa-1,2,4a-triaza-phenanthren-3-one;
6-(Azetidin-3-ylamino)-4-methyl-7-(tetrahydro-pyran-4-yl)-2,10-dihydro-9-oxa-1,2,4a-triaza-phenanthren-3-one;
4-Methyl-6-(1-methyl-azetidin-3-ylamino)-2,10-dihydro-9-oxa-1,2,4a-triaza-phenanthren-3-one;
(R)-6-(Azetidin-3-ylamino)-7-isopropyl-4-methyl-2,10-dihydro-9-oxa-1,2,4a-triaza-phenanthren-3-one;
6-(Azetidin-3-yl-methyl-amino)-7-fluoro-4-methyl-2,10-dihydro-9-oxa-1,2,4a-triaza-phenanthren-3-one;
6-(Azetidin-3-ylamino)-7-methoxy-4-methyl-2,10-dihydro-9-oxa-1,2,4a-triaza-phenanthren-3-one;
4-Methyl-6-(1-methyl-piperidin-4-yl)-2,10-dihydro-9-oxa-1,2,4a-triaza-phenanthren-3-one;
4-Methyl-6-pyrrolidin-3-yl-2,10-dihydro-9-oxa-1,2,4a-triaza-phenanthren-3-one;
6-(Azetidin-3-yl-cyclopropyl-amino)-2,10-dihydro-9-oxa-1,2,4a-triaza-phenanthren-3-one;
(1R,8r)-8-(2,6-difluorophenyl)-9-((3R,4R)-1,3-dimethylpiperidin-4-yl)-1-methyl-3,5-dihydrobenzo[5,6][1,4]oxazino[3,4-c][1,2,4]triazin-2(1H)-one;
R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-6-(3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(S)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-7-(3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-7-(2,6-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;

(R)-6-((2R,5S)-2,5-Dimethyl-piperazin-1-yl)-7-(2-fluoro-phenyl)-4-methyl-2,10-dihydro-9-oxa-1,2,4a-triaza-phenanthren-3-one hydrochloride;

(R)-7-(2-Fluoro-phenyl)-4-methyl-6-((2R,5S)-2,4,5-trim-ethyl-piperazin-1-yl)-2,10-dihydro-9-oxa-1,2,4a-triaza-phenanthren-3-one; or (R)-7-(2-Fluoro-phenyl)-4-methyl-6-((2S,5S)-2,4,5-trim-ethyl-piperazin-1-yl)-2,10-dihydro-9-oxa-1,2,4a-triaza-phenanthren-3-one.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKCtheta is a member of the nPKC sub-family (Baier, G., et al., *J. Biol. Chem.*, 1993, 268, 4997). It has a restricted expression pattern, found predominantly in T cells, platelets and skeletal muscle (Mischak, H. et al., *FEBS Lett.*, 1993, 326, p. 51), with some expression reported in mast cells (Liu, Y. et al., *J. Leukoc. Biol.*, 2001, 69, p. 831) and endothelial cells (Mattila, P. et al., *Life Sci.*, 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., *Nature*, 1997, 385, p. 83), placing it in proximity with other signaling enzymes that mediate T cell activation processes.

In another study (Baier-Bitterlich, G. et al., *Mol. Cell. Biol.*, 1996, 16, p. 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

Other studies showed that PKCtheta, via activation of IκB kinase beta, mediates activation of NF-κB induced by T cell receptor/CD28 co-stimulation (N. Coudronniere et al., *Proc. Nat. Acad. Sci. U.S.A.*, 2000, 97, p. 3394; and Lin, X. et al., *Mol. Cell. Biol.*, 2000, 20, p. 2933).

Proliferation of peripheral T cells from PKCtheta knockout mice, in response to T cell receptor (TCR)/CD28 stimulation was greatly diminished compared to T cells from wild type mice. In addition, the amount of IL-2 released from the T cells was also greatly reduced (Sun, Z. et al., *Nature*, 2000, 404, p. 402). It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., *J. Exp. Med.*, 2004, 199, p. 743; Marsland, B. J. et al., *J. Exp. Med.*, 2004, 200, p. 181). The impaired Th2 cell response results in reduced levels of IL-4 and immunoglobulin E (IgE), contributing to the AHR and inflammatory pathophysiology. Otherwise, the PKCtheta knockout mice seemed normal and fertile.

Recent reports, using PKCtheta knockout mice demonstrate that PKCtheta plays an important role in controlling T cell activation and significantly reduce T cell-mediated autoimmune diseases. These publications show impaired TH1, TH2 and TH17 responses (Healy et al., *J Immunol*, 2006, 177 (3), p. 1886; Salek-Ardakani et al., *J. Immunol*, 2005, 173 (10), p. 6440).

Regulatory T cells (Treg; CD4+CD25highFoxP3+) have been shown to play an important role in controlling autoimmunity by suppressing inflammatory responses (reviewed in Sakaguchi, *Cell*, 2008, 133 (5), p. 775). A recent study suggests that PKCtheta negatively regulates Treg differentiation and function (Ma et al., *J. Immunol*, 2012, 188 (11), p. 5337) and demonstrates that inhibiting PKCtheta, using knock out or inhibitor, increases Treg generation in vitro and in vivo. Another report (Zanin-Zhorov et al., *Science*, 2010, 328, p. 372) shows that PKCtheta inhibition enhances function of Tregs in autoimmune disease. These data suggest that enhancement of Treg differentiation and function through PKCtheta inhibition may be beneficial in controlling autoimmunity.

The studies cited above and others studies confirm the critical role of PKCtheta in T cell activation. Thus an inhibitor of PKCtheta would be of therapeutic benefit in treating immunological disorders and other diseases mediated by the inappropriate activation of T cells.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, rheumatoid arthritis, ankylosing spondilitis, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer Helicobacter related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), and Mesopram. Preferred combinations include methotrexate or leflunomide and in moderate or severe rheumatoid arthritis cases, cyclosporin and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as TNFα or IL-1 (e.g. NIK, IKK, or MAP kinase inhibitors); IL-1β converting enzyme inhibitors; TNFα converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2a, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent is replaced by $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_{12})$ alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylacetyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)$alkyl$)_2$ or glycosyl (the radical resulting from detachment of the hydroxyl of the hemiacetal of a carbohydrate).

Other exemplary pro-drugs release an amine of Formula (I) wherein the free hydrogen of the amine group is replaced by —C(O)alkyl, —C(O)O-alkyl, N-phosphonoxyalkyl, alkyl, cycloalkyl, aryl, heteroaryl or heterocyclyl, wherein the alkyl, cycloalkyl, aryl, heteroaryl or heterocyclyl can be optionally substituted with, for example, halogen and hydroxyl.

As used herein "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

As used herein, "hydrate" is a solvate wherein the solvent molecule is water.

As used herein, the term "bridged ($C_5$-$C_{12}$) cycloalkyl group" means a saturated or unsaturated, bicyclic or polycyclic bridged hydrocarbon group having two or three $C_3$-$C_{10}$ cycloalkyl rings. Non bridged cycloalkyls are excluded. For purposes of exemplification, which should not be construed as limiting the scope of this invention, bridged cyclic hydrocarbon may include bicyclo[2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "bridged ($C_2$-$C_{10}$) heterocyclyl" means bicyclic or polycyclic bridged hydrocarbon groups containing one or more heteroatoms such as nitrogen, oxygen and sulfur. For purposes of exemplification, which should not be construed as limiting the scope of this invention, bridged ($C_2$-$C_{10}$) heterocyclyl may include azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0]nonanyl, and azabicyclo[3.3.1]nonanyl.

As used herein, "spirocyclic ($C_2$-$C_{10}$) heterocyclyl" means bicyclic or polycyclic hydrocarbon group having two or three ($C_3$-$C_{10}$) rings at least one of which contains a heteroatom such as nitrogen, oxygen or sulfur. For purposes of exemplification, which should not be construed as limiting the scope of this invention, spirocyclic ($C_2$-$C_{10}$) heterocyclyl may include diazaspiro[3.5]nonane and diazaspiro[4.5]decane.

As used herein, "spirocyclic ($C_5$-$C_{11}$) carbocyclyl" means a saturated or unsaturated, bicyclic or polycyclic hydrocarbon group having two or three ($C_3$-$C_{10}$) cycloalkyl rings. For purposes of exemplification, which should not be construed as limiting the scope of this invention, spirocyclic ($C_5$-$C_{11}$) carbocyclyl includes spiro[5.5]undecane, spiro[4.5]decane and spiro[4.4]nonane.

The term "heterocyclic", "heterocyclyl" or "heterocyclylene", as used herein, include non-aromatic ring systems, including, but not limited to, monocyclic, bicyclic, and tricyclic rings, which can be completely saturated or which can contain one or more units of unsaturation. (for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzoxadiazolyl, 6,7-dihydro-5H-cyclopentapyrimidinyl, furanyl, imidazolyl, imidazopyridinyl, indolyl, indazolyl, isoxazolyl, isothiazolyl, octahydro-pyrrolopyrrolyl, oxadiazolyl, oxazolyl, phthalazinyl, pteridinyl, purinyl, pyranyl, 5,8-dihydro-6H-pyrano[3,4-d]pyridinyl, pyrazinyl, pyrazolyl, pyridinyl, pyrido[2,3-d]pyrimidinyl, pyrido[4,3-d]pyrimidinyl, pyrido[3,4-d]pyrimidinyl, pyrimidinyl, pyrimido[4,5-d]pyrimidinyl, pyrrolyl, pyrrolo[2,3-d]pyrimidinyl, pyrazolo[3,4-d]pyrimidinyl, quinolinyl, quinazolinyl, 5,6,7,8-tetrahydroquinazolinyl, triazolyl, thiazolyl, thieno[2,3-d]pyrimidinyl, thieno[3,2-d]pyrimidinyl, thiophenyl, tetrazolyl, thiadiazolyl, thienyl, [1,3,5]triazinyl, 5,6,7,8-tetrahydro-imidazo[1,5-a]pyrazinyl, and 5,6,7,8-tetrahydro-triazolo[1,2,4]pyrazinyl.

As used herein, "alkyl" and "alkylene" include straight chained or branched hydrocarbons which are completely saturated. For purposes of exemplification, which should not be construed as limiting the scope of this invention, examples of alkyls are methyl, ethyl, propyl, isopropyl, butyl, pentyl, hexyl and isomers thereof.

As used herein, "alkenyl", "alkenylene", "alkynylene" and "alkynyl" mean hydrocarbon moieties containing two to eight carbons and include straight chained or branched hydrocarbons which contain one or more units of unsaturation, one or more double bonds for alkenyl and one or more triple bonds for alkynyl. For purposes of exemplification, which should not be construed as limiting the scope of this invention, examples of alkenyl are ethenyl, propenyl and butenyl, and examples of alkynyl are ethynyl, propynyl and butynyl.

As used herein, "aryl" or "arylene" groups include aromatic carbocyclic ring systems (e.g. phenyl) and fused polycyclic aromatic ring systems. For purposes of exemplification, which should not be construed as limiting the scope of this invention, aryl groups include naphthyl, biphenyl and 1,2,3,4-tetrahydronaphthyl.

As used herein, "cycloalkyl" or "cycloalkylene" means $C_3$-$C_{12}$ monocyclic or multicyclic (e.g., bicyclic, tricyclic, etc.) hydrocarbons that are completely saturated or have one or more unsaturated bonds but do not amount to an aromatic group. For purposes of exemplification, which should not be construed as limiting the scope of this invention, examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: deuterium, optionally substituted ($C_1$-$C_8$)alkyl groups, optionally substituted ($C_2$-$C_8$)alkenyl groups, ($C_2$-$C_8$)alkynyl groups, optionally substituted ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, —OH, —S—($C_1$-$C_8$)alkyl groups, —SH, —NH($C_1$-$C_8$)alkyl groups, —N(($C_1$-$C_8$)alkyl)$_2$ groups, —NH$_2$, —NH—($C_1$-$C_6$)alkyl-optionally substituted heterocycle, —NH-heterocycle, —C(O)NH$_2$, —C(O)NH($C_1$-$C_8$)alkyl groups, —C(O)N(($C_1$-$C_8$)alkyl)$_2$, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)NH$_2$, —NHC(O)NH($C_1$-$C_8$)alkyl groups, —N(($C_1$-$C_8$)alkyl)C(O)NH$_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$) alkyl groups, —CN, —NO$_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, —NHOH, —NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$) alkyl groups (for example but not limited to —S(O)$_2CF_3$), —S-halogenated ($C_1$-$C_8$)alkyl groups (for example but not limited to —$SCF_3$), —($C_1$-$C_6$)alkyl-optionally substituted heterocycle (for example but not limited to azetidine, piperidine, piperazine, pyrrolidine, tetrahydrofuran, pyran or morpholine), —($C_1$-$C_6$)alkyl-heteroaryl (for example but not limited to tetrazole, imidazole, furan, pyrazine or pyrazole), -optionally substituted phenyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$) alkyl groups, or —C(=N—O—($C_1$-$C_6$)alkyl)-($C_1$-$C_6$)alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few h up to over several days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in EtOH:DCM (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

Abbreviations
Ac Acetyl
AcOH Acetic acid
ATP Adenosine triphosphate
BINAP 2,2'-bis(diphenylphosphino)-1,1'-binaphthalene
Boc t-Butoxycarbonyl
$Boc_2O$ Di-tert-butyl dicarbonate
BOP-Cl Bis(2-oxo-3-oxazolidinyl)phosphonic chloride
BSA Bovine serum albumin
n-BuLi n-Butyllithium
t-BuLi t-Butyllithium
$Bu_4NBr_3$ Tetrabutylammonium tribromide
$CaCl_2$ Calcium chloride
$CO_2$ Carbon dioxide
CT Computed tomography
$Cs_2CO_3$ Cesium carbonate
d Doublet
DCE Dichloroethane
DCM Dichloromethane (methylene chloride)
dd Doublet of doublets
ddd Doublet of doublets of doublets DIEA N,N-Diisopropylethylamine
DMEM Dulbecco's Modified Eagle Medium
DMF N,N-Dimethylformamide
DMSO Dimethyl sulfoxide
Dppf 1,1'-bis(diphenylphosphino)ferrocene
DTT Dithiothreitol
EDC.HCl N-(3-Dimethylaminopropyl)-N'-ethylcarbodiimide hydrochloride
EDTA Ethylene diamine tetraacetic acid
EGTA Ethylene glycol-O,O'-bis(2-aminoethyl)-N,N,N',N'-tetraacetic acid
equiv Equivalent(s)
EtOAc Ethyl acetate
$Et_2O$ Diethyl ether
EtOH Ethanol
FBS Fetal bovine serum
g Gram(s)
h Hour(s)
HATU O-(7-Azabenzotriazol-1-yl)-N,N,N',N'-tetramethyluronium hexafluorophosphate
HCl Hydrochloric acid
HEPES N-2-Hydroxyethylpiperazine-N'-2-ethanesulfonic acid
HOBt Hydroxybenzotriazole
HPLC High-pressure liquid chromatography
IBCF Isobutylchloroformate
i.d. Intradermal
KF Potassium fluoride
$K_2CO_3$ Potassium carbonate
KOt-Bu Potassium tert-butoxide
LC/MS Liquid chromatography/mass spectrometry
LDA Lithium diisopropylamide
$LiAlH_4$ Lithium aluminum hydride
$LiBH_4$ Lithium borohydride
LiBr Lithium bromide
LiHMDS Lithium bis(trimethylsilyl)amide
m Multiplet
M Molar
$MgCl_2$ Magnesium chloride
MeCN Acetonitrile
MeOH Methyl alcohol
$MgSO_4$ Magnesium sulfate
min Minute(s)
mmol Millimole
MOPS 3-(N-Morpholino)-2-hydroxypropanesulfonic acid
Ms Methanesulfonate
MS Mass spectrometry
MsCl Methanesulfonyl chloride
MTT 3-(4,5-Dimethylthiazol-2-yl)-2,5-diphenyltetrazolium bromide
N Normal
$Na(AcO)_3BH$ Sodium triacetoxyborohydride
NaCl Sodium chloride
NaF Sodium fluoride
NaH Sodium hydride
$NaHCO_3$ Sodium bicarbonate
$NaBH_3CN$ Sodium cyanoborohydride
$Na_2CO_3$ Sodium carbonate
NaOH Sodium hydroxide
$Na_2SO_4$ Sodium sulfate
$Na_3VO_4$ Sodium orthovanadate
$NH_3$ Ammonia
$NH_4Cl$ Ammonium chloride
$NH_4OAc$ Ammonium acetate
$NH_4OH$ Ammonium hydroxide
NMP N-Methylpyrrolidinone
NMR Nuclear magnetic resonance
P para
PBS Phosphate buffered saline
Pd/C Palladium on carbon
$PdCl_2$(dppf) Dichloro[1,1'-bis(diphenylphosphino)ferrocene]palladium(II)
$Pd_2(dba)_3$ Bis(dibenzylideneacetone)palladium(0)
$Pd(OAc)_2$ Palladium(II) acetate
$Pd(PPh_3)_4$ Tetrakis(triphenylphosphine)palladium(0)
pH $-\log [H^+]$
Ph Phenyl
PHA Phytohaemagglutinin
ppm Parts per million
PrOH Propanol
PSI Pounds per square inch
PTLC Preparatory thin layer chromatography
PVDF Polyvinylidene fluoride
RB Reaction buffer
RP-HPLC Reverse-phase high-pressure liquid chromatography
RPMI Roswell park memorial institute
rpm Revolutions per minute
$R_t$ Retention time
rt Room temperature
s Singlet
SDS-PAGE Sodium dodecyl sulfate polyacrylamide gel electrophoresis
sec Second
SEM 2-(trimethylsilyl)ethoxymethyl
$SOCl_2$ Thionyl chloride
t Triplet
t- Tertiary
TBAF Tetrabutylammonium fluoride
TBS t-butyldimethylsilyl
TBTU 2-(1H-Benzo[d][1,2,3]triazol-1-yl)-1,1,3,3-tetramethyluronium tetrafluoroborate
td Triplet of doublets
TEA Triethylamine
Tf Trifluoromethanesulfonate
TFA Trifluoroacetic acid
tert- Tertiary
THF Tetrahydrofuran
TLC Thin layer chromatography Assays In Vitro Enzyme Assays PKC kinase activity was assayed by time-resolved fluorescence in vitro kinase assay. Unless otherwise indicated, all reagents used for enzyme assays were obtained from Sigma. Specifically, 5 µL N- or C-terminal His6-tagged, recombinant, human PKC, expressed by baculovirus in Sf21 cells (Millipore) was mixed with 5 µL inhibitor (various concentrations, 5% final DMSO), 5 µL Bio-cdc peptide (Biotin-Ahx-AKVSRSGLYRSPSMPENLNRPR, 2 µM final concentration, New England Peptide) and 5 µL of ATP (100 µM or 1000 µM final concentration) in 1× reaction buffer, 20 µL final volume. (PKC 1×RB: 20 mM MOPS, pH 7.2, 10 mM $MgCl_2$, 5 mM EGTA, 1.1 mM DTT, 0.01% Triton-X-100, 7.5 mM β-phospho-glycerol, 1.1 mM $Na_3VO_4$, 0.05 mg/mL phosphatidylserine, 0.005 mg/mL diacylglycerol, 0.1 mM $CaCl_2$ (Millipore PKC Lipid Activator cat#20133); PKC alpha or theta 1× RB was as described above except $CaCl_2$ concentration was 1.1 mM. Reactions were initiated by addition of enzyme in a black ½ area 96 or 384 well flat bottomed polystyrene plate (Corning).

Following a sixty minute incubation at room temperature, the reaction was quenched with 5 µL of 0.5 M EDTA pH 7.5. Detection buffer is added to each well (50 mM Hepes pH 7.0, 0.4 M KF, 0.01% Tween (BioRad), 0.1% BSA, 0.9 ng/well batch 2 Phospho-(Ser) 14-3-3 Binding Motif 4E2 Monoclonal Antibody-K (Cell Signaling #9606, labeled by Perkin Elmer W1024), and 0.055 µg/well CR130-100 (Perkin Elmer). Plates are incubated for 10 min at rt and read on the RubyStar HTRF micro-plate analyzer, measuring fluorescence counts at 665 nm and 620 nm (20 counts/sec).

Background counts from a minus enzyme control is subtracted from all data. Data (after background correction) are converted to percent activity by dividing by the signal obtained from PKC without drug sample. $IC_{50}$ values are determined by fitting the percent activity vs. inhibitor concentration data set to percent activity=$1/1+[I]/IC_{50}$ by non-linear least means squares curve fitting.

T-Blasts CD3/CD28 Induced IL-2 Assay

Human T-Blasts are generated using PHA following standard protocols. T-Blasts are freeze aliquoted and vials thawed as required. To set up the assay, thaw vial and wash cells using standard growth medium (RPMI 1640 medium with 2 mM L-glutamine, 10 mM HEPES, 100 U/mL Pen/Strep, and 10% FBS) Count and resuspend cells at $2 \times 10^6$/mL in growth medium. Seed $2 \times 10^5$/100 µL cell suspension per well in flat bottomed 96 well plate. Compound dilutions are prepared from 100% DMSO stocks. A total of 8 serial dilutions are made (1/3 in 100% DMSO). Compounds are diluted 1/50 in growth medium to prepare 4x stocks of each tested concentration. 50 µL from each 4x stock concentration is added to the 100 µL cell suspension and incubated for 30 minutes prior stimulus addition. A 4x stimulus stock is prepared using anti-CD3+anti-CD28 antibodies. Antibody mix is added to the cell/compounds suspension in 50 µL at 5 µg/mL final concentration. Compounds are tested in duplicates. Plates are transferred to 37° C./$CO_2$ incubator for 24 hours. After incubation 130 µL of supernatant is collected for IL-2 determination while MTT toxicity analysis is performed on remaining cells/medium.

| Reagent | Vendor | Catalog Number |
| --- | --- | --- |
| DMSO | Sigma | D2650 |
| 96-well assay plates, flat bottom | Costar | 3599 |
| RPMI | Gibco | 11875093 |
| FBS (Heat-inactivated) | Gibco | 10438026 |
| 200 mM L-Glutamine | Gibco | 25030-081 |
| Pen/Strep | Gibco | 15140-122 |
| 1M HEPES | Gibco | 15630-080 |
| Anti-human CD3 antibody @ 1 mg/mL | BD Bioscience | 555336 |
| Anti-human CD28 antibody @ 0.5 mg/mL | BD Bioscience | 555726 |

T-Blasts CD3/CD28 Induced P-IκB-α Assay

Human T-Blasts are generated using PHA following standard protocols. T-Blasts are freeze aliquoted and vials thawed as required. To set up the assay, vial is thawed and cells washed using standard growth medium (RPMI 1640 medium with 2 mM L-glutamine, 10 mM HEPES, 100 U/mL Pen/Strep, and 10% FBS). Maintain cells in culture with growth medium plus 50 µ/mL rhIL-2 for 48 hours prior stimulation. Count and resuspend cells at $6 \times 10^6$/mL in growth medium. Add $1.5 \times 10^6$/250 µL cell suspension to 1.5 mL Eppendorf tubes. Compounds dilutions are prepared from 100% DMSO stocks. A total of 6 serial dilutions are made (1/3 in 100% DMSO) Compounds are diluted 1/4 in growth medium to prepare 25x stocks of each tested concentration. 10 µL from each 25x stock concentration is added to the 250 µL cell suspension and incubated for 30 minutes prior stimulus addition. A 50x stimulus stock is prepared using anti-CD3+anti-CD28 antibodies. Antibody mix is added to the cell/compounds suspension in 5 µL at 5 µg/mL final concentration. Tubes are transferred to 37° C./$CO_2$ incubator for 60 min. After incubation, cells are collected by quick centrifugation in table top Eppendorf centrifuge (12,000 rpm/20 sec.) and washed quickly using 750 µL of ice cold PBS containing 1 mM sodium orthovanadate. Cells are collected by centrifugation (12,000 rpm/20 sec.) and lysed using 50 µL of buffer A. Incubate lysates on ice for 30 min and clear lysates by centrifugation in table top Eppendorf centrifuge (12,000 rpm/10 min./4° C.) Cleared lysates are transferred to new Eppendorf tubes and 50 µL of 2x reducing sample buffer added. Samples are incubated at 90° C. for 5 min before being loaded into gels and separated by SDS-PAGE. Western blot analysis is performed after transferring the gels onto PVDF membranes. A specific monoclonal antibody recognizing a phosphorylated S32/S36 form of IκB-α is used.

| Reagent | Vendor | Catalog Number |
| --- | --- | --- |
| DMSO | Sigma | D2650 |
| RPMI | Gibco | 11875093 |
| FBS (Heat-inactivated) | Gibco | 10438026 |
| 200 mM L-Glutamine | Gibco | 25030-081 |
| Pen/Strep | Gibco | 15140-122 |
| 1M HEPES | Gibco | 15630-080 |
| PBS | Gibco | 14190 |
| Anti-human CD3 antibody @ 1 mg/mL | BD Bioscience | 555336 |
| Anti-human CD28 antibody @ 0.5 mg/mL | BD Bioscience | 555726 |
| Anti-P-IκB-α (S32/S36) | Cell Signaling | 9246 |
| Complete EDTA-free | Roche | 1873580 |

Buffer A Composition:

25 mM Tris pH 7.5, 150 mM NaCl, 1% Trition X-100, 20 mM NaF, 10 mM sodium pyrophosphate, 1 mM DTT, 1 mM EDTA, 1 mM EGTA, 1 mM sodium orthovanadate (added fresh), ½ tablet per 25 mL Complete EDTA-free. (added fresh) protease inhibitor cocktail.

In Vivo

Concanavalin A (Con A)-Induced Cytokine Production in Lewis Rats

The test compound is formulated in an inert vehicle (for example but not limited to 0.5% hydroxypropylmethyl cellulose/0.02% Tween 80 in water) at the desired concentration to achieve doses in the range of 0.01-100 mg/kg. Eight-week-old male Lewis rats (200 g) (Charles River Laboratories) are dosed with the compound orally, at time zero (0 min). After about 60 min the rats are injected intravenously (i.v.) with 10 mg/kg Concanavalin A dissolved in PBS About 2 h later, the rats are cardiac bled and their plasma is analyzed for levels of IL-2 (ELISA kit) and IFN-γ (ELISA kit).

| Reagent | Vendor | Catalog Number |
| --- | --- | --- |
| 0.5% hydroxypropylmethyl cellulose | Sigma | H3785 |
| 0.02% Tween 80 | Sigma | P4780 |
| Concanavalin A (Con A) | Amersham Bioscience | 17-0450-01 |
| PBS | Invitrogen | 14190 |
| IL-2 ELISA kit | R&D Systems | R2000 |
| IFN-γ ELISA kit | R&D Systems | RIF00 |

Glucose-6-Phosphate Isomerase (G6PI) Induced Arthritis in DBA/J Mice

Male DBA/J mice were immunized intradermally (i.d.) at the base of the tail with 100 µL of 1:1 (v/v) emulsion containing 300 µg of G6PI and 200 µg of heat-inactivated *Mycobacterium tuberculosis* H37Ra (Complete Freund's Adjuvant, Difco, Laurence, Kans.).

Preparation of 4× Complete Freund's Adjuvant (CFA). (Difco-VWR-#90002-206).

Start with a volume of cold CFA 4× the volume of the collagen solution, because ¾ of the CFA oil will be discarded. Keep the CFA on ice. Centrifuge CFA @ 1,000 rpm for 10 minutes at 4° C., remove ¾ of the oil (7.5 mL) and discard it, then resuspend the remaining CFA.

To Prepare Emulsion: Load two Luer-Lok glass syringes. Using a long hypodermic needle, load one glass syringe with 4×CFA or 1×IFA, then load a second glass syringe with an equal amount of collagen. Wear goggles for this step in case some of the liquid sprays out. Connect the 2 syringes with a metal Luer-Lok connector and inject the two solutions back and forth to mix them. Keep the apparatus on ice, alternating with forcing the liquid back and forth between the syringes 8-10 times every few minutes until emulsified. To test for emulsification, remove one syringe and let one drop of the liquid fall into a beaker of water. The drop should hold together in the water without spreading over the surface. Keep the collagen/adjuvant on ice after emulsification and while injecting into the animals.

The mice were dosed according to the study design with vehicle, compound or dexamethasone at 1 mg/kg from day 0-17. Seven days after immunization, mice were monitored for arthritis. Rear paws were evaluated for paw-edema using Dyer spring calipers on days 7, 10, 13, 15, and 17. Mice began to show signs of paw swelling between day 7 and 10. At the termination of the experiment, a full 12 hour exposure AUC was performed on the final day.

Adjuvant Induced Arthritis (AIA) in a Lewis Rat

Female Lewis rats, (8 weeks of age, 170 g in weight from Charles River Laboratories) are immunized intradermally (i.d.) in the right hind-footpad with 100 μL of a suspension of mineral oil and containing 200 μg M. tuberculosis (H37RA). The inflammation appears in the contra-lateral (left) hind paw seven days after the initial immunization. Seven days post immunization, the compound is formulated in an inert vehicle (for example but not limited to 0.5% hydroxypropylmethyl cellulose/0.02% Tween 80 in water) and dosed orally once or twice a day for at least 10 days. Baseline paw volume is taken on day 0 using a water displacement pleythsmograph (Vgo Basile North America Inc. PA 19473, Model #7140). Rats are lightly anesthetized with an inhalant anesthetic (isoflurane) and the contra-lateral (left) hind paw is dipped into the plethysmograph and the paw volume is recorded. The rats are scored every other day up to day 17 after immunization. On day 17 after immunization, all rats are exsanguinated by cardiac puncture under isoflurane anesthesia, and the left hind paw is collected to assess the impact on bone erosion using micro-CT or histology. For assessing bone erosion by micro CT, paw samples are scanned (SCANCO Medical, Southeastern, PA, Model # μCT 40) at a voxel size of 18 μm, a threshold of 400, sigma-gauss 0.8, support-gauss 1.0. Bone volume and density is determined for a 360 μm (200 slice) vertical section encompassing the tarsal section of the paw. The 360 μm section is analyzed from the base of the metatarsals to the top of the tibia, with the lower reference point fixed at the tibio-talar junction. In addition, the changes in bone are assessed by histology. Essentially, the left hind paws are collected from various groups and are fixed and decalcified in Cal-Rite following which the paws are embedded in paraffin blocks. 5 μm sections are cut, routinely de-paraffinized and stained by standard hematoxylin and eosin procedure. The sections are then evaluated for inflammation, bone and cartilage erosion using a subjective scoring system with a scale of 0-5. Drug exposure is determined in the plasma using LC/MS.

| Reagent | Vendor | Catalog Number |
|---|---|---|
| Mineral Oil | Sigma | M5904 |
| M. tuberculosis, H37RA | Difco | 231141 |
| 0.5% hydroxypropylmethyl cellulose | Sigma | H3785 |
| 0.02% Tween 80 | Sigma | P4780 |
| Cal-Rite | Richard-Allen Scientific | 5501 |

The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using the synthetic transformations illustrated in Schemes I-VI. Starting materials are commercially available or may be prepared by the procedures described herein, by literature procedures, or by procedures that would be well known to one skilled in the art of organic chemistry. All times and temperatures are approximate. All drying reagents are anhydrous. Unless stated, all aqueous solutions are saturated. If desired, chiral separation of compounds may be accomplished by methods known to one skilled in the art such as chiral SFC or chiral preparative HPLC.

Methods for preparing 3,5-dihydrobenzo[5,6][1,4]oxazino[3,4-c][1,2,4]triazin-2(1H)-one and 3,5-dihydrobenzo[5,6][1,4]thiazino[3,4-c][1,2,4]triazin-2(1H)-one compounds of the invention are illustrated in Schemes I-V. In Scheme I, step a, commercially available 2-amino-4-nitrophenols are reacted with chloroacetyl chloride using conditions described in Preparation #2, Step A, or by methods known to one skilled in the art (for example, *Organic Preparations and Procedures International* 1982, 14 (3), 195-197) to give benzooxazinones 3. Alternatively, 4-chloro-5-nitroanilines are cyclized with methyl 2-mercaptoacetate as described in Example #97, Step A to give benzothiazinones 4. In Scheme I, step c, benzooxazinones 3 or benzothiazinones 4 can be alkylated using conditions such as those described in Preparation #2, Step B, or Example #97, Step B, or by methods known to one skilled in the art (for example, *Indian Journal of Pharmaceutical Sciences* 1991, 53 (4), 180-183). Conversion of lactams 5 and 6 to thiolactams 7 or 8, respectively, may be accomplished using conditions such as those described in Preparation #2, Step C, or Example #97, Step C, or by methods known to one skilled in the art (for example, *Indian Journal of Pharmaceutical Sciences* 1991, 53 (4), 180-183). The materials may be cyclized to dihydrobenzooxazinotriazinones 9 and dihydrobenzothiazinotriazinones 10 using conditions such as those described in Preparation #2, Step D, or Example #97, Step D or by methods known to one skilled in the art (for example, *Indian Journal of Pharmaceutical Sciences* 1991, 53 (4), 180-183). In Scheme I, step g, the materials 9 and 10 may be reduced to the anilines 12 and 13, respectively using methods such as those described in Preparation #2, Step E, or Example #97, Step E, or by a variety of methods known to one skilled in the art (for example, Larock, R. C. "Comprehensive Organic Transformations: A Guide to Functional Group Preparations, $2^{nd}$ edition", 1999, Wiley-VCH). Alternatively, reduction of compounds 7 (Scheme I, step f) followed by cyclization (Scheme I, step h) to give dihydrobenzooxazinotriazinones 9 may be accomplished using methods known to one skilled in the art (for example, Example #56, Steps E and F). Anilines 12 or 13 may undergo further functionalization using reactions known to one skilled in the art (for example, Larock, R. C. referenced above). For example, formation of secondary anilines 14 and 15 may be accomplished using standard conditions such as those described in Example #1, Step A, or Example #97, Step F, or Example #79, Step A, or by methods known to one skilled in the art (for example, Larock, R. C. referenced above). Additional functionalization of secondary anilines 14 to form compounds 16, if desired, can be performed using conditions such as those described in Example #55, Step B, or using reactions known to one skilled in the art (for example, Larock, R. C. referenced above). If $R_2$ or $R_3$ contain a protecting group, deprotection of dihydrobenzooxazinotriazinone and dihydrobenzothiazinotriazinone compounds 14, 15, or 16 can be performed using conditions such as those described in Greene, T. W. and Wuts. P. G. M "Protective Groups in Organic Synthesis, $3^{rd}$ Edition, 1999, Wiley-Interscience". For example, a protecting group such as a t-butyloxycarbonyl (Boc) group can be removed from a protected amine to yield the unprotected amine (for example, Example #55, Step C) and the deprotected compound 14, 15, or 16 may then be reacted further as described above. A protecting group such as a benzylhydryl group can be removed from a protected amine to yield the unprotected amine (for example, Example #80, Step H) and the deprotected compound 14, 15, or 16 may then be reacted further as described above. If desired, chiral separation of compounds 5, 6, 9, 10, 12, 13, 14, 15, or 16 may be done using methods known to one skilled in the art such as chiral SFC or chiral preparative HPLC (for example, Example #1, Step C).

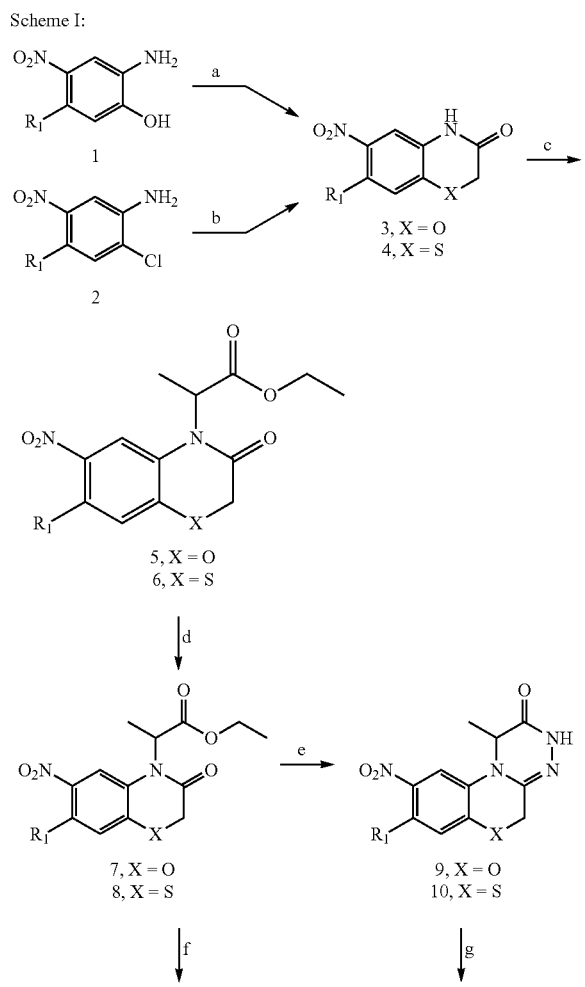

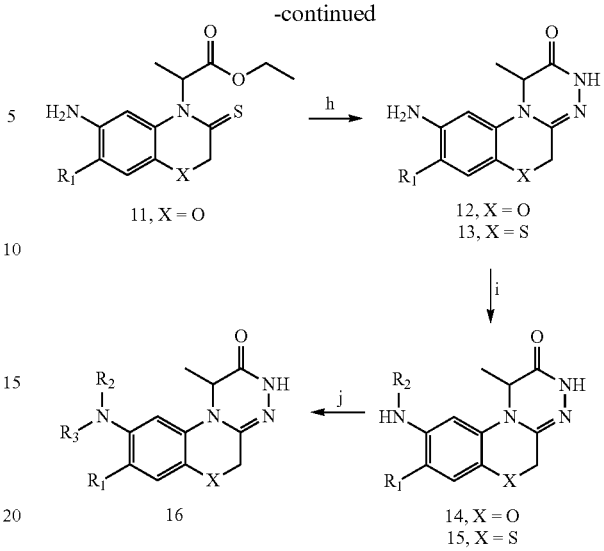

In Scheme II, step a, nitration of commercially available 4-bromophenols 17 provides nitrophenols 18 using methods known to one skilled in the art (for example, Example #53, Step A). Reduction to aminophenols 19 may be accomplished using methods such as those described in Example #53, Step B, or by a variety of methods known to one skilled in the art (for example, Larock, R. C. "Comprehensive Organic Transformations: A Guide to Functional Group Preparations, $2^{nd}$ edition", 1999, Wiley-VCH). In Scheme II, step c, cyclization of aminophenols 19 with chloroacetyl chloride and subsequent alkylation is performed using conditions described in Example #53, Step C, or using reactions known to one skilled in the art (for example, Larock, R. C. referenced above, and *Indian Journal of Pharmaceutical Sciences* 1991, 53 (4), 180-183). The material may be cyclized to dihydrobenzooxazinotriazinones 21 using conditions such as those described in Example #53, Step D, or by methods known to one skilled in the art (for example, *Indian Journal of Pharmaceutical Sciences* 1991, 53 (4), 180-183). Dihydrobenzooxazinotriazinones 21 may be 2-(trimethylsilyl)ethoxymethyl (SEM) protected using conditions such as those described in Example #53, Step E, or by methods known to one skilled in the art (for example, Greene, T. W. and Wuts. P. G. M "Protective Groups in Organic Synthesis, $3^{rd}$ Edition, 1999, Wiley-Interscience".) In Scheme II, step f, an amine is introduced by reaction with dihydrobenzooxazinotriazinones 22 under Buchwald-Hartwig amination conditions (for example, Example #53, Step F, or *Advanced Synthesis & Catalysis* 2004, 346, 1599-1626) to give dihydrobenzooxazinotriazinones 23. Deprotection of dihydrobenzooxazinotriazinones 23 may be accomplished using conditions such as those described in Example #53, Step G, or by methods known to one skilled in the art (for example, the books from Larock, R. C. or Greene, T. W. and Wuts, P. G. M. referenced above). If $R_2$ and/or $R_3$ contain a protecting group, deprotection of compound 24 can be performed using conditions such as those described in Example #53, Step H, or Greene, T. W. and Wuts, P. G. M. described above. For example, a protecting group such as a t-butoxycarbonyl group can be removed with acid using conditions such as those described in Example #53, Step H or by methods known to one skilled in the art (for example, the books from Larock, R. C. or Greene, T. W. and Wuts, P. G. M. referenced above). If desired, chiral separation of compounds 20-24 may be accomplished using methods known to one skilled in the art such as chiral SFC or chiral preparative HPLC (for example, Example #53, Step G). Alternatively $R_1$ can be introduced at a later stage, for example after step f or step g, utilizing the methodology outlined in Scheme IV, steps a and b, or steps a, c and d.

the art (for example, *Indian Journal of Pharmaceutical Sciences* 1991, 53 (4), 180-183). Alternatively, formation of the boronic esters 32 from dihydrobenzooxazinotriazinones 22 (Scheme III, step g) can be performed using conditions such as those described in Example #107, Step A, or using reactions known to one skilled in the art (for example, *Journal of Organic Chemistry* 1995 60, 7508-7510). Formation of phenols 33 can be accomplished by oxidative cleavage using methods known to one skilled in the art (for example, Scheme II:

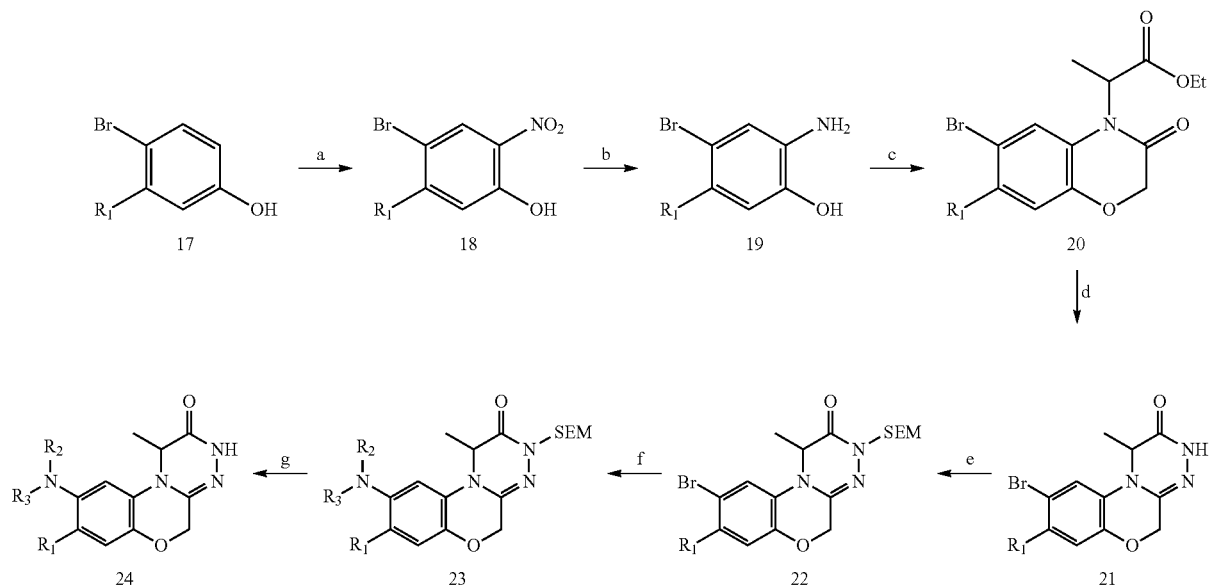

In Scheme III, step a, dihydrobenzooxazinones 25 can be alkylated using conditions such as those described in Example #65, Step A, or by methods known to one skilled in the art (for example, *Indian Journal of Pharmaceutical Sciences* 1991, 53 (4), 180-183). The formation of esters 26 by oxidative rearrangement is accomplished using conditions such as those described in Example #65, Step B or by methods known to one skilled in the art (for example, Larock, R. C. "Comprehensive Organic Transformations: A Guide to Functional Group Preparations, $2^{nd}$ edition", 1999, Wiley-VCH). Deprotection of compounds 27 to yield phenols 28 can be performed using conditions such as those described in Example #65, Step C, or Greene, T. W. and Wuts. P. G. M "Protective Groups in Organic Synthesis, $3^{rd}$ Edition, 1999, Wiley-Interscience". The formation of ethers 29 can be achieved by reaction of phenols 28 with appropriately substituted alkyl mesylates by methods known to one skilled in the art (for example, Example #65, Step D, or Larock, R. C. referenced above). In Scheme III, step e, conversion to thiolactams 30 may be achieved using methods known to one skilled in the art (for example, *Indian Journal of Pharmaceutical Sciences* 1991, 53 (4), 180-183, or Example #65, Step E). Thiolactams 30 may be cyclized to dihydrobenzooxazinotriazinones 31 using conditions such as those described in Example #65, Step F or by methods known to one skilled in Example #107, Step B, or Larock, R. C. referenced above). The formation of ethers 34 can be achieved by methods known to one skilled in the art (for example, Example #107, Step C, or Larock, R. C. referenced above). Deprotection of dihydrobenzooxazinotriazinones 34 may be accomplished using methods known to one skilled in the art (for example, the books from Larock, R. C. or Greene, T. W. and Wuts, P. G. M. referenced above, or Example #107, Step D). If $R_2$ contains a protecting group, deprotection of compounds 29, 30, 31 or 34 can be performed using conditions such as those described in Example #80, Step L, or Example #107, Step D, or Greene, T. W. and Wuts, P. G. M. described above. For example, a protecting group such as a t-butoxycarbonyl group can be removed with acid using conditions such as those described in Example #80, Step L, or by methods known to one skilled in the art (for example, the books from Larock, R. C. or Greene, T. W. and Wuts, P. G. M. referenced above). A protecting group such as a benzylhydryl group can be removed from a protected amine to yield the unprotected amine (for example, Example #107, Step D). The deprotected compounds 29, 30, 31, or 34 may then be reacted further as described above. If desired, chiral separation of compounds 22, 31 or 34 may be done using methods known to one skilled in the art such as chiral SFC or chiral preparative HPLC (for example, Example #96, Step A).

Scheme III:
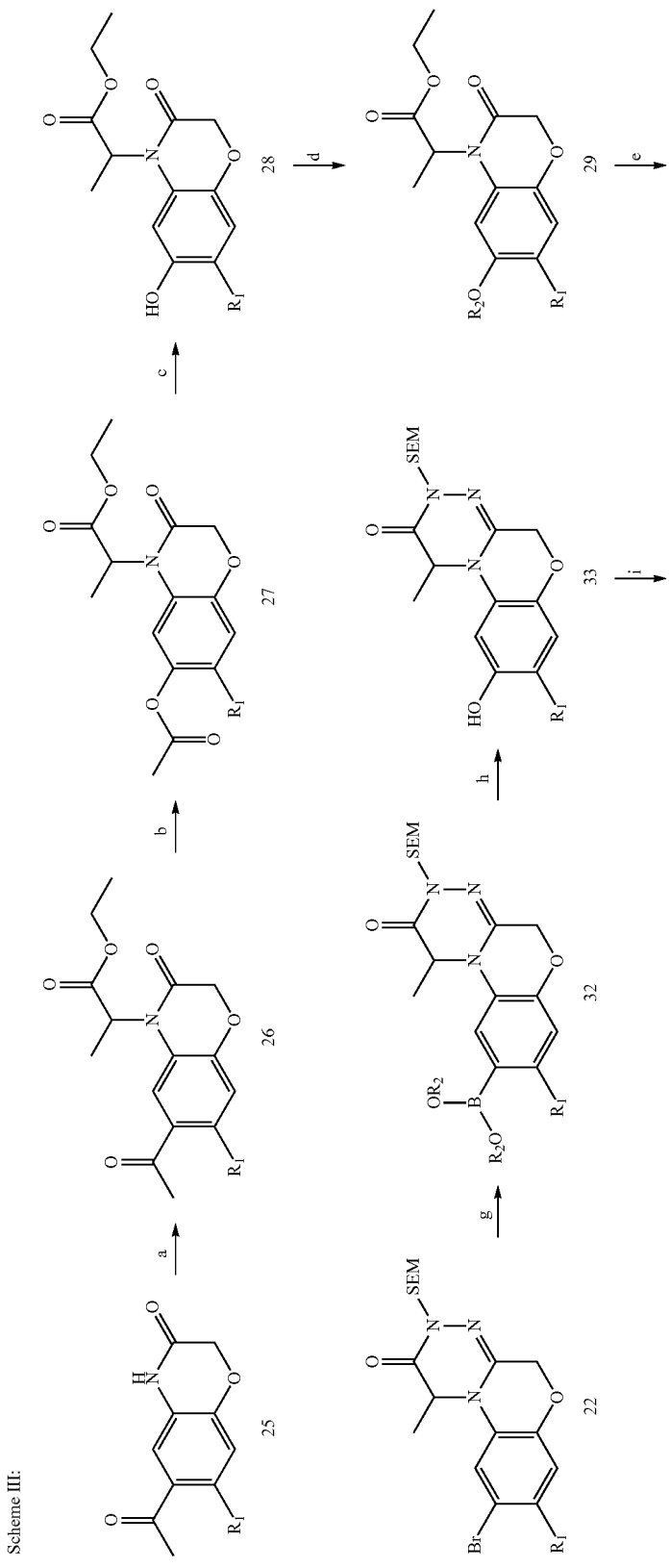

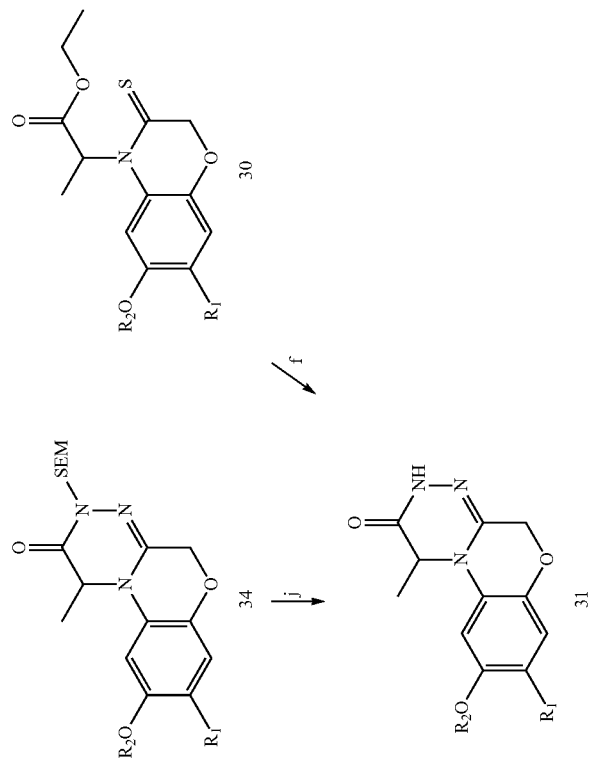

In Scheme IV, step a, bromination of dihydrobenzooxazinones 35 can be accomplished using conditions such as those described in Example #1, Step B, or by methods known to one skilled in the art (for example, Larock, R. C. "Comprehensive Organic Transformations: A Guide to Functional Group Preparations, $2^{nd}$ edition", 1999, Wiley-VCH). Further functionalization of dihydrobenzooxazinones 36 can be performed to yield substituted dihydrobenzooxazinones 37 using reactions known to one skilled in the art (for example, Example #1, Step C or Larock, R. C. referenced above). Alternatively, substituted dihydrobenzooxazinones 39 may be generated by introducing a substituted alkenyl group using conditions such as those described in Example #112, Step A, followed by reduction using reactions known to one skilled in the art (for example, Example #112, Step B, or Larock, R. C. referenced above). If $R_1$ contains a protecting group, deprotection of compounds 37, 38 or 39 can be performed using conditions such as those described in Example #112, Step C, or Greene, T. W. and Wuts. P. G. M "Protective Groups in Organic Synthesis, $3^{rd}$ Edition, 1999, Wiley-Interscience". For example, a protecting group such as a t-butoxycarbonyl group can be removed with acid using conditions such as those described in Example #112, Step C, or by methods known to one skilled in the art (for example, the books from Larock, R. C. or Greene, T. W. and Wuts, P. G. M. referenced above). If desired, chiral separation of compounds 35-39 may be done using methods known to one skilled in the art such as chiral SFC or chiral preparative HPLC (for example, Example #1, Step C).

Scheme IV:

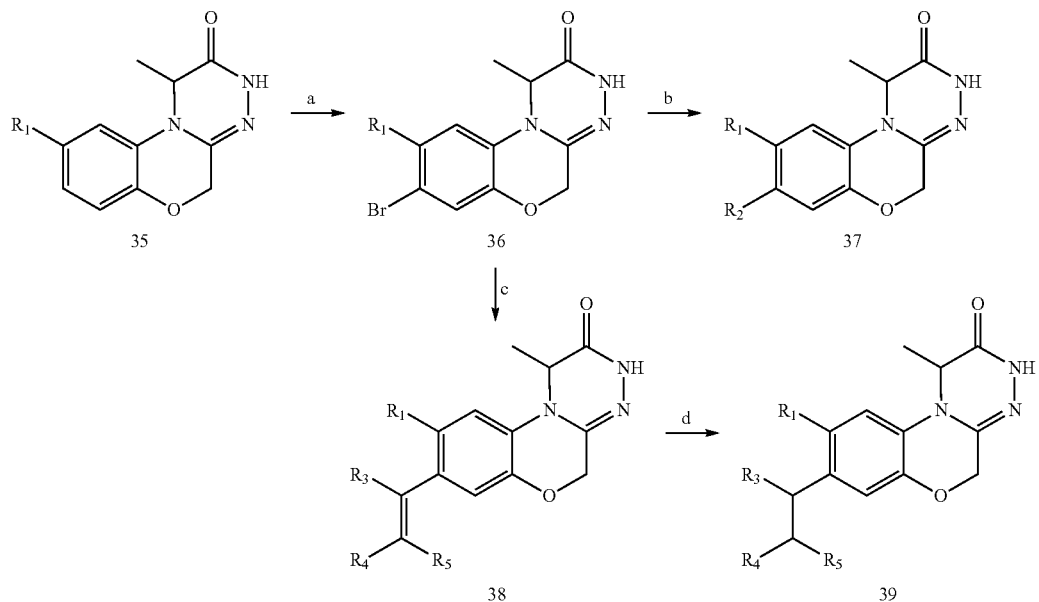

In Scheme V, step a, an alkenyl group is introduced by reaction of bromodihydrooxazinotriazinones 21 (Scheme II, step d) under Suzuki or Heck cross-coupling conditions (for example, Example #71, Step A, or Example #76, Step A, or de Meijere, A. and Diederich, F. "Metal-Catalyzed Cross-Coupling Reactions, $2^{nd}$ edition", 2004, Wiley-VCH). Reduction of compounds 41 to yield dihydrooxazinotriazinones 42 can be performed using conditions such as those described in Example #71, Step B, or by methods known to one skilled in the art (for example, Larock, R. C. "Comprehensive Organic Transformations: A Guide to Functional Group Preparations, $2^{nd}$ edition", 1999, Wiley-VCH). Alternatively, the Suzuki coupling can be performed from the boronic ester dihydrooxazinotriazinones 40 to provide compounds 41 using conditions such as those described in Example #86, Step B, or de Meijere, A. and Deiderich, F. as referenced above.

Scheme V:

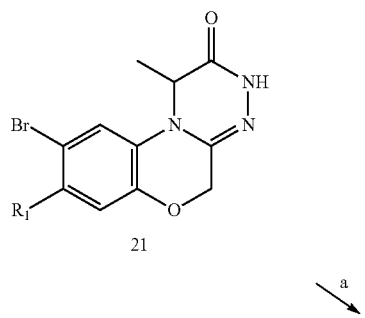

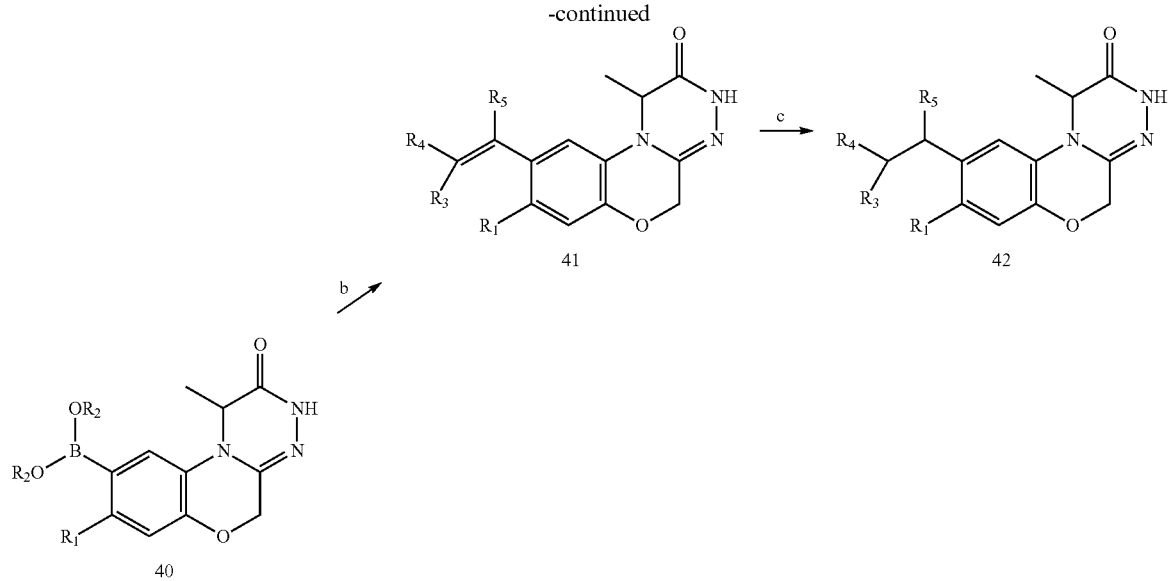

Methods for preparing 5,6-dihydro-1H-[1,2,4]triazino[4,3-a]quinolin-2(3H)-one compounds of the invention are illustrated in Scheme VI. In Scheme VI, step a, protection of aminodihydroquinolinones 43 (prepared by methods described in *Journal of Medicinal Chemistry* 2005, 48 (1), 71-90) to yield dimethylpyrrolodihydroquinolinones 44 can be performed using conditions known to one skilled in the art (for example, Example #108, Step C, or Greene, T. W. and Wuts. P. G. M. "Protective Groups in Organic Synthesis, 3$^{rd}$ Edition, 1999, Wiley-Interscience"). In Scheme VI, step b, dihydroquinolinones 44 can be alkylated using conditions such as those described in Example #108, Step D, or by methods known to one skilled in the art (for example, Larock, R. C. referenced above). Conversion to thiolactams 46 is accomplished using conditions such as those described in Example #108, Step E. Dihydrotriazinoquinolinones 47 can be prepared by reaction of thiolactams 46 with hydrazine (for example, Example #108, Step F). Deprotection of compounds 47 to yield aminodihydrotriazinoquinolinones 48 can be performed using conditions such as those described in Example #108, Step G, or Greene, T. W. and Wuts, P. G. M. referenced above. Aminodihydrotriazinoquinolinones 48 may undergo further functionalization using reactions known to one skilled in the art (for example, Larock, R. C. referenced above). For example, formation of secondary amines 49 may be accomplished using standard conditions such as those described in Example #108, Step H, or by methods known to one skilled in the art (for example, the books from Larock, R. C. referenced above). If $R_1$ contains a protecting group, deprotection of compounds 49 can be performed using conditions such as those described in Greene, T. W. and Wuts. P. G. M. referenced above. For example, a protecting group such as a t-butoxycarbonyl group can be removed from a protected amine to yield the unprotected amine (for example, Example #108, Step I) and the deprotected compound may then be reacted further as described above. Alternatively $R_1$ can be introduced at a later stage, for example after step a, step b, or step c, utilizing the methodology outlined in Scheme IV, steps a and b, or steps a, c and d.

Scheme VI:

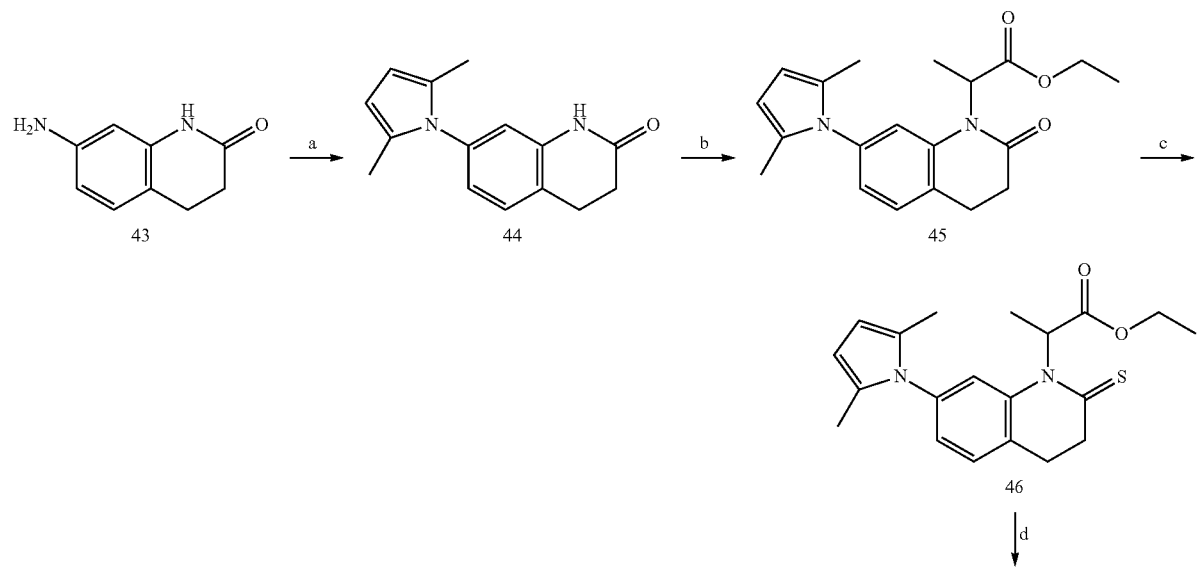

-continued

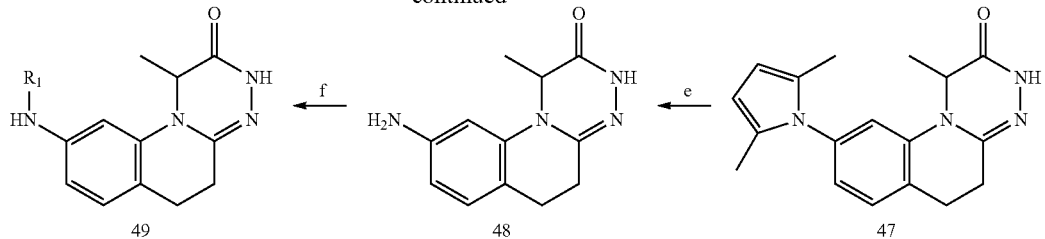

Bruker Avance III 400 MHz FT-NMR spectrometer, 5 mm BBO(F) probe.
Varian 400 MHz, 1H/19F/31P/13C 5 mm PFG 4Nuc probe Analytical Methods Analytical data is included within the procedures below, in the illustrations of the general procedures, or in the tables of examples. Unless otherwise stated, all $^1$H NMR data were collected on a Bruker Avance III 400 MHz FT-NMR spectrometer with 5 mm BBO(F) probe or a Varian 400 MHz, 1H/19F/31P/13C 5 mm PFG 4Nuc probe instrument and chemical shifts are quoted in parts per million (ppm). LC/MS was performed on instrument with Shimadzu pump LC-20AB, PDA SPD-M20, MS MS-2010EV. LC/MS and HPLC data is referenced to LC/MS and HPLC conditions using the method number provided in Table 1.

TABLE 1

LC/MS and SFC analysis methods

| Method | Conditions |
|---|---|
| 1 | SFC condition: Column: Chiralpak AS-H 150 × 4.6 mm I.D., 5 μm; Mobile phase: ethanol (0.05% DEA) in supercritical $CO_2$, from 5% to 40%; Flow rate: 3 mL/min; Wavelength: 220 nm |
| 2 | LC/MS analysis condition: Column: Ultimate XB-C18, 3 μm, 30 × 2.1 mm; Mobile phase: MeCN (0.02% TFA) in water (0.04% TFA), from 10% to 80% within 2 min; Flow rate: 1.2 mL/min; Wavelength: 220 nm |
| 3 | LC/MS analysis condition: Column: Ultimate XB-C18, 3 μm, 30 × 2.1 mm; Mobile phase: MeCN (0.02% TFA) in water (0.04% TFA), from 0% to 60% within 2 min; Flow rate: 1.2 mL/min; Wavelength: 220 nm |
| 4 | LC/MS analysis condition: Column: Ultimate XB-C18, 3 μm, 30 × 2.1 mm; Mobile phase: MeCN (0.02% TFA) in water (0.04% TFA), from 10% to 80% within 4 min; Flow rate: 1.2 mL/min; Wavelength: 220 nm |
| 5 | LC/MS analysis condition: Column: Ultimate XB-C18, 3 μm, 30 × 2.1 mm; Mobile phase: MeCN (0.02% TFA) in water (0.04% TFA), from 0% to 60% within 4 min; Flow rate: 1.2 mL/min; Wavelength: 220 nm |
| 6 | SFC analysis condition: Column: Chiralpak AD-H 250 × 4.6 mm I.D., 5 μm. Mobile phase: ethanol (0.05% DEA) in supercritical $CO_2$ from 5% to 40%. Flow rate: 2.35 mL/min. Wavelength: 220 nm. |
| 7 | SFC analysis condition: Column: Chiralcel OJ-H 250 × 4.6 mm I.D., 5 μm. Mobile phase: ethanol in supercritical $CO_2$ from 5% to 40%. Flow rate: 2.35 mL/min. Wavelength: 220 nm. |
| 8 | SFC analysis condition: Column: Chiralpak AS-H 150 × 4.6 mm I.D., 5 μm; Mobile phase: methanol (0.05% DEA) in supercritical $CO_2$ from 5% to 40%; Flow rate: 3 mL/min; Wavelength: 220 nm. |
| 9 | SFC analysis condition: Column: Chiralpak AS-H 150 × 4.6 mm I.D., 5 μm; Mobile phase: ethanol (0.1% ethanolamine) in supercritical $CO_2$ from 5% to 40%; Flow rate: 3 mL/min; Wavelength: 220 nm. |
| 10 | SFC analysis condition: Column: Chiralpak AD-3 150 × 4.6 mm I.D., 3 μm; Mobile phase: IPA (0.05% DEA) in supercritical $CO_2$ from 5% to 40%; Flow rate: 2.5 mL/min; Wavelength: 220 nm |
| 11 | SFC analysis condition: Column: Chiralpak AS-H 150 × 4.6 mm I.D., 5 μm; Mobile phase: ethanol (0.05% DEA) in supercritical $CO_2$ from 5% to 40%; Flow rate: 3 mL/min; Wavelength: 254 nm. |
| 12 | SFC analysis condition: Column: Chiralpak AS-H 250 × 4.6 mm I.D., 5 μm; Mobile phase: methanol (0.05% DEA) in supercritical $CO_2$ from 5% to 40%; Flow rate: 2.5 mL/min; Wavelength: 220 nm. |
| 13 | SFC analysis condition: Column: Chiralpak AD-3 150 × 4.6 mm I.D., 3 μm; Mobile phase: methanol (0.05% DEA) in supercritical $CO_2$ from 5% to 40%; Flow rate: 4.0 mL/min; Wavelength: 220 nm |
| 14 | SFC analysis condition: Column: Chiralcel OJ-3 50 × 4.6 mm I.D., 3 μm. Mobile phase: methanol (0.05% DEA) in supercritical $CO_2$ from 5% to 40%. Flow rate: 4.0 mL/min. Wavelength: 220 nm. |
| 15 | SFC analysis condition: Column: Chiralpak AD-3 150 × 4.6 mm I.D., 3 μm; Mobile phase: ethanol (0.05% DEA) in supercritical $CO_2$ from 5% to 40%; Flow rate: 4.0 mL/min; Wavelength: 220 nm |
| 16 | SFC analysis condition: Column: Chiralpak AD-3 150 × 4.6 mm I.D., 3 μm; Mobile phase: methanol (0.05% DEA) in supercritical $CO_2$ from 5% to 40%; Flow rate: 2.5 mL/min; Wavelength: 220 nm |
| 17 | SFC analysis condition: Column: Chiralpak AD-3 150 × 4.6 mm I.D., 3 μm; Mobile phase: isopropanol (0.05% DEA) in supercritical $CO_2$ from 5% to 40%; Flow rate: 2.5 mL/min; Wavelength: 220 nm |
| 18 | SFC analysis condition: Column: Chiralpak AD-3 150 × 4.6 mm I.D., 5 μm; Mobile phase: isopropanol (0.05% DEA) in supercritical $CO_2$ from 5% to 40%; Flow rate: 2.4 mL/min; Wavelength: 220 nm |
| 19 | SFC analysis condition: Column: Chiralpak AD-3 150 × 4.6 mm I.D., 5 μm; Mobile phase: methanol (0.05% DEA) in supercritical $CO_2$ from 5% to 40%; Flow rate: 2.5 mL/min; Wavelength: 220 nm |
| 20 | SFC analysis condition: Column: Chiralpak AD-3 150 × 4.6 mm I.D., 5 μm; Mobile phase: isopropanol (0.05% DEA) in supercritical $CO_2$ from 5% to 40%; Flow rate: 2.5 mL/min; Wavelength: 220 nm |
| 21 | SFC analysis condition: Column: Chiralpak AS-H 150 × 4.6 mm I.D., 5 μm; Mobile phase: ethanol (0.05% DEA) in supercritical $CO_2$ from 5% to 40%; Flow rate: 3.0 mL/min; Wavelength: 220 nm |
| 22 | SFC analysis condition: Column: Chiralpak AD-3 150 × 4.6 mm I.D., 5 um; Mobile phase: methanol (0.05% DEA) in supercritical $CO_2$ 40%; Flow rate: 2.5 mL/min; Wavelength: 220 nm |
| 23 | SFC analysis condition: Column: Chiralcel OJ-H 250 × 4.6 mm I.D., 5 μm. Mobile phase: ethanol in supercritical $CO_2$ from 5% to 40%. Flow rate: 2.35 mL/min. Wavelength: 220 nm. |
| 24 | SFC analysis condition: Column: Chiralcel AD-H 250 × 4.6 mm I.D., 5 μm. Mobile phase: ethanol (0.05% DEA) in supercritical $CO_2$ from 5% to 40%. Flow rate: 2.35 mL/min. Wavelength: 220 nm. |

TABLE 1-continued

LC/MS and SFC analysis methods

| Method | Conditions |
|---|---|
| 25 | LC/MS analysis condition: Column: Merck, 3 µm, 25 × 2 mm; Mobile phase: MeCN (0.02% TFA) in water (0.04% TFA), from 5% to 95% within 0.7 min, keep at 95% for 0.4 min, keep at 5% within 0.4 min; Flow rate: 1.5 mL/min; Wavelength: 220 nm |
| 26 | SFC analysis condition: Column: IC 250 × 4.6 mm I.D., 5 µm Mobile phase: 40% ethanol (0.05% DEA) in supercritical $CO_2$ Flow rate: 2.35 mL/min Wavelength: 220 nm |
| 27 | LC/MS analysis condition: Column: Ultimate XB-C18, 3 µm, 30 × 2.1 mm; Mobile phase: MeCN (0.02% TFA) in water (0.04% TFA), from 30% to 90% within 2 min; Flow rate: 1.2 mL/min; Wavelength: 220 nm |
| 28 | SFC analysis condition: Column: Chiralcel OD-3 150 × 4.6 mm I.D., 3 µm Mobile phase: methanol (0.05% DEA) in supercritical $CO_2$ from 5% to 40%. Flow rate: 2.5 mL/min Wavelength: 220 nm |
| 29 | SFC analysis condition: Column: Chiralpak AD-H 250 × 4.6 mm I.D., 5 µm Mobile phase: methanol (0.05% DEA) in supercritical $CO_2$ from 5%-40%. Flow rate: 2.35 mL/min. Wavelength: 220 nm |
| 30 | SFC analysis condition: Column: Chiralcel OD-H 150 × 4.6 mm I.D., 5 µm Mobile phase: methanol (0.05% DEA) in supercritical $CO_2$ from 5%-40%. Flow rate: 2.35 mL/min. Wavelength: 220 nm |
| 31 | SFC analysis condition: Column: Chiralpak AS-H 250 × 4.6 mm I.D., 5 µm Mobile phase: methanol (0.05% DEA) in supercritical $CO_2$ from 5%-40%. Flow rate: 2.35 mL/min. Wavelength: 254 nm |
| 32 | SFC analysis condition: Column: Chiralpak AS-H 250 × 4.6 mm I.D., 5 µm Mobile phase: ethanol (0.05% DEA) in supercritical $CO_2$ from 5%-40%. Flow rate: 2.35 mL/min. Wavelength: 220 nm |
| 33 | SFC analysis condition: Column: Chiralpak AS-H 150 × 4.6 mm I.D., 5 µm; Mobile phase: ethanol (0.05% DEA) in supercritical $CO_2$ from 5% to 40%. Flow rate: 3 mL/min; Wavelength: 220 nm |
| 34 | SFC analysis condition: Column: Chiralpak AD-3 50 × 4.6 mm I.D., 3 µm Mobile phase: isopropanol (0.05% DEA) in supercritical $CO_2$ from 5% to 40%. Flow rate: 4 mL/min Wavelength: 220 nm |
| 35 | SFC analysis condition: Column: Chiralcel OJ-H 250 × 4.6 mm I.D., 5 µm Mobile phase: methanol (0.05% DEA) in supercritical $CO_2$ from 5% to 40%. Flow rate: 2.35 mL/min Wavelength: 220 nm |
| 36 | SFC analysis condition: Column: Chiralcel OD-H 150 × 4.6 mm I.D., 5 µm Mobile phase: methanol (0.05% DEA) in supercritical $CO_2$ from 5% to 40%. Flow rate: 2.35 mL/min Wavelength: 220 nm |
| 37 | SFC analysis condition: Column: Chiralpak AD-H 250 × 4.6 mm I.D., 5 µm Mobile phase: methanol (0.05% DEA) in supercritical $CO_2$ from 5% to 40%. Flow rate: 3 mL/min. Wavelength: 220 nm |
| 38 | SFC analysis condition: Column: Chiralcel OJ-H 250 × 4.6 mm I.D., 5 µm Mobile phase: 40% ethanol (0.05% DEA) in supercritical $CO_2$. Flow rate: 2.35 mL/min Wavelength: 220 nm |
| 39 | SFC analysis condition: Column: Chiralcel OJ-H 250 × 4.6 mm I.D., 5 µm Mobile phase: methanol (0.05% DEA) in supercritical $CO_2$ from 5% to 40%. Flow rate: 2.5 mL/min Wavelength: 220 nm |
| 40 | SFC anslysis condition: Column: Chiralpak AD-3 150 × 4.6 mm I.D., 3 µm Mobile phase: 40% of isopropanol (0.05% DEA) in supercritical $CO_2$. Flow rate: 2.5 mL/min Wavelength: 254 nm |
| 41 | LC/MS analysis condition: Column: Ultimate XB-C18, 3 um, 30 × 2.1 mm; Mobile phase: MeCN (0.02% TFA) in water (0.04% TFA), from 0% to 30% within 4 min; Flow rate: 1.2 mL/min; Wavelength: 220 nm |
| 42 | SFC anslysis condition: Column: Chiralcel OJ-H 250 × 4.6 mm I.D., 5 µm Mobile phase: methanol (0.05% DEA) in supercritical $CO_2$ from5% to 40% Flow rate: 2.35 mL/min Wavelength: 220 nm |
| 43 | SFC anslysis condition: Column: Chiralpak AS-H 150 × 4.6 mm I.D., 5 µm Mobile phase: methanol (0.05% DEA) in supercritical $CO_2$ from 5% to 40% Flow rate: 3 mL/min Wavelength: 220 nm |
| 44 | LC/MS analysis condition: Column: Ultimate XB-C18, 3 µm, 30 × 2.1 mm; Mobile phase: MeCN (0.02% TFA) in water (0.04% TFA), from 10% to 80% within 7 min; Flow rate: 1.2 mL/min; Wavelength: 220 nm |
| 45 | SFC analysis condition: Chiralcel OD-3 150 × 4.6 mm I.D., 3 µm Mobile phase: ethanol (0.05% DEA) in supercritical $CO_2$ from 5% to 40% Flow rate: 2.5 mL/min Wavelength: 220 nm |
| 46 | SFC analysis condition: Chiralpak AD-3 150 × 4.6 mm I.D., 3 µm Mobile phase: methanol (0.05% DEA) in supercritical $CO_2$ from 5% to 40% Flow rate: 2.5 mL/min Wavelength: 310 nm |
| 47 | SFC analysis condition: Column: Chiralcel OJ-3 50 × 4.6 mm I.D., 3 µm Mobile phase: methanol (0.05% DEA) in supercritical $CO_2$ from 5% to 40% Flow rate: 4 mL/min Wavelength: 220 nm |
| 48 | SFC analysis condition: Column: Chiralpak AS-H 150 × 4.6 mm I.D., 5 µum Mobile phase: ethanol (0.05% DEA) in supercritical $CO_2$ from 5% to 40% Flow rate: 3 mL/min Wavelength: 220 nm |
| 49 | SFC analysis condition: Column: Chiralpak AD-H 250 × 4.6 mm I.D., 5 µm; Mobile phase: 40% methanol (0.05% DEA) in supercritical $CO_2$ from 5% to 40%; Flow rate: 2.35 mL/min; Wavelength: 220 nm |
| 50 | SFC analysis condition: Column: Chiralpak IC-3 150 × 4.6 mm I.D., 3 µm Mobile phase: 40% methanol (0.05% DEA) in supercritical $CO_2$ Flow rate: 2.35 mL/min Wavelength: 314 nm |
| 51 | SFC analysis condition: Column: Chiralcel OJ-H 250 × 4.6 mm I.D., 5 µm Mobile phase: methanol (0.05% DEA) in supercritical $CO_2$ from 5% to 40% Flow rate: 2.35 mL/min Wavelength: 220 nm |
| 52 | SFC analysis condition: Column: Chiralpak AS-H 150 × 4.6 mm I.D., 5 µm; Mobile phase: ethanol (0.05% DEA) in supercritical $CO_2$, from 5% to 40%; Flow rate: 3 mL/min; Wavelength: 220 nm |
| 53 | SFC analysis condition: Column: Chiralpak AD-3 50 × 4.6 mm I.D., 3 µm Mobile phase: methanol (0.05% DEA) in supercritical $CO_2$ from 5% to 40% Flow rate: 4 mL/min Wavelength: 220 nm |
| 54 | SFC analysis condition: Column: Chiralpak AD-3 50 × 4.6 mm I.D., 3 µum Mobile phase: ethanol (0.05% DEA) in supercritical $CO_2$ from 5% to 40% Flow rate: 4 mL/min Wavelength: 220 nm |
| 55 | SFC analysis methods: Column: Chiralpak AD-H 250 × 4.6 mm I.D., 5 um; Mobile phase: ethanol (0.05% DEA) in supercritical $CO_2$ from 5% to 40%; Flow rate: 2.35 mL/min; Wavelength: 220 nm |
| 56 | SFC analysis condition: Column: Chiralpak AD-H 250 × 4.6 mm I.D., 5 um Mobile phase: 40% ethanol (0.05% DEA) in supercritical $CO_2$; Flow rate: 2.35 mL/min Wavelength: 220 nm |

Chiral Preparative SFC Purification

Chiral purification is performed using Varian 218 LC pumps, a Varian CVM 500 with switching valves and heaters for automatic solvent, column and temperature control and a Varian 701 Fraction collector. Detection methods include a Varian 210 variable wavelength detector, an in-line polarimeter (PDR-chiral advanced laser polarimeter, model ALP2002) used to measure qualitative optical rotation (+/−) and an evaporative light scattering detector (ELSD) (a PS-ELS 2100 (Polymer Laboratories)) using a 100:1 split flow. ELSD settings are as follows: evaporator: 46° C., nebulizer: 24° C. and gas flow: 1.1 SLM.

TABLE 2

Chiral SFC separation methods

| Method | Conditions |
|---|---|
| 1 | Column: Chiralpak AS 250 × 30 mm I.D., 20 μm; Mobile phase: supercritical $CO_2$/MeOH = 65/35; Flow rate: 80 mL/min; Wavelength: 220 nm |
| 2 | Column: Chiralpak AD 250 × 30 mm I.D., 5 μm; Mobile phase: supercritical $CO_2$/EtOH = 65/35; Flow rate: 55 mL/min; Wavelength: 220 nm |
| 3 | Column: Chiralcel OD 250 × 30 mm I.D., 10 μm; Mobile phase: supercritical $CO_2$/MeOH = 60/40; Flow rate: 80 mL/min; Wavelength: 220 nm |
| 4 | Column: Chiralpak AD 250 × 30 mm I.D., 20 μm; Mobile phase: Supercritical $CO_2$/IPA = 70/30; Flow rate: 80 mL/min; Wavelength: 220 nm. |
| 5 | Column: Chiralpak AS 250 × 30 mm I.D., 5 μm; Mobile phase: Supercritical $CO_2$/MeOH = 70/30; Flow rate: 80 mL/min; Wavelength: 220 nm |
| 6 | Column: Chiralpak AS 250 × 30 mm I.D., 20 μm; Mobile phase: Supercritical $CO_2$/MeOH (0.2% $NH_3 \cdot H_2O$) = 60/40; Flow rate: 80 mL/min; Wavelength: 220 nm |
| 7 | Column: Chiralpak AD 250 × 30 mm I.D., 20 μm; Mobile phase: Supercritical $CO_2$/MeOH (0.2% $NH_3 \cdot H_2O$) = 50/50; Flow rate: 80 mL/min; Wavelength: 220 nm. |
| 8 | Column: Chiralpak AD 250 × 30 mm I.D., 5 μm; Mobile phase: Supercritical $CO_2$/IPA (0.2% $NH_3 \cdot H_2O$) = 65/35; Flow rate: 60 mL/min; Wavelength: 220 nm. |
| 9 | Column: Chiralpak AD 250 × 30 mm I.D., 20 μm; Mobile phase: Supercritical $CO_2$/EtOH (0.2% $NH_3 \cdot H_2O$) = 65/35; Flow rate: 80 mL/min; Wavelength: 220 nm. |
| 10 | Column: Chiralpak AD 250 × 30 mm I.D., 5 μm; Mobile phase: Supercritical $CO_2$/MeOH (0.2% $NH_3 \cdot H_2O$) = 75/25; Flow rate: 80 mL/min; Wavelength: 220 nm. |
| 11 | Column: Chiralpak AD 250 × 30 mm I.D., 5 μm; Mobile phase: Supercritical $CO_2$/MeOH (0.2% $NH_3 \cdot H_2O$) = 80/20; Flow rate: 70 mL/min; Wavelength: 220 nm. |
| 12 | Column: Chiralpak AD 250 × 30 mm I.D., 5 μm; Mobile phase: Supercritical $CO_2$/MeOH (0.2% $NH_3 \cdot H_2O$) = 80/20; Flow rate: 60 mL/min; Wavelength: 220 nm. |
| 13 | Column: Chiralpak OJ 250 × 30 mm I.D., 10 μm; Mobile phase: Supercritical $CO_2$/MeOH (0.2% $NH_3 \cdot H_2O$) = 60/40; Flow rate: 240 mL/min; Wavelength: 220 nm. |
| 14 | Column: Chiralpak AD 250 × 30 mm I.D., 5 μm; Mobile phase: Supercritical $CO_2$/MeOH = 90/10; Flow rate: 160 mL/min; Wavelength: 220 nm. |
| 15 | Column: Chiralpak OJ 250 × 30 mm I.D., 5 μm; Mobile phase: Supercritical $CO_2$/MeOH (0.2% $NH \cdot_3 H_2O$) = 75/25; Flow rate: 60 mL/min; Wavelength: 220 nm. |
| 16 | Column: Chiralpak AD 250 × 30 mm I.D., 20 μm; Mobile phase: Supercritical $CO_2$/MeOH (0.2% $NH_3 \cdot H_2O$) = 55/45; Flow rate: 80 mL/min; Wavelength: 220 nm. |
| 17 | SFC separation condition: Column: Chiralcel AD-H 250 × 30 mm I.D., 5 μm. Mobile phase: ethanol (0.1% $NH_3 \cdot H_2O$) in supercritical $CO_2$ from 40% to 60%, Flow rate: 50 mL/min. Wavelength: 220 nm |
| 18 | SFC separation methods: Column: Chiralpak AD 250 × 30 mm I.D., 20 μm; Mobile phase: supercritical $CO_2$/IPA (0.1% $NH_3 \cdot H_2O$) = 65/35; Flow rate: 80 mL/min; Wavelength: 220 nm |
| 19 | SFC separation methods: Column: Chiralcel OJ 250 × 30 mm I.D., 5 μm; Mobile phase: supercritical $CO_2$/MeOH (0.1% $NH_3 \cdot H_2O$) = 90/10; Flow rate: 60 mL/min; Wavelength: 220 nm |
| 20 | SFC separation methods: Column: Chiralpak AD 250 × 30 mm I.D., 20 μm; Mobile phase: supercritical $CO_2$/IPA (0.1% $NH_3 \cdot H_2O$) = 60/40; Flow rate: 80 mL/min; Wavelength: 220 nm |
| 21 | SFC separation methods: Column: Chiralpak OD 250 × 30 mm I.D., 5 μm; Mobile phase: supercritical $CO_2$/MeOH (0.1% $NH_3 \cdot H_2O$) = 75/25; Flow rate: 60 mL/min; Wavelength: 220 nm |
| 22 | SFC separation methods: Column: Chiralpak AD 300 × 50 mm I.D., 10 μm; Mobile phase: Supercritical $CO_2$/EtOH (0.1% $NH_3 \cdot H_2O$) = 60/40 at 220 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm |
| 23 | SFC separation methods: Column: Chiralcel OJ 250 × 30 mm I.D., 20 μm; Mobile phase: Supercritical $CO_2$/MeOH (0.1% $NH_3 \cdot H_2O$) = 45/55 at 80 mL/min; Column Temp: 38° C.; Nozzle Pressure: 100 Bar; NozzleTemp: 60° C.; Evaporator Temp: 20° C.; Trimmer Temp: 25° C.; Wavelength: 220 nm |
| 24 | SFC separation methods: Column: Chiralpak OJ 250 × 30 mm I.D., 5 μm; Mobile phase: supercritical $CO_2$/EtOH (0.1% $NH_3 \cdot H_2O$) = 80/20; Flow rate: 60 mL/min; Wavelength: 220 nm |
| 25 | SFC separation methods: Column: Chiralpak AD 250 × 30 mm I.D., 5 m; Mobile phase: Supercritical CO2/EtOH (0.1% NH3•H2O) = 60/40 at 50 mL/min; Wavelength: 220 nm |
| 26 | SFC separation methods: Column: Chiralpak AD 300 × 50 mm I.D., 5 um; Mobile phase: Supercritical CO2/EtOH (0.1% NH3•H2O) = 65/35 at 200 mL/min; Wavelength: 220 nm |
| 27 | SFC analysis methods: Column: Chiralpak AS-H 150 × 4.6 mm I.D., 5 um; Mobile phase: methanol (0.05% DEA) in supercritical $CO_2$ from 5% to 40%; Flow rate: 3 mL/min; Wavelength: 220 nm |
| 28 | SFC analysis condition: Column: Chiralpak AD-3 150 × 4.6 mm I.D., 3 um Mobile phase: ethanol (0.05% DEA) in $CO_2$ from 5% to 40% Flow rate: 2.5 mL/min Wavelength: 220 nm |
| 29 | SFC separation methods: Column: Chiralpak AD 300 × 50 mm I.D., 10 um; Mobile phase: Supercritical $CO_2$/EtOH (0.1% $NH_3 \cdot H_2O$) = 45/55; Flow rate: 70 mL/min; Wavelength: 220 nm |

Purification Methods

For the general procedures, intermediate and final compounds may be purified by any technique or combination of techniques known to one skilled in the art. Some examples that are not limiting include flash chromatography with a solid phase (i.e. silica gel, alumina, etc.) and a solvent (or combination of solvents, i.e. heptane, EtOAc, DCM, MeOH, MeCN, water, etc.) that elutes the desired compounds; preparatory TLC with a solid phase (i.e. silica gel, alumina etc.) and a solvent (or combination of solvents, i.e. heptane, EtOAc, DCM, MeOH, MeCN, water, etc.) that elutes the desired compounds; reverse phase HPLC (see Table 1 for some non-limiting conditions); recrystallization from an appropriate solvent (i.e. MeOH, EtOH, i-PrOH, EtOAc, toluene, etc.) or combination of solvents (i.e. EtOAc/heptane, EtOAc/MeOH, etc.); chiral chromatography with a solid phase and an appropriate solvent (i.e. EtOH/heptane, MeOH/heptane, i-PrOH/heptane, etc. with or without a modifier such as diethylamine, TFA, etc.) to elute the desired compound; precipitation from a combination of solvents (i.e. DMF/water, DMSO/DCM, EtOAc/heptane, etc.); trituration with an appropriate solvent (i.e. EtOAc, DCM, MeCN, MeOH, EtOH, i-PrOH, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Descriptions of these techniques can be found in the following references: Gordon, A. J. and Ford, R. A. "The Chemist's Companion", 1972; Palleros, D. R. "Experimental Organic Chemistry", 2000; Still, W. C., Kahn and M. Mitra, A. *J. Org. Chem.* 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, $4^{th}$ Ed.", 1993; Skoog, D. A. and Leary, J. J. "Principles of Instrumental Analysis, $4^{th}$ Ed." 1992; G. Subramanian, "Chiral Separation Techniques $3^{rd}$ Edition" 2007; Y. Kazakevich, R. Lobrutto, "HPLC for Pharmaceutical Scientists" 2007.

TABLE 3

Preparative HPLC separation methods

| Method | Conditions |
|---|---|
| 1 | Column: Phenomenex Gemini C18 200 × 25 mm, 10 μm. Mobile phase: MeCN in water (0.125% formic acid and 0.025% hydrochloric acid), from 10% to 30% in 10 min; Flow rate: 25 mL/min. Wavelength: 220 nm. |
| 2 | Column: Phenomenex Gemini C18 250 × 80 mm, 10 μm. Mobile phase: MeCN in water (0.05% ammonia solution), from 30% to 60% in 30 min; Flow rate: 80 mL/min. Wavelength: 220 nm. |
| 3 | Column: YMC-Actus Triart C18 150 × 30 mm, 5 μm. Mobile phase: MeCN in water (0.075% TFA), from 60% to 90% in 11 min; Flow rate: 25 mL/min. Wavelength: 220 nm. |
| 4 | Column: Phenomenex Gemini C18 150 × 25 mm, 10 μm. Mobile phase: MeCN in water (0.05% ammonia solution), from 40% to 70% in 12 min; Flow rate: 25 mL/min. Wavelength: 220 nm. |
| 5 | Column: YMC-Actus Triart C18 150 × 30 mm, 5 μm. Mobile phase: MeCN in water (0.075% TFA), from 13% to 33% in 12 min; Flow rate: 25 mL/min. Wavelength: 220 nm. |
| 6 | Column: YMC-pack ODS-AQ C18 250 × 30 mm, 5 μm. Mobile phase: MeCN in water (0.075% TFA), from 30% to 60% in 15 min; Flow rate: 25 mL/min. Wavelength: 220 nm. |
| 7 | Column: YMC-Actus Triart C18 150 × 30 mm, 5 μm. Mobile phase: MeCN in water (0.075% TFA), 29% in 12 min; Flow rate: 25 mL/min. Wavelength: 220 nm. |
| 8 | Column: YMC-Actus Triart C18 150 × 30 mm, 5 μum. Mobile phase: MeCN in water (0.075% TFA), from 27% to 47% in 11 min; Flow rate: 25 mL/min. Wavelength: 220 nm. |
| 9 | Column: Diamonsil 150 × 25 mm, 5 μm. Mobile phase: MeCN in water (0.225% TFA), from 7% to 12% in 12 min; Flow rate: 25 mL/min. Wavelength: 220 nm |
| 10 | Column: YMC-Actus Triart C18 150 × 30 mm, 5 μm. Mobile phase: MeCN in water (0.225% TFA), 28% in 12 min; Flow rate: 25 mL/min. Wavelength: 220 nm. |
| 11 | Column: YMC-Actus Triart C18 150 × 30 mm, 5 m. Mobile phase: MeCN in water (0.075% TFA), from 40% to 90% in 13 min; Flow rate: 25 mL/min. Wavelength: 220 nm |
| 12 | Column: YMC-Actus Triart C18 150 × 30 mm, 5 μm. Mobile phase: MeCN in water (0.075% TFA), from 15% to 35% in 11 min; Flow rate: 25 mL/min. Wavelength: 220 nm |
| 13 | Column: YMC-Actus Triart C18 150 × 30 mm, 5 μm. Mobile phase: MeCN in water (0.075% TFA), from 27% to 47% in 11 min; Flow rate: 25 mL/min. Wavelength: 220 nm |
| 14 | Column: YMC-Actus Triart C18 150 × 30 mm, 5 μm. Mobile phase: MeCN in water (0.075% TFA), 22% in 11 min; Flow rate: 25 mL/min. Wavelength: 220 nm |
| 15 | Column: YMC-Actus Triart C18 150 × 30 mm, 5 μm. Mobile phase: MeCN in water (0.075% TFA), from 28% to 40% in 11 min; Flow rate: 25 mL/min. Wavelength: 220 nm |
| 16 | Column: YMC-Actus Triart C18 150 × 30 mm, 5 μm. Mobile phase: MeCN in water (0.075% TFA), from 25% to 45% in 11 min; Flow rate: 25 mL/min. Wavelength: 220 nm |
| 17 | Column: YMC-Actus Triart C18 150 × 30 mm, 5 μm. Mobile phase: MeCN in water (0.075% TFA), from 60% to 77% in 11 min; Flow rate: 25 mL/min. Wavelength: 220 nm |
| 18 | Column: YMC-Actus Triart C18 150 × 30 mm, 5 μm. Mobile phase: MeCN in water (0.075% TFA), from 20% to 40% in 11 min; Flow rate: 25 mL/min. Wavelength: 220 nm |
| 19 | Column: YMC-Actus Triart C18 150 × 30 mm, 5 μm. Mobile phase: MeCN in water (0.075% TFA), from 22% to 52% in 11 min; Flow rate: 25 mL/min. Wavelength: 220 nm |
| 20 | Column: Phenomenex Gemini C18 150 × 25 mm, 10 μm. Mobile phase: MeCN in water (0.075% TFA), from 10% to 40% in 10 min; Flow rate: 25 mL/min. Wavelength: 220 nm |
| 21 | Column: YMC-Actus Triart C18 150 × 30 mm, 5 μm. Mobile phase: MeCN in water (0.075% TFA), from 23% to 40% in 10 min; Flow rate: 25 mL/min. Wavelength: 220 nm |
| 22 | Column: YMC-Actus Triart C18 150 × 30 mm, 5 μm. Mobile phase: MeCN in water (0.075% TFA), from 18% to 38% in 10 min; Flow rate: 25 mL/min. Wavelength: 220 nm |
| 23 | Column: YMC-Actus Triart C18 150 × 30 mm, 5 μm. Mobile phase: MeCN in water (0.075% TFA), from 55% to 75% in 10 min; Flow rate: 25 mL/min. Wavelength: 220 nm |
| 24 | Column: YMC-Actus Triart C18 150 × 30 mm, 5 μm. Mobile phase: MeCN in water (0.075% TFA), from 47% to 67% in 11 min; Flow rate: 25 mL/min. Wavelength: 220 nm |
| 25 | Column: Phenomenex Gemini C18 200 × 25 mm, 10 μm. Mobile phase: MeCN in water (0.05% ammonia solution), from 41% to 61% in 10 min; Flow rate: 25 mL/min. Wavelength: 220 nm |
| 26 | Column: Agella Venusil ASB C18 150 × 21.2 mm, 5 μm. Mobile phase: MeCn in water (0.075% TFA), from 10% to 40% in 11 min; Flow rate: 25 mL/min. Wavelength: 220 nm |
| 27 | Column: Agella Venusil ASB C18 150 × 21.2 mm, 5 μm. Mobile phase: MeCN in hydrochloric acid water, from 30% to 40% in 10 min; Flow rate: 25 mL/min. Wavelength: 220 nm. |
| 28 | Column: YMC-Actus Pro C18 150 × 30 mm, 5 μm. Mobile phase: MeCN in water (0.075% TFA), from 22% to 42% in 11 min; Flow rate: 25 mL/min. Wavelength: 220 nm |
| 29 | Column: Phenomenex Gemini C18 200 × 25 mm, 10 μm. Mobile phase: MeCN in water (0.025% hydrochloric acid, from 20% to 40% in 10 min; Flow rate: 25 mL/min. Wavelength: 220 nm |
| 30 | Column: ASB 150 × 25 mm × 5 μm. Mobile phase: MeCn in water (0.025% hydrochloric acid), 16% in 10 min; Flow rate: 30 mL/min. Wavelength: 220 nm |
| 31 | Column: ASB 150 × 25 mm × 5 μm. Mobile phase: MeCN in water (0.075% HCl), from 19% to 44% in 12 min; Flow rate: 30 mL/min. Wavelength: 220 nm |

TABLE 3-continued

Preparative HPLC separation methods

| Method | Conditions |
|---|---|
| 32 | Column: Durashell 250 × 21.2 mm × 5 μm. Mobile phase: MeCN in basic water (0.05% NH₃ H₂O), from 30% to 60% in 12 min; Flow rate: 25 mL/min. Wavelength: 220 nm |
| 33 | Column: Phenomenex Gemini C18 200 × 25 mm, 10 μm. Mobile phase: MeCNe in water (0.125% formic acid and 0.025% hydrochloric acid), from 10% to 30% in 10 min; Flow rate: 25 mL/min. Wavelength: 220 nm |
| 34 | Column: Sunfire C8 30 * 100 mm * 5um. Mobile phase: HCl water in acetonitrile, from 13% to 38% in 12 min; Flow rate: 30 mL/min. Wavelength: 220 nm |
| 35 | Column: Phenomenex Gemini C18 200 × 25 mm, 10 um. Mobile phase: MeCN in water (0.1% TFA), from 20% to 45% in 10 min; Flow rate: 25 mL/min. Wavelength: 220 nm |
| 36 | Column: Phenomenex Gemini C18 200 × 25 mm, 10 um. Mobile phase: acetonitrile in water (0.05% hydrochloric acid), from 51% to 81% in 10 min; Flow rate: 25 mL/min. Wavelength: 220 nm |

Degassing Methods

Preparations of intermediate and final compounds obtained via the General Procedures can be optionally degassed using one or more of the Degassing Methods described below. The reaction mixtures may be degassed by a single or multiple applications of any technique or combination of techniques known to one skilled in the art. Some examples that are not limiting include bubbling a continuous stream of an inert gas (e.g. nitrogen, argon, etc.) through a mixture of reagents and a solvent suitable for the transformation (e.g. THF, 1,4-dioxane, EtOAc, DCM, toluene, MeOH, EtOH, DMF, MeCN, water, etc.); freeze-thawing of a mixture of reagents in a solvent (e.g. THF, 1,4-dioxane, EtOAc, DCM, toluene, MeOH, EtOH, DMF, MeCN, water, etc.) where the resulting solution is cooled below its freezing point and evacuated under reduced pressure, then allowed to warm above the freezing point and purged with an atmosphere of inert gas (e.g. nitrogen, argon, etc.); evacuation under reduced pressure of a mixture of reagents with or without a suitable solvent for the transformation (e.g. THF, 1,4-dioxane, EtOAc, DCM, toluene, MeOH, EtOH, DMF, MeCN, water, etc.) followed by purging of the mixture with an inert gas (e.g. nitrogen, argon, etc.); evacuation under reduced pressure of a mixture of reagents in a suitable solvent for the transformation (e.g. THF, 1,4-dioxane, EtOAc, DCM, toluene, MeOH, EtOH, DMF, MeCN, water, etc.) with the aid of mechanical agitation (e.g. stirring, shaking, sonication, etc.) followed by purging of the mixture with an inert gas (e.g. nitrogen, argon, etc.). Some descriptions of these techniques can be found in the following references, Gordon, A. J. and Ford, R. A. "The Chemist's Companion", 1972; Palleros, D. R. "Experimental Organic Chemistry", 2000; Harwood, L. M., Moody, C. J. and Percy, J. M. "Experimental Organic Chemistry Standard and Microscale, 2$^{nd}$ Edition", 1999; Landgrebe, J. A. "Theory and Practice in the Organic Laboratory, 4$^{th}$ Edition", 1993; Leonard, J., Lygo, B. and Procter, G. "Advanced Practical Organic Chemistry, 2$^{nd}$ Edition", 1998; Meyers, A. G.; Dragovich, P. S. *Organic Syntheses*, 1995, 72, 104; Hajos, Z. G., Parrish, D. R. *Organic Syntheses*, 1985, 63, 26.

PREPARATIONS AND EXAMPLES

All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® Chem-Draw Ultra 9.0.7, CambridgeSoft® Chemistry E-Notebook 9.0.127, or AutoNom 2000. None of the specific conditions and reagents noted herein is to be construed as limiting the scope of the invention and are provided for illustrative purposes only. All reactions were run under a nitrogen atmosphere.

Example #1

6-(Azetidin-3-ylamino)-4-(R)-methyl-7-phenyl-2,10-dihydro-9-oxa-1,2,4a-triaza-phenanthren-3-one trifluoroacetic acid (Example #1-1, Enantiomer 1) and 6-(azetidin-3-ylamino)-4-(S)-methyl-7-phenyl-2,10-dihydro-9-oxa-1,2,4a-triaza-phenanthren-3-one trifluoroacetic acid (Example #1-2, Enantiomer 2)

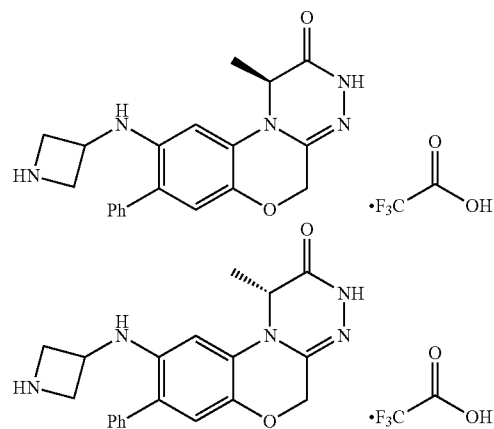

Step A. 3-(4-Methyl-3-oxo-2,3,4,10-tetrahydro-9-oxa-1,2,4a-triaza-phenanthren-6-ylamino)-azetidine-1-carboxylic acid tert-butyl ester

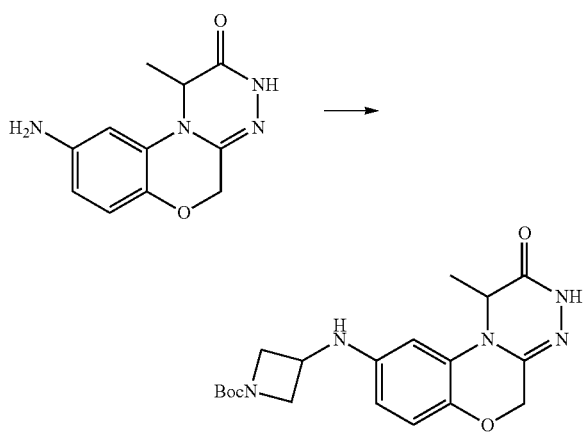

A solution of 6-amino-4-methyl-2,10-dihydro-9-oxa-1,2,4a-triaza-phenanthren-3-one (Preparation #2, Step E; 5 g, 21.6 mmol) and 3-oxo-azetidine-1-carboxylic acid tert-butyl ester (7.37 g, 43.1 mmol) in MeOH (90 mL) and HOAc (10 mL) was stirred at rt for 2 h. Sodium cyanoborohydride (2.7 g, 43.1 mmol) was added in portions and the resulting dark solution was stirred at rt for 2 h. The solvent was removed in vacuo and the residue was washed with aqueous Na₂CO₃ (100 mL) and extracted with EtOAc (4×100 mL). The combined organic phase was dried over Na₂SO₄, filtered and concentrated in vacuo. The residue was purified by column chromatography on silica gel (eluting with 10-50% EtOAc in petroleum ether) to give 3-(4-methyl-3-oxo-2,3,4,10-tetrahydro-9-oxa-1,2,4a-triaza-phenanthren-6-ylamino)-azetidine-1-carboxylic acid tert-butyl ester (4.48 g, 54%) as a solid. ¹H NMR (CDCl₃, 400 MHz): δ 8.28 (brs, 1H), 6.87 (d, J=8.4 Hz, 1H), 6.15 (s, 1H), 6.13 (d, J=8.4 Hz, 1H), 4.70 (m, 1H), 4.58 (d, J=13.2 Hz, 2H), 4.30 (m, 2H), 4.17 (m, 1H), 4.01 (m, 1H), 3.75 (m, 2H), 1.51 (d, J=6.8 Hz, 3H), 1.47 (s, 9H).

Step B. 3-(7-Bromo-4-methyl-3-oxo-2,3,4,10-tetrahydro-9-oxa-1,2,4a-triaza-phenanthren-6-ylamino)-azetidine-1-carboxylic acid tert-butyl ester

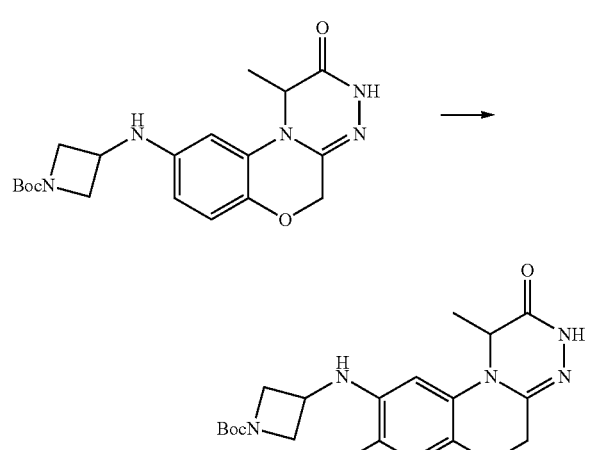

To a solution of 3-(4-methyl-3-oxo-2,3,4,10-tetrahydro-9-oxa-1,2,4a-triaza-phenanthren-6-ylamino)-azetidine-1-carboxylic acid tert-butyl ester (4.48 g, 11.6 mmol) in DCM (65 mL) and MeOH (35 mL) was added tetra-N-butylammonium tribromide (5.6 g, 11.6 mmol) in portions. The mixture was stirred at rt for 2 h then aqueous Na₂S₂O₃ (30 mL) and aqueous NaHCO₃ (30 mL) were added. The organic phase was separated and the aqueous phase was extracted with DCM (3×50 mL). The combined organic phase was dried over Na₂SO₄, filtered and concentrated in vacuo to give the crude product, which was purified by column chromatography on silica gel (eluting with 10-33% EtOAc in petroleum ether) to give 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (3.4 g, 7.3 mmol, 63%) as pale yellow powder. ¹H NMR (CDCl₃, 400 MHz): δ 7.95 (br s, 1H), 7.09 (s, 1H), 5.82 (s, 1H), 4.58 (m, 1H), 4.45 (m, 2H), 4.38 (m, 1H), 4.28 (m, 2H), 4.09 (m, 1H), 3.72 (m, 2H), 1.42 (d, J=6.8 Hz, 3H), 1.39 (s, 9H).

Step C. 3-(4(S)-Methyl-3-oxo-7-phenyl-2,3,4,10-tetrahydro-9-oxa-1,2,4a-triaza-phenanthren-6-ylamino)-azetidine-1-carboxylic acid tert-butyl ester & 3-(4(R)-methyl-3-oxo-7-phenyl-2,3,4,10-tetrahydro-9-oxa-1,2,4a-triaza-phenanthren-6-ylamino)-azetidine-1-carboxylic acid tert-butyl ester

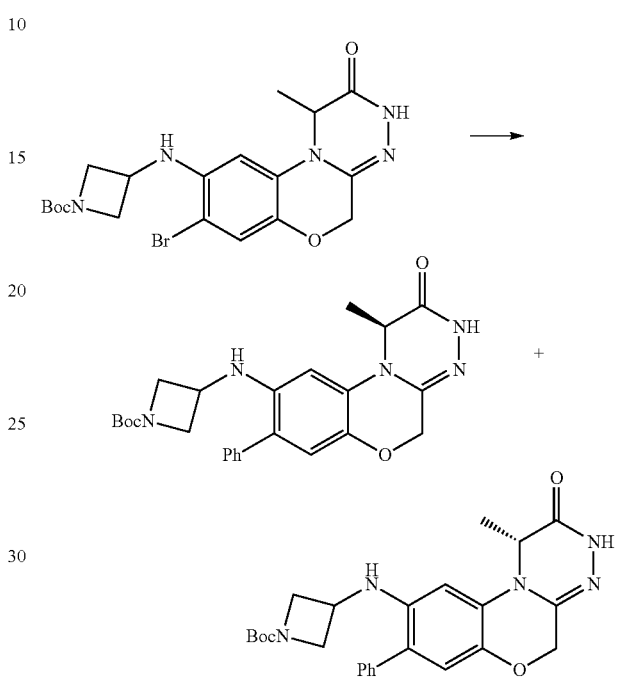

A mixture of 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (1 g, 2.1 mmol), phenylboronic acid (0.79 g, 6.4 mmol), 1,1'-bis(diphenylphosphino)ferrocene-palladium(II)dichloride dichloromethane complex (0.351 g, 0.43 mmol) and K₂CO₃ (0.890 g, 6.4 mmol) in dioxane (24 mL) and water (4 mL) was heated at 110° C. overnight. The reaction mixture was cooled to ambient temperature and the solvent was removed in vacuo to give the crude product, which was purified by column chromatography (eluting with 10-40% EtOAc in petroleum ether) to give 3-(4-methyl-3-oxo-7-phenyl-2,3,4,10-tetrahydro-9-oxa-1,2,4a-triaza-phenanthren-6-ylamino)-azetidine-1-carboxylic acid tert-butyl ester (0.710 g racemate, 1.5 mmol, 71%) as an off-white powder. The racemic material was further separated by chiral SFC (Table 2, Method 1) to give two isomers: 3-(4(R)-methyl-3-oxo-7-phenyl-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 1), R$_t$=3.374 min., 0.281 g, 0.61 mmol, 29%) and 3-(4(S)-methyl-3-oxo-7-phenyl-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 1), R$_t$=4.333 min., 0.252 g, 26%). LC/MS (Table 1, Method 2) R$_t$=1.25 min.; MS m/z: 464 [M+H]⁺.

Step D. 6-(Azetidin-3-ylamino)-4(R)-methyl-7-phenyl-2,10-dihydro-9-oxa-1,2,4a-triaza-phenanthren-3-one trifluoroacetic acid

Step E. 6-(azetidin-3-ylamino)-4(S)-methyl-7-phenyl-2,10-dihydro-9-oxa-1,2,4a-triaza-phenanthren-3-one trifluoroacetic acid

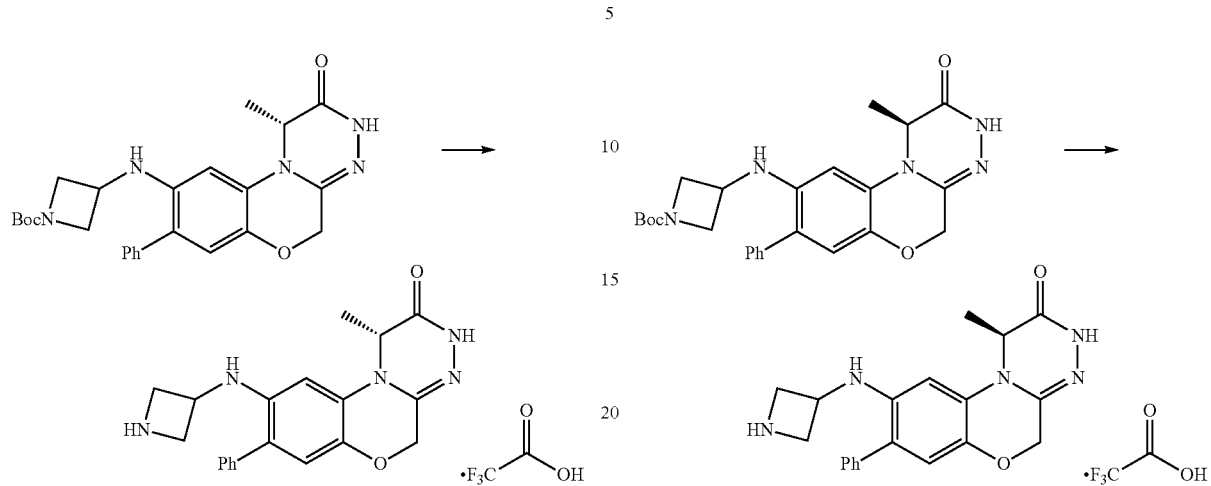

A solution of 3-(4(R)-methyl-3-oxo-7-phenyl-2,3,4,10-tetrahydro-9-oxa-1,2,4a-triaza-phenanthren-6-ylamino)-azetidine-1-carboxylic acid tert-butyl ester (enantiomer 1, SFC (Table 1, Method 1), $R_t$=3.374 min., 0.281 g, 0.61 mmol) in TFA (4 mL) and DCM (24 mL) was stirred at ambient temperature for 3 h. The solvent was removed in vacuo to give 6-(azetidin-3-ylamino)-4(R)-methyl-7-phenyl-2,10-dihydro-9-oxa-1,2,4a-triaza-phenanthren-3-one trifluoroacetic acid (Example #1-1, Enantiomer 1, SFC (Table 1, Method 1), $R_t$=4.541 min., 0.192 g, 65%) as yellow solid. LC/MS (Table 1, Method 5) $R_t$=2.074 min.; MS m/z: 364 [M+H]$^+$.

A solution of 3-(4(S)-methyl-3-oxo-7-phenyl-2,3,4,10-tetrahydro-9-oxa-1,2,4a-triaza-phenanthren-6-ylamino)-azetidine-1-carboxylic acid tert-butyl ester (enantiomer 2, SFC (Table 1, Method 1), $R_t$=4.333 min., 0.252 g, 0.54 mmol) in TFA (4 mL) and DCM (24 mL) was stirred at ambient temperature for 3 h. The solvent was removed in vacuo to give 6-(azetidin-3-ylamino)-4(S)-methyl-7-phenyl-2,10-dihydro-9-oxa-1,2,4a-triaza-phenanthren-3-one trifluoroacetic acid (Example #1-2, Enantiomer 2, SFC (Table 1, Method 1), $R_t$=5.572 min, 0.261 g, 100%) as yellow solid. LC/MS (Table 1, Method 5) $R_t$=2.117 min.; MS m/z: 364 [M+H]$^+$

TABLE 4

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-E and substituting the appropriate boronic acid.

| Structure | Example # | Boronic acid | $R_t$ min (method) | m/z ESI+ (M + H)$^+$ |
|---|---|---|---|---|
| 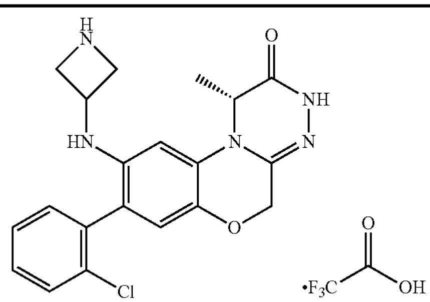 | 2 |  | 1.825 (Table 1, Method 5) | 398 |
| 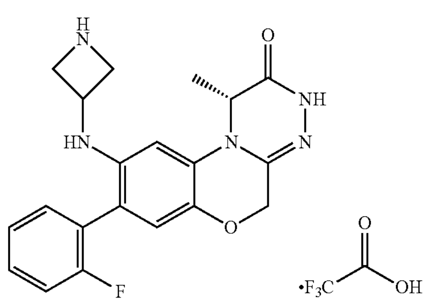 | 3 |  | 2.373 (Table 1, Method 5) | 382 |

TABLE 4-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-E and substituting the appropriate boronic acid.

| Structure | Example # | Boronic acid | R$_t$ min (method) | m/z ESI+ (M + H)+ |
|---|---|---|---|---|
| 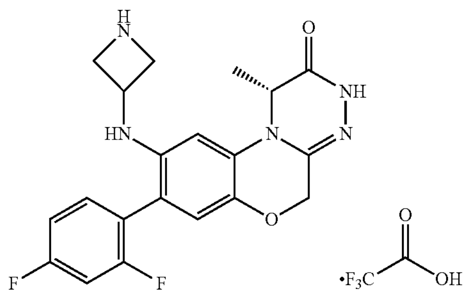 | 4 | 2,4-difluorophenylboronic acid | 1.808 (Table 1, Method 5) | 400 |
| 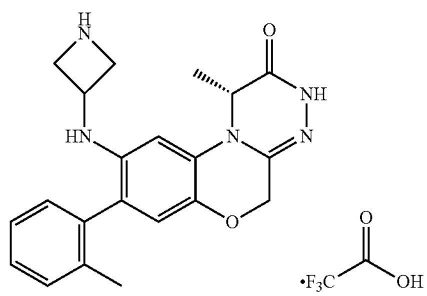 | 5 | 2-methylphenylboronic acid | 1.670 (Table 1, Method 4) | 378 |
| 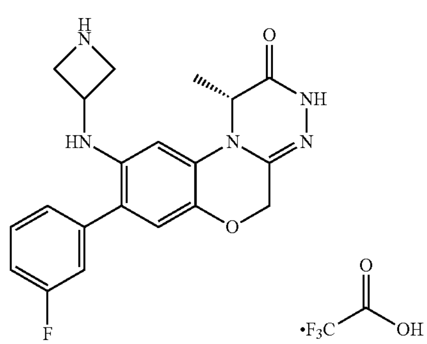 | 6 | 3-fluorophenylboronic acid | 2.317 (Table 1, Method 5) | 382 |
| 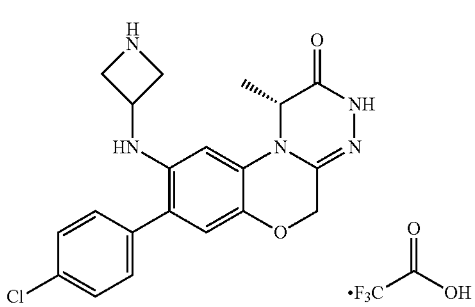 | 7 | 4-chlorophenylboronic acid | 2.482 (Table 1, Method 5) | 398 |

TABLE 4-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-E and substituting the appropriate boronic acid.

| Structure | Example # | Boronic acid | $R_t$ min (method) | m/z ESI+ (M + H)+ |
|---|---|---|---|---|
| 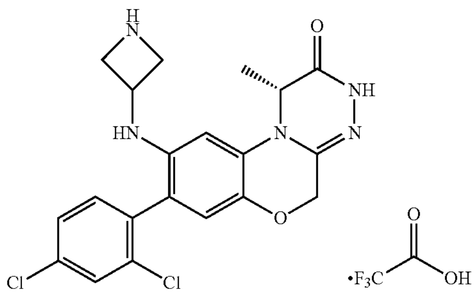 | 8 |  | 1.839 (Table 1, Method 4) | 432 |
| 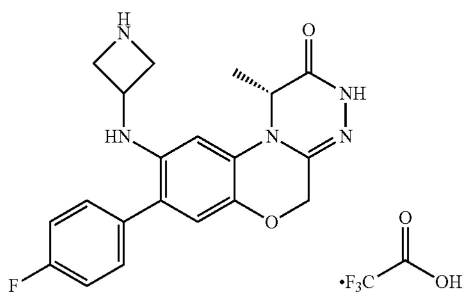 | 9 |  | 2.313 (Table 1, Method 5) | 382 |
| 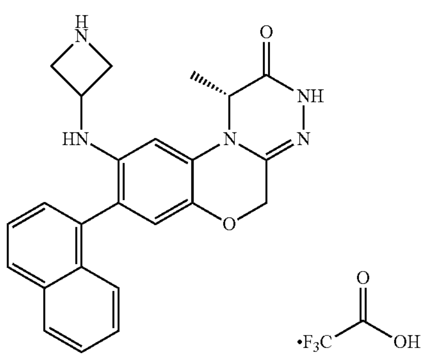 | 10 |  | 2.457 (Table 1, Method 5) | 414 |
| 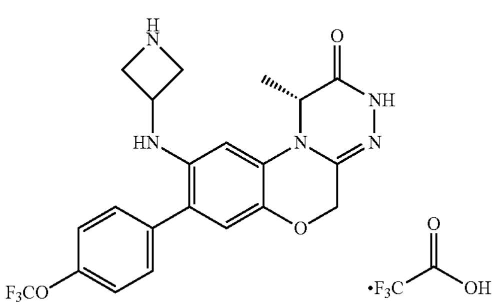 | 11 |  | 1.973 (Table 1, Method 4) | 448 |

TABLE 5

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | R$_t$ min (method) | m/z ESI+ (M + H)$^+$ |
|---|---|---|---|---|
| 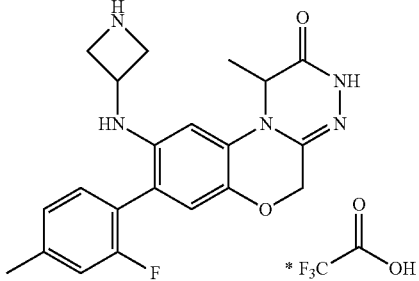 | 12 | 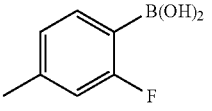 | 1.160 (Table 1, Method 5) | 396 |
| 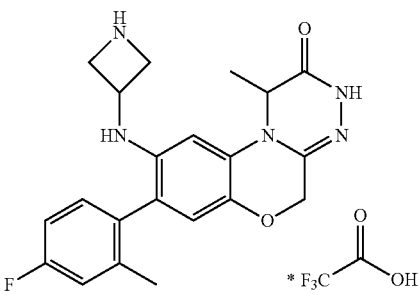 | 13 | 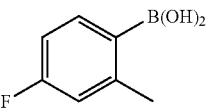 | 2.433 (Table 1, Method 5) | 396 |
| 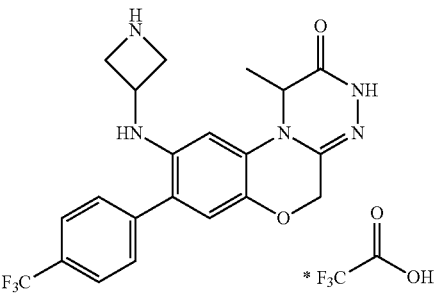 | 14 | 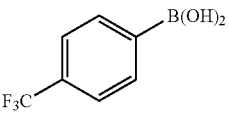 | 1.962 (Table 1, Method 4) | 432 |
| 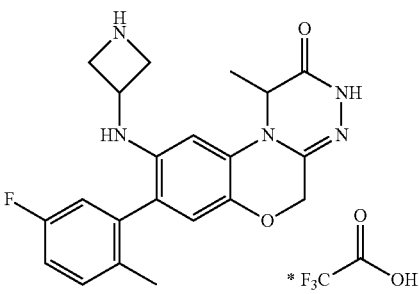 | 15 | 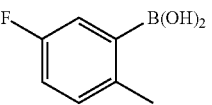 | 2.435 (Table 1, Method 5) | 396 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 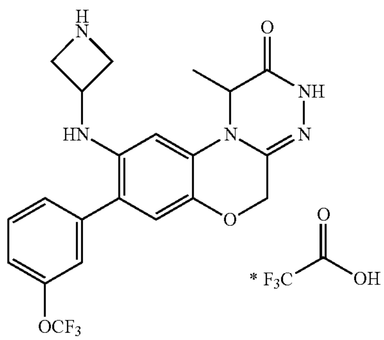 | 16 | 3-(OCF₃)C₆H₄-B(OH)₂ | 1.985 (Table 1, Method 4) | 448 |
| 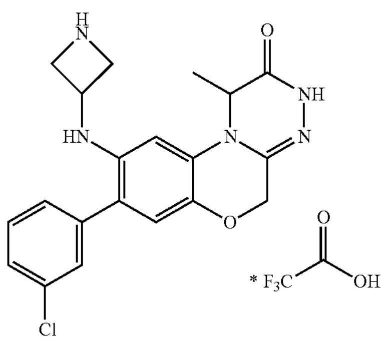 | 17 | 3-Cl-C₆H₄-B(OH)₂ | 1.849 (Table 1, Method 4) | 398 |
| 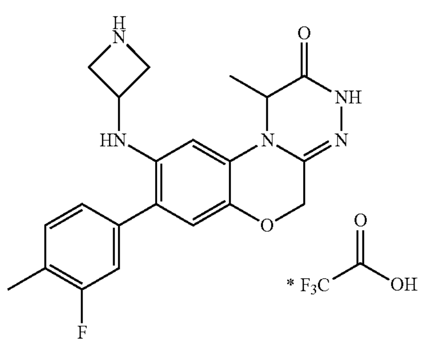 | 18 | 3-F-4-Me-C₆H₃-B(OH)₂ | 2.494 (Table 1, Method 5) | 396 |
| 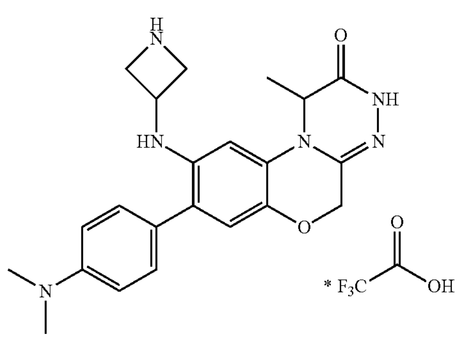 | 19 | 4-(NMe₂)C₆H₄-B(OH)₂ | 1.784 (Table 1, Method 5) | 407 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 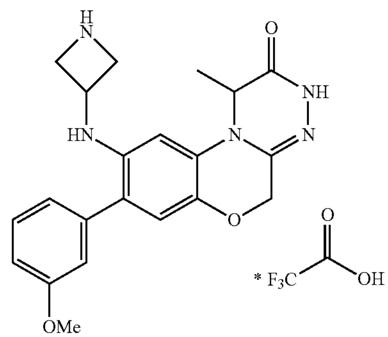 | 20 | 3-methoxyphenylboronic acid | 1.675 (Table 1, Method 4) | 394 |
| 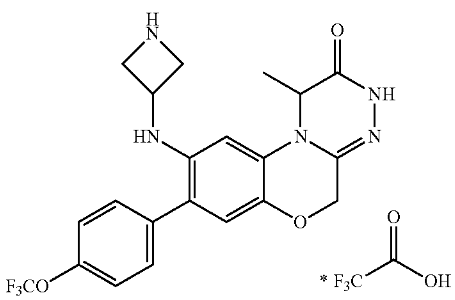 | 21 | 4-trifluoromethoxyphenylboronic acid | 2.012 (Table 1, Method 4) | 448 |
| 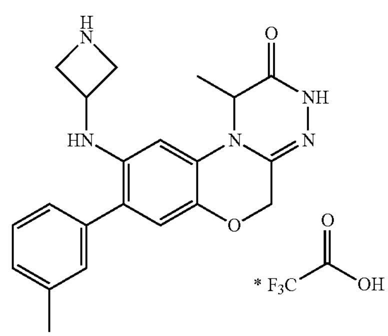 | 22 | 3-methylphenylboronic acid | 2.318 (Table 1, Method 5) | 378 |
| 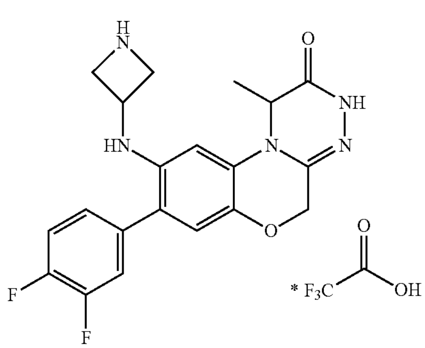 | 23 | 3,4-difluorophenylboronic acid | 2.417 (Table 1, Method 5) | 400 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | R$_t$ min (method) | m/z ESI+ (M + H)+ |
|---|---|---|---|---|
| 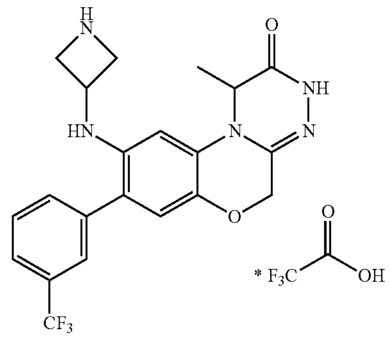 | 24 | | 1.940 (Table 1, Method 4) | 432 |
| 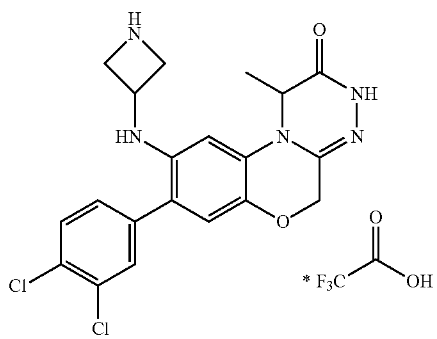 | 25 | | 2.015 (Table 1, Method 4) | 432 |
| 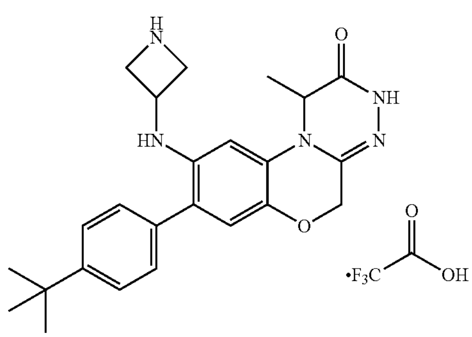 | 26 | | 2.105 (Table 1, Method 4) | 420 |
| 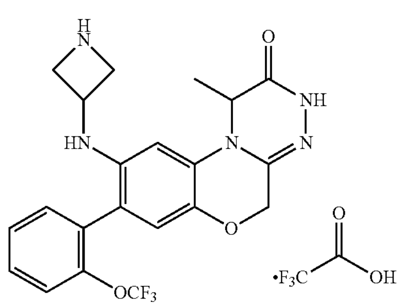 | 27 | | 1.846 (Table 1, Method 4) | 448 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 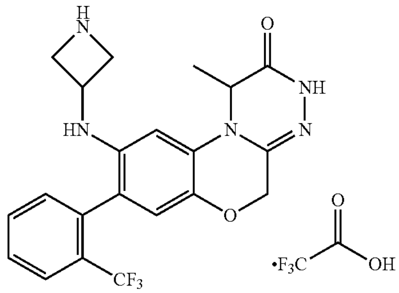 | 28 | 2-CF₃-phenyl B(OH)₂ | 1.770 (Table 1, Method 4) | 432 |
| 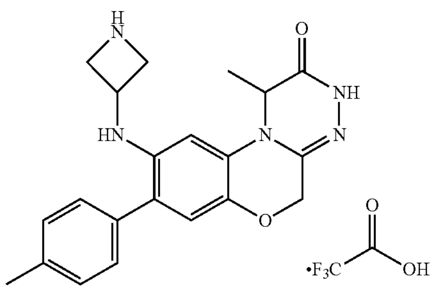 | 29 | 4-methylphenyl B(OH)₂ | 2.401 (Table 1, Method 5) | 378 |
| 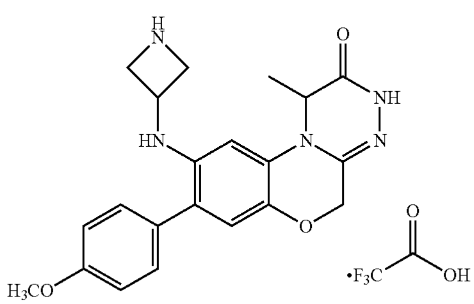 | 30 | 4-methoxyphenyl B(OH)₂ | 2.318 (Table 1, Method 5) | 394 |
| 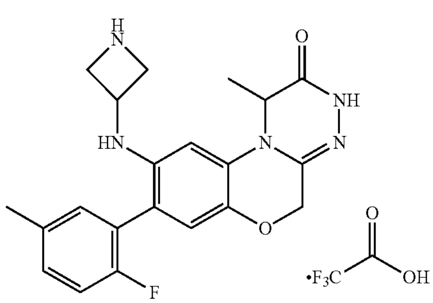 | 31 | 5-methyl-2-fluorophenyl B(OH)₂ | 2.407 (Table 1, Method 5) | 396 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ $(M + H)^+$ |
|---|---|---|---|---|
| 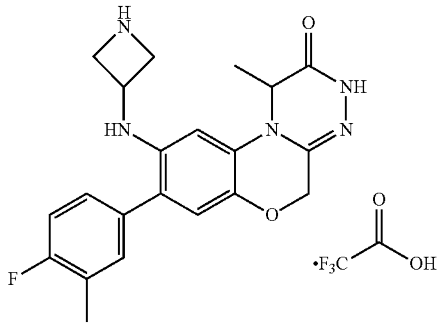 | 32 | | 2.506 (Table 1, Method 5) | 396 |
| 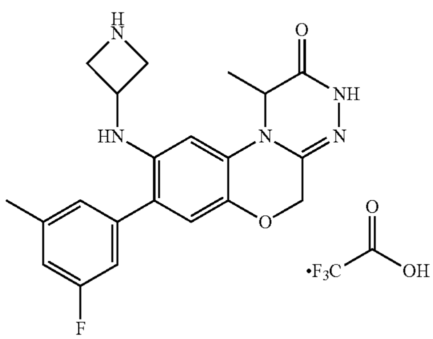 | 33 | | 2.413 (Table 1, Method 5) | 396 |
| 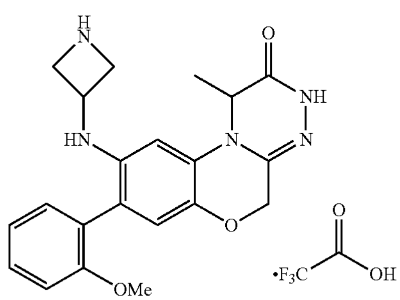 | 34 | | 2.240 (Table 1, Method 5) | 394 |
| 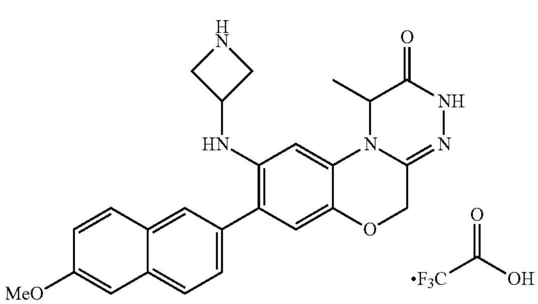 | 35 | | 1.980 (Table 1, Method 4) | 444 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 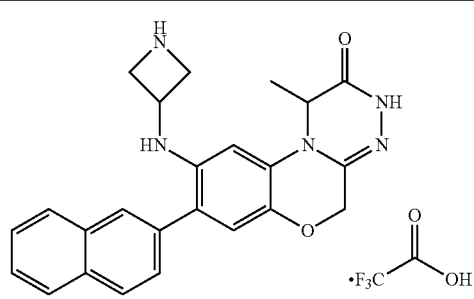 | 36 | 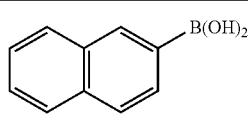 | 1.972 (Table 1, Method 4) | 414 |
| 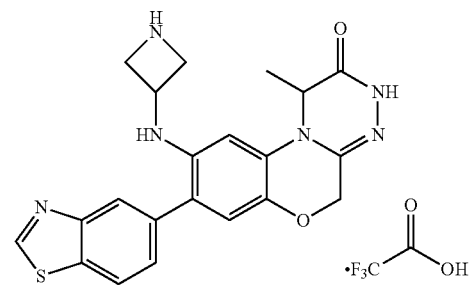 | 37 | 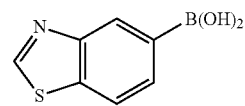 [SMILES: OB(O)c1ccc2scnc2c1] | 1.579 (Table 1, Method 4) | 421 |
| 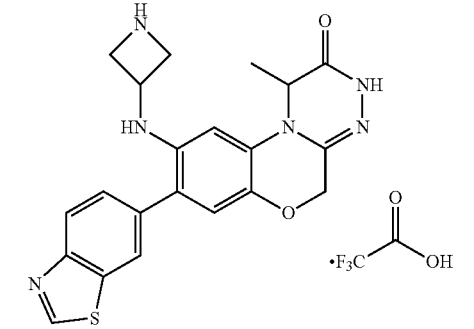 | 38 | 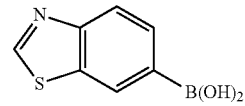 [SMILES: OB(O)c1ccc2ncsc2c1] | 1.564 (Table 1, Method 4) | 421 |
| 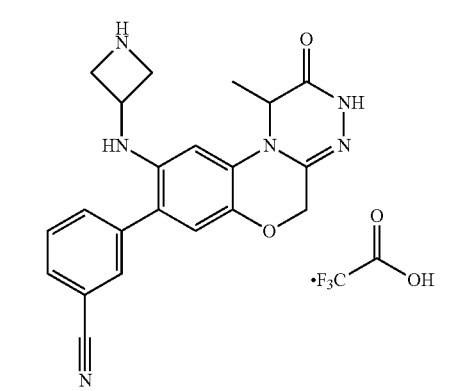 | 39 | 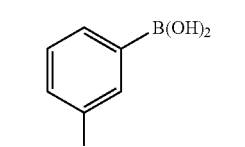 | 1.610 (Table 1, Method 4) | 389 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ $(M + H)^+$ |
|---|---|---|---|---|
| 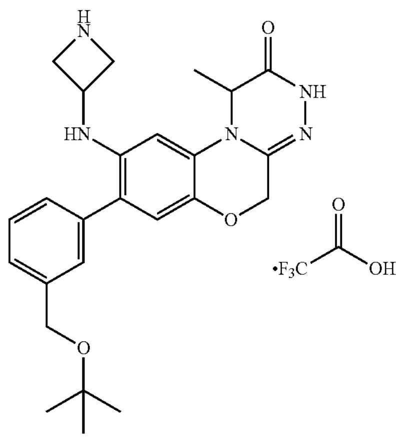 | 40 | | 1.937 (Table 1, Method 4) | 450 |
| 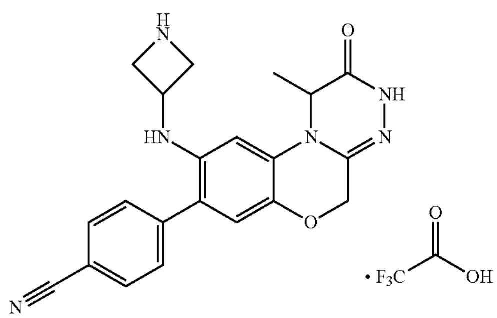 | 41 | | 1.646 (Table 1, Method 4) | 389 |
| 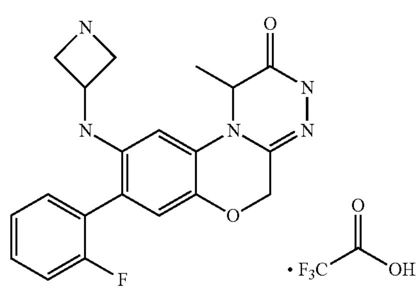 | 42 | | 2.162 (Table 1, Method 5) | 328 |
| 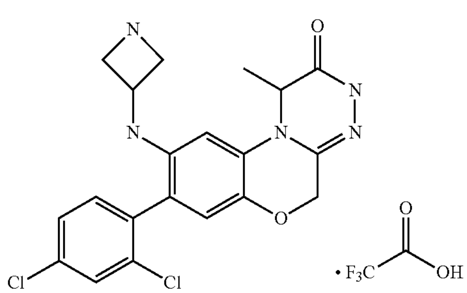 | 43 | | 1.774 (Table 1, Method 4) | 432 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 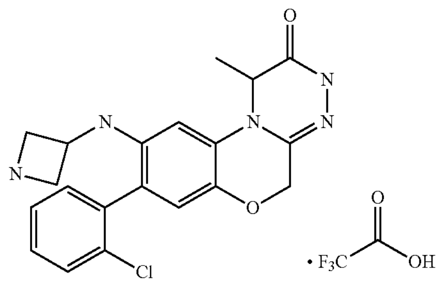 | 44 | 2-chlorophenylboronic acid | 1.717 (Table 1, Method 4) | 398 |
| 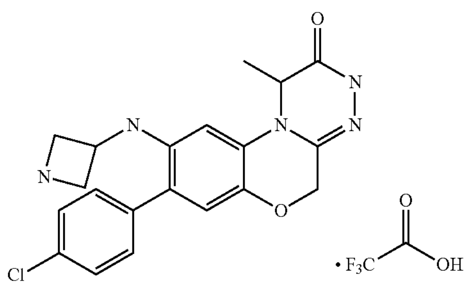 | 45 | 4-chlorophenylboronic acid | 1.844 (Table 1, Method 4) | 398 |
| 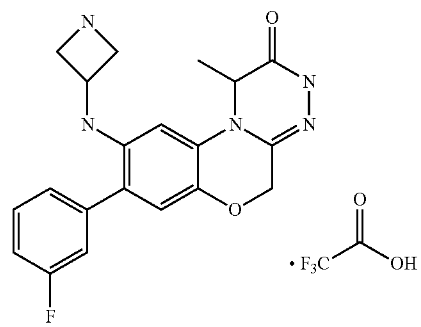 | 46 | 3-fluorophenylboronic acid | 2.336 (Table 1, Method 5) | 382 |
| 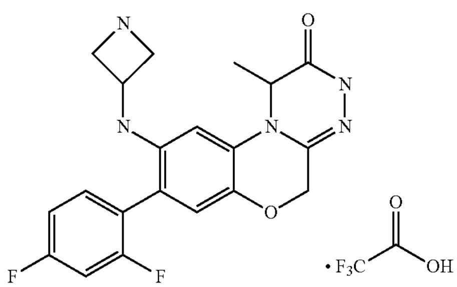 | 47 | 2,4-difluorophenylboronic acid | 2.329 (Table 1, Method 5) | 400 |
| 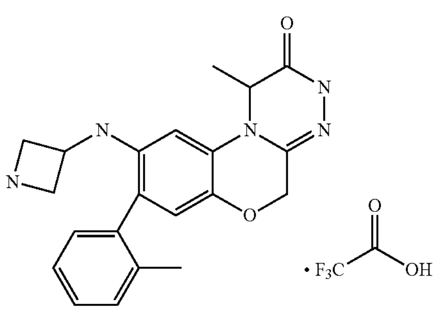 | 48 | 2-methylphenylboronic acid | 2.276 (Table 1, Method 5) | 378 |

TABLE 5-continued

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #1, Step C-D and substituting the appropriate boronic acid. No SFC separation was performed in Step C; the isolated racemate was carried on to the final deprotection, Step D, as a mixture of two enantiomers:

| Structure | Example # | Boronic acid | $R_t$ min (method) | m/z ESI+ (M + H)+ |
|---|---|---|---|---|
| 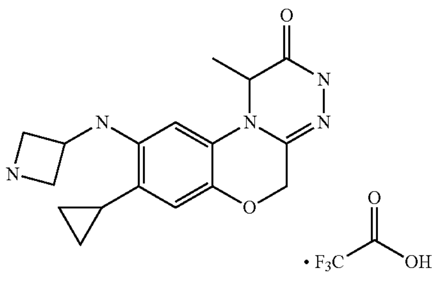 | 49 | cyclopropyl-B(OH)$_2$ | 1.935 (Table 1, Method 5) | 328 |
| 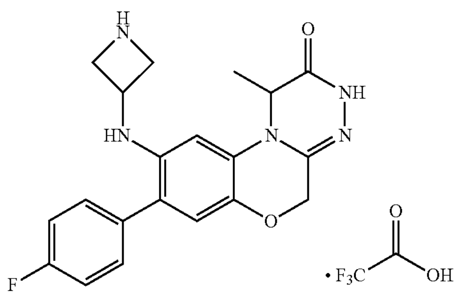 | 50 | 4-fluorophenyl-B(OH)$_2$ | 2.322 (Table 1, Method 5) | 382 |
| 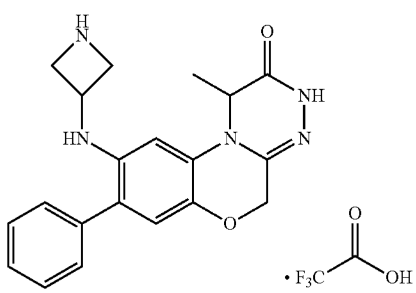 | 51 | phenyl-B(OH)$_2$ | 2.167 (Table 1, Method 5) | 364 |
| 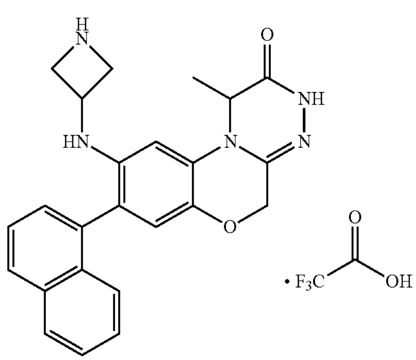 | 52 | 1-naphthyl-B(OH)$_2$ | 2.364 (Table 1, Method 5) | 414 |

Example #53

6-(Azetidin-3-ylamino)-4(S)-methyl-7-trifluoromethyl-2,10-dihydro-9-oxa-1,2,4a-triaza-phenanthren-3-one trifluoroacetic acid (Example #53-1, Enantiomer 1) and 6-(azetidin-3-ylamino)-4(R)-methyl-7-trifluoromethyl-2,10-dihydro-9-oxa-1,2,4a-triaza-phenanthren-3-one trifluoroacetic acid (Example #53-2, Enantiomer 2)

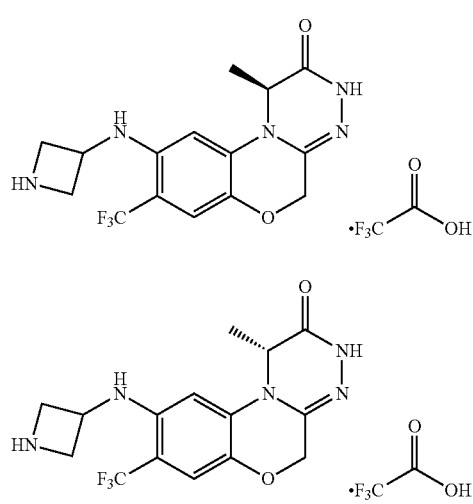

Step A. 4-Bromo-2-nitro-5-(trifluoromethyl)phenol

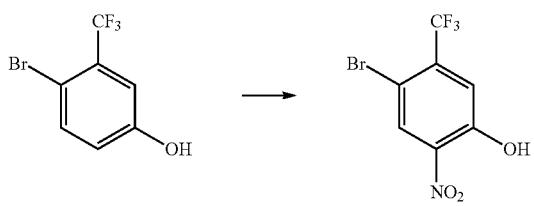 [SMILES: Oc1ccc(Br)c(C(F)(F)F)c1 ; O=[N+]([O-])c1cc(Br)c(C(F)(F)F)cc1O]

To a 0° C. mixture of 4-bromo-3-(trifluoromethyl)phenol (Apollo, 10.8 g, 44.8 mmol) in AcOH (40 mL) was added concentrated sulfuric acid (1.5 mL) followed by fuming nitric acid (5.2 g) and the mixture was stirred for 30 min. Additional concentrated sulfuric acid (9 mL) was added and the temperature was allowed to rise to ambient temperature and stirred for 3 h at rt. The mixture was poured into ice water (500 mL) and the aqueous solution was extracted with EtOAc (3×50 mL). The combined organic phase was washed with brine (50 mL), dried over anhydrous $Na_2SO_4$ and filtered. The filtrate was evaporated in vacuo and the residue was purified by column chromatography on silica gel (eluting with 10-20% EtOAc in petroleum ether) to give 4-bromo-2-nitro-5-(trifluoromethyl) phenol (4.7 g, 36%) as yellow oil. $^1$H NMR (DMSO-$d_6$, 400 MHz): δ 12.0 (brs, 1H), 8.31 (s, 1H), 7.54 (s, 1H).

Step B. 2-Amino-4-bromo-5-(trifluoromethyl)phenol

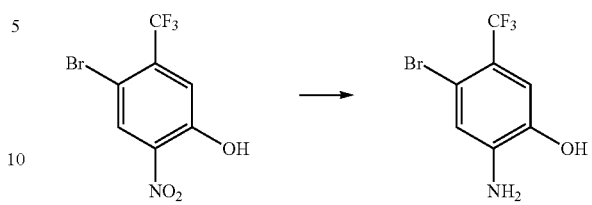

To a mixture of zinc powder (16.23 g, 248 mmol) and ammonium chloride (13.28 g, 248 mmol) in MeOH (80 mL) was added 4-bromo-2-nitro-5-(trifluoromethyl)phenol (7.1 g, 24.8 mmol) and the reaction mixture was stirred overnight at ambient temperature. The reaction mixture was filtered and the filtrate was evaporated in vacuo. The residue was partitioned between EtOAc (100 mL) and water (300 mL). The organic phase was separated and washed with brine (30 mL), dried over $Na_2SO_4$, filtered and concentrated in vacuo to give 2-amino-4-bromo-5-(trifluoromethyl)phenol as a black oil (5.9 g, 93%), which was used in the next step without further purification. $^1$H NMR (DMSO-$d_6$, 400 MHz): δ 9.89 (brs 1H), 6.98 (s, 1H), 6.92 (s, 1H), 5.53 (brs, 2H).

Step C. Ethyl 2-(6-bromo-3-oxo-7-(trifluoromethyl)-2H-benzo[b][1,4]oxazin-4(3H)-yl)propanoate

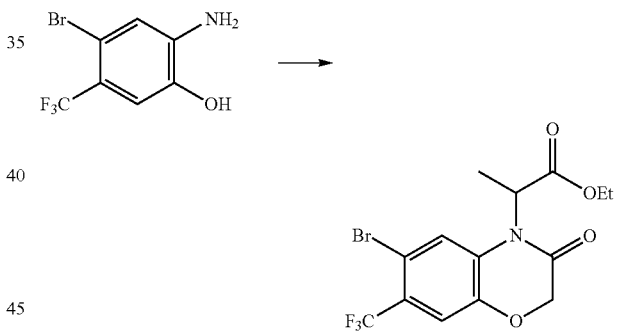

To a mixture of 6-amino-3-bromo-2-(trifluoromethyl)phenol (5.9 g, 23.05 mmol) and $K_2CO_3$ (9.55 g, 69.01 mmol) in DMF (80 mL) was added 2-chloroacetyl chloride (2.86 g, 25.3 mmol) dropwise at rt and the mixture was stirred for 16 h at ambient temperature. $Cs_2CO_3$ (7.51 g, 23.05 mmol) and ethyl 2-bromopropanoate (6.26 g, 34.6 mmol) were added sequentially and the mixture was stirred for an additional 3 h at ambient temperature. The reaction mixture was poured into water (150 mL) and the aqueous mixture was extracted with EtOAc (3×50 mL). The combined organic phase was washed with brine (30 mL) and dried over $Na_2SO_4$, filtered and the filtrate was evaporated in vacuo. The residue was purified by column chromatography on silica gel (eluting with 10-17% EtOAc in petroleum ether) to give ethyl 2-(6-bromo-3-oxo-7-(trifluoromethyl)-2H-benzo[b][1,4]xazin-4(3H)-yl)propanoate as yellow oil (4.2 g, 46%). $^1$H NMR (CDCl$_3$, 400 MHz): δ 7.35 (s 1H), 7.15 (s, 1H), 5.26 (q, J=8.0 Hz, 1H), 4.68 (dd, J=11.6 Hz, 2H), 4.24 (q, J=6.8 Hz, 2H), 1.65 (d, J=7.2 Hz, 3H), 1.24 (t, J=7.2 Hz, 3H).

Step D. 6-Bromo-4-methyl-7-trifluoromethyl-2,10-dihydro-9-oxa-1,2,4a-triaza-phenanthren-3-one

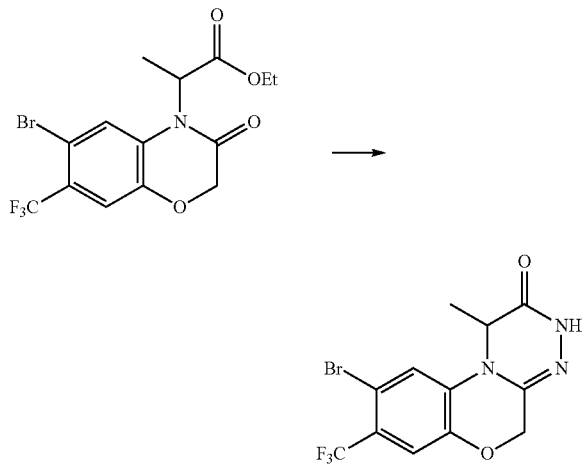

A mixture of ethyl 2-(6-bromo-3-oxo-7-(trifluoromethyl)-2H-benzo[b][1,4]oxazin-4(3H)-yl)propanoate (7.7 g, 19.44 mmol) and Lawesson reagent (8.65 g, 21.38 mmol) in toluene (20 mL) was heated at reflux for 1 h. The reaction mixture was cooled to ambient temperature, hydrazine hydrate (4.98 g, 155 mmol) was added and the reaction mixture was heated at 80° C. for 1 h. The reaction mixture was cooled to ambient temperature and the solvent was evaporated in vacuo. The residue was purified by column chromatography on silica gel (eluting with 16-33% EtOAc in petroleum ether) to give 6-bromo-4-methyl-7-trifluoromethyl-2,10-dihydro-9-oxa-1,2,4a-triaza-phenanthren-3-one as white solid (1.30 g, 18%). $^1$H NMR (DMSO-$d_6$, 400 MHz): δ 10.92 (s, 1H), 7.66 (s, 1H), 7.34 (s, 1H), 4.88 (q, J=6.8 Hz, 1H), 4.72 (d, J=13.2 Hz, 1H), 4.64 (d, J=13.2 Hz, 1H), 1.30 (d, J=6.8 Hz, 3H).

Step E. 6-Bromo-4-methyl-7-trifluoromethyl-2-(2-trimethylsilanyl-ethoxymethyl)-2,10-dihydro-9-oxa-1,2,4a-triaza-phenanthren-3-one

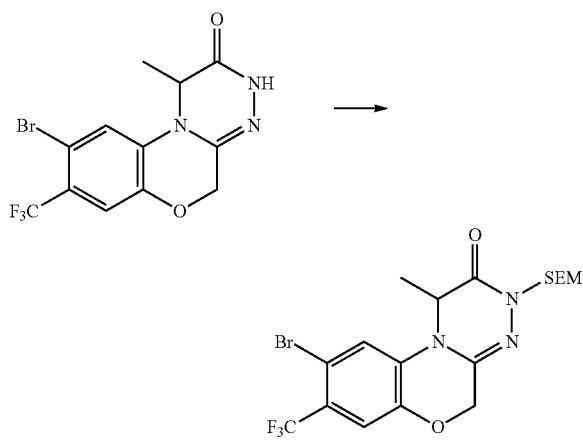

To a 0° C. solution of 6-bromo-4-methyl-7-trifluoromethyl-2,10-dihydro-9-oxa-1,2,4a-triaza-phenanthren-3-one (0.364 g, 1.0 mmol) in THF (50 mL) was added sodium hydride (60% in mineral oil, 0.080 g, 2 mmol) and the reaction mixture was stirred for 0.5 h. (2-(chloromethoxy)ethyl)trimethylsilane (0.250 g, 1.5 mmol) was added and the mixture was stirred at ambient temperature for 2 h. The reaction was quenched with water (100 mL) and the aqueous mixture was extracted with EtOAc (2×30 mL). The combined organic layers were washed with brine (30 mL), dried over $Na_2SO_4$, filtered and evaporated in vacuo. The residue was purified by column chromatography on silica gel (eluting with 3-20% EtOAc in petroleum ether) to give 6-bromo-4-methyl-7-trifluoromethyl-2-(2-trimethylsilanyl-ethoxymethyl)-2,10-dihydro-9-oxa-1,2,4a-triaza-phenanthren-3-one as a white solid (0.330 g, 67%). $^1$H NMR (CDCl$_3$, 400 MHz): δ 7.32 (s, 1H), 7.16 (s, 1H), 5.11 (q, J=8.8 Hz, 2H), 4.75 (d, J=12.6 Hz, 1H), 4.69 (q, J=6.4 Hz, 1H), 4.57 (d, J=12.6 Hz, 1H), 3.65 (t, J=8.4 Hz, 2H), 1.51 (d, J=6.8 Hz, 3H), 0.99 (t, J=8.4 Hz, 2H), 0.01 (s, 9H).

Step F. 3-[4-Methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester

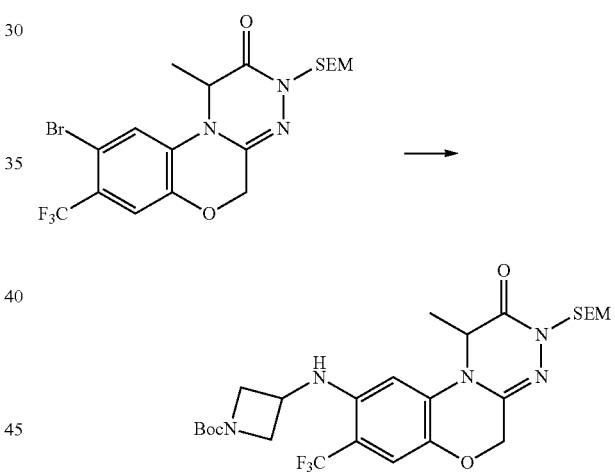

A mixture of 6-bromo-4-methyl-7-trifluoromethyl-2-(2-trimethylsilanyl-ethoxymethyl)-2,10-dihydro-9-oxa-1,2,4a-triaza-phenanthren-3-one (2.0 g, 4.05 mmol), tert-butyl 3-amino azetidine-1-carboxylate (1.39 g, 8.09 mmol), diacetoxypalladium (0.27 g, 1.21 mmol), $Cs_2CO_3$ (1.32 g, 4.05 mmol) and BINAP (1.0 g, 1.62 mmol) in toluene (10 mL) was heated at reflux for 2 h. The reaction mixture was cooled to ambient temperature and filtered. The filtrate was concentrated in vacuo. The residue was purified by column chromatography on silica gel (eluting with 20% EtOAc in petroleum ether) to give 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (2.1 g, 89%) as a pale yellow solid. $^1$H NMR (CDCl$_3$, 400 MHz): δ 7.14 (s, 1H), 5.86 (s, 1H), 5.10 (q, J=9.2 Hz, 2H), 4.63 (m, 2H), 4.51 (m, 2H), 4.33 (m, 2H), 4.18 (m, 1H), 3.77 (m, 2H), 3.65 (t, J=8.4 Hz, 2H), 1.47 (d, J=6.4 Hz, 3H), 1.45 (s, 9H), 0.99 (t, J=8.4 Hz, 2H), 0.00 (s, 9H).

Step G. 3-(4(R)-Methyl-3-oxo-7-trifluoromethyl-2,3,4,10-tetrahydro-9-oxa-1,2,4a-triaza-phenanthren-6-ylamino)-azetidine-1-carboxylic acid tert-butyl ester and 3-(4(S)-Methyl-3-oxo-7-trifluoromethyl-2,3,4,10-tetrahydro-9-oxa-1,2,4a-triaza-phenanthren-6-ylamino)-azetidine-1-carboxylic acid tert-butyl ester

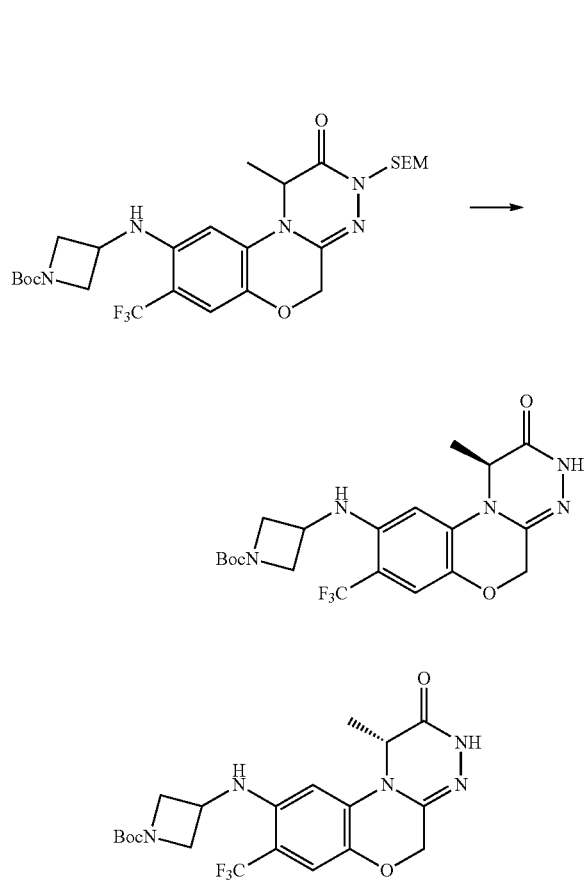

To a solution of 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (1.6 g, 2.73 mmol) in THF (5 mL) was added a solution of TBAF (1 M in THF, 4.1 mL, 4.1 mmol). The reaction mixture was heated at reflux for 3 days then cooled to ambient temperature. The solvent was removed in vacuo and the residue was purified by chiral SFC separation (Table 2, Method 2) to give 3-(4(S)-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 6), $R_t$=8.78 min., 0.280 g, 22%) and 3-(4(R)-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 6), $R_t$=10.53 min., 0.260 g, 21%). $^1$H NMR (CDCl$_3$, 400 MHz): δ 8.18 (s, 1H), 7.18 (s 1H), 5.91 (s, 1H), 4.68 (q, J=6.8 Hz, 1H), 4.61 (d, J=12.8 Hz, 1H), 4.52 (m, 1H), 4.51 (d, J=12.8 Hz, 1H), 4.36 (m, 2H), 4.22 (m, 1H), 3.80 (m, 2H), 1.55 (d, J=6.8 Hz, 3H), 1.49 (m, 9H).

Step H. 6-(Azetidin-3-ylamino)-4(S)-methyl-7-trifluoromethyl-2,10-dihydro-9-oxa-1,2,4a-triaza-phenanthren-3-one trifluoroacetic acid (Example #53-1, Enantiomer 1)

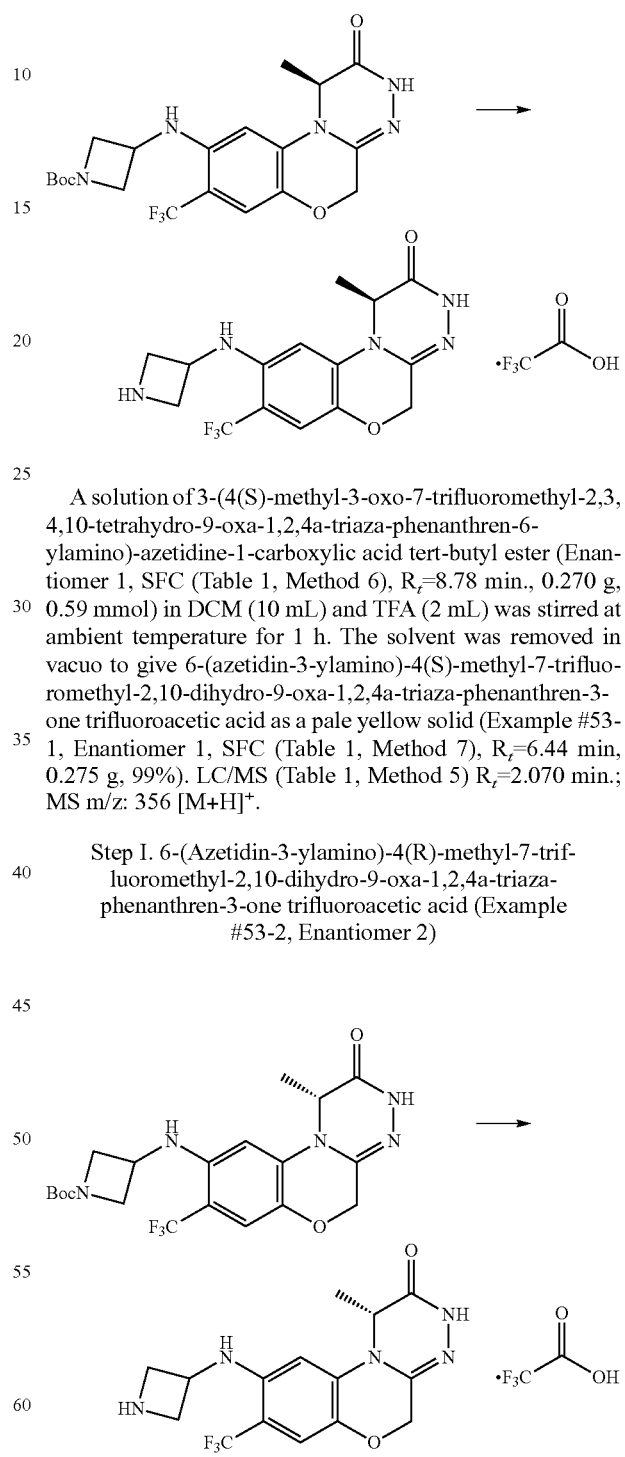

A solution of 3-(4(S)-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 6), $R_t$=8.78 min., 0.270 g, 0.59 mmol) in DCM (10 mL) and TFA (2 mL) was stirred at ambient temperature for 1 h. The solvent was removed in vacuo to give 6-(azetidin-3-ylamino)-4(S)-methyl-7-trifluoromethyl-2,10-dihydro-9-oxa-1,2,4a-triaza-phenanthren-3-one trifluoroacetic acid as a pale yellow solid (Example #53-1, Enantiomer 1, SFC (Table 1, Method 7), $R_t$=6.44 min, 0.275 g, 99%). LC/MS (Table 1, Method 5) $R_t$=2.070 min.; MS m/z: 356 [M+H]$^+$.

Step I. 6-(Azetidin-3-ylamino)-4(R)-methyl-7-trifluoromethyl-2,10-dihydro-9-oxa-1,2,4a-triaza-phenanthren-3-one trifluoroacetic acid (Example #53-2, Enantiomer 2)

A solution of 3-(4(R)-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester ((Enantiomer 2, SFC (Table 1, Method 6), $R_t$=10.53 min., 0.260 g, 0.57 mmol) in DCM (10 mL) and TFA (2 mL) was stirred at ambient temperature for 1 h. The solvent was removed in vacuo to give 6-(azetidin-3-ylamino)-4(R)-methyl-7-trifluoromethyl-2,10-dihydro-9-oxa-1,2,4a-triaza-phenanthren-3-one trifluoroacetic acid as a pale yellow solid (Example #53-2, Enantiomer 2, SFC (Table 1, Method 7), $R_t$=7.98 min, 0.260 g, 97%). LC/MS (Table 1, Method 5) $R_t$=2.068 min.; MS m/z: 356 [M+H]$^+$.

Example #54

6-(Azetidin-3-ylamino)-4(R),7-dimethyl-2,10-dihydro-9-oxa-1,2,4a-triaza-phenanthren-3-one trifluoroacetic acid (Example #54-1, Enantiomer 1) & 6-(azetidin-3-ylamino)-4(S),7-dimethyl-2,10-dihydro-9-oxa-1,2,4a-triaza-phenanthren-3-one trifluoroacetic acid (Example #54-2, Enantiomer 2)

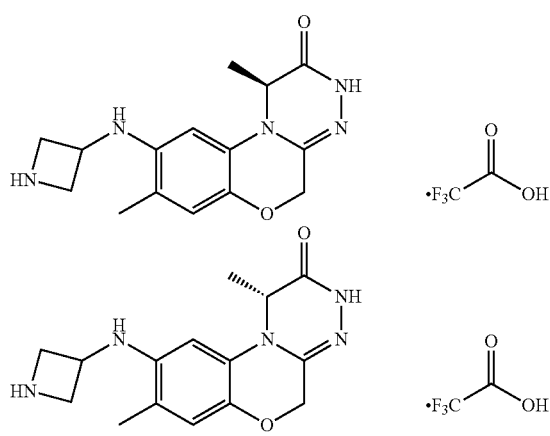

Step A.
7-Methyl-6-nitro-4H-benzo[1,4]oxazin-3-one

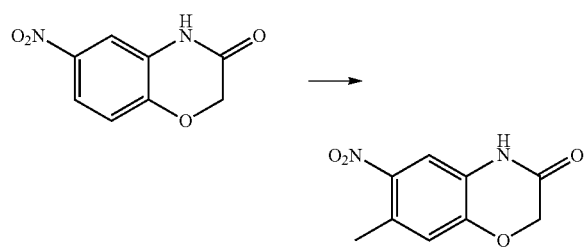

To a solution of 6-nitro-2H-benzo[b][1,4]oxazin-3(4H)-one (Preparation #2, Step A, 5 g, 25.8 mmol) in THF (80 mL) at 0° C. was added methylmagnesium bromide solution (3N in THF, 25.8 mL, 77.4 mmol, 3 equiv) dropwise. The reaction mixture was stirred for 15 min at 0° C. then allowed to warm to ambient temperature and stirred for 1 h. The reaction mixture was cooled to 0° C. and additional methylmagnesium bromide solution (3N in THF, 25.8 mL, 77.4 mmol) was added dropwise. The reaction mixture was allowed to warm to ambient temperature and stirred for an additional 1 h. The reaction mixture was poured into a 0° C. solution of KMnO$_4$ (0.270 g) in acetone (4 mL) and water (4 mL) and stirred for 15 min. The reaction mixture was allowed to warm to rt over 15 min. The resulting mixture was filtered and washed with EtOAc (25 mL). The aqueous solution was separated and the organic phase was concentrated in vacuo to give the crude product (0.870 g, crude) as a 1:1 mixture of 6-nitro-4H-benzo[1,4]oxazin-3-one and 7-methyl-6-nitro-4H-benzo[1,4]oxazin-3-one which was used in the next step directly. $^1$H NMR (CDCl$_3$, 400 MHz): δ 8.51 (brs, 1H), 7.56 (s, 1H), 6.84 (s, 1H), 4.65 (s, 2H), 2.52 (s, 3H).

Step B. 2-(7-Methyl-6-nitro-3-oxo-2,3-dihydrobenzo[1,4]oxazin-4-yl)-propionic acid ethyl ester

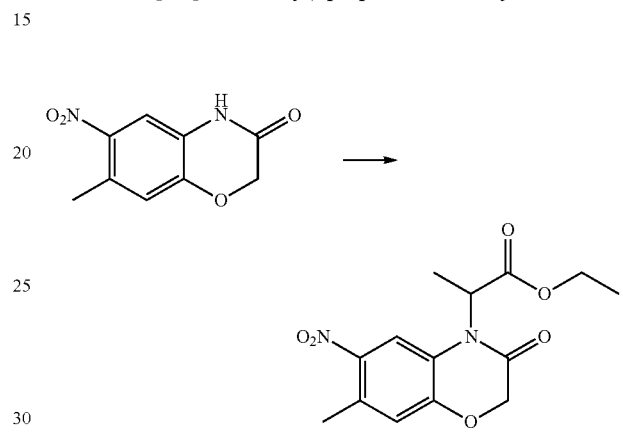

To 7-methyl-6-nitro-4H-benzo[1,4]oxazin-3-one (50% purity; 0.870 g, 1.44 mmol) and K$_2$CO$_3$ (1.15 g, 8.36 mmol) in acetone (20 mL) was added 2-bromo-propionic acid ethyl ester (1.5 g, 8.36 mmol) and the mixture was heated at 70° C. for 5 h. The reaction mixture was cooled to ambient temperature and the solvent was removed in vacuo and the residue was dissolved in DCM (15 mL). The solution was washed with water (15 mL), dried over anhydrous Na$_2$SO$_4$, filtered and the filtrate was evaporated in vacuo. The residue was purified by chromatography on silica gel (eluting with 20% EtOAc in petroleum ether) to give a mixture of the title compound as a yellow solid (total 0.5 g crude, 48% desired product as indicated by HPLC at 254 or 220 nm), HPLC (Column: Ultimate XB-C18, 3 um, 50×3.0 mm; Mobile phase: MeCN (0.02% TFA) in water (0.04% TFA), from 30% to 90% within 7 min; Flow rate: 1.5 mL/min; Wavelength: 220 nm) $R_t$=3.42 min.), which was used directly in the next step.

Step C. 2-(7-Methyl-6-nitro-3-thioxo-2,3-dihydrobenzo[1,4]oxazin-4-yl)-propionic acid ethyl ester

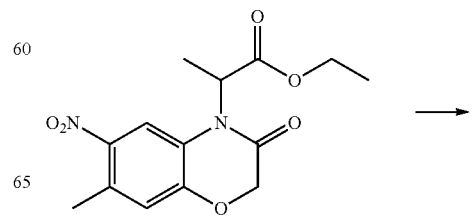

-continued

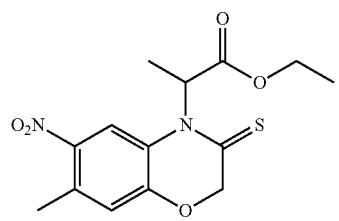

A solution of 2-(7-methyl-6-nitro-3-oxo-2,3-dihydro-benzo[1,4]oxazin-4-yl)-propionic acid ethyl ester (0.5 g crude, 48% pure, 0.81 mmol) and Lawesson's reagent (0.656 g, 1.62 mmol) in toluene (30 mL) was heated at 120° C. for 20 h. The reaction mixture was cooled to ambient temperature and the solvent was removed in vacuo to give the crude product, which was purified by chromatography on silica gel (eluting with 20% EtOAc in petroleum ether) and further purified by preparative TLC (eluting with 20% EtOAc in petroleum ether) to give 2-(7-methyl-6-nitro-3-thioxo-2,3-dihydro-benzo[1,4]oxazin-4-yl)-propionic acid ethyl ester (0.130 g, 50%) as a solid. $^1$H NMR (CDCl$_3$, 400 MHz): δ 7.64 (s, 1H), 6.90 (s, 1H), 6.61 (s, 1H), 4.90 (q, J=15.6 Hz, 2H), 4.20 (q, J=7.2 Hz, 2H), 2.54 (s, 3H), 1.65 (d, J=7.2 Hz, 3H), 1.21 (t, J=7.2 Hz, 3H).

Step D. 4,7-Dimethyl-6-nitro-2,10-dihydro-9-oxa-1,2,4a-triaza-phenanthren-3-one

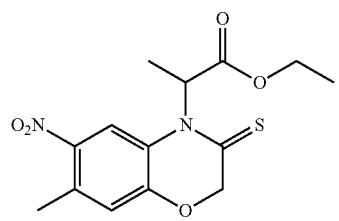

To a solution of 2-(7-methyl-6-nitro-3-thioxo-2,3-dihydro-benzo[1,4]oxazin-4-yl)-propionic acid ethyl ester (0.130 g, 0.40 mmol) in EtOH (8 mL) was added hydrazine hydrate (98%, 1.4 mmol, 0.070 g) and the reaction mixture was heated at 120° C. for 4 h. The reaction mixture was cooled to ambient temperature and the solvent was removed in vacuo to give 4,7-dimethyl-6-nitro-2,10-dihydro-9-oxa-1,2,4a-triaza-phenanthren-3-one (0.085 g, 75%) as yellow solid, which was used directly in the next step. TLC (eluting with 25% EtOAc in petroleum ether) R$_f$=0.4.

Step E. 6-Amino-4,7-dimethyl-2,10-dihydro-9-oxa-1,2,4a-triaza-phenanthren-3-one

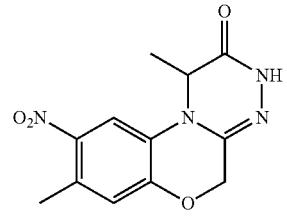

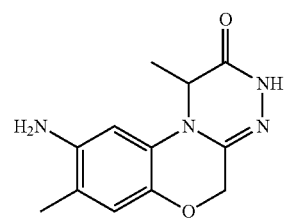

To a solution of 4,7-dimethyl-6-nitro-2,10-dihydro-9-oxa-1,2,4a-triaza-phenanthren-3-one (0.085 g, 0.31 mmol) and ammonium chloride (0.164 g, 3.1 mmol) in MeOH (10 mL) and THF (10 mL) was added zinc powder (0.200 g, 3.1 mmol) and the resulting mixture was heated at 70° C. for 4 h. The reaction mixture was cooled to ambient temperature, filtered and the filtrate was washed with MeOH (15 mL). The filtrate was concentrated in vacuo and the residue was dissolved in water (20 mL). The aqueous solution was extracted with EtOAc (3×15 mL) and the combined organic phase was dried over anhydrous Na$_2$SO$_4$, filtered and concentrated to give 6-amino-4,7-dimethyl-2,10-dihydro-9-oxa-1,2,4a-triaza-phenanthren-3-one (0.060 g, 0.24 mmol, 79%) as a solid, which was used directly in the next step. TLC (eluting with 25% EtOAc in petroleum ether) R$_f$=0.2.

Step F. 3-(4(S),7-Dimethyl-3-oxo-2,3,4,10-tetrahydro-9-oxa-1,2,4a-triaza-phenanthren-6-ylamino)-azetidine-1-carboxylic acid tert-butyl ester and 3-(4(R),7-dimethyl-3-oxo-2,3,4,10-tetrahydro-9-oxa-1,2,4a-triaza-phenanthren-6-ylamino)-azetidine-1-carboxylic acid tert-butyl ester

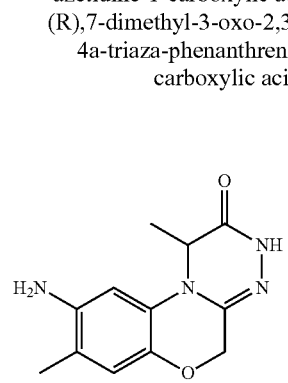

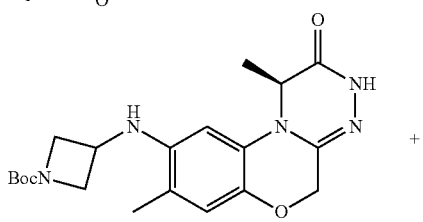

+

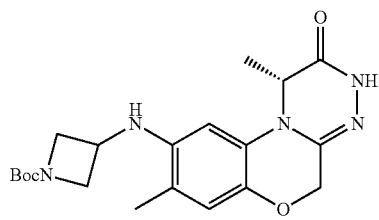

A solution of 6-amino-4,7-dimethyl-2,10-dihydro-9-oxa-1,2,4a-triaza-phenanthren-3-one (1.1 g, 4.5 mmol) and 3-oxo-azetidine-1-carboxylic acid tert-butyl ester (1.53 g, 8.9 mmol) in methanol (45 mL) and acetic acid (5 mL) was stirred at rt for 2 h. Sodium cyanoborohydride (0.563 g, 8.9 mmol) was added and the resulting dark solution was stirred at rt for 14 h. The solvent was removed in vacuo to give the crude product, which was purified by column chromatography on silica gel (eluting with 33% EtOAc in petroleum ether) to give 3-(4,7-dimethyl-3-oxo-2,3,4,10-tetrahydro-9-oxa-1,2,4a-triaza-phenanthren-6-ylamino)-azetidine-1-carboxylic acid tert-butyl ester (racemate, 0.580 g, 1.45 mmol, 32%) as an off-white powder. The racemate was further separated by chiral SFC (Table 2, Method 3) to give two enantiomers: 3-(4(R),7-dimethyl-3-oxo-2,3,4,10-tetrahydro-9-oxa-1,2,4a-triaza-phenanthren-6-ylamino)-azetidine-1-carboxylic acid tert-butyl ester (enantiomer 1, SFC (Table 1, Method 8), $R_t$=3.090 min, 0.250 g, 14%) and 3-(4(S),7-dimethyl-3-oxo-2,3,4,10-tetrahydro-9-oxa-1,2,4a-triaza-phenanthren-6-ylamino)-azetidine-1-carboxylic acid tert-butyl ester (enantiomer 2, SFC (Table 1, Method 8), $R_t$=4.151 min, 0.240 g, 13%). LC/MS (Table 1, Method 2) $R_t$=1.065 min.; MS m/z: 424 [M+23]$^+$.

Step G. 6-(Azetidin-3-ylamino)-4(R),7-dimethyl-2,10-dihydro-9-oxa-1,2,4a-triaza-phenanthren-3-one trifluoroacetic acid (Example #54-1, Enantiomer 1)

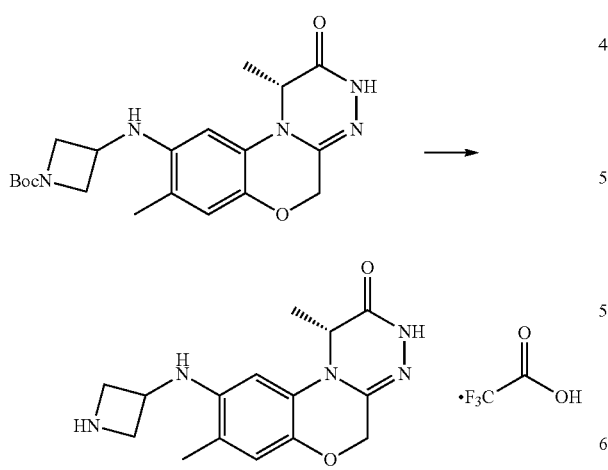

A solution of 3-(4(R),7-dimethyl-3-oxo-2,3,4,10-tetrahydro-9-oxa-1,2,4a-triaza-phenanthren-6-ylamino)-azetidine-1-carboxylic acid tert-butyl ester ((Enantiomer 1, SFC (Table 1, Method 8), $R_t$=3.090 min, 0.250 g, 0.62 mmol) in TFA (4 mL) and DCM (24 mL) was stirred at 25° C. for 3 h. The solvent was removed in vacuo to give 6-(azetidin-3-ylamino)-4(R),7-dimethyl-2,10-dihydro-9-oxa-1,2,4a-triaza-phenanthren-3-one trifluoroacetic acid (Example #54-1, Enantiomer 1, SFC (Table 1, Method 9), $R_t$=4.110 min, 0.240 g, 93%) as yellow solid. LC/MS (Table 1, Method 5) $R_t$=2.048 min.; MS m/z: 302 [M+H]$^+$.

Step H. 6-(Azetidin-3-ylamino)-4(S),7-dimethyl-2,10-dihydro-9-oxa-1,2,4a-triaza-phenanthren-3-one trifluoroacetic acid (Example #54-2, Enantiomer 2)

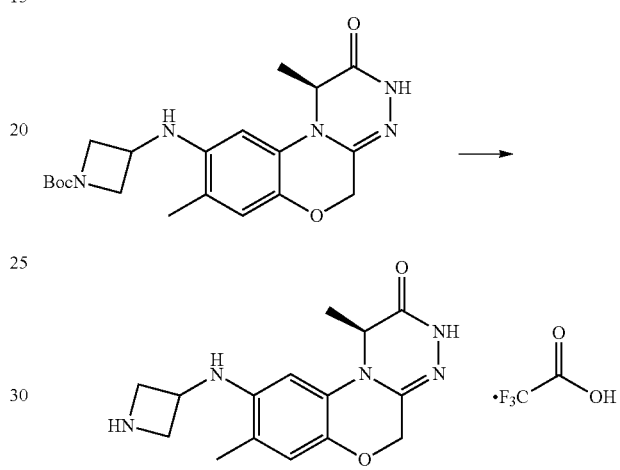

A solution of 3-(4(S),7-dimethyl-3-oxo-2,3,4,10-tetrahydro-9-oxa-1,2,4a-triaza-phenanthren-6-ylamino)-azetidine-1-carboxylic acid tert-butyl ester (enantiomer 2, SFC (Table 1, Method 8), $R_t$=4.151 min, 0.240 g, 0.60 mmol) in TFA (4 mL) and DCM (24 mL) was stirred at 25° C. for 3 h. The solvent was removed in vacuo to give 6-(azetidin-3-ylamino)-4(S),7-dimethyl-2,10-dihydro-9-oxa-1,2,4a-triaza-phenanthren-3-one trifluoroacetic acid (Example #54-2, Enantiomer 2, SFC (Table 1, Method 9), $R_t$=4.945 min, 0.246 g, 98%) as a yellow solid. LC/MS (Table 1, Method 5) $R_t$=2.048 min.; MS m/z: 302 [M+H]$^+$.

Example #55

6-(Azetidin-3-yl-methyl-amino)-4,7-dimethyl-2,10-dihydro-9-oxa-1,2,4a-triaza-phenanthren-3-one trifluoroacetic acid

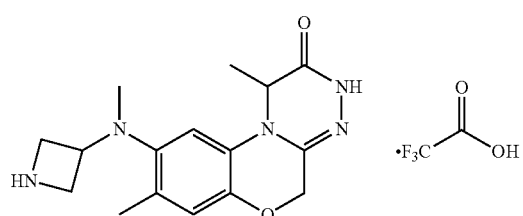

Step A. 3-(4,7-Dimethyl-3-oxo-2,3,4,10-tetrahydro-9-oxa-1,2,4a-triaza-phenanthren-6-ylamino)-azetidine-1-carboxylic acid tert-butyl ester

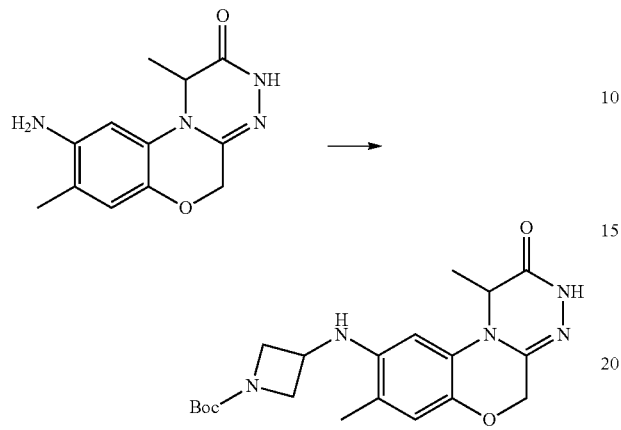

A solution of 6-amino-4,7-dimethyl-2,10-dihydro-9-oxa-1,2,4a-triaza-phenanthren-3-one ((Example #54, Step E, 0.060 g, 0.24 mmol) and 3-oxo-azetidine-1-carboxylic acid tert-butyl ester (0.083 g, 0.41 mmol) in MeOH (4.5 mL) and acetic acid (0.5 mL) was stirred at ambient temperature for 1 h. Sodium cyanoborohydride (0.031 g, 0.41 mmol) was added and the resulting dark solution was stirred at ambient temperature for 14 h. The solvent was removed in vacuo to give the crude product, which was purified by preparative TLC (eluting with 33% EtOAc in petroleum ether) to give 3-(4,7-dimethyl-3-oxo-2,3,4,10-tetrahydro-9-oxa-1,2,4a-triaza-phenanthren-6-ylamino)-azetidine-1-carboxylic acid tert-butyl ester (0.042 g, 44%) as an off-white solid. LC/MS (Table 1, Method 2) $R_t$=1.065 min.; MS m/z: 424 [M+23]$^+$.

Step B. 3-[(4,7-Dimethyl-3-oxo-2,3,4,10-tetrahydro-9-oxa-1,2,4a-triaza-phenanthren-6-yl)-methyl-amino]-azetidine-1-carboxylic acid tert-butyl ester

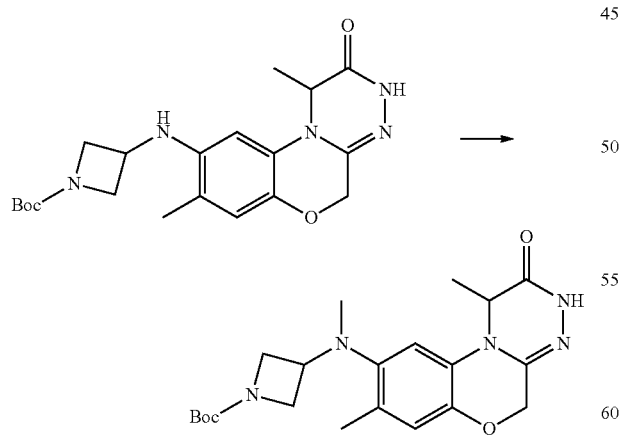

A solution of 3-(4,7-dimethyl-3-oxo-2,3,4,10-tetrahydro-9-oxa-1,2,4a-triaza-phenanthren-6-ylamino)-azetidine-1-carboxylic acid tert-butyl ester (0.16 g, 0.40 mmol) and paraformaldehyde (neat, 0.024 g, 0.80 mmol) in MeOH (10 mL) and HOAc (1 mL) was heated at 70° C. for 14 h. The mixture was cooled to ambient temperature and sodium cyanoborohydride (0.050 g, 0.80 mmol) was added. The resulting dark solution was stirred at 70° C. for 3 h. The solvent was removed in vacuo and the residue was purified by column chromatography on silica gel (eluting with 33-60% EtOAc in petroleum ether) to give 3-[(4,7-dimethyl-3-oxo-2,3,4,10-tetrahydro-9-oxa-1,2,4a-triaza-phenanthren-6-yl)-methyl-amino]-azetidine-1-carboxylic acid tert-butyl ester as yellow solid (0.081 g, 49%). LC/MS (Table 1, Method 2) $R_t$=1.168 min.; MS m/z: 416 [M+H]$^+$.

Step C. 6-(Azetidin-3-yl-methyl-amino)-4,7-dimethyl-2,10-dihydro-9-oxa-1,2,4a-triaza-phenanthren-3-one trifluoroacetic acid

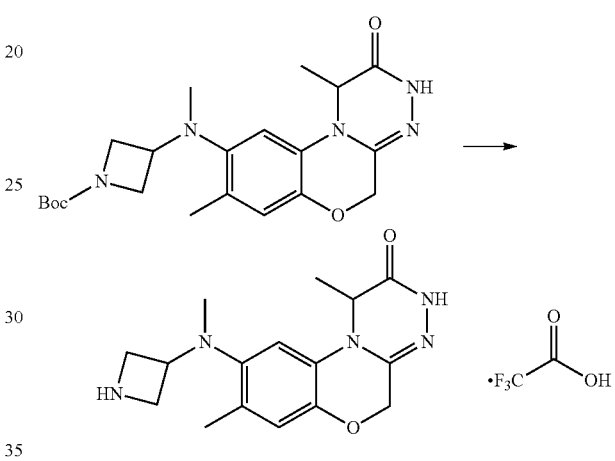

A solution of 3-[(4,7-dimethyl-3-oxo-2,3,4,10-tetrahydro-9-oxa-1,2,4a-triaza-phenanthren-6-yl)-methyl-amino]-azetidine-1-carboxylic acid tert-butyl ester (0.018 g, 0.043 mmol) in TFA (0.5 mL) and DCM (3 mL) was stirred at 25° C. for 2 h. The solvent was removed in vacuo to give 6-(azetidin-3-yl-methyl-amino)-4,7-dimethyl-2,10-dihydro-9-oxa-1,2,4a-triaza-phenanthren-3-one trifluoroacetic acid (0.010 g, 56%). LC/MS (Table 1, Method 5) $R_t$=1.994 min.; MS m/z: 316 [M+H]$^+$.

Example #56

6-(Azetidin-3-ylamino)-7-fluoro-4(S)-methyl-2,10-dihydro-9-oxa-1,2,4a-triaza-phenanthren-3-one trifluoroacetic acid (Example #56-1, Enantiomer 1) and 6-(azetidin-3-ylamino)-7-fluoro-4(R)-methyl-2,10-dihydro-9-oxa-1,2,4a-triaza-phenanthren-3-one trifluoroacetic acid (Example #56-2, Enantiomer 2)

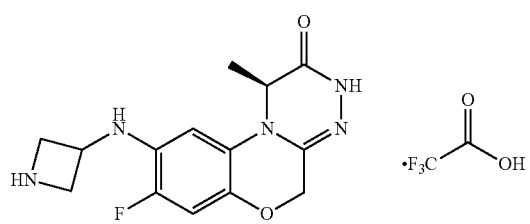

-continued

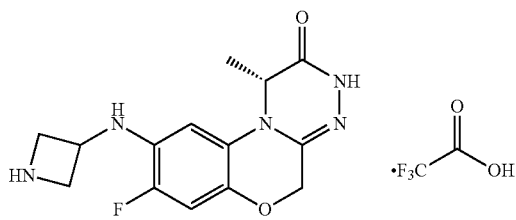

Step A. 7-Fluoro-4H-benzo[1,4]oxazin-3-one

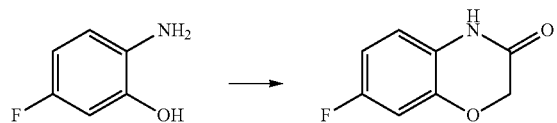 [SMILES: Nc1ccc(F)cc1O ; O=C1COc2cc(F)ccc2N1]

To a suspension of 2-amino-5-fluorophenol (Alfa, 15.00 g, 118 mmol), K$_2$CO$_3$ (48.9 g, 354 mmol) and tetrabutyl-ammonium bromide (3.80 g, 11.80 mmol) in MeCN (200 mL) was added 2-chloroacetyl chloride (14.66 g, 130 mmol) dropwise at 0° C. The reaction mixture was warmed to rt and then heated at reflux overnight. The reaction mixture was cooled to ambient temperature and concentrated in vacuo. The solid was collected, washed with water (100 mL) and dried in vacuo to give 7-fluoro-4H-benzo[1,4]oxazin-3-one as a pale solid (17.2 g, 87%). $^1$H NMR (DMSO-d$_6$, 400 MHz): δ10.71 (s, 1H), 6.84-6.88 (m, 2H), 6.76-6.81 (m, 1H), 4.57 (s, 2H).

Step B. 7-Fluoro-6-nitro-4H-benzo[1,4]oxazin-3-one

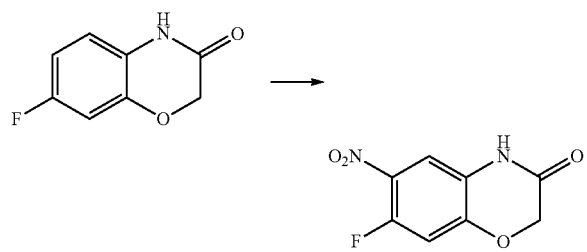

To a solution of 7-fluoro-4H-benzo[1,4]oxazin-3-one (3.00 g, 17.95 mmol) in concentrated H$_2$SO$_4$ (12 mL) at –10° C. was added a mixture of fuming nitric acid (1.131 g, 17.95 mmol, 0.75 mL) and concentrated H$_2$SO$_4$ (0.75 mL) dropwise, keeping the internal temperature below 0° C. After addition, the reaction mixture was stirred at –10° C. for 10 min. The reaction mixture was poured onto crushed ice (200 g) with care. The precipitate was collected by filtration, washed with water (50 mL) and dried in vacuo to give 7-fluoro-6-nitro-4H-benzo[1,4]oxazin-3-one as a light yellow solid (3.5 g, 92%). $^1$H NMR (DMSO-d$_6$, 400 MHz): δ 11.02 (s, 1H), 7.61 (d, J=7.6 Hz, 1H), 7.23 (d, J=12.0 Hz, 1H), 4.77 (s, 2H).

Step C. 2-(7-Fluoro-6-nitro-3-oxo-2,3-dihydro-benzo[1,4]oxazin-4-yl)-propionic acid ethyl ester

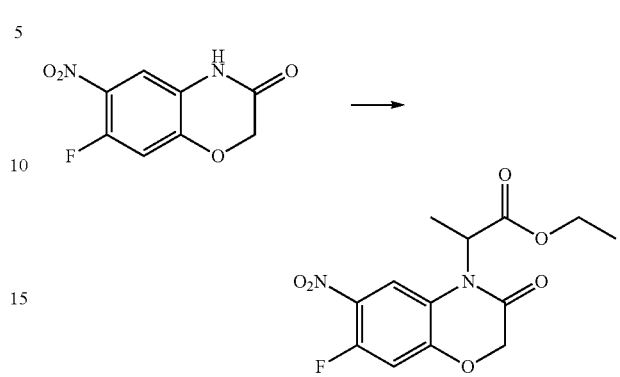

A suspension of 7-fluoro-6-nitro-4H-benzo[1,4]oxazin-3-one (3.50 g, 16.50 mmol) and K$_2$CO$_3$ (3.42 g, 24.75 mmol) in acetone (100 mL) was stirred at rt for 15 min. A solution of ethyl 2-bromopropanoate (5.97 g, 33.0 mmol) in acetone (60 mL) was added dropwise and the reaction mixture was heated at reflux for 5 h. The reaction mixture was cooled to ambient temperature and concentrated in vacuo. The residue was dissolved in DCM (50 mL) and washed with water (50 mL). The organic phase was separated and dried over anhydrous Na$_2$SO$_4$, filtered and the filtrate was concentrated in vacuo. The residue was purified by column chromatography on silica gel (eluting with 0-30% EtOAc in petroleum ether) to give 2-(7-fluoro-6-nitro-3-oxo-2,3-dihydro-benzo[1,4]oxazin-4-yl)-propionic acid ethyl ester as a white solid (3.29 g, 64%). $^1$H NMR (DMSO-d$_6$, 400 MHz): δ 7.89 (d, J=7.2 Hz, 1H), 7.39 (d, J=11.6 Hz, 1H), 5.28 (q, J=7.2 Hz 1H), 4.86 (s, 2H), 4.02-4.16 (m, 2H), 1.48 (d, J=7.2 Hz, 3H), 1.12 (t, J=7.2 Hz, 3H).

Step D. 2-(7-Fluoro-6-nitro-3-thioxo-2,3-dihydro-benzo[1,4]oxazin-4-yl)-propionic acid ethyl ester

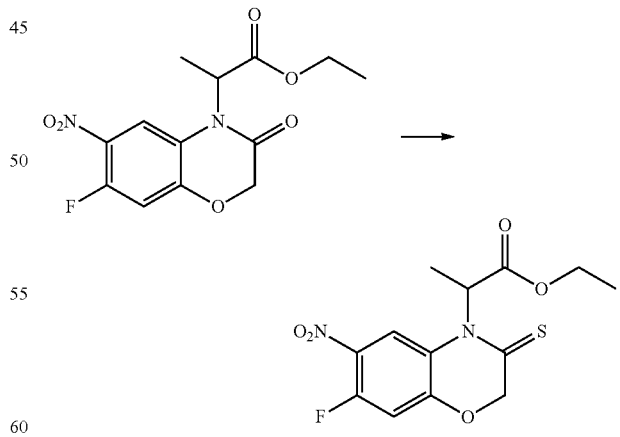

A suspension of 2-(7-fluoro-6-nitro-3-oxo-2,3-dihydro-benzo[1,4]oxazin-4-yl)-propionic acid ethyl ester (1.170 g, 3.75 mmol) and Lawesson's reagent (1.516 g, 3.75 mmol) in toluene (40 mL) was heated at reflux for 3 h then cooled to ambient temperature. The reaction mixture was filtered and the filtrate was concentrated in vacuo. The residue was purified by column on silica gel (eluting with 0%~10% EtOAc in petroleum ether) to give 2-(7-fluoro-6-nitro-3-thioxo-2,3-dihydro-benzo[1,4]oxazin-4-yl)-propionic acid ethyl ester as a light yellow solid (1.05 g, 85%). ¹H NMR (DMSO-$d_6$, 400 MHz): δ 7.86 (d, J=6.8 Hz, 1H), 7.43 (d, J=11.6 Hz, 1H), 6.16 (brs, 1H), 5.07 (s, 2H), 4.02-4.10 (q, J=7.2 Hz, 2H), 1.58 (d, J=6.8 Hz, 3H), 1.04 (t, J=7.2 Hz, 3H).

Step E. 2-(6-Amino-7-fluoro-3-thioxo-2,3-dihydro-benzo[1,4]oxazin-4-yl)-propionic acid ethyl ester

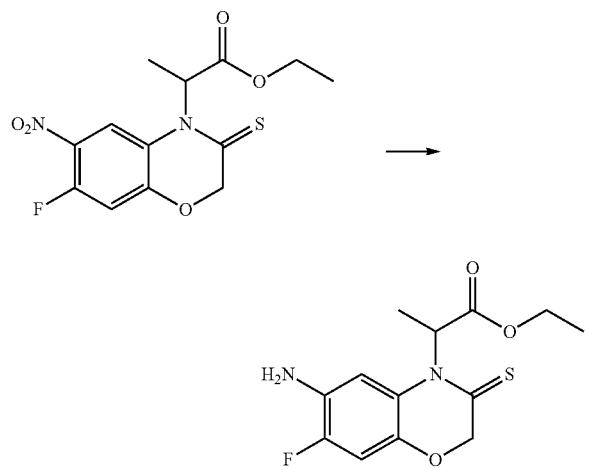

To a solution of 2-(7-fluoro-6-nitro-3-thioxo-2,3-dihydro-benzo[1,4]oxazin-4-yl)-propionic acid ethyl ester (3.05 g, 9.29 mmol) in MeOH (45 ml) and THF (45 mL) was added zinc powder (6.07 g, 92.9 mmol) and ammonium chloride (4.97 g, 92.9 mmol). The reaction mixture was heated to reflux for 3 h then cooled to ambient temperature. The reaction mixture was filtered through a pad of Celite® and the filtrate was concentrated in vacuo. The residue was purified by column on silica gel (eluting with 0-30% EtOAc in petroleum ether to give 2-(6-amino-7-fluoro-3-thioxo-2,3-dihydro-benzo[1,4]oxazin-4-yl)-propionic acid ethyl ester (0.458 g, 16%). ¹H NMR (DMSO-$d_6$, 400 MHz): δ 6.89 (d, J=11.2 Hz, 1H), 6.61 (d, J=8.4 Hz, 1H), 6.21 (brs, 1H), 5.04 (brs, 2H), 4.78 (s, 2H), 3.99-4.03 (m, 2H), 1.62 (d, J=7.2 Hz, 3H), 1.07 (t, J=7.2 Hz, 3H).

Step F. 6-Amino-7-fluoro-4-methyl-2,10-dihydro-9-oxa-1,2,4a-triaza-phenanthren-3-one

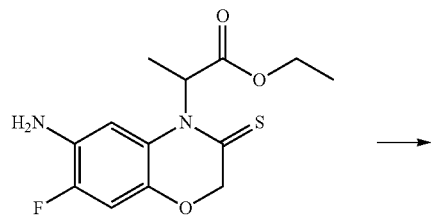

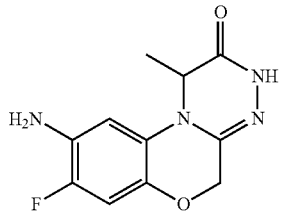

To a solution of 2-(6-amino-7-fluoro-3-thioxo-2,3-dihydro-benzo[1,4]oxazin-4-yl)-propionic acid ethyl ester (0.400 g, 1.34 mmol) in EtOH (15 mL) was added hydrazine hydrate (98%, 0.430 g, 13.4 mmol) and the reaction mixture was stirred at 90° C. for 2 h. The reaction mixture was cooled to ambient temperature then concentrated in vacuo and the residue was purified by column on silica gel (basified by treatment with triethyl amine, eluting with 10-20% MeOH in DCM) to give 6-amino-7-fluoro-4-methyl-2,10-dihydro-9-oxa-1,2,4a-triaza-phenanthren-3-one as a light yellow solid (0.316 g, 94%). ¹H NMR (DMSO-$d_6$, 400 MHz): δ 10.73 (s, 1H), 6.78 (d, J=11.6 Hz, 1H), 6.62 (d, J=8.8 Hz 1H), 4.84 (brs, 2H), 4.44-4.53 (m, 3H), 1.29 (d, J=6.8 Hz, 3H).

Step G. 3-(7-Fluoro-4-methyl-3-oxo-2,3,4,10-tetrahydro-9-oxa-1,2,4a-triaza-phenanthren-6-ylamino)-azetidine-1-carboxylic acid tert-butyl ester

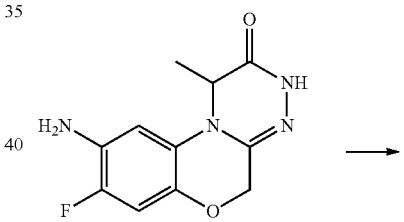

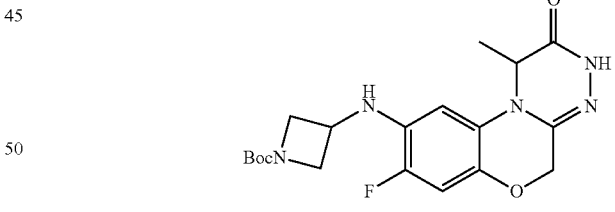

A solution of 6-amino-7-fluoro-4-methyl-2,10-dihydro-9-oxa-1,2,4a-triaza-phenanthren-3-one (0.100 g, 0.400 mmol) and tert-butyl 3-oxoazetidine-1-carboxylate (0.171 g, 0.999 mmol) in MeOH (10 mL) and HOAc (1 mL) was stirred at rt for 1 h. Sodium cyanoborohydride (0.176 g, 2.80 mmol) was added and the reaction mixture was stirred at rt for 3 h. The reaction mixture was concentrated in vacuo and the residue was purified by column on silica gel (eluting with 0-10% MeOH in DCM to give 3-(7-fluoro-4-methyl-3-oxo-2,3,4,10-tetrahydro-9-oxa-1,2,4a-triaza-phenanthren-6-ylamino)-azetidine-1-carboxylic acid tert-butyl ester (0.115 g, 71%) as a crude gum, which was used directly in the next step. LC/MS (Table 1, Method 3) $R_t$=1.374 min.; MS m/z: 428 [M+23]⁺.

Step H. 6-(Azetidin-3-ylamino)-7-fluoro-4-methyl-2,10-dihydro-9-oxa-1,2,4a-triaza-phenanthren-3-one hydrochloric acid

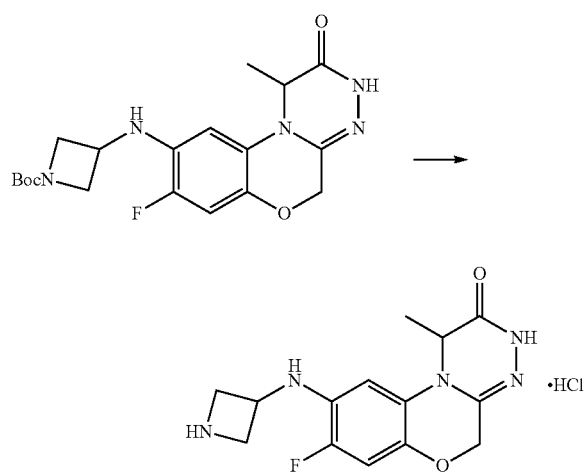

To a suspension of 3-(7-fluoro-4-methyl-3-oxo-2,3,4,10-tetrahydro-9-oxa-1,2,4a-triaza-phenanthren-6-ylamino)-azetidine-1-carboxylic acid tert-butyl ester (0.110 g, 0.271 mmol) in EtOAc (10 mL) was added an EtOAc solution saturated with hydrogen chloride (3 mL). The reaction mixture was stirred at rt for 3 h then concentrated in vacuo and the residue was purified by preparative HPLC (Table 3, Method 1)) to give 6-(azetidin-3-ylamino)-7-fluoro-4-methyl-2,10-dihydro-9-oxa-1,2,4a-triaza-phenanthren-3-one hydrochloric acid as a white solid (0.026 g, 31%). LC/MS (Table 1, Method 5) $R_t$=1.853 min.; MS m/z: 306 [M+H]$^+$.

Step I. 3-(7-Fluoro-4(R)-methyl-3-oxo-2,3,4,10-tetrahydro-9-oxa-1,2,4a-triaza-phenanthren-6-ylamino)-azetidine-1-carboxylic acid tert-butyl ester and 3-(7-fluoro-4(S)-methyl-3-oxo-2,3,4,10-tetrahydro-9-oxa-1,2,4a-triaza-phenanthren-6-ylamino)-azetidine-1-carboxylic acid tert-butyl ester

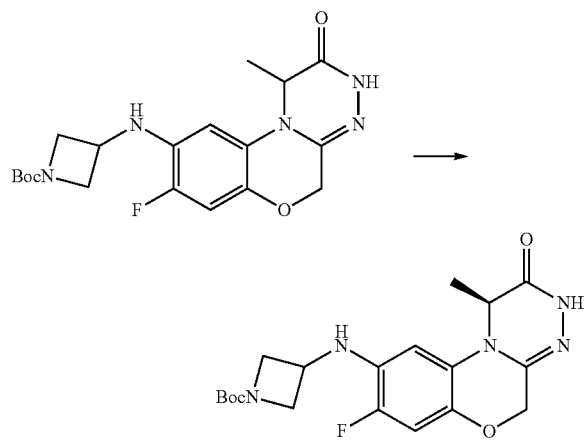

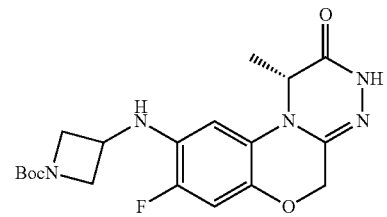

Racemic 3-(7-fluoro-4-methyl-3-oxo-2,3,4,10-tetrahydro-9-oxa-1,2,4a-triaza-phenanthren-6-ylamino)-azetidine-1-carboxylic acid tert-butyl ester (Example #56, Step G, 0.38 g, 0.937 mmol) was separated by chiral SFC (Table 2, Method 4) to give (7-fluoro-4(S)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 10), $R_t$=8.01 min., 0.180 g, 47%) and 3-(7-fluoro-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 10), $R_t$=9.31 min., 0.190 g, 50%).

Step J. 6-(Azetidin-3-ylamino)-7-fluoro-4(S)-methyl-2,10-dihydro-9-oxa-1,2,4a-triaza-phenanthren-3-one trifluoroacetic acid (Example #56-1, Enantiomer 1)

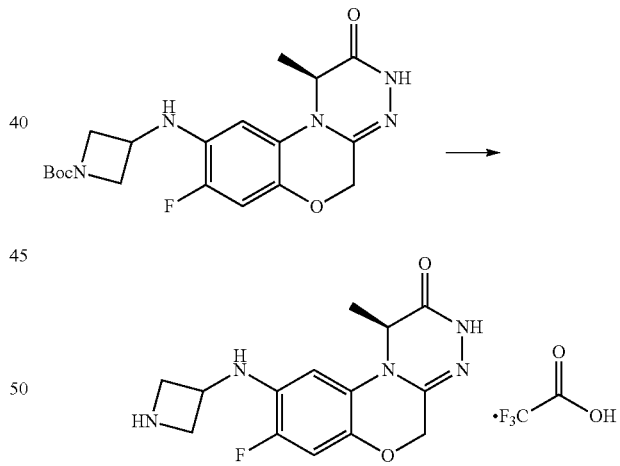

A mixture of (7-fluoro-4(S)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 10), $R_t$=8.01 min., 0.180 g, 0.444 mmol) in DCM (8 mL) and TFA (2 mL) was stirred at ambient temperature for 1 h. The solvent was removed in vacuo to give 6-(azetidin-3-ylamino)-7-fluoro-4(S)-methyl-2,10-dihydro-9-oxa-1,2,4a-triaza-phenanthren-3-one trifluoroacetic acid as a pale yellow solid (Example #56-1, Enantiomer 1, SFC (Table 1, Method 10), $R_t$=10.43 min., 0.190 g, 99%). LC/MS (Table 1, Method 5) $R_t$=1.735 min.; MS m/z: 306 [M+H]$^+$.

129

Step K. 6-(Azetidin-3-ylamino)-7-fluoro-4(R)-methyl-2,10-dihydro-9-oxa-1,2,4a-triaza-phenanthren-3-one trifluoroacetic acid (Example #56-2, Enantiomer 2)

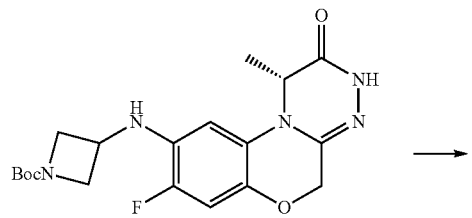

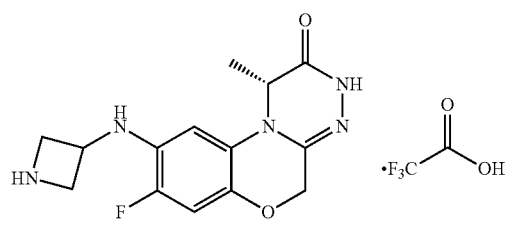

A mixture of (7-fluoro-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 10), $R_t$=9.31 min., 0.190 g, 0.469 mmol) in DCM (8 mL) and TFA (2 mL) was stirred at ambient temperature for 1 h. The solvent was removed in vacuo to give 6-(azetidin-3-ylamino)-7-fluoro-4(R)-methyl-2,10-dihydro-9-oxa-1,2,4a-triaza-phenanthren-3-one trifluoroacetic acid as a pale yellow solid (Example #2, Enantiomer 2, SFC (Table 1, Method 10), $R_t$=9.55 min., 0.185 g, 99%). LC/MS (Table 1, Method 5) $R_t$=1.724 min.; MS m/z: 306 [M+H]$^+$.

Example #57

6-(Azetidin-3-ylamino)-7-isopropyl-4(R)-methyl-2,10-dihydro-9-oxa-1,2,4a-triaza-phenanthren-3-one trifluoroacetic acid (Example #57-1, Enantiomer 1) and 6-(azetidin-3-ylamino)-7-isopropyl-4(S)-methyl-2,10-dihydro-9-oxa-1,2,4a-triaza-phenanthren-3-one trifluoroacetic acid (Example #57-2, Enantiomer 2)

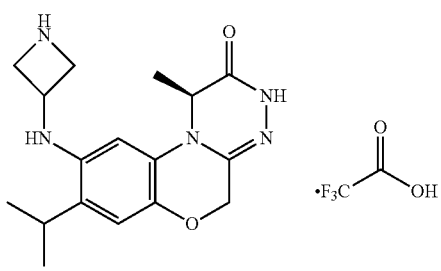

130

-continued

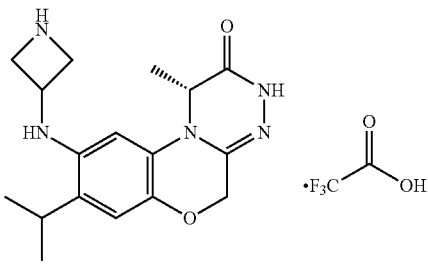

Step A. 3-(7-Isopropenyl-4-methyl-3-oxo-2,3,4,10-tetrahydro-9-oxa-1,2,4a-triaza-phenanthren-6-ylamino)-azetidine-1-carboxylic acid tert-butyl ester

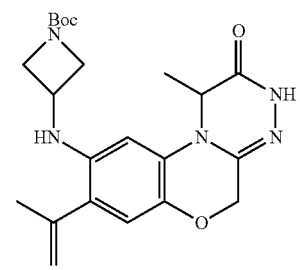

A mixture of 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example 1, Step B, 1.5 g, 3.22 mmol), 4,4,5,5-tetramethyl-2-(prop-1-en-2-yl)-1,3,2-dioxaborolane (1.62 g, 9.66 mmol), K$_2$CO$_3$ (1.33 g, 9.66 mmol) and [1,1'-Bis(diphenylphosphino)ferrocene]palladium(II) chloride (0.544 g, 0.64 mmol) in a mixture of 10% water in dioxane (35 mL) was heated at 80° C. for 2 h. The reaction mixture was cooled to ambient temperature and concentrated in vacuo. The residue was purified by column chromatography on silica gel (eluting with 20% EtOAc in petroleum ether) to give 3-(7-isopropenyl-4-methyl-3-oxo-2,3,4,10-tetrahydro-9-oxa-1,2,4a-triaza-phenanthren-6-ylamino)-azetidine-1-carboxylic acid tert-butyl ester (1.15 g, 84%) as a pale solid. LC/MS (Table 1, Method 2) $R_t$=1.202 min.; MS m/z: 428 [M+H]$^+$.

Step B. 3-(7-Isopropyl-4-methyl-3-oxo-2,3,4,10-tetrahydro-9-oxa-1,2,4a-triaza-phenanthren-6-ylamino)-azetidine-1-carboxylic acid tert-butyl ester

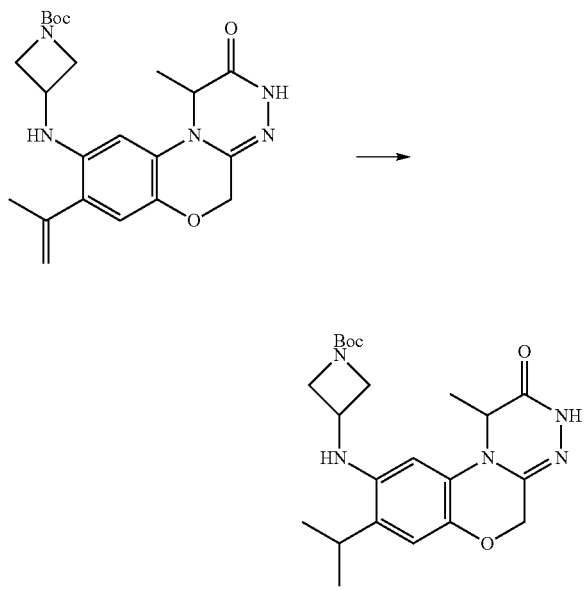

A suspension of 3-(7-isopropenyl-4-methyl-3-oxo-2,3,4,10-tetrahydro-9-oxa-1,2,4a-triaza-phenanthren-6-ylamino)-azetidine-1-carboxylic acid tert-butyl ester (1.15 g, 2.69 mmol) and 10% Pd/C (0.2 g) in MeOH (150 mL) was stirred under $H_2$ at 55 PSI overnight. The reaction mixture was filtered through a pad of Celite® and the filtrate was evaporated in vacuo. The residue was purified by preparative HPLC (Table 3, Method 2) to give 3-(7-isopropyl-4-methyl-3-oxo-2,3,4,10-tetrahydro-9-oxa-1,2,4a-triaza-phenanthren-6-ylamino)-azetidine-1-carboxylic acid tert-butyl ester as a white solid (0.86 g, 74%). LC/MS (Table 1, Method 2) $R_t$=1.186 min.; MS m/z: 452.1 [M+23]$^+$.

Step C. 3-(7-Isopropyl-4 (S)-methyl-3-oxo-2,3,4,10-tetrahydro-9-oxa-1,2,4a-triaza-phenanthren-6-ylamino)-azetidine-1-carboxylic acid tert-butyl ester and 3-(7-isopropyl-4(R)-methyl-3-oxo-2,3,4,10-tetrahydro-9-oxa-1,2,4a-triaza-phenanthren-6-ylamino)-azetidine-1-carboxylic acid tert-butyl ester

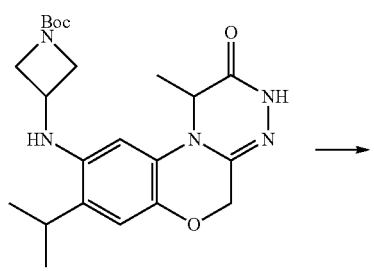

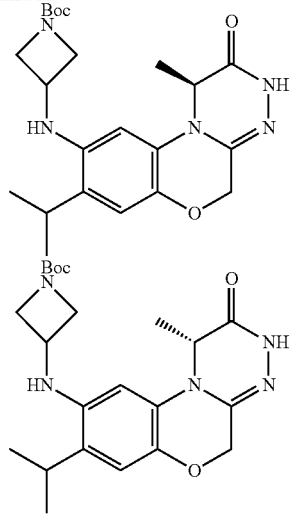

The racemic mixture of 3-(7-isopropyl-4-methyl-3-oxo-2,3,4,10-tetrahydro-9-oxa-1,2,4a-triaza-phenanthren-6-ylamino)-azetidine-1-carboxylic acid tert-butyl ester (0.86 g, 2.00 mmol) was separated by chiral SFC (Table 2, Method 5) to give 3-(7-isopropyl-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 11) $R_t$=2.948 min.; 0.33 g, 38%) and 3-(7-isopropyl-4(S)-methyl-3-oxo-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 11) $R_t$=4.715 min, 0.32 g, 37%).

Step D. 6-(Azetidin-3-ylamino)-7-isopropyl-4(R)-methyl-2,10-dihydro-9-oxa-1,2,4a-triaza-phenanthren-3-one trifluoacetic acid (Example #57-1, Enantiomer 1)

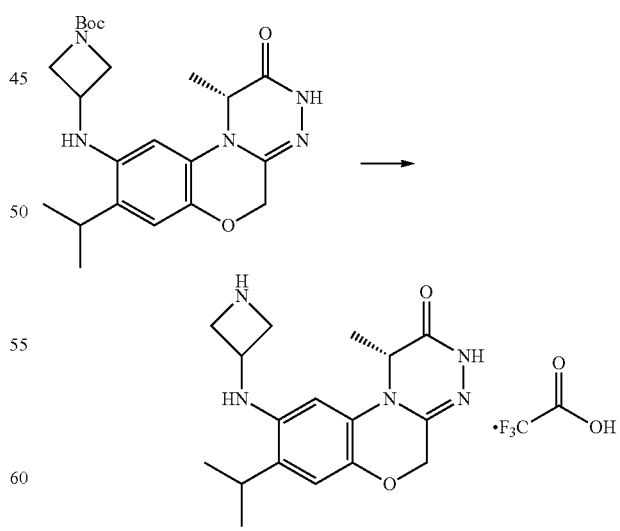

A solution of 3-(7-isopropyl-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 11) $R_t$=2.948 min.; 0.33 g, 0.77 mmol)

in DCM (8 mL) and TFA (2 mL) was stirred at ambient temperature for 2 h. The solvent was removed in vacuo to give 6-(azetidin-3-ylamino)-7-isopropyl-4(R)-methyl-2,10-dihydro-9-oxa-1,2,4a-triaza-phenanthren-3-one trifluoroacetic acid as a pale yellow solid (Example #57-1, Enantiomer 1, SFC (Table 1, Method 11) $R_t$=3.79 min, 0.31 g, 92%). LC/MS (Table 1, Method 5) $R_t$=1.676 min.; MS m/z: 330 [M+H]$^+$.

Step E. 6-(Azetidin-3-ylamino)-7-isopropyl-4(S)-methyl-2,10-dihydro-9-oxa-1,2,4a-triaza-phenanthren-3-one trifluoacetic acid (Example #57-2, Enantiomer 2)

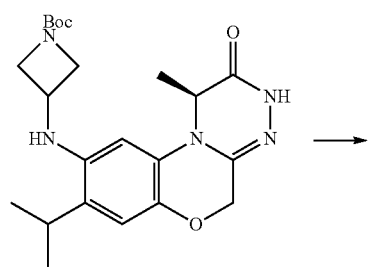

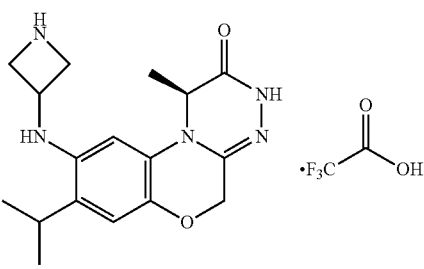

A solution of 3-(7-isopropyl-4(S)-methyl-3-oxo-2,3,4,10-tetrahydro-9-oxa-1,2,4a-triaza-phenanthren-6-ylamino)-azetidine-1-carboxylic acid tert-butyl ester (Enantiomer 2, SFC (Table 1, Method 11) $R_t$=4.715 min, 0.32 g, 0.75 mmol) in DCM (8 mL) and TFA (2 mL) was stirred at ambient temperature for 2 h. The solvent was removed in vacuo to give 6-(azetidin-3-ylamino)-7-isopropyl-4(S)-methyl-2,10-dihydro-9-oxa-1,2,4a-triaza-phenanthren-3-one trifluoacetic acid as a pale yellow solid (Example #57-2, Enantiomer 2, SFC (Table 1, Method 11) $R_t$=4.92 min, 0.31 g, 92%). LC/MS (Table 1, Method 5) $R_t$=1.688 min.; MS m/z: 330 [M+H]$^+$.

TABLE 6

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #57, Steps A, B and D.

| Structure | Example # | Boronic acid | $R_t$ min (method) | m/z ESI+ (M + H)$^+$ |
|---|---|---|---|---|
| 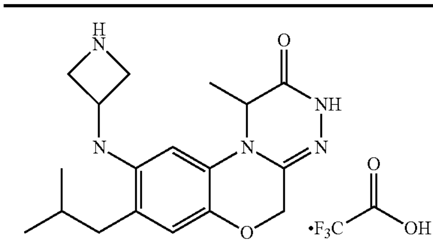 | 58 | | 2.285 (Table 1, Method 5) | 344 |
| 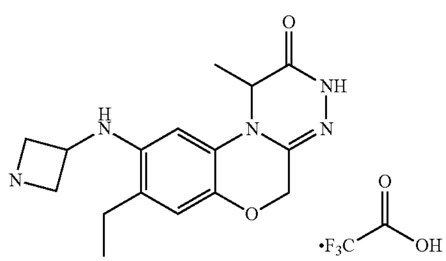 | 59 | | 1.878 (Table 1, Method 5) | 316 |
| 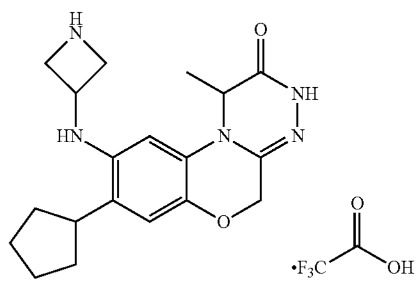 | 60 | | 1.666 (Table 1, Method 4) | 356 |

TABLE 7

The following analogs were prepared from 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B) using the procedure detailed in Example #57 Steps A-E.

| Structure | Example # | Boronic acid/ boronate | $R_t$ min (method) | m/z ESI+ (M + H)+ |
|---|---|---|---|---|
| 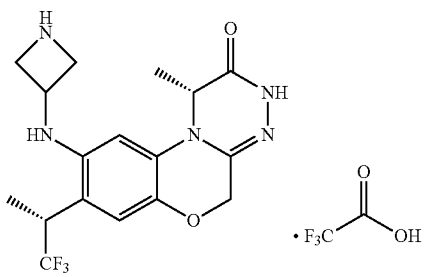 | 61 |  | 1.553 (Table 1, Method 4) | 384 |
| 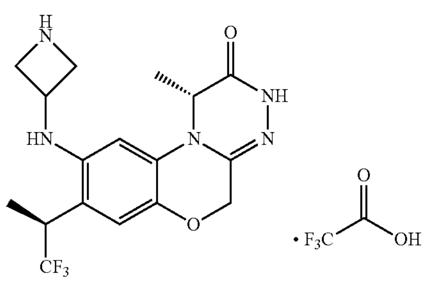 | 62 |  | 1.572 (Table 1, Method 4) | 384 |

TABLE 8

The following analogs were prepared from 6-(1-benzhydryl-3-methyl-azetidin-3-ylamino)-7-bromo-4-methyl-2,10-dihydro-9-oxa-1,2,4a-triaza-phenanthren-3-one (Example #79, Step B) using the procedure detailed in Example #57, Steps A-B and Example #79, Step D.

| Structure | Example # | Boronic acid/ boronate | $R_t$ min (method) | m/z ESI+ (M + H)+ |
|---|---|---|---|---|
| 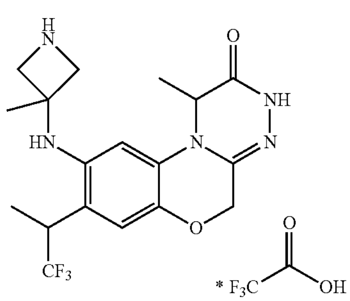 | 63 |  | 1.559 (Table 1, Method 4) | 398 |

Example #64

6-(Azetidin-3-ylamino)-7-cyclopropyl-4(R)-methyl-2,10-dihydro-9-oxa-1,2,4a-triaza-phenanthren-3-one trifluoroacetic acid (Example #64-1, Enantiomer 1) and 6-(azetidin-3-ylamino)-7-cyclopropyl-4(S)-methyl-2,10-dihydro-9-oxa-1,2,4a-triaza-phenanthren-3-one trifluoroacetic acid (Example #64-2, Enantiomer 2)

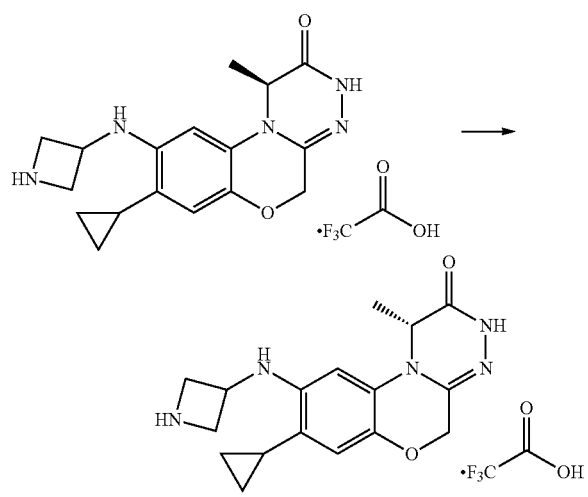

Step A. 6-Amino-7-bromo-4-methyl-2,10-dihydro-9-oxa-1,2,4a-triaza-phenanthren-3-one

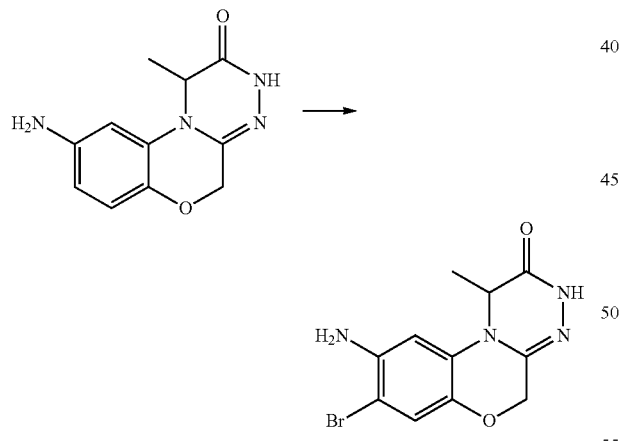

To a 30° C. solution of 6-amino-4-methyl-2,10-dihydro-9-oxa-1,2,4a-triaza-phenanthren-3-one (Preparation #2, Step E, 3.0 g, 12.92 mmol) in MeOH (15 mL) and DCM (7.5 mL) was added tetrabutylammonium tribromide (3.31 g, 12.92 mmol) in portions and the resulting black solution was stirred for 1 h. The solvent was removed in vacuo and the residue was purified by column chromatography on silica gel (eluting with 1-50% EtOAc in petroleum ether) to give 6-amino-7-bromo-4-methyl-2,10-dihydro-9-oxa-1,2,4a-triaza-phenanthren-3-one (1.2 g, 3.86 mmol, 30%). LC/MS (Table 1, Method 4) $R_t$=1.337 min.; MS m/z: 311/313 [M+H]$^+$.

Step B. 6-Amino-7-cyclopropyl-4-methyl-2,10-dihydro-9-oxa-1,2,4a-triaza-phenanthren-3-one

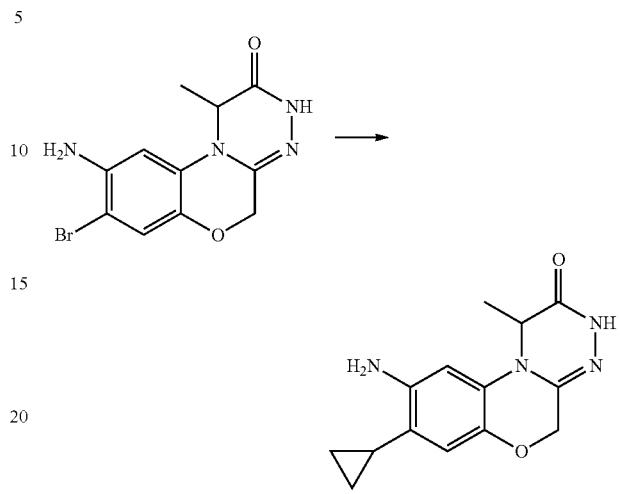

A mixture of 6-amino-7-bromo-4-methyl-2,10-dihydro-9-oxa-1,2,4a-triaza-phenanthren-3-one (0.500 g, 1.607 mmol), cyclopropylboronic acid (1.38 g, 16.07 mmol), $K_2CO_3$ (0.888 g, 6.43 mmol), and [1,1'-bis(diphenylphosphino)ferrocene]dichloropalladium(II) (0.262 g, 0.321 mmol) in water (10 mL) and dioxane (60 mL) was heated at 130° C. for 2 h. The reaction mixture was cooled to ambient temperature and the solution was concentrated in vacuo. The residue was purified by column chromatography on silica gel (eluting with 30-100% EtOAc in petroleum ether) to give 6-amino-7-cyclopropyl-4-methyl-2,10-dihydro-9-oxa-1,2,4a-triaza-phenanthren-3-one (0.235 g, 0.863 mmol, 54%). $^1$H NMR (DMSO-$d_6$, 400 MHz): δ 10.71 (s 1H), 6.50 (s, 1H), 6.45 (s, 1H), 4.75 (brs, 2H), 4.45 (m, 3H), 1.60 (m, 1H), 1.31 (d, J=6.8 Hz, 3H), 0.83 (m, 2H), 0.46 (m, 2H).

Step C. 3-(7-Cyclopropyl-4(S)-methyl-3-oxo-2,3,4,10-tetrahydro-9-oxa-1,2,4a-triaza-phenanthren-6-ylamino)-azetidine-1-carboxylic acid tert-butyl ester

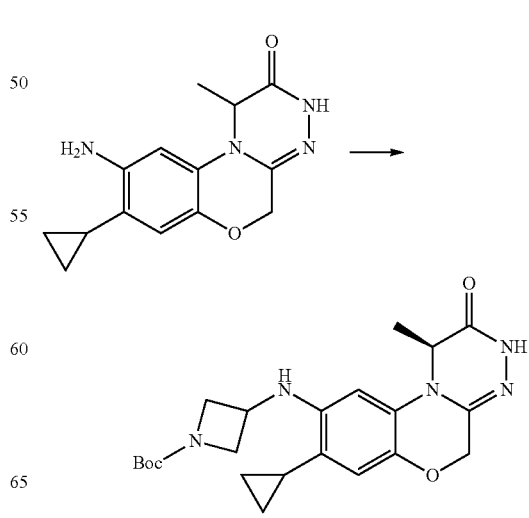

-continued

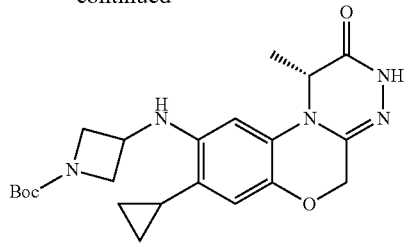

A solution of 6-amino-7-cyclopropyl-4-methyl-2,10-dihydro-9-oxa-1,2,4a-triaza-phenanthren-3-one (0.860 g, 3.16 mmol) and tert-butyl 3-oxoazetidine-1-carboxylate (2.703 g, 15.79 mmol) in EtOH (25 mL) and HOAc (2.5 mL) was heated to reflux overnight. The reaction mixture was cooled to ambient temperature and sodium cyanoborohydride (0.073 g, 1.159 mmol) was added. The reaction mixture was stirred overnight and concentrated in vacuo. The residue was purified by preparative HPLC (Table 3, Method 3) to give 3-(7-cyclopropyl-4-methyl-3-oxo-2,3,4,10-tetrahydro-9-oxa-1,2,4a-triaza-phenanthren-6-ylamino)-azetidine-1-carboxylic acid tert-butyl ester (0.560 g, 41%). The racemic product was separated by chiral SFC (Table 2, Method 6) to give 3-(7-cyclopropyl-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 12) $R_t$=6.01 min., 0.300 g, 22%) and 3-[7-(2,4-dichloro-phenyl)-4(S)-methyl-3-oxo-2,3,4,10-tetrahydro-9-oxa-1,2,4a-triaza-phenanthren-6-ylamino]-azetidine-1-carboxylic acid tert-butyl ester (Enantiomer 2, SFC (Table 1, Method 12) $R_t$=8.89 min., 0.280 g, 20%).

Step D. 6-(Azetidin-3-ylamino)-7-cyclopropyl-4(R)-methyl-2,10-dihydro-9-oxa-1,2,4a-triaza-phenanthren-3-one trifluoroacetic acid (Example #64-1, Enantiomer 1)

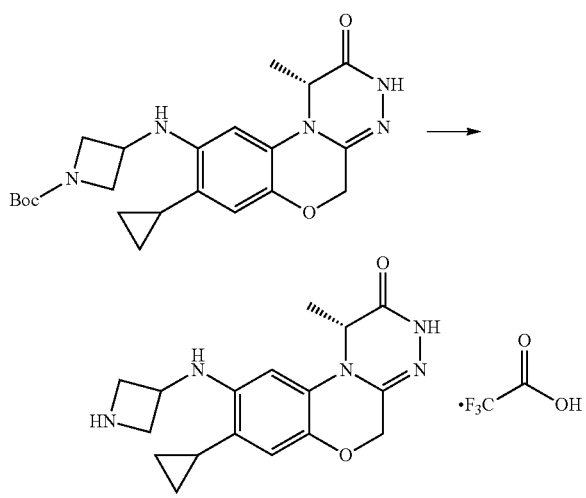

To a solution of 3-(7-cyclopropyl-4(R)-methyl-3-oxo-2,3,4,10-tetrahydro-9-oxa-1,2,4a-triaza-phenanthren-6-ylamino)-azetidine-1-carboxylic acid tert-butyl ester (Enantiomer 1, SFC (Table 1, Method 12) $R_t$=6.01 min., 0.300 g, 0.702 mmol) in DCM (9 mL) was added TFA (1.5 mL) and the reaction mixture was stirred for 2 h at ambient temperature. The solution was concentrated in vacuo to give 6-(azetidin-3-ylamino)-7-cyclopropyl-4(R)-methyl-2,10-dihydro-9-oxa-1,2,4a-triaza-phenanthren-3-one trifluoroacetic acid (Example #64-1, Enantiomer 1, SFC (Table 1, Method 1) $R_t$=4.205 min., 0.291 g, 0.661 mmol, 94%). LC/MS (Table 1, Method 4) $R_t$=1.333 min.; MS m/z: 328 [M+H]$^+$.

Step E. 6-(Azetidin-3-ylamino)-7-cyclopropyl-4(S)-methyl-2,10-dihydro-9-oxa-1,2,4a-triaza-phenanthren-3-one trifluoroacetic acid (Example #64-2, Enantiomer 2)

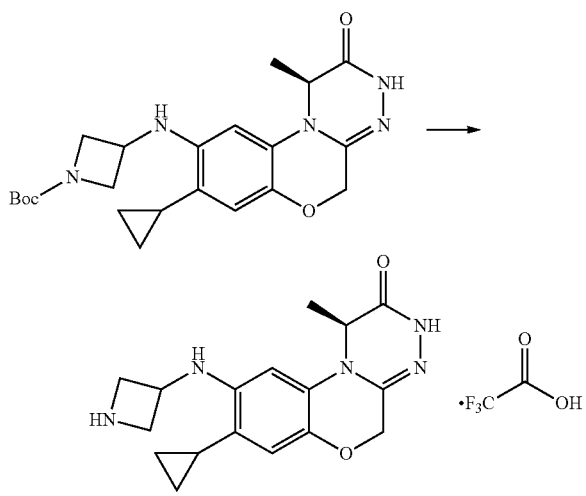

To a solution of 3-[7-(2,4-dichloro-phenyl)-4(S)-methyl-3-oxo-2,3,4,10-tetrahydro-9-oxa-1,2,4a-triaza-phenanthren-6-ylamino]-azetidine-1-carboxylic acid tert-butyl ester (Enantiomer 2, SFC (Table 1, Method 12) $R_t$=8.89 min., 0.280 g, 0.655 mmol) in DCM (9 mL) was added TFA (1.5 mL) and the reaction mixture was stirred for 2 h at ambient temperature. The solution was concentrated in vacuo to give 6-(azetidin-3-ylamino)-7-cyclopropyl-4(S)-methyl-2,10-dihydro-9-oxa-1,2,4a-triaza-phenanthren-3-one trifluoroacetic acid (Example #64-2, Enantiomer 2, SFC (Table 1, Method 1) $R_t$=5.859 min., 0.275 g, 0.624 mmol, 95%). LC/MS (Table 1, Method 4) $R_t$=1.331 min.; MS m/z: 328 [M+H]$^+$.

Example #65

6-(Azetidin-3-yloxy)-7-cyclopropyl-4-methyl-2,10-dihydro-9-oxa-1,2,4a-triaza-phenanthren-3-one trifluoroacetic acid

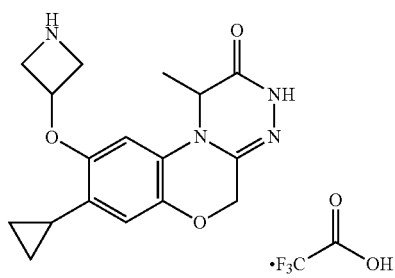

Step A. 2-(6-Acetyl-3-oxo-2,3-dihydro-benzo[1,4]oxazin-4-yl)-propionic acid ethyl ester

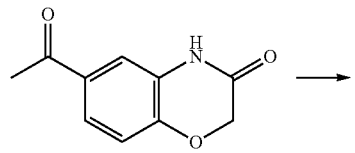

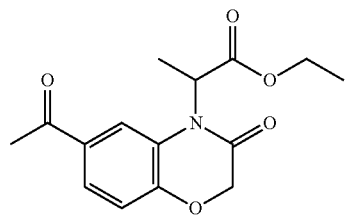

To a mixture of 6-acetyl-4H-benzo[1,4]oxazin-3-one (Alfa, 5 g, 26.18 mmol) and $K_2CO_3$ (5.4 g, 39.2 mmol) in acetone (50 mL) was added 2-bromo-propionic acid ethyl ester (14.14 g, 78.54 mmol) and the mixture was heated to reflux for 3 h. The reaction mixture was cooled to ambient temperature and evaporated in vacuo. The residue was purified by column chromatography on silica gel (eluting with 5% EtOAc in petroleum ether) to give 2-(6-acetyl-3-oxo-2,3-dihydro-benzo[1,4]oxazin-4-yl)-propionic acid ethyl ester as a white solid (6.14 g, 86%). $^1$H NMR (CDCl$_3$, 400 MHz): δ 7.62 (dd, J=2 Hz, J=8.4 Hz, 1H), 7.52 (d, J=2 Hz, 1H), 7.07 (d, J=8.4 Hz, 1H), 5.29 (t, J=6.8 Hz, 1H), 4.68 (d, J=15.6 Hz, 2H), 4.22 (q, J=7.2 Hz, 2H), 2.56 (s, 3H), 1.65 (d, J=6.8 Hz, 3H), 1.22 (t, J=7.2 Hz, 3H).

Step B. 2-(6-Acetoxy-3-oxo-2,3-dihydro-benzo[1,4]oxazin-4-yl)-propionic acid ethyl ester

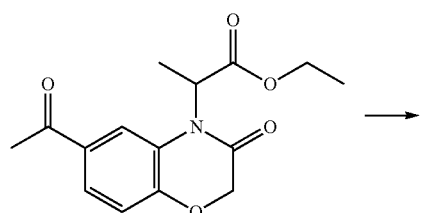

To a suspension of urea-hydrogen peroxide (5.93 g, 63 mmol) and NaHCO$_3$ (5.93 g, 63 mmol) in DCM (60 mL) at 0° C. was added 2-(6-acetyl-3-oxo-2,3-dihydro-benzo[1,4]oxazin-4-yl)-propionic acid ethyl ester (6.14 g, 21 mmol). The reaction mixture was stirred for 10 min and TFAA (5.84 mL, 42 mmol) was added dropwise. The reaction mixture was stirred at 0° C. for 1 h and then 3 days at ambient temperature. The reaction mixture was diluted with DCM (60 mL), quenched with saturated Na$_2$S$_2$O$_3$ solution (30 mL) and washed with water (30 mL). The combined organic phase was dried over anhydrous Na$_2$SO$_4$, filtered and concentrated in vacuo to give 2-(6-acetoxy-3-oxo-2,3-dihydro-benzo[1,4]oxazin-4-yl)-propionic acid ethyl ester, which was used in the next step directly without purification. TLC (eluting with 25% EtOAc/heptane) R$_f$=0.4.

Step C. 2-(6-Hydroxy-3-oxo-2,3-dihydro-benzo[1,4]oxazin-4-yl)-propionic acid ethyl ester

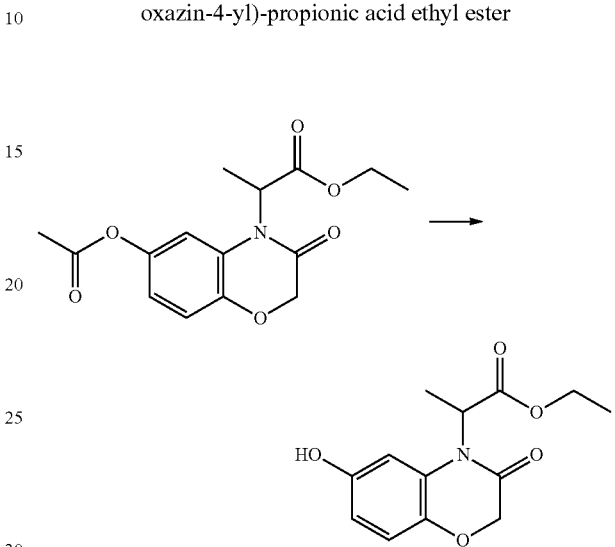

To a solution of the crude 2-(6-acetoxy-3-oxo-2,3-dihydro-benzo[1,4]oxazin-4-yl)-propionic acid ethyl ester in THF (80 mL) was added morpholine (5.5 mL, 63 mmol) and the mixture was heated to reflux overnight. The reaction mixture was cooled to ambient temperature and diluted with EtOAc (100 mL). The mixture was washed with brine (30 mL) and the combined organic phase was dried over anhydrous Na$_2$SO$_4$, filtered and concentrated in vacuo. The residue was purified by column chromatograph on silica gel (eluting with 10% EtOAc in petroleum ether) to give 2-(6-hydroxy-3-oxo-2,3-dihydro-benzo[1,4]oxazin-4-yl)-propionic acid ethyl ester as a white solid (3.2 g, 57% over two steps). $^1$H NMR (CDCl$_3$, 400 MHz): δ 6.88 (d, J=8.8 Hz, 1H), 6.47 (dd, J=2.8 Hz, J=8.8 Hz, 1H), 6.39 (d, J=2.8 Hz, 1H), 5.24 (q, J=6.8 Hz, 1H), 4.54 (d, J=14.8 Hz, 2H), 4.20 (q, J=7.2 Hz, 2H), 1.62 (d, J=6.8 Hz, 3H), 1.21 (t, J=7.2 Hz, 3H). The phenol OH was not observed in CDCl$_3$.

Step D. 3-[4-(1-Ethoxycarbonyl-ethyl)-3-oxo-3,4-dihydro-2H-benzo[1,4]oxazin-6-yloxy]-azetidine-1-carboxylic acid tert-butyl ester

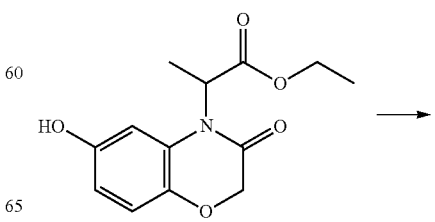

-continued

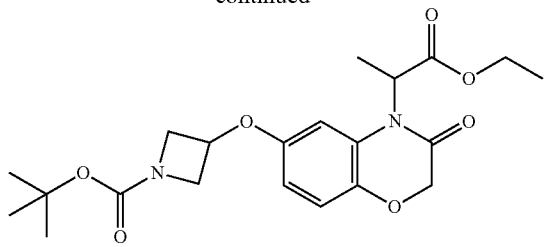

A mixture of ethyl 2-(6-hydroxy-3-oxo-2,3-dihydro-benzo[1,4]oxazin-4-yl)-propionic acid ethyl ester (1.08 g, 4.07 mmol), 3-methanesulfonyloxy-azetidine-1-carboxylic acid tert-butyl ester (1.12 g, 4.48 mmol) and $Cs_2CO_3$ (2.65 g, 8.12 mmol) in DMF (20 mL) was stirred at 90° C. for 3 h. The reaction mixture was cooled to ambient temperature and poured into water (150 mL). The aqueous mixture was extracted with EtOAc (3×20 mL) and the combined organic phase was washed with brine (50 mL), dried over anhydrous $Na_2SO_4$, filtered and evaporated in vacuo. The residue was purified by column chromatography on silica gel (eluting with 10% EtOAc in petroleum ether) to give 3-[4-(1-ethoxycarbonyl-ethyl)-3-oxo-3,4-dihydro-2H-benzo[1,4]oxazin-6-yloxy]-azetidine-1-carboxylic acid tert-butyl ester as a white solid (0.7 g, 41%). $^1$H NMR ($CDCl_3$, 400 MHz): δ 6.94 (d, J=8.4 Hz, 1H), 6.30 (m, 2H), 5.30 (q, J=7.2 Hz, 1H), 4.78 (m, 1H), 4.59 (d, J=15.2 Hz, 2H), 4.27 (m, 4H), 3.95 (m, 2H), 1.62 (d, J=7.2 Hz, 3H), 1.45 (s, 9H), 1.21 (t, J=7.2 Hz, 3H).

Step E. 3-[4-(1-Ethoxycarbonyl-ethyl)-3-thioxo-3,4-dihydro-2H-benzo[1,4]oxazin-6-yloxy]-azetidine-1-carboxylic acid tert-butyl ester

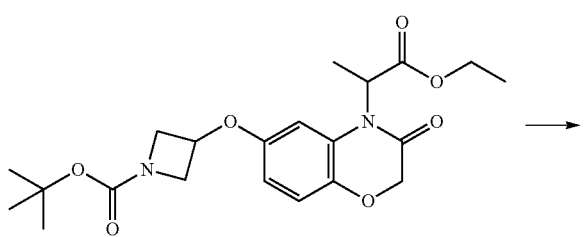

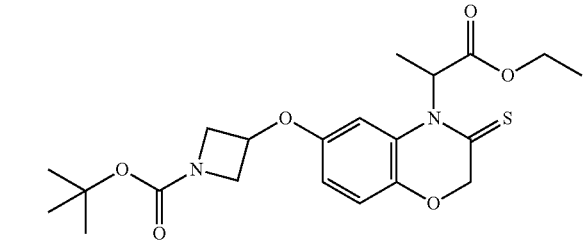

To a solution of 3-[4-(1-ethoxycarbonyl-ethyl)-3-oxo-3,4-dihydro-2H-benzo[1,4]oxazin-6-yloxy]-azetidine-1-carboxylic acid tert-butyl ester (0.700 g, 1.66 mmol) in toluene (15 mL) and DME (15 mL) was added Lawesson's reagent (1.058 g, 2.66 mmol) and the mixture was heated to reflux for 4 h. The mixture was cooled to ambient temperature and concentrated in vacuo. The residue was purified by column chromatography on silica gel (eluting with 15% EtOAc in petroleum ether) to give 3-[4-(1-ethoxycarbonyl-ethyl)-3-thioxo-3,4-dihydro-2H-benzo[1,4]oxazin-6-yloxy]-azetidine-1-carboxylic acid tert-butyl ester (0.540 g, 74%) as a white solid. $^1$H NMR ($CDCl_3$, 400 MHz): δ 6.94 (d, J=8.8 Hz, 1H), 6.67 (br, 1H), 6.39 (m, 1H), 6.36 (m, 1H), 4.88 (d, J=15.2 Hz, 2H), 4.74 (m, 1H), 4.27 (m, 2H), 4.19 (m, 2H), 3.97 (m, 2H), 1.68 (d, J=7.2 Hz, 3H), 1.45 (s, 9H), 1.14 (t, J=7.2 Hz, 3H).

Step F. 3-(4-Methyl-3-oxo-2,3,4,10-tetrahydro-9-oxa-1,2,4a-triaza-phenanthren-6-yloxy)-azetidine-1-carboxylic acid tert-butyl ester

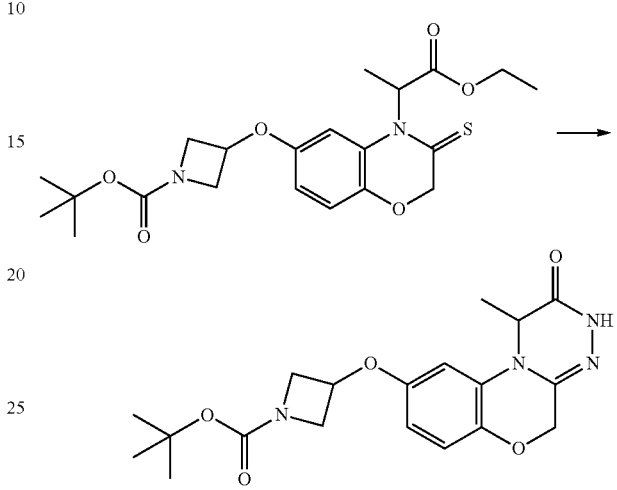

To a solution of 3-[4-(1-ethoxycarbonyl-ethyl)-3-thioxo-3,4-dihydro-2H-benzo[1,4]oxazin-6-yloxy]-azetidine-1-carboxylic acid tert-butyl ester (0.530 g, 1.22 mmol) in EtOH (10 mL) was added hydrazine hydrate (0.486 g, 9.72 mmol) and the mixture was heated at reflux for 2 h. The reaction mixture was cooled to ambient temperature, concentrated in vacuo and the residue was purified by column chromatography on silica gel (eluting with 20% EtOAc in petroleum ether) to give 3-(4-methyl-3-oxo-2,3,4,10-tetrahydro-9-oxa-1,2,4a-triaza-phenanthren-6-yloxy)-azetidine-1-carboxylic acid tert-butyl ester (0.234 g, 52%) as a white solid. LC/MS (Table 1, Method 3) $R_t$=1.332 min.; MS m/z: 389 [M+H]$^+$.

Step G. 3-(7-Bromo-4-methyl-3-oxo-2,3,4,10-tetrahydro-9-oxa-1,2,4a-triaza-phenanthren-6-yloxy)-azetidine-1-carboxylic acid tert-butyl ester

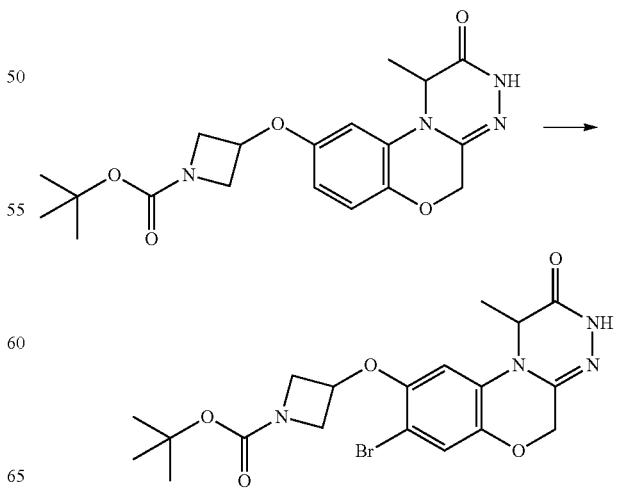

To a solution of 3-(4-methyl-3-oxo-2,3,4,10-tetrahydro-9-oxa-1,2,4a-triaza-phenanthren-6-yloxy)-azetidine-1-carboxylic acid tert-butyl ester (0.234 g, 0.603 mmol) in DCM (4 mL) and MeOH (2 mL) was added tetrabutylammonium tribromide (0.291 g, 0.603 mmol) and the mixture was stirred at ambient temperature for 2 h. The solvent was removed in vacuo and the residue was purified by column chromatography on silica gel (eluting with 30% EtOAc in petroleum ether) to give 3-(7-bromo-4-methyl-3-oxo-2,3,4,10-tetrahydro-9-oxa-1,2,4a-triaza-phenanthren-6-yloxy)-azetidine-1-carboxylic acid tert-butyl ester (0.267 g, 95%). LC/MS (Table 1, Method 2) $R_f$=1.217 min.; MS m/z: 467/469 [M+H]$^+$.

Step H. 3-(7-Cyclopropyl-4-methyl-3-oxo-2,3,4,10-tetrahydro-9-oxa-1,2,4a-triaza-phenanthren-6-yloxy)-azetidine-1-carboxylic acid tert-butyl ester

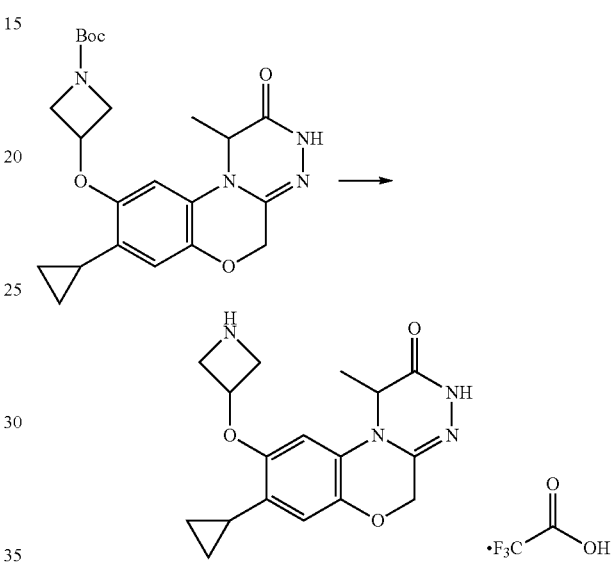

A mixture of 3-(7-bromo-4-methyl-3-oxo-2,3,4,10-tetrahydro-9-oxa-1,2,4a-triaza-phenanthren-6-yloxy)-azetidine-1-carboxylic acid tert-butyl ester (0.080 g, 0.17 mmol), cyclopropyl boronic acid (0.044 g, 0.52 mmol), K$_2$CO$_3$ (0.047 g, 0.34 mmol) and Pd(dppf)Cl$_2$·CH$_2$Cl$_2$ (0.014 g, 0.017 mmol) in dioxane (3 mL) and H$_2$O (0.5 mL) was stirred at 100° C. for 15 h. The mixture was cooled to ambient temperature and the solvent was removed in vacuo. The residue was purified by preparative HPLC (Table 3, Method 4) to give 3-(7-cyclopropyl-4-methyl-3-oxo-2,3,4,10-tetrahydro-9-oxa-1,2,4a-triaza-phenanthren-6-yloxy)-azetidine-1-carboxylic acid tert-butyl ester as a pale yellow solid (0.029 g, 33%). LC/MS (Table 1, Method 2) $R_f$=1.228 min.; MS m/z: 429 [M+H]$^+$.

Step I. 6-(Azetidin-3-yloxy)-7-cyclopropyl-4-methyl-2,10-dihydro-9-oxa-1,2,4a-triaza-phenanthren-3-one trifluoroacetic acid

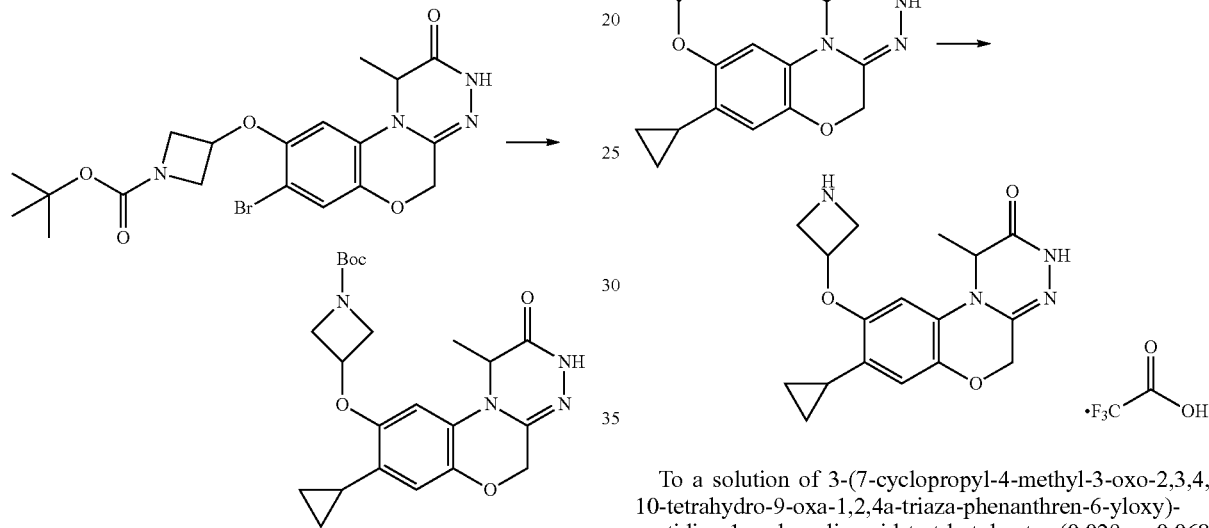

To a solution of 3-(7-cyclopropyl-4-methyl-3-oxo-2,3,4,10-tetrahydro-9-oxa-1,2,4a-triaza-phenanthren-6-yloxy)-azetidine-1-carboxylic acid tert-butyl ester (0.029 g, 0.068 mmol) in DCM (2 mL) was added TFA (0.35 mL) dropwise and the mixture was stirred at ambient temperature for 2 h. The solvent was removed in vacuo to give 6-(azetidin-3-yloxy)-7-cyclopropyl-4-methyl-2,10-dihydro-9-oxa-1,2,4a-triaza-phenanthren-3-one trifluoroacetic acid as a white solid (0.020 g, 90%). LC/MS (Table 1, Method 5) $R_f$=2.056 min.; MS m/z: 329 [M+H]$^+$.

TABLE 9

The following analogs were prepared from 3-(7-bromo-4-methyl-3-oxo-2,3,4,10-tetrahydro-9-oxa-1,2,4a-triaza-phenanthren-6-yloxy)-azetidine-1-carboxylic acid tert-butyl ester (Example #65, Step G) using the procedure detailed in Example #65, Steps H-I.

| Structure | Example # | Boronic acid | $R_t$ min (method) | m/z ESI+ (M + H)$^+$ |
|---|---|---|---|---|
| 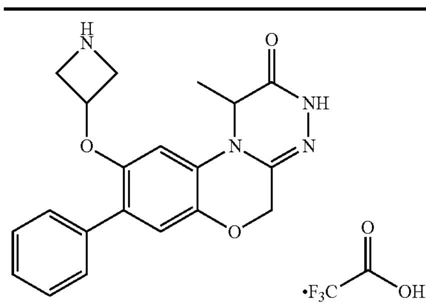 | 66 | Ph-B(OH)$_2$ | 2.280 (Table 1, Method 5) | 365 |

TABLE 9-continued

The following analogs were prepared from 3-(7-bromo-4-methyl-3-oxo-2,3,4,10-tetrahydro-9-oxa-1,2,4a-triaza-phenanthren-6-yloxy)-azetidine-1-carboxylic acid tert-butyl ester (Example #65, Step G) using the procedure detailed in Example #65, Steps H-I.

| Structure | Example # | Boronic acid | $R_t$ min (method) | m/z ESI+ $(M + H)^+$ |
|---|---|---|---|---|
| 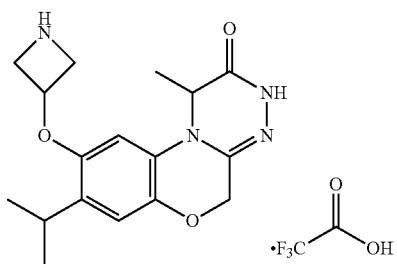 | 67 | ⟍B(OH)₂ | 1.706 (Table 1, Method 5) | 303 |

Example #68

6-(Azetidin-3-yloxy)-7-isopropyl-4-methyl-2,10-dihydro-9-oxa-1,2,4a-triaza-phenanthren-3-one trifluoroacetic acid

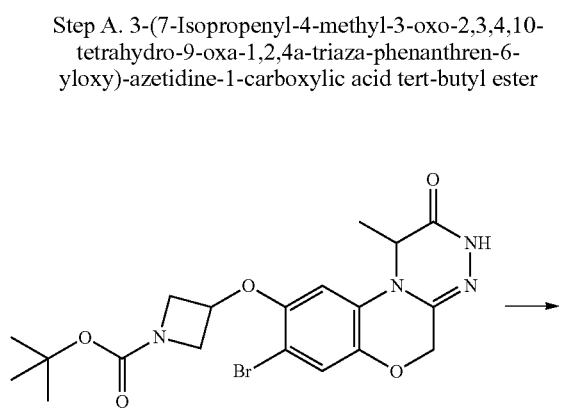

Step A. 3-(7-Isopropenyl-4-methyl-3-oxo-2,3,4,10-tetrahydro-9-oxa-1,2,4a-triaza-phenanthren-6-yloxy)-azetidine-1-carboxylic acid tert-butyl ester

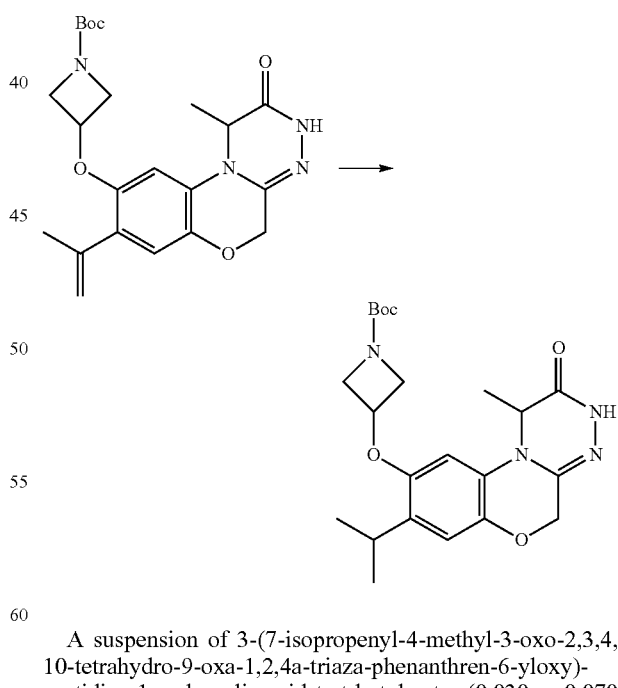

A mixture of 3-(7-bromo-4-methyl-3-oxo-2,3,4,10-tetrahydro-9-oxa-1,2,4a-triaza-phenanthren-6-yloxy)-azetidine-1-carboxylic acid tert-butyl ester (Example #65, Step G, 0.030 g, 0.064 mmol), isopropenyl boronic acid (0.032 g, 0.193 mmol), K₂CO₃ (0.018 g, 0.13 mmol) and Pd(dppf)Cl₂·CH₂Cl₂ (0.011 g, 0.013 mmol) in dioxane (3 mL) and H₂O (0.5 mL) was stirred at 80° C. for 15 h. The mixture was cooled to ambient temperature and the solvent was removed in vacuo. The residue was purified by preparative TLC (eluting with 20% EtOAc in petroleum ether) to give 3-(7-isopropenyl-4-methyl-3-oxo-2,3,4,10-tetrahydro-9-oxa-1,2,4a-triaza-phenanthren-6-yloxy)-azetidine-1-carboxylic acid tert-butyl ester as a white solid (0.09 g, 33%). LC/MS (Table 1, Method 2) R$_t$=1.241 min.; MS m/z: 429 [M+H]⁺.

Step B. 3-(7-Isopropyl-4-methyl-3-oxo-2,3,4,10-tetrahydro-9-oxa-1,2,4a-triaza-phenanthren-6-yloxy)-azetidine-1-carboxylic acid tert-butyl ester

A suspension of 3-(7-isopropenyl-4-methyl-3-oxo-2,3,4,10-tetrahydro-9-oxa-1,2,4a-triaza-phenanthren-6-yloxy)-azetidine-1-carboxylic acid tert-butyl ester (0.030 g, 0.070 mmol) and 10% Pd/C (10 mg) in MeOH (10 mL) was stirred under H₂ (50 psi) at ambient temperature overnight. The reaction mixture was filtered and the filtrate was evaporated in vacuo. The residue was purified by preparative TLC (eluting with 30% EtOAc in petroleum ether) to give 3-(7-isopropyl-4-methyl-3-oxo-2,3,4,10-tetrahydro-9-oxa-1,2,4a-triaza-phenanthren-6-yloxy)-azetidine-1-carboxylic acid tert-butyl ester as a white solid (0.016 g, 53%). LC/MS (Table 1, Method 2) R$_f$=1.275 min.; MS m/z: 431 [M+H]$^+$.

Step C. 6-(Azetidin-3-yloxy)-7-isopropyl-4-methyl-2,10-dihydro-9-oxa-1,2,4a-triaza-phenanthren-3-one trifluoroacetic acid

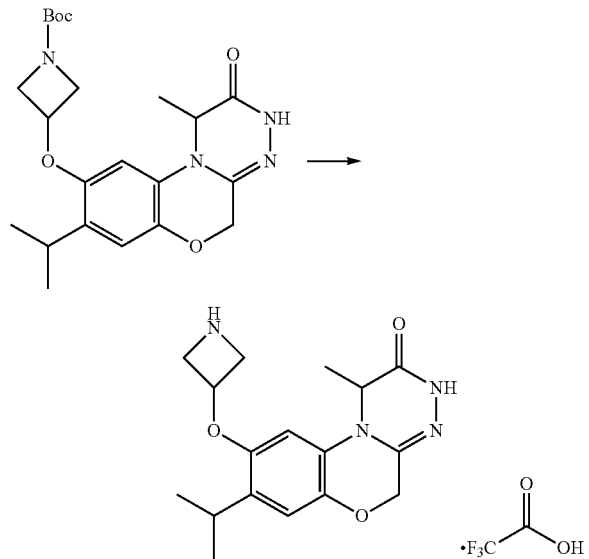

To a solution of 3-(7-isopropyl-4-methyl-3-oxo-2,3,4,10-tetrahydro-9-oxa-1,2,4a-triaza-phenanthren-6-yloxy)-azetidine-1-carboxylic acid tert-butyl ester (0.016 g, 0.067 mmol) in DCM (2 mL) was added TFA (0.35 mL) and the mixture was stirred at ambient temperature for 2 h. The solvent was removed in vacuo to give 6-(azetidin-3-yloxy)-7-isopropyl-4-methyl-2,10-dihydro-9-oxa-1,2,4a-triaza-phenanthren-3-one trifluoroacetic acid as a pale solid (0.015 g, 51%). LC/MS (Table 1, Method 5) R$_f$=2.160 min.; MS m/z: 331 [M+H]$^+$.

Example #69

4-Methyl-6-(3-methyl-azetidin-3-yloxy)-2,10-dihydro-9-oxa-1,2,4a-triaza-phenanthren-3-one trifluoroacetic acid

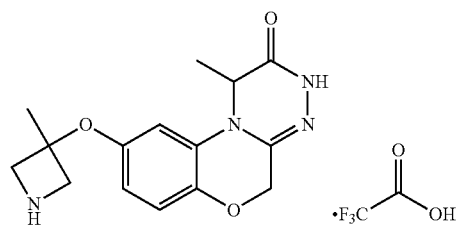

Step A. 2-[6-(1-Benzhydryl-3-methyl-azetidin-3-yloxy)-3-oxo-2,3-dihydro-benzo[1,4]oxazin-4-yl]-propionic acid ethyl ester

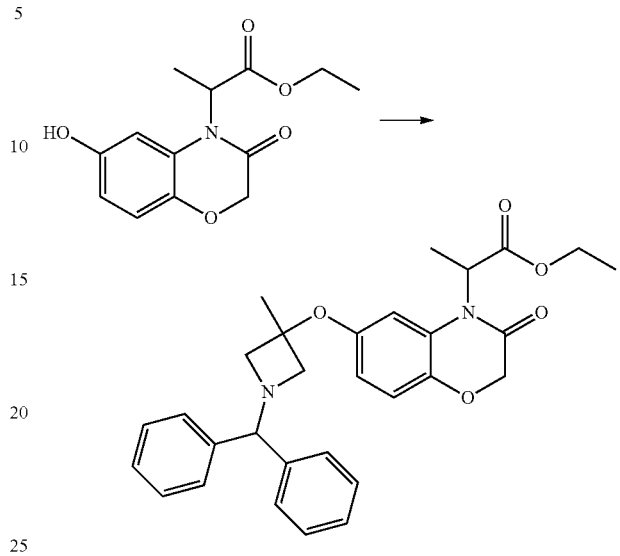

A mixture of ethyl 2-(6-hydroxy-3-oxo-2,3-dihydro-benzo[1,4]oxazin-4-yl)-propionic acid ethyl ester (Example #65, Step C, 0.200 g, 0.754 mmol), methanesulfonic acid 1-benzhydryl-3-methyl-azetidin-3-yl ester (0.275 g, 0.829 mmol) and Cs$_2$CO$_3$ (0.491 g, 1.508 mmol) in DMF (8 mL) was stirred at 90° C. for 3 h. The reaction mixture was cooled to ambient temperature and poured into water (150 mL). The aqueous mixture was extracted with EtOAc (3×20 mL) and the combined organic phase was washed with brine (3×20 mL), dried over anhydrous Na$_2$SO$_4$, filtered and evaporated in vacuo. The residue was purified by column chromatography on silica gel (eluting with 5% to 10% EtOAc in petroleum ether) to give 2-[6-(1-benzhydryl-3-methyl-azetidin-3-yloxy)-3-oxo-2,3-dihydro-benzo[1,4]oxazin-4-yl]-propionic acid ethyl ester as a white solid (0.300 g, 79%). $^1$H NMR (CDCl$_3$, 400 MHz): δ 7.44 (m, 4H), 7.30 (m, 3H), 7.29 (m, 1H), 7.28 (m, 2H), 6.87 (d, J=8.8 Hz, 1H), 6.28 (d, J=8.8 Hz, 1H), 6.22 (s, 1H), 5.32 (q, J=7.2 Hz, 1H), 4.55 (d, J=17.6 Hz, 2H), 4.42 (s, 1H), 4.09 (q, J=7.2 Hz, 2H), 3.38 (m, 2H), 3.19 (m, 2H), 1.59 (m, 6H), 1.16 (t, J=7.2 Hz, 3H).

Step B. 2-[6-(3-Methyl-azetidin-3-yloxy)-3-oxo-2,3-dihydro-benzo[1,4]oxazin-4-yl]-propionic acid ethyl ester

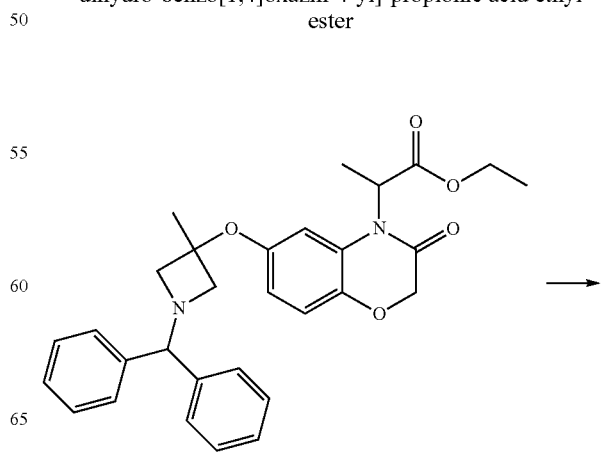

151
-continued

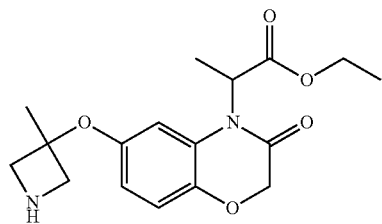

A suspension of 2-[6-(1-benzhydryl-3-methyl-azetidin-3-yloxy)-3-oxo-2,3-dihydro-benzo[1,4]oxazin-4-yl]-propionic acid ethyl ester (0.300 g, 0.070 mmol) and Pd(OH)$_2$/C (10%, 0.170 g) in EtOH (15 mL) was stirred under H$_2$ (50 psi) at ambient temperature overnight. The reaction mixture was filtered and the filtrate was evaporated in vacuo to give 2-[6-(3-methyl-azetidin-3-yloxy)-3-oxo-2,3-dihydro-benzo[1,4]oxazin-4-yl]-propionic acid ethyl ester (0.250 g, crude) as an oil, which was used in the next step directly. LC/MS (Table 1, Method 2) R$_t$=0.806 min.; MS m/z: 335 [M+H]$^+$.

Step C. 3-[4-(1-Ethoxycarbonyl-ethyl)-3-oxo-3,4-dihydro-2H-benzo[1,4]oxazin-6-yloxy]-3-methyl-azetidine-1-carboxylic acid tert-butyl ester

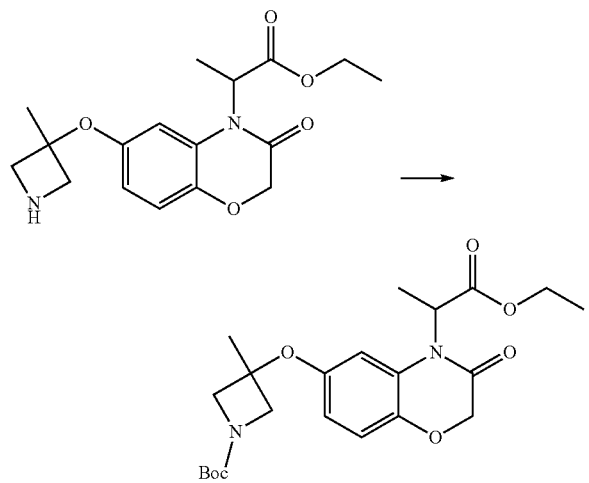

To a solution of 2-[6-(3-methyl-azetidin-3-yloxy)-3-oxo-2,3-dihydro-benzo[1,4]oxazin-4-yl]-propionic acid ethyl ester (0.250 g, crude) in THF (10 mL) was added aqueous NaOH (0.748 mL, 2M) and Boc$_2$O (0.196 g, 0.897 mmol). The mixture was stirred at ambient temperature overnight. The solvent was removed in vacuo and the residue was purified by column chromatography on silica gel (eluting with 5-10% EtOAc in petroleum ether) to give 3-[4-(1-ethoxycarbonyl-ethyl)-3-oxo-3,4-dihydro-2H-benzo[1,4]oxazin-6-yloxy]-3-methyl-azetidine-1-carboxylic acid tert-butyl ester as a white solid (0.250 g, 96% over two steps). $^1$H NMR (CDCl$_3$, 400 MHz): δ 6.94 (d, J=8.4 Hz, 1H), 6.28 (m, 2H), 5.32 (m, 1H), 4.58 (d, J=15.2 Hz, 2H), 4.25 (q, J=7.2 Hz, 2H), 4.18 (m, 2H), 3.88 (m, 2H), 1.63 (m, 6H), 1.47 (s, 9H), 1.24 (t, J=7.2 Hz, 3H).

152

Step D. 3-[4-(1-Ethoxycarbonyl-ethyl)-3-thioxo-3,4-dihydro-2H-benzo[1,4]oxazin-6-yloxy]-3-methyl-azetidine-1-carboxylic acid tert-butyl ester

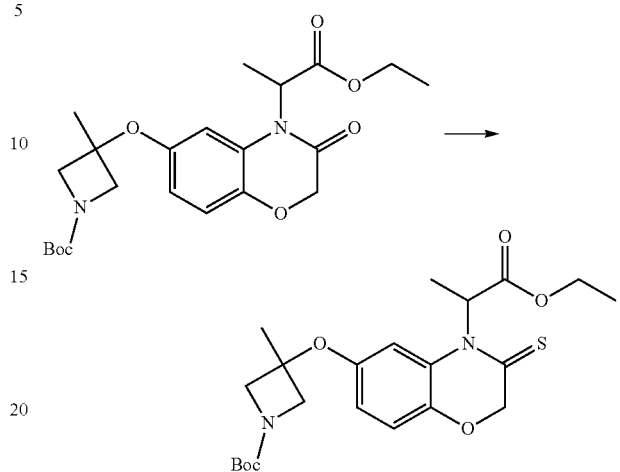

To a solution of 3-[4-(1-ethoxycarbonyl-ethyl)-3-oxo-3,4-dihydro-2H-benzo[1,4]oxazin-6-yloxy]-3-methyl-azetidine-1-carboxylic acid tert-butyl ester (0.250 g, 0.575 mmol) in toluene (5 mL) and DME (5 mL) was added Lawesson reagent (0.372 g, 0.920 mmol) and the mixture was heated to reflux for 4 h. The mixture was cooled to ambient temperature and concentrated in vacuo. The residue was purified by column chromatography on silica gel (eluting with 5% to 10% EtOAc in petroleum ether) to give 3-[4-(1-ethoxycarbonyl-ethyl)-3-thioxo-3,4-dihydro-2H-benzo[1,4]oxazin-6-yloxy]-3-methyl-azetidine-1-carboxylic acid tert-butyl ester (0.095 g, 36.6%) as a pale yellow solid. $^1$H NMR (CDCl$_3$, 400 MHz): δ 6.90 (d, J=8.8 Hz, 1H), 6.67 (brs, 1H), 6.38 (m, 1H), 6.31 (s, 1H), 4.85 (d, J=15.2 Hz, 2H), 4.14 (m, 4H), 3.87 (m, 2H), 1.64 (d, J=7.2 Hz, 3H), 1.59 (s, 3H), 1.42 (s, 9H), 1.13 (t, J=7.2 Hz, 3H).

Step E. 3-Methyl-3-(4-methyl-3-oxo-2,3,4,10-tetrahydro-9-oxa-1,2,4a-triaza-phenanthren-6-yloxy)-azetidine-1-carboxylic acid tert-butyl ester

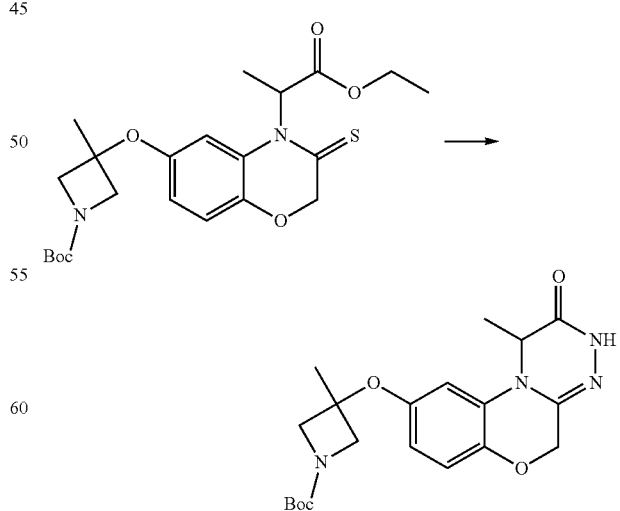

To a solution of 3-[4-(1-ethoxycarbonyl-ethyl)-3-thioxo-3,4-dihydro-2H-benzo[1,4]oxazin-6-yloxy]-3-methyl-azetidine-1-carboxylic acid tert-butyl ester (0.095 g, 0.211 mmol) in EtOH (5 mL) was added hydrazine hydrate (0.105 g, 2.109 mmol) and the mixture was heated at reflux for 2 h. The reaction mixture was cooled to ambient temperature, concentrated in vacuo and the residue was purified by preparative TLC (eluting with 30% EtOAc in petroleum ether) to give 3-methyl-3-(4-methyl-3-oxo-2,3,4,10-tetrahydro-9-oxa-1,2,4a-triaza-phenanthren-6-yloxy)-azetidine-1-carboxylic acid tert-butyl ester (0.064 g, 75%) as a white solid. LC/MS (Table 1, Method 2) $R_t$=1.143 min.; MS m/z: 403 [M+H]$^+$.

Step F. 4-Methyl-6-(3-methyl-azetidin-3-yloxy)-2,10-dihydro-9-oxa-1,2,4a-triaza-phenanthren-3-one trifluoroacetic acid

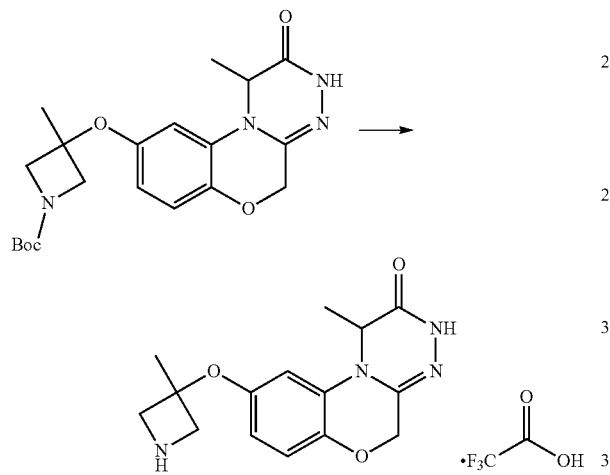

To a solution of 3-methyl-3-(4-methyl-3-oxo-2,3,4,10-tetrahydro-9-oxa-1,2,4a-triaza-phenanthren-6-yloxy)-azetidine-1-carboxylic acid tert-butyl ester (0.064 g, 0.159 mmol) in DCM (2 mL) was added TFA (0.5 mL) dropwise and the mixture was stirred at ambient temperature for 2 h. The solvent was removed in vacuo to give 4-methyl-6-(3-methyl-azetidin-3-yloxy)-2,10-dihydro-9-oxa-1,2,4a-triaza-phenanthren-3-one trifluoroacetic acid as white solid (0.045 g, 68%). LC/MS (Table 1, Method 5) $R_t$=1.691 min; MS m/z: 303 [M+H]$^+$.

Example #70

6-(1,3-Dimethyl-azetidin-3-ylamino)-4-methyl-7-trifluoromethyl-2,10-dihydro-9-oxa-1,2,4a-triaza-phenanthren-3-one trifluoroacetic acid

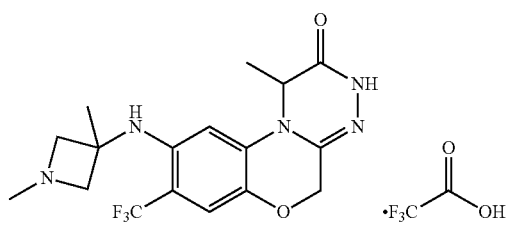

Step A. 6-(1-Benzhydryl-3-methyl-azetidin-3-ylamino)-4-methyl-7-trifluoromethyl-2-(2-trimethylsilanyl-ethoxymethyl)-2,10-dihydro-9-oxa-1,2,4a-triaza-phenanthren-3-one

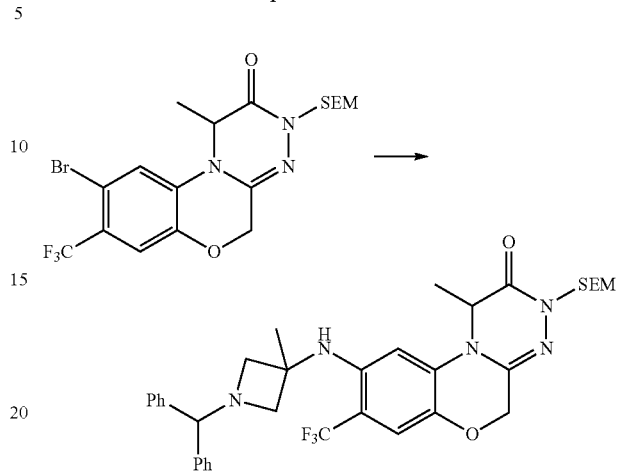

A mixture of 6-bromo-4-methyl-7-trifluoromethyl-2-(2-trimethylsilanyl-ethoxymethyl)-2,10-dihydro-9-oxa-1,2,4a-triaza-phenanthren-3-one (Example #53, Step E, 0.100 g, 0.20 mmol), 1-benzhydryl-3-methy 1-azetidin-3-ylamine (0.102 g, 0.40 mmol), diacetoxypalladium (0.0136 g, 0.06 mmol) Ce$_2$CO$_3$ (0.099 g, 0.30 mmol) and BINAP (0.050 g, 0.08 mmol) in toluene (2 mL) was heated to reflux for 5 h. The reaction mixture was cooled to ambient temperature, filtered and the filtrate concentrated in vacuo. The residue was purified by column chromatography on silica gel (eluting with 15% EtOAc in petroleum ether) to give 6-(1-benzhydryl-3-methyl-azetidin-3-ylamino)-4-methyl-7-trifluoromethyl-2-(2-trimethylsilanyl-ethoxymethyl)-2,10-dihydro-9-oxa-1,2,4a-triaza-phenanthren-3-one as a yellow solid (0.060 g, 45%). LC/MS (Table 1, Method 2) $R_t$=1.258 min.; MS m/z: 666 [M+H]$^+$.

Step B. 6-(1-Benzhydryl-3-methyl-azetidin-3-ylamino)-4-methyl-7-trifluoromethyl-2,10-dihydro-9-oxa-1,2,4a-triaza-phenanthren-3-one

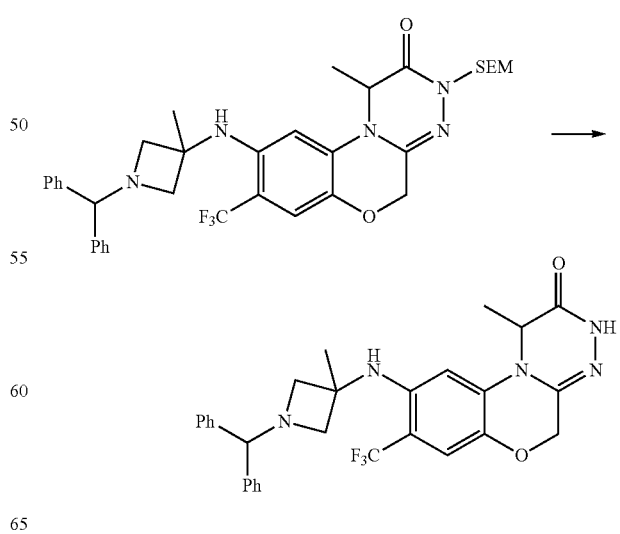

A solution of 6-(1-benzhydryl-3-methyl-azetidin-3-ylamino)-4-methyl-7-trifluoromethyl-2-(2-trimethylsilanylethoxymethyl)-2,10-dihydro-9-oxa-1,2,4a-triaza-phenanthren-3-one (0.020 g, 0.034 mmol) in DCM (0.5 mL) and TFA (0.25 mL) was stirred at ambient temperature for 1 h. The solvent was removed in vacuo. The residue was dissolved in THF (0.5 mL) and aqueous ammonium hydroxide solution (25%, 0.25 mL) was added. The mixture was stirred for additional 2 h at ambient temperature. The mixture was diluted with water (10 mL) and extracted with EtOAc (3×10 mL). The combined organic phase was washed with brine (10 mL), dried over $Na_2SO_4$ and filtered. The filtrate was evaporated in vacuo to give crude 6-(1-benzhydryl-3-methyl-azetidin-3-ylamino)-4-methyl-7-trifluoromethyl-2,10-dihydro-9-oxa-1,2,4a-triaza-phenanthren-3-one as a yellow solid (0.015 g, 84%), which was used in next step directly. LC/MS (Table 1, Method 2) $R_t$=0.997 min.; MS m/z: 536 $[M+H]^+$.

Step C. 6-(1,3-Dimethyl-azetidin-3-ylamino)-4-methyl-7-trifluoromethyl-2,10-dihydro-9-oxa-1,2,4a-triaza-phenanthren-3-one trifluoroacetic acid

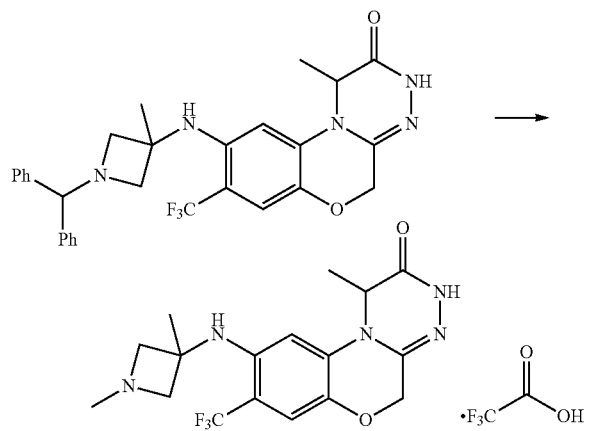

6-(1-Benzhydryl-3-methyl-azetidin-3-ylamino)-4-methyl-7-trifluoromethyl-2,10-dihydro-9-oxa-1,2,4a-triaza-phenanthren-3-one (0.005 g, 0.019 mmol) and $Pd(OH)_2/C$ (0.05 g) in MeOH (1 mL) was stirred at ambient temperature under $H_2$ (50 psi) for 60 h. After filtration, the residue was purified by preparative HPLC (Table 3, Method 16) to give 6-(1,3-dimethyl-azetidin-3-ylamino)-4-methyl-7-trifluoromethyl-2,10-dihydro-9-oxa-1,2,4a-triaza-phenanthren-3-one trifluoroacetic acid as a pale white solid (0.003 g, 65%). LC/MS (Table 1, Method 5) $R_t$=2.135 min.; MS m/z: 384 $[M+H]^+$.

Example #71

4-Methyl-6-piperidin-4-yl-2,10-dihydro-9-oxa-1,2,4a-triaza-phenanthren-3-one trifluoroacetic acid

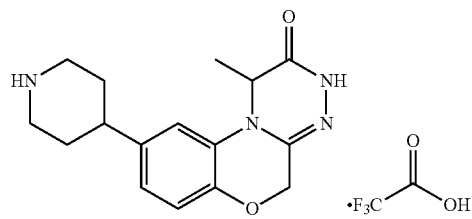

Step A. 4-(4-Methyl-3-oxo-2,3,4,10-tetrahydro-9-oxa-1,2,4a-triaza-phenanthren-6-yl)-3,6-dihydro-2H-pyridine-1-carboxylic acid tert-butyl ester

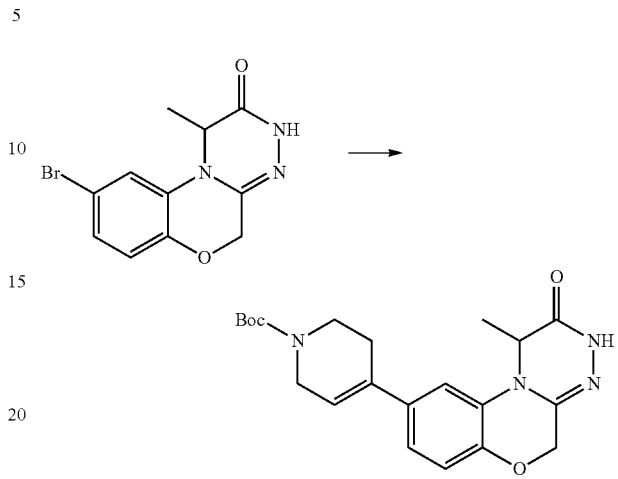

A degassed mixture of 4-(7-bromo-4-methyl-3-oxo-2,3,4,10-tetrahydro-9-oxa-1,2,4a-triaza-phenanthren-6-yl)-piperidine-1-carboxylic acid tert-butyl ester (Preparation #1, Step D, 1.70 g, 5.74 mmol), 4-(4,4,5,5-tetramethyl-[1,3,2]dioxaborolan-2-yl)-3,6-dihydro-2H-pyridine-1-carboxylic acid tert-butyl ester (3.55 g, 11.48 mmol), [1,1'-bis(diphenylphosphino)ferrocene]dichloropalladium(II)dichloride dichloromethane complex (0.494 g, 0.675 mmol) and $K_2CO_3$ (1.58 g, 11.48 mmol) in dioxane (10 mL) and water (2 mL) was heated to reflux for 6 h. The reaction mixture was cooled to ambient temperature and filtered through a pad of Celite®. The filtrate was concentrated in vacuo. The residue was purified by column chromatography on silica gel (eluting with 40% EtOAc in petroleum ether) to give 4-(4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (2.0 g, 87%) as a pale white solid. LC/MS (Table 1, Method 3) $R_t$=1.398 min.; MS m/z: 399 $[M+H]^+$.

Step B. 4-(4-Methyl-3-oxo-2,3,4,10-tetrahydro-9-oxa-1,2,4a-triaza-phenanthren-6-yl)-piperidine-1-carboxylic acid tert-butyl ester

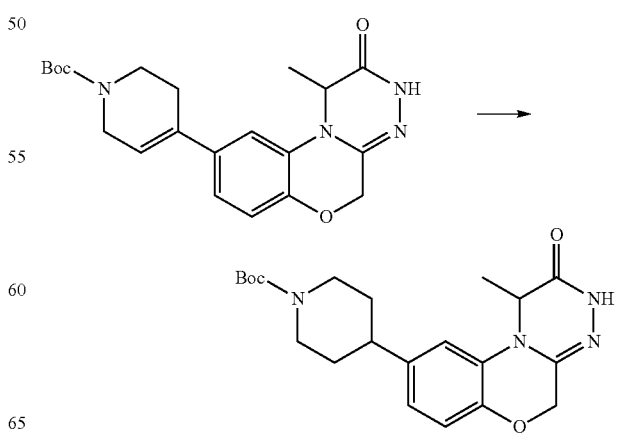

To a solution of 4-(4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (1.1 g, 2.76 mmol) in MeOH (15 mL) was added Pd/C (10%, 0.110 g) and the reaction mixture was stirred under $H_2$ (1 atm) for 10 h. The catalyst was removed by filtration, washing with methanol (3×5 mL). The filtrate was concentrated in vacuo to give 4-(4-methyl-3-oxo-2,3,4,10-tetrahydro-9-oxa-1,2,4a-triaza-phenanthren-6-yl)-piperidine-1-carboxylic acid tert-butyl ester (1.05 g, 100%). LC/MS (Table 1, Method 3) $R_t$=1.428 min.; MS m/z: 401 $[M+H]^+$.

Step C. 4-Methyl-6-piperidin-4-yl-2,10-dihydro-9-oxa-1,2,4a-triaza-phenanthren-3-one trifluoroacetic acid

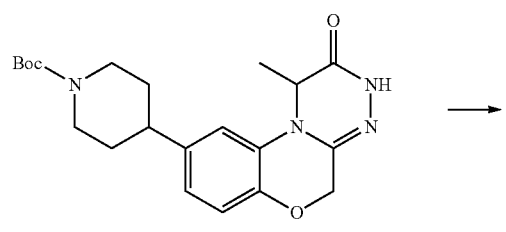

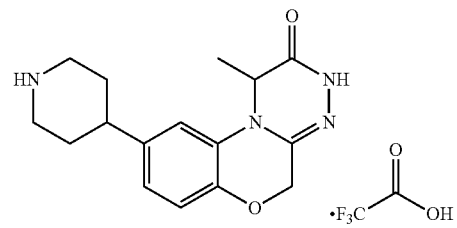

A solution of 4-(4-methyl-3-oxo-2,3,4,10-tetrahydro-9-oxa-1,2,4a-triaza-phenanthren-6-yl)-piperidine-1-carboxylic acid tert-butyl ester (0.020 g, 0.050 mmol) in DCM (6 mL) and TFA (1 mL) was stirred at ambient temperature for 1.5 h. The solvent was removed in vacuo to give 4-methyl-6-piperidin-4-yl-2,10-dihydro-9-oxa-1,2,4a-triaza-phenanthren-3-one trifluoroacetic acid as a pale yellow solid (0.019 g, 99%). LC/MS (Table 1, Method 5) $R_t$=1.684 min.; MS m/z: 301 $[M+H]^+$.

TABLE 10

The following analogs were prepared from 9-bromo-8-fluoro-1-methyl-3,5-dihydrobenzo[5,6][1,4]oxazino[3,4-c][1,2,4]triazin-2(1H)-one (Preparation #7, Step F) using the procedure detailed in Example #71, Steps A-C.

| Structure | Example # | Boronic acid/boronate | $R_t$ min (method) | m/z ESI+ $(M + H)^+$ |
|---|---|---|---|---|
| 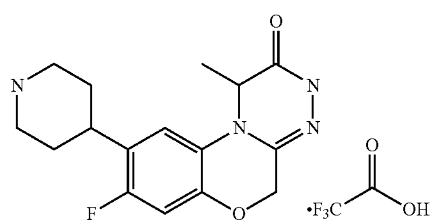 | 72 |  | 1.784 (Table 1, Method 5) | 319 |

TABLE 11

The following analogs were prepared from 1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (Preparation #1, Step D) using the procedure detailed in Example #71, Steps A-C.

| Structure | Example # | Boronic acid/boronate | $R_t$ min (method) | m/z ESI+ $(M + H)^+$ |
|---|---|---|---|---|
| 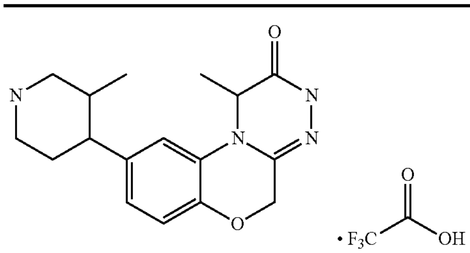 | 73 |  | 1.694 (Table 1, Method 5) | 315 |

TABLE 11-continued

The following analogs were prepared from 1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (Preparation #1, Step D) using the procedure detailed in Example #71, Steps A-C.

| Structure | Example # | Boronic acid/boronate | R$_t$ min (method) | m/z ESI+ (M + H)$^+$ |
|---|---|---|---|---|
| 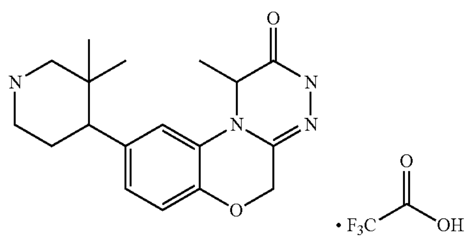 | 74 | | 0.985 (Table 1, Method 3) | 329 |

Example #75

4,7-Dimethyl-6-piperidin-4-yl-2,10-dihydro-9-oxa-1,2,4a-triaza-phenanthren-3-one trifluoroacetic acid

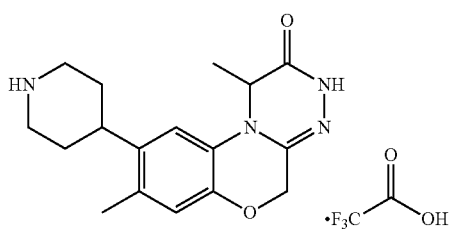

Step A. 4-(7-Bromo-4-methyl-3-oxo-2,3,4,10-tetrahydro-9-oxa-1,2,4a-triaza-phenanthren-6-yl)-piperidine-1-carboxylic acid tert-butyl ester

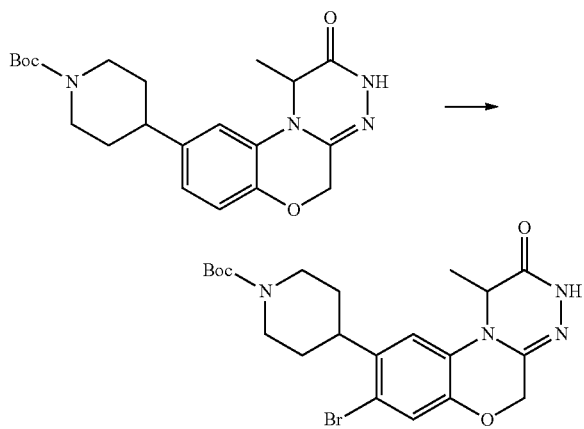

To a solution of 4-(4-methyl-3-oxo-2,3,4,10-tetrahydro-9-oxa-1,2,4a-triaza-phenanthren-6-yl)-piperidine-1-carboxylic acid tert-butyl ester (Example #71, Step B, 0.50 g, 1.249 mmol) in DCM (5 mL) and MeOH (5 mL) was added tetrabutylammonium tribromide (0.662 g, 1.373 mmol) in portions and the mixture was stirred for 30 min at ambient temperature. The reaction was quenched by addition of saturated aqueous Na$_2$S$_2$O$_3$ solution (5 mL) and the pH was adjusted to 7 with saturated aqueous NaHCO$_3$ solution. The mixture was extracted with DCM (3×20 mL). The combined organic phase was washed with brine (20 mL), dried over anhydrous Na$_2$SO$_4$, filtered and concentrated in vacuo. The residue was purified by column chromatography on silica gel (eluting with 20% EtOAc in petroleum ether) to give 4-(7-bromo-4-methyl-3-oxo-2,3,4,10-tetrahydro-9-oxa-1,2,4a-triaza-phenanthren-6-yl)-piperidine-1-carboxylic acid tert-butyl ester (0.34 g, 57%). LC/MS (Table 1, Method 2) R$_t$=1.289 min.; MS m/z: 479/481 [M+H]$^+$.

Step B. 4-(4,7-Dimethyl-3-oxo-2,3,4,10-tetrahydro-9-oxa-1,2,4a-triaza-phenanthren-6-yl)-piperidine-1-carboxylic acid tert-butyl ester

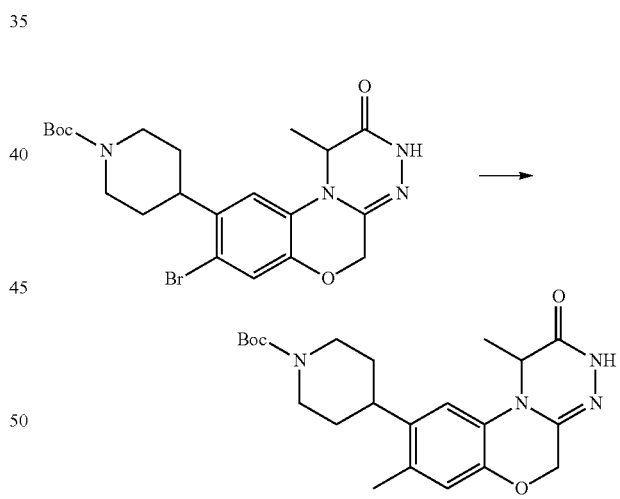

A degassed mixture of 4-(7-bromo-4-methyl-3-oxo-2,3,4,10-tetrahydro-9-oxa-1,2,4a-triaza-phenanthren-6-yl)-piperidine-1-carboxylic acid tert-butyl ester (0.08 g, 0.167 mmol), 2,4,6-trimethyl-1,3,5,2,4,6-trioxatriborinane (0.042 g, 0.334 mmol), [1,1'-bis(diphenylphosphino)ferrocene]dichloropalladium(II)dichloride dichloromethane complex (0.027 g, 0.033 mmol) and K$_2$CO$_3$ (0.046 g, 0.334 mmol) in dioxane (1 mL) and water (0.2 mL) was heated to reflux for 8 h. The reaction mixture was cooled to ambient temperature and filtered. The filtrate was concentrated in vacuo and the residue was purified by preparative-TLC (eluting with 50% EtOAc in petroleum ether) to give 4-(4,7-dimethyl-3-oxo-2,3,4,10-tetrahydro-9-oxa-1,2,4a-triaza-phenanthren-6-yl)-piperidine- 1-carboxylic acid tert-butyl ester (0.03 g, 43%) as a pale white solid. LC/MS (Table 1, Method 3) $R_t$=1.415 min.; MS m/z: 415 [M+H]$^+$.

Step C. 4,7-Dimethyl-6-piperidin-4-yl-2,10-dihydro-9-oxa-1,2,4a-triaza-phenanthren-3-one trifluoroacetic acid

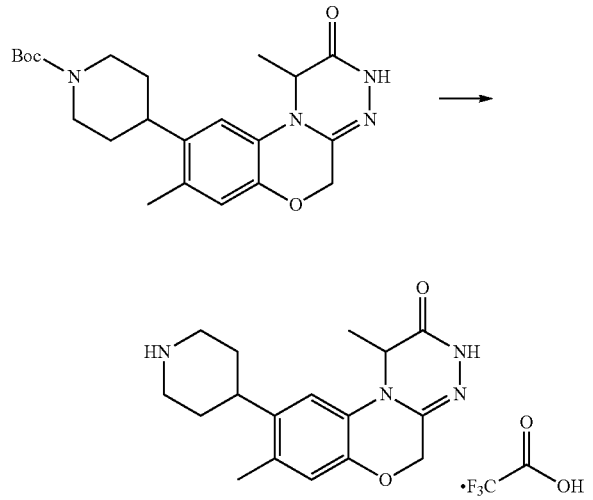

A solution of 4-(4,7-dimethyl-3-oxo-2,3,4,10-tetrahydro-9-oxa-1,2,4a-triaza-phenanthren-6-yl)-piperidine-1-carboxylic acid tert-butyl ester (0.015 g, 0.036 mmol) in DCM (6 mL) and trifluoroacetic acid (1 mL) was stirred at ambient temperature for 1.5 h. The solvent was removed in vacuo to give 4,7-dimethyl-6-piperidin-4-yl-2,10-dihydro-9-oxa-1,2,4a-triaza-phenanthren-3-one trifluoroacetic acid as a pale yellow solid (0.015 g, 97%). LC/MS (Table 1, Method 5) $R_t$=1.939 min.; MS m/z: 315 [M+H]$^+$.

Example #76

7-Isopropyl-4-methyl-6-piperidin-4-yl-2,10-dihydro-9-oxa-1,2,4a-triaza-phenanthren-3-one trifluoroacetic acid

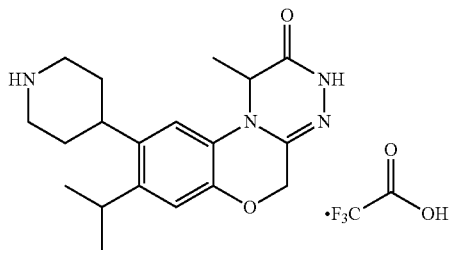

Step A. 4-(7-Isopropenyl-4-methyl-3-oxo-2,3,4,10-tetrahydro-9-oxa-1,2,4a-triaza-phenanthren-6-yl)-piperidine-1-carboxylic acid tert-butyl ester

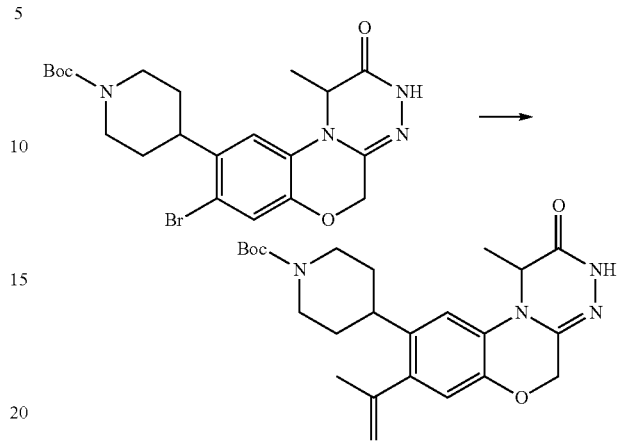

A mixture of 4-(7-bromo-4-methyl-3-oxo-2,3,4,10-tetrahydro-9-oxa-1,2,4a-triaza-phenanthren-6-yl)-piperidine-1-carboxylic acid tert-butyl ester (Example #75, Step A, 0.05 g, 0.104 mmol), 4,4,5,5-tetramethyl-2-(prop-1-en-2-yl)-1,3,2-dioxaborolane (0.035 g, 0.209 mmol), [1,1'-bis(diphenylphosphino)ferrocene]dichloropalladium(II) dichloride dichloromethane complex (0.017 g, 0.021 mmol) and K$_2$CO$_3$ (0.029 g, 0.209 mmol) in dioxane (1 mL) and water (0.2 mL) was heated to reflux for 8 h. The reaction mixture was cooled to ambient temperature and filtered and the filtrate was concentrated in vacuo. The residue was purified by preparative-TLC (eluting with 50% EtOAc in petroleum ether) to give 4-(7-isopropenyl-4-methyl-3-oxo-2,3,4,10-tetrahydro-9-oxa-1,2,4a-triaza-phenanthren-6-yl)-piperidine-1-carboxylic acid tert-butyl ester (0.035 g, 76%) as a pale-white solid. LC/MS (Table 1, Method 5) $R_t$=3.653 min.; MS m/z: 441 [M+H]$^+$.

Step B. 4-(7-Isopropyl-4-methyl-3-oxo-2,3,4,10-tetrahydro-9-oxa-1,2,4a-triaza-phenanthren-6-yl)-piperidine-1-carboxylic acid tert-butyl ester

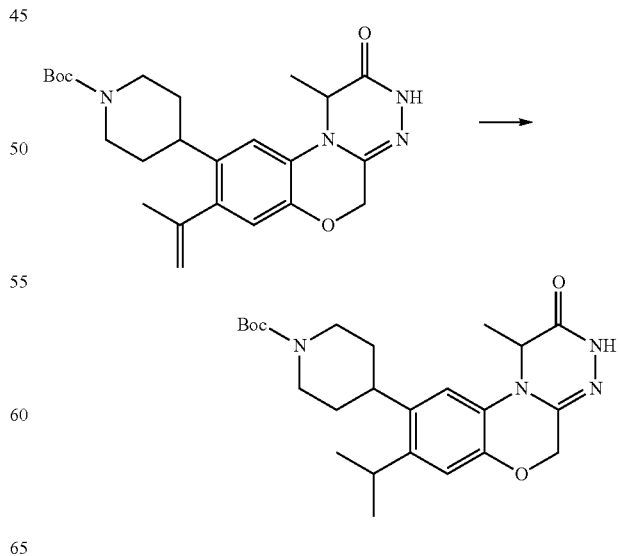

To a solution of 4-(7-isopropenyl-4-methyl-3-oxo-2,3,4,10-tetrahydro-9-oxa-1,2,4a-triaza-phenanthren-6-yl)-piperidine-1-carboxylic acid tert-butyl ester (0.035 g, 2.76 mmol) in MeOH (15 mL) was added Pd/C (10%, 0.005 g, 0.005 mmol). The reaction mixture was stirred under an H₂ atmosphere (50 psi) for 10 h. The catalyst was removed by filtration and washed with methanol (3×5 mL). The filtrate was concentrated in vacuo to give 4-(7-isopropyl-4-methyl-3-oxo-2,3,4,10-tetrahydro-9-oxa-1,2,4a-triaza-phenanthren-6-yl)-piperidine-1-carboxylic acid tert-butyl ester (0.035 g, 100%). LC/MS (Table 1, Method 5) $R_f$=3.554 min.; MS m/z: 443 [M+H]⁺.

Step C. 7-Isopropyl-4-methyl-6-piperidin-4-yl-2,10-dihydro-9-oxa-1,2,4a-triaza-phenanthren-3-one trifluoroacetic acid

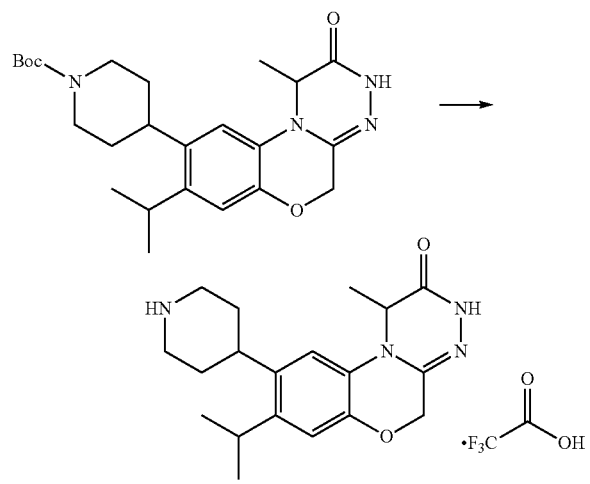

A solution of 4-(7-isopropyl-4-methyl-3-oxo-2,3,4,10-tetrahydro-9-oxa-1,2,4a-triaza-phenanthren-6-yl)-piperidine-1-carboxylic acid tert-butyl ester (0.035 g, 0.036 mmol) in DCM (6 mL) and trifluoroacetic acid (1 mL) was stirred at ambient temperature for 1.5 h. The solvent was removed in vacuo to give 7-isopropyl-4-methyl-6-piperidin-4-yl-2,10-dihydro-9-oxa-1,2,4a-triaza-phenanthren-3-one trifluoroacetic acid as pale yellow solid (0.033 g, 89%). LC/MS (Table 1, Method 5) $R_f$=2.217 min.; MS m/z: 343 [M+H]⁺.

Example #77

7-Cyclopropyl-4-methyl-6-piperidin-4-yl-2,10-dihydro-9-oxa-1,2,4a-triaza-phenanthren-3-one trifluoroacetic acid

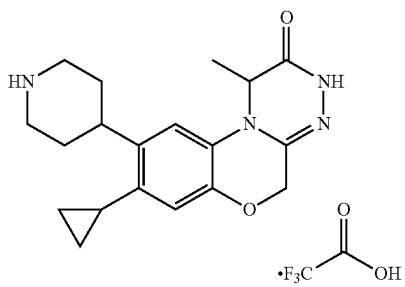

Step A. 4-(7-Cyclopropyl-4-methyl-3-oxo-2,3,4,10-tetrahydro-9-oxa-1,2,4a-triaza-phenanthren-6-yl)-piperidine-1-carboxylic acid tert-butyl ester

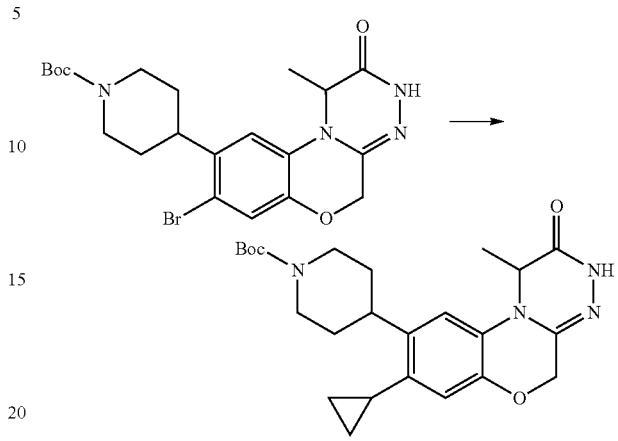

A degassed mixture of 4-(7-bromo-4-methyl-3-oxo-2,3,4,10-tetrahydro-9-oxa-1,2,4a-triaza-phenanthren-6-yl)-piperidine-1-carboxylic acid tert-butyl ester (Example #75, Step A, 0.06 g, 0.127 mmol), cyclopropylboronic acid (0.021 g, 0.250 mmol), [1,1'-bis(diphenylphosphino)ferrocene]dichloropalladium(II)dichloride dichloromethane complex (0.020 g, 0.025 mmol) and K₂CO₃ (0.035 g, 0.250 mmol) in dioxane (1 mL) and water (0.2 mL) was heated to reflux for 8 h. The reaction mixture was cooled to ambient temperature and filtered. The filtrate was concentrated in vacuo and the residue was purified by preparative TLC (eluting with 50% EtOAc in petroleum ether) to give 4-(7-cyclopropyl-4-methyl-3-oxo-2,3,4,10-tetrahydro-9-oxa-1,2,4a-triaza-phenanthren-6-yl)-piperidine-1-carboxylic acid tert-butyl ester (0.024 g, 44%) as a pale-white solid. LC/MS (Table 1, Method 2) $R_f$=1.223 min.; MS m/z: 441 [M+H]⁺.

Step B. 7-Cyclopropyl-4-methyl-6-piperidin-4-yl-2,10-dihydro-9-oxa-1,2,4a-triaza-phenanthren-3-one trifluoroacetic acid

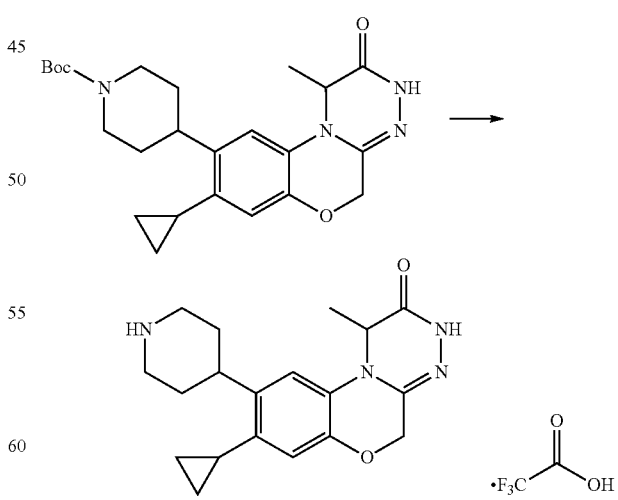

A solution of 4-(7-cyclopropyl-4-methyl-3-oxo-2,3,4,10-tetrahydro-9-oxa-1,2,4a-triaza-phenanthren-6-yl)-piperidine-1-carboxylic acid tert-butyl ester (0.030 g, 0.068 mmol) in DCM (6 mL) and trifluoroacetic acid (1 mL) was stirred at ambient temperature for 1.5 h. The solvent was removed in vacuo to give 7-cyclopropyl-4-methyl-6-piperidin-4-yl-2,10-dihydro-9-oxa-1,2,4a-triaza-phenanthren-3-one trifluoroacetic acid as a pale yellow solid (0.0275 g, 87%). LC/MS (Table 1, Method 5) $R_t$=2.041 min.; MS m/z: 341 [M+H]$^+$.

Example #78

6-Azetidin-3-ylmethyl-4-methyl-2,10-dihydro-9-oxa-1,2,4a-triaza-phenanthren-3-one trifluoroacetic acid

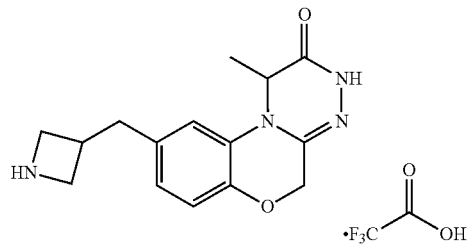

Step A. 3-(4-Methyl-3-oxo-2,3,4,10-tetrahydro-9-oxa-1,2,4a-triaza-phenanthren-6-ylmethylene)-azetidine-1-carboxylic acid tert-butyl ester

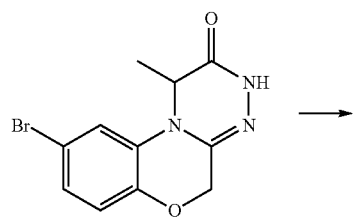

A solution of 6-bromo-4-methyl-2,10-dihydro-9-oxa-1,2,4a-triaza-phenanthren-3-one (Preparation #1, Step D, 0.30 g, 1.013 mmol), 3-methylene-azetidine-1-carboxylic acid tert-butyl ester (0.343 g, 2.026 mmol), Pd(OAc)$_2$ (0.023 g, 0.101 mmol), tri-O-tolylphosphine (0.0617 g, 0.203 mmol) and triethylamine (0.308 mg, 3.04 mmol) in CH$_3$CN (10 mL) was heated at 110° C. for 14 h. The mixture was cooled to ambient temperature and the solvent was removed in vacuo. The residue was purified by preparative TLC (eluting with 50% EtOAc in petroleum ether) to give 3-(4-methyl-3-oxo-2,3,4,10-tetrahydro-9-oxa-1,2,4a-triaza-phenanthren-6-ylmethylene)-azetidine-1-carboxylic acid tert-butyl ester as yellow solid (0.201 g, 52%), which was used directly in the next step. LC/MS (Table 1, Method 2) $R_t$=1.264 min; MS m/z: 385 [M+H]$^+$.

Step B. 3-(4-Methyl-3-oxo-2,3,4,10-tetrahydro-9-oxa-1,2,4a-triaza-phenanthren-6-ylmethyl)-azetidine-1-carboxylic acid tert-butyl ester

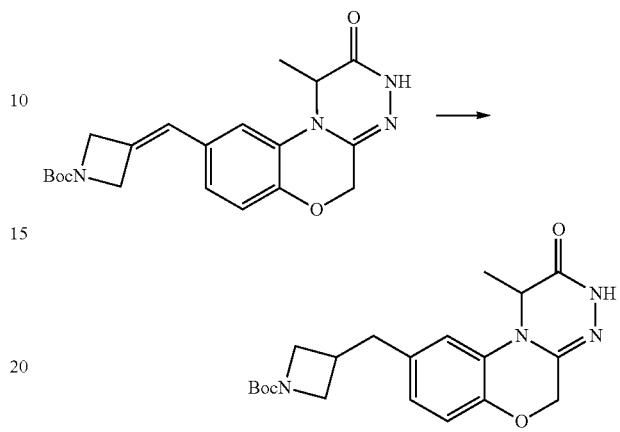

To a solution of 3-(4-methyl-3-oxo-2,3,4,10-tetrahydro-9-oxa-1,2,4a-triaza-phenanthren-6-ylmethylene)-azetidine-1-carboxylic acid tert-butyl ester (0.1 g, 0.16 mmol) in MeOH (10 mL) was added Pd/C (10%, 0.02 g) and the mixture was stirred under H$_2$ (50 psi) for 14 h. The reaction mixture was filtered and the filtrate was concentrated in vacuo and the residue was purified by preparative TLC (eluting with 50% EtOAc in petroleum ether) to give 3-(4-methyl-3-oxo-2,3,4,10-tetrahydro-9-oxa-1,2,4a-triaza-phenanthren-6-ylmethyl)-azetidine-1-carboxylic acid tert-butyl ester (0.075 mg, 69%) as a pale yellow powder. LC/MS (Table 1, Method 2) $R_t$=1.217 min; MS m/z: 409 [M+23]$^+$.

Step C. 6-Azetidin-3-ylmethyl-4-methyl-2,10-dihydro-9-oxa-1,2,4a-triaza-phenanthren-3-one trifluoroacetic acid

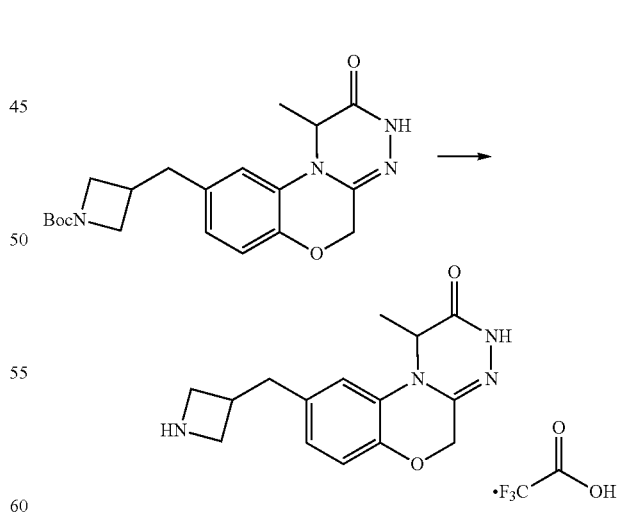

A solution of 3-[(4,7-dimethyl-3-oxo-2,3,4,10-tetrahydro-9-oxa-1,2,4a-triaza-phenanthren-6-yl)-methyl-amino]-azetidine-1-carboxylic acid tert-butyl ester (0.035 g, 0.091 mmol) in DCM (3 mL) and TFA (0.5 mL) was stirred at 25° C. for 2 h. The solvent was removed in vacuo to give 6-azetidin-3-ylmethyl-4-methyl-2,10-dihydro-9-oxa-1,2,4a-triazaphenanthren-3-one trifluoroacetic acid (0.0376 g, 100%). LC/MS (Table 1, Method 4) R$_f$=1.769 min; MS m/z: 287 [M+H]$^+$.

Example #79

4-Methyl-6-(3-methyl-azetidin-3-ylamino)-7-phenyl-2,10-dihydro-9-oxa-1,2,4a-triaza-phenanthren-3-one trifluoroacetic acid

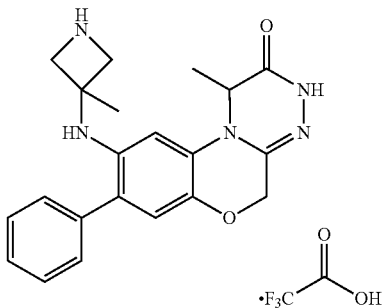

Step A. 6-(1-Benzhydryl-3-methyl-azetidin-3-ylamino)-4-methyl-2,10-dihydro-9-oxa-1,2,4a-triaza-phenanthren-3-one

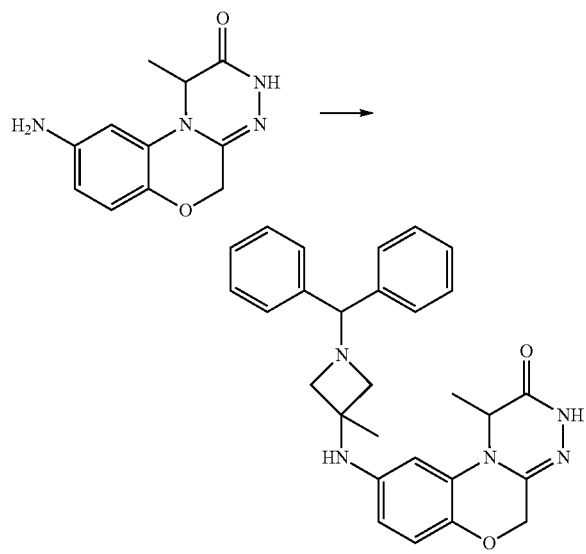

A mixture of K$_2$CO$_3$ (0.238 g, 1.722 mmol), 6-amino-4-methyl-2,10-dihydro-9-oxa-1,2,4a-triaza-phenanthren-3-one (Preparation #2, Step E, 0.20 g, 0.861 mmol), and 1-benzhydryl-3-methylazetidin-3-yl methanesulfonate (Preparation #3, Step B, 0.428 g, 1.292 mmol) in propan-2-ol (10 ml) was stirred at 80° C. overnight. The solution was concentrated in vacuo and the residue was purified by column chromatography on silica gel (eluting with 0 to 50% EtOAc in petroleum ether) to give 6-(1-benzhydryl-3-methyl-azetidin-3-ylamino)-4-methyl-2,10-dihydro-9-oxa-1,2,4a-triaza-phenanthren-3-one (0.234 g, 58%). LC/MS (Table 1, Method 2) R$_f$=0.948 min; MS m/z: 468 [M+H]$^+$.

Step B. 6-(1-Benzhydryl-3-methyl-azetidin-3-ylamino)-7-bromo-4-methyl-2,10-dihydro-9-oxa-1,2,4a-triaza-phenanthren-3-one

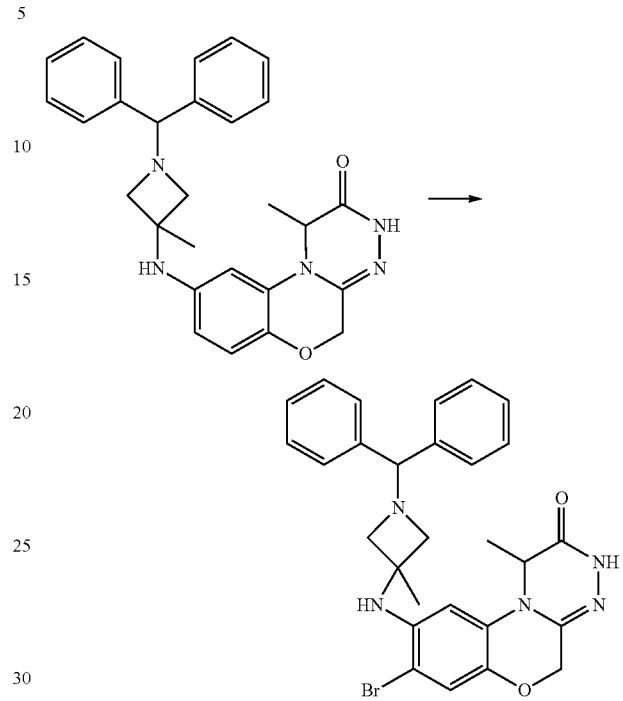

To a solution of 6-(1-benzhydryl-3-methyl-azetidin-3-ylamino)-4-methyl-2,10-dihydro-9-oxa-1,2,4a-triaza-phenanthren-3-one (0.250 g, 0.535 mmol) in DCM (10 mL) and MeOH (10 mL), was added tetra-N-butylammonium tribromide (0.258 g, 0.535 mmol) in portions at ambient temperature. The resulting yellow solution was stirred for 0.5 h. The solvent was removed in vacuo and the residue was purified by column chromatography on silica gel (eluting with 50% EtOAc in petroleum ether) to give 6-(1-benzhydryl-3-methyl-azetidin-3-ylamino)-7-bromo-4-methyl-2,10-dihydro-9-oxa-1,2,4a-triaza-phenanthren-3-one (0.180 g, 62%) as an off-white solid. $^1$H NMR (CDCl$_3$, 400 MHz): δ 8.77 (brs, 1H), 7.35 (m, 4H), 7.20 (m, 4H), 7.12 (m, 2H), 7.04 (s, 1H), 5.84 (s, 1H), 4.46 (q, J=6.4 Hz, 1H), 4.40 (s, 2H), 4.37 (s, 1H), 4.24 (brs, 1H), 3.29 (m, 2H), 3.06 (m, 2H), 1.56 (s, 3H), 1.30 (d, J=6.4 Hz, 3H).

Step C. 6-(1-Benzhydryl-3-methyl-azetidin-3-ylamino)-4-methyl-7-phenyl-2,10-dihydro-9-oxa-1,2,4a-triaza-phenanthren-3-one

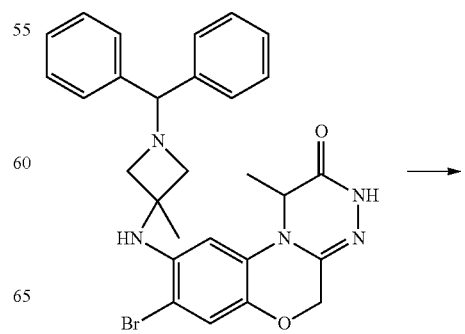

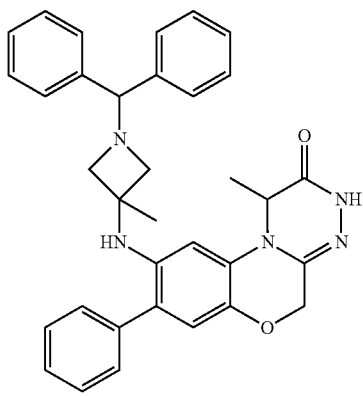

A degassed mixture of [1,1'-bis(diphenylphosphino)ferrocene]dichloropalladium(II) (0.175 g, 0.214 mmol), 6-(1-benzhydryl-3-methyl-azetidin-3-ylamino)-7-bromo-4-methyl-2,10-dihydro-9-oxa-1,2,4a-triaza-phenanthren-3-one (0.220 g, 0.403 mmol), K₂CO₃ (0.167 g, 1.208 mmol), and phenylboronic acid (0.123 g, 1.006 mmol) in water (0.5 mL) and dioxane (3 mL) was stirred at 100° C. overnight. The mixture was cooled to ambient temperature, the solution was concentrated in vacuo and the residue was purified by column chromatography on silica gel (eluting with 0 to 50% EtOAc in petroleum ether) to give 6-(1-benzhydryl-3-methyl-azetidin-3-ylamino)-4-methyl-7-phenyl-2,10-dihydro-9-oxa-1,2,4a-triaza-phenanthren-3-one (0.120 g, 55%). ¹H NMR (CDCl₃, 400 MHz): δ 8.09 (brs, 1H), 7.31 (m, 7H), 7.19 (m, 6H), 7.12 (m, 2H), 6.73 (s, 1H), 5.85 (s, 1H), 4.54 (q, J=6.8 Hz, 1H), 4.49 (d, J=12.8 Hz, 2H), 4.32 (s, 1H), 3.96 (brs, 1H), 3.22 (m, 2H), 2.93 (m, 2H), 1.52 (s, 3H), 1.37 (d, J=6.8 Hz, 3H).

Step D. 4-Methyl-6-(3-methyl-azetidin-3-ylamino)-7-phenyl-2,10-dihydro-9-oxa-1,2,4a-triaza-phenanthren-3-one trifluoroacetic acid

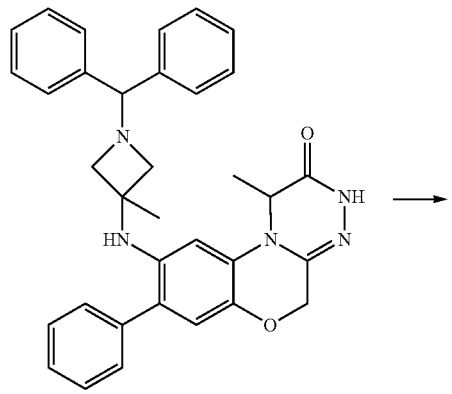

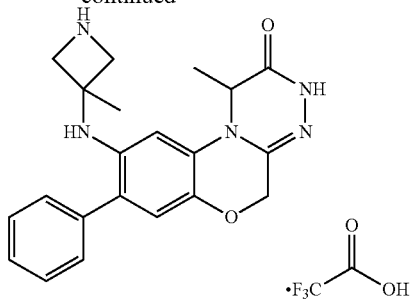

A mixture of 6-(1-benzhydryl-3-methyl-azetidin-3-ylamino)-4-methyl-7-phenyl-2,10-dihydro-9-oxa-1,2,4a-triaza-phenanthren-3-one (0.120 g, 0.221 mmol) and Pd(OH)₂/C (10%, 0.100 g, 0.07 mmol) in MeOH (10 mL) was stirred under an atmosphere of hydrogen (55 psi) for 72 h at rt. The reaction mixture was filtered, the filtrate was concentrated in vacuo and the residue was purified by preparative HPLC (Table 3, Method 3) to give 4-methyl-6-(3-methyl-azetidin-3-ylamino)-7-phenyl-2,10-dihydro-9-oxa-1,2,4a-triaza-phenanthren-3-one trifluoroacetic acid (0.0118 g, 14%). LC/MS (Table 1, Method 4) R_f=1.572 min; MS m/z: 378 [M+H]⁺.

Example #80

7-Fluoro-4-methyl-6-(3-methyl-azetidin-3-yloxy)-2,10-dihydro-9-oxa-1,2,4a-triaza-phenanthren-3-one trifluoroacetic acid

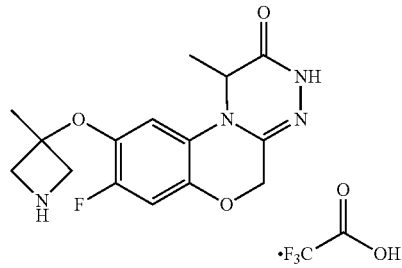

Step A.
1-(2-Fluoro-4-hydroxy-5-nitro-phenyl)-ethanone

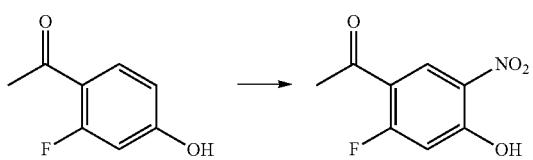

To a mixture of 1-(2-fluoro-4-hydroxy-phenyl)-ethanone (5 g, 32.5 mmol) in concentrated sulfuric acid (50 mL) at −5° C. was added KNO₃ (3.29 g, 32.6 mmol) in portions and the mixture was stirred for 3 h at −5° C. The mixture was poured into ice water (120 mL) and the aqueous solution was extracted with EtOAc (3×50 mL). The combined organic phase was washed with brine (100 mL), dried over anhydrous Na₂SO₄ and filtered. The filtrate was evaporated in vacuo and the residue was purified by column chromatography on silica gel (eluting with 2-10% EtOAc in petroleum ether) to give 1-(2-fluoro-4-hydroxy-5-nitro-phenyl)-ethanone as a yellow solid (4.59 g, 71%). ¹H-NMR (CDCl₃, 400 MHz): δ 10.95 (s 1H), 8.79 (d, J=7.2 Hz, 1H), 6.92 (d, J=11.2 Hz, 1H), 2.63 (d, J=5.2 Hz, 3H).

Step B. 1-(5-Amino-2-fluoro-4-hydroxy-phenyl)-ethanone

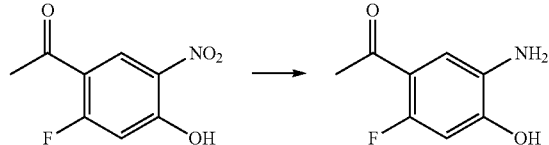

To a solution of 1-(2-fluoro-4-hydroxy-5-nitro-phenyl)-ethanone (3 g, 15.7 mmol) in EtOH (30 mL) and THF (6 mL) was added Pd/C (10%, 1.5 g, 1.4 mmol) and the reaction mixture was stirred at ambient temperature for 2 h. The reaction mixture was filtered and the filtrate was evaporated in vacuo to give 1-(5-amino-2-fluoro-4-hydroxy-phenyl)-ethanone as a black solid (2.5 g, crude), which was used in the next step directly without further purification. ¹H-NMR (DMSO-d₆, 400 MHz): δ 7.01 (d, J=8.0 Hz, 1H), 6.48 (d, J=12.4 Hz, 1H), 2.39 (d, J=4.8 Hz, 3H).

Step C. Ethyl 2-(6-bromo-3-oxo-7-(trifluoromethyl)-2H-benzo[b][1,4]oxazin-4(3H)-yl)propanoate

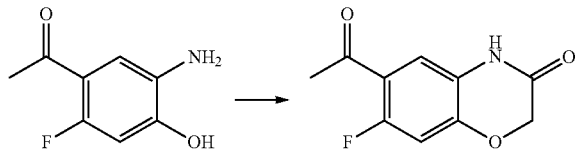

To a mixture of 1-(5-amino-2-fluoro-4-hydroxyphenyl)ethanone (13.2 g, 78 mmol) and NaHCO₃ (19.67 g, 234 mmol) in water (90 mL) and 4-methyl-2-pentanone (90 mL) at 0° C. was added 2-chloroacetyl chloride (13.22 g, 117 mmol) dropwise. After addition, the reaction mixture was stirred at rt for 0.5 h. Then, the reaction mixture was stirred at 80° C. for 18 h. The reaction mixture was filtered to give ethyl 2-(6-bromo-3-oxo-7-(trifluoromethyl)-2H-benzo[b][1,4]oxazin-4(3H)-yl)propanoate as a gray solid (12 g, crude) which was used in next step directly without further purification. ¹H-NMR (DMSO-d₆, 400 MHz): δ 10.90 (s 1H), 7.35 (d, J=7.6 Hz, 1H), 7.02 (d, J=11.6 Hz, 1H), 4.71 (s, 2H), 2.47 (d, J=4.8 Hz, 3H).

Step D. Ethyl 2-(6-acetyl-7-fluoro-3-oxo-2H-benzo[b][1,4]oxazin-4(3H)-yl)propanoate

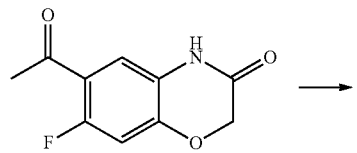

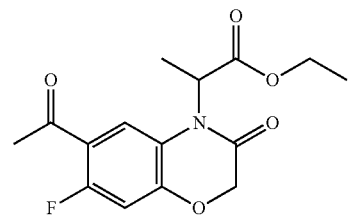

To a mixture of 6-acetyl-7-fluoro-2H-benzo[b][1,4]oxazin-3(4H)-one (12 g, 57.4 mmol) and K₂CO₃ (11.89 g, 86 mmol) in acetone (120 mL) was added ethyl 2-bromopropanoate (23.6 mL, 172 mmol) and the mixture was stirred and heated at 80° C. for 16 h. The mixture was cooled to ambient temperature and the solvent was removed in vacuo. The residue was purified by column chromatography on silica gel (eluting with 5-10% EtOAc in petroleum ether) to give ethyl 2-(6-acetyl-7-fluoro-3-oxo-2H-benzo[b][1,4]oxazin-4(3H)-yl)propanoate as a gray solid (13.2 g, 74.4%). ¹H-NMR (CDCl₃, 400 MHz): δ 7.40 (d, J=6.4 Hz, 1H), 6.80 (d, J=10.8 Hz, 1H), 5.24 (q, J=11.2 Hz, 1H), 4.66 (q, J=15.2 Hz, 2H), 4.23 (m, 2H), 2.60 (d, J=5.2 Hz, 3H), 1.63 (d, J=7.2 Hz, 3H), 1.23 (t, 3H).

Step E. Ethyl 2-(6-acetoxy-7-fluoro-3-oxo-2H-benzo[b][1,4]oxazin-4(3H)-yl)propanoate

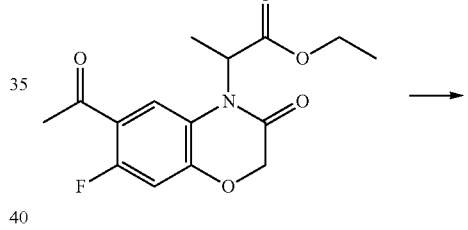

To a mixture of NaHCO₃ (5.38 g, 64.0 mmol) and urea hydrogen peroxide (6.02 g, 64.0 mmol) in DCM (60 mL) at 0° C. was added ethyl 2-(6-acetyl-7-fluoro-3-oxo-2H-benzo[b][1,4]oxazin-4(3H)-yl)propanoate (6.6 g, 21.34 mmol). The reaction mixture was stirred for 10 min then TFAA (5.94 mL, 42.7 mmol) was added dropwise. The reaction mixture was stirred at 0° C. for 1 h and then allowed to warm to ambient temperature and stirred for 3 days. The reaction mixture was diluted with DCM (30 mL) and washed with water (30 mL). The combined organic layers were dried over anhydrous MgSO₄, filtered and concentrated in vacuo. The residue was purified by column chromatography on silica gel (eluting with 15% EtOAc in petroleum ether) to give ethyl 2-(6-acetoxy-7-fluoro-3-oxo-2H-benzo[b][1,4]oxazin-4(3H)-yl)propanoate and starting material as a white solid (5.9 g, 85%). ¹H NMR (CDCl₃, 400 MHz): δ 6.85 (d, J=10 Hz, 1H), 6.59 (d, J=6.8 Hz, 1H), 5.23 (m, 1H), 4.57 (q, J₁=15.2 Hz, J₂=14.8 Hz, 2H), 4.17 (m, 2H), 2.29 (s, 3H), 1.58 (d, J=7.2 Hz, 3H), 1.17 (t, 3H).

Step F. Ethyl 2-(7-fluoro-6-hydroxy-3-oxo-2H-benzo[b][1,4]oxazin-4(3H)-yl)propanoate

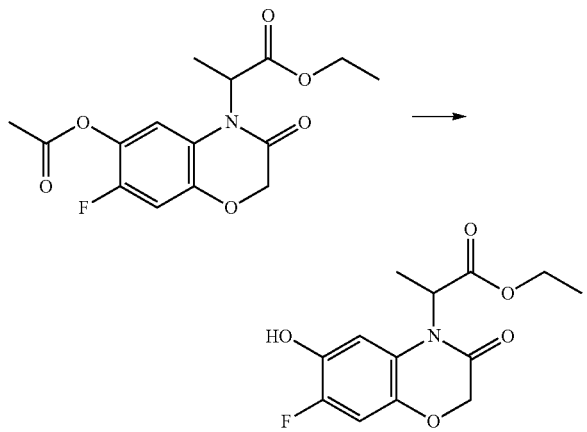

To a solution of ethyl 2-(6-acetoxy-7-fluoro-3-oxo-2H-benzo[b][1,4]oxazin-4(3H)-yl)propanoate (13 g, 40.0 mmol) in THF (100 mL) was added morpholine (10.4 mL, 120 mmol) and the reaction mixture was heated at reflux for 18 h. The reaction mixture was cooled to ambient temperature, filtered and the filtrate was concentrated in vacuo. The residue was purified by column chromatography on silica gel (eluting with 5% EtOAc in petroleum ether) to give ethyl 2-(7-fluoro-6-hydroxy-3-oxo-2H-benzo[b][1,4]oxazin-4(3H)-yl)propanoate (11 g, 80%) as a white solid. $^1$H NMR (CDCl$_3$, 400 MHz): δ 6.78 (d, J=10.4 Hz, 1H), 6.49 (d, J=8.4 Hz, 1H), 5.20 (m, 2H), 4.57 (q, J=14.8 Hz, 2H), 4.20 (m, 2H), 1.58 (d, J=7.2 Hz, 3H), 1.19 (t, 3H).

Step G. 2-[7-Fluoro-6-(1-benzhydryl-3-methyl-azetidin-3-yloxy)-3-oxo-2,3-dihydro-benzo[1,4]oxazin-4-yl]-propionic acid ethyl ester

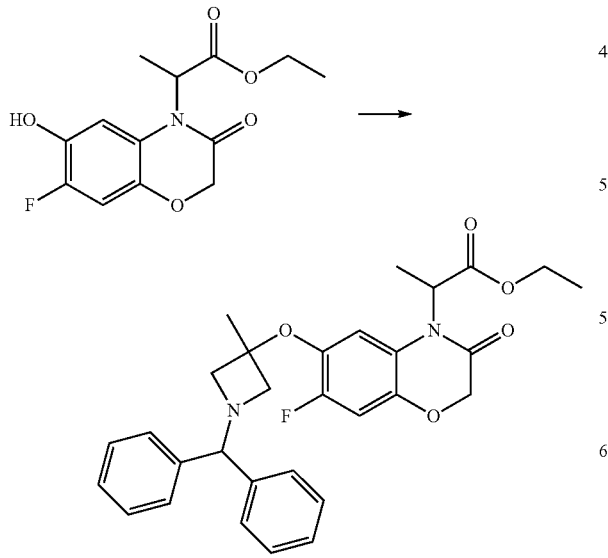

A mixture of ethyl 2-(7-fluoro-6-hydroxy-3-oxo-2,3-dihydro-benzo[1,4]oxazin-4-yl)-propionic acid ethyl ester (0.200 g, 0.706 mmol), methanesulfonic acid 1-benzhydryl-3-methyl-azetidin-3-yl ester (Preparation #3, Step B, 0.257 g, 0.777 mmol) and Cs$_2$CO$_3$ (0.460 g, 1.412 mmol) in DMF (8 mL) was stirred at 90° C. for 3 h. The reaction mixture was cooled to ambient temperature and poured into water (150 mL). The aqueous mixture was extracted with EtOAc (3×20 mL) and the combined organic phase was washed with brine (3×20 mL), dried over anhydrous Na$_2$SO$_4$, filtered and evaporated in vacuo. The residue was purified by column chromatography on silica gel (eluting with 5-10% EtOAc in petroleum ether) to give 2-[7-fluoro-6-(1-benzhydryl-3-methyl-azetidin-3-yloxy)-3-oxo-2,3-dihydro-benzo[1,4]oxazin-4-yl]-propionic acid ethyl ester as a white solid (0.280 g, 76%). $^1$H NMR (CDCl$_3$, 400 MHz): δ 7.44 (m, 4H), 7.31 (m, 2H), 7.29 (m, 2H), 7.27 (m, 2H), 6.87 (d, J=10.4 Hz, 1H), 6.22 (d, J=7.6 Hz, 1H), 5.45 (q, J=7.2 Hz, 1H), 4.55 (d, J=15.2 Hz, 2H), 4.41 (s, 1H), 3.98 (q, J=7.2 Hz, 2H), 3.34 (d, J=7.6 Hz, 2H), 3.19 (d, J=7.6 Hz, 2H), 1.59 (s, 3H), 1.56 (d, J=7.2 Hz, 3H), 1.16 (t, J=7.2 Hz, 3H).

Step H. 2-[7-Fluoro-6-(3-methyl-azetidin-3-yloxy)-3-oxo-2,3-dihydro-benzo[1,4]oxazin-4-yl]-propionic acid ethyl ester

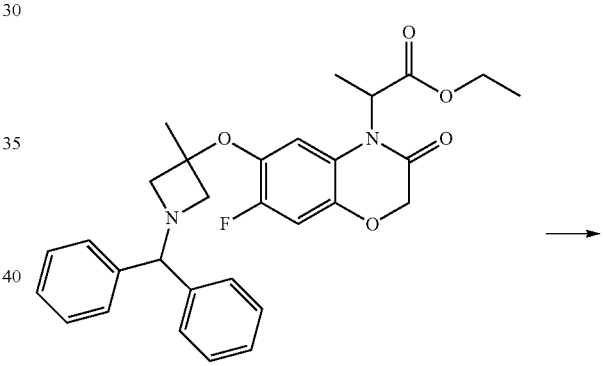

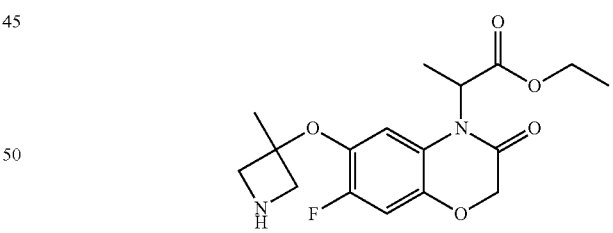

A suspension of 2-[7-fluoro-6-(1-benzhydryl-3-methyl-azetidin-3-yloxy)-3-oxo-2,3-dihydro-benzo[1,4]oxazin-4-yl]-propionic acid ethyl ester (0.280 g, 0.540 mmol) and Pd(OH)$_2$/C (10%, 0.140 g, 0.1 mmol) in EtOH (15 mL) was stirred under H$_2$ (50 psi) at ambient temperature overnight. The reaction mixture was filtered and the filtrate was evaporated in vacuo to give 2-[7-fluoro-6-(3-methyl-azetidin-3-yloxy)-3-oxo-2,3-dihydro-benzo[1,4]oxazin-4-yl]-propionic acid ethyl ester (0.275 g, crude) as an oil, which was used in the next step directly. LC/MS (Table 1, Method 3) R$_t$=1.026 min.; MS m/z: 353 [M+H]$^+$.

Step I. 3-[4-(1-Ethoxycarbonyl-ethyl)-7-fluoro-3-oxo-3,4-dihydro-2H-benzo[1,4]oxazin-6-yloxy]-3-methyl-azetidine-1-carboxylic acid tert-butyl ester

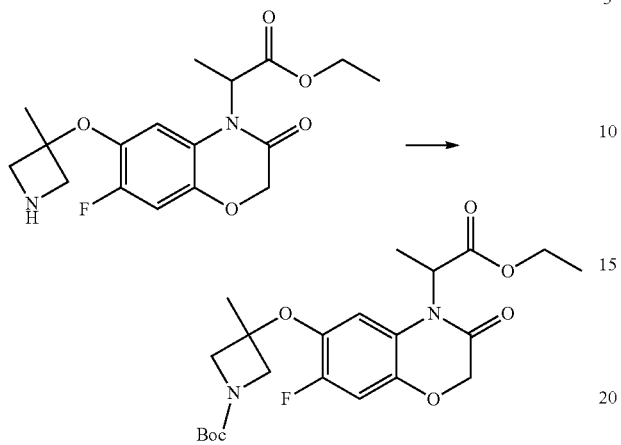

To a solution of 2-[7-fluoro-6-(3-methyl-azetidin-3-yloxy)-3-oxo-2,3-dihydro-benzo[1,4]oxazin-4-yl]-propionic acid ethyl ester (0.275 g, crude from previous step) in THF (10 mL) was added aqueous NaOH solution (2M, 0.78 mL) and Boc$_2$O (0.204 g, 0.937 mmol). The mixture was stirred at ambient temperature overnight. The solvent was removed in vacuo and the residue was purified by column chromatography on silica gel (eluting with 5-10% EtOAc in petroleum ether) to give 3-[4-(1-ethoxycarbonyl-ethyl)-7-fluoro-3-oxo-3,4-dihydro-2H-benzo[1,4]oxazin-6-yloxy]-3-methyl-azetidine-1-carboxylic acid tert-butyl ester as a white solid (0.164 g, 67% over two steps). $^1$H NMR (CDCl$_3$, 400 MHz): δ 6.83 (d, J=10.8 Hz, 1H), 6.35 (d, J=8.0 Hz, 1H), 5.45 (q, J=7.2 Hz, 1H), 4.58 (d, J=14.8, 2H), 4.25 (q, J=7.2 Hz, 2H), 4.15 (m, 2H), 3.85 (m, 2H), 1.61 (s, 3H), 1.59 (d, J=7.2 Hz, 3H), 1.45 (s, 9H), 1.24 (t, J=7.2 Hz, 3H).

Step J. 3-[4-(1-Ethoxycarbonyl-ethyl)-7-fluoro-3-thioxo-3,4-dihydro-2H-benzo[1,4]oxazin-6-yloxy]-3-methyl-azetidine-1-carboxylic acid tert-butyl ester

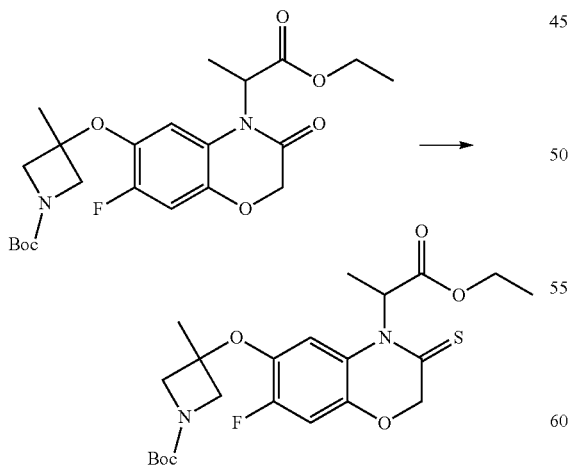

To a solution of 3-[4-(1-ethoxycarbonyl-ethyl)-7-fluoro-3-oxo-3,4-dihydro-2H-benzo[1,4]oxazin-6-yloxy]-3-methyl-azetidine-1-carboxylic acid tert-butyl ester (0.164 g, 0.362 mmol) in toluene (3 mL) and DME (3 mL) was added Lawesson's reagent (0.117 g, 0.290 mmol) and the mixture was heated to reflux for 4 h. The mixture was cooled to ambient temperature and concentrated in vacuo. The residue was purified by column chromatography on silica gel (eluting with 5% to 10% EtOAc in petroleum ether) to give 3-[4-(1-ethoxycarbonyl-ethyl)-7-fluoro-3-thioxo-3,4-dihydro-2H-benzo[1,4]oxazin-6-yloxy]-3-methyl-azetidine-1-carboxylic acid tert-butyl ester (0.080 g, 47%) as a pale yellow solid. $^1$H NMR (CDCl$_3$, 400 MHz): δ 6.82 (d, J=10.0 Hz, 1H), 6.72 (brs, 1H), 6.47 (d, J=6.8 Hz, 1H), 4.89 (d, J=13.2 Hz, 2H), 4.16 (m, 4H), 3.85 (m, 2H), 1.64 (d, J=7.2 Hz, 3H), 1.56 (s, 3H), 1.43 (s, 9H), 1.16 (t, J=6.8 Hz, 3H).

Step K. 3-(7-Fluoro-4-methyl-3-oxo-2,3,4,10-tetrahydro-9-oxa-1,2,4a-triaza-phenanthren-6-yloxy)-3-methyl-azetidine-1-carboxylic acid tert-butyl ester

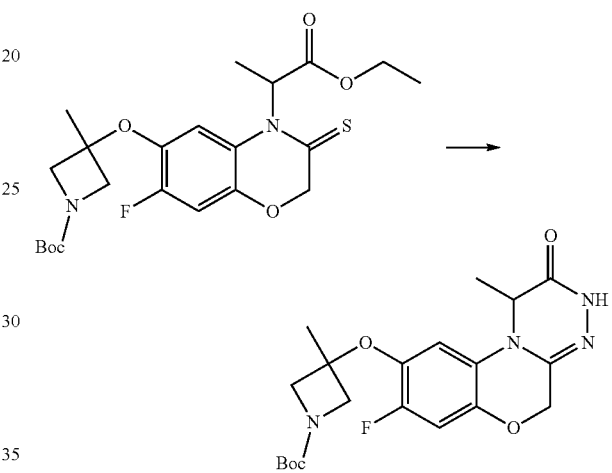

To a solution of 3-[4-(1-ethoxycarbonyl-ethyl)-7-fluoro-3-thioxo-3,4-dihydro-2H-benzo[1,4]oxazin-6-yloxy]-3-methyl-azetidine-1-carboxylic acid tert-butyl ester (0.080 g, 0.171 mmol) in EtOH (5 mL) was added hydrazine hydrate (0.085 g, 1.707 mmol) and the mixture was heated to reflux for 2 h. The reaction mixture was cooled to ambient temperature and concentrated in vacuo. The residue was purified by preparative TLC (eluting with 30% EtOAc in petroleum ether) to give 3-(7-fluoro-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.033 g, 46%) as a white solid. LC/MS (Table 1, Method 2) R$_t$=1.144 min.; MS m/z: 421 [M+H]$^+$.

Step L. 7-Fluoro-4-methyl-6-(3-methyl-azetidin-3-yloxy)-2,10-dihydro-9-oxa-1,2,4a-triaza-phenanthren-3-one trifluoroacetic acid

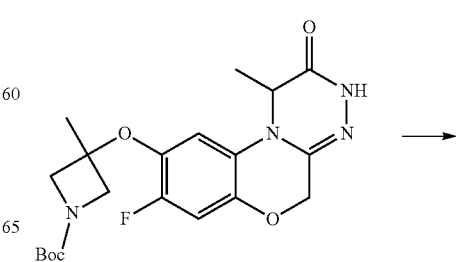

-continued

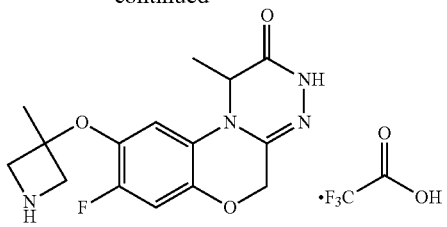

To a solution of 3-(7-fluoro-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.033 g, 0.078 mmol) in DCM (2 mL) was added TFA (0.5 mL) dropwise and the mixture was stirred at ambient temperature for 2 h. The solvent was removed in vacuo to give 7-fluoro 4-methyl-6-(3-methyl-azetidin-3-yloxy)-2,10-dihydro-9-oxa-1,2,4a-triaza-phenanthren-3-one trifluoroacetic acid as a white solid (0.017 g, 67%). LC/MS (Table 1, Method 5) $R_t$=1.806 min; MS m/z: 321 [M+H]$^+$.

Example #81

4-Methyl-6-(3-methyl-azetidin-3-ylamino)-7-trifluoromethyl-2,10-dihydro-9-oxa-1,2,4a-triaza-phenanthren-3-one

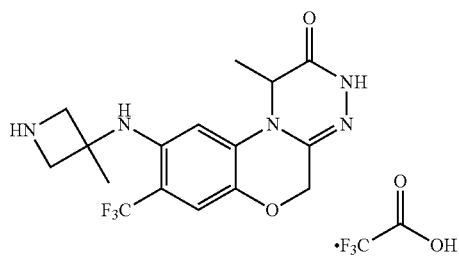

Step A. 3-Methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester

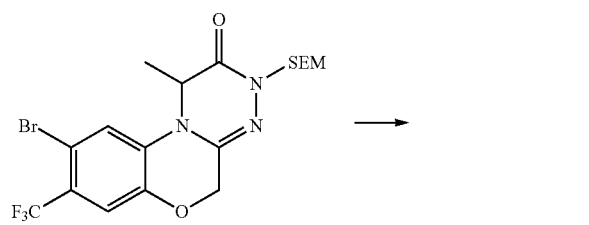

A mixture of 6-bromo-4-methyl-7-trifluoromethyl-2-(2-trimethylsilanyl-ethoxymethyl)-2,10-dihydro-9-oxa-1,2,4a-triaza-phenanthren-3-one (Example #53, Step E, 0.110 g, 0.223 mmol), tert-butyl 3-amino-3-methylazetidine-1-carboxylate (0.062 g, 0.334 mmol), Pd(OAc)$_2$ (0.010 g, 0.045 mmol), cesium carbonate (0.109 g, 0.334 mmol) and BINAP (0.042 g, 0.067 mmol) in toluene (5 mL) was heated at reflux for 5 h. The reaction mixture was cooled to ambient temperature and filtered. The filtrate was concentrated and the residue was purified by column chromatography on silica gel (eluting with 20% EtOAc in petroleum ether) to give 3-methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (0.090 g, 67%) as a white solid. $^1$H NMR (CDCl$_3$, 400 MHz): δ 7.13 (s, 1H), 5.93 (s, 1H), 5.10 (q, J=10.4 Hz, 2H), 4.62 (d, J=12.8 Hz, 1H), 4.58 (m, 1H), 4.49 (d, J=12.8 Hz, 1H), 4.37 (s, 1H), 4.00 (m, 2H), 3.95 (m, 2H), 3.66 (t, J=8.0 Hz, 2H), 1.63 (s, 3H), 1.47 (d, J=6.8 Hz, 3H) 1.45 (s, 9H), 0.99 (m, 2H), 0.00 (s, 9H).

Step B. 3-Methyl-3-(4-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester

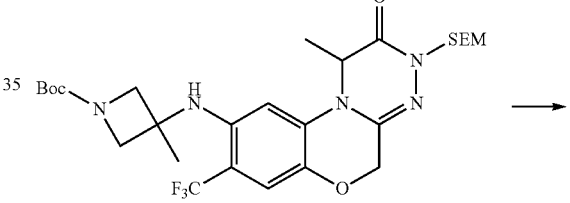

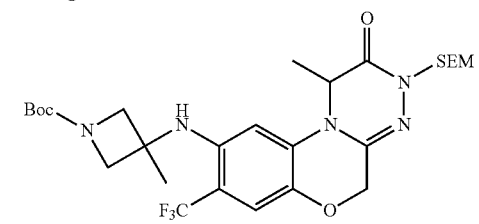

To a solution of 3-methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (0.085 g, 0.142 mmol) in THF (5 mL) was added a solution of TBAF in THF (1M, 0.709 mL, 0.709 mmol). The reaction mixture was heated to reflux overnight. The reaction mixture was cooled to ambient temperature and the solvent was removed in vacuo. The residue was purified by preparative HPLC (Table 3, Method 9) to give 3-methyl-3-(4-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester as a pale yellow solid (0.010 g, 15%). LC/MS (Table 1, Method 5) $R_t$=1.207 min; MS m/z: 492 [M+23]$^+$.

Step C. 4-Methyl-6-(3-methyl-azetidin-3-ylamino)-7-trifluoromethyl-2,10-dihydro-9-oxa-1,2,4a-triaza-phenanthren-3-one trifluoroacetic acid

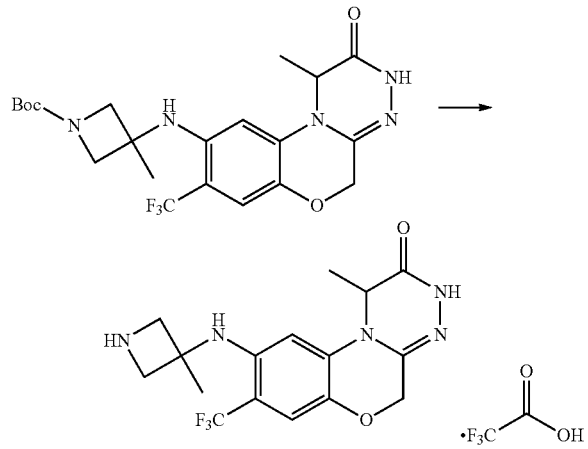

A solution of 3-methyl-3-(4-methyl-3-oxo-7-trifluoromethyl-2,3,4,10-tetrahydro-9-oxa-1,2,4a-triaza-phenanthren-6-ylamino)-azetidine-1-carboxylic acid tert-butyl ester (0.010 g, 0.021 mmol) in DCM (1 mL) and TFA (0.25 mL) was stirred for 1 h at ambient temperature. The solvent was removed in vacuo and the residue was purified by preparative HPLC (Table 3, Method 10) to give 4-methyl-6-(3-methyl-azetidin-3-ylamino)-7-trifluoromethyl-2,10-dihydro-9-oxa-1,2,4a-triaza-phenanthren-3-one trifluoroacetic acid as a white solid (0.0045 g, 44%). LC/MS (Table 1, Method 4) $R_t$=1.441 min; MS m/z: 370 [M+H]$^+$.

Example #82

6-(Azetidin-3-yloxy)-7-isopropyl-4-methyl-2,10-dihydro-9-oxa-1,2,4a-triaza-phenanthren-3-one trifluoroacetic acid

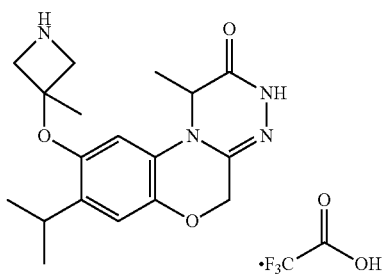

Step A. 3-(7-Bromo-4-methyl-3-oxo-2,3,4,10-tetrahydro-9-oxa-1,2,4a-triaza-phenanthren-6-yloxy)-3-methyl-azetidine-1-carboxylic acid tert-butyl ester

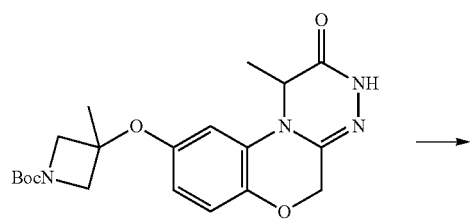

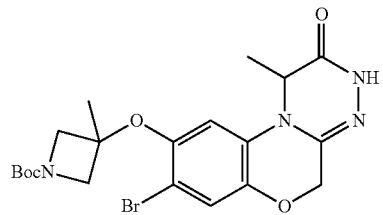

To a solution of 3-(4-methyl-3-oxo-2,3,4,10-tetrahydro-9-oxa-1,2,4a-triaza-phenanthren-6-yloxy)-azetidine-1-carboxylic acid tert-butyl ester (Example #69, Step E, 0.400 g, 0.994 mmol) in DCM (4 mL) and MeOH (2 mL) was added tetra-N-butylammonium tribromide (0.483 g, 0.994 mmol) and the mixture was stirred at ambient temperature for 2 h. The solvent was removed in vacuo and the residue was purified by column chromatography on silica gel (eluting with 25% EtOAc in petroleum ether) to give 3-(7-bromo-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.422 g, 88%). LC/MS (Table 1, Method 2) $R_t$=1.198 min.; MS m/z: 481/483 [M+H]$^+$ Step B. 3-(7-Isopropenyl-4-methyl-3-oxo-2,3,4,10-tetrahydro-9-oxa-1,2,4a-triaza-phenanthren-6-yloxy)-3-methyl-azetidine-1-carboxylic acid tert-butyl ester

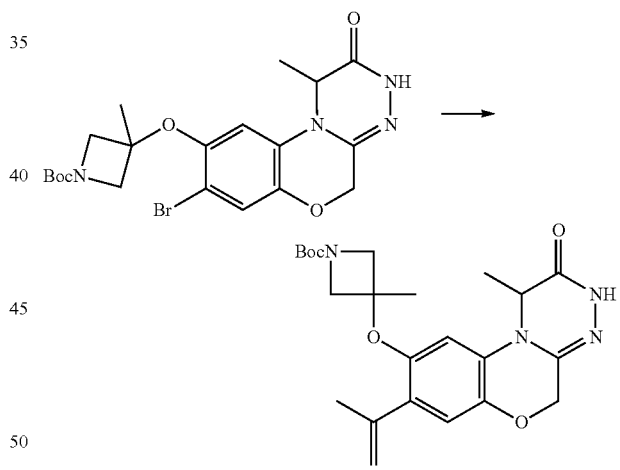

A mixture of 3-(7-bromo-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.080 g, 0.166 mmol), 4,4,5,5-tetramethyl-2-(prop-1-en-2-yl)-1,3,2-dioxaborolane (0.084 g, 0.499 mmol), $K_2CO_3$ (0.046 g, 0.332 mmol) and Pd(dppf)Cl$_2$.CH$_2$Cl$_2$ (0.014 g, 0.017 mmol) in dioxane (3 mL) and H$_2$O (0.5 mL) was stirred at 90° C. for 15 h. The solvent was removed in vacuo and the residue was purified by preparative TLC (eluting with 30% EtOAc in petroleum ether) to give 3-(7-isopropenyl-4-methyl-3-oxo-2,3,4,10-tetrahydro-9-oxa-1,2,4a-triaza-phenanthren-6-yloxy)-3-methyl-azetidine-1-carboxylic acid tert-butyl ester as a white solid (0.055 g, 75%). LC/MS (Table 1, Method 2) $R_t$=1.240 min.; MS m/z: 443 [M+H]$^+$.

Step C. 3-(7-Isopropyl-4-methyl-3-oxo-2,3,4,10-tetrahydro-9-oxa-1,2,4a-triaza-phenanthren-6-yloxy)-3-methyl-azetidine-1-carboxylic acid tert-butyl ester

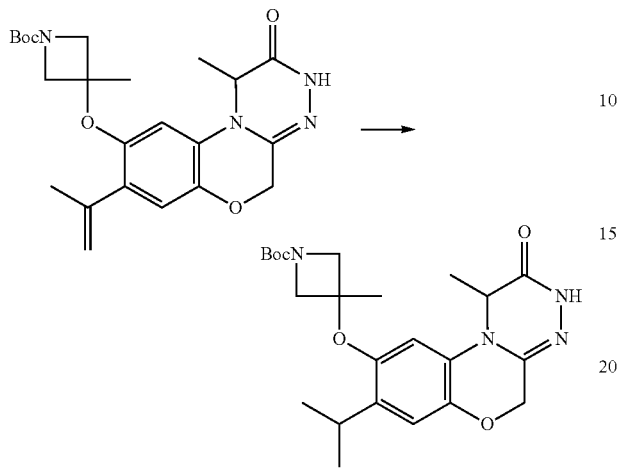

A suspension of 3-(7-isopropenyl-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.054 g, 0.122 mmol) and Pd/C (10%, 0.015 g) in MeOH (10 mL) was stirred under $H_2$ (50 psi) at ambient temperature overnight. The reaction mixture was filtered and the filtrate was evaporated in vacuo. The residue was purified by preparative TLC (eluting with 30% EtOAc in petroleum ether) to give 3-(7-isopropyl-4-methyl-3-oxo-2,3,4,10-tetrahydro-9-oxa-1,2,4a-triaza-phenanthren-6-yloxy)-3-methyl-azetidine-1-carboxylic acid tert-butyl ester as a white solid (0.049 g, 95%). LC/MS (Table 1, Method 2) $R_f$=1.327 min.; MS m/z: 467 $[M+23]^+$.

Step D. 7-Isopropyl-4-methyl-6-(3-methyl-azetidin-3-yloxy)-2,10-dihydro-9-oxa-1,2,4a-triaza-phenanthren-3-one trifluoroacetic acid

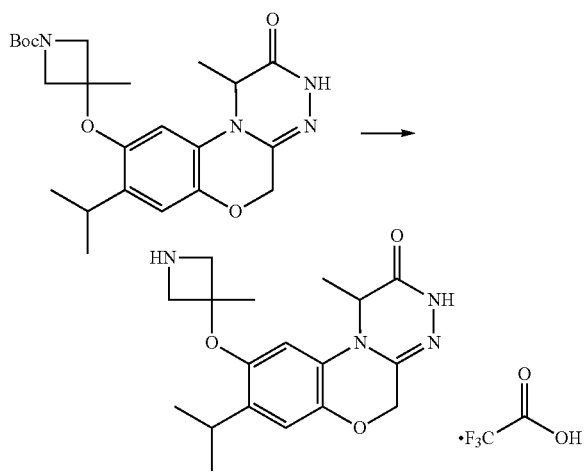

To a solution of 3-(7-isopropyl-4-methyl-3-oxo-2,3,4,10-tetrahydro-9-oxa-1,2,4a-triaza-phenanthren-6-yloxy)-3-methyl-azetidine-1-carboxylic acid tert-butyl ester (0.049 g, 0.110 mmol) in DCM (2 mL) was added TFA (0.35 mL) and the mixture was stirred at ambient temperature for 2 h. The solvent was removed in vacuo. The residue was purified by preparative HPLC (Table 3, Method 7) to give 7-isopropyl-4-methyl-6-(3-methyl-azetidin-3-yloxy)-2,10-dihydro-9-oxa-1,2,4a-triaza-phenanthren-3-one trifluoroacetic acid as a pale solid (0.042 g, 82%). LC/MS (Table 1, Method 5) $R_f$=2.233 min.; MS m/z: 345 $[M+H]^+$ Example #83

4,7-Dimethyl-6-(3-methyl-azetidin-3-yloxy)-2,10-dihydro-9-oxa-1,2,4a-triaza-phenanthren-3-one trifluoroacetic acid

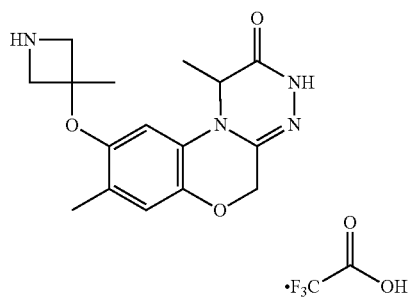

Step A. 3-(4,7-Dimethyl-3-oxo-2,3,4,10-tetrahydro-9-oxa-1,2,4a-triaza-phenanthren-6-yloxy)-3-methyl-azetidine-1-carboxylic acid tert-butyl ester

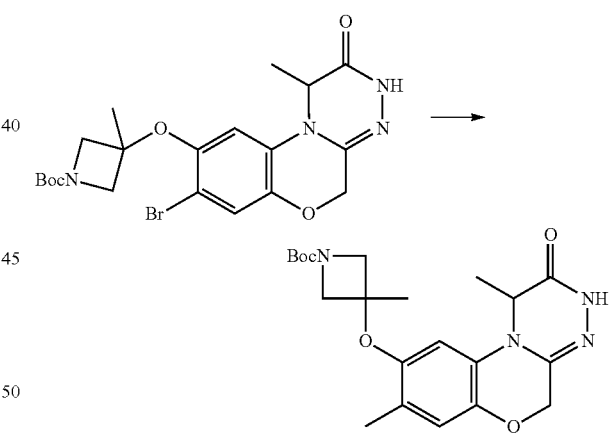

A mixture of 3-(7-bromo-4-methyl-3-oxo-2,3,4,10-tetrahydro-9-oxa-1,2,4a-triaza-phenanthren-6-yloxy)-3-methyl-azetidine-1-carboxylic acid tert-butyl ester (Example #82, Step A, 0.032 g, 0.066 mmol), 2,4,6-trimethyl-cyclotriboroxane (0.025 g, 0.199 mmol), $K_2CO_3$ (0.018 g, 0.133 mmol) and Pd(dppf)$Cl_2$·$CH_2Cl_2$ (0.006 g, 0.007 mmol) in dioxane (3 mL) and water (0.5 mL) was stirred at 110° C. for 4 h. The solvent was removed in vacuo and the residue was purified by preparative TLC (eluting with 30% EtOAc in petroleum ether) to give 3-(4,7-dimethyl-3-oxo-2,3,4,10-tetrahydro-9-oxa-1,2,4a-triaza-phenanthren-6-yloxy)-3-methyl-azetidine-1-carboxylic acid tert-butyl ester as a white solid (0.024 g, 87%). LC/MS (Table 1, Method 2) $R_f$=1.160 min.; MS m/z: 417 $[M+H]^+$.

Step B. 4,7-Dimethyl-6-(3-methyl-azetidin-3-yloxy)-2,10-dihydro-9-oxa-1,2,4a-triaza-phenanthren-3-one trifluoroacetic acid

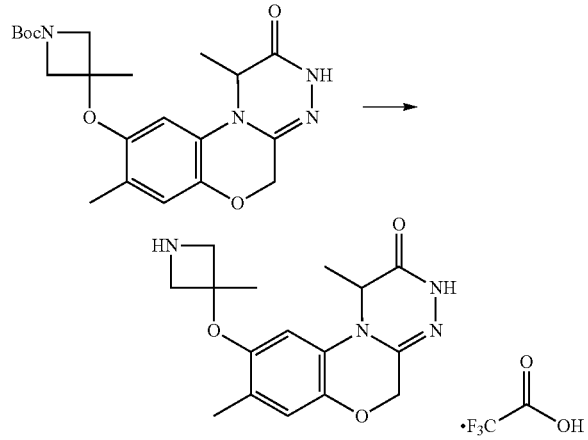

To a solution of 3-(4,7-dimethyl-3-oxo-2,3,4,10-tetrahydro-9-oxa-1,2,4a-triaza-phenanthren-6-yloxy)-3-methyl-azetidine-1-carboxylic acid tert-butyl ester (0.024 g, 0.058 mmol) in DCM (2 mL) was added TFA (0.35 mL) and the mixture was stirred at ambient temperature for 2 h. The solvent was removed in vacuo. The residue was purified by preparative HPLC (Table 3, Method 6) to give 4,7-dimethyl-6-(3-methyl-azetidin-3-yloxy)-2,10-dihydro-9-oxa-1,2,4a-triaza-phenanthren-3-one trifluoroacetic acid as a pale solid (0.008 g, 44%). LC/MS (Table 1, Method 5) $R_t$=1.913 min.; MS m/z: 317 [M+H]$^+$

Example #84

8-Fluoro-1-methyl-9-((3-methylazetidin-3-yl)amino)-3,5-dihydrobenzo[5,6][1,4]oxazino[3,4-c][1,2,4]triazin-2(1H)-one trifluoroacetic acid

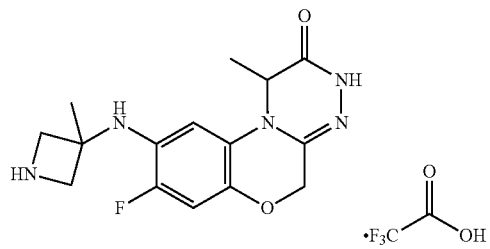

Step A. 6-(1-Benzhydryl-3-methyl-azetidin-3-ylamino)-7-fluoro-4-methyl-2,10-dihydro-9-oxa-1,2,4a-triaza-phenanthren-3-one

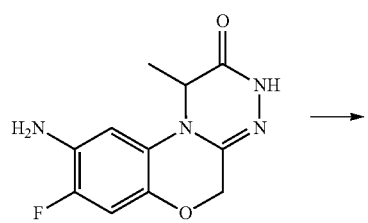

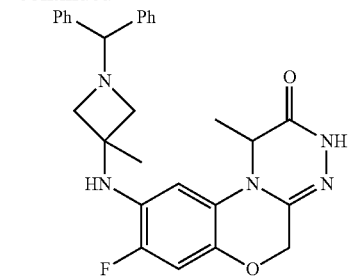

A mixture of 6-amino-7-fluoro-4-methyl-2,10-dihydro-9-oxa-1,2,4a-triaza-phenanthren-3-one (Example #56, Step F, 0.100 g, 0.400 mmol), methanesulfonic acid 1-benzhydryl-3-methyl-azetidin-3-yl ester (Preparation #3, Step B, 0.159 g, 0.480 mmol) and K$_2$CO$_3$ (0.166 g, 1.199 mmol) in DMF (2 mL) was stirred at 80° C. overnight. The reaction mixture was cooled to ambient temperature and poured into water (8 mL). The aqueous mixture was extracted with EtOAc (3×10 mL) and the combined organic phase was washed with brine (3×10 mL), dried over anhydrous Na$_2$SO$_4$, filtered and evaporated in vacuo. The residue was purified by column chromatography on silica gel (eluting with 5-10% EtOAc in petroleum ether) to give 6-(1-benzhydryl-3-methyl-azetidin-3-ylamino)-7-fluoro-4-methyl-2,10-dihydro-9-oxa-1,2,4a-triaza-phenanthren-3-one as a white solid (0.055 g, 28%). LC/MS (Table 1, Method 2) $R_t$=1.199 min.; MS m/z: 486 [M+H]$^+$.

Step B. 8-Fluoro-1-methyl-9-((3-methylazetidin-3-yl)amino)-3,5-dihydrobenzo[5,6][1,4]oxazino[3,4-c][1,2,4]triazin-2(1H)-one trifluoroacetic acid

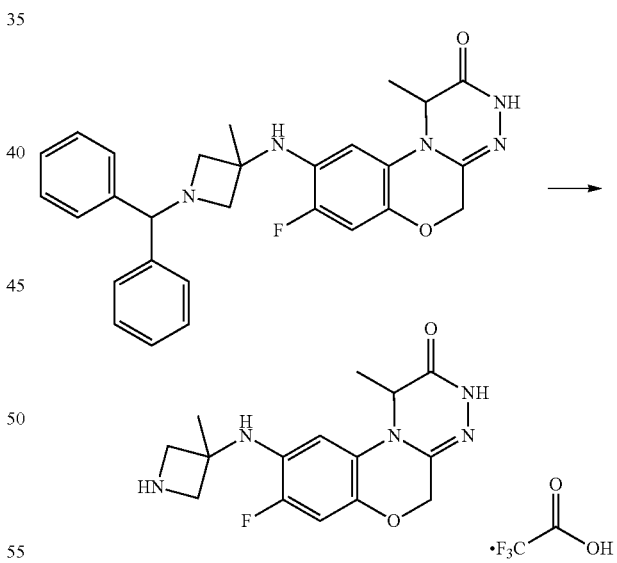

To a solution of 9-((1-benzhydryl-3-methylazetidin-3-yl)amino)-8-fluoro-1-methyl-3,5-dihydrobenzo[5,6][1,4]oxazino[3,4-c][1,2,4]triazin-2(1H)-one (0.055 g, 0.113 mmol) in EtOH (4 mL) and THF (1 mL) was added Pd(OH)$_2$/C (10%, 0.100 g, 0.07 mmol) under an atmosphere of argon and the mixture was stirred at ambient temperature for 18 h under an atmosphere of H$_2$ (50 psi). The mixture was filtered and the filtrate was concentrated in vacuo. The residue was purified by preparative HPLC (Table 3, Method 5) to give 8-fluoro-1-methyl-9-((3-methylazetidin-3-yl)amino)-3,5-dihydrobenzo[5,6][1,4]oxazino[3,4-c][1,2,4]-triazin-2(1H)-one trifluoroacetic acid as a pale solid (0.015 g, 31%). LC/MS (Table 1, Method 5) $R_t$=1.472 min; MS m/z: 320 [M+H]$^+$.

Example #85

6-(Azetidin-3-ylamino)-7-bromo-4-methyl-2,10-dihydro-9-oxa-1,2,4a-triaza-phenanthren-3-one trifluoroacetic acid

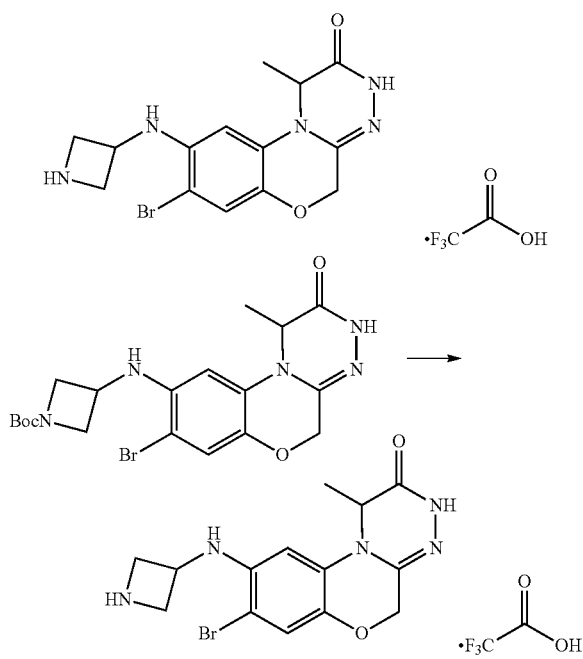

To a solution of 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example 1, Step B, 0.053 g, 0.114 mmol) in DCM (2 mL) was added TFA (0.5 mL) and the mixture was stirred at ambient temperature for 2 h. The solvent was removed in vacuo to give 6-(azetidin-3-ylamino)-7-bromo-4-methyl-2,10-dihydro-9-oxa-1,2,4a-triaza-phenanthren-3-one trifluoroacetic acid (0.040 g, 76%) as a white solid. LC/MS (Table 1, Method 5) $R_t$=1.865 min.; MS m/z: 366 [M+H]$^+$.

Example #86

9-(2-Benzylpiperidin-4-yl)-1-methyl-3,5-dihydrobenzo[5,6][1,4]oxazino[3,4-c][1,2,4]triazin-2(1H)-one trifluoroacetic acid

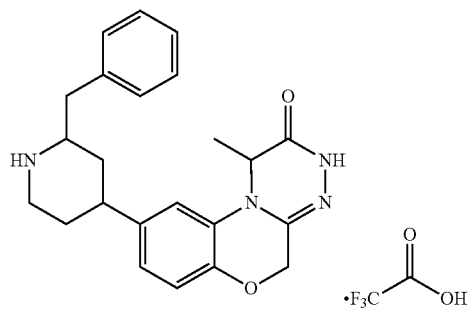

Step A. tert-Butyl 6-benzyl-4-(((trifluoromethyl)sulfonyl)oxy)-5,6-dihydropyridine-1(2H)-carboxylate

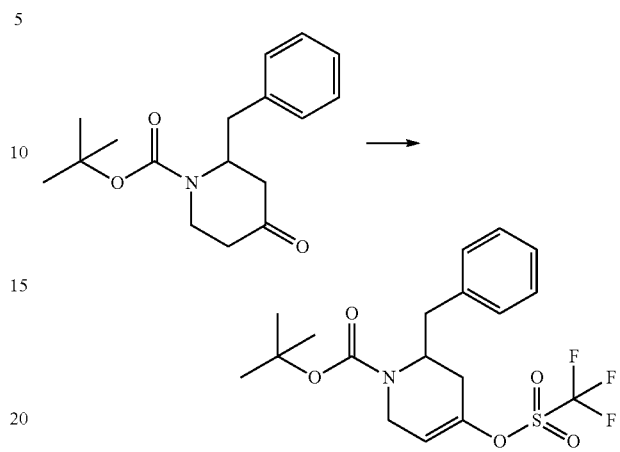

To a solution of 2-benzylpiperidin-4-one (BETAPHARMA, 0.868 g, 3 mmol) in anhydrous THF (10 mL) was added LiHMDS (1M solution in THF, 6 mL) dropwise at −78° C. After addition, the mixture was allowed to warm to −30° C. and stirred for 20 min. The mixture was cooled to −78° C. again and 1,1,1-trifluoro-N-phenyl-N-(trifluoromethylsulfonyl)methanesulfonamide (2.144 g, 6 mmol) was added. The mixture was allowed to warm to ambient temperature and stirred for 2 h. The solvent was removed in vacuo and the residue was purified by flash column chromatography on silica gel (eluting with 2% EtOAc in petroleum ether) to give tert-butyl 6-benzyl-4-(((trifluoromethyl)sulfonyl)oxy)-5,6-dihydropyridine-1(2H)-carboxylate as an oil (0.72 g, crude), which was used in the next step without further purification. TLC (eluting with 10% EtOAc/PE) $R_f$=0.5.

Step B. tert-Butyl 6-benzyl-4-(1-methyl-2-oxo-1,2,3,5-tetrahydrobenzo[5,6][1,4]oxazino[3,4-c][1,2,4]triazin-9-yl)-5,6-dihydropyridine-1(2H)-carboxylate

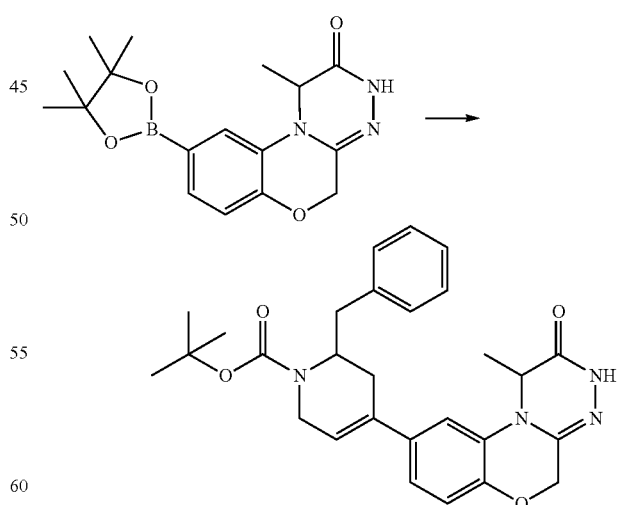

A mixture of methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (prepared from the corresponding bromide (Preparation #1, Step D) following similar procedure as describe in Example #109, Step B, 0.103 g, 0.3 mmol), tert-butyl 6-benzyl-4-(trifluoromethylsulfonyloxy)-5,6-dihydropyridine-1(2H)-carboxylate (0.253 g, 0.6 mmol), Pd(dppf)Cl₂—CH₂Cl₂ complex (0.073 g, 0.09 mmol) and K₂CO₃ (0.124 g, 0.9 mmol) in 1,4-dioxane (2 mL) and water (0.5 mL) was heated at 90° C. for 10 h. The reaction was cooled to ambient temperature. The solvent was removed in vacuo and the residue was purified by PTLC (eluting with 50% EtOAc in petroleum ether) to give tert-butyl 6-benzyl-4-(1-methyl-2-oxo-1,2,3,5-tetrahydrobenzo[5,6][1,4]oxazino[3,4-c][1,2,4]triazin-9-yl)-5,6-dihydropyridine-1(2H)-carboxylate (0.147 g, 99%). LC/MS (Table 1, Method 2) $R_t$=1.308 min; MS m/z: 489 [M+H]⁺.

Step C. tert-Butyl 2-benzyl-4-(1-methyl-2-oxo-1,2,3,5-tetrahydrobenzo[5,6][1,4]oxazino[3,4-e][1,2,4]triazin-9-yl)piperidine-1-carboxylate

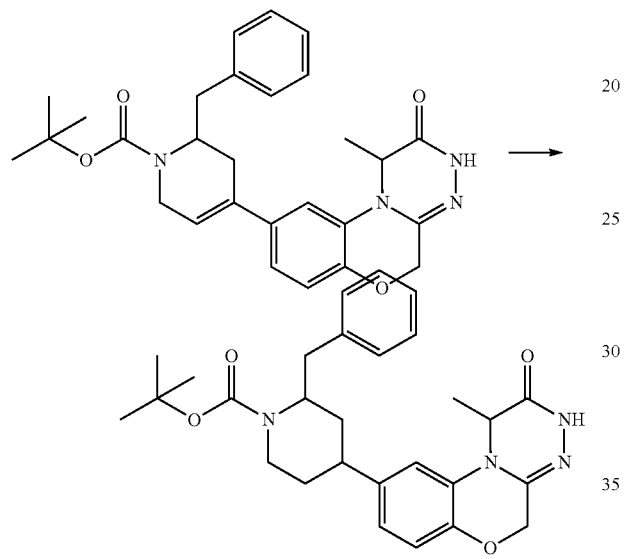

To a solution of tert-butyl 6-benzyl-4-(1-methyl-2-oxo-1,2,3,5-tetrahydrobenzo[5,6][1,4]oxazino[3,4-c][1,2,4]triazin-9-yl)-5,6-dihydropyridine-1(2H)-carboxylate (0.147 g, 0.3 mmol) in MeOH (30 mL) was added Pd/C (10%, 0.096 g, 0.1 mmol) and the mixture was stirred under an atmosphere of H₂ (50 psi) for 12 h. After filtration, the filtrate was concentrated in vacuo to give tert-butyl 2-benzyl-4-(1-methyl-2-oxo-1,2,3,5-tetrahydrobenzo[5,6][1,4]oxazino[3,4-c][1,2,4]triazin-9-yl)piperidine-1-carboxylate (0.147 g), which was used in the next step without further purification. LC/MS (Table 1, Method 2) $R_t$=2.453 min; MS m/z: 491 [M+H]⁺.

Step D. 9-(2-Benzylpiperidin-4-yl)-1-methyl-3,5-dihydrobenzo[5,6][1,4]oxazino[3,4-e][1,2,4]triazin-2(1H)-one trifluoroacetic acid

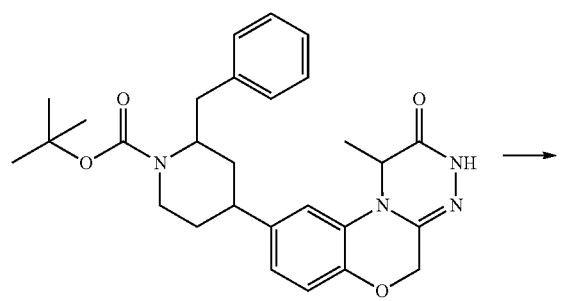

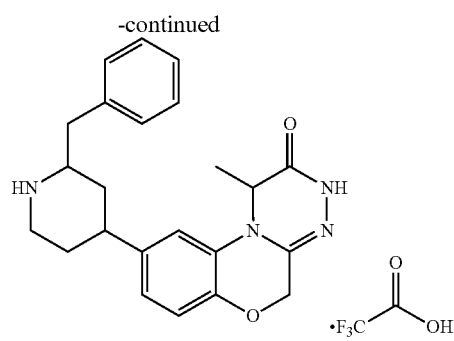

To a solution of tert-butyl 2-benzyl-4-(1-methyl-2-oxo-1,2,3,5-tetrahydrobenzo[5,6][1,4]oxazino[3,4-c][1,2,4]triazin-9-yl)piperidine-1-carboxylate (0.147 g, 0.3 mmol) in DCM (2.5 mL) was added TFA (0.5 mL) and the mixture was stirred at ambient temperature for 2 h. The solvent was removed in vacuo and EtOAc (2 mL) was added to the residue. The precipitate was collected by filtration and washed with EtOAc (1 mL) and petroleum ether (2 mL) to give 9-(2-benzylpiperidin-4-yl)-1-methyl-3,5-dihydrobenzo[5,6][1,4]oxazino[3,4-c][1,2,4]triazin-2(1H)-one trifluoroacetic acid (0.030 g, 20% yield for three steps) as a solid. LC/MS (Table 1, Method 4) $R_t$=1.651 min; MS m/z: 391 [M+H]⁺.

Example #87

6-[(1,3-Dimethyl-azetidin-3-yl)-methyl-amino]-4-methyl-7-phenyl-2,10-dihydro-9-oxa-1,2,4a-triaza-phenanthren-3-one trifluoroacetic acid

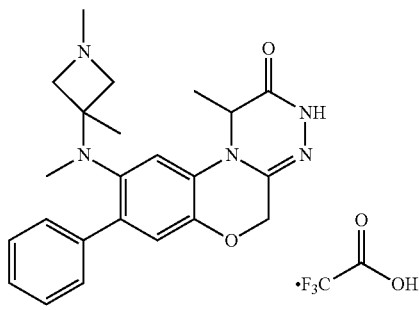

Step A. 6-[(1,3-Dimethyl-azetidin-3-yl)-methyl-amino]-4-methyl-7-phenyl-2,10-dihydro-9-oxa-1,2,4a-triaza-phenanthren-3-one trifluoroacetic acid

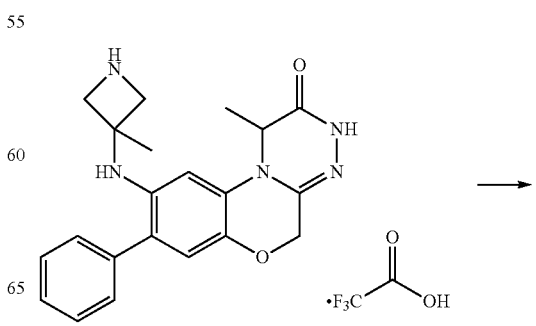

189
-continued

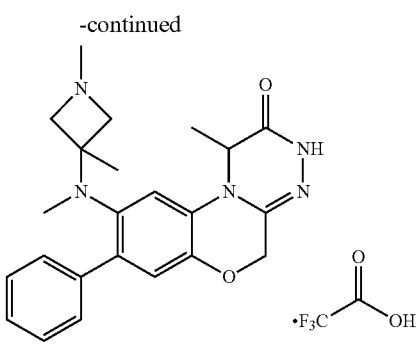

190

A mixture of paraformaldehyde (0.016 g, 0.053 mmol) in methanol (10 mL) and AcOH (1 mL) was heated to reflux overnight. The reaction was cooled to ambient temperature and 4-methyl-6-(3-methyl-azetidin-3-ylamino)-7-phenyl-2,10-dihydro-9-oxa-1,2,4a-triaza-phenanthren-3-one trifluoroacetic acid (Example #79, Step D, 0.020 g, 0.053 mmol) was added into the solution and the mixture was stirred for 2 h. Sodium cyanoborohydride (0.013 g, 0.212 mmol) was added and the mixture was stirred overnight at rt. The solvent was removed in vacuo and the residue was purified by prep-HPLC (Table 3, Method 8) to give 6-[(1,3-dimethyl-azetidin-3-yl)-methyl-amino]-4-methyl-7-phenyl-2,10-dihydro-9-oxa-1,2,4a-triaza-phenanthren-3-one trifluoroacetic acid (0.015 g, 0.036 mmol, 68%). LC/MS (Table 1, Method 4) $R_t$=1.689 min.; MS m/z: 406 [M+H]$^+$.

TABLE 12

The following analogs were prepared from 6-(1-benzhydryl-3-methyl-azetidin-3-ylamino)-7-bromo-4-methyl-2,10-dihydro-9-oxa-1,2,4a-triaza-phenanthren-3-one (Example #79, Step B) using the procedure detailed in Example #79, Steps C-D and Example #87, Step A.

| Structure | Example # | Boronic acid | $R_t$ min (method) | m/z ESI+ (M + H)$^+$ |
|---|---|---|---|---|
| 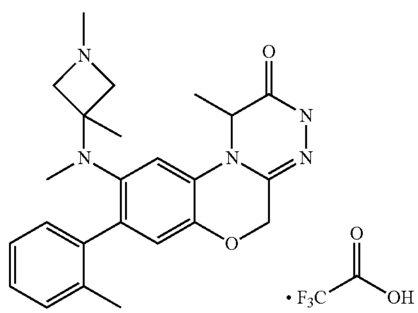 | 88 | 2-methylphenyl B(OH)$_2$ | 1.883 (Table 1, Method 4) | 420 |
| 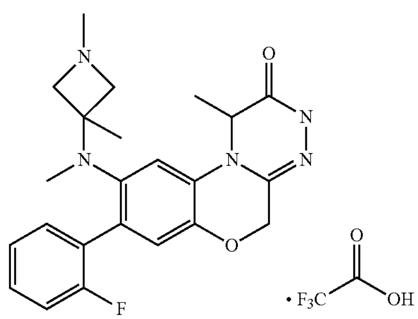 | 89 | 2-fluorophenyl B(OH)$_2$ | 1.797 (Table 1, Method 4) | 424 |
| 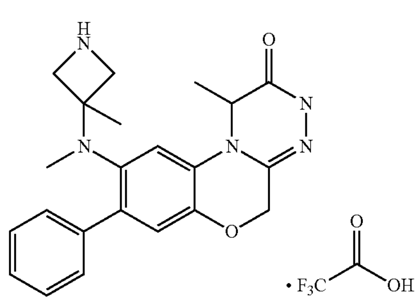 | 90 | phenyl B(OH)$_2$ | 1.801 (Table 1, Method 4) | 392 |

TABLE 13

The following analogs were prepared from 4-methyl-6-[methyl-(3-methyl-azetidin-3-yl)-amino]-7-phenyl-2,10-dihydro-9-oxa-1,2,4a-triaza-phenanthren-3-one (prepared from 6-(1-benzhydryl-3-methyl-azetidin-3-ylamino)-4-methyl-7-phenyl-2,10-dihydro-9-oxa-1,2,4a-triaza-phenanthren-3-one (Example #79, Step C) using the procedure detailed in Example #87, Step A with paraformaldehyde and Example #79, Step D) using the procedure detailed in Example #87, Step A, with the aldehyde or ketone in place of paraformaldehyde.

| Structure | Example # | Aldehyde or ketone | $R_t$ min (method) | m/z ESI+ $(M + H)^+$ |
|---|---|---|---|---|
| 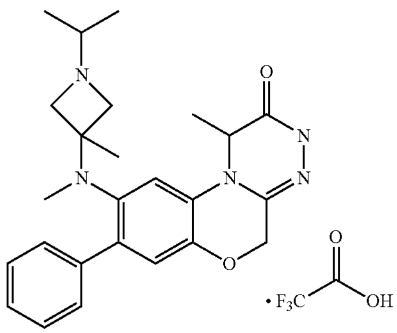 | 91 | acetone | 1.926 (Table 1, Method 4) | 434 |
| 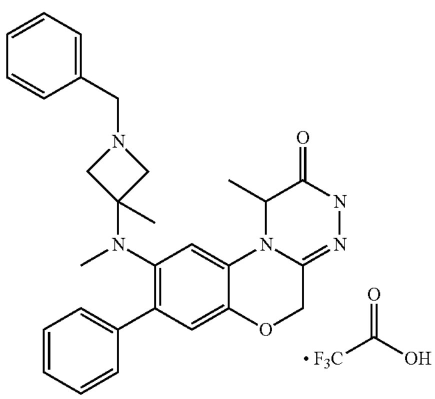 | 92 | benzaldehyde | 2.087 (Table 1, Method 4) | 482 |
| 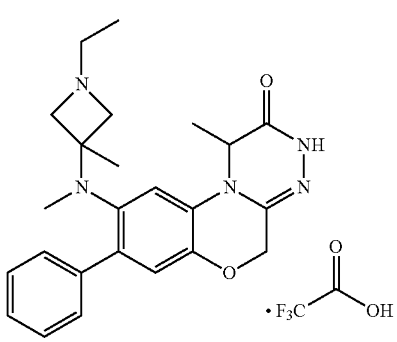 | 93 | acetaldehyde | 1.856 (Table 1, Method 4) | 420 |

TABLE 13-continued

The following analogs were prepared from 4-methyl-6-[methyl-(3-methyl-azetidin-3-yl)-amino]-7-phenyl-2,10-dihydro-9-oxa-1,2,4a-triaza-phenanthren-3-one (prepared from 6-(1-benzhydryl-3-methyl-azetidin-3-ylamino)-4-methyl-7-phenyl-2,10-dihydro-9-oxa-1,2,4a-triaza-phenanthren-3-one (Example #79, Step C) using the procedure detailed in Example #87, Step A with paraformaldehyde and Example #79, Step D) using the procedure detailed in Example #87, Step A, with the aldehyde or ketone in place of paraformaldehyde.

| Structure | Example # | Aldehyde or ketone | $R_t$ min (method) | m/z ESI+ $(M + H)^+$ |
|---|---|---|---|---|
| 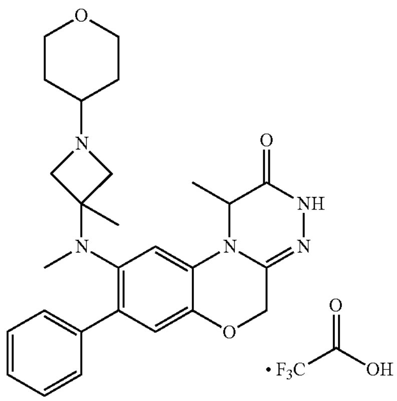 | 94 | | 1.848 (Table 1, Method 4) | 476 |
| 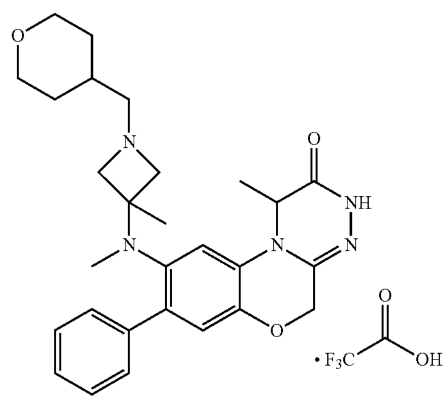 | 95 | | 1.836 (Table 1, Method 4) | 490 |

Example #96

(R)-9-(Azetidin-3-yloxy)-8-isopropyl-1-methyl-3,5-dihydrobenzo[5,6][1,4]oxazino[3,4-c][1,2,4]triazin-2(1H)-one trifluoroacetic acid Step A. 3-(7-Isopropyl-4(S)-methyl-3-oxo-2,3,4,10-tetrahydro-9-oxa-1,2,4a-triaza-phenanthren-6-yloxy)-azetidine-1-carboxylic acid tert-butyl ester and 3-(7-isopropyl-4(R)-methyl-3-oxo-2,3,4,10-tetrahydro-9-oxa-1,2,4a-triaza-phenanthren-6-yloxy)-azetidine-1-carboxylic acid tert-butyl ester

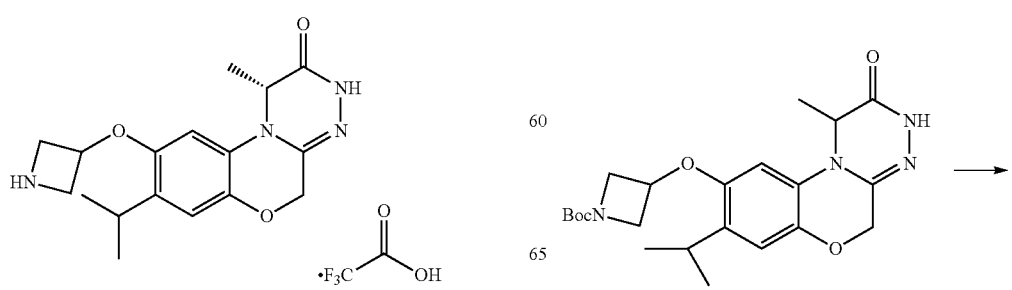

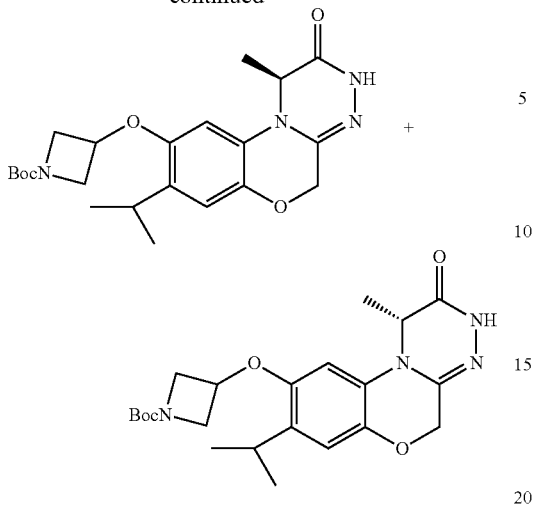

Racemic 3-(7-isopropyl-4-methyl-3-oxo-2,3,4,10-tetrahydro-9-oxa-1,2,4a-triaza-phenanthren-6-yloxy)-azetidine-1-carboxylic acid tert-butyl ester (prepared from the corresponding bromide (Example #65, Step G) with similar procedure as descried in Example #57, Step A-B, 0.090 g, 0.210 mmol) was separated by chiral SFC (Table 2, Method 7) to give 3-(7-isopropyl-4(S)-methyl-3-oxo-2,3,4,10-tetrahydro-9-oxa-1,2,4a-triaza-phenanthren-6-yloxy)-azetidine-1-carboxylic acid tert-butyl ester (Enantiomer 1, SFC (Table 1, Method 13) R$_t$=1.572 min.; 0.045 g, 50%) and 3-(7-isopropyl-4(R)-methyl-3-oxo-2,3,4,10-tetrahydro-9-oxa-1,2,4a-triaza-phenanthren-6-yloxy)-azetidine-1-carboxylic acid tert-butyl ester (Enantiomer 2, SFC (Table 1, Method 13) R$_t$=2.104 min, 0.042 g, 47%).

Step B. 6-(Azetidin-3-yloxy)-7-isopropyl-4(R)-methyl-2,10-dihydro-9-oxa-1,2,4a-triaza-phenanthren-3-one trifluoacetic acid salt

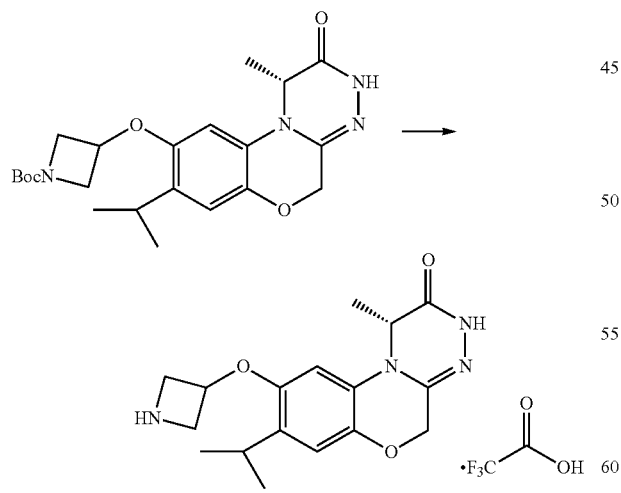

A solution of 3-(7-isopropyl-4(R)-methyl-3-oxo-2,3,4,10-tetrahydro-9-oxa-1,2,4a-triaza-phenanthren-6-yloxy)-azetidine-1-carboxylic acid tert-butyl ester (Enantiomer 2, SFC (Table 1, Method 13) R$_t$=2.104 min, 0.042 g, 0.098 mmol) in DCM (2 mL) and TFA (0.5 mL) was stirred at 25° C. for 2 h.

The solvent was removed in vacuo to give 6-(azetidin-3-yloxy)-7-isopropyl-4(R)-methyl-2,10-dihydro-9-oxa-1,2,4a-triaza-phenanthren-3-one trifluoroacetic acid (SFC (Table 1, Method 14), R$_t$=1.610 min, 0.036 g, 86%) as a pale yellow solid. LC/MS (Table 1, Method 5) R$_t$=2.077 min.; MS m/z: 331 [M+H]$^+$.

Example #97

6-(Azetidin-3-ylamino)-4-methyl-2,10-dihydro-9-thia-1,2,4a-triaza-phenanthren-3-one hydrochloric acid salt

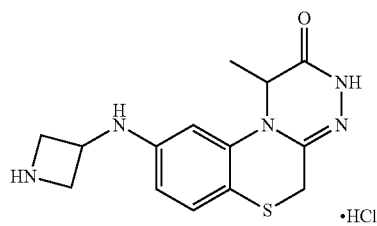 [SMILES: CC1C(=O)NN=C2CSc3ccc(NC4CNC4)cc3N21 ; Cl]

Step A. 6-Nitro-2H-benzo[b][1,4]thiazin-3(4H)-one

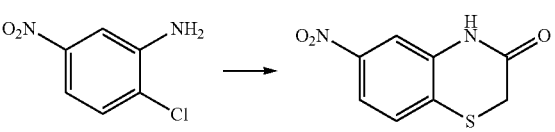 [SMILES: Nc1cc([N+](=O)[O-])ccc1Cl ; O=C1CSc2ccc([N+](=O)[O-])cc2N1]

A mixture of 2-chloro-5-nitroaniline (15 g, 87 mmol), methyl 2-mercaptoacetate (13.8 g, 130 mmol) and sodium hydroxide (10.4 g, 261 mmol) in EtOH/water (250 mL, v/v=10:1) was heated at reflux for 16 h. The reaction mixture was cooled to ambient temperature, the solvent was removed in vacuo and the residue was purified by column chromatography on silica gel (eluting with 17% EtOAc in petroleum ether) to give 6-nitro-2H-benzo[b][1,4]thiazin-3(4H)-one (2.1 g, 11%). LC/MS (Table 1, Method 2) R$_t$=0.790 min; MS m/z: 211 [M+H]$^+$.

Step B. Ethyl 2-(6-nitro-3-oxo-2H-benzo[b][1,4]thiazin-4(3H)-yl)propanoate

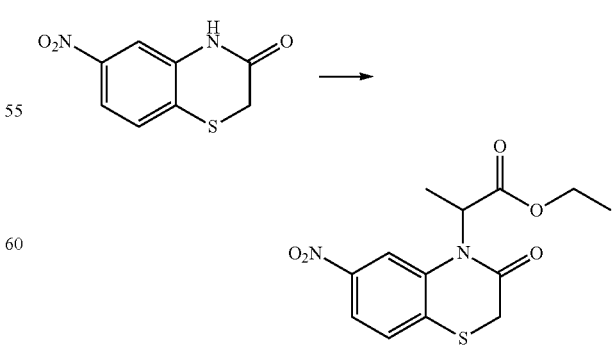

A mixture of 6-nitro-2H-benzo[b][1,4]thiazin-3(4H)-one (0.512 g, 2.436 mmol), ethyl 2-bromopropanoate (0.573 g, 3.17 mmol) and K₂CO₃ (1.01 g, 7.31 mmol) in acetone (40 mL) was heated at reflux for 16 h. After cooling to ambient temperature, the mixture was filtered and the filtrate was evaporated in vacuo. The residue was purified by column chromatography on silica gel (eluting with 9% EtOAc in petroleum ether) to give ethyl 2-(6-nitro-3-oxo-2H-benzo[b] [1,4]thiazin-4(3H)-yl)propanoate (0.376 g, 50%). TLC (eluting with 20% EtOAc/PE) R$_f$=0.6.

Step C. Ethyl 2-(6-nitro-3-thioxo-2H-benzo[b][1,4]thiazin-4(3H)-yl)propanoate

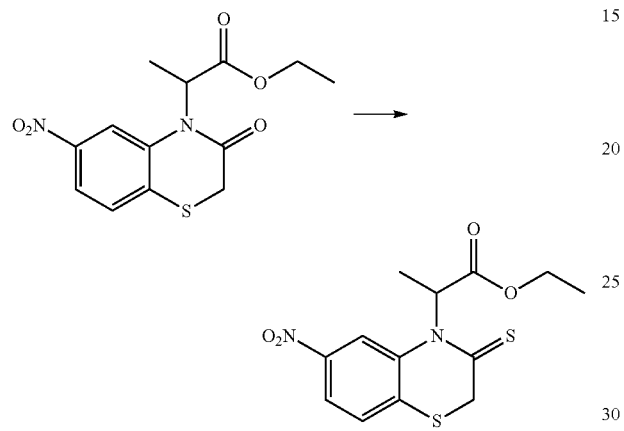

A mixture of ethyl 2-(6-nitro-3-oxo-2H-benzo[b][1,4]thiazin-4(3H)-yl)propanoate (0.189 g, 0.61 mmol) and Lawesson's reagent (0.493 g, 1.22 mmol) in toluene (40 mL) was heated at reflux for 16 h. After cooling to ambient temperature, the mixture was concentrated in vacuo. The residue was purified by column chromatography on silica gel (eluting with 8% EtOAc in petroleum ether) to give ethyl 2-(6-nitro-3-thioxo-2H-benzo[b][1,4]thiazin-4(3H)-yl)propanoate (0.109 g, 55%). TLC (eluting with 25% EtOAc in petroleum ether) R$_f$=0.3.

Step D. 1-Methyl-9-nitro-3,5-dihydrobenzo[5,6][1,4]thiazino[3,4-c][1,2,4]triazin-2(1H)-one

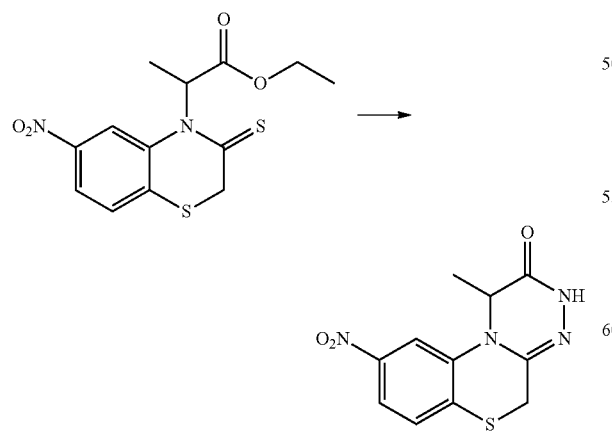

To a solution of ethyl 2-(6-nitro-3-thioxo-2H-benzo[b][1,4]thiazin-4(3H)-yl)propanoate (0.475 g, 1.455 mmol) in EtOH (30 mL) was added hydrazine hydrate (0.364 g, 7.28 mmol) and the mixture was then heated at reflux for 16 h. After cooling to ambient temperature gradually, the precipitate was collected by filtration to give 1-methyl-9-nitro-3,5-dihydrobenzo[5,6][1,4]thiazino[3,4-c][1,2,4]-triazin-2(1H)-one (0.312 g, 77%), which was used in the next step directly without further purification. TLC (eluting with 33% EtOAc in petroleum ether) R$_f$=0.3.

Step E. 9-Amino-1-methyl-3,5-dihydrobenzo[5,6][1,4]thiazino[3,4-c][1,2,4]triazin-2(1H)-one

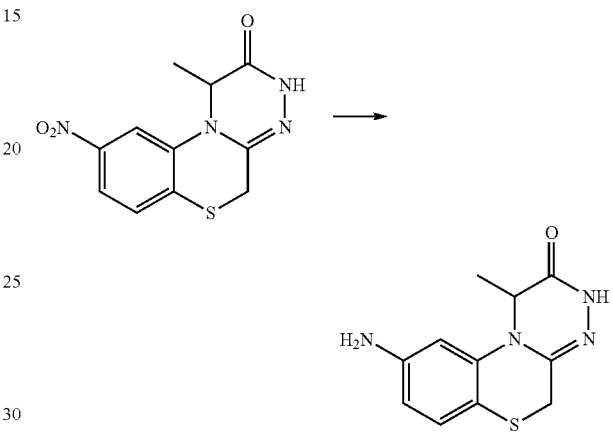

To a solution of 1-methyl-9-nitro-3,5-dihydrobenzo[5,6][1,4]thiazino[3,4-c][1,2,4]triazin-2(1H)-one (0.308 g, 1.11 mmol) in MeOH (25 mL) and THF (25 mL) was added powdered zinc (0.724 g, 11.1 mmol) and NH₄Cl (0.592 g, 11.1 mmol) and the mixture was heated at reflux for 16 h. After cooling to ambient temperature, the mixture was filtered to give crude 9-amino-1-methyl-3,5-dihydrobenzo[5,6][1,4]thiazino[3,4-c][1,2,4]triazin-2(1H)-one (100%), which was used in the next step directly without further purification. TLC (eluting with 50% EtOAc/PE) R$_f$=0.3.

Step F. tert-Butyl 3-((1-methyl-2-oxo-1,2,3,5-tetrahydrobenzo[5,6][1,4]thiazino[3,4-c][1,2,4]triazin-9-yl)amino)azetidine-1-carboxylate

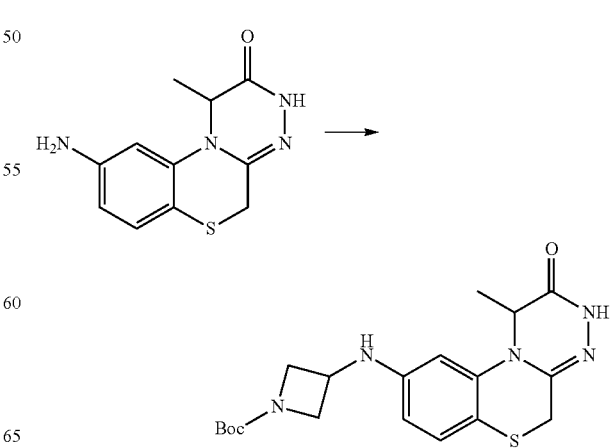

A mixture of 9-amino-1-methyl-3,5-dihydrobenzo[5,6][1,4]thiazino[3,4-c][1,2,4]triazin-2(1H)-one (0.700 g, 2.82 mmol) and tert-butyl 3-oxoazetidine-1-carboxylate (0.145 g, 8.46 mmol) in MeOH/AcOH (50 mL, v:v=10:1) was stirred for 1 h at ambient temperature. NaBH₃CN (0.007 g, 0.121 mmol) was added and the mixture was heated at 60° C. for 2 h. The reaction mixture was cooled to ambient temperature, the solvent was removed in vacuo and the residue was purified by column chromatography on silica gel (eluting with 17% EtOAc in petroleum ether) to give 3-((1-methyl-2-oxo-1,2,3,5-tetrahydrobenzo[5,6][1,4]thiazino[3,4-c][1,2,4]triazin-9-yl)amino)azetidine-1-carboxylate (0.369 g, 32%). TLC (eluting with 50% EtOAc/PE) R$_f$=0.5.

Step G. 6-(Azetidin-3-ylamino)-4-methyl-2,10-dihydro-9-thia-1,2,4a-triaza-phenanthren-3-one hydrochloric acid

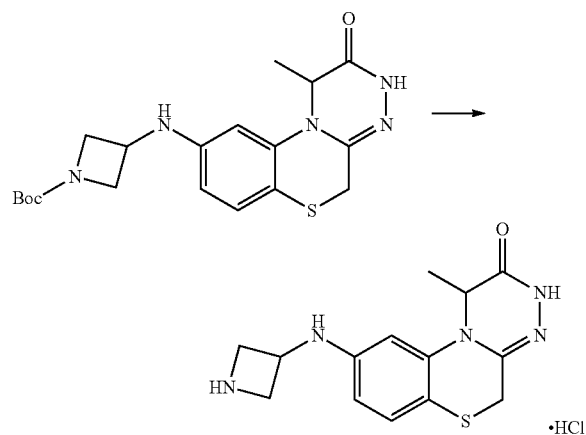

A mixture of 3-((1-methyl-2-oxo-1,2,3,5-tetrahydrobenzo[5,6][1,4]thiazino[3,4-c][1,2,4]triazin-9-yl)amino)azetidine-1-carboxylate (0.112 g, 0.278 mmol) and HCl (2N in EtOAc, 40 mL) was stirred at ambient temperature for 2 h. The solvent was removed in vacuo to give 6-(azetidin-3-ylamino)-4-methyl-2,10-dihydro-9-thia-1,2,4a-triazphenanthren-3-one hydrochloric acid (0.063 g, 74%). LC/MS (Table 1, Method 5) R$_t$=1.866 min; MS m/z: 304 [M+H]⁺

Example #98

4,7-Dimethyl-6-(3-methyl-azetidin-3-ylamino)-2,10-dihydro-9-oxa-1,2,4a-triaza-phenanthren-3-one trifluoroacetic acid

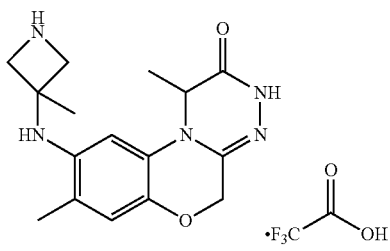

Step A. 6-(1-Benzhydryl-3-methyl-azetidin-3-ylamino)-4,7-dimethyl-2,10-dihydro-9-oxa-1,2,4a-triaza-phenanthren-3-one

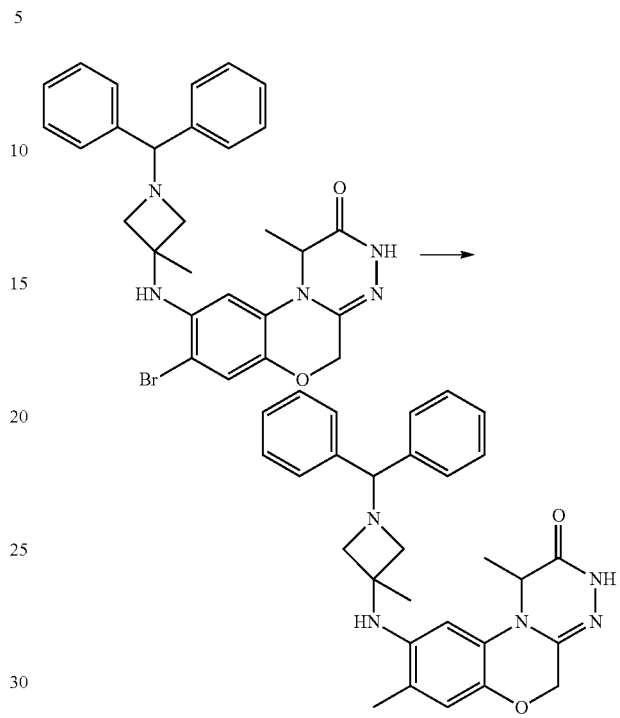

A mixture of [1,1'-bis(diphenylphosphino)ferrocene]dichloropalladium(II) (0.0598 g, 0.073 mmol), 6-(1-benzhydryl-3-methyl-azetidin-3-ylamino)-7-bromo-4-methyl-2,10-dihydro-9-oxa-1,2,4a-triaza-phenanthren-3-one (Example #79, Step B, 0.20 g, 0.366 mmol), K₂CO₃ (0.152 g, 1.098 mmol), 2,4,6-trimethyl-1,3,5,2,4,6-trioxatriborinane (0.138 g, 1.098 mmol) in water (1 mL) and dioxane (6 mL) was stirred at 120° C. overnight. The reaction mixture was cooled to ambient temperature and the solvent was removed in vacuo. The residue was purified by preparative HPLC (Table 3, Method 13) to give 6-(1-benzhydryl-3-methyl-azetidin-3-ylamino)-4,7-dimethyl-2,10-dihydro-9-oxa-1,2,4a-triaza-phenanthren-3-one (0.10 g, 56%). LC/MS (Table 1, Method 2) R$_t$=0.959 min; MS m/z: 482 [M+H]⁺.

Step B. 4,7-Dimethyl-6-(3-methyl-azetidin-3-ylamino)-2,10-dihydro-9-oxa-1,2,4a-triaza-phenanthren-3-one trifluoroacetic acid

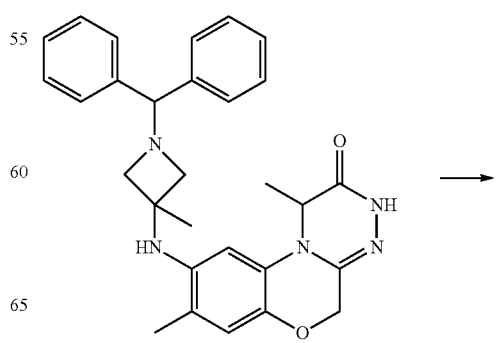

-continued

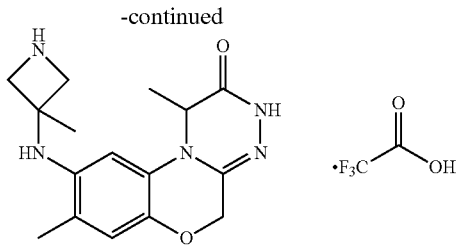

A mixture of 6-(1-benzhydryl-3-methyl-azetidin-3-ylamino)-4,7-dimethyl-2,10-dihydro-9-oxa-1,2,4a-triaza-phenanthren-3-one (0.070 g, 0.145 mmol) and Pd(OH)$_2$/C (10%, 0.020 g, 0.014 mmol) in MeOH (10 mL) was stirred for 40 h under an atmosphere of hydrogen (55 psi) at ambient temperature. After filtration, the solvent was removed in vacuo and the residue was purified by preparative HPLC (Table 3, Step 12) to give 4,7-dimethyl-6-(3-methyl-azetidin-3-ylamino)-2,10-dihydro-9-oxa-1,2,4a-triaza-phenanthren-3-one trifluoroacetic acid (0.043 g, 94%). LC/MS (Table 1, Method 3) R$_t$=0.966 min; MS m/z: 316 [M+H]$^+$.

Example #99

6-Azetidin-3-ylmethyl-4-methyl-7-trifluoromethyl-2,10-dihydro-9-oxa-1,2,4a-triaza-phenanthren-3-one trifluoroacetic acid

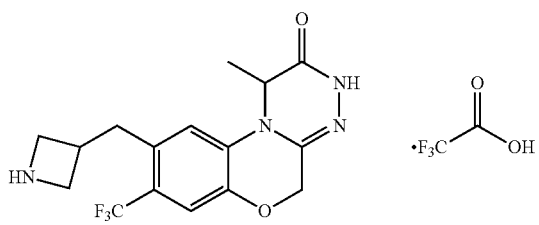

Step A. 3-[4-Methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethylene]-azetidine-1-carboxylic acid tert-butyl ester

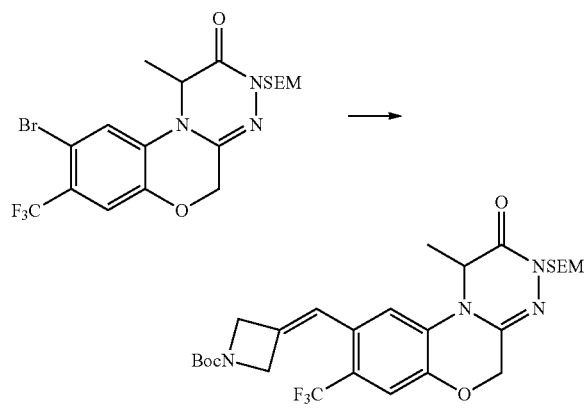

A solution of 6-bromo-4-methyl-7-trifluoromethyl-2-(2-trimethylsilanyl-ethoxymethyl)-2,10-dihydro-9-oxa-1,2,4a-triaza-phenanthren-3-one (Example #53, Step E, 0.30 g, 0.61 mmol), 3-methylene-azetidine-1-carboxylic acid tert-butyl ester (0.123 g, 0.73 mmol), Pd(OAc)$_2$ (0.027 g, 0.12 mmol), tri-O-tolylphosphine (0.074 g, 0.24 mmol) and triethylamine (0.184 g, 1.82 mmol) in CH$_3$CN (10 mL) was heated at 110° C. for 14 hr. The reaction mixture was cooled to ambient temperature and the solvent was removed in vacuo. The residue was purified by preparative TLC (eluting with 25% EtOAc in petroleum ether) to give 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethylene]-azetidine-1-carboxylic acid tert-butyl ester (0.072 g, 20%) as a yellow solid. LC/MS (Table 1, Method 2) R$_t$=1.523 min.; MS m/z: 605 [M+23]$^+$.

Step B. 3-[4-Methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethyl]-azetidine-1-carboxylic acid tert-butyl ester

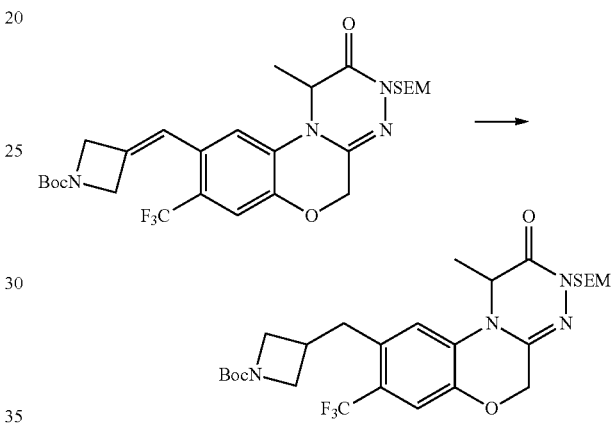

To a solution of 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethylene]-azetidine-1-carboxylic acid tert-butyl ester (0.072 g, 0.127 mmol) in CH$_3$OH (10 mL) was added Pd(OH)$_2$/C (0.02 g) and the mixture was stirred under an atmosphere of H$_2$ (50 psi) for 14 hr. The reaction mixture was filtered and the filtrate was concentrated to give 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethyl]-azetidine-1-carboxylic acid tert-butyl ester (0.052 g, 70%) as a pale yellow powder. LC/MS (Table 1, Method 2) R$_t$=1.502 min.; MS m/z: 607 [M+23]$^+$.

Step C. 3-(4-Methyl-3-oxo-7-trifluoromethyl-2,3,4,10-tetrahydro-9-oxa-1,2,4a-triaza-phenanthren-6-ylmethyl)-azetidine-1-carboxylic acid tert-butyl ester

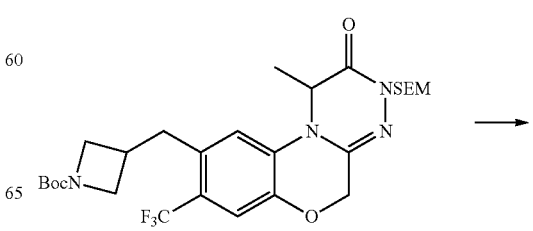

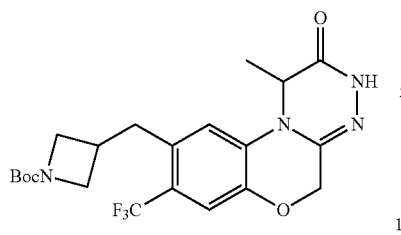

To a solution of 3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylmethyl]-azetidine-1-carboxylic acid tert-butyl ester (0.052 g, 0.08 mmol) in THF (1 mL) was added TBAF (1M in THF, 1 mL) and the solution was heated to 80° C. for 14 h. The reaction mixture was cooled to ambient temperature and the solvent was removed in vacuo. The residue was partioned between EtOAc (5 mL) and water (5 mL). The aqueous phase was extracted with EtOAc (3×10 mL). The combined organic portion was dried over anhydrous $Na_2SO_4$, filtered and concentrated in vacuo. The residue was purified by preparative TLC (eluting with 50% EtOAc in petroleum ether) to give 3-(4-methyl-3-oxo-7-trifluoromethyl-2,3,4,10-tetrahydro-9-oxa-1,2,4a-triaza-phenanthren-6-ylmethyl)-azetidine-1-carboxylic acid tert-butyl ester (0.019 g, 44%). LC/MS (Table 1, Method 2) $R_t$=1.230 min.; MS m/z: 477 $[M+23]^+$.

Step D. 6-Azetidin-3-ylmethyl-4-methyl-7-trifluoromethyl-2,10-dihydro-9-oxa-1,2,4a-triaza-phenanthren-3-one trifluoroacetic acid

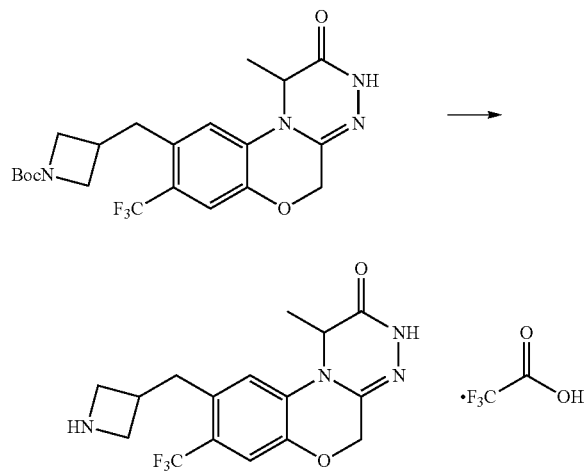

A solution of 3-(4-methyl-3-oxo-7-trifluoromethyl-2,3,4,10-tetrahydro-9-oxa-1,2,4a-triaza-phenanthren-6-ylmethyl)-azetidine-1-carboxylic acid tert-butyl ester (0.019 g, 0.042 mmol) in TFA (0.5 mL) and DCM (3 mL) was stirred at 25° C. for 2 h. The solvent was removed in vacuo to give 6-azetidin-3-ylmethyl-4-methyl-7-trifluoromethyl-2,10-dihydro-9-oxa-1,2,4a-triaza-phenanthren-3-one trifluoroacetic acid (0.002 g, 100%). LC/MS (Table 1, Method 5) $R_t$=2.023 min; MS m/z: 355 $[M+H]^+$.

Example #100

(R)-1-Methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (Example #100-1, Enantiomer 1) and (S)-1-methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (Example #100-2, Enantiomer 2)

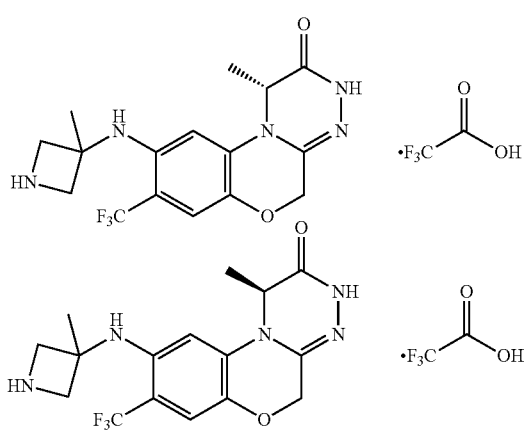

Step A. 3-Methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester

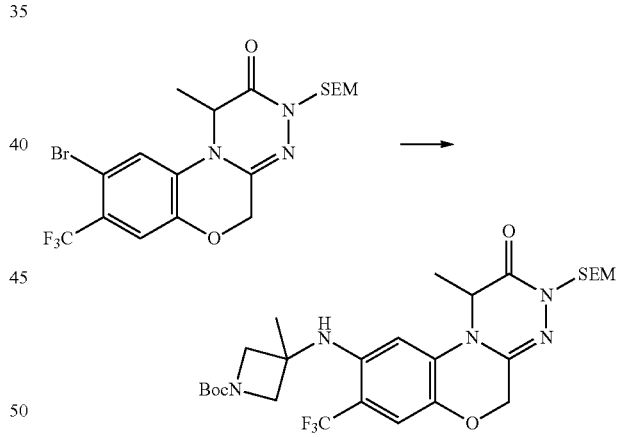

A mixture of 6-bromo-4-methyl-7-trifluoromethyl-2-(2-trimethylsilanyl-ethoxymethyl)-2,10-dihydro-9-oxa-1,2,4a-triaza-phenanthren-3-one (Example #53, Step E, 2.0 g, 4.05 mmol), tert-butyl 3-amino azetidine-1-carboxylate (0.904 g, 4.85 mmol), diacetoxypalladium (0.091 g, 0.405 mmol), $Cs_2CO_3$ (2.64 g, 8.10 mmol) and BINAP (0.252 g, 0.405 mmol) in toluene (10 mL) was heated at reflux for 10 h. The reaction mixture was cooled to ambient temperature and filtered. The filtrate was concentrated in vacuo and the residue was purified by column chromatography on silica gel (eluting with 10% EtOAc in petroleum ether) to give 3-methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (2.2 g, 91%) as a pale yellow solid. $^1H$ NMR (CDCl₃, 400 MHz): δ 7.16 (s, 1H), 5.96 (brs, 1H), 5.13 (q, J=9.2 Hz, 2H), 4.61 (m, 1H), 4.56 (q, J=13.2 Hz, 2H), 4.41 (brs, 1H), 4.04 (m, 2H), 3.95 (d, J=12.4 Hz, 2H), 3.68 (m, 2H), 1.66 (s, 3H), 1.47 (d, J=6.4 Hz, 3H), 1.46 (s, 9H), 0.99 (m, 2H), 0.02 (s, 9H).

Step B. (R)-tert-Butyl 3-methyl-3-((1-methyl-2-oxo-8-(trifluoromethyl)-1,2,3,5-tetrahydrobenzo[5,6][1,4]oxazino[3,4-c][1,2,4]triazin-9-yl)amino)azetidine-1-carboxylate

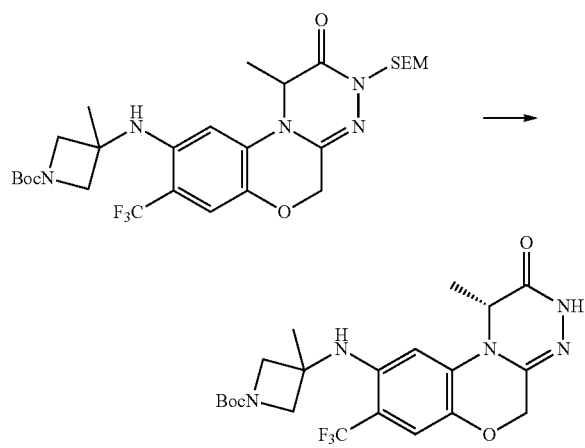

To a solution of 3-methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (4 g, 6.67 mmol) in THF (10 mL) was added a solution of TBAF (1M in THF, 80 mL, 80 mmol) The reaction mixture was heated at 80° C. for 15 h. The reaction mixture was cooled to ambient temperature and solvent was removed in vacuo. The residue was purified by preparative HPLC (Table 3, Method 17) and further separated by chiral SFC (Table 2, Method 10) to give (R)-tert-butyl 3-methyl-3-((1-methyl-2-oxo-8-(trifluoromethyl)-1,2,3,5-tetrahydrobenzo[5,6][1,4]oxazino[3,4-c][1,2,4]triazin-9-yl)amino)azetidine-1-carboxylate (Enantiomer 1, SFC (Table 1, Method 16) Rt: 6.686 min, 0.600 g, 19%) as a white solid, LC/MS (Table 1, Method 2) R_t=1.192 min.; MS m/z: 492 [M+23]⁺.

Step C. (R)-1-Methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (Example #100-1, Enantiomer 1)

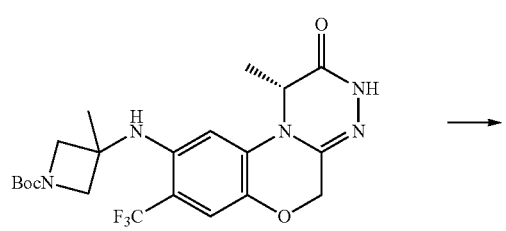

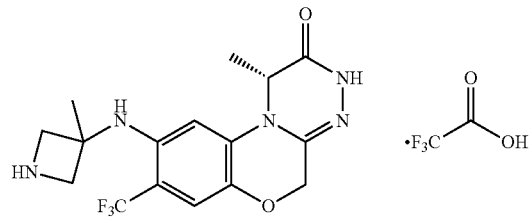

To a solution of (R)-tert-butyl 3-methyl-3-((1-methyl-2-oxo-8-(trifluoromethyl)-1,2,3,5-tetrahydrobenzo[5,6][1,4]oxazino[3,4-c][1,2,4]triazin-9-yl)amino)azetidine-1-carboxylate (Enantiomer 1, SFC (Table 1, Method 16) Rt: 6.686 min, 0.270 g, 0.55 mmol) in DCM (10 mL) was added TFA (2 mL) and the mixture was stirred at ambient temperature for 2 h. The solvent was removed in vacuo to give (R)-1-methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (Example #100-1, Enantiomer 1, SFC (Table 1, Method 18) Rt: 9.62 min, 0.275 g, 99%) as a pale solid. LC/MS (Table 1, Method 5) R_t=2.005 min; MS m/z: 370 [M+H]⁺.

Step D. (S)-1-Methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoacetic acid salt (Example #100-2, Enantiomer 2)

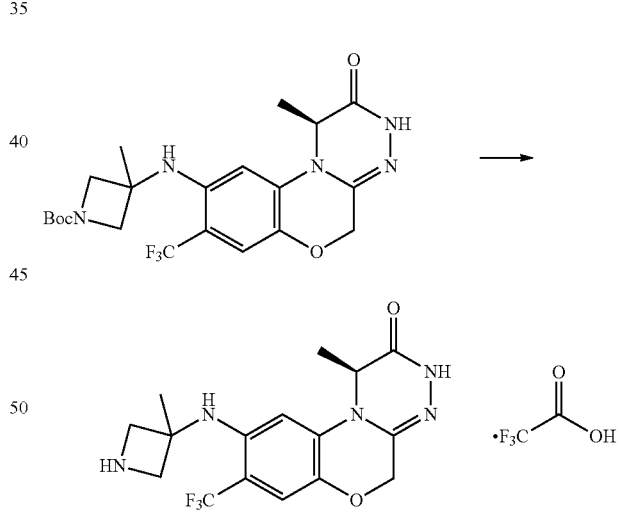

Using a similar procedure as described in Example #100, Step B-C, (S)-1-methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoacetic acid salt (Example #100-2, Enantiomer 2, SFC (Table 1, Method 18) Rt: 10.30 min, 0.26 g) was prepared from (S)-tert-butyl 3-methyl-3-((1-methyl-2-oxo-8-(trifluoromethyl)-1,2,3,5-tetrahydrobenzo[5,6][1,4]oxazino[3,4-c][1,2,4]triazin-9-yl)amino)azetidine-1-carboxylate (0.6 g). LC/MS (Table 1, Method 5) R_t=2.068 min; MS m/z: 370 [M+H]⁺

Example #101

(S)-9-(1,3-Dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-1, Enantiomer 1) and (R)-9-(1,3-dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-2, Enantiomer 2)

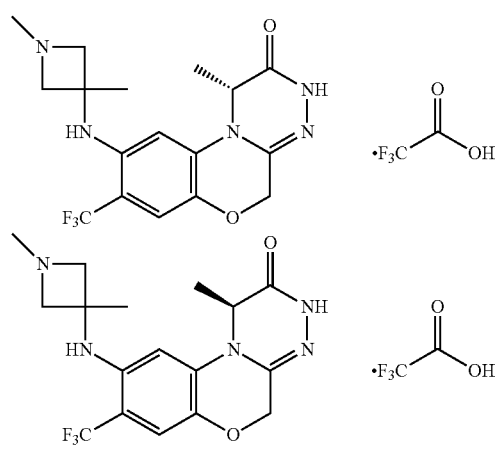

Step A. (S)-9-(1,3-Dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-1, Enantiomer 1) and (R)-9-(1,3-dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-2, Enantiomer 2)

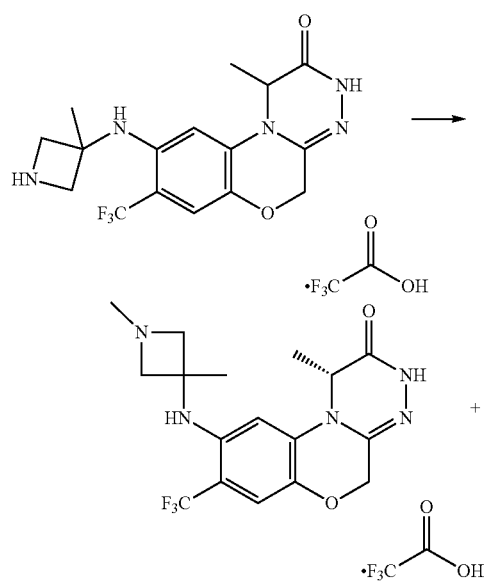

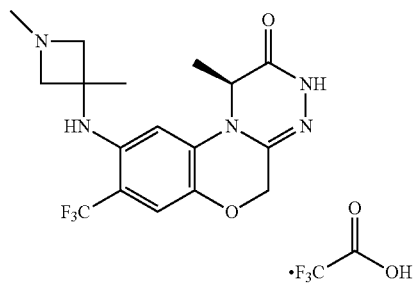

To a mixture of 1-methyl-9-((3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (Example #100, Step C, 0.120 g, 0.250 mmol) in MeOH (5 mL) and AcOH (0.5 mL) was added paraformaldehyde (neat, 0.060 g, 2 mmol). The reaction mixture was stirred at ambient temperature for 30 min then NaBH$_3$CN (0.126 g, 2 mmol) was added and the reaction mixture was heated at 50° C. for 5 h. The reaction mixture was cooled to ambient temperature and the solvent was removed in vacuo. The residue was purified by preparative HPLC (Table 3, Method 18) and further separated by chiral SFC (Table 2, Method 11) to give (S)-9-((1,3-dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-1, Enantiomer 1, SFC (Table 1, Method 16) R$_t$=5.21 min, 0.019 g, 12%) and (R)-9-((1,3-dimethylazetidin-3-yl)amino)-1-methyl-8-(trifluoromethyl)-3,5-dihydrobenzo[5,6][1,4]oxazino[3,4-c][1,2,4]triazin-2(1H)-one trifluoroacetic acid (Example #101-2, Enantiomer 2, SFC (Table 1, Method 16) R$_t$=5.89 min, 0.020 g, 12%) as white solids.

Enantiomer 1: LC/MS (Table 1, Method 5) R$_t$=1.683 min; MS m/z: 384 [M+H]$^+$.

Enantiomer 1: LC/MS (Table 1, Method 5) R$_t$=1.672 min; MS m/z: 384 [M+H]$^+$.

Example #102

(R)-1-Methyl-9-(methyl(3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid

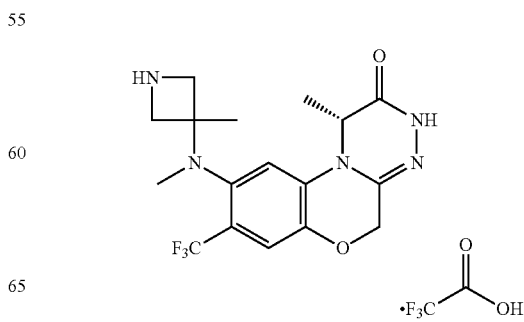

Step A. tert-Butyl 3-methyl-3-(methyl(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)amino)azetidine-1-carboxylate

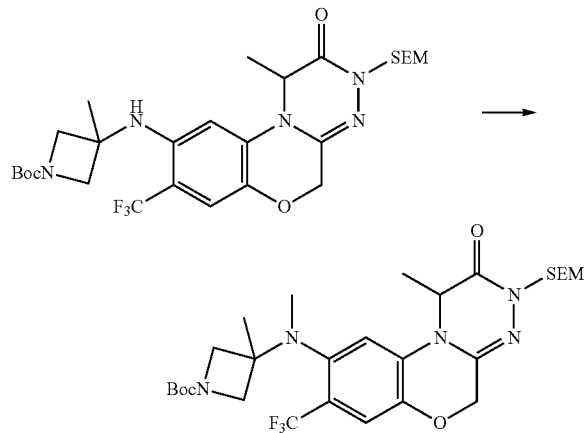

A mixture of 3-methyl-3-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-ylamino]-azetidine-1-carboxylic acid tert-butyl ester (Example #100, Step A, 0.250 g, 0.417 mmol) and paraformaldehyde (neat, 0.250 g, 8.34 mmol) in iPrOH (5 mL) and AcOH (0.5 ml) was stirred at 110° C. for 2 days. The reaction mixture was cooled to ambient temperature and the solvent was removed in vacuo. Then, MeOH (5 mL), AcOH (2.5 mL) and NaBH₃CN (0.524 g, 8.34 mmol) were added. The mixture was stirred at 60° C. for 1 h. The reaction mixture was cooled to ambient temperature and solvent was removed in vacuo. The residue was purified by column chromatography on silica gel (eluting with 5-10% EtOAc in petroleum ether) to give tert-butyl 3-methyl-3-(methyl(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)amino)azetidine-1-carboxylate (0.135 g, 53%). $^1$H NMR (CDCl₃, 400 MHz): δ 7.25 (s, 1H), 6.72 (s, 1H), 5.10 (m, 2H), 4.65 (m, 1H), 4.66 (q, J=13.2 Hz, 2H), 4.03 (d, J=8.8 Hz, 1H), 3.90 (d, J=12.4 Hz, 1H), 3.66 (t, 2H), 3.58 (t, 2H), 2.68 (s, 3H), 1.48 (s, 3H), 1.47 (d, J=6.4 Hz, 3H), 1.42 (s, 9H), 0.99 (m, 2H), 0.00 (s, 9H).

Step B. (R)-1-Methyl-9-(methyl(3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid

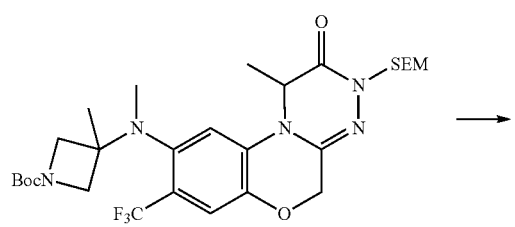

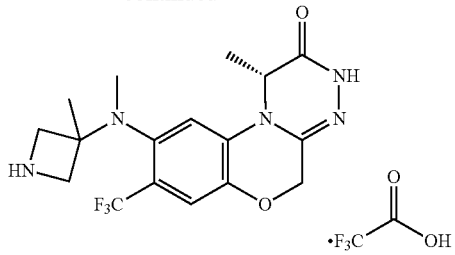

To a solution of tert-butyl 3-methyl-3-(methyl(1-methyl-2-oxo-8-(trifluoromethyl)-3-((2-(tri methylsilyl)ethoxy)methyl)-1,2,3,5-tetrahydrobenzo[5,6][1,4]oxazino[3,4-c][1,2,4]triazin-9-yl)amino)azetidine-1-carboxylate (0.586 g, 0.360 mmol) in DCM (4 mL) was added TFA (0.8 mL) and the mixture was stirred at ambient temperature for 1.5 h. The solvent was removed in vacuo and dioxane (1 mL) and ammonium hydroxide (25%, 1 mL) were added and the reaction mixture was stirred for 1.5 h at ambient temperature. The solvent was removed in vacuo and the residue was purified by HPLC (Table 3, Method 19) and further separated by chiral SFC (Table 2, Method 12) to give (R)-1-methyl-9-(methyl(3-methylazetidin-3-yl)amino)-8-(trifluoromethyl)-3,5-dihydrobenzo[5,6][1,4]oxazino[3,4-c][1,2,4]triazin-2(1H)-one trifluoroacetic acid (SFC (Table 1, Method 17) R$_t$: 6.57 min, 0.033 g, 7%)) as a pale solid. LC/MS (Table 1, Method 5) R$_t$=2.319 min.; MS m/z: 384 [M+H]⁺.

Example #103

10-(Azetidin-3-yl)-1-methyl-5,10-dihydro-1H-[1,2,4]triazino[4',3':4,5][1,4]oxazino[2,3-f]indol-2(3H)-one trifluoroacetic acid

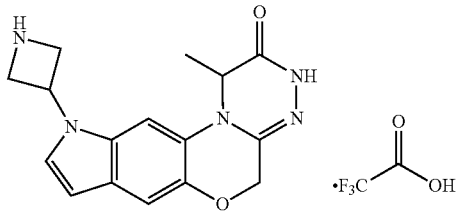

Step A. (E)-tert-Butyl 3-((8-(2-ethoxyvinyl)-1-methyl-2-oxo-1,2,3,5-tetrahydrobenzo[5,6][1,4]oxazino[3,4-c][1,2,4]triazin-9-yl)amino)azetidine-1-carboxylate

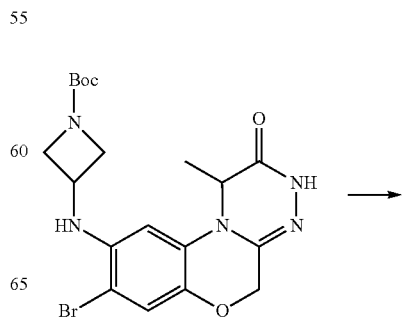

211
-continued

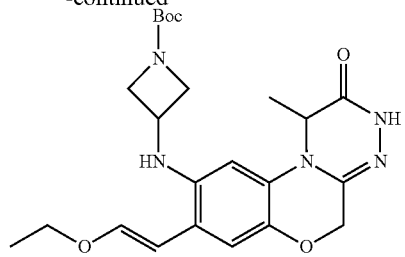

To a solution of tert-butyl 3-((8-bromo-1-methyl-2-oxo-1,2,3,5-tetrahydrobenzo[5,6][1,4]oxazino[3,4-c][1,2,4]triazin-9-yl)amino)azetidine-1-carboxylate (Example 1, Step B, 0.20 g, 0.43 mmol), (E)-2-(2-ethoxyvinyl)-4,4,5,5-tetramethyl-1,3,2-dioxaborolane (0.1 g, 0.5 mmol) in dioxane (6 mL) and water (1 mL) was added $PdCl_2(dppf)\cdot CH_2Cl_2$ adduct (0.035 g, 0.043 mmol) and $K_2CO_3$ (0.118 g, 0.85 mmol). The reaction mixture was stirred at 100° C. overnight. The reaction mixture was cooled to ambient temperature, the solvent was removed in vacuo and the residue was purified by chromatography on silica gel (eluting with 2% MeOH in DCM) to give (E)-tert-butyl 3-((8-(2-ethoxyvinyl)-1-methyl-2-oxo-1,2,3,5-tetrahydrobenzo[5,6][1,4]oxazino[3,4-c][1,2,4]triazin-9-yl)amino)azetidine-1-carboxylate (0.10 g, 51%) as a yellow solid. LC/MS (Table 1, Method 2) $R_t$=1.352 min.; MS m/z: 458 [M+H]$^+$.

Step B. 10-(Azetidin-3-yl)-1-methyl-5,10-dihydro-1H-[1,2,4]triazino[4',3':4,5][1,4]oxazino[2,3-f]indol-2(3H)-one trifluoroacetic acid

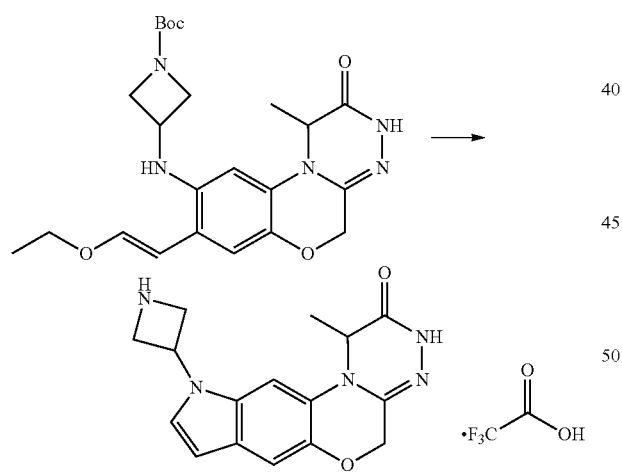

To a mixture of (E)-tert-butyl 3-((8-(2-ethoxyvinyl)-1-methyl-2-oxo-1,2,3,5-tetrahydrobenzo[5,6][1,4]oxazino[3,4-c][1,2,4]triazin-9-yl)amino)azetidine-1-carboxylate (0.020 g, 0.044 mmol) in THF (5 mL) was added aqueous HCl (1N, 1 mL) and the reaction mixture was stirred at rt overnight. The solvent was removed in vacuo to give the residue, which was purified by prep-HPLC (Table 3, Method 14) to give 10-(azetidin-3-yl)-1-methyl-5,10-dihydro-1H-[1,2,4]-triazino[4',3':4,5]oxazino[2,3-f]indol-2(3H)-one trifluoroacetic acid (0.0052 g, 38%) as a pale yellow powder. LC/MS (Table 1, Method 5) $R_t$=1.748 min.; MS m/z: 312 [M+H]$^+$.

212
Example #104

6-[(1,3-Dimethyl-azetidin-3-yl)-methyl-amino]-4(R)-methyl-7-phenyl-2,10-dihydro-9-oxa-1,2,4a-triaza-phenanthren-3-one trifluoroacetic acid (Example #104-1, Enantiomer 1) and 6-[(1,3-dimethyl-azetidin-3-yl)-methyl-amino]-4(S)-methyl-7-phenyl-2,10-dihydro-9-oxa-1,2,4a-triaza-phenanthren-3-one trifluoroacetic acid (Example #104-2, Enantiomer 2)

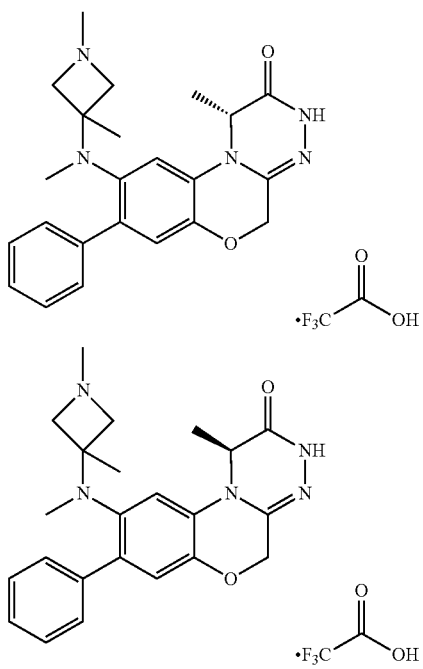

Step A. 6-[(1,3-Dimethyl-azetidin-3-yl)-methyl-amino]-4(R)-methyl-7-phenyl-2,10-dihydro-9-oxa-1,2,4a-triaza-phenanthren-3-one trifluoroacetic acid (Example #104-1, Enantiomer 1) and 6-[(1,3-dimethyl-azetidin-3-yl)-methyl-amino]-4(S)-methyl-7-phenyl-2,10-dihydro-9-oxa-1,2,4a-triaza-phenanthren-3-one trifluoroacetic acid (Example #104-2, Enantiomer 2)

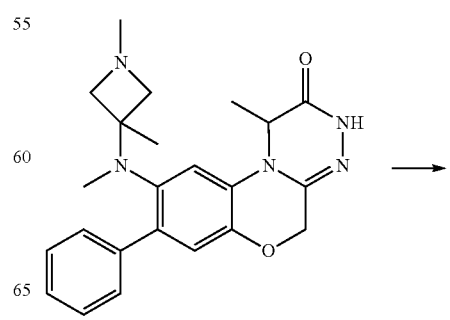

-continued

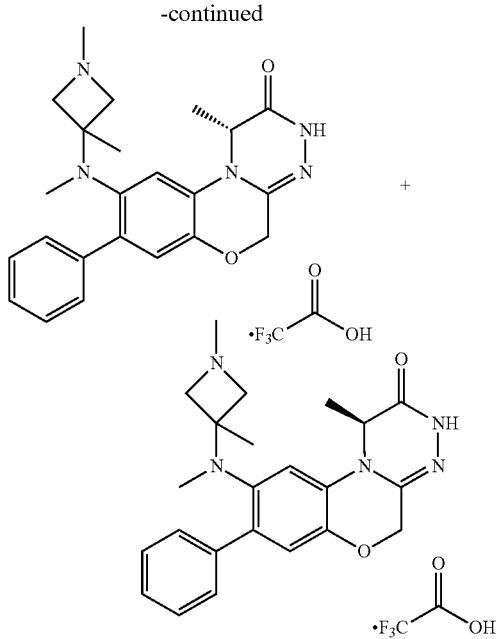

The racemic compound 6-[(1,3-dimethyl-azetidin-3-yl)-methyl-amino]-4-methyl-7-phenyl-2,10-dihydro-9-oxa-1,2,4a-triaza-phenanthren-3-one (Example #87, Step A, 0.12 g, 0.30 mmol) was separated by chiral SFC (Table 2, Method 9) to give 6-[(1,3-dimethyl-azetidin-3-yl)-methyl-amino]-4(R)-methyl-7-phenyl-2,10-dihydro-9-oxa-1,2,4a-triaza-phenanthren-3-one. The material was treated with TFA using a similar procedure as described in Example #1, Step E, to give 6-[(1,3-dimethyl-azetidin-3-yl)-methyl-amino]-4(R)-methyl-7-phenyl-2,10-dihydro-9-oxa-1,2,4a-triaza-phenanthren-3-one trifluoroacetic acid (Example #104-1, Enantiomer 1, SFC (Table 1, Method 15) $R_t$=1.693 min, 0.0685 g, 39%) and 6-[(1,3-dimethyl-azetidin-3-yl)-methyl-amino]-4(S)-methyl-7-phenyl-2,10-dihydro-9-oxa-1,2,4a-triaza-phenanthren-3-one trifluoroacetic acid (Example #104-2, Enantiomer 2, SFC (Table 1, Method 15) $R_t$=1.889 min, 0.0291 g, 16%).

Example #104-1, Enantiomer 1

LC/MS (Table 1, Method 4) $R_t$=1.797 min.; MS m/z: 406 [M+H]$^+$.

Example #104-2, Enantiomer 2

LC/MS (Table 1, Method 4) $R_t$=1.796 min.; MS m/z: 406 [M+H]$^+$.

Example #105
6-(1,3-Dimethyl-azetidin-3-ylamino)-4-methyl-7-phenyl-2,10-dihydro-9-oxa-1,2,4a-triaza-phenanthren-3-one trifluoroacetic acid

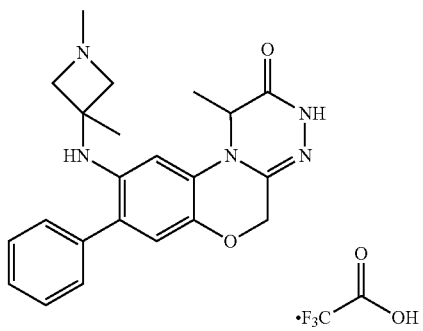

Step A. 4-Methyl-6-(3-methyl-azetidin-3-ylamino)-7-phenyl-2,10-dihydro-9-oxa-1,2,4a-triaza-phenanthren-3-one

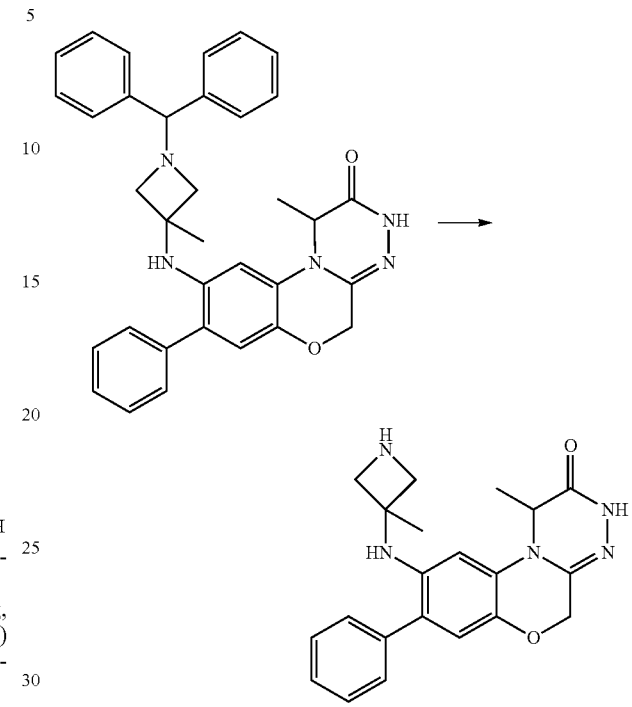

To a solution of 6-(1-benzhydryl-3-methyl-azetidin-3-ylamino)-4-methyl-7-phenyl-2,10-dihydro-9-oxa-1,2,4a-triaza-phenanthren-3-one (Example #79, Step C, 0.10 g, 0.18 mmol) in THF (20 mL), MeOH (20 mL) and aqueous HCl (12N, 0.3 mL) was added Pd(OH)$_2$/C (10%, 0.02 g, 0.014 mmol) and the solution was heated at 50° C. under an atmosphere of H$_2$ (55 psi) for 4 h. The reaction mixture was cooled to ambient temperature and filtered. The filtrate was evaporated in vacuo to give 4-methyl-6-(3-methyl-azetidin-3-ylamino)-7-phenyl-2,10-dihydro-9-oxa-1,2,4a-triaza-phenanthren-3-one (0.095 g, 57% pure, 82%), which was used in the next step directly without further purification. LC/MS (Table 1, Method 2) $R_t$=0.890 min; MS m/z: 378 [M+H]$^+$.

Step B. 6-(1,3-Dimethyl-azetidin-3-ylamino)-4-methyl-7-phenyl-2,10-dihydro-9-oxa-1,2,4a-triaza-phenanthren-3-one trifluoroacetic acid

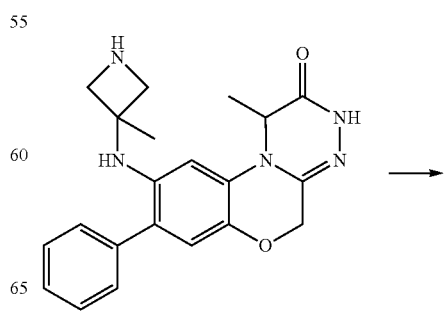

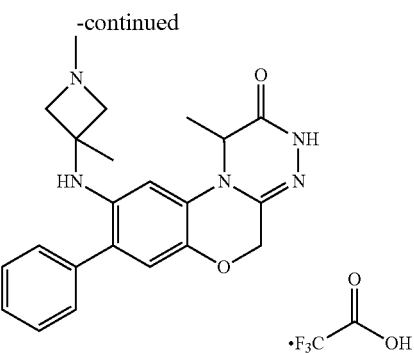

A solution of 4-methyl-6-(3-methyl-azetidin-3-ylamino)-7-phenyl-2,10-dihydro-9-oxa-1,2,4a-triaza-phenanthren-3-one (0.095 g, 57% purity, 0.15 mmol) and paraformaldehyde (0.015 g, 0.45 mmol) in MeOH (10 mL) and AcOH (1 mL) was heated at 80° C. for 2 h. NaBH$_3$CN (0.019 g, 0.30 mmol) was added and the reaction mixture was stirred at 80° C. for 0.5 h. The reaction mixture was cooled to ambient temperature. The solvent was removed in vacuo and the residue was washed with aqueous saturated Na$_2$CO$_3$ solution (2 mL). The aqueous phase was extracted with EtOAc (4×20 mL). The combined organic layer was dried, filtered and concentrated in vacuo to give crude 6-(1,3-dimethyl-azetidin-3-ylamino)-4-methyl-7-phenyl-2,10-dihydro-9-oxa-1,2,4a-triaza-phenanthren-3-one (0.060 g, 78% over two steps), which was used in the next step directly. LC/MS (Table 1, Method 2) R$_t$=0.924 min; MS m/z: 392 [M+H]$^+$. A solution of 6-(1,3-dimethyl-azetidin-3-ylamino)-4-methyl-7-phenyl-2,10-dihydro-9-oxa-1,2,4a-triaza-phenanthren-3-one (0.060 g, 0.15 mmol) in ammonium hydroxide (25%, 5 mL) and dioxane (5 mL) was stirred at ambient temperature for 2 h. The solvent was removed in vacuo and the residue was purified by preparative HPLC (Table 3, Method 16) to give 6-(1,3-dimethyl-azetidin-3-ylamino)-4-methyl-7-phenyl-2,10-dihydro-9-oxa-1,2,4a-triaza-phenanthren-3-one trifluoroacetic acid (0.022 g, 27%). LC/MS (Table 1, Method 4) R$_t$=1.722 min; MS m/z: 392 [M+H]$^+$.

Example #106

6-(Azetidin-3-ylamino)-4-methyl-7-phenoxy-2,10-dihydro-9-oxa-1,2,4a-triaza-phenanthren-3-one trifluoroacetic acid

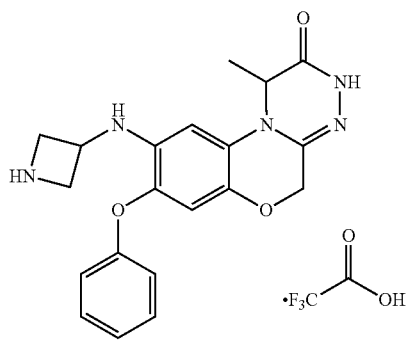

Step A. 7-Fluoro-4-methyl-6-nitro-2,10-dihydro-9-oxa-1,2,4a-triaza-phenanthren-3-one

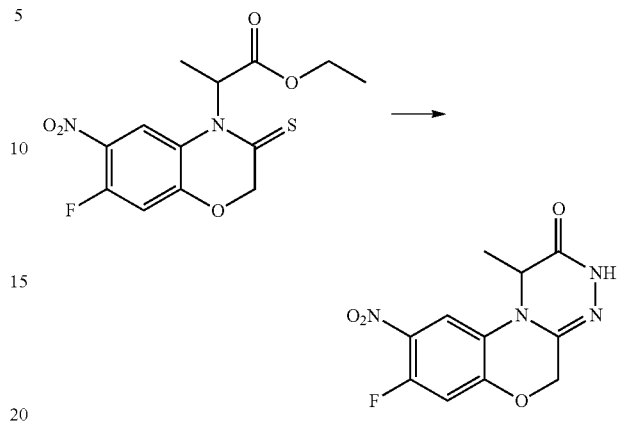

To a solution of 7-fluoro-6-nitro-2H-benzo[b][1,4]oxazine-3(4H)-thione (Example #56, Step D, 1.0 g, 3.05 mmol) in MeOH (10 mL) was added hydrazine (55% wt, 0.2 mL, 3.4 mmol) at ambient temperature and the reaction mixture was stirred at ambient temperature overnight. The precipitate was collected by filtration to give 7-fluoro-4-methyl-6-nitro-2,10-dihydro-9-oxa-1,2,4a-triaza-phenanthren-3-one (0.63 g, 74%) as an orange solid. LC/MS (Table 1, Method 2) R$_t$=0.884 min; MS m/z: 281 [M+H]$^+$ Step B. 4-Methyl-6-nitro-7-phenoxy-2,10-dihydro-9-oxa-1,2,4a-triaza-phenanthren-3-one

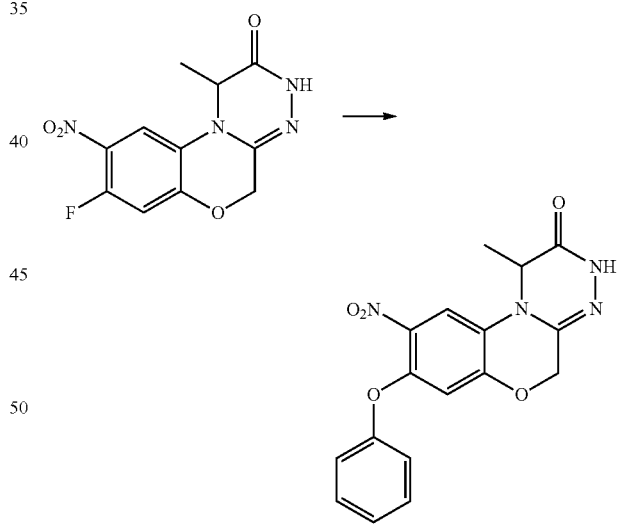

A mixture of 7-fluoro-4-methyl-6-nitro-2,10-dihydro-9-oxa-1,2,4a-triaza-phenanthren-3-one (0.30 g, 1.07 mmol), K$_2$CO$_3$ (0.296 g, 2.14 mmol) and phenol (0.151 g, 1.61 mmol) in acetone (10 mL) was stirred at ambient temperature for 48 h and then heated to reflux for 3 h. After cooling to ambient temperature, the solvent was removed in vacuo and the residue was partitioned between EtOAc (30 mL) and water (10 mL). The organic portion was washed with brine (10 mL), dried over Na$_2$SO$_4$, filtered and concentrated in vacuo. The residue was purified by chromatography on silical gel (eluting with 15% EtOAc in petroleum ether) to give 4-methyl-6-nitro-7-phenoxy-2,10-dihydro-9-oxa-1,2,4a- triaza-phenanthren-3-one (0.090 g, 24%) as an orange solid. LC/MS (Table 1, Method 2) $R_t$=1.117 min; MS m/z: 355 [M+H]$^+$ Step C. 6-Amino-4-methyl-7-phenoxy-2,10-dihydro-9-oxa-1,2,4a-triaza-phenanthren-3-one

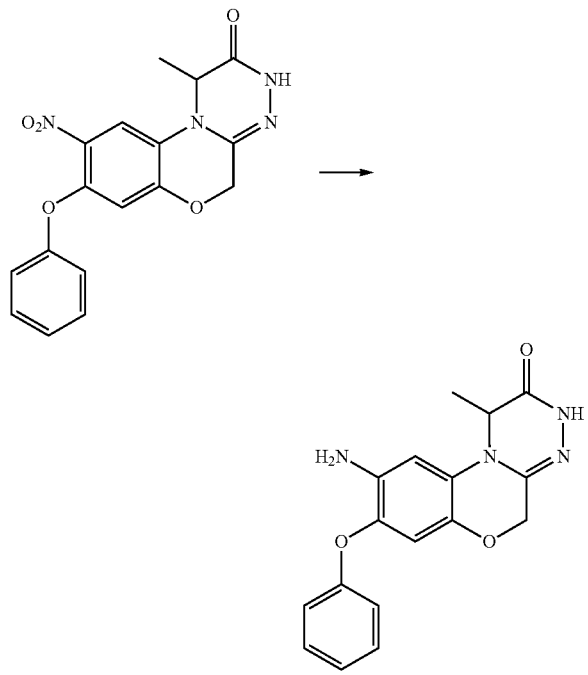

A mixture of 4-methyl-6-nitro-7-phenoxy-2,10-dihydro-9-oxa-1,2,4a-triaza-phenanthren-3-one (0.090 g, 0.25 mmol) and Raney Ni (0.030 g) in MeOH (5 mL) was stirred overnight under an atmosphere of H$_2$ (30 psi) at ambient temperature. The reaction mixture was filtered and the filtrate was concentrated in vacuo to give 6-amino-4-methyl-7-phenoxy-2,10-dihydro-9-oxa-1,2,4a-triaza-phenanthren-3-one as a colorless oil (0.090 g, crude), which was used in next step without further purification. LC/MS (Table 1, Method 2) $R_t$=0.938 min; MS m/z: 325 [M+H]$^+$ Step D. 3-(4-Methyl-3-oxo-7-phenoxy-2,3,4,10-tetrahydro-9-oxa-1,2,4a-triaza-phenanthren-6-ylamino)-azetidine-1-carboxylic acid tert-butyl ester

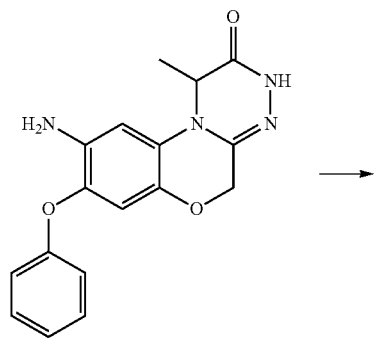

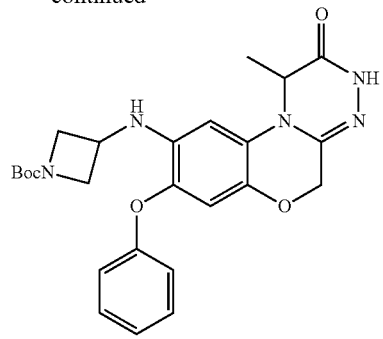

A mixture of 6-amino-4-methyl-7-phenoxy-2,10-dihydro-9-oxa-1,2,4a-triaza-phenanthren-3-one (0.090 g, crude from previous step), tert-butyl 3-aminoazetidine-1-carboxylate (0.087 g, 0.51 mmol) and sodium cyanoborohydride (0.00032 g, 0.51 mmol) in MeOH (2.7 mL) and AcOH (0.3 mL) was heated at reflux overnight. The reaction mixture was cooled to ambient temperature and diluted with MeOH (10 mL). The solution was purified by preparative HPLC (Table 3, Method 3) to give 3-(4-methyl-3-oxo-7-phenoxy-2,3,4,10-tetrahydro-9-oxa-1,2,4a-triaza-phenanthren-6-ylamino)-azetidine-1-carboxylic acid tert-butyl ester (0.015 g, 12% over 2 steps) as a colorless oil. LC/MS (Table 1, Method 2) $R_t$=1.188 min; MS m/z: 502 [M+23]$^+$ Step E. 6-(Azetidin-3-ylamino)-4-methyl-7-phenoxy-2,10-dihydro-9-oxa-1,2,4a-triaza-phenanthren-3-one trifluoroacetic acid

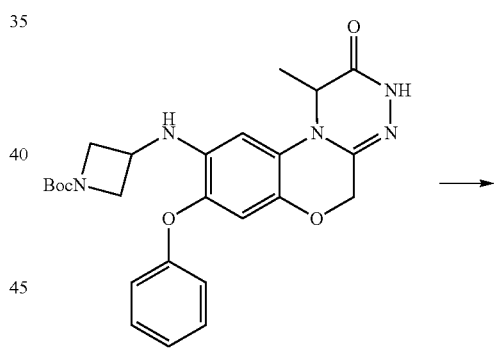

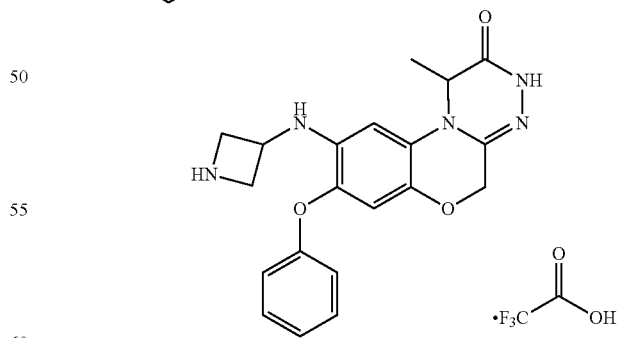

A solution of 6-(azetidin-3-ylamino)-4-methyl-7-phenoxy-2,10-dihydro-9-oxa-1,2,4a-triaza-phenanthren-3-one (0.015 g, 0.031 mmol) in DCM (3 mL) and TFA (0.5 mL) was stirred for 2 h at ambient temperature. The solvent was removed in vacuo to give 6-(azetidin-3-ylamino)-4-methyl-7-phenoxy-2,10-dihydro-9-oxa-1,2,4a-triaza-phenanthren- 3-one trifluoroacetic acid (0.009 mg, 58%) as a white solid. LC/MS (Table 1, Method 5) $R_t$=2.166 min; MS m/z: 380 [M+H]$^+$

Example #107

4-Methyl-6-(3-methyl-azetidin-3-yloxy)-7-trifluoromethyl-2,10-dihydro-9-oxa-1,2,4a-triaza-phenanthren-3-one trifluoroacetic acid

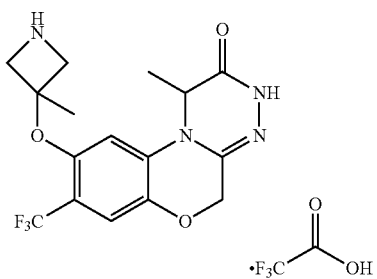

Step A. 4-Methyl-6-(4,4,5,5-tetramethyl-[1,3,2]diox-aborolan-2-yl)-7-trifluoromethyl-2-(2-trimethylsilanyl-ethoxymethyl)-2,10-dihydro-9-oxa-1,2,4a-triaza-phenanthren-3-one

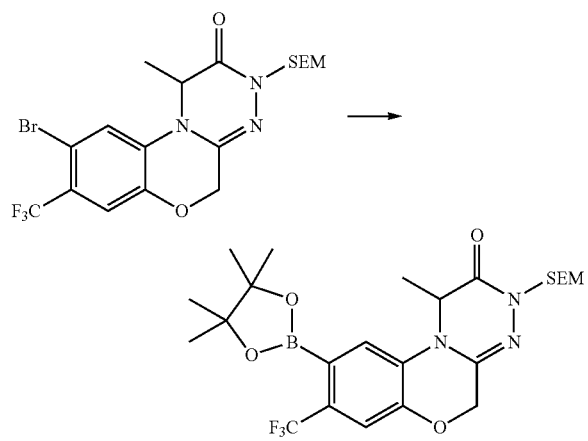

A mixture of 6-bromo-4-methyl-7-trifluoromethyl-2-(2-trimethylsilanyl-ethoxymethyl)-2,10-dihydro-9-oxa-1,2,4a-triaza-phenanthren-3-one (Example #53, Step E, 0.610 g, 1.234 mmol), 4,4,4',4',5,5,5',5'-octamethyl-2,2'-bi(1,3,2-dioxaborolane) (0.627 g, 2.468 mmol), Pd(dppf)Cl$_2$ (0.180 g, 0.405 mmol) and KOAc (0.303 g, 3.08 mmol) in dioxane (20 mL) was stirred at 90° C. overnight. The reaction mixture was cooled to ambient temperature and the solvent was removed in vacuo. The residue was purified by column chromatography on silica gel (eluting with 5-10% EtOAc in petroleum ether) to give 4-methyl-6-(4,4,5,5-tetramethyl-[1,3,2]diox-aborolan-2-yl)-7-trifluoromethyl-2-(2-trimethylsilanyl-ethoxymethyl)-2,10-dihydro-9-oxa-1,2,4a-triaza-phenanthren-3-one (0.500 g, crude) as a white solid containing 20% of the de-Br byproduct and was used in the next step directly. LC/MS (Table 1, Method 2) $R_t$=1.499 min.; MS m/z: 564 [M+23]$^+$.

Step B. 6-Hydroxy-4-methyl-7-trifluoromethyl-2-(2-trimethylsilanyl-ethoxymethyl)-2,10-dihydro-9-oxa-1,2,4a-triaza-phenanthren-3-one

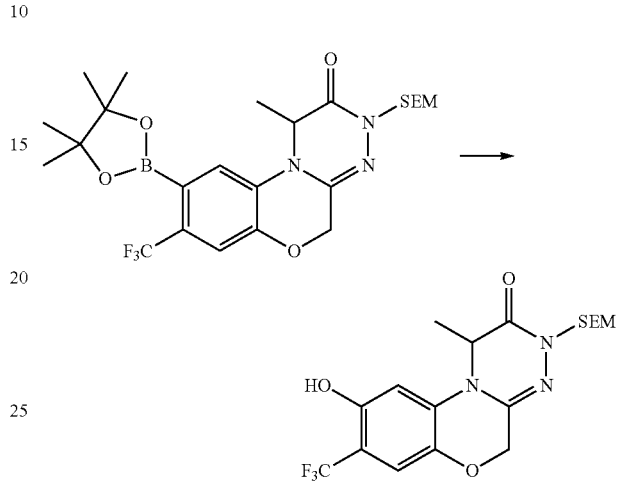

To a solution of 4-methyl-6-(4,4,5,5-tetramethyl-[1,3,2] dioxaborolan-2-yl)-7-trifluoromethyl-2-(2-trimethylsilanyl-ethoxymethyl)-2,10-dihydro-9-oxa-1,2,4a-triaza-phenanthren-3-one (0.500 g, 0.923 mmol) in dioxane (25 mL) was added AcOH (2.5 mL) and hydrogen peroxide (30%, 5 mL) and the reaction mixture was stirred at ambient temperature overnight. The solution was quenched by the addition of saturated Na$_2$SO$_3$ solution and the volatiles were evaporated in vacuo. The aqueous residue was extracted with EtOAc (3×20 mL) and the combined organic phases were dried over anhydrous Na$_2$SO$_4$, filtered and the filtrate was concentrated in vacuo. The residue was purified by column chromatography on silica gel (eluting with 5-20% EtOAc in petroleum ether) to give 6-hydroxy-4-methyl-7-trifluoromethyl-2-(2-trimethylsilanyl-ethoxymethyl)-2,10-dihydro-9-oxa-1,2,4a-triaza-phenanthren-3-one (0.200 g, 50%) as a white solid. $^1$H NMR (CDCl$_3$, 400 MHz): δ 7.15 (s, 1H), 6.59 (s, 1H), 6.00 (s, 1H), 5.14 (m, 2H), 4.69 (m, 2H), 4.56 (m, 1H), 3.69 (t, J=8.4 Hz, 2H), 1.53 (d, J=6.4 Hz, 3H), 1.02 (m, 2H), 0.04 (s, 9H).

Step C. 6-(1-Benzhydryl-3-methyl-azetidin-3-yloxy)-4-methyl-7-trifluoromethyl-2-(2-trimethylsi-lanyl-ethoxymethyl)-2,10-dihydro-9-oxa-1,2,4a-triaza-phenanthren-3-one

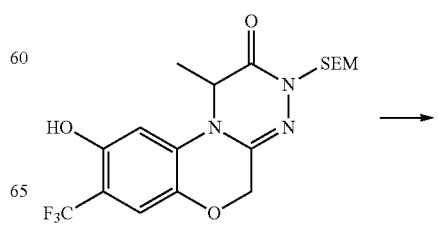

-continued

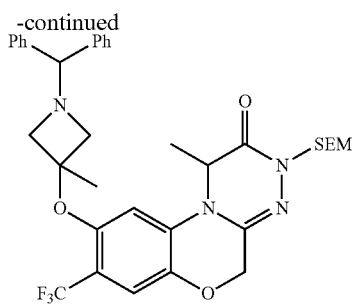

A mixture of 6-hydroxy-4-methyl-7-trifluoromethyl-2-(2-trimethylsilanyl-ethoxymethyl)-2,10-dihydro-9-oxa-1,2,4a-triaza-phenanthren-3-one (0.055 g, 0.127 mmol), 1-benzhydryl-3-methylazetidin-3-ylmethanesulfonate (Preparation #3, Step B, 0.084 g, 0.255 mmol) and $Cs_2CO_3$ (0.083 g, 0.255 mmol) in DMF (2 mL) was stirred at 80° C. overnight. The reaction mixture was cooled to ambient temperature and poured into water (150 mL). The aqueous mixture was extracted with EtOAc (3×20 mL) and the combined organic phase was washed with brine (3×20 mL), dried over anhydrous $Na_2SO_4$, filtered and concentrated in vacuo. The residue was purified by column chromatography on silica gel (eluting with 5-10% EtOAc in petroleum ether) to give 6-(1-benzhydryl-3-methyl-azetidin-3-yloxy)-4-methyl-7-trifluoromethyl-2-(2-trimethylsilanyl-ethoxymethyl)-2,10-dihydro-9-oxa-1,2,4a-triaza-phenanthren-3-one (0.031 g, 36%) as an oil. LC/MS (Table 1, Method 2) $R_t$=1.024 min.; MS m/z: 667 [M+H]$^+$.

Step D. 4-Methyl-6-(3-methyl-azetidin-3-yloxy)-7-trifluoromethyl-2,10-dihydro-9-oxa-1,2,4a-triaza-phenanthren-3-one trifluoroacetic acid

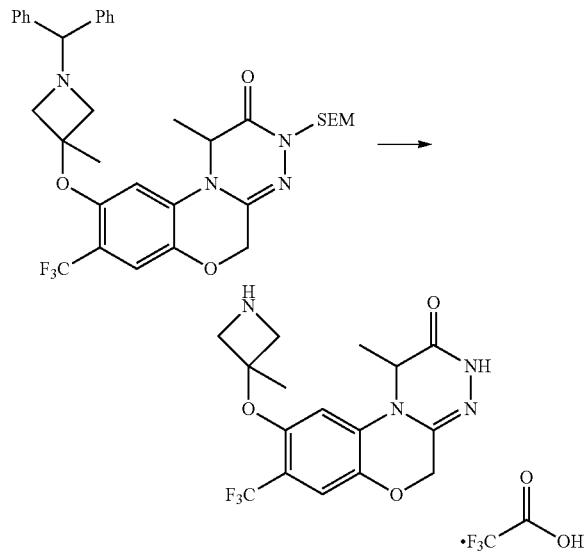

A suspension of 6-(1-benzhydryl-3-methyl-azetidin-3-yloxy)-4-methyl-7-trifluoromethyl-2-(2-trimethylsilanyl-ethoxymethyl)-2,10-dihydro-9-oxa-1,2,4a-triaza-phenanthren-3-one (0.031 g, 0.046 mmol) and Pd(OH)$_2$/C (10%, 0.030 g) in EtOH (10 mL) was stirred at 50° C. under an atmosphere of $H_2$ (50 psi) overnight. The reaction mixture was cooled to ambient temperature and filtered. The filtrate was evaporated in vacuo to give 4-methyl-6-(3-methyl-azetidin-3-yloxy)-7-trifluoromethyl-2-(2-trimethylsilanyl-ethoxymethyl)-2,10-dihydro-9-oxa-1,2,4a-triaza-phenanthren-3-one (0.021 g crude) as an oil, which was used directly without purification. To a solution of 4-methyl-6-(3-methyl-azetidin-3-yloxy)-7-trifluoromethyl-2-(2-trimethylsilanyl-ethoxymethyl)-2,10-dihydro-9-oxa-1,2,4a-triaza-phenanthren-3-one (0.021 g, 0.042 mmol) in DCM (3 mL) was added TFA (1 mL). The reaction was stirred at ambient temperature for 1.5 h then the solvent was removed in vacuo and the residue was diluted with dioxane (1 mL). Aqueous ammonium hydroxide (25%, 1 mL) was added and the reaction mixture was stirred at ambient temperature for 1.5 h. The solvent was removed in vacuo and the residue was purified by preparative HPLC (Table 3, Method 15) to give 4-methyl-6-(3-methyl-azetidin-3-yloxy)-7-trifluoromethyl-2,10-dihydro-9-oxa-1,2,4a-triaza-phenanthren-3-one trifluoroacetic acid (0.0039 g, 25%). LC/MS (Table 1, Method 5) $R_t$=2.088 min; MS m/z: 371 [M+H]$^+$.

Example #108

9-(Azetidin-3-ylamino)-1-methyl-5,6-dihydro-1H-[1,2,4]triazino[4,3-a]quinolin-2(3H)-one hydrochloric acid

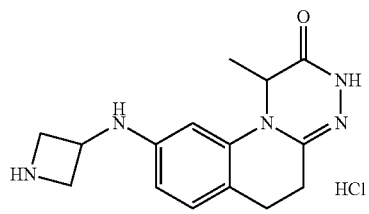 [SMILES: CC1C(=O)NN=C2CCc3ccc(NC4CNC4)cc3N21 ; Cl]

Step A. (E)-ethyl 3-(2,4-dinitrophenyl)acrylate

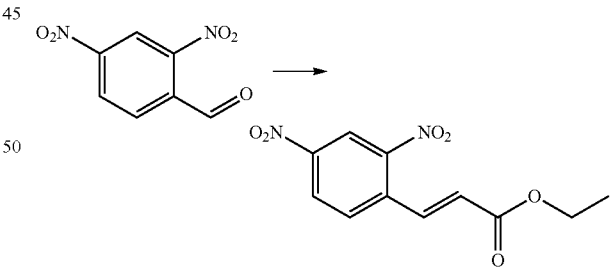

To a mixture of 2,4-dinitrobenzaldehyde (12.0 g, 61.2 mmol), N-ethyl-N-isopropylpropan-2-amine (11.9 g, 91.8 mmol) and lithium chloride (3.1 g, 24.1 mmol) in $CH_3CN$ (100 mL) was added slowly ethyl 2-(diethoxyphosphoryl)acetate (16.5 g, 64.3 mmol) and the reaction mixture was stirred at ambient temperature for 12 h. After filtration, the solvent was removed in vacuo and the residue was purified by column chromatography on silica gel (eluting with 4% EtOAc in petroleum ether) to give (E)-ethyl 3-(2,4-dinitrophenyl)acrylate (13 g, 84%). $^1$H NMR (CDCl$_3$, 400 MHz): δ 8.83 (s, 1H), 8.42 (d, J=8.8 Hz, 1H), 8.02 (d, J=16.0 Hz, 1H), 7.77 (d, J=8.8 Hz, 1H), 6.39 (d, J=16.0 Hz, 1H), 4.24 (q, J=7.2 Hz, 2H), 1.29 (t, J=7.2 Hz, 3H).

Step B. 7-Amino-3,4-dihydro-1H-quinolin-2-one

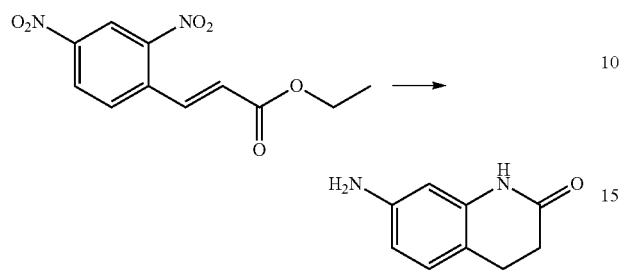

A suspension of Pd(OH)$_2$/C (10%, 3.0 g) and (E)-ethyl 3-(2,4-dinitrophenyl)acrylate (12.0 g, 45.1 mmol) in MeOH (80 mL) was stirred at 25° C. under an atmosphere of H$_2$ (45 psi) for 15 h. The mixture was filtered and the filtrate was concentrated in vacuo to give 3-(2,4-diamino-phenyl)-propionic acid ethyl ester (8.6 g, 98%), which was used directly in the next step without further purification. A solution of ethyl 3-(2,4-diaminophenyl)propanoate (8.6 g, 41.3 mmol) in EtOH (50 mL) was stirred at 85-100° C. for 48 h. The reaction mixture was cooled to ambient temperature and the solvent was removed in vacuo. EtOAc (10 mL) was added to the residue and the precipitate was collected by filtration to give 7-amino-3,4-dihydro-1H-quinolin-2-one (5.8 g, 87%). $^1$H NMR (DMSO-d$_6$, 400 MHz): δ 9.83 (brs, 1H), 6.76 (d, J=7.6 Hz, 1H), 6.12 (m, 2H), 4.95 (brs, 2H), 2.65 (t, J=7.2 Hz, 2H), 2.36 (t, J=7.2 Hz, 2H).

Step C. 7-(2,5-Dimethyl-pyrrol-1-yl)-3,4-dihydro-1H-quinolin-2-one

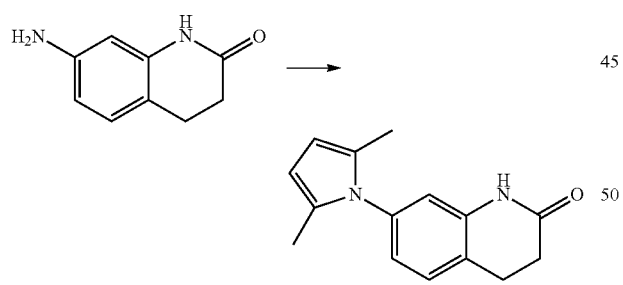

A mixture of 7-amino-3,4-dihydroquinolin-2(1H)-one (3.0 g, 18.50 mmol), hexane-2,5-dione (3.0 g, 25.9 mmol) and 4-methylbenzenesulfonic acid (3.2 g, 18.50 mmol) in toluene (40 mL) was stirred at 100° C. for 30 min. The reaction mixture was cooled to ambient temperature, concentrated in vacuo and the residue was purified by flash column chromatography on silica gel (eluting with 10% EtOAc in petroleum ether) to give 7-(2,5-dimethyl-pyrrol-1-yl)-3,4-dihydro-1H-quinolin-2-one (3.0 g, 67%). $^1$H NMR (CDCl$_3$, 400 MHz): δ 8.72 (brs, 1H), 7.23 (d, J=8.0 Hz, 1H), 6.83 (d, J=8.0 Hz, 1H), 6.67 (s, 1H), 5.89 (s, 2H), 3.02 (t, J=8.0 Hz, 2H), 2.68 (m, 2H), 2.03 (s, 6H).

Step D. Ethyl 2-(7-(2,5-dimethyl-1H-pyrrol-1-yl)-2-oxo-3,4-dihydroquinolin-1(2H)-yl)propanoate

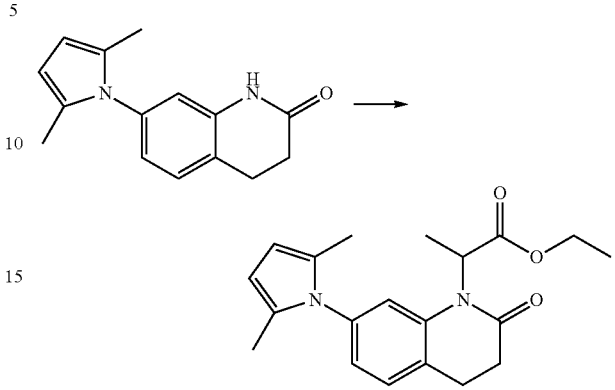

A mixture of 7-(2,5-dimethyl-1H-pyrrol-1-yl)-3,4-dihydroquinolin-2(1H)-one (1.4 g, 5.8 mmol) and potassium carbonate (2.4 g, 17.5 mmol) in ACN (40 mL) was stirred for 30 min then ethyl 2-bromopropanoate (2.1 g, 11.6 mmol) was added and the mixture was heated to reflux overnight. The reaction mixture was cooled to ambient temperature and the solvent was removed in vacuo. EtOAc (50 mL) and water (30 mL) was added to the residue and the organic layer was separated, dried over anhydrous Na$_2$SO$_4$, filtered and concentrated in vacuo. The residue was purified by column chromatography on silica gel (eluting with 0-30% EtOAc in petroleum ether) to give ethyl 2-(7-(2,5-dimethyl-1H-pyrrol-1-yl)-2-oxo-3,4-dihydroquinolin-1(2H)-yl)propanoate (1.6 g, 81%). $^1$H NMR (CDCl$_3$, 400 MHz): δ 7.26 (d, J=7.2 Hz, 1H), 6.87 (d, J=7.6 Hz, 1H), 6.71 (s, 1H), 5.91 (s, 2H), 4.98 (q, J=6.8 Hz, 1H), 4.17 (q, J=7.2 Hz, 2H), 2.96 (m, 2H), 2.72 (m, 2H), 2.05 (s, 6H), 1.61 (d, J=7.2 Hz, 3H), 1.19 (t, J=7.2 Hz, 3H).

Step E. Ethyl 2-(7-(2,5-dimethyl-1H-pyrrol-1-yl)-2-thioxo-3,4-dihydroquinolin-1(2H)-yl)propanoate

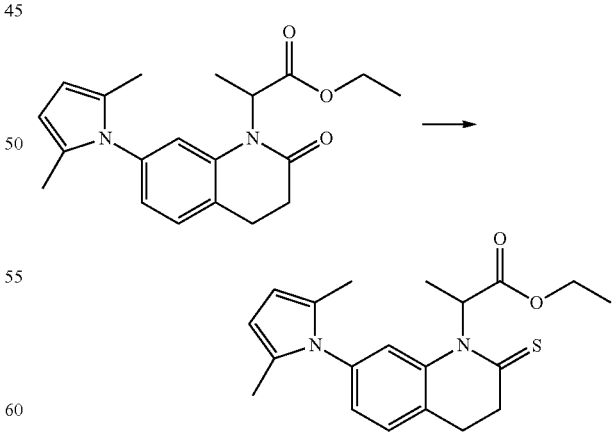

A solution of ethyl 2-(7-(2,5-dimethyl-1H-pyrrol-1-yl)-2-oxo-3,4-dihydroquinolin-1(2H)-yl)propanoate (1.6 g, 4.70 mmol) and Lawesson reagent (1.9 g, 4.70 mmol) in toluene (20 mL) was heated to reflux for 2 h. The reaction mixture was cooled to ambient temperature and the mixture was concentrated in vacuo. The residue was purified by column chromatography on silica gel (eluting with 0-5% EtOAc in petroleum ether) to give ethyl 2-(7-(2,5-dimethyl-1H-pyrrol-1-yl)-2-thioxo-3,4-dihydroquinolin-1(2H)-yl)propanoate (0.20 g, 12%). ¹H NMR (CDCl₃, 400 MHz): δ 7.27 (d, J=8.0 Hz, 1H), 6.94 (d, J=8.06 Hz, 1H), 6.82 (s, 1H), 6.58 (m, 1H), 5.91 (s, 2H), 4.13 (q, J=7.2 Hz, 2H), 3.24 (m, 2H), 2.85 (m, 2H), 2.03 (s, 6H), 1.71 (d, J=7.2 Hz, 3H), 1.13 (t, J=7.2 Hz, 3H).

Step F. 9-(2,5-Dimethyl-1H-pyrrol-1-yl)-1-methyl-5,6-dihydro-1H-[1,2,4]triazino[4,3-a]quinolin-2(3H)-one

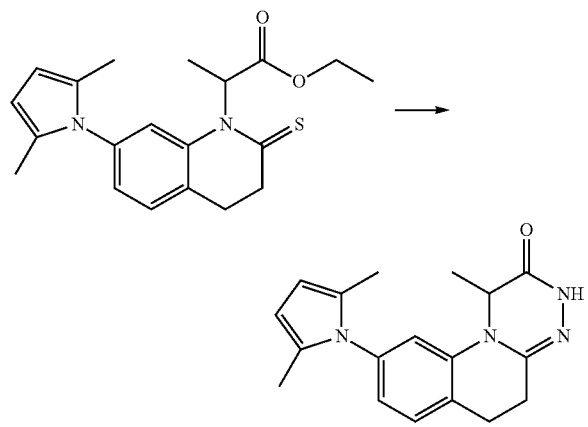

To a solution of ethyl 2-(7-(2,5-dimethyl-1H-pyrrol-1-yl)-2-thioxo-3,4-dihydroquinolin-1(2H)-yl)propanoate (0.2 g, 0.561 mmol) in EtOH (10 mL) was added hydrazine hydrate (6 mL) and the solution was heated to reflux overnight. The reaction mixture was cooled to ambient temperature and the solvent was removed in vacuo. Water (10 mL) was added to the residue and the mixture was extracted with EtOAc (2×30 mL). The combined organic layer was dried over anhydrous Na₂SO₄, filtered and concentrated in vacuo. The residue was purified by column chromatography on silica gel (eluting with 30-50% EtOAc in petroleum ether) to give 9-(2,5-dimethyl-1H-pyrrol-1-yl)-1-methyl-5,6-dihydro-1H-[1,2,4]-triazino[4,3-a]quinolin-2(3H)-one (0.14 g, 81%). ¹H NMR (CDCl₃, 400 MHz): δ 8.04 (brs, 1H), 7.21 (d, J=8.0 Hz, 1H), 6.82 (d, J=8.0 Hz, 1H), 6.73 (s, 1H), 5.89 (s, 2H), 4.56 (q, J=6.8 Hz, 1H), 2.93 (m, 2H), 2.63 (m, 2H), 2.05 (s, 6H), 1.42 (d, J=6.8 Hz, 3H).

Step G. 9-Amino-1-methyl-5,6-dihydro-1H-[1,2,4]triazino[4,3-a]quinolin-2(3H)-one

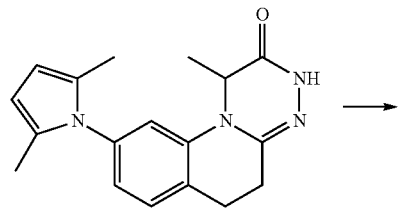

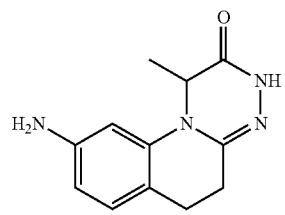

To a solution of 9-(2,5-dimethyl-1H-pyrrol-1-yl)-1-methyl-5,6-dihydro-1H-[1,2,4]triazino[4,3-a]quinolin-2(3H)-one (0.140 g, 0.45 mmol) and triethylamine (0.138 g, 1.362 mmol) in EtOH (9 mL) was added a solution of hydroxylamine hydrochloride (0.095 g, 1.362 mmol) in water (3 mL) and the reaction mixture was heated to reflux for 3 h. The reaction mixture was cooled to ambient temperature and the solvent was removed in vacuo. The residue was purified by column chromatography on silica gel (eluting with 50-100% EtOAc in petroleum ether) to give 9-amino-1-methyl-5,6-dihydro-1H-[1,2,4]-triazino[4,3-a]quinolin-2(3H)-one (0.070 g, 67%). ¹H NMR (CDCl₃, 400 MHz): δ 8.06 (brs, 1H), 6.91 (d, J=8.0 Hz, 1H), 6.31 (d, J=8.0 HZ, 1H), 6.26 (s, 1H), 4.60 (q, J=6.8 HZ, 1H), 3.63 (brs, 2H), 2.67 (m, 2H), 2.53 (m, 2H), 1.42 (d, J=6.8 Hz, 3H).

Step H. tert-Butyl 3-(1-methyl-2-oxo-2,3,5,6-tetrahydro-1H-[1,2,4]triazino[4,3-a]quinolin-9-ylamino)azetidine-1-carboxylate

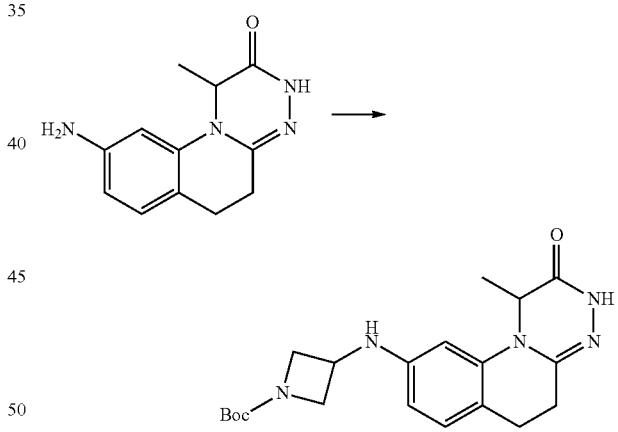

A solution of 9-amino-1-methyl-5,6-dihydro-1H-[1,2,4]triazino[4,3-a]quinolin-2(3H)-one (0.035 g, 0.152 mmol) and tert-butyl 3-oxoazetidine-1-carboxylate (0.078 g, 0.45 mmol) in MeOH (5 mL) and AcOH (0.5 mL) was stirred for 1 h at rt. Sodium cyanoborohydride (0.028 g, 0.456 mmol) was added and the reaction mixture was stirred at ambient temperature overnight. The solution was concentrated in vacuo and the residue was purified by preparative TLC (eluting with 50% EtOAc in petroleum ether) to give tert-butyl 3-(1-methyl-2-oxo-2,3,5,6-tetrahydro-1H-[1,2,4]triazino[4,3-a]quinolin-9-ylamino)azetidine-1-carboxylate (0.020 g, 34%). LC/MS (Table 1, Method 2) R_t=1.104 min; MS m/z: 386 [M+H]⁺.

227

Step I. 9-(Azetidin-3-ylamino)-1-methyl-5,6-dihydro-1H-[1,2,4]triazino[4,3-a]quinolin-2(3H)-one hydrochloric acid

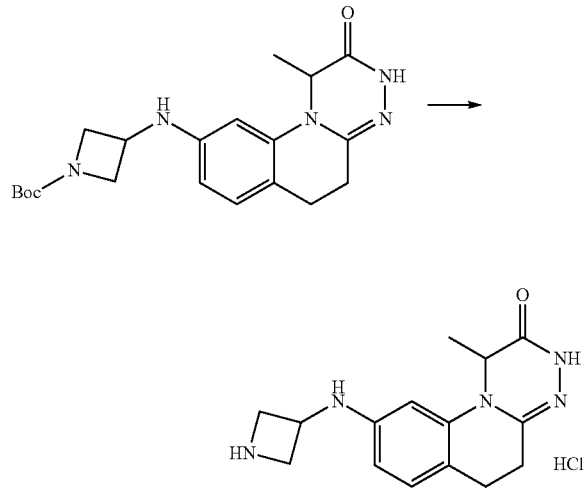

To a solution of HCl in EtOAc (4M, 5 mL, 20 mmol) was added slowly tert-butyl-3-(1-methyl-2-oxo-2,3,5,6-tetrahydro-1H-[1,2,4]triazino[4,3-a]quinolin-9-ylamino)azetidine-1-carboxylate (0.022 g, 0.057 mmol) and the reaction mixture was stirred at ambient temperature for 2 h. The solution was concentrated in vacuo to give 9-(azetidin-3-ylamino)-1-methyl-5,6-dihydro-1H-[1,2,4]triazino[4,3-a]quinolin-2(3H)-one hydrochloric acid (0.015 g, 95%). LC/MS (Table 1, Method 5) $R_t$=2.252 min; MS m/z: 286 [M+H]$^+$.

Example #109

(R)-9-((2S,4S)-2-Benzylpiperidin-4-yl)-1-methyl-3,5-dihydrobenzo[5,6][1,4]oxazino[3,4-c][1,2,4]triazin-2(1H)-one trifluoroacetic acid (Example #109-1, Enantiomer 1) & (R)-9-((2S,4R)-2-Benzylpiperidin-4-yl)-1-methyl-3,5-dihydrobenzo[5,6][1,4]oxazino[3,4-c][1,2,4]triazin-2(1H)-one trifluoroacetic acid (Example #109-2, Enantiomer 2)

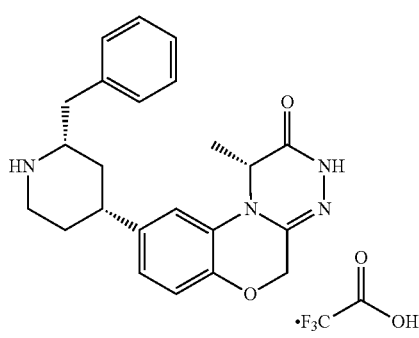

228

-continued

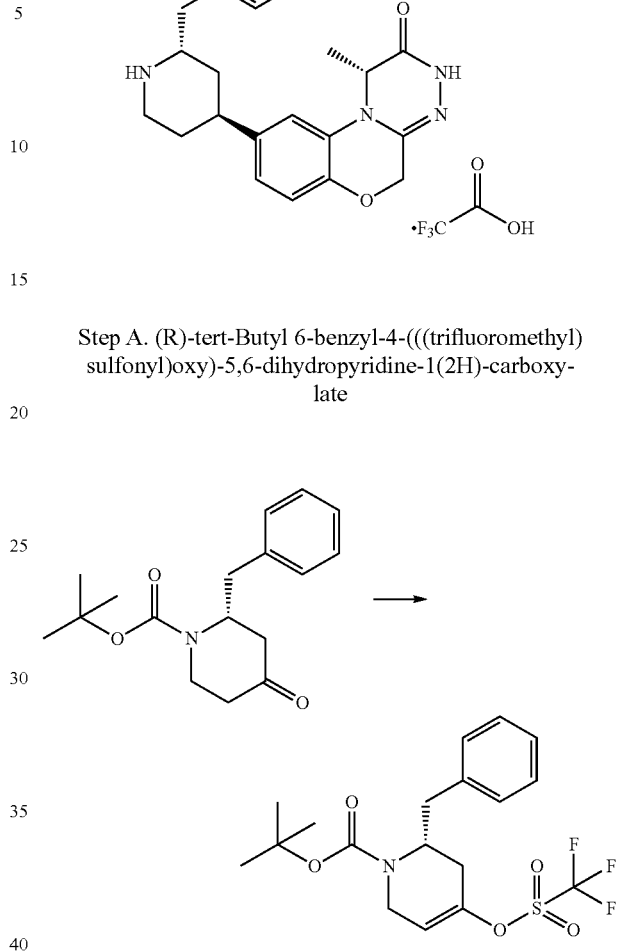

Step A. (R)-tert-Butyl 6-benzyl-4-(((trifluoromethyl)sulfonyl)oxy)-5,6-dihydropyridine-1(2H)-carboxylate Chiral SFC (Table 2, Method 14) separation of racemic compound tert-butyl 2-benzyl-4-oxopiperidine-1-carboxylate (BETAPHARMA) gave (S)-tert-butyl 2-benzyl-4-oxopiperidine-1-carboxylate (enantiomer 1, SFC (Table 1, Method 19) $R_t$=2.14 min) and (R)-tert-butyl 2-benzyl-4-oxopiperidine-1-carboxylate (enantiomer 2, SFC (Table 1, Method 19) $R_t$=3.17 min).

To a solution of (R)-tert-butyl 2-benzyl-4-oxopiperidine-1-carboxylate (enantiomer 2, SFC (Table 1, Method 19) $R_t$=3.17 min, 0.579 g, 2 mmol) in anhydrous THF (15 mL) was added LiHMDS solution (1M, 3 mL, 3 mmol) dropwise at −78° C. The mixture was allowed to warm to −30° C. and stirred for 20 min then cooled to −78° C. 1,1,1-Trifluoro-N-phenyl-N-(trifluoromethylsulfonyl)methanesulfonamide (1.072 g, 3 mmol) was added. The mixture was allowed to warm to rt and stirred for 2 h. The solvent was removed in vacuo and the residue was purified by flash column chromatography on silica gel (eluting with 2% EtOAc in petroleum ether) to give (R)-tert-butyl 6-benzyl-4-(((trifluoromethyl)sulfonyl)oxy)-5,6-dihydropyridine-1(2H)-carboxylate as oil (0.9 g, 99%). TLC (eluting with 10% EtOAc in petroleum ether) $R_f$=0.4.

Step B. (R)-1-Methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one

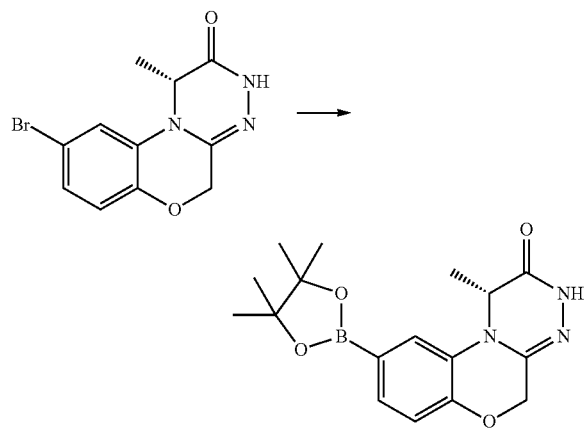

Chiral SFC (Table 2, Method 13) separation of racemic compound 9-bromo-1-methyl-3,5-dihydrobenzo[5,6][1,4]oxazino[3,4-c][1,2,4]triazin-2(1H)-one (Preparation #1, Step D) gave (S)-9-bromo-1-methyl-3,5-dihydrobenzo[5,6][1,4]oxazino[3,4-c][1,2,4]triazin-2(1H)-one (enantiomer 1, SFC (Table 1, Method 22) $R_t$=6.01 min) and (R)-9-bromo-1-methyl-3,5-dihydrobenzo[5,6][1,4]oxazino[3,4-c][1,2,4]triazin-2(1H)-one (enantiomer 2, SFC (Table 1, Method 22) $R_t$=8.43 min).

To a solution of (R)-9-bromo-1-methyl-3,5-dihydrobenzo[5,6][1,4]oxazino[3,4-c][1,2,4]triazin-2(1H)-one (enantiomer 2, SFC (Table 1, Method 22) $R_t$=8.43 min, 1.481 g, 5 mmol), potassium acetate (1.227 g, 12.5 mmol) and Pd(dppf)Cl$_2$ (1.098 g, 1.5 mmol) in 1,4-dioxane (15 mL) was added bis(pinacolato)diboron (2.54 g, 10 mmol) and the mixture was stirred at 90° C. for 3 h. The reaction mixture was cooled to ambient temperature and concentrated in vacuo. The residue was purified by column chromatography on silica gel (eluting with 30% EtOAc in petroleum ether) to give (R)-1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (1 g, 58%). $^1$H NMR (DMSO-d$_6$, 400 MHz): δ 10.79 (s, 1H), 7.30-7.28 (m, 2H), 7.05-7.00 (m, 1H), 4.77 (q, J=6.8 Hz, 1H), 4.65-6.60 (m, 2H), 1.32 (d, J=6.8 Hz, 3H), 1.30 (s, 12H).

Step C. (R)-tert-Butyl 6-benzyl-4-((R)-1-methyl-2-oxo-1,2,3,5-tetrahydrobenzo[5,6][1,4]oxazino[3,4-c][1,2,4]triazin-9-yl)-5,6-dihydropyridine-1(2H)-carboxylate

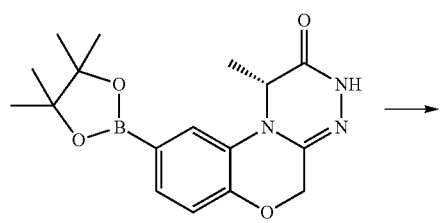

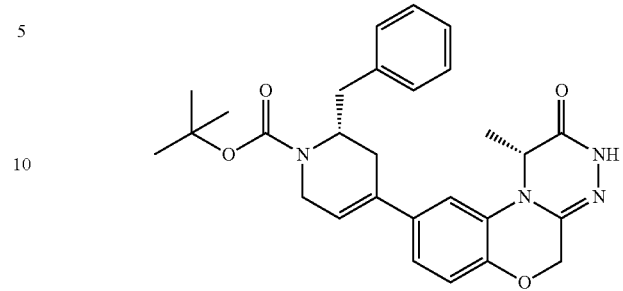

A mixture of (R)-1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (0.515 g, 1.5 mmol), (R)-tert-butyl 6-benzyl-4-((((trifluoromethyl)sulfonyl)oxy)-5,6-dihydropyridine-1(2H)-carboxylate (0.900 g, 2.13 mmol), Pd(dppf)Cl$_2$—CH$_2$Cl$_2$ complex (0.309 g, 0.375 mmol) and K$_2$CO$_3$ (0.622 g, 4.50 mmol) in 1,4-dioxane (15 mL) and water (5 mL) was heated at 90° C. for 4 h. The reaction was cooled to ambient temperature. The solvent was removed in vacuo and the residue was purified by column chromatography on silica gel (eluting with 30% EtOAc in petroleum ether) to give (R)-tert-butyl 6-benzyl-4-((R)-1-methyl-2-oxo-1,2,3,5-tetrahydrobenzo[5,6][1,4]oxazino[3,4-c][1,2,4]triazin-9-yl)-5,6-dihydropyridine-1(2H)-carboxylate (0.330 g, 45%).

Step D. (2S,4S)-tert-Butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate and (2S,4R)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate

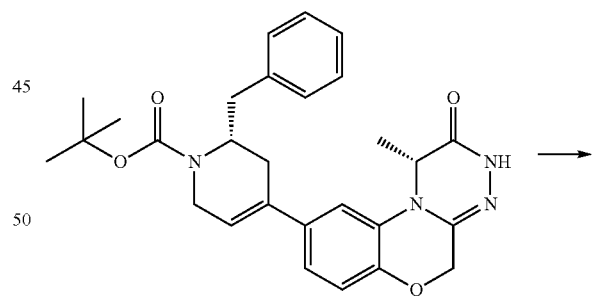

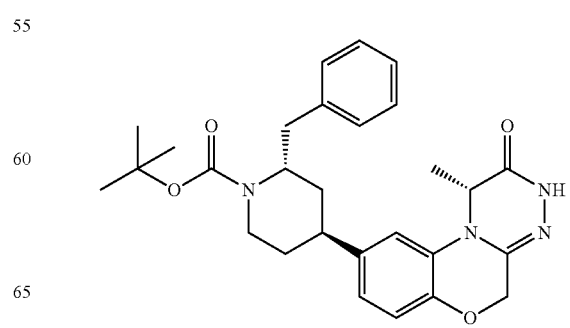

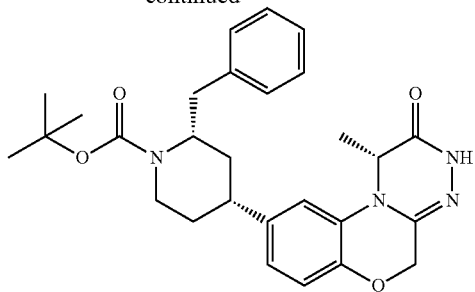

To a solution of (R)-tert-butyl 6-benzyl-4-((R)-1-methyl-2-oxo-1,2,3,5-tetrahydrobenzo[5,6][1,4]oxazino[3,4-c][1,2,4]triazin-9-yl)-5,6-dihydropyridine-1(2H)-carboxylate (0.330 g, 0.675 mmol) in MeOH (20 mL) was added Pd/C (10%, 0.033 g, 0.028 mmol) and the mixture was stirred under an atmosphere of $H_2$ (50 psi) at 50° C. for 12 h. The reaction mixture was cooled to ambient temperature and filtered. The filtrate was concentrated in vacuo to give crude (2S)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate (0.320 g). LC/MS (Table 1, Method 4) $R_t$=2.813 min; MS m/z: 513 [M+23]$^+$.

Chiral SFC (Table 2, Method 8) separation gave (2S,4S)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate (isomer 1, SFC (Table 1, Method 20) $R_t$=8.4 min, 0.120 g, 36%) and (2S,4R)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate (isomer 2, SFC (Table 1, Method 20) $R_t$=8.79 min, 0.190 g, 57%).

Step E. (R)-9-((2S,4S)-2-Benzylpiperidin-4-yl)-1-methyl-3,5-dihydrobenzo[5,6][1,4]oxazino[3,4-c][1,2,4]triazin-2(1H)-one trifluoroacetic acid (Example #109-1, Enantiomer 1)

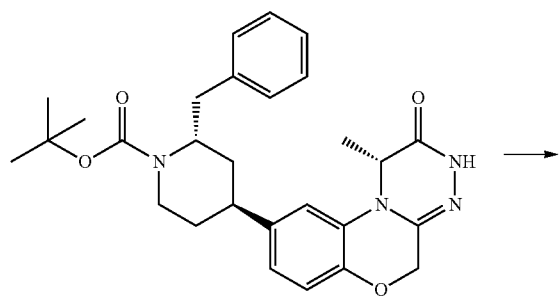

To a solution of (2S,4S)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate (isomer 1, SFC (Table 1, Method 20) $R_t$=8.4 min, 0.120 g, 0.245 mmol) in DCM (3 mL) was added TFA (1 mL) and the reaction mixture was stirred at ambient temperature for 1 h. The solvent was removed in vacuo and EtOAc (2 mL) was added to the residue. The precipitate was collected by filtration and washed with EtOAc (1 mL) and petroleum ether (2 mL) to give (R)-9-((2S,4S)-2-benzylpiperidin-4-yl)-1-methyl-3,5-dihydrobenzo[5,6][1,4]oxazino[3,4-c][1,2,4]triazin-2(1H)-one trifluoroacetic acid (Example #109-1, Enantiomer 1, SFC (Table 1, Method 21) $R_t$=4.912 min, 0.115 g, 93%) as a solid. LC/MS (Table 1, Method 4) $R_t$=1.617 min; MS m/z: 391 [M+H]$^+$.

Step F. (R)-9-((2S,4R)-2-Benzylpiperidin-4-yl)-1-methyl-3,5-dihydrobenzo[5,6][1,4]oxazino[3,4-c][1,2,4]triazin-2(1H)-one trifluoroacetic acid (Example #109-2, Enantiomer 2)

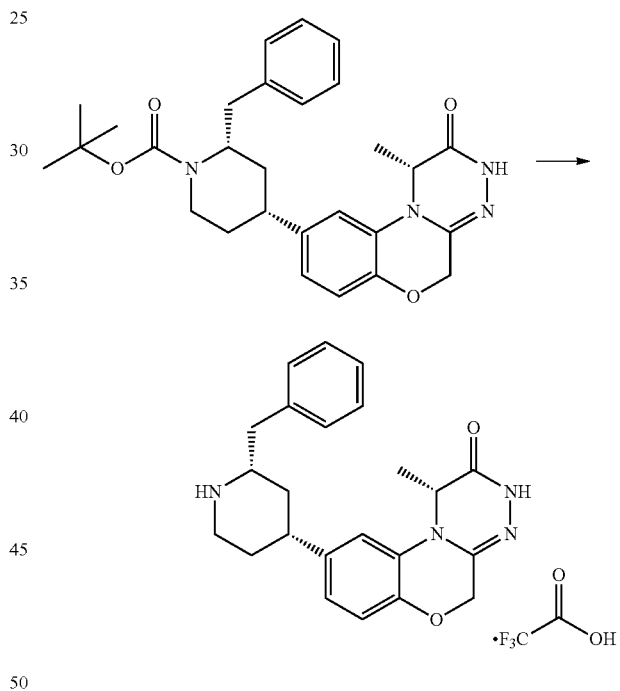

To a solution of (2S,4R)-tert-butyl 2-benzyl-4-((R)-1-methyl-2-oxo-1,2,3,5-tetrahydrobenzo[5,6][1,4]oxazino[3,4-c][1,2,4]triazin-9-yl)piperidine-1-carboxylate (0.190 g, 0.387 mmol) in DCM (3 mL) was added TFA (1 mL) and the mixture was stirred at ambient temperature for 1 h. The solvent was removed in vacuo and EtOAc (2 mL) was added to the residue. The precipitate was collected by filtration and washed with EtOAc (1 mL) and petroleum ether (2 mL) to give (R)-9-((2S,4R)-2-benzylpiperidin-4-yl)-1-methyl-3,5-dihydrobenzo[5,6][1,4]oxazino[3,4-c][1,2,4]triazin-2(1H)-one trifluoroacetic acid (Example #109-2, Enantiomer 2, SFC (Table 1, Method 21) $R_t$=4.521 min, 0.190 g, 97%) as a solid. LC/MS (Table 1, Method 4) $R_t$=1.617 min; MS m/z: 391 [M+H]$^+$.

TABLE 14

The following analogs were prepared from (R)-1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (Example #109, Step B) and 3-(1-trifluoromethanesulfonyloxy-vinyl)-azetidine-1-carboxylic acid tert-butyl ester (Preparation #4, Step C) using the procedure detailed in Example #109, Step C-F.

| Structure | Example # | R$_t$ min (method) | m/z ESI+ (M + H)+ |
|---|---|---|---|
| 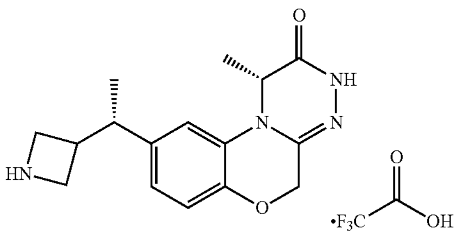 | 110 | 2.429 (Table 1, Method 5) | 301 |
| 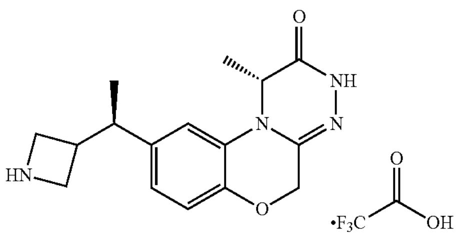 | 111 | 2.433 (Table 1, Method 5) | 301 |

Absolute configuration of benzylic position not determined.

Example #112

9-(Azetidin-3-ylamino)-1-methyl-8-(1,1,1-trifluoro-propan-2-yl)-3,5-dihydrobenzo[5,6][1,4]oxazino[3,4-c][1,2,4]triazin-2(1H)-one trifluoroacetic acid salt

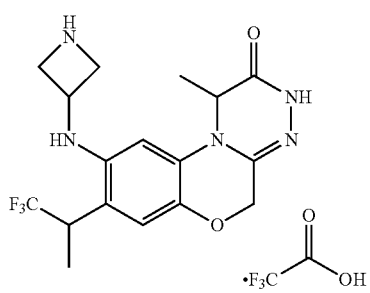

Step A. 3-[4-Methyl-3-oxo-7-(1-trifluoromethyl-vinyl)-2,3,4,10-tetrahydro-9-oxa-1,2,4a-triaza-phenanthren-6-ylamino]-azetidine-1-carboxylic acid tert-butyl ester

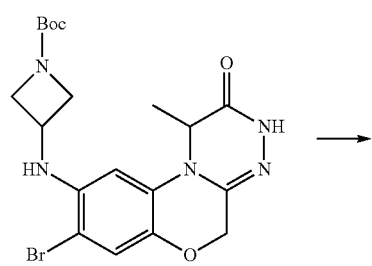

-continued

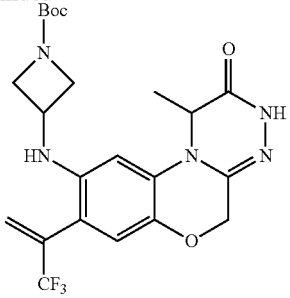

A mixture of K$_2$CO$_3$ (0.12 g, 0.86 mmol), Pd(PPh$_3$)$_4$ (0.099 g, 0.086 mmol), 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester ((Example 1, Step B, 0.20 g, 0.43 mmol) and 4,4,6-trimethyl-2-(3,3,3-trifluoro-prop-1-en-2-yl)-1,3,2-dioxaborinane (0.38 g, 1.7 mmol) in DME (15 mL) and water (2.5 mL) was stirred at 80° C. overnight. The reaction mixture was cooled to ambient temperature. EtOAc (50 mL) and water (30 mL) were added and the organic portion was separated, dried over anhydrous Na$_2$SO$_4$, filtered and concentrated in vacuo. The residue was purified by preparative TLC (eluting with 50% EtOAc in petroleum ether) to give 3-[4-methyl-3-oxo-7-(1-trifluoromethyl-vinyl)-2,3,4,10-tetrahydro-9-oxa-1,2,4a-triaza-phenanthren-6-ylamino]-azetidine-1-carboxylic acid tert-butyl ester (0.14 g, 68%). $^1$H NMR (CDCl$_3$, 400 MHz): δ 8.14 (brs, 1H), 6.83 (s, 1H), 6.28 (s, 1H), 5.92 (s, 1H), 5.73 (s, 1H), 4.66 (q, J=6.8 Hz, 1H), 4.56 (d, J=12.8 Hz, 2H), 4.26 (m, 2H), 4.16 (m, 1H), 4.04 (m, 1H), 3.70 (m, 2H), 1.53 (t, J=6.8 Hz, 3H), 1.48 (s, 9H).

235

Step B. 3-[4-Methyl-3-oxo-7-(2,2,2-trifluoro-1-methyl-ethyl)-2,3,4,10-tetrahydro-9-oxa-1,2,4a-triaza-phenanthren-6-ylamino]-azetidine-1-carboxylic acid tert-butyl ester

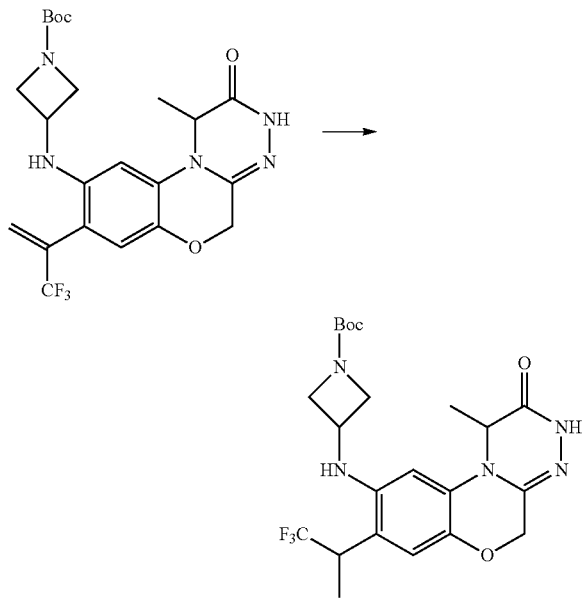

A mixture of 3-[4-methyl-3-oxo-7-(1-trifluoromethyl-vinyl)-2,3,4,10-tetrahydro-9-oxa-1,2,4a-triaza-phenanthren-6-ylamino]-azetidine-1-carboxylic acid tert-butyl ester (0.12 g, 0.25 mmol) and Pd/C (10%, 0.10 g, 0.1 mmol) in EtOAc (60 mL) was stirred under an atmosphere of $H_2$ (40 psi) overnight. The mixture was filtered and the filtrate was concentrated in vacuo to give a residue which was purified by preparative TLC (eluting with 50% EtOAc in petroleum ether) to give 3-[4-methyl-3-oxo-7-(2,2,2-trifluoro-1-methyl-ethyl)-2,3,4,10-tetrahydro-9-oxa-1,2,4a-triaza-phenanthren-6-ylamino]-azetidine-1-carboxylic acid tert-butyl ester (0.020 g, 17%). $^1$H NMR (CDCl$_3$, 400 MHz): δ 8.62 (brs, 1H), 7.29 (s, 1H), 6.97 (s, 1H), 6.97 (s, 1H), 4.72 (m, 1H), 4.53 (m, 2H), 4.33 (m, 2H), 4.11 (m, 1H), 3.77 (m, 2H), 3.63 (m, 1H), 1.50 (m, 15H).

Step C. 9-(Azetidin-3-ylamino)-1-methyl-8-(1,1,1-trifluoropropan-2-yl)-3,5-dihydrobenzo[5,6][1,4]oxazino[3,4-c][1,2,4]triazin-2(1H)-one trifluoroacetic acid

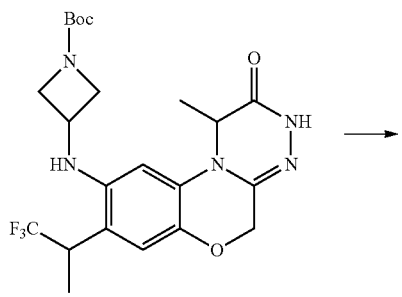

236

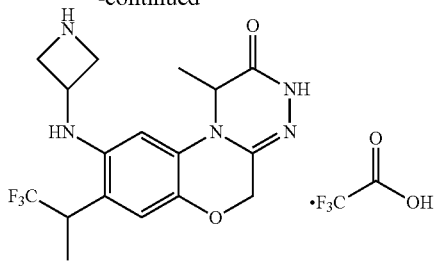

To a solution of 3-[4-methyl-3-oxo-7-(2,2,2-trifluoro-1-methyl-ethyl)-2,3,4,10-tetrahydro-9-oxa-1,2,4a-triaza-phenanthren-6-ylamino]-azetidine-1-carboxylic acid tert-butyl ester (0.020 g, 0.041 mmol) in DCM (3 mL) was added in TFA (0.5 mL) and the solution was stirred for 2 h. The solvent was removed in vacuo to give 9-(azetidin-3-ylamino)-1-methyl-8-(1,1,1-trifluoropropan-2-yl)-3,5-dihydrobenzo[5,6][1,4]oxazino[3,4-c][1,2,4]triazin-2(1H)-one trifluoroacetic acid (0.015 g, 95%). LC/MS (Table 1, Method 5) $R_f$=2.166 min; MS m/z: 384 [M+H]$^+$ Example #113

9-((3-Isopropylazetidin-3-yl)amino)-1-methyl-3,5-dihydrobenzo[5,6][1,4]oxazino[3,4-c][1,2,4]triazin-2(1H)-one trifluoroacetic acid

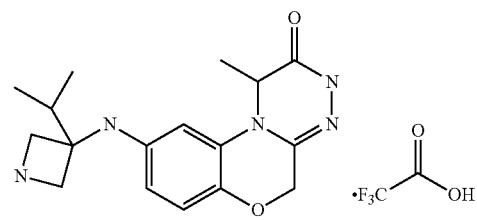

Step A. tert-Butyl 3-isopropyl-3-((1-methyl-2-oxo-3-((2-(trimethylsilyl)ethoxy)methyl)-1,2,3,5-tetrahydrobenzo[5,6][1,4]oxazino[3,4-c][1,2,4]triazin-9-yl)amino)azetidine-1-carboxylate

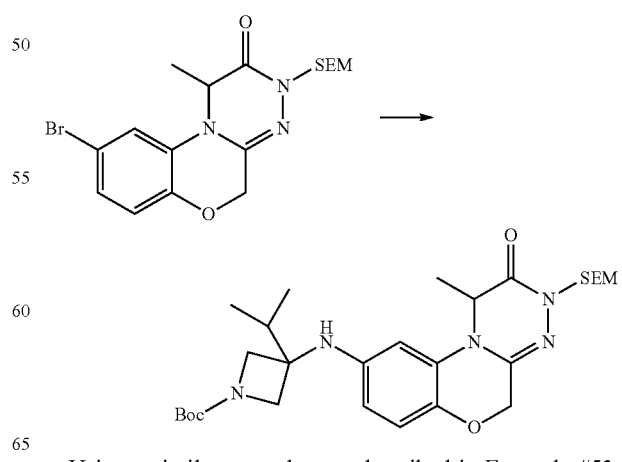

Using a similar procedure as described in Example #53, Step F, tert-butyl 3-isopropyl-3-((1-methyl-2-oxo-3-((2-(trimethylsilyl)ethoxy)methyl)-1,2,3,5-tetrahydrobenzo[5,6][1,4]oxazino[3,4-c][1,2,4]triazin-9-yl)amino)azetidine-1-carboxylate (0.025 g, 0.045 mmol) was prepared from 9-bromo-1-methyl-3-((2-(trimethylsilyl)ethoxy)methyl)-3,5-dihydrobenzo[5,6][1,4]oxazino[3,4-c][1,2,4]triazin-2(1H)-one (Preparation #1, Step E, 0.05 g, 0.117 mmol) and tert-butyl 3-amino-3-isopropylazetidine-1-carboxylate (UKRORGSYN, 0.038 g, 0.176 mmol). LC/MS (Table 1, Method 2) $R_t$=1.398 min.; MS m/z: 582 [M+23]$^+$ Step B. 9-((3-Isopropylazetidin-3-yl)amino)-1-methyl-3,5-dihydrobenzo[5,6][1,4]oxazino[3,4-c][1,2,4]triazin-2(1H)-one trifluoroacetic acid

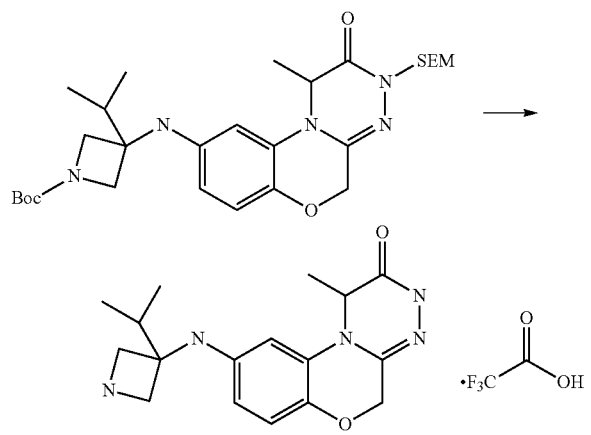

Using a similar procedure as described in Example #53, Steps G and H, 9-((3-isopropylazetidin-3-yl)amino)-1-methyl-3,5-dihydrobenzo[5,6][1,4]oxazino[3,4-c][1,2,4]triazin-2(1H)-one trifluoroacetic acid (0.0018 g, 9%) was prepared from tert-butyl 3-isopropyl-3-((1-methyl-2-oxo-1,2,3,5-tetrahydrobenzo[5,6][1,4]oxazino[3,4-c][1,2,4]triazin-9-yl)amino)azetidine-1-carboxylate (0.025 g, 0.045 mmol). LC/MS (Table 1, Method 5) $R_t$=1.950 min.; MS m/z: 330 [M+H]$^+$.

Example #114

9-(Azetidin-3-ylamino)-7,8-difluoro-1-methyl-3,5-dihydrobenzo[5,6][1,4]oxazino[3,4-c][1,2,4]triazin-2(1H)-one trifluoroacetic acid

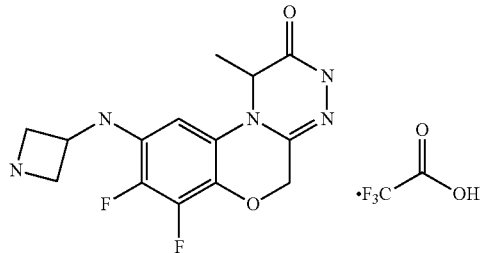

Using a similar procedure as described in Example #56, Step A-H, 9-(azetidin-3-ylamino)-7,8-difluoro-1-methyl-3,5-dihydrobenzo[5,6][1,4]oxazino[3,4-c][1,2,4]triazin-2(1H)-one trifluoroacetic acid (0.0014 g, 0.04%) was prepared from 2,3-difluoro-6-nitrophenol (5 g, 28.6 mmol). LC/MS (Table 1, Method 5) $R_t$=1.854 min; MS m/z: 324 [M+H]$^+$ Example #115

1,8-Dimethyl-9-(1,7-diazaspiro[3.5]nonan-1-yl)-3,5-dihydrobenzo[5,6][1,4]oxazino[3,4-c][1,2,4]triazin-2(1H)-one trifluoroacetic acid

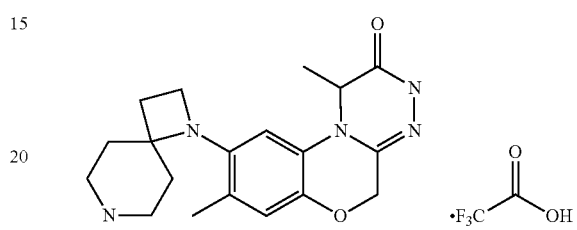

Step A. tert-Butyl 1-(1,8-dimethyl-2-oxo-3-((2-(trimethylsilyl)ethoxy)methyl)-1,2,3,5-tetrahydrobenzo[5,6][1,4]oxazino[3,4-e][1,2,4]triazin-9-yl)-1,7-diazaspiro[3.5]nonane-7-carboxylate

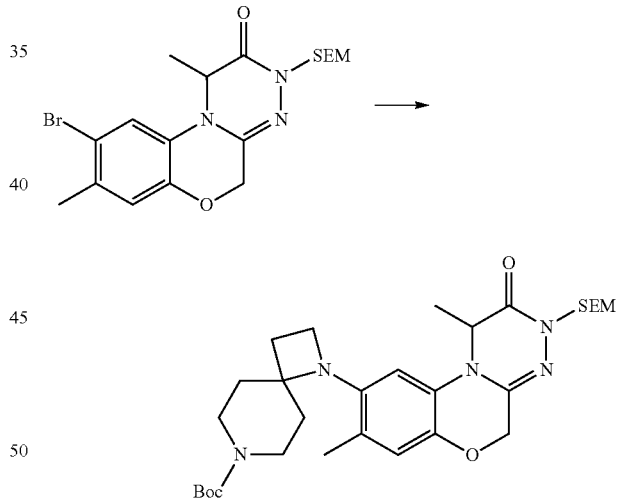

Using a similar procedure as described in Example #53, Step F, tert-butyl 1-(1,8-dimethyl-2-oxo-3-((2-(trimethylsilyl)ethoxy)methyl)-1,2,3,5-tetrahydrobenzo[5,6][1,4]oxazino[3,4-c][1,2,4]triazin-9-yl)-1,7-diazaspiro[3.5]nonane-7-carboxylate (0.026 g, 19%) was prepared from 9-bromo-1,8-dimethyl-3-((2-(trimethylsilyl)ethoxy)methyl)-3,5-dihydrobenzo[5,6][1,4]oxazino[3,4-c][1,2,4]triazin-2(1H)-one (Preparation #6, Step F, 0.1 g, 0.227 mmol) and tert-butyl 1,7-diazaspiro[3.5]nonane-7-carboxylate (0.062 g, 0.272 mmol). LC/MS (Table 1, Method 2) $R_t$=0.948 min.; MS m/z: 608 [M+23]$^+$

239

Step B. 1,8-Dimethyl-9-(1,7-diazaspiro[3.5]nonan-1-yl)-3,5-dihydrobenzo[5,6][1,4]oxazino[3,4-c][1,2,4]triazin-2(1H)-one trifluoroacetic acid

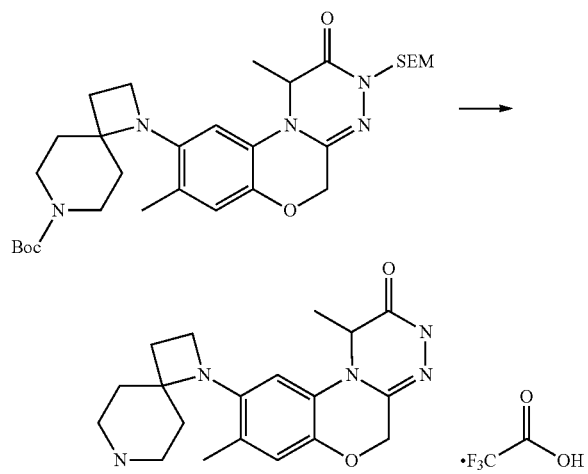

Using a similar procedure as described in Example #53, Steps G and H, 1,8-dimethyl-9-(1,7-diazaspiro[3.5]nonan-1-yl)-3,5-dihydrobenzo[5,6][1,4]oxazino[3,4-c][1,2,4]triazin-2(1H)-one trifluoroacetic acid (0.0049 g, 0.014 mmol) was prepared from tert-butyl 1-(1,8-dimethyl-2-oxo-1,2,3,5-tetrahydrobenzo[5,6][1,4]oxazino[3,4-c][1,2,4]triazin-9-yl)-1,7-diazaspiro[3.5]nonane-7-carboxylate (0.026 g, 0.044 mmol). LC/MS (Table 1, Method 5) $R_t$=1.556 min; MS m/z: 356 [M+H]$^+$

Example #116

9-(2-Benzylpiperidin-4-yl)-1-methyl-8-(trifluoromethyl)-3,5-dihydrobenzo[5,6][1,4]oxazino[3,4-c][1,2,4]triazin-2(1H)-one trifluoroacetic acid

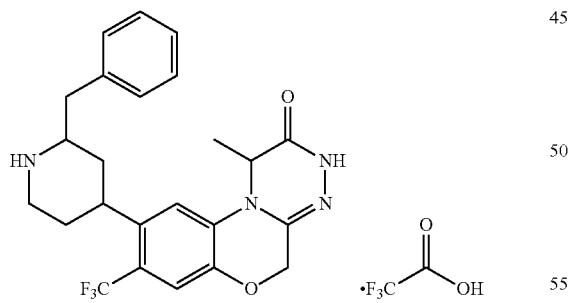

Using a similar procedure as described in Example #86, Step A-D, 9-(2-benzylpiperidin-4-yl)-1-methyl-8-(trifluoromethyl)-3,5-dihydrobenzo[5,6][1,4]oxazino[3,4-c][1,2,4]triazin-2(1H)-one trifluoroacetic acid (0.042 g, 10%) was prepared from 1-methyl-9-(4,4,5,5-tetramethyl-1,3,2-dioxaborolan-2-yl)-8-(trifluoromethyl)-3-((2-(trimethylsilyl)ethoxy)methyl)-3,5-dihydrobenzo[5,6][1,4]oxazino[3,4-c][1,2,4]triazin-2(1H)-one (Example #109, Step B, 0.379 g, 0.700 mmol). LC/MS (Table 1, Method 4) $R_t$=2.003 min; MS m/z: 459 [M+H]$^+$

Example #117

6-(2-Aminomethyl-pyrrolidin-1-yl)-4-methyl-2,10-dihydro-9-oxa-1,2,4a-triaza-phenanthren-3-one trifluoroacetic acid

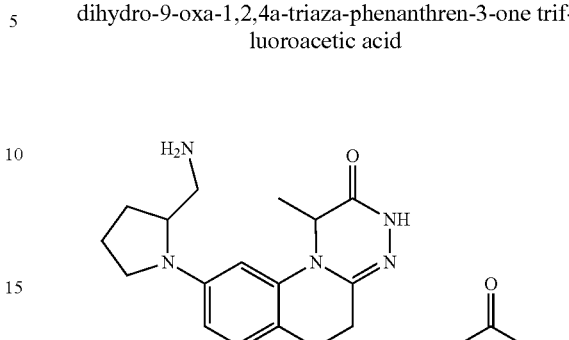

A mixture of 6-bromo-4-methyl-2-(2-trimethylsilanyl-ethoxymethyl)-2,10-dihydro-9-oxa-1,2,4a-triaza-phenanthren-3-one (Preparation #1, Step E, 0.050 g, 0.117 mmol), cesium carbonate (0.076 g, 0.235 mmol), tert-butyl (pyrrolidin-2-ylmethyl)carbamate (0.047 g, 0.235 mmol), Pd(OAc)$_2$ (0.008 g, 0.035 mmol) and BINAP (0.022 g, 0.035 mmol) in toluene (2 mL) was heated at reflux overnight. The reaction mixture was cooled to ambient temperature, filtered and concentrated in vacuo to give crude tert-butyl ((1-(1-methyl-2-oxo-3-((2-(trimethylsilyl)ethoxy)methyl)-1,2,3,5-tetrahydrobenzo[5,6][1,4]oxazino[3,4-c][1,2,4]triazin-9-yl)pyrrolidin-2-yl)methyl)carbamate as brown solid, which was used for next step without further purification.

A mixture of crude {1-[4-methyl-3-oxo-2-(2-trimethylsilanyl-ethoxymethyl)-2,3,4,10-tetrahydro-9-oxa-1,2,4a-triaza-phenanthren-6-yl]-pyrrolidin-2-ylmethyl}-carbamic acid tert-butyl ester (0.117 mol) in DCM (2 mL) and TFA (1 mL) was stirred for 1 h at ambient temperature. The solvent was removed in vacuo and the residue was re-dissolved in MeOH (2 mL) and aqueous ammonium hydroxide (25%, 0.5 mL). The mixture was stirred for 2 h then purified by preparative HPLC (Table 3, Method 20) to give 6-(2-aminomethyl-pyrrolidin-1-yl)-4-methyl-2,10-dihydro-9-oxa-1,2,4a-triaza-phenanthren-3-one trifluoroacetic acid as white solid (0.0068 g, 13% for 2 steps). LC/MS (Table 1, Method 4) $R_t$=1.111 min; MS m/z: 316 [M+H]$^+$

Example #118

4-Methyl-6-(2-methyl-azetidin-3-ylamino)-2,10-dihydro-9-oxa-1,2,4a-triaza-phenanthren-3-one trifluoroacetic acid

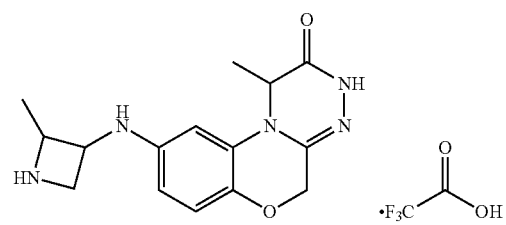

241

Step A. (3-Diazo-1-methyl-2-oxo-propyl)-carbamic acid tert-butyl ester

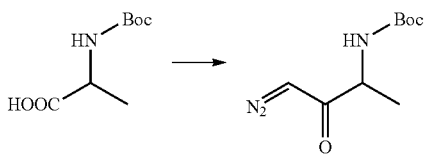

To a −15° C. solution of 2-((tert-butoxycarbonyl)amino)propanoic acid (2.5 g, 13.21 mmol) in THF (66 mL) was added Et₃N (1.337 g, 13.21 mmol) and ethyl carbonochloridate (1.434 g, 13.21 mmol). The reaction mixture was stirred for 15 min then allowed to warm to 0° C. A solution of diazomethane (prepared according to the standard procedure (*Organic Syntheses, Coll.* Vol. 5, p. 351 (1973); Vol. 41, p. 16 (1961)) in Et₂O (150 mL) was added, until the rich yellow color persisted. The reaction mixture was allowed to warm to rt and stirred for 3 h. Excess $CH_2N_2$ was destroyed by the addition of a small amount of aqueous AcOH (20%, 3 mL). The reaction mixture was extracted with saturated $NaHCO_3$ (20 mL), and the organic portion was separated and washed with saturated aqueous $NH_4Cl$ (20 mL) and brine (20 mL). The organic portion was separated, dried over $Na_2SO_4$, filtered and evaporated in vacuo. The residue was purified by column chromatography on silica gel (eluting with 5-20% EtOAc in petroleum ether) to give (3-diazo-1-methyl-2-oxo-propyl)-carbamic acid tert-butyl ester (2.8 g, 99%) as a brown solid. ¹H NMR (DMSO-d₆, 400 MHz): δ 7.27 (d, J=7.2, 1H), 6.02 (s, 1H), 4.01 (m, 1H), 1.39 (s, 9H), 1.20 (m, 3H).

Step B. 2-Methyl-3-(4-methyl-3-oxo-2,3,4,10-tetrahydro-9-oxa-1,2,4a-triaza-phenanthren-6-ylamino)-azetidine-1-carboxylic acid tert-butyl ester

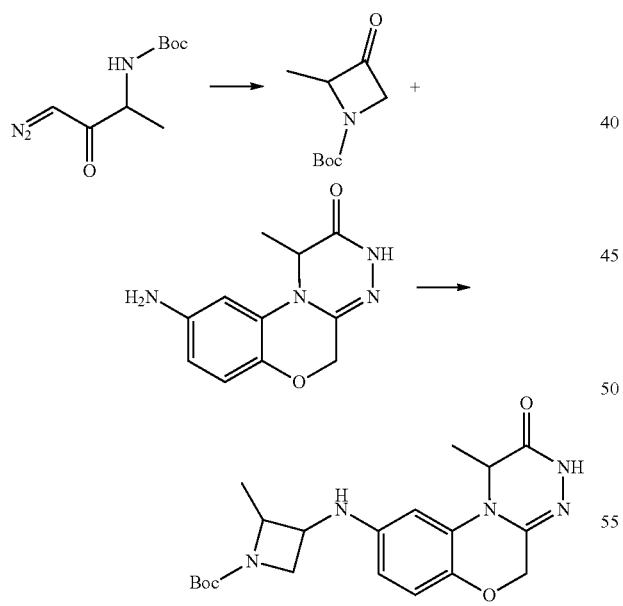

(3-Diazo-1-methyl-2-oxo-propyl)-carbamic acid tert-butyl ester (0.250 g, 1.17 mmol) was dissolved in anhydrous DCM (6 mL) and Et₃N (1.18 mg, 0.012 mmol) was added. The reaction mixture was cooled to 0° C. and rhodium (II) acetate (0.010 g, 0.023 mmol) was added. The reaction mixture was stirred at 0° C. for 1 h then concentrated in vacuo to give 2-methyl-3-oxo-azetidine-1-carboxylic acid tert-butyl ester, which was used in the next step without further purification. TLC (eluting with 20% EtOAc/heptane) $R_f$=0.3.

242

To a mixture of 2-methyl-3-oxo-azetidine-1-carboxylic acid tert-butyl ester (crude, 1.17 mmol) in MeOH (5 mL) and AcOH (0.5 mL) was added 6-amino-4-methyl-2,10-dihydro-9-oxa-1,2,4a-triaza-phenanthren-3-one (Preparation #2, Step E, 0.050 g, 0.215 mmol). The reaction mixture was stirred at ambient temperature for 0.5 h then NaBH₃CN (0.068 g, 1.076 mmol) was added. The mixture was stirred at ambient temperature overnight then concentrated in vacuo. The residue was purified by preparative HPLC (Table 3, Method 24) to give 2-methyl-3-(4-methyl-3-oxo-2,3,4,10-tetrahydro-9-oxa-1,2,4a-triaza-phenanthren-6-ylamino)-azetidine-1-carboxylic acid tert-butyl ester (0.016 g, 18%). LC/MS (Table 1, Method 5) $R_t$=1.087 min; MS m/z: 424 [M+23]⁺.

Step C. 4-Methyl-6-(2-methyl-azetidin-3-ylamino)-2,10-dihydro-9-oxa-1,2,4a-triaza-phenanthren-3-one trifluoroacetic acid

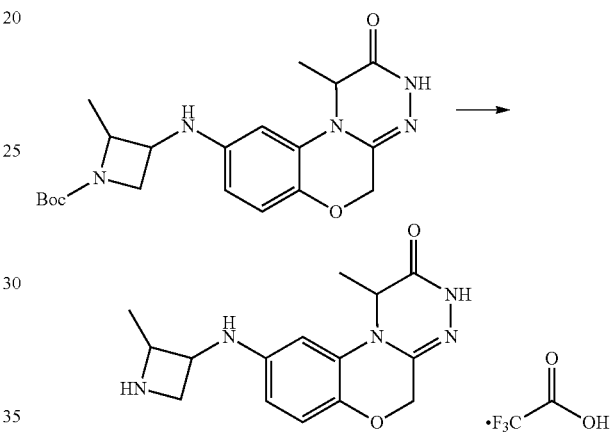

To a solution of 2-methyl-3-(4-methyl-3-oxo-2,3,4,10-tetrahydro-9-oxa-1,2,4a-triaza-phenanthren-6-ylamino)-azetidine-1-carboxylic acid tert-butyl ester (0.016 g, 0.040 mmol) in DCM (2 mL) was added TFA (0.4 mL) and the mixture was stirred at ambient temperature for 2 h. The solvent was removed in vacuo to give 4-methyl-6-(2-methyl-azetidin-3-ylamino)-2,10-dihydro-9-oxa-1,2,4a-triaza-phenanthren-3-one trifluoroacetic acid (0.012 g, 100%) LC/MS (Table 1, Method 5) $R_t$=1.582 min.; MS m/z: 302 [M+H]⁺.

Example #119

1-Methyl-8-phenyl-9-(piperidin-4-yl)-3,5-dihydrobenzo[5,6][1,4]oxazino[3,4-c][1,2,4]triazin-2(1H)-one trifluoroacetic acid

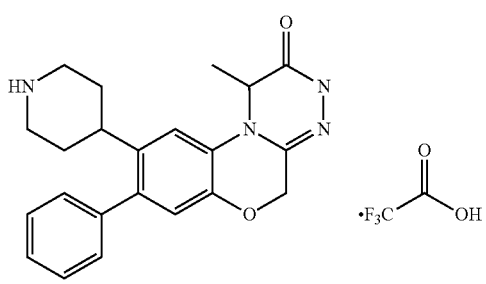

Step A. 4-(7-Bromo-4-methyl-3-oxo-2,3,4,10-tetrahydro-9-oxa-1,2,4a-triaza-phenanthren-6-yl)-piperidine-1-carboxylic acid tert-butyl ester

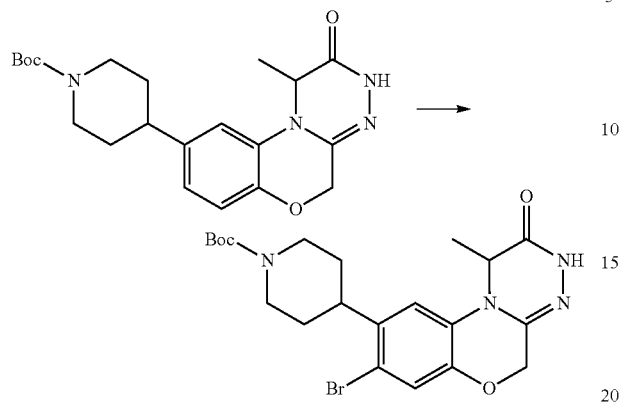

To a solution of 4-(4-methyl-3-oxo-2,3,4,10-tetrahydro-9-oxa-1,2,4a-triaza-phenanthren-6-yl)-piperidine-1-carboxylic acid tert-butyl ester (Example #71, Step B, 0.50 g, 1.249 mmol) in DCM (5 mL) and MeOH (5 mL) was added tetrabutylammonium tribromide (0.662 g, 1.373 mmol) portionwise and the reaction mixture was stirred for 30 min at ambient temperature. Saturated aqueous $Na_2S_2O_3$ solution (5 mL) was added and the pH was adjusted to 7 by the addition of saturated aqueous $NaHCO_3$ solution. The mixture was extracted with DCM (3×20 mL). The combined organic layers were washed with brine (20 mL), dried over anhydrous $Na_2SO_4$ and concentrated in vacuo. The residue was purified by column chromatography on silica gel (eluting with 20% EtOAc in petroleum ether) to give 4-(7-bromo-4-methyl-3-oxo-2,3,4,10-tetrahydro-9-oxa-1,2,4a-triaza-phenanthren-6-yl)-piperidine-1-carboxylic acid tert-butyl ester (0.34 g, 57%). LC/MS (Table 1, Method 2) $R_t$=1.289 min.; MS m/z: 479/481 $[M+H]^+$.

Step B. tert-Butyl 4-(1-methyl-2-oxo-8-phenyl-1,2,3,5-tetrahydrobenzo[5,6][1,4]oxazino[3,4-e][1,2,4]triazin-9-yl)piperidine-1-carboxylate

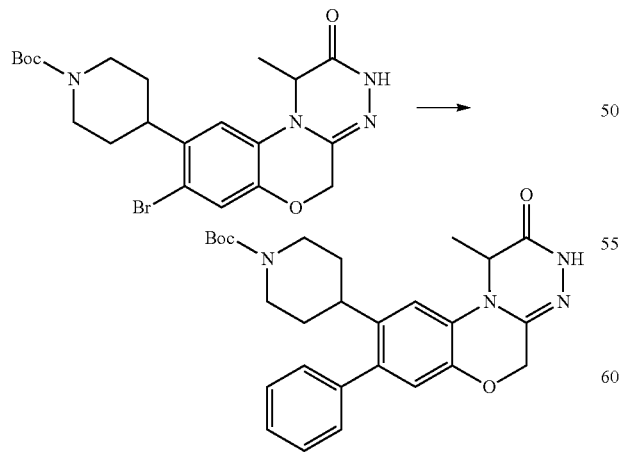

A mixture of 4-(7-bromo-4-methyl-3-oxo-2,3,4,10-tetrahydro-9-oxa-1,2,4a-triaza-phenanthren-6-yl)-piperidine-1-carboxylic acid tert-butyl ester (0.02 g, 0.042 mmol), phenylboronic acid (0.01 g, 0.083 mmol), [1,1'-bis(diphenylphosphino)ferrocene]dichloropalladium(II) dichloride dichloromethane complex (0.007 g, 0.008 mmol) and $K_2CO_3$ (0.012 g, 0.083 mmol) in dioxane (1 mL) and water (0.2 mL) was heated to reflux for 8 h. The reaction mixture was cooled to ambient temperature and filtered. The filtrate was concentrated in vacuo and the residue was purified by preparative TLC (eluting with 50% EtOAc in petroleum ether) to give tert-butyl-4-(1-methyl-2-oxo-8-phenyl-1,2,3,5-tetrahydrobenzo[5,6][1,4]oxazino[3,4-c][1,2,4]triazin-9-yl)piperidine-1-carboxylate (0.02 g, 100%) as a pale-white solid. LC/MS (Table 1, Method 3) $R_t$=1.596 min.; MS m/z: 477 $[M+H]^+$.

Step C. 1-Methyl-8-phenyl-9-(piperidin-4-yl)-3,5-dihydrobenzo[5,6][1,4]oxazino[3,4-e][1,2,4]triazin-2(1H)-one trifluoroacetic acid

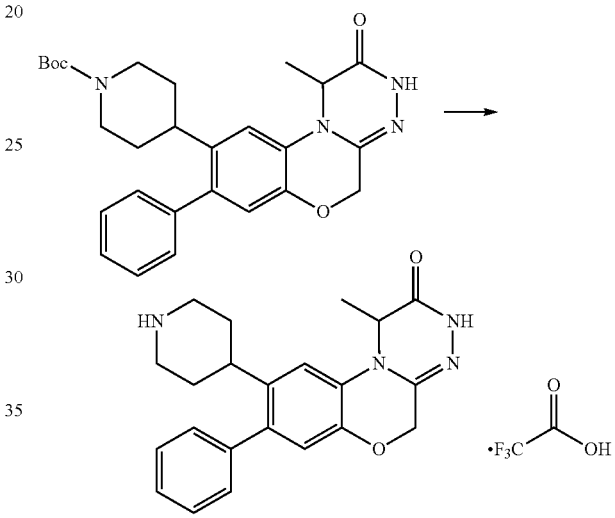

A solution of tert-butyl 4-(1-methyl-2-oxo-8-phenyl-1,2,3,5-tetrahydrobenzo[5,6][1,4]oxazino[3,4-c][1,2,4]triazin-9-yl)piperidine-1-carboxylate (0.020 g, 0.042 mmol) in DCM (6 mL) and TFA (1 mL) was stirred at ambient temperature for 1.5 h. The solvent was removed in vacuo to give 1-methyl-8-phenyl-9-(piperidin-4-yl)-3,5-dihydrobenzo[5,6][1,4]oxazino[3,4-c][1,2,4]triazin-2(1H)-one trifluoroacetic acid (0.016 g, 78%) as a pale yellow solid. LC/MS (Table 1, Method 5) $R_t$=2.314 min.; MS m/z: 377 $[M+H]^+$.

Example #120

1-Methyl-9-(piperidin-4-yl)-8-(trifluoromethyl)-3,5-dihydrobenzo[5,6][1,4]oxazino[3,4-c][1,2,4]triazin-2(1H)-one trifluoroacetic acid

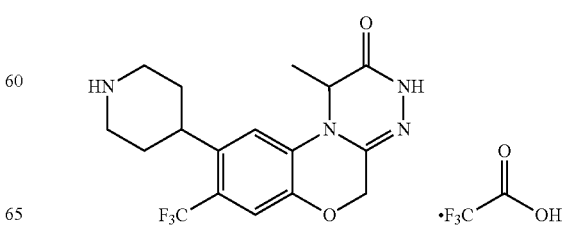

Step A. tert-butyl 4-(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)-5,6-dihydropyridine-1(2H)-carboxylate

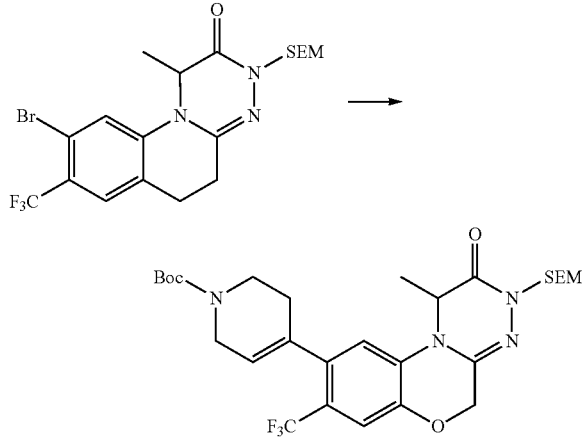

A mixture of 9-bromo-1-methyl-8-(trifluoromethyl)-3-((2-(trimethylsilyl)ethoxy)methyl)-3,5-dihydrobenzo[5,6][1,4]oxazino[3,4-c][1,2,4]triazin-2(1H)-one (Example #53, Step E, 0.08 g, 0.162 mmol), 4-(4,4,5,5-tetramethyl-[1,3,2]dioxaborolan-2-yl)-3,6-dihydro-2H-pyridine-1-carboxylic acid tert-butyl ester (0.10 g, 0.324 mmol), [1,1'-bis(diphenylphosphino)ferrocene]dichloropalladium(II)dichloride dichloromethane complex (0.026 g, 0.032 mmol) and $K_2CO_3$ (0.045 g, 0.324 mmol) in dioxane (1.2 mL) and water (0.2 mL) was heated at reflux for 6 h. The reaction mixture was cooled to ambient temperature and filtered. The filtrate was concentrated in vacuo and the residue was purified by column chromatography on silica gel (eluting with 40% EtOAc in petroleum ether) to give tert-butyl 4-(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)-5,6-dihydropyridine-1(2H)-carboxylate (0.07 g, 73%) as a pale-white solid. $^1$H NMR (methanol-$d_4$, 400 MHz): δ 7.28 (s, 1H), 7.10 (s, 1H), 5.64 (s, 1H), 5.11 (q, J=10.4 Hz, 2H), 4.97 (q, J=6.8 Hz, 1H), 4.69 (d, J=13.2 Hz, 2H), 4.04 (s, 2H), 3.70 (m, 4H), 2.39 (s, 2H), 1.51 (s, 9H), 1.47 (d, J=6.8 Hz, 3H), 0.96 (t, J=8.4 Hz, 2H), 0.00 (s, 9H).

Step B. tert-Butyl 4-(1-methyl-2-oxo-8-(trifluoromethyl)-1,2,3,5-tetrahydrobenzo[5,6][1,4]oxazino[3,4-c][1.2.4]-triazin-9-yl)piperidine-1-carboxylate

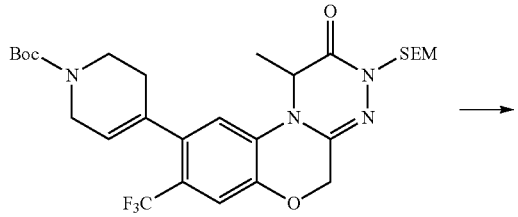

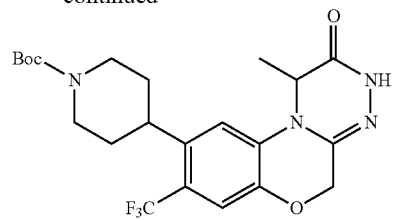

To a solution of tert-butyl 4-(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)-5,6-dihydropyridine-1(2H)-carboxylate (0.07 g, 0.117 mmol) in MeOH (15 mL) was added Pd/C (10%, 0.010 g) and the reaction mixture was stirred under an atmosphere of $H_2$ (1 atm) for 20 h. The reaction mixture was filtered, washing with methanol (3×5 mL). The filtrate was concentrated in vacuo to give tert-butyl 4-(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)piperidine-1-carboxylate (0.07 g, 100%), which was used directly in the next step.

To a solution of tert-butyl 4-(1-methyl-2-oxo-8-(trifluoromethyl)-3-((2-(trimethylsilyl)ethoxy)methyl)-1,2,3,5-tetrahydrobenzo[5,6][1,4]oxazino[3,4-c][1,2,4]triazin-9-yl)piperidine-1-carboxylate (0.07 g, 0.117 mmol) in THF (2 mL) was added a solution of TBAF in THF (1M, 0.58 mL, 0.585 mmol) and the reaction mixture was heated at reflux for 24 h. The reaction mixture was cooled to rt and the solvent was removed in vacuo. The residue was purified by preparative HPLC (Table 3, Method 23) to give tert-butyl 4-(1-methyl-2-oxo-8-(trifluoromethyl)-1,2,3,5-tetrahydrobenzo[5,6][1,4]oxazino[3,4-c][1,2,4]triazin-9-yl)piperidine-1-carboxylate (0.04 g, 73%). LC/MS (Table 1, Method 3) $R_t$=1.665 min; MS m/z: 469 [M+H]$^+$.

Step C 1-Methyl-9-(piperidin-4-yl)-8-(trifluoromethyl)-3,5-dihydrobenzo[5,6][1,4]oxazino[3,4-c][1,2,4]triazin-2(1H)-one trifluoroacetic acid

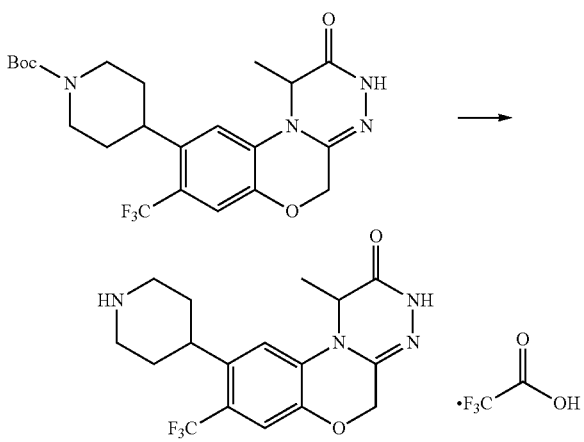

A solution of tert-butyl 4-(1-methyl-2-oxo-8-(trifluoromethyl)-1,2,3,5-tetrahydrobenzo[5,6][1,4]oxazino[3,4-c][1,2,4]triazin-9-yl)piperidine-1-carboxylate (0.01 g, 0.021 mmol) in DCM (5 mL) and TFA (1 mL) was stirred for 1 h at ambient temperature. The solvent was removed in vacuo to give 1-methyl-9-(piperidin-4-yl)-8-(trifluoromethyl)-3,5-dihydrobenzo[5,6][1,4]oxazino[3,4-c][1,2,4]triazin-2(1H)-one trifluoacetic acid salt as a pale yellow solid (0.01 g, 97%). LC/MS (Table 1, Method 5) R$_f$=3.057 min.; MS m/z: 369 [M+H]$^+$.

Example #121

(R)-8-Isopropyl-1-methyl-9-((3-methylazetidin-3-yl)oxy)-3,5-dihydrobenzo[5,6][1,4]oxazino[3,4-c][1,2,4]triazin-2(1H)-one trifluoroacetic acid (Example #121-1, Enantiomer 1) and (S)-8-isopropyl-1-methyl-9-((3-methylazetidin-3-yl)oxy)-3,5-dihydrobenzo[5,6][1,4]oxazino[3,4-c][1,2,4]triazin-2(1H)-one trifluoroacetic acid (Example #121-2, Enantiomer 2)

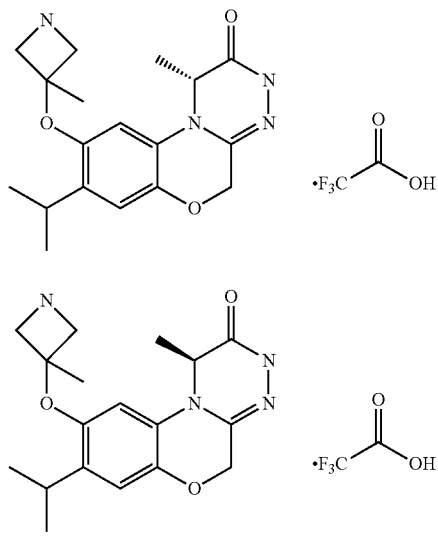

Step A. (R)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate and (S)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate

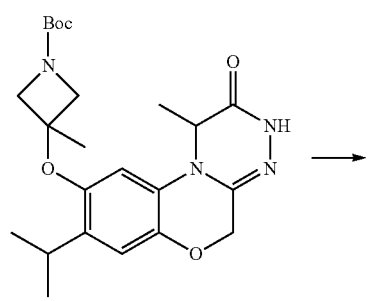

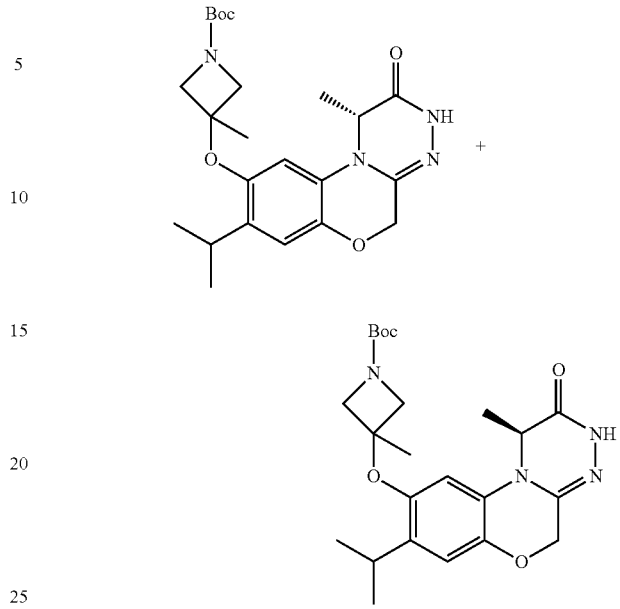

Racemic compound tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate (Example #82, Step C, 0.240 g) was separated by chiral SFC (Table 2, Method 16) to give two isomers: (S)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate (enantiomer 1, SFC (Table 1, Method 24), R$_f$=8.741 min., 0.095 g, 39%) and (R)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate (enantiomer 2, SFC (Table 1, Method 1), R$_f$=9.756 min., 0.095 g, 39%)

Enantiomer 1: LC/MS (Table 1, Method 2) R$_f$=1.40 min.; MS m/z: 445 [M+H]$^+$.

Enantiomer 2: LC/MS (Table 1, Method 2) R$_f$=1.39 min.; MS m/z: 445 [M+H]$^+$.

Step B. (S)-8-Isopropyl-1-methyl-9-((3-methylazetidin-3-yl)oxy)-3,5-dihydrobenzo[5,6][1,4]oxazino[3,4-c][1,2,4]triazin-2(1H)-one trifluoroacetic acid (Example #121-1, Enantiomer 1)

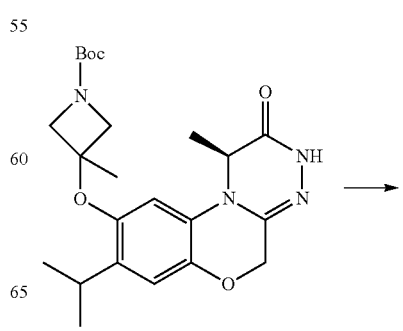

-continued

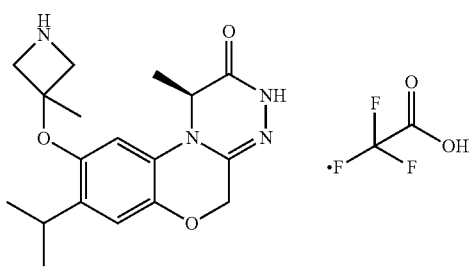

To a solution of (S)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate (enantiomer 1, SFC (Table 1, Method 24), $R_t$=8.741 min., 0.095 g, 0.213 mmol) in DCM (3 mL) was added TFA (0.5 mL) and the mixture was stirred at ambient temperature for 2 h. The solvent was removed in vacuo to give (S)-8-isopropyl-1-methyl-9-((3-methylazetidin-3-yl)oxy)-3,5-dihydrobenzo[5,6][1,4]oxazino[3,4-c][1,2,4]-triazin-2(1H)-one trifluoroacetic acid (Example #121-1, Enantiomer 1, SFC (Table 1, Method 24), $R_t$=3.745 min, 0.085 g, 97%). LC/MS (Table 1, Method 5) $R_t$=2.175 min.; MS m/z: 345 [M+H]$^+$.

Step C. (R)-8-isopropyl-1-methyl-9-((3-methylazetidin-3-yl)oxy)-3,5-dihydrobenzo[5,6][1,4]oxazino[3,4-c][1,2,4]triazin-2(1H)-one trifluoroacetic acid (Example #121-2, Enantiomer 2)

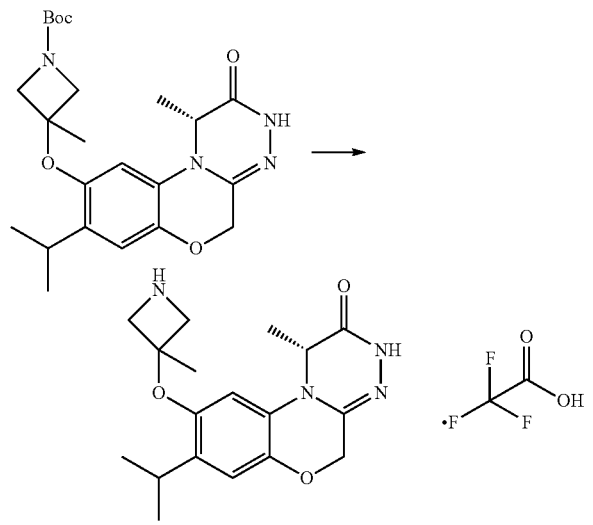

To a solution of (R)-tert-butyl 3-((8-isopropyl-1-methyl-2-oxo-1,2,3,5-tetrahydrobenzo[5,6][1,4]oxazino[3,4-c][1,2,4]triazin-9-yl)oxy)-3-methylazetidine-1-carboxylate ((enantiomer 2, SFC (Table 1, Method 24), $R_t$=9.756 min., 0.095 g, 0.213 mmol) in DCM (3 mL) was added TFA (0.5 mL) and the mixture was stirred at ambient temperature for 2 h. The solvent was removed in vacuo to give (R)-8-isopropyl-1-methyl-9-((3-methylazetidin-3-yl)oxy)-3,5-dihydrobenzo[5,6][1,4]oxazino[3,4-c][1,2,4]triazin-2(1H)-one trifluoroacetic acid (Example #121-2, Enantiomer 2, SFC (Table 1, Method 24), $R_t$=3.331 min, 0.085 g, 97%). LC/MS (Table 1, Method 5) $R_t$=2.175 min.; MS m/z: 345 [M+H]$^+$.

Example #122

9-(Azetidin-3-ylamino)-1,8-dimethyl-3,5-dihydrobenzo[5,6][1,4]oxazino[3,4-c][1,2,4]triazin-2(1H)-one ditrifluoroacetic acid

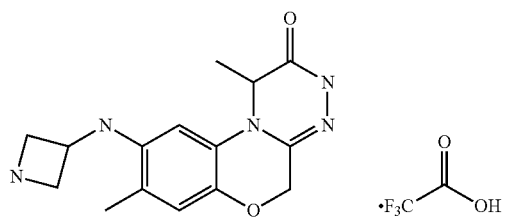

Using a similar procedure as described in Example #54, Step A-H, 9-(azetidin-3-ylamino)-1,8-dimethyl-3,5-dihydrobenzo[5,6][1,4]oxazino[3,4-c][1,2,4]triazin-2(1H)-one ditrifluoroacetic acid was prepared from 6-nitro-2H-benzo[b][1,4]oxazin-3(4H)-one (Preparation #2, Step A). LC/MS (Table 1, Method 5) $R_t$=2.048 min; MS m/z: 302 [M+H]$^+$ Example #123

9-(Azetidin-3-yloxy)-8-fluoro-1-methyl-3,5-dihydrobenzo[5,6][1,4]oxazino[3,4-c][1,2,4]triazin-2(1H)-one trifluoroacetic acid

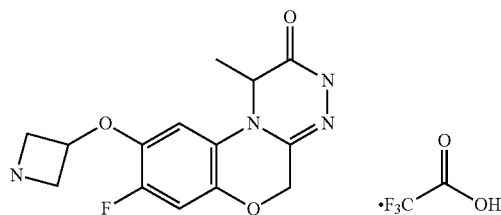

Using a similar procedure as described in Example #65, Step A-1,9-(azetidin-3-yloxy)-8-fluoro-1-methyl-3,5-dihydrobenzo[5,6][1,4]oxazino[3,4-c][1,2,4]triazin-2(1H)-one trifluoroacetic acid was prepared from 6-acetyl-7-fluoro-2H-benzo[b][1,4]oxazin-3(4H)-one (Preparation #5, Step C). LC/MS (Table 1, Method 5) $R_t$=1.711 min; MS m/z: 307 [M+H]$^+$ Example #124

(R)-9-(Azetidin-3-yloxy)-8-fluoro-1-methyl-3,5-dihydrobenzo[5,6][1,4]oxazino[3,4-c][1,2,4]triazin-2(1H)-one trifluoroacetic acid

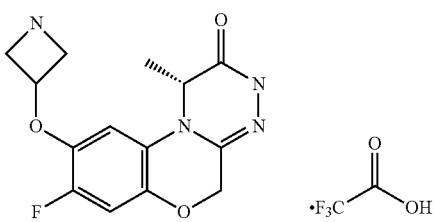

Using a similar procedure as described in Example #65, Step A-F and I, (R)-9-(azetidin-3-yloxy)-8-fluoro-1-methyl-3,5-dihydrobenzo[5,6][1,4]oxazino[3,4-c][1,2,4]triazin-2(1H)-one trifluoroacetic acid was prepared from 6-acetyl-7- fluoro-2H-benzo[b][1,4]oxazin-3(4H)-one (Preparation #5, Step C). LC/MS (Table 1, Method 5) R$_t$=1.669 min; MS m/z: 307 [M+H]$^+$

Example #125

1,8-Dimethyl-9-((1-methylazetidin-3-yl)amino)-3,5-dihydrobenzo[5,6][1,4]oxazino[3,4-c][1,2,4]triazin-2(1H)-one trifluoroacetic acid

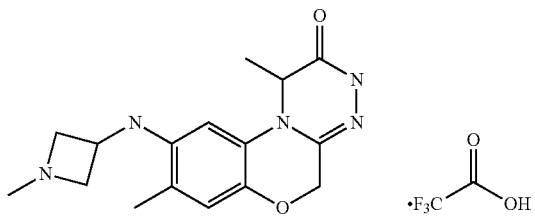

Using a similar procedure as described in Example #54, Step A-H, and Example #101, Step A, 1,8-dimethyl-9-((1-methylazetidin-3-yl)amino)-3,5-dihydrobenzo[5,6][1,4]oxazino[3,4-c][1,2,4]triazin-2(1H)-one trifluoroacetic acid was prepared from 6-amino-4,7-dimethyl-2,10-dihydro-9-oxa-1,2,4a-triaza-phenanthren-3-one (Example #54, Step E). LC/MS (Table 1, Method 5) R$_t$=1.871 min.; MS m/z: 316 [M+H]$^+$

Example #126

9-((1-Isopropyl-3-methylazetidin-3-yl)amino)-1-methyl-8-(tetrahydro-2H-pyran-4-yl)-3,5-dihydrobenzo[5,6][1,4]oxazino[3,4-c][1,2,4]triazin-2(1H)-one trifluoroacetic acid

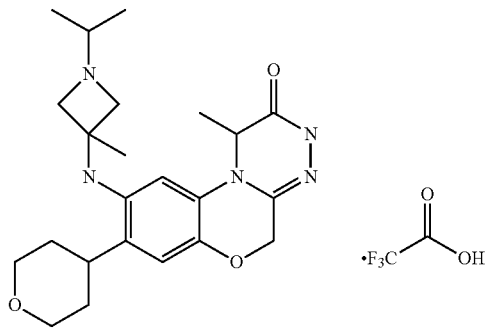

Using a similar procedure as described in Example #79, Step C-D and Example #57, Step B, 9-((1-isopropyl-3-methylazetidin-3-yl)amino)-1-methyl-8-(tetrahydro-2H-pyran-4-yl)-3,5-dihydrobenzo[5,6][1,4]oxazino[3,4-c][1,2,4]triazin-2(1H)-one trifluoroacetic acid was prepared from 6-(1-benzhydryl-3-methyl-azetidin-3-ylamino)-7-bromo-4-methyl-2,10-dihydro-9-oxa-1,2,4a-triaza-phenanthren-3-one (Example #79, Step B) and 3,6-dihydro-2H-pyran-4-ylboronic acid (Apollo). LC/MS (Table 1, Method 4) R$_t$=1.458 min; MS m/z: 428 [M+H]$^+$

Example #127

6-(Azetidin-3-ylamino)-7-benzyloxy-4-methyl-2,10-dihydro-9-oxa-1,2,4a-triaza-phenanthren-3-one trifluoroacetic acid

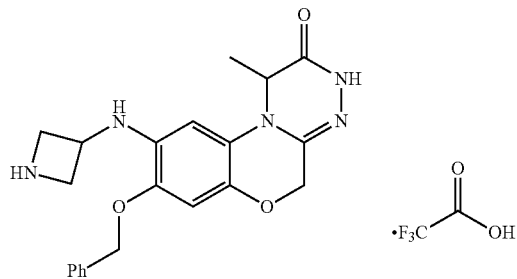

Step A. 7-Hydroxy-4-methyl-6-nitro-2,10-dihydro-9-oxa-1,2,4a-triaza-phenanthren-3-one

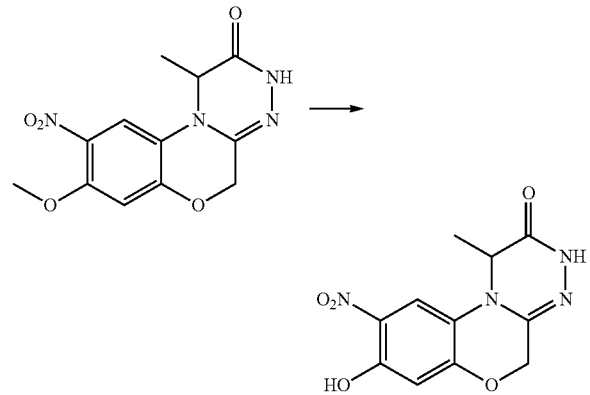

A solution of 7-methoxy-4-methyl-6-nitro-2,10-dihydro-9-oxa-1,2,4a-triaza-phenanthren-3-one (prepared from 2-amino-5-methoxyphenol using the similar procedure detailed in Example #56, Step A-D and Example #106, Step A, 1 g, 3.42 mmol) and lithium chloride (0.44 g, 10.27 mmol) in DMF (10 mL) was heated at 150° C. for 3 h. The reaction mixture was cooled to ambient temperature and the solvent was removed in vacuo. The residue was purified by column chromatography on silica gel (eluting with 50% EtOAc in petroleum ether) to give 7-hydroxy-4-methyl-6-nitro-2,10-dihydro-9-oxa-1,2,4a-triaza-phenanthren-3-one (0.65 g, 68%) as a red solid. TLC (eluting with 50% EtOAc in petroleum ether) R$_f$=0.5.

Step B. 7-Benzyloxy-4-methyl-6-nitro-2,10-dihydro-9-oxa-1,2,4a-triaza-phenanthren-3-one

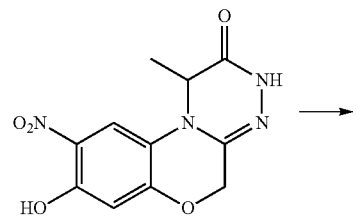

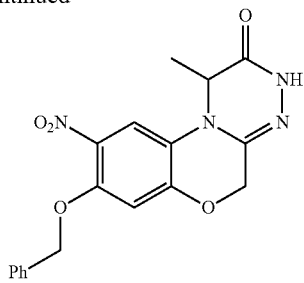

To a solution of 7-hydroxy-4-methyl-6-nitro-2,10-dihydro-9-oxa-1,2,4a-triaza-phenanthren-3-one (0.2 g, 0.72 mmol) and K$_2$CO$_3$ (0.30 g, 2.16 mmol) in DMF (10 mL) was added benzyl bromide (0.37 g, 2.16 mmol) dropwise. The solution was heated at 70° C. for 14 h. The reaction mixture was cooled to ambient temperature and brine (30 mL) was added. The aqueous phase was extracted with EtOAc (3×15 mL) and the combined organic layer was dried over Na$_2$SO$_4$, filtered and concentrated in vacuo. The residue was purified by column chromatography on silica gel (eluting with 50% EtOAc in petroleum ether) to give 7-benzyloxy-4-methyl-6-nitro-2,10-dihydro-9-oxa-1,2,4a-triaza-phenanthren-3-one (0.140 g, 53%) as yellow solid. $^1$H NMR (CDCl$_3$, 400 MHz): δ 8.08 (s, 1H), 7.62 (s, 1H), 7.49 (m, 2H), 7.44 (m, 2H), 7.39 (m, 1H), 6.81 (s, 1H), 5.23 (s, 2H), 4.70 (m, 3H), 1.56 (d, J=6.8 Hz, 3H).

Step C. 6-Amino-7-benzyloxy-4-methyl-2,10-dihydro-9-oxa-1,2,4a-triaza-phenanthren-3-one

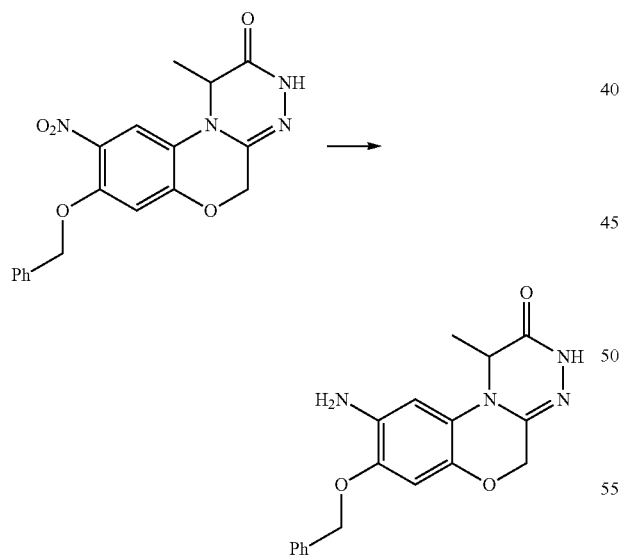

To a solution of 7-benzyloxy-4-methyl-6-nitro-2,10-dihydro-9-oxa-1,2,4a-triaza-phenanthren-3-one (0.14 g, 0.38 mmol) in MeOH (10 mL) was added Raney-Ni (0.03 g). Then the mixture was stirred under an atmosphere of H$_2$ (1 atm) at rt for 2 h. The reaction mixture was filtered and washed with 10% MeOH/DCM (3×10 mL). The filtrate was concentrated in vacuo to give 6-amino-7-benzyloxy-4-methyl-2,10-dihydro-9-oxa-1,2,4a-triaza-phenanthren-3-one (0.065 g, 54%), which was used in the next step directly without further purification. TLC (eluting with 50% EtOAc in petroleum ether) R$_f$=0.3.

Step D. 3-(7-Benzyloxy-4-methyl-3-oxo-2,3,4,10-tetrahydro-9-oxa-1,2,4a-triaza-phenanthren-6-ylamino)-azetidine-1-carboxylic acid tert-butyl ester

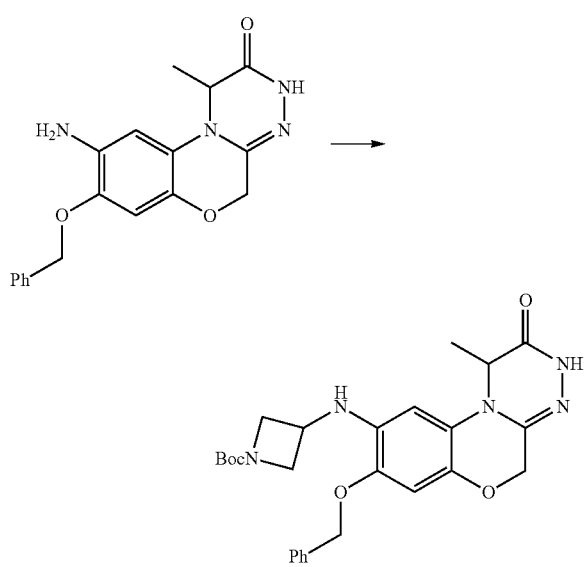

A solution of 6-amino-7-benzyloxy-4-methyl-2-(2-trimethylsilanyl-ethoxymethyl)-2,10-dihydro-9-oxa-1,2,4a-triaza-phenanthren-3-one (0.065 g, 0.19 mmol) and tert-butyl 3-oxoazetidine-1-carboxylate (0.061 g, 0.36 mmol) in MeOH (10 mL) and AcOH (1 mL) was heated at 70° C. for 14 h. The reaction mixture was cooled to ambient temperature and sodium cyanoborohydride (0.022 g, 0.36 mmol) was added. The reaction mixture was heated at 70° C. for 1 hr then cooled to ambient temperature. The solvent was removed in vacuo and the residue was purified by preparative TLC (eluting with 50% EtOAc in petroleum ether) to give 3-(7-benzyloxy-4-methyl-3-oxo-2,3,4,10-tetrahydro-9-oxa-1,2,4a-triaza-phenanthren-6-ylamino)-azetidine-1-carboxylic acid tert-butyl ester (0.028 g, 32%). LC/MS (Table 1, Method 2) R$_t$=1.205 min; MS m/z: 516 [M+23]$^+$ Step E. 6-(Azetidin-3-ylamino)-7-benzyloxy-4-methyl-2,10-dihydro-9-oxa-1,2,4a-triaza-phenanthren-3-one trifluoroacetic acid

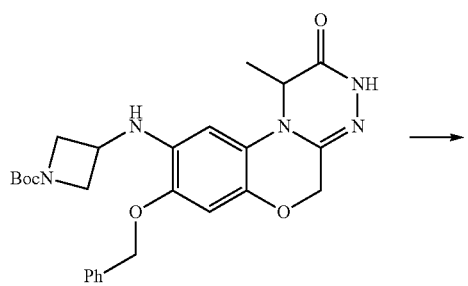

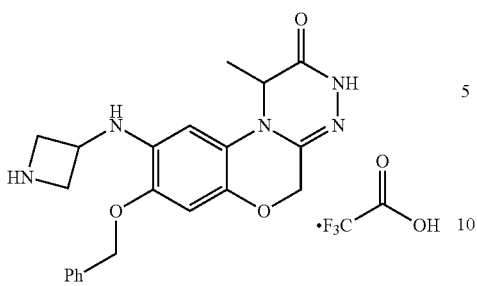

A solution of 3-(7-benzyloxy-4-methyl-3-oxo-2,3,4,10-tetrahydro-9-oxa-1,2,4a-triaza-phenanthren-6-ylamino)-azetidine-1-carboxylic acid tert-butyl ester (0.028 g, 0.057 mmol) in TFA (0.5 mL) and DCM (3 mL) was stirred at rt for 2 h. The solvent was removed in vacuo and the residue was purified by preparative HPLC (Table 3, Method 18) to give 6-(azetidin-3-ylamino)-7-benzyloxy-4-methyl-2,10-dihydro-9-oxa-1,2,4a-triaza-phenanthren-3-one trifluoroacetic acid (0.013 g, 58%). LC/MS (Table 1, Method 5) $R_t$=2.201 min; MS m/z: 394 [M+H]$^+$ Example #128

6-(Azetidin-3-ylamino)-4-methyl-7-phenylamino-2,10-dihydro-9-oxa-1,2,4a-triaza-phenanthren-3-one trifluoroacetic acid

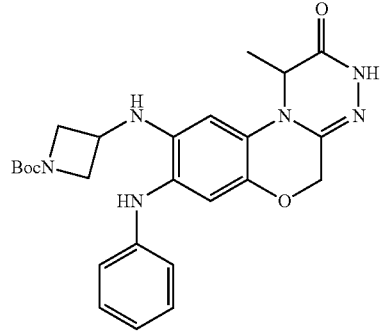

A solution of 3-(7-bromo-4-methyl-3-oxo-2,3,4,10-tetrahydro-9-oxa-1,2,4a-triaza-phenanthren-6-ylamino)-azetidine-1-carboxylic acid tert-butyl ester (Example #1, Step B, 0.1 g, 0.21 mmol), aniline (0.06 g, 0.64 mmol), Pd$_2$(dba)$_3$ (0.039 g, 0.04 mmol), Xantphos (0.0496 g, 0.09 mmol), and Cs$_2$CO$_3$ (0.14 g, 0.43 mmol) in anhydrous dioxane (10 mL) was heated at 130° C. for 14 h. The reaction mixture was cooled to ambient temperature and concentrated in vacuo. The residue was purified by chromatography on silica gel (eluting with 50% EtOAc in petroleum ether) to give 3-(4-methyl-3-oxo-7-phenylamino-2,3,4,10-tetrahydro-9-oxa-1,2,4a-triaza-phenanthren-6-ylamino)-azetidine-1-carboxylic acid tert-butyl ester (0.014 g, 14%) as brown solid. LC/MS (Table 1, Method 2) $R_t$=1.205 min; MS m/z: 542 [M+23+41]$^+$ Step B. 6-Azetidin-3-ylmethyl-4-methyl-7-trifluoromethyl-2,10-dihydro-9-oxa-1,2,4a-triaza-phenanthren-3-one trifluoroacetic acid

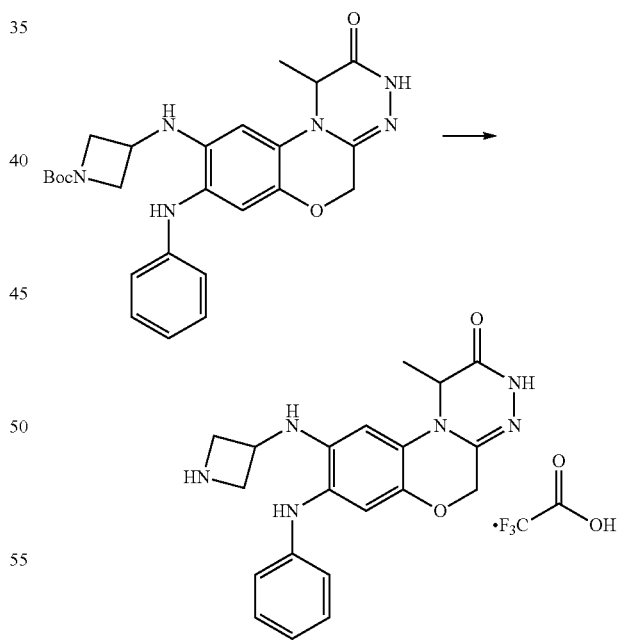

Step A. 3-(4-methyl-3-oxo-7-phenylamino-2,3,4,10-tetrahydro-9-oxa-1,2,4a-triaza-phenanthren-6-ylamino)-azetidine-1-carboxylic acid tert-butyl ester

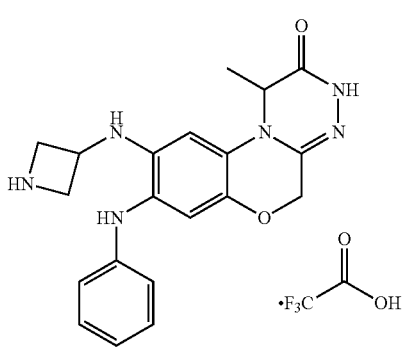

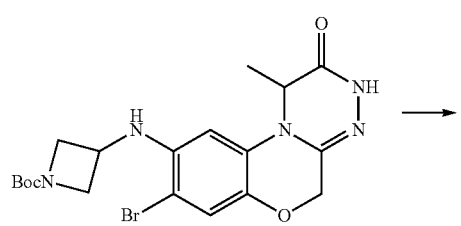

A solution of 3-(4-methyl-3-oxo-7-phenylamino-2,3,4,10-tetrahydro-9-oxa-1,2,4a-triaza-phenanthren-6-ylamino)-azetidine-1-carboxylic acid tert-butyl ester (0.014 g, 0.029 mmol) in TFA (1 mL) and DCM (6 mL) was stirred at ambient temperature for 2 h. The solvent was removed in vacuo to give 6-azetidin-3-ylmethyl-4-methyl-7-trifluoromethyl-2,10-dihydro-9-oxa-1,2,4a-triaza-phenanthren-3-one trifluoroacetic acid (0.0112 g, 100%). LC/MS (Table 1, Method 5) $R_t$=2.173 min; MS m/z: 379 [M+H]$^+$

Example #129

1-Methyl-9-(1-(3-methylazetidin-3-yl)ethyl)-3,5-dihydrobenzo[5,6][1,4]oxazino[3,4-c][1,2,4]triazin-2(1H)-one trifluoroacetic acid

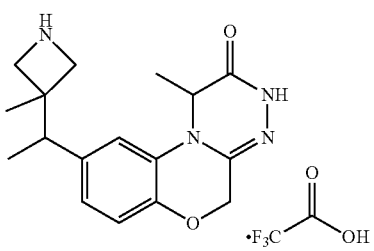

Using a similar procedure as described in Example #109, Step C, D (with no chiral SFC), and E, 1-methyl-9-(1-(3-methylazetidin-3-yl)ethyl)-3,5-dihydrobenzo[5,6][1,4]oxazino[3,4-c][1,2,4]triazin-2(1H)-one trifluoroacetic acid was prepared from (R)-1-methyl-9-(4,4,5,5-tetramethyl-1,3,2-dioxaborolan-2-yl)-3,5-dihydrobenzo[5,6][1,4]oxazino[3,4-c][1,2,4]triazin-2(1H)-one (0.515 g, 1.5 mmol) (Example #109, Step B) and 3-(1-iodo-vinyl)-3-methyl-azetidine-1-carboxylic acid tert-butyl ester (Preparation #21). LC/MS (Table 1, Method 5) $R_f$=1.905 min; MS m/z: 315 [M+H]$^+$

Example #130

(R)-7-(2-Fluoro-6-piperazin-1-yl-phenyl)-4-methyl-2,10-dihydro-9-oxa-1,2,4a-triaza-phenanthren-3-one trifluoroacetic acid

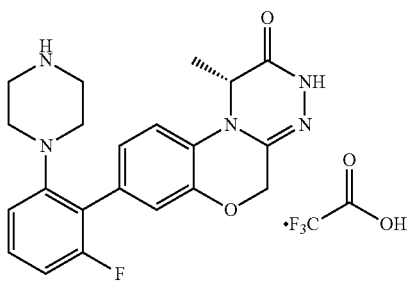

Step A. 4-(2-Bromo-3-fluoro-phenyl)-piperazine-1-carboxylic acid tert-butyl ester

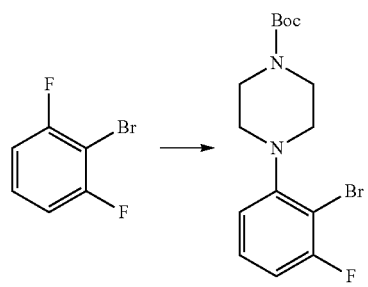 [SMILES: Fc1cccc(F)c1Br ; CC(C)(C)OC(=O)N1CCN(c2cccc(F)c2Br)CC1]

A mixture of 2-bromo-1,3-difluorobenzene (0.2 g, 1.03 mmol) and tert-butyl piperazine-1-carboxylate (0.39 g, 2.07 mmol), and N,N-dimethylpyridin-4-amine (0.06 g, 0.52 mmol) was stirred at 120° C. overnight. The reaction mixture was cooled to ambient temperature and concentrated in vacuo. The residue was purified by column chromatography on silica gel (eluting with 5% EtOAc in petroleum ether) to give 4-(2-bromo-3-fluoro-phenyl)-piperazine-1-carboxylic acid tert-butyl ester (0.06 g, 16%). $^1$H NMR (CDCl$_3$, 400 MHz): δ 7.25 (m, 1H), 6.87 (m, 1H), 6.81 (d, J=8.4 Hz, 1H), 3.63 (t, J=4.8 Hz, 4H), 3.01 (t, J=4.8 Hz, 4H), 1.5 (s, 9H). LC/MS (Table 1, Method 2) $R_f$=1.300 min; MS m/z: 303 [M+H−56]$^+$ and 305 [M+H−56]$^+$.

Step B. 4-[3-Fluoro-2-(4-methyl-3-oxo-2,3,4,10-tetrahydro-9-oxa-1,2,4a-triaza-phenanthren-7-yl)-phenyl]-piperazine-1-carboxylic acid tert-butyl ester

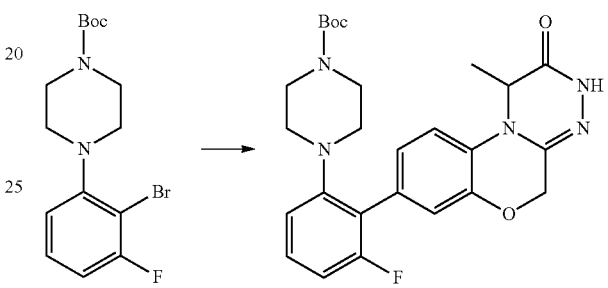

To a solution of 4-methyl-7-(4,4,5,5-tetramethyl-[1,3,2]dioxaborolan-2-yl)-2,10-dihydro-9-oxa-1,2,4a-triaza-phenanthren-3-one (Preparation #19, 0.057 g, 0.174 mmol), 4-(2-bromo-3-fluoro-phenyl)-piperazine-1-carboxylic acid tert-butyl ester (0.06 g, 0.174 mmol) and Pd(dppf)Cl$_2$ (0.012 g, 0.017 mmol) in EtOH (4 mL) and water (1 mL) was added sodium carbonate (0.036 g, 0.34 mmol) and the reaction mixture was stirred at 100° C. for 4 h. The reaction mixture was cooled to ambient temperature and concentrated in vacuo. The residue was purified by column chromatography on silica gel (eluting with 30% EtOAc in petroleum ether) to give 4-[3-fluoro-2-(4-methyl-3-oxo-2,3,4,10-tetrahydro-9-oxa-1,2,4a-triaza-phenanthren-7-yl)-phenyl]-piperazine-1-carboxylic acid tert-butyl ester (0.040 g, 58%). LC/MS (Table 1, Method 25) $R_f$=0.920 min; MS m/z: 496 [M+H]$^+$ Step C. 4-[3-Fluoro-2-((R)-4-methyl-3-oxo-2,3,4,10-tetrahydro-9-oxa-1,2,4a-triaza-phenanthren-7-yl)-phenyl]-piperazine-1-carboxylic acid tert-butyl ester and 4-[3-fluoro-2-((S)-4-methyl-3-oxo-2,3,4,10-tetrahydro-9-oxa-1,2,4a-triaza-phenanthren-7-yl)-phenyl]-piperazine-1-carboxylic acid tert-butyl ester

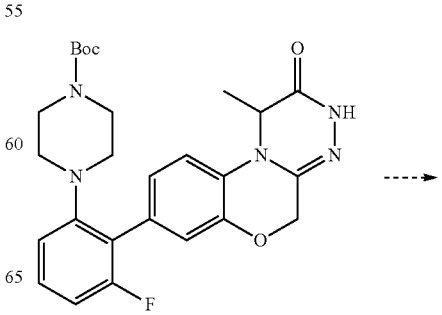

Step D. (R)-7-(2-Fluoro-6-piperazin-1-yl-phenyl)-4-methyl-2,10-dihydro-9-oxa-1,2,4a-triaza-phenanthren-3-one trifluoroacetic acid

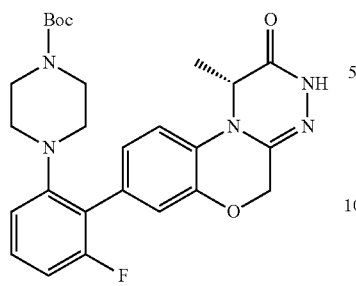

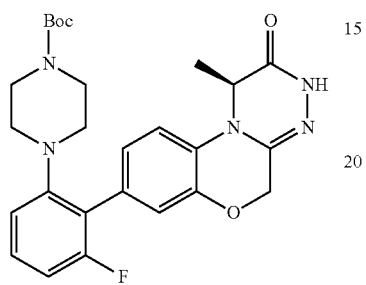

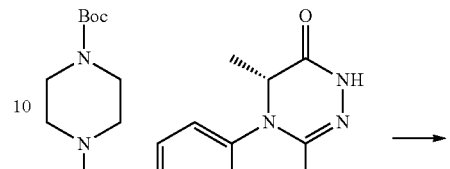

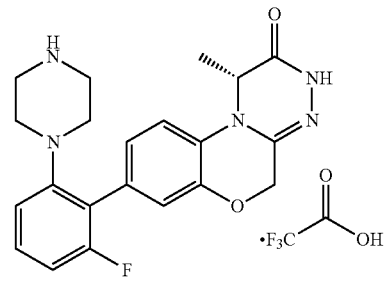

Chiral SFC (Table 2, Method 20) separation of 4-[3-fluoro-2-(4-methyl-3-oxo-2,3,4,10-tetrahydro-9-oxa-1,2,4a-triaza-phenanthren-7-yl)-phenyl]-piperazine-1-carboxylic acid tert-butyl ester (0.15 g, 0.43 mmol) gave 4-[3-fluoro-2-((R)-4-methyl-3-oxo-2,3,4,10-tetrahydro-9-oxa-1,2,4a-triaza-phenanthren-7-yl)-phenyl]-piperazine-1-carboxylic acid tert-butyl ester (enantiomer 1, SFC (Table 1, Method 34) $R_t$=1.688 min, 0.07 g, 0.141 mmol) and 4-[3-fluoro-2-((S)-4-methyl-3-oxo-2,3,4,10-tetrahydro-9-oxa-1,2,4a-triaza-phenanthren-7-yl)-phenyl]-piperazine-1-carboxylic acid tert-butyl ester (enantiomer 2, SFC (Table 1, Method 34) $R_t$=1.858 min, 0.02 g, 0.04 mmol).

To a solution of 4-[3-fluoro-2-((R)-4-methyl-3-oxo-2,3,4,10-tetrahydro-9-oxa-1,2,4a-triaza-phenanthren-7-yl)-phenyl]-piperazine-1-carboxylic acid tert-butyl ester (enantiomer 1, 0.070 g, 0.141 mmol) in DCM (3 mL) was added TFA (1 mL) and the reaction mixture was stirred at ambient temperature for 1 h. The solvent was removed in vacuo to give (R)-7-(2-fluoro-6-piperazin-1-yl-phenyl)-4-methyl-2,10-dihydro-9-oxa-1,2,4a-triaza-phenanthren-3-one trifluoroacetic acid (0.06 g, 85%) as a solid. $^1$H NMR (CD$_3$OD, 400 MHz): δ 7.36 (m, 1H), 7.27 (m, 2H), 7.18 (s, 1H), 6.96 (m, 2H), 4.87 (m, 1H), 4.66 (d, J=13.0 Hz, 2H), 3.08 (s, 8H), 1.51 (d, J=6.8 Hz, 3H). LC/MS (Table 1, Method 4) $R_t$=1.684 min; MS m/z: 396 [M+H]$^+$. SFC (Table 1, Method 33) $R_t$=4.921 min.

TABLE 15

The following analogs were prepared from (R)-4-methyl-7-(4,4,5,5-tetramethyl-[1,3,2]dioxaborolan-2-yl)-2,10-dihydro-9-oxa-1,2,4a-triaza-phenanthren-3-one (Preparation #10, Step F) using the procedure detailed in Example #130, Steps A-B & Step D.

| Structure | Example # | Halogen | $R_t$ min (method) | m/z ESI+ (M + H)$^+$ |
|---|---|---|---|---|
| 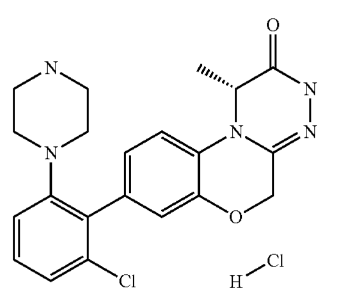 | 131 | Br, Br, Cl | 1.792 (Table 1, Method 4) | 412 |

TABLE 15-continued

The following analogs were prepared from (R)-4-methyl-7-(4,4,5,5-tetramethyl-[1,3,2]dioxaborolan-2-yl)-2,10-dihydro-9-oxa-1,2,4a-triaza-phenanthren-3-one (Preparation #10, Step F) using the procedure detailed in Example #130, Steps A-B & Step D.

| Structure | Example # | Halogen | $R_t$ min (method) | m/z ESI+ $(M + H)^+$ |
|---|---|---|---|---|
| 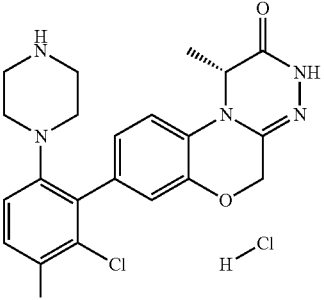 | 132 | Br, Br, Cl, Cl (See Preparation #12, Step B for intermediate synthesis) | 2.454 (Table 1, Method 5) | 446 |

Example #133

(R)-7-Isopropyl-4-methyl-6-[(R)-1-(3-methyl-azetidin-3-yl)-ethyl]-2,10-dihydro-9-oxa-1,2,4a-triaza-phenanthren-3-one hydrochloric acid

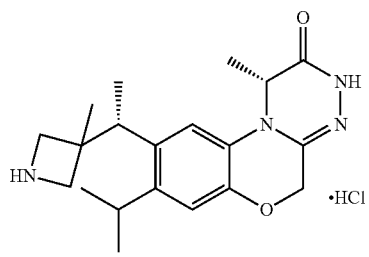 [SMILES: CC(C)c1cc2c(cc1[C@@H](C)C1(C)CNC1)N1C(=NNC(=O)[C@H]1C)CO2 ; Cl]

Step A. 3-Methyl-3-[1-((R)-4-methyl-3-oxo-2,3,4,10-tetrahydro-9-oxa-1,2,4a-triaza-phenanthren-6-yl)-vinyl]-azetidine-1-carboxylic acid tert-butyl ester

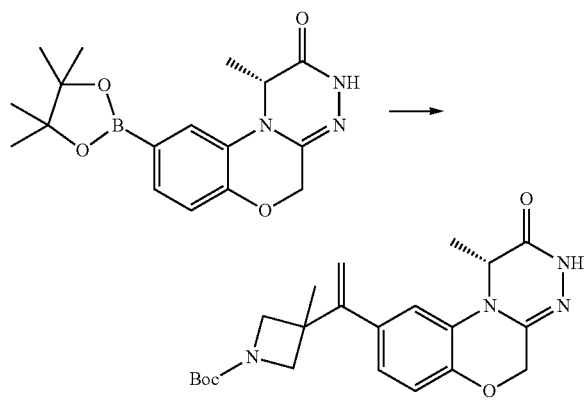

A mixture of (R)-4-methyl-6-(4,4,5,5-tetramethyl-[1,3,2]dioxaborolan-2-yl)-2,10-dihydro-9-oxa-1,2,4a-triaza-phenanthren-3-one (Preparation #11, Step E, 2 g, 5.83 mmol), 3-methyl-3-(1-trifluoromethanesulfonyloxy-vinyl)-azetidine-1-carboxylic acid tert-butyl ester (Preparation #20 3.02 g, 8.74 mmol), $Na_2CO_3$ (1.235 g, 11.66 mmol) and $Pd(Ph_3P)_4$ (3.37 g, 2.91 mmol) in dioxane (20 mL) and water (5 mL) was stirred at 90° C. overnight. The reaction mixture was cooled to ambient temperature. The solvent was removed in vacuo and the residue was purified by column chromatography on silica gel (eluting with 0-30% EtOAc in petroleum ether) to give 3-methyl-3-[1-((R)-4-methyl-3-oxo-2,3,4,10-tetrahydro-9-oxa-1,2,4a-triaza-phenanthren-6-yl)-vinyl]-azetidine-1-carboxylic acid tert-butyl ester (0.610 g, 25%) as a solid. LC/MS (Table 1, Method 25) $R_t$=0.867 min.; MS m/z: 413 $[M+H]^+$ and 357 $[M+H-56]^+$. $^1$H NMR ($CDCl_3$, 400 MHz): δ 8.10 (br. s., 1H), 6.98 (d, J=8.4 Hz, 1H), 6.83 (d, J=8.4 Hz, 1H), 6.78 (s, 1H), 5.33 (s, 1H), 5.10 (s, 1H), 4.74 (m, 1H), 4.67-4.56 (d, J=15.2 Hz, 2H), 4.11 (m, 2H), 3.79 (m, 2H), 1.61 (d, J=15.2 Hz, 3H), 1.55 (m, 3H). 1.46 (s, 9H).

Step B. 3-Methyl-3-[1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester

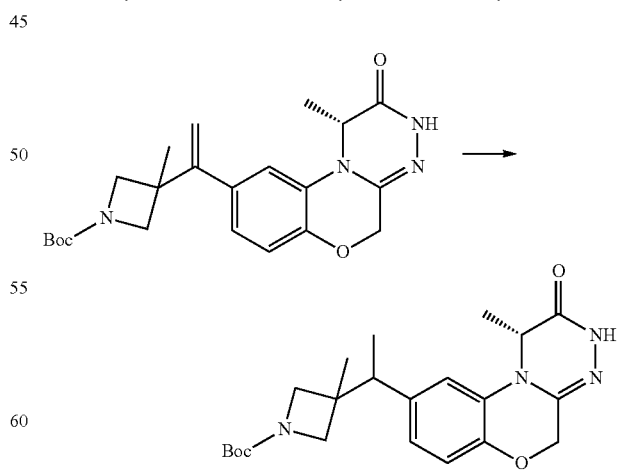

A mixture of 3-methyl-3-[1-((R)-4-methyl-3-oxo-2,3,4,10-tetrahydro-9-oxa-1,2,4a-triaza-phenanthren-6-yl)-vinyl]-azetidine-1-carboxylic acid tert-butyl ester (0.5 g, 1.212 mmol) and Pd/C (0.258 g, 0.242 mmol, 10%) in MeOH (10 mL) was stirred under H$_2$ at ambient temperature for 1 h. The reaction mixture was filtered and the filtrate was evaporated in vacuo to give 3-methyl-3-[1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester (0.484 g, 96%) as a solid. LC/MS (Table 1, Method 25) R$_t$=0.858 min.; MS m/z: 415 [M+H]$^+$ and 359 [M+H−56]$^+$. $^1$H NMR (CDCl$_3$, 400 MHz): δ 8.08 (brs, 1H), 6.96 (d, J=8.4 Hz, 1H), 6.83 (d, J=8.4 Hz, 1H), 6.73 (s, 1H), 4.78 (m, 1H), 4.63-4.56 (m, 2H), 3.84 (m, 2H), 3.57 (d, J=8.0 Hz, 1H), 3.35 (d, J=8.0 Hz, 1H), 2.98 (m, 1H), 1.66-1.49 (m, 12H), 1.27 (d, J=7.3 Hz, 3H), 1.21 (s, 3H).

Step C. 3-Methyl-3-[(R)-1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester and 3-methyl-3-[(S)-1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester

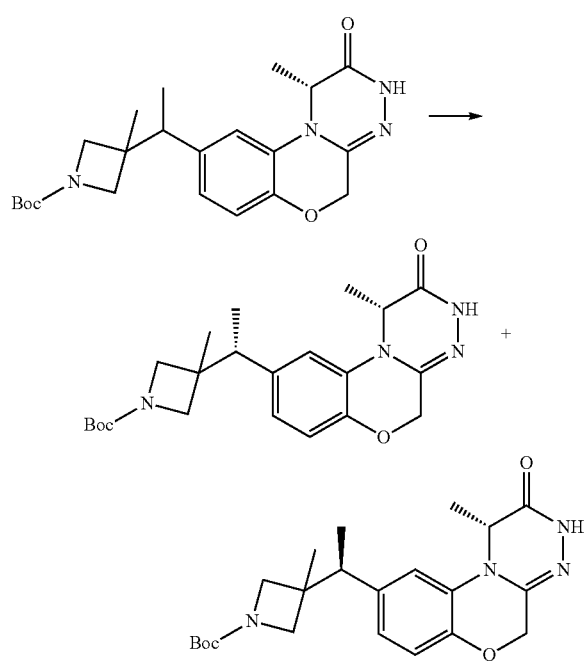

3-Methyl-3-[1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester (0.484 g, 1.168 mmol) was separated by chiral SFC separation (Table 2, Method 17) to give two diastereomers: 3-methyl-3-[(R)-1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester (diastereomer 1, 0.178 g, 36%, LC/MS (Table 1, Method 25) R$_t$=0.868 min.; MS m/z: 437 [M+Na]$^+$, SFC (Table 1, Method 24) R$_t$=9.201 min.) and 3-methyl-3-[(S)-1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester (diastereomer 2, 0.2284 g, 47%, LC/MS (Table 1, Method 25) R$_t$=0.872 min.; MS m/z: 437 [M+Na]$^+$, SFC (Table 1, Method 24) R$_t$=9.819 min.).

Step D. 3-[(R)-1-((R)-7-Bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester To a solution of 3-methyl-3-[(R)-1-((R)-4-methyl-3-oxo-2,3,4,10-tetrahydro-9-oxa-1,2,4a-triaza-phenanthren-6-yl)-ethyl]-azetidine-1-carboxylic acid tert-butyl ester (diastereomer 1, 0.283 g, 0.683 mmol) in AcOH (1 mL) was added a solution of bromine (0.070 mL, 1.366 mmol) in AcOH (1 mL) drop-wise and the reaction mixture was stirred for 1 h at ambient temperature. The reaction mixture was quenched by the addition of saturated aqueous NaS$_2$O$_3$ solution and aqueous NaHCO$_3$ solution to pH 7-8. MeOH (5 mL), TEA (0.146 g, 1.439 mmol) and di-tert-butyl dicarbonate (0.188 g, 0.864 mmol) were added in sequence to the above mixture and the reaction mixture was stirred at ambient temperature for 1.5 h. The aqueous solution was extracted with EtOAc (3×10 mL) and the combined organic phase was washed with saturated brine (10 mL), dried over Na$_2$SO$_4$ and filtered. The filtrate was evaporated to dryness and the residue was purified by prep-TLC (eluting with 50% EtOAc in petroleum ether) to give 3-[(R)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.128 g, 36%) as a solid. LC/MS (Table 1, Method 25) R$_t$=0.913 min.; MS m/z: 437 [M+H−56]$^+$ and 439 [M+H−56]$^+$. $^1$H NMR (CDCl$_3$, 400 MHz): δ 8.26 (brs, 1H), 7.25 (s, 1H), 6.70 (s, 1H), 4.75-4.70 (m, 1H), 4.60 (d, J=12.8 Hz, 2H), 3.98-3.91 (m, 2H), 3.55 (m, 2H), 3.44 (d, J=8.4 Hz, 1H), 1.52 (d, J=6.8 Hz, 3H), 1.46 (s, 9H), 1.32-1.27 (m, 6H).

Step E. 3-[(R)-1-((R)-7-Isopropenyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester

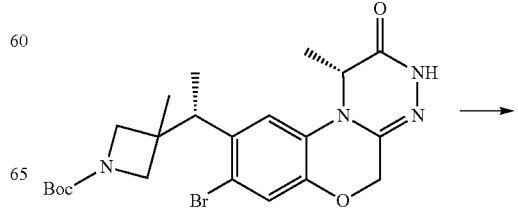

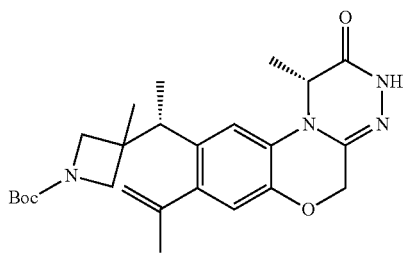

A mixture of 3-[(R)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.128 g, 0.26 mmol), 2-isopropenyl-4,4,5,5-tetramethyl-[1,3,2]dioxaborolane (0.044 g, 0.259 mmol), $Na_2CO_3$ (0.055 g, 0.519 mmol) and $PdCl_2(dppf)\cdot CH_2Cl_2$ adduct (0.042 g, 0.052 mmol) in dioxane (4 mL) and water (1 mL) was stirred at 90° C. for 4 h. The reaction mixture was cooled to ambient temperature. The solvent was removed in vacuo and the residue was purified by prep-TLC (eluting with 50% EtOAc in petroleum ether) to give 3-[(R)-1-((R)-7-isopropenyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.109 g, 59%) as a solid. LC/MS (Table 1, Method 25) $R_t$=0.925 min.; MS m/z: 455 [M+H]$^+$ and 399 [M+H−56]$^+$. $^1$H NMR (CDCl$_3$, 400 MHz): δ 8.06 (brs, 1H), 6.79 (s, 1H), 6.65 (s, 1H), 5.25 (s, 1H), 4.86 (s, 1H), 4.70 (q, J=6.8 Hz, 1H), 4.64-4.54 (d, J=13.8 Hz, 2H), 3.96 (d, J=8.0 Hz, 1H), 3.82 (d, J=8.0 Hz, 1H), 3.56 (d, J=8.0 Hz, 1H), 3.42 (d, J=8.0 Hz, 1H), 3.21 (m, 1H), 2.03 (s, 3H), 1.67 (m, 3H), 1.45 (s, 9H), 1.32 (d, J=7.2 Hz, 3H), 1.25 (d, J=15.2 Hz, 3H).

Step F. 3-[(R)-1-((R)-7-Isopropyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester

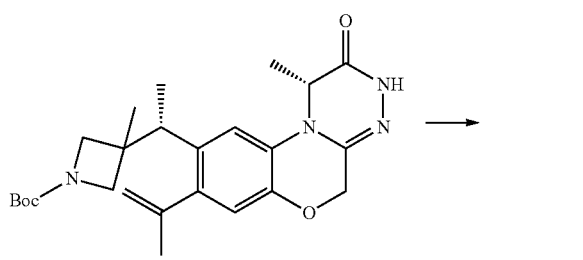

A mixture of 3-[(R)-1-((R)-7-isopropenyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.0795 g, 0.175 mmol) and 10% Pd/C (0.037 g, 0.035 mmol) in MeOH (10 mL) was stirred under H$_2$ for 1 h at rt. The reaction mixture was filtered, the filtrate was evaporated to dryness and the residue was purified by prep-TLC (eluting with 50% EtOAc in petroleum ether) to give 3-[(R)-1-((R)-7-isopropyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.061 g, 76%) as a solid. LC/MS (Table 1, Method 4) $R_t$=2.972 min.; MS m/z: 457 [M+H]$^+$. $^1$H NMR (CDCl$_3$, 400 MHz): δ 8.03 (brs, 1H), 7.00-6.92 (m, 1H), 6.64 (brs, 1H), 4.77-4.70 (m, 1H), 4.65-4.52 (m, 2H), 3.92-3.79 (m, 2H), 3.57-3.51 (m, 1H), 3.45 (m, 1H), 3.30 (m, 1H), 3.23-3.14 (m, 1H), 1.55-1.45 (m, 12H), 1.34-1.24 (m, 12H).

Step G. (R)-7-Isopropyl-4-methyl-6-[(R)-1-(3-methyl-azetidin-3-yl)-ethyl]-2,10-dihydro-9-oxa-1,2,4a-triaza-phenanthren-3-one hydrochloric acid

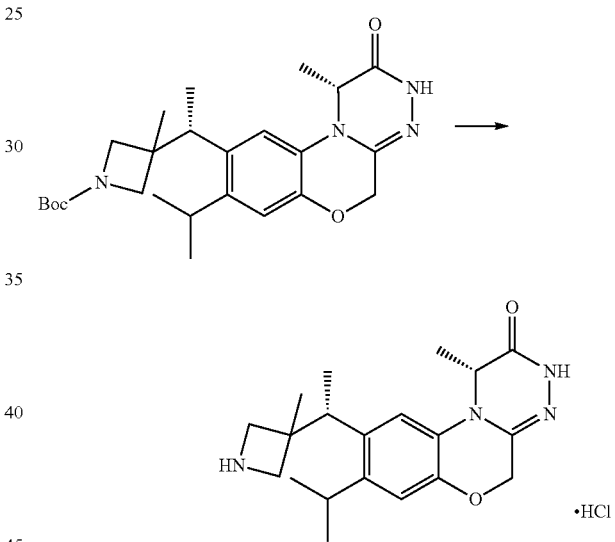

A solution of 3-[(R)-1-((R)-7-isopropyl-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (0.0736 g, 0.162 mmol) in HCl (4M in EtOAc, 0.8 mL) was stirred for 1.5 h at ambient temperature. The reaction mixture was concentrated in vacuo and the residue was purified by prep-HPLC (Table 3, Method 27) to give (R)-7-isopropyl-4-methyl-6-[(R)-1-(3-methyl-azetidin-3-yl)-ethyl]-2,10-dihydro-9-oxa-1,2,4a-triaza-phenanthren-3-one hydrochloric acid (0.026 g, 44%) as a solid. $^1$H NMR (CD$_3$OD-d$_4$, 400 MHz): δ 7.01 (s, 1H), 6.83 (s, 1H), 4.87-4.82 (m, 1H), 4.60 (s, 2H), 4.16 (d, J=10.8 Hz, 1H), 4.02 (d, J=10.8 Hz, 1H), 3.64 (d, J=10.8 Hz, 1H), 3.55 (d, J=10.8 Hz, 1H), 3.42-3.37 (m, 1H), 3.18-3.11 (m, 1H), 1.52 (s, 3H), 1.45 (d, J=6.8 Hz, 3H), 1.38 (d, J=6.8 Hz, 3H), 1.30 (d, J=6.8 Hz, 3H), 1.16 (d, J=6.8 Hz, 3H). LC/MS (Table 1, Method 5) $R_t$=2.401 min.; MS m/z: 357 [M+H]$^+$. SFC (Table 1, Method 26) $R_t$=7.575 min.

Example #134

(R)-6-[(R)-1-(1,3-Dimethyl-azetidin-3-yl)-ethyl]-7-isopropyl-4-methyl-2,10-dihydro-9-oxa-1,2,4a-triaza-phenanthren-3-one

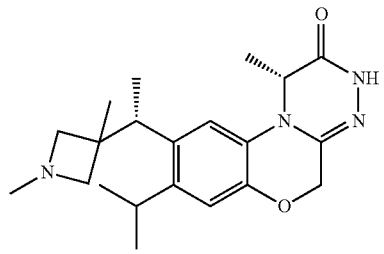 [SMILES: CC(C)c1cc2c(cc1[C@@H](C)C1(C)CN(C)C1)N1C(=NNC(=O)[C@H]1C)CO2]

Step A. (R)-6-[(R)-1-(1,3-Dimethyl-azetidin-3-yl)-ethyl]-7-isopropyl-4-methyl-2,10-dihydro-9-oxa-1,2,4a-triaza-phenanthren-3-one

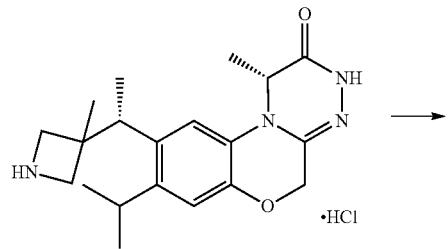

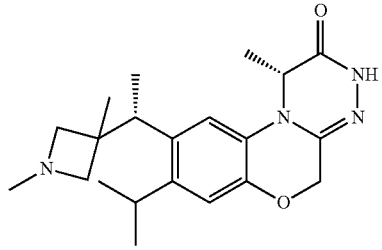

To a solution of (R)-7-isopropyl-4-methyl-6-[(R)-1-(3-methyl-azetidin-3-yl)-ethyl]-2,10-dihydro-9-oxa-1,2,4a-triaza-phenanthren-3-one hydrochloric acid (Example #133, Step G, 0.0227 g, 0.064 mmol) in MeOH (2 mL) and acetic acid (0.2 mL) was added paraformaldehyde (0.765 mL, 0.255 mmol) and the reaction mixture was stirred at ambient temperature for 0.5 h. NaBH$_3$CN (0.008 g, 0.127 mmol) was added and the reaction mixture was stirred at ambient temperature for 0.5 h. The reaction mixture was concentrated in vacuo and the residue was purified by prep-TLC (eluting with 10% MeOH in dichloromethane) to give (R)-6-[(R)-1-(1,3-dimethyl-azetidin-3-yl)-ethyl]-7-isopropyl-4-methyl-2,10-dihydro-9-oxa-1,2,4a-triaza-phenanthren-3-one (0.0199 g, 84%) as a solid. $^1$H NMR (CD$_3$OD-d$_4$, 400 MHz): δ 7.00 (s, 1H), 6.79 (s, 1H), 4.83 (br. s., 1H), 4.60 (s, 2H), 3.96 (m, 1H), 3.91 (m, 1H), 3.76 (d, J=9.8 Hz, 1H), 3.67 (d, J=9.8 Hz, 1H), 3.38 (m, 1H), 3.18 (m, 1H), 2.71 (s, 3H), 1.48-1.43 (m, 6H), 1.38 (d, J=6.8 Hz, 3H), 1.30 (d, J=6.8 Hz, 3H), 1.15 (d, J=6.8 Hz, 3H). LC/MS (Table 1, Method 4) R$_t$=1.601 min.; MS m/z: 371 [M+H]$^+$. SFC (Table 1, Method 24) R$_t$=7.354 min.

TABLE 16

The following analogs were prepared from 3-[(S)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (Example #133, Step D) using the similar procedure detailed in Example #133, Step E, G and Example #134, Step A.

| Structure | Example # | Reagent | R$_t$ min (method) | m/z ESI+ (M + H)$^+$ |
|---|---|---|---|---|
| 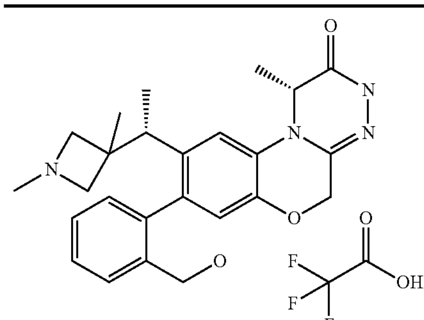 | 135 | 2-(hydroxymethyl)phenylboronic acid; trifluoroacetic acid | 1.379 & 1.595 (Table 1, Method 4) | 435 |
| 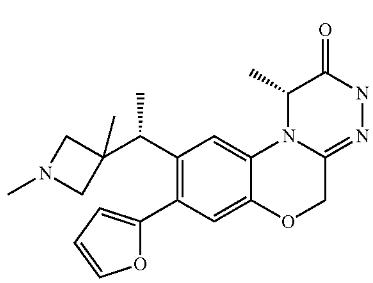 [SMILES: C[C@@H]1C(=O)NN=C2COc3cc(-c4ccco4)c([C@@H](C)C4(C)CN(C)C4)cc3N21] | 136 | furan-2-ylboronic acid | 1.688 (Table 1, Method 4) | 395 |

Example #137

(R)-6-[(R)-1-(1,3-Dimethyl-azetidin-3-yl)-ethyl]-7-[2-(1-hydroxy-1-methyl-ethyl)-phenyl]-4-methyl-2,10-dihydro-9-oxa-1,2,4a-triaza-phenanthren-3-one

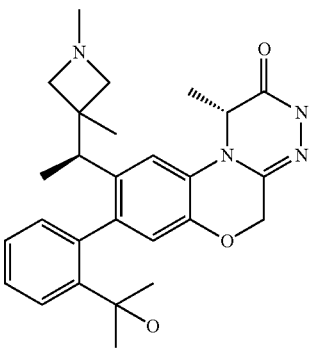 [SMILES: C[C@@H]1C(=O)NN=C2COc3cc(-c4ccccc4C(C)(C)O)c([C@@H](C)C4(C)CN(C)C4)cc3N21]

Using a similar procedure as detailed in Example #133, Steps E and G followed by Example #134, Step A, and Preparation #14, Step A, (R)-6-[(R)-1-(1,3-dimethyl-azetidin-3-yl)-ethyl]-7-[2-(1-hydroxy-1-methyl-ethyl)-phenyl]-4-methyl-2,10-dihydro-9-oxa-1,2,4a-triaza-phenanthren-3-one was prepared from 3-[(S)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (Example #133, Step D) and (2-acetylphenyl)boronic acid. LC/MS (Table 1, Method 4) $R_t$=1.542 min.; MS m/z: 463 [M+H]$^+$.

Example #138

(R)-6-{(R)-1-[1-(2-Hydroxy-ethyl)-3-methyl-azetidin-3-yl]-ethyl}-7-isopropyl-4-methyl-2,10-dihydro-9-oxa-1,2,4a-triaza-phenanthren-3-one hydrochloric acid

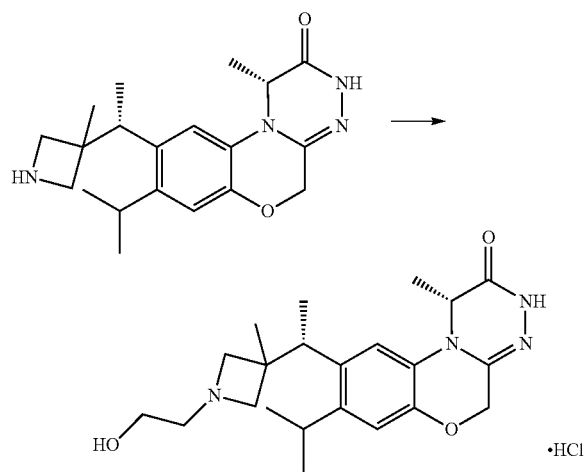

To a solution of (R)-7-isopropyl-4-methyl-6-[(R)-1-(3-methyl-azetidin-3-yl)-ethyl]-2,10-dihydro-9-oxa-1,2,4a-triaza-phenanthren-3-one hydrochloric acid (Example #133, Step G, 0.083 g, 0.233 mmol) in MeOH (3 mL) and acetic acid (0.3 mL) was added 2-((tert-butyldimethylsilyl)oxy)acetaldehyde (0.122 g, 0.699 mmol) and the reaction mixture was stirred at 70° C. overnight. NaBH$_3$CN (0.073 g, 1.164 mmol) was added and the reaction mixture was stirred at 70° C. for 1 h. The reaction mixture was cooled to ambient temperature. The solvent was removed in vacuo and the residue was purified by prep-HPLC (Table 3, Method 26) to give (R)-6-{(R)-1-[1-(2-hydroxy-ethyl)-3-methyl-azetidin-3-yl]-ethyl}-7-isopropyl-4-methyl-2,10-dihydro-9-oxa-1,2,4a-triaza-phenanthren-3-one hydrochloric acid (0.0291 g, 31%) as a solid. $^1$H NMR (CD$_3$OD-d$_4$, 400 MHz): δ 7.04 (s, 1H), 6.84 (s, 1H), 4.81-4.78 (m, 1H), 4.62 (s, 2H), 4.15 (d, J=10.8 Hz, 1H), 4.04 (d, J=10.8 Hz, 1H), 3.93 (d, J=10.8 Hz, 1H), 3.86 (d, J=10.8 Hz, 1H), 3.77-3.69 (m, 2H), 3.38 (m, 2H), 3.12-3.04 (m, 2H), 1.56 (s, 3H), 1.45 (d, J=6.8 Hz, 3H), 1.42-1.35 (m, 3H), 1.34-1.27 (m, 3H), 1.19-1.12 (m, 3H). LC/MS (Table 1, Method 4) $R_t$=1.761 min.; MS m/z: 401 [M+H]$^+$. SFC (Table 1, Method 28) $R_t$=5.52 min.

Example #139

(R)-7-(2-Fluoro-phenyl)-6-{(R)-1-[1-((S)-2-hydroxy-propyl)-3-methyl-azetidin-3-yl]-ethyl}-4-methyl-2,10-dihydro-9-oxa-1,2,4a-triaza-phenanthren-3-one hydrochloric acid

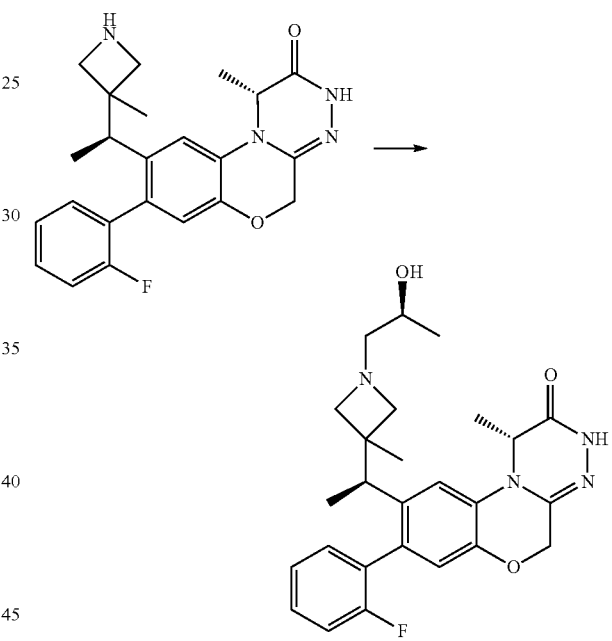

To a mixture of (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one (Example #146, Step B, 0.050 g, 0.24 mmol) and 2-methyloxirane (0.036 g, 0.61 mmol) in EtOH (2 mL) was added DIEA (0.050 g, 0.37 mmol) and the reaction mixture was stirred at 85° C. under microwave irradiation (Biotage Initiator 60 Exp) for 2.5 h. The reaction mixture was cooled to ambient temperature and the solvent was removed in vacuo. The residue was purified by prep-TLC (eluting with 10% MeOH in DCM) and prep-HPLC (Table 3, Method 34) to give (R)-7-(2-fluoro-phenyl)-6-{(R)-1-[1-((S)-2-hydroxy-propyl)-3-methyl-azetidin-3-yl]-ethyl}-4-methyl-2,10-dihydro-9-oxa-1,2,4a-triaza-phenanthren-3-one hydrochloric acid (0.020 g, 35%) as a white solid. $^1$H NMR (400 MHz, methanol-d$_4$) d 7.49 (brs, 1H), 7.41-7.18 (m, 3H), 6.97 (s, 1H), 6.87 (m, 1H), 4.94-4.91 (m, 1H), 4.66 (s, 2H), 4.04 (m, 1H), 3.94-3.57 (m, 4H), 3.25-3.02 (m, 1H), 2.94-2.59 (m, 2H), 1.50 (d, J=6.4 Hz, 3H), 1.44-1.36 (m, 3H), 1.34-1.24 (m, 3H), 1.22-1.09 (m, 3H). LC/MS (Table 1, Method 4) $R_t$=1.736 min; MS (ESI): m/z 467 [M+H]$^+$.

TABLE 17a

The following analogs were prepared from (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one hydrochloric acid (Example #146, Step B) using the similar procedure detailed in Example #139.

| Structure | Example # | Reagent | $R_t$ min (method) | m/z ESI+ $(M + H)^+$ |
|---|---|---|---|---|
| 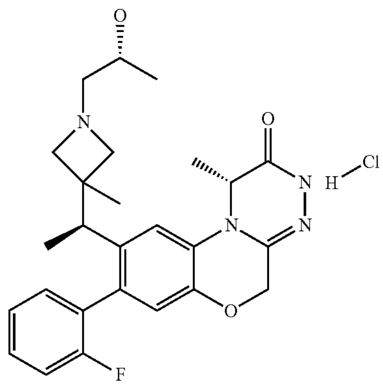 | 140 | | 1.79 (Table 1, Method 4) | 467 |
| 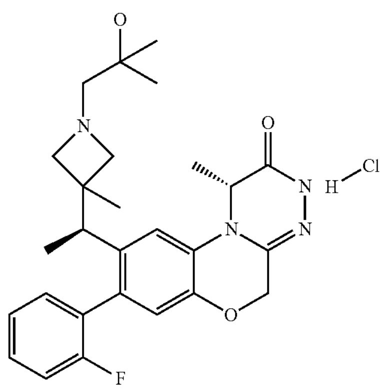 | 143 | | 1.771 (Table 1, Method 4) | 481 |

TABLE 17

The following analogs were prepared from (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one hydrochloric acid (Example #146, Step B) using the similar procedure detailed in Example #134, Step A. In cases where a TBS group was present, the TBS group was also removed under the reaction conditions.

| Structure | Example # | Reagent | $R_t$ min (method) | m/z ESI+ $(M + H)^+$ |
|---|---|---|---|---|
| 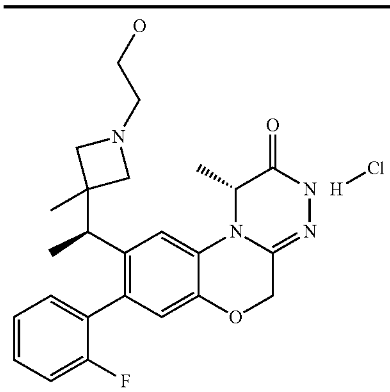 | 141 | OTBS CHO | 1.869 (Table 1, Method 4) | 453 |

TABLE 17-continued

The following analogs were prepared from (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one hydrochloric acid (Example #146, Step B) using the similar procedure detailed in Example #134, Step A. In cases where a TBS group was present, the TBS group was also removed under the reaction conditions.

| Structure | Example # | Reagent | R, min (method) | m/z ESI+ (M + H)+ |
|---|---|---|---|---|
| 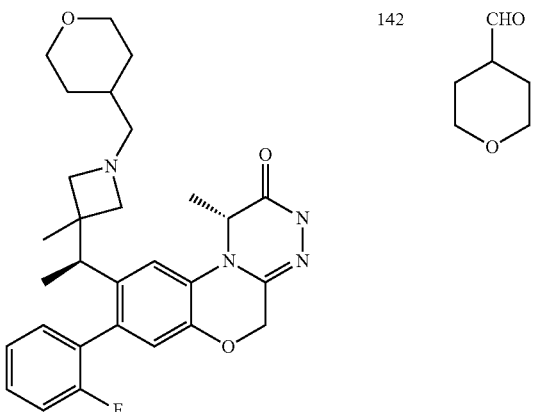 | 142 | CHO (tetrahydropyran) | 1.973 (Table 1, Method 4) | 507 |
| 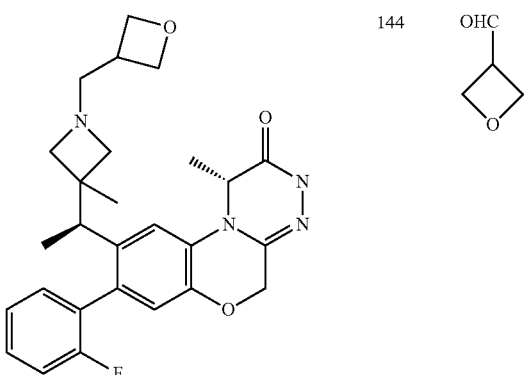 | 144 | OHC (oxetane) | 1.785 (Table 1, Method 4) | 479 |
| 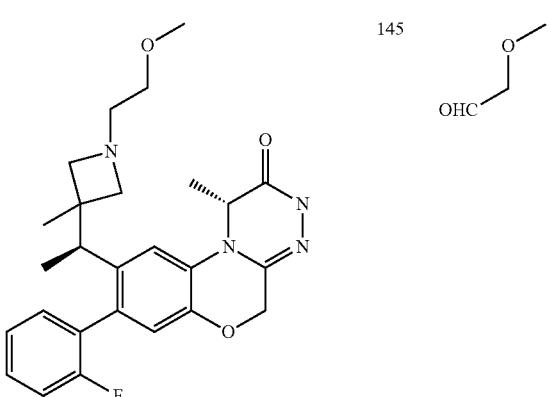 | 145 | OHC-CH2-O-CH3 | 1.817 (Table 1, Method 4) | 467 |

Example #146

(R)-7-(2-Fluoro-phenyl)-4-methyl-6-[(R)-1-(3-methyl-azetidin-3-yl)-ethyl]-2,10-dihydro-9-oxa-1,2,4a-triaza-phenanthren-3-one

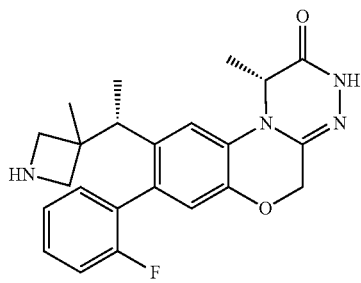 [SMILES: C[C@@H]1C(=O)NN=C2COc3cc(-c4ccccc4F)c([C@@H](C)C4(C)CNC4)cc3N21]

Step A. 3-{(R)-1-[(R)-7-(2-Fluoro-phenyl)-4-methyl-3-oxo-2,3,4,10-tetrahydro-9-oxa-1,2,4a-triaza-phenanthren-6-yl]-ethyl}-3-methyl-azetidine-1-carboxylic acid tert-butyl ester

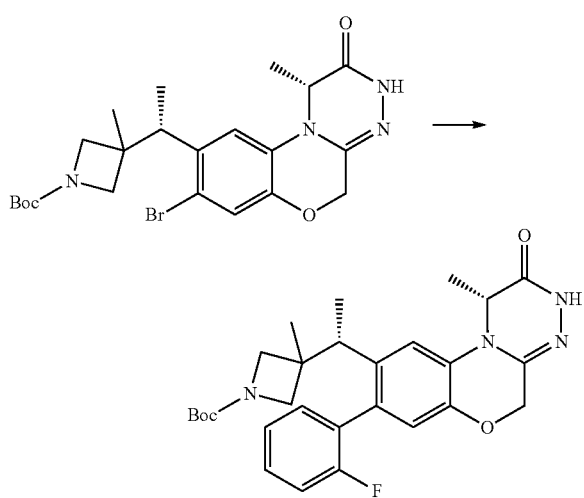

To a solution of 3-[(S)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (Example #133, Step D, 0.08 g, 0.162 mmol), (2-fluorophenyl)boronic acid (0.027 g, 0.195 mmol) and sodium carbonate (0.034 g, 0.324 mmol) in 1,4-dioxane (2.0 mL) and water (0.5 mL) was added PdCl$_2$(dppf)-DCM adduct (0.013 g, 0.016 mmol) and the reaction mixture was stirred at 90° C. overnight. The reaction mixture was cooled to ambient temperature and filtered. The filtrate was partitioned between EtOAc (30 mL) and water (30 mL). The organic layer was separated and the aqueous phase was extracted with EtOAc (3×50 mL). The combined organic phase was dried over anhydrous sodium sulfate and filtered. The filtrate was evaporated in vacuo and the residue was purified by prep-TLC (eluting with 5% methanol in dichloromethane) to give 3-{(R)-1-[(R)-7-(2-fluoro-phenyl)-4-methyl-3-oxo-2,3,4,10-tetrahydro-9-oxa-1,2,4a-triaza-phenanthren-6-yl]-ethyl}-3-methyl-azetidine-1-carboxylic acid tert-butyl ester (0.083 g, 100%). $^1$H NMR (CDCl$_3$, 400 MHz): δ 8.12 (br. s, 1H), 7.37 (m, 1H), 7.08-7.26 (m, 3H), 6.84-6.91 (m, 1H), 6.79 (m, 1H), 4.73-4.87 (m, 1H), 4.59-4.68 (m, 2H), 3.57 (m, 1H), 3.44- 3.51 (m, 1H), 3.33-3.41 (m, 1H), 3.25 (m, 1H), 2.86 (m, 1H), 1.55 (d, J=6.8 Hz, 3H), 1.35-1.47 (m, 9H), 1.22-1.35 (m, 3H), 1.07-1.21 (m, 3H). LC/MS (Table 1, Method 25) R$_t$=0.883 min; MS (ESI): m/z 531 [M+Na]$^+$ and 453 [M+H−56]$^+$.

Step B. (R)-7-(2-Fluoro-phenyl)-4-methyl-6-[(R)-1-(3-methyl-azetidin-3-yl)-ethyl]-2,10-dihydro-9-oxa-1,2,4a-triaza-phenanthren-3-one

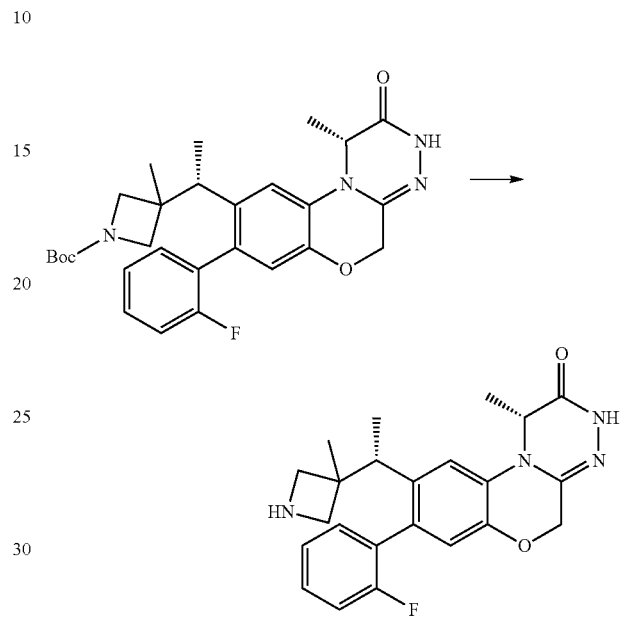

A solution of 3-{(R)-1-[(R)-7-(2-fluoro-phenyl)-4-methyl-3-oxo-2,3,4,10-tetrahydro-9-oxa-1,2,4a-triaza-phenanthren-6-yl]-ethyl}-3-methyl-azetidine-1-carboxylic acid tert-butyl ester (0.073 g, 0.144 mmol) in HCl (4M in EtOAc, 1 mL) was stirred at ambient temperature for 1 h. The reaction mixture was concentrated in vacuo to give (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one (0.06 g, 100%), which was used directly in the next step without further purification. $^1$H NMR (CD$_3$OD, 400 MHz): δ 7.45 (m, 1H), 7.16-7.34 (m, 3H), 6.90-6.96 (m, 1H), 6.86 (s, 1H), 4.92-4.98 (m, 1H), 4.57-4.68 (m, 2H), 4.24 (m, 1H), 3.69-3.76 (m, 1H), 3.46-3.55 (m, 1H), 3.38 (m, 1H), 2.97 (m, 1H), 1.36-1.51 (m, 6H), 1.20-1.27 (m, 3H). LC/MS (Table 1, Method 25) R$_t$=0.673 min; MS (ESI): m/z 409 [M+H]$^+$.

Step C. (R)-6-[(R)-1-(1,3-Dimethyl-azetidin-3-yl)-ethyl]-7-(2-fluoro-phenyl)-4-methyl-2,10-dihydro-9-oxa-1,2,4a-triaza-phenanthren-3-one

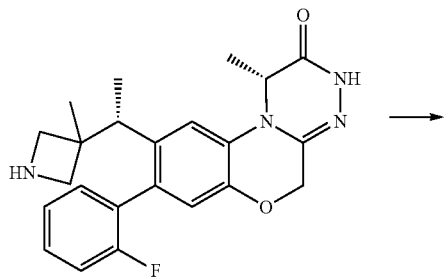

-continued

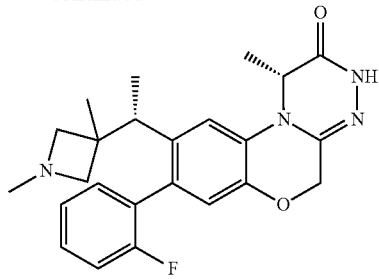

To a solution of (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one (0.04 g, 0.098 mmol) in AcOH (0.5 mL) and MeOH (5 mL) was added paraformaldehyde (0.029 g, 0.979 mmol) and the resulting mixture was stirred at ambient temperature for 1 h. NaBH$_3$CN (0.015 g, 0.245 mmol) was added and the reaction mixture was stirred at ambient temperature overnight. Aqueous NaHCO$_3$ (10 mL) was added and the aqueous solution was extracted with EtOAc (3×30 mL). The combined organic phase was dried over anhydrous sodium sulfate and filtered. The filtrate was evaporated in vacuo and the residue was purified by prep-HPLC (Table 3, Method 25) to give (R)-6-[(R)-1-(1,3-dimethyl-azetidin-3-yl)-ethyl]-7-(2-fluoro-phenyl)-4-methyl-2,10-dihydro-9-oxa-1,2,4a-triaza-phenanthren-3-one (0.017 g, 40%). $^1$H NMR (CD$_3$OD, 400 MHz): δ 7.40-7.48 (m, 1H), 7.15-7.32 (m, 3H), 6.91 (s, 1H), 6.84 (s, 1H), 4.83 (m, 1H), 4.58-4.69 (m, 2H), 2.87-3.19 (m, 3H), 2.73-2.87 (m, 2H), 2.10-2.22 (m, 3H), 1.50 (m, 3H), 1.25-1.35 (m, 3H), 1.13-1.23 (m, 3H). LC/MS (Table 1, Method 4) R$_t$=1.858 min; MS m/z: 423 [M+H]$^+$. SFC (Table 1, Method 15) R$_t$=1.592 min.

Example #147

(R)-4-Methyl-6-[(R)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-1, Enantiomer 1) & (R)-4-Methyl-6-[(S)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-2, Enantiomer 2)

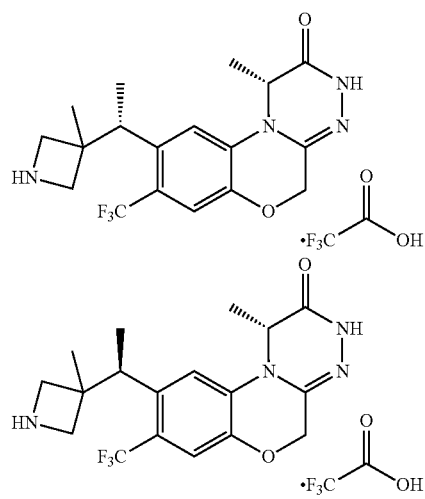

Step A. 3-Methyl-3-{1-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-yl]-vinyl}-azetidine-1-carboxylic acid tert-butyl ester

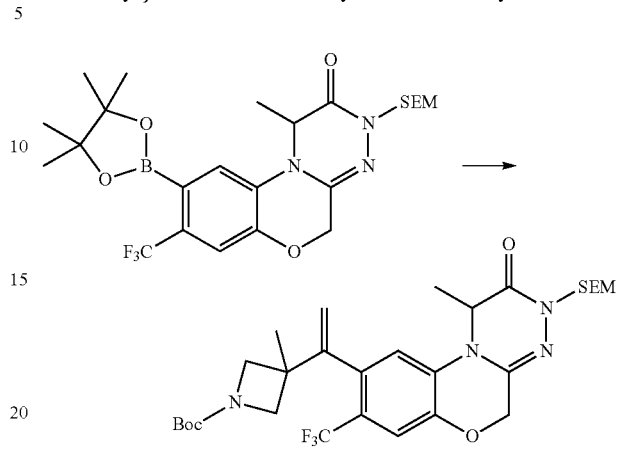

A mixture of 4-methyl-6-(4,4,5,5-tetramethyl-[1,3,2]dioxaborolan-2-yl)-7-trifluoromethyl-2-(2-trimethylsilanyl-ethoxymethyl)-2,10-dihydro-9-oxa-1,2,4a-triaza-phenanthren-3-one (Example #107, Step A, 4.87 g, 6.279 mmol), tert-butyl 3-methyl-3-(1-(trifluoromethylsulfonyloxy)vinyl)azetidine-1-carboxylate (Prepared from 1-(tert-butoxycarbonyl)-3-methylazetidine-3-carboxylic acid using the procedure detailed in Preparation #4, Steps A-C, 2.168 g, 6.279 mmol), PdCl$_2$(dppf)-CH$_2$Cl$_2$ adduct (0.513 g, 0.628 mmol) and K$_2$CO$_3$ (1.735 g, 12.554 mmol) in dioxane (48 mL) and water (8 mL) was stirred at 90° C. for 3 h. The reaction mixture was cooled to ambient temperature. The solvent was removed in vacuo and the residue was purified by column chromatography on silica gel (eluting with 0% to 20% EtOAc in petroleum ether) to give 3-methyl-3-{1-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-yl]-vinyl}-azetidine-1-carboxylic acid tert-butyl ester (1.214 g, 31%). LC/MS (Table 1, Method 27) R$_t$=1.481 min; MS m/z: 633 [M+Na]$^+$.

Step B. 3-Methyl-3-[1-(4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester

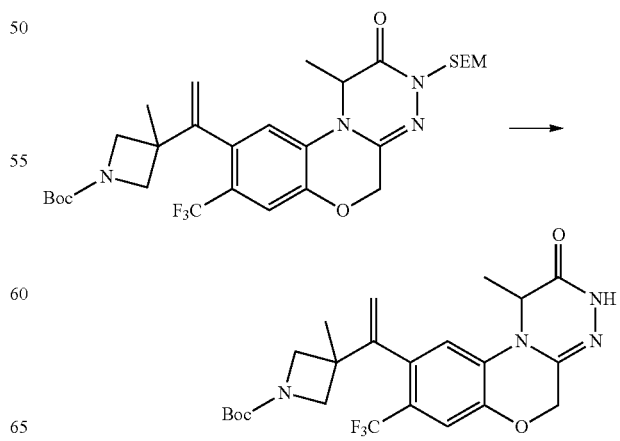

A mixture of 3-methyl-3-{1-[4-methyl-3-oxo-7-trifluoromethyl-2-(2-trimethylsilanyl-ethoxymethyl)-2,3,4,10-tetrahydro-9-oxa-1,2,4a-triaza-phenanthren-6-yl]-vinyl}-azetidine-1-carboxylic acid tert-butyl ester (1.214 g, 1.662 mmol) and tetrabutylammonium fluoride (1M in THF, 22.9 mL, 22.9 mmol) was stirred at 80° C. overnight. The reaction was cooled to ambient temperature. The solvent was removed in vacuo and the residue was purified by column chromatography on silica gel (eluting with 0-10% EtOAc in petroleum ether) to give 3-methyl-3-[1-(4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester (0.330 g, 45%). $^1$H NMR (CDCl$_3$, 400 MHz): δ 8.25 (s, 1H), 7.35 (s, 1H), 6.66 (s, 1H), 5.46 (s, 1H), 5.15 (s, 1H), 4.7 (m, 2H), 4.6 (m, 1H), 3.95 (m, 1H), 3.86 (m, 1H), 3.65 (m, 2H), 1.55 (m, 3H), 1.50 (m, 3H), 1.40 (s, 9H). LC/MS (Table 1, Method 25) R$_t$=0.923 min; MS m/z: 503 [M+Na]$^+$.

Step C. 3-Methyl-3-[1-((R)-4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester and 3-methyl-3-[1-((S)-4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester

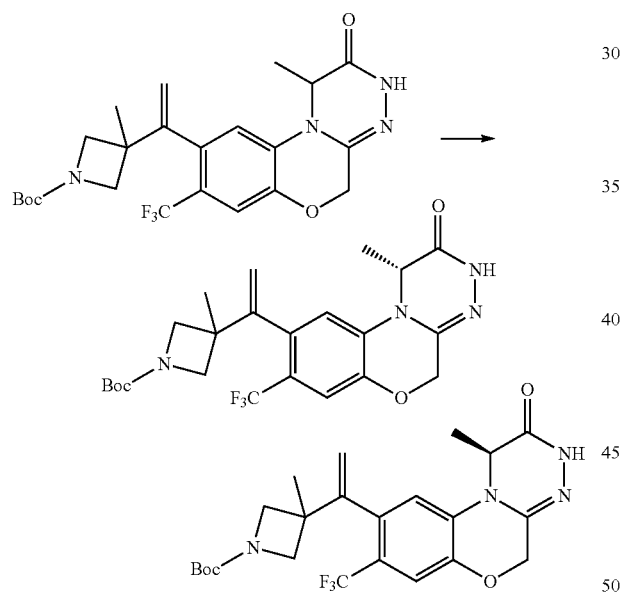

3-Methyl-3-[1-(4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester (0.310 g, 0.645 mmol) was separated by Chiral SFC separation (Table 2, Method 18) to give two enantiomers: 3-methyl-3-[1-((S)-4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester (enantiomer 1, SFC (Table 1, Method 10), R$_t$=5.93 min., 0.133 g, 42%, LC/MS (Table 1, Method 25) R$_t$=0.911 min; MS m/z: 503 [M+Na]$^+$) and 3-methyl-3-[1-((R)-4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester (enantiomer 2, SFC (Table 1, Method 10), R$_t$=7.69 min., 0.089 g, 28%, LC/MS (Table 1, Method 25) R$_t$=0.918 min; MS m/z: 503 [M+Na]$^+$).

Step D. 3-Methyl-3-[1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester

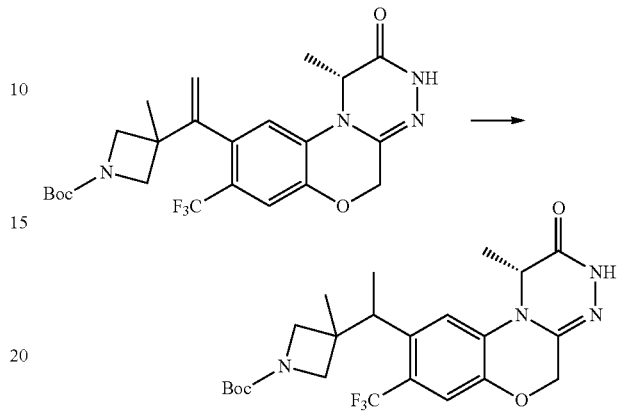

To a solution of 3-methyl-3-[1-((R)-4-methyl-3-oxo-7-trifluoromethyl-2,3,4,10-tetrahydro-9-oxa-1,2,4a-triaza-phenanthren-6-yl)-vinyl]-azetidine-1-carboxylic acid tert-butyl ester (enantiomer 2, 0.089 g, 0.185 mmol) in MeOH (12 mL) was added 10% Pd/C (0.039 g, 0.037 mmol) and the reaction mixture was stirred under H$_2$ at ambient temperature for 1 h. The reaction mixture was filtered and the filtrate was concentrated in vacuo to give 3-methyl-3-[1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (0.084 g, 94%). LC/MS (Table 1, Method 25) R$_t$=0.934 min; MS m/z: 427 [M+H−56]$^+$.

Step E. 3-Methyl-3-[(R)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester and 3-methyl-3-[(S)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester

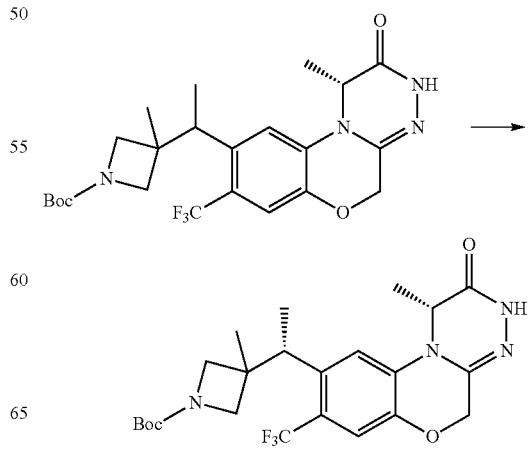

-continued

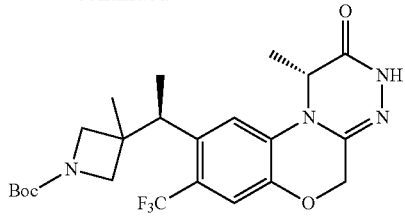

3-Methyl-3-[1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (0.084 g, 0.174 mmol) was separated by Chiral SFC (Table 2, Method 19) to give 3-methyl-3-[(R)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (diastereomer 1, SFC (Table 1, Method 35) $R_t$=2.905 min., 0.062 g, 73%, LC/MS (Table 1, Method 25) $R_t$=0.934 min; MS m/z: 427 [M+H–56]$^+$) and 3-methyl-3-[(S)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (diastereomer 2, SFC (Table 1, Method 35) $R_t$=3.387 min., 0.009 g, 10%, LC/MS (Table 1, Method 25) $R_t$=0.938 min; MS m/z: 427 [M+H–56]$^+$).

Step F. (R)-4-Methyl-6-[(R)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-1, Enantiomer 1)

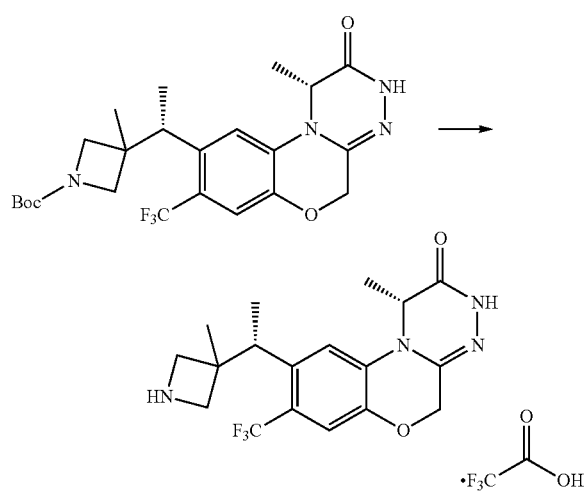

To a solution of 3-methyl-3-[(R)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (diastereomer 1, 0.062 g, 0.128 mmol) in DCM (4 mL) was added TFA (1 mL) and the reaction mixture was stirred at ambient temperature for 1.5 h. The solvent was removed in vacuo to give (R)-4-methyl-6-[(R)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-1, Enantiomer 1, 0.060 g, 94%) as a solid. $^1$H NMR (CD$_3$OD-d$_4$, 400 MHz): δ 7.46 (s, 1H), 7 (s, 1H), 4.95 (m, 1H), 4.70 (d, J=13.2 Hz, 2H), 4.3 (d, J=10.8 Hz, 1H), 3.95 (d, J=10.8 Hz, 1H), 3.65 (t, J=10.0 Hz, 2H), 3.26 (m, 1H), 1.55 (s, 3H), 1.49 (d, J=7.2 Hz, 3H), 1.44 (d, J=7.2 Hz, 3H). LC/MS (Table 1, Method 4) $R_t$=1.741 min; MS m/z: 383 [M+H]$^+$. SFC (Table 1, Method 36) $R_t$=4.264 min.

Step G. (R)-4-Methyl-6-[(S)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-2, Enantiomer 2)

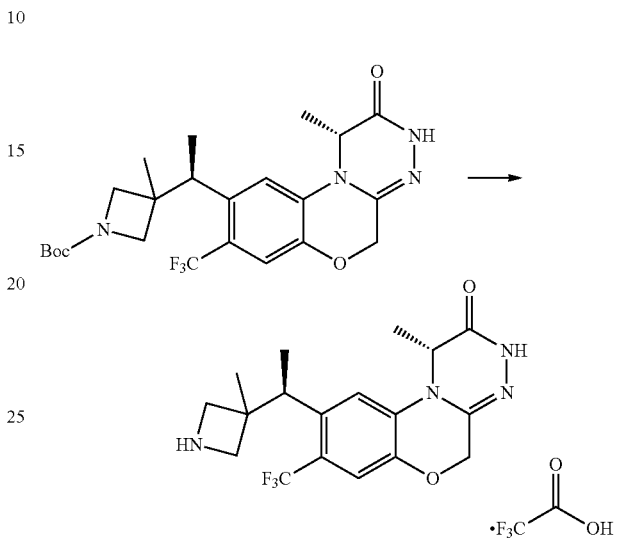

To a solution of 3-methyl-3-[(S)-1-((R)-4-methyl-3-oxo-7-trifluoromethyl-2,3,4,10-tetrahydro-9-oxa-1,2,4a-triaza-phenanthren-6-yl)-ethyl]-azetidine-1-carboxylic acid tert-butyl ester (diastereomer 2, 0.009 g, 0.019 mmol) in DCM (2 mL) was added TFA (0.5 mL) and the reaction mixture was stirred at ambient temperature for 1.5 h. The solvent was removed in vacuo and the residue was purified by prep-HPLC (Table 3, Method 28) to give (R)-4-methyl-6-[(S)-1-(3-methyl-azetidin-3-yl)-ethyl]-7-trifluoromethyl-2,10-dihydro-9-oxa-1,2,4a-triaza-phenanthren-3-one trifluoroacetic acid (Example #147-2, Enantiomer 2, 0.006 g, 84%) as a solid. $^1$H NMR (CD$_3$OD-d$_4$, 400 MHz): δ 7.35 (s, 1H), 6.9 (s, 1H), 4.95 (m, 1H), 4.7 (d, J=12.0 Hz, 2H), 4.4 (d, J=11.2 Hz, 1H), 4.2 (d, J=11.2 Hz, 1H), 3.65 (t, J=8.4 Hz, 2H), 3.26 (m, 1H), 1.5 (m, 6H), 1.45 (m, 3H). LC/MS (Table 1, Method 5) $R_t$=2.310 min; MS m/z: 383 [M+H]$^+$. SFC (Table 1, Method 36) $R_t$=4.712 min.

Example #148

(R)-1-Methyl-10-(3-methyl-azetidin-3-yl)-3,5-dihydro-10H-6-oxa-3,4,10,11b-tetraaza-cyclopenta[b]phenanthren-2-one hydrochloride

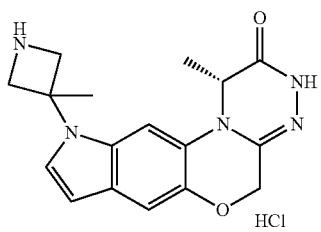 [SMILES: C[C@@H]1C(=O)NN=C2COc3cc4ccn(C5(C)CNC5)c4cc3N21 ; Cl]

Step A. (R)-2-(6-Nitro-3-oxo-2,3-dihydro-benzo[1,4]oxazin-4-yl)-propionic acid ethyl ester

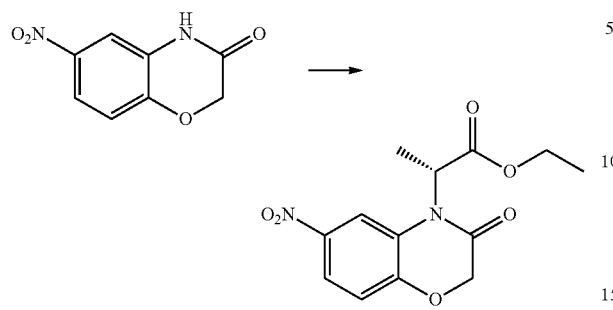

To a 0° C. suspension of 6-nitro-4H-benzo[1,4]oxazin-3-one (Preparation #2, Step A, 55 g, 283 mmol) in THF (1.1 L) was added drop-wise KHMDS (1M solution in THF, 283 mL, 283 mmol) and the reaction mixture was stirred for 30 min. (S)-2-trifluoromethanesulfonyloxy-propionic acid ethyl ester (Preparation #10, Step B, 142 g, 567 mmol) was added drop-wise and the reaction mixture was stirred for 30 min. Water (1 L) was added and the aqueous solution was extracted with EtOAc (3×1 L). The combined organic phase was dried over anhydrous $Na_2SO_4$ and filtered. The filtrate was concentrated to give a residue, which was purified by column chromatography on silica gel (eluting with 10% EtOAc in petroleum ether) to give (R)-2-(6-nitro-3-oxo-2,3-dihydro-benzo[1,4]oxazin-4-yl)-propionic acid ethyl ester (80.0 g, 96%) as an oil. $^1$H NMR (CDCl$_3$, 400 MHz): δ 7.96 (dd, J=2.4, 8.8 Hz, 1H), 7.76 (d, J=2.4 Hz, 1H), 7.12 (d, J=8.8 Hz, 1H), 5.34 (q, J=7.2 Hz, 1H), 4.81-4.66 (m, 2H), 4.29 (q, J=7.2 Hz, 2H), 1.68 (d, J=7.2 Hz, 3H), 1.25 (t, J=7.2 Hz, 3H). SFC (Table 2, Method 3) R$_t$=5.39 min.

Step B. (R)-2-(6-Nitro-3-thioxo-2,3-dihydro-benzo[1,4]oxazin-4-yl)-propionic acid ethyl ester

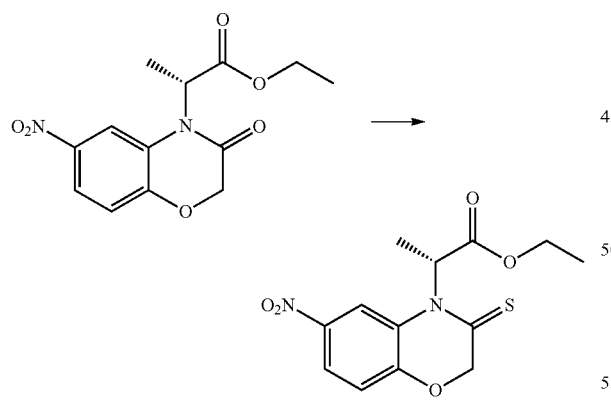

A mixture of (R)-2-(6-nitro-3-oxo-2,3-dihydro-benzo[1,4]oxazin-4-yl)-propionic acid ethyl ester (80.0 g, 272.0 mmol) and Lawesson's Reagent (66 g, 163.0 mmol) in toluene (1 L) was heated at 120° C. for 3 h. The reaction mixture was cooled to ambient temperature and the solvent was removed in vacuo. The residue was purified by column chromatography on silica gel (eluting with 3% EtOAc in petroleum ether) to give (R)-2-(6-nitro-3-thioxo-2,3-dihydro-benzo[1,4]oxazin-4-yl)-propionic acid ethyl ester (75.0 g, 89%) as a yellow solid. $^1$H NMR (CDCl$_3$, 400 MHz): δ 8.06 (dd, J=2.4, 8.8 Hz, 1H), 7.87 (d, J=2.4 Hz, 1H), 7.21 (d, J=8.8 Hz, 1H), 6.71 (m, 1H), 5.06 (d, J=15.6 Hz, 2H), 4.32 (q, J=7.2 Hz, 2H), 1.76 (d, J=7.6 Hz, 3H), 1.28-1.21 (t, J=7.2 Hz, 3H). SFC (Table 2, Method 3) R$_t$=4.04 min.

Step C. (R)-4-Methyl-6-nitro-2,10-dihydro-9-oxa-1,2,4a-triaza-phenanthren-3-one

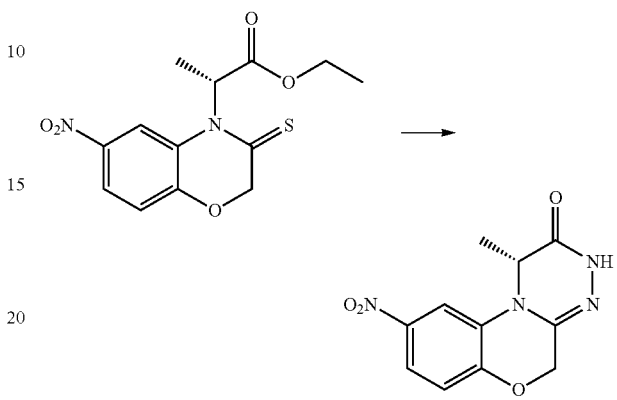

To a solution of (R)-2-(6-nitro-3-thioxo-2,3-dihydro-benzo[1,4]oxazin-4-yl)-propionic acid ethyl ester (150.0 g, 483.0 mmol) in ethanol (1.5 L) was added hydrazine hydrate (98%, 48.4 g, 967.0 mmol) and the reaction mixture was stirred at 25° C. for 16 h. The reaction mixture was filtered and the filter cake was washed with EtOH (3×100 mL) to give (R)-1-methyl-9-nitro-3,5-dihydrobenzo[5,6][1,4]oxazino[3,4-c][1,2,4]triazin-2(1H)-one (100.0 g, 79%). SFC (Table 2, Method 4) R$_t$=3.19 min. $^1$H NMR (DMSO-d$_6$, 400 MHz): δ 10.92 (s, 1H), 7.98 (d, J=2.4 Hz, 1H), 7.87 (dd, J=2.4, 8.8 Hz, 1H), 7.22 (d, J=8.8 Hz, 1H), 4.98 (q, J=6.8 Hz, 1H), 4.83-4.74 (d, J=12.8 Hz, 2H), 1.36 (d, J=6.8 Hz, 3H). The crude (R)-1-methyl-9-nitro-3,5-dihydrobenzo[5,6][1,4]oxazino[3,4-c][1,2,4]triazin-2(1H)-one (33 g, 142 mmol, e.e. =77%) was dissolved in refluxing MeOH (2.1 L) and then cooled slowly to ambient temperature. The crystals were removed by filtration and the filtrate was concentrated in vacuo to give (R)-4-methyl-6-nitro-2,10-dihydro-9-oxa-1,2,4a-triaza-phenanthren-3-one (26 g, 79%) as a yellow solid. SFC (Table 2, Method 4) R$_t$=3.06 min, e.e. =98%.

Step D. (R)-6-Amino-4-methyl-2,10-dihydro-9-oxa-1,2,4a-triaza-phenanthren-3-one

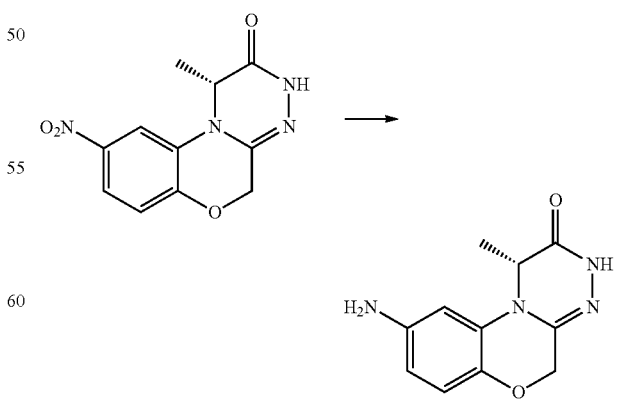

To a solution of (R)-4-methyl-6-nitro-2,10-dihydro-9-oxa-1,2,4a-triaza-phenanthren-3-one (50 g, 191 mmol) and ammonium chloride (102 g, 1907 mmol) in MeOH (700 mL)

and THF (700 mL) was added zinc powder (125 g, 1907 mmol) in portions. After addition, the reaction mixture was stirred at 50° C. for 16 h. The reaction mixture was cooled to ambient temperature and filtered. The filter cake was washed with hot MeOH (3×1 L) and the combined organic phase was concentrated in vacuo. The residue was washed with THF (3×500 mL) and the combined organic phase was concentrated to give the crude (R)-6-amino-4-methyl-2,10-dihydro-9-oxa-1,2,4a-triaza-phenanthren-3-one (50 g, 215 mmol, containing residual NH$_4$Cl), which was used in the next step without further purification. $^1$H NMR (CDCl$_3$, 400 MHz): δ 6.68 (d, J=8.4 Hz, 1H), 6.43 (d, J=2.4 Hz, 1H), 6.16 (dd, J=2.4, 8.4 Hz, 1H), 4.83 (br. s., 1H), 4.56-4.52 (m, 1H), 4.47-4.39 (m, 2H), 1.31 (d, J=6.5 Hz, 3H). LCMS (Table 1, Method 3) R$_t$=0.803 min; MS m/z: 233 [M+H]$^+$.

Step E. (R)-6-(1-Benzhydryl-3-methyl-azetidin-3-ylamino)-4-methyl-2,10-dihydro-9-oxa-1,2,4a-triaza-phenanthren-3-one

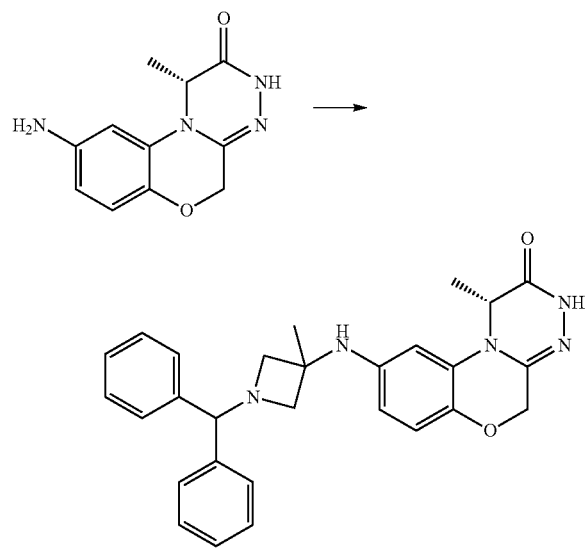

A mixture of (R)-6-amino-4-methyl-2,10-dihydro-9-oxa-1,2,4a-triaza-phenanthren-3-one (50 g, 172 mmol), methansulfonic acid 1-benzhydryl-3-methylazetidin-3-yl ester (Preparation #14, Step B, 95 g, 258 mmol) and K$_2$CO$_3$ (47.6 g, 344 mmol) in iPrOH (1 L) was stirred at 90° C. for 16 h. The reaction mixture was cooled to ambient temperature and concentrated in vacuo. The residue was dissolved in water (1 L) and extracted with EtOAc (3×500 mL). The combined organic phase was dried over anhydrous Na$_2$SO$_4$ and filtered. The filtrate was concentrated and the residue was purified by column chromatography on silica gel (eluting with 30-60% EtOAc in petroleum ether) to give (R)-6-(1-benzhydryl-3-methyl-azetidin-3-ylamino)-4-methyl-2,10-dihydro-9-oxa-1,2,4a-triaza-phenanthren-3-one (31 g, 38%) as a yellow solid. $^1$H NMR (CDCl$_3$, 400 MHz): δ 8.47 (s, 1H), 7.45-7.40 (m, 4H), 7.30-7.26 (m, 4H), 7.22-7.16 (m, 2H), 6.78 (d, J=9.0 Hz, 1H), 6.08-6.02 (m, 2H), 4.64-4.57 (t, J=6.8 Hz, 1H), 4.53-4.41 (d, J=14.8 Hz, 3H), 3.30 (m, 2H), 3.15 (m, 2H), 1.65 (s, 3H), 1.46 (d, J=6.8 Hz, 3H). SFC (Table 1, Method 1) R$_t$=4.36 min.

Step F. 3-Methyl-3-((R)-4-methyl-3-oxo-2,3,4,10-tetrahydro-9-oxa-1,2,4a-triaza-phenanthren-6-ylamino)-azetidine-1-carboxylic acid tert-butyl ester

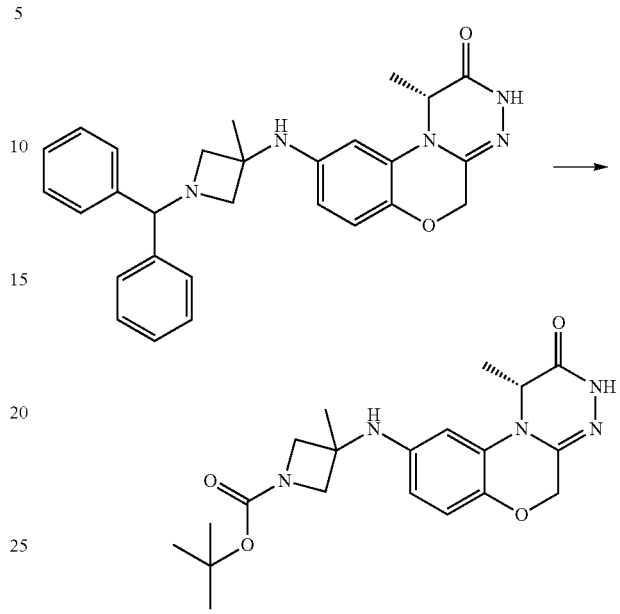

To a solution of (R)-6-(1-benzhydryl-3-methyl-azetidin-3-ylamino)-4-methyl-2,10-dihydro-9-oxa-1,2,4a-triaza-phenanthren-3-one (31 g, 66.3 mmol) and di-tert-butyl dicarbonate (57.9 g, 265 mmol) in MeOH (1 L) was added Pd(OH)$_2$/C (10%, 15.5 g, 110 mmol) and the reaction mixture was stirred at 50° C. under an atmosphere of H$_2$ (50 psi) for 3 h. The reaction mixture was cooled to ambient temperature and filtered. The filtrate cake was washed with hot MeOH (3×200 mL) and the combined filtrate was concentrated in vacuo. The residue was purified by column chromatography on silica gel (eluting with 10-50% EtOAc in petroleum ether) to give 3-methyl-3-((R)-4-methyl-3-oxo-2,3,4,10-tetrahydro-9-oxa-1,2,4a-triaza-phenanthren-6-ylamino)-azetidine-1-carboxylic acid tert-butyl ester (20 g, 75%) as a white solid. $^1$H NMR (CDCl$_3$, 400 MHz): δ 8.47 (s, 1H), 6.80 (d, J=8.4 Hz, 1H), 6.08 (m, 2H), 4.62 (m, 1H), 4.52 (m, 2H), 4.12 (m, 2H), 3.88 (m, 2H), 1.60 (s, 3H), 1.48 (m, 3H), 1.45 (s, 9H). LCMS (Table 1, Method 25) R$_t$=0.777 min; MS m/z: 402 [M+H]$^+$. SFC (Table 1, Method 31) R$_t$=5.344 min.

Step G. 3-((R)-7-Bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester

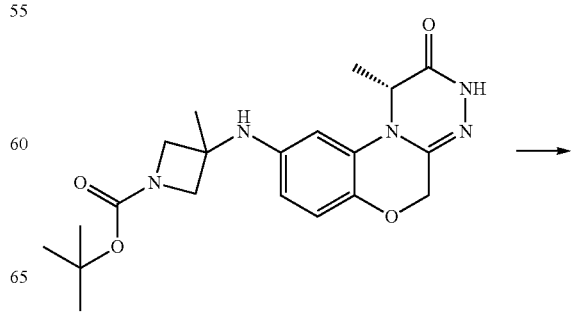

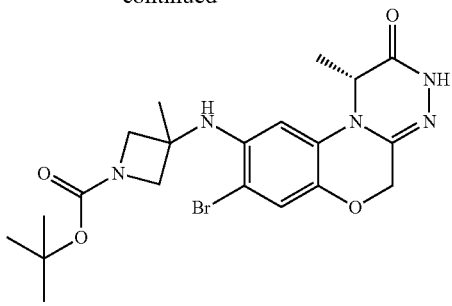

To a solution of 3-methyl-3-((R)-4-methyl-3-oxo-2,3,4,10-tetrahydro-9-oxa-1,2,4a-triaza-phenanthren-6-ylamino)-azetidine-1-carboxylic acid tert-butyl ester (20 g, 49.8 mmol) in CH$_2$Cl$_2$ (240 mL) and MeOH (120 mL) was added tetra-n-butylammonium tribromide (24.02 g, 49.8 mmol) in portions and the reaction mixture was stirred for 4 h. Saturated aqueous Na$_2$S$_2$O$_3$ solution (100 mL) and saturated aqueous NaHCO$_3$ solution (50 mL) was added to quench the reaction. The aqueous solution was extracted with CH$_2$Cl$_2$ (3×50 mL). The combined organic phase was dried over anhydrous Na$_2$SO$_4$ and filtered. The filtrate was concentrated in vacuo and the residue was purified by column chromatography on silica gel (eluting with 20-50% EtOAc in petroleum ether) to give 3-((R)-7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester (20 g, 84%) as a yellow solid. $^1$H NMR (CDCl$_3$, 400 MHz): δ 8.68 (brs, 1H), 7.14 (s, 1H), 4.63-4.57 (m, 1H), 4.56-4.45 (m, 2H), 4.34 (s, 1H), 4.08-4.01 (m, 2H), 3.96-3.90 (m, 2H), 1.62 (s, 3H), 1.51-1.45 (m, 12H). LCMS (Table 1, Method 25) R$_t$=0.867 min; MS m/z: 482 [M+H+2]$^+$ & 480 [M+H]$^+$. SFC (Table 1, Method 31) R$_t$=5.402 min.

Step H. 3-[(R)-7-((E)-2-Ethoxy-vinyl)-4-methyl-3-oxo-2,3,4,10-tetrahydro-9-oxa-1,2,4a-triaza-phenanthren-6-ylamino]-3-methyl-azetidine-1-carboxylic acid tert-butyl ester

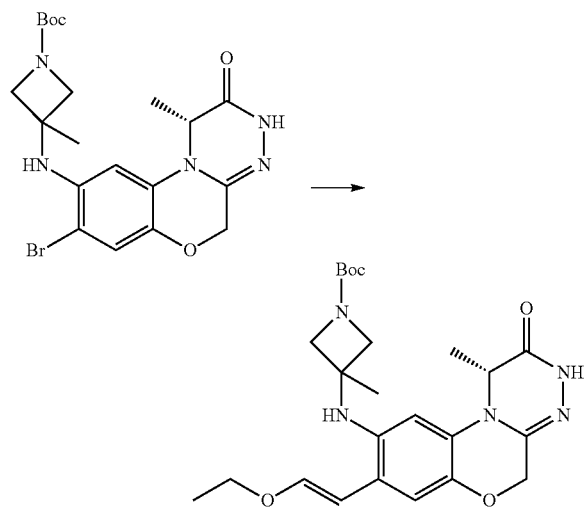

A mixture of 3-((R)-7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester (12.7 g, 26.4 mmol), (E)-2-(2-ethoxyvinyl)-4,4,5,5-tetramethyl-1,3,2-dioxaborolane (7.85 g, 39.7 mmol), Pd(dppf)Cl$_2$·CH$_2$Cl$_2$ adduct (4.32 g, 5.29 mmol) and K$_2$CO$_3$ (7.31 g, 52.9 mmol) in dioxane (210 mL) and water (35 mL) was stirred at 80° C. overnight. The reaction mixture was cooled to ambient temperature and concentrated in vacuo. The residue was purified by column chromatography on silica gel (eluting with 20-50% EtOAc in petroleum ether) to give 3-[(R)-7-((E)-2-ethoxy-vinyl)-4-methyl-3-oxo-2,3,4,10-tetrahydro-9-oxa-1,2,4a-triaza-phenanthren-6-ylamino]-3-methyl-azetidine-1-carboxylic acid tert-butyl ester (9 g, 72%). $^1$H NMR (CD$_3$OD, 400 MHz): δ 6.88 (s, 1H), 6.81 (d, J=12.5 Hz, 1H), 5.99 (brs, 1H), 5.85 (d, J=12.5 Hz, 1H), 4.97-4.93 (m, 1H), 4.70 (m, 2H), 4.06 (m, 2H), 3.93 (m, 4H), 1.61 (s, 3H), 1.48-1.44 (m, 12H), 1.33 (s, 3H).

Step I. (R)-1-Methyl-10-(3-methyl-azetidin-3-yl)-3,5-dihydro-10H-6-oxa-3,4,10,11b-tetraaza-cyclopenta[b]phenanthren-2-one hydrochloride

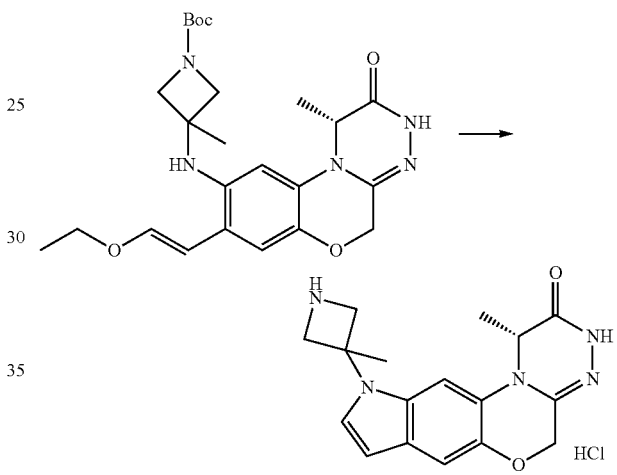

To a solution of HCl (4M in EtOAc, 160 mL) was added 3-[(R)-7-((E)-2-ethoxy-vinyl)-4-methyl-3-oxo-2,3,4,10-tetrahydro-9-oxa-1,2,4a-triaza-phenanthren-6-ylamino]-3-methyl-azetidine-1-carboxylic acid tert-butyl ester (16 g, 33.9 mmol) at 0° C. and the reaction mixture was stirred for 30 min. The reaction mixture was concentrated in vacuo to give crude (R)-1-methyl-10-(3-methyl-azetidin-3-yl)-3,5-dihydro-10H-6-oxa-3,4,10,11b-tetraaza-cyclopenta[b]phenanthren-2-one hydrochloride (10 g, 91%), which was used in the next step without further purification. LC/MS (Table 1, Method 25) R$_t$=0.627 min; MS m/z: 326 [M+H]$^+$ Step J. 3-Methyl-3-((R)-1-methyl-2-oxo-1,2,3,5-tetrahydro-6-oxa-3,4,10,11b-tetraaza-cyclopenta[b]phenanthren-10-yl)-azetidine-1-carboxylic acid tert-butyl ester

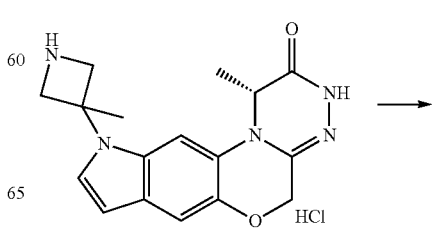

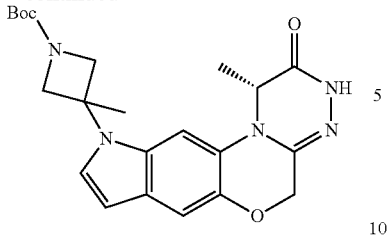

To a mixture of (R)-1-methyl-10-(3-methyl-azetidin-3-yl)-3,5-dihydro-10H-6-oxa-3,4,10,11b-tetraaza-cyclopenta[b]phenanthren-2-one hydrochloride (36 g, 111 mmol) in DCM (800 mL) was added dropwise TEA (33.6 g, 332 mmol) at 0° C. The reaction mixture was stirred for 10 min then Boc$_2$O (48.3 g, 221 mmol) was added. The reaction mixture was stirred at ambient temperature for 1.5 h then washed with water (2×100 mL). The separated organic phase was concentrated in vacuo and the residue was purified by column chromatography on silica gel (eluting with 10-50% EtOAc in petroleum ether) to give 3-methyl-3-((R)-1-methyl-2-oxo-1,2,3,5-tetrahydro-6-oxa-3,4,10,11b-tetraaza-cyclopenta[b]phenanthren-10-yl)-azetidine-1-carboxylic acid tert-butyl ester (26 g, 55%). $^1$H NMR (CD$_3$OD, 400 MHz): δ 7.25-7.19 (m, 2H), 6.87 (s, 1H), 6.42 (d, J=3.0 Hz, 1H), 4.96 (q, J=6.6 Hz, 1H), 4.62-4.51 (m, 4H), 4.30 (m, 2H), 1.81 (s, 3H), 1.51-1.48 (m, 12H). LC/MS (Table 1, Method 4) R$_t$=2.569 min; MS m/z: 426 [M+1]$^+$.

Step K. (R)-1-Methyl-10-(3-methyl-azetidin-3-yl)-3,5-dihydro-10H-6-oxa-3,4,10,11b-tetraaza-cyclopenta[b]phenanthren-2-one hydrochloride

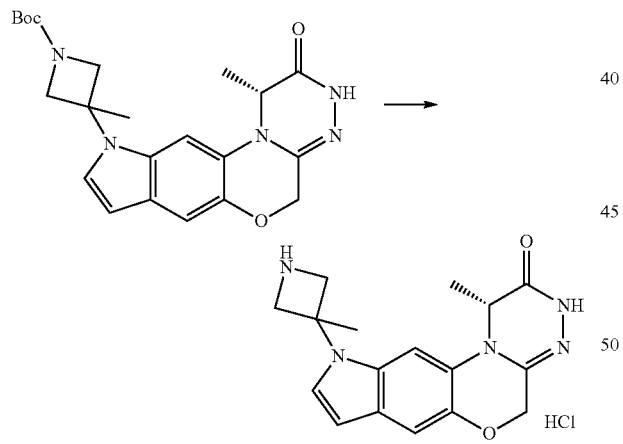

To a solution of HCl (4M in EtOAc, 40 mL) was added 3-methyl-3-((R)-1-methyl-2-oxo-1,2,3,5-tetrahydro-6-oxa-3,4,10,11b-tetraaza-cyclopenta[b]phenanthren-10-yl)-azetidine-1-carboxylic acid tert-butyl ester (4 g, 9.4 mmol) at 0° C. and the reaction mixture was stirred for 30 min. The resulting precipitate was collected by filtration and recrystallized in EtOH to give (R)-1-Methyl-10-(3-methyl-azetidin-3-yl)-3,5-dihydro-10H-6-oxa-3,4,10,11b-tetraaza-cyclopenta[b]phenanthren-2-one hydrochloride (2.6 g, 85%). $^1$H NMR (CD$_3$OD, 400 MHz): δ 7.27 (d, J=12.8 Hz, 2H), 6.84 (s, 1H), 6.50 (s, 1H), 5.04 (d, J=6.5 Hz, 1H), 4.79 (m, 2H), 4.62-4.55 (m, 4H), 1.89 (s, 3H), 1.47 (d, J=6.5 Hz, 3H). LC/MS (Table 1, Method 5) R$_t$=1.988 min; MS m/z: 326 [M+1]$^+$. SFC (Table 1, Method 37) R$_t$=2.169 min.

Example #149

8-Deuterated-1-methyl-10-(3-methyl-azetidin-3-yl)-3,5-dihydro-10H-6-oxa-3,4,10,11b-tetraaza-cyclopenta[b]phenanthren-2-one hydrochloride

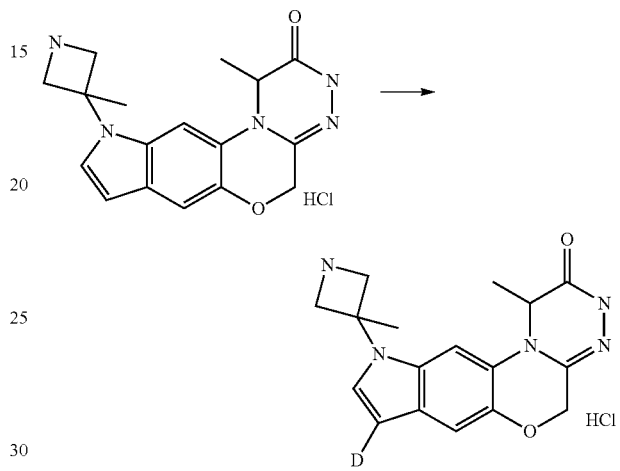

1-Methyl-10-(3-methyl-azetidin-3-yl)-3,5-dihydro-10H-6-oxa-3,4,10,11b-tetraaza-cyclopenta[b]phenanthren-2-one hydrochloride (Example 148, Step K, 0.005 g, 0.015 mmol) was dissolved in deuterated methanol (0.5 mL) and stirred for 10 min. The solvent was removed in vacuo to give 8-deuterated-1-methyl-10-(3-methyl-azetidin-3-yl)-3,5-dihydro-10H-6-oxa-3,4,10,11b-tetraaza-cyclopenta[b]phenanthren-2-one hydrochloride (0.004 g, 80%). $^1$H NMR (CD$_3$OD, 400 MHz): δ 7.27 (d, J=12.8 Hz, 2H), 6.83 (s, 1H), 5.04 (m, 1H), 4.79 (m, 2H), 4.62-4.55 (m, 4H), 1.88 (s, 3H), 1.47 (d, J=6.5 Hz, 3H). LC/MS (Table 1, Method 4) R$_t$=1.388 min.; MS m/z: 327 [M+H]+.

TABLE 18

The following analog was prepared from (R)-6-amino-4-methyl-2,10-dihydro-9-oxa-1,2,4a-triaza-phenanthren-3-one (Example #148, Step D) and methanesulfonic acid 1-benzhydryl-3-ethyl-azetidin-3-yl ester (Preparation #17) using the procedure detailed in Example #148, Steps E-K.

| Structure | Example # | R$_t$ min (method) | m/z ESI+ (M + H)$^+$ |
|---|---|---|---|
| 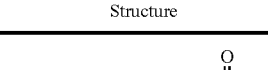 | 150 | 2.882 (Table 1, Method 41) | 340 |

Example #151

(R)-1-Methyl-10-(S)-pyrrolidin-3-yl-3,5-dihydro-10H-6-oxa-3,4,10,11b-tetraaza-cyclopenta[b]phenanthren-2-one hydrochloric acid (Example #151-1, Enantiomer 1) and (R)-1-Methyl-10-(R)-pyrrolidin-3-yl-3,5-dihydro-10H-6-oxa-3,4,10,11b-tetraaza-cyclopenta[b]phenanthren-2-one hydrochloric acid (Example #151-2, Enantiomer 2)

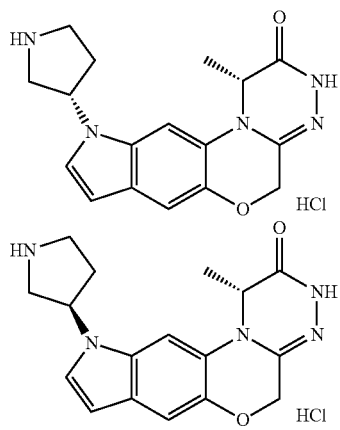

Step A. (R)-3-((R)-4-Methyl-3-oxo-2,3,4,10-tetrahydro-9-oxa-1,2,4a-triaza-phenanthren-6-ylamino)-pyrrolidine-1-carboxylic acid tert-butyl ester and (S)-3-((R)-4-methyl-3-oxo-2,3,4,10-tetrahydro-9-oxa-1,2,4a-triaza-phenanthren-6-ylamino)-pyrrolidine-1-carboxylic acid tert-butyl ester

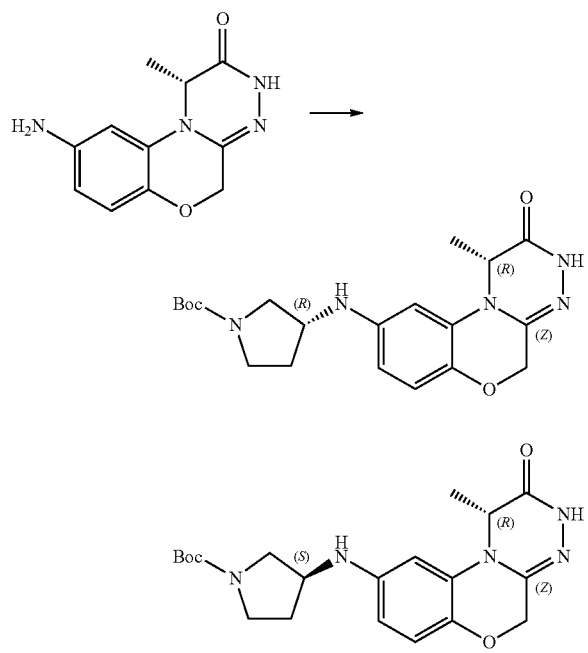

A solution of (R)-6-amino-4-methyl-2,10-dihydro-9-oxa-1,2,4a-triaza-phenanthren-3-one (Example #148, Step D, 2.4 g, 10.32 mmol) and tert-butyl 3-oxopyrrolidine-1-carboxylate (Aldrich, 2.0 g, 6.23 mmol) was stirred at 15° C. for 10 min and then acetic acid (7 mL) was added. The reaction mixture was stirred for 30 min and sodium cyanoborohydride (0.68 g, 11 mmol) was added. The reaction mixture was stirred at ambient temperature overnight then concentrated in vacuo. The residue was purified by column chromatography on silica gel (eluting with 100% EtOAc) to give 3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (2.3 g, 53%) as a yellow solid. $^1$H-NMR (400 MHz, DMSO-$d_6$): δ 10.71 (s, 1H), 6.75 (d, J=8.4 Hz, 1H), 6.42 (s, 1H), 6.20 (d, J=8.4 Hz, 1H), 5.63-5.53 (m, 1H), 4.73 (m, 1H), 4.52-4.41 (m, 2H), 4.06-3.99 (m, 1H), 3.62-3.37 (m, 2H), 3.15-2.92 (m, 1H), 2.10 (m, 1H), 1.64 (m, 1H), 1.38 (s, 9H), 1.30 (m, 3H). LCMS (Table 1, Method 2) $R_t$=1.059 min.; MS m/z: 424 [M+Na]+.

Chiral SFC (Table 2, Method 19) separation of racemic compound 3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (2.5 g) gave (R)-3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (diastereomer 1, 1.2 g, SFC (Table 1, Method 47) $R_t$=4.647 min.) and (S)-3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (diastereomer 2, 1.1 g, SFC (Table 1, Method 47) $R_t$=5.021 min.).

Step B. (R)-3-((R)-7-Bromo-4-methyl-3-oxo-2,3,4,10-tetrahydro-9-oxa-1,2,4a-triaza-phenanthren-6-ylamino)-pyrrolidine-1-carboxylic acid tert-butyl ester

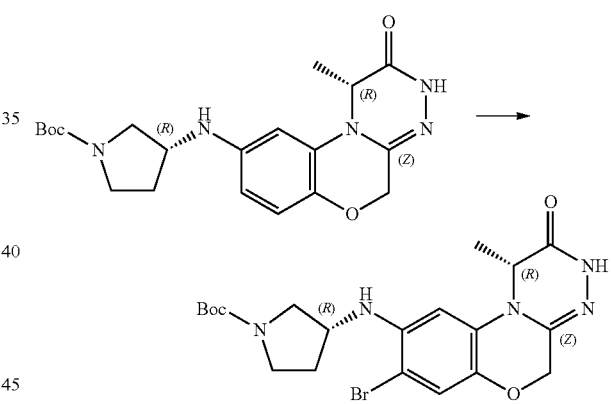

To a solution of (R)-3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (Step A, diastereomer 1, 0.65 g, 1.62 mmol) in DCM (20 mL) and MeOH (10 mL) was added tetra-N-butylammonium tribromide (0.82 g, 1.70 mmol) and the resulting solution was stirred at 15° C. for 1.5 h. The reaction mixture was quenched by the addition of saturated NaHCO$_3$ (10 mL) and Na$_2$S$_2$O$_3$ (5 mL). The aqueous solution was extracted with EtOAc (5×10 mL) and the combined organic phase was dried over anhydrous Na$_2$SO$_4$. After filtration, the filtrate was concentrated in vacuo and the residue was purified by column chromatography on silica gel (eluting with 80% EtOAc in petroleum ether) to give (R)-3-((R)-7-bromo-4-methyl-3-oxo-2,3,4,10-tetrahydro-9-oxa-1,2,4a-triaza-phenanthren-6-ylamino)-pyrrolidine-1-carboxylic acid tert-butyl ester (0.6 g, 92%) as a yellow solid. $^1$H NMR (400 MHz, CDCl$_3$): δ 8.31 (m, 1H), 7.07 (s, 1H), 6.19 (s, 1H), 4.72 (d, J=6.8 Hz, 1H), 4.51 (s, 2H), 4.23 (m, 1H), 3.99 (m, 1H), 3.71 (m, 1H), 3.50 (m, 1H), 3.30 (m, 1H), 2.29 (m, 1H), 1.93 (m, 1H), 1.47-1.51 (m, 12H). SFC (Table 1, Method 39) $R_t$=6.77 min.

293

Step C. (R)-3-[(R)-7-((E)-2-Ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester

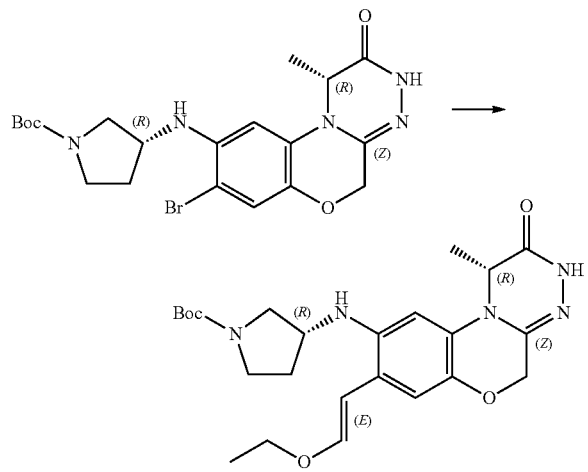

To a mixture of (R)-3-((R)-7-bromo-4-methyl-3-oxo-2,3,4,10-tetrahydro-9-oxa-1,2,4a-triaza-phenanthren-6-ylamino)-pyrrolidine-1-carboxylic acid tert-butyl ester (0.5 g, 0.625 mmol), PdCl$_2$(dppf)-CH$_2$Cl$_2$ adduct (0.05 g, 0.06 mmol) and K$_2$CO$_3$ (0.43 g, 1.87 mmol) in dioxane (24 mL) and water (4 mL) was added 2-((E)-2-ethoxy-vinyl)-4,4,5,5-tetramethyl-[1,3,2]dioxaborolane (0.123 g, 0.62 mmol) and the reaction mixture was stirred at 100° C. for 3 h. The reaction mixture was cooled to ambient temperature and concentrated in vacuo to give the crude product, which was purified by column chromatography on silica gel (eluting with 50% EtOAc in petroleum ether) to give (R)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (0.22 g, 74%) as a light yellow solid. $^1$H NMR (400 MHz, CDCl$_3$): δ 8.16 (s, 1H), 6.73 (s, 1H), 6.61 (d, J=12.4 Hz, 1H), 6.07 (s, 1H), 5.56 (d, J=12.4 Hz, 1H), 4.65 (m, 1H), 4.48 (m, 2H), 3.90 (m, 1H), 3.80 (m, 2H), 3.64 (m, 1H), 3.40 (m, 2H), 3.09-3.30 (m, 1H), 2.22 (m, 1H), 1.82 (m, 1H), 1.42 (m, 12H), 1.28 (t, J=7.2 Hz, 3H). LC/MS (Table 1, Method 2) R$_t$=1.100 min.; MS m/z: 472 [M+H]+. SFC (Table 1, Method 37) R$_t$=2.183 min.

Step D. (R)-1-Methyl-10-(R)-pyrrolidin-3-yl-3,5-dihydro-10H-6-oxa-3,4,10,11b-tetraaza-cyclopenta[b]phenanthren-2-one hydrochloric acid (Example #151-2, Diastereomer 2)

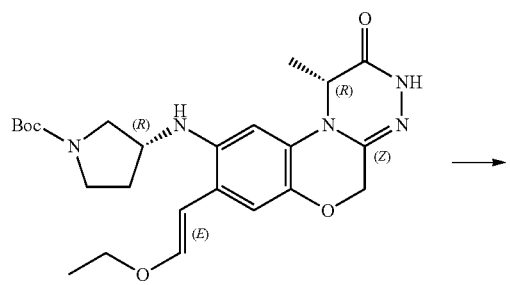

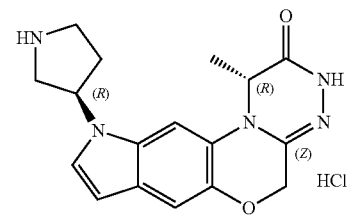

A mixture of (R)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (0.1 g, 0.212 mmol) in TFA (1 mL) was stirred at ambient temperature for 0.5 h. After concentration in vacuo, the crude product was purified by prep-HPLC (Table 3, Method 27) to give (R)-1-methyl-10-(R)-pyrrolidin-3-yl-3,5-dihydro-10H-6-oxa-3,4,10,11b-tetraaza-cyclopenta[b]phenanthren-2-one hydrochloric acid (Example #151-2, Diastereomer 2, 0.025 g, 36%). $^1$H NMR (400 MHz, DMSO-d$_6$) δ 10.75 (s, 1H), 9.40-9.80 (m, 2H), 7.55 (d, J=3.2 Hz, 1H), 7.43 (s, 1H), 7.15 (s, 1H), 6.40 (d, J=3.2 Hz, 1H), 5.40 (m, 1H), 4.97 (q, J=6.8 Hz, 1H), 4.53 (s, 2H), 3.66-3.81 (m, 1H), 3.20-3.39 (m, 4H), 2.25 (m, 1H), 1.32 (d, J=6.8 Hz, 3H). LCMS (Table 1, Method 4) R$_t$=1.238 min.; MS m/z: 326 [M+H]+. SFC (Table 1, Method 38) R$_t$=7.285 min.

Step E. (S)-3-((R)-7-Bromo-4-methyl-3-oxo-2,3,4,10-tetrahydro-9-oxa-1,2,4a-triaza-phenanthren-6-ylamino)-pyrrolidine-1-carboxylic acid tert-butyl ester

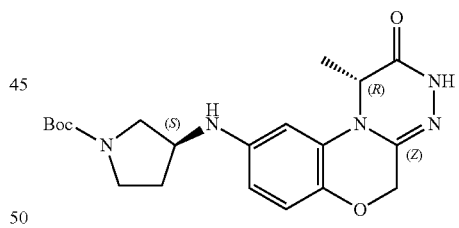

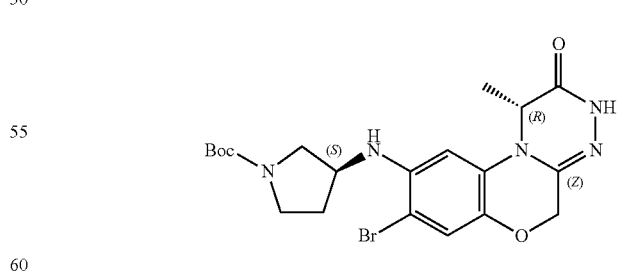

To a solution of (S)-3-((R)-4-methyl-3-oxo-2,3,4,10-tetrahydro-9-oxa-1,2,4a-triaza-phenanthren-6-ylamino)-pyrrolidine-1-carboxylic acid tert-butyl ester (Step A, diastereomer 2, 0.6 g, 1.495 mmol) in DCM (20 mL) and MeOH (10 mL) was added tetra-N-butylammonium tribromide (0.76 g, 1.569 mmol) and the reaction mixture was stirred at 15° C. for 1.5 h. The reaction was quenched by the addition of saturated aqueous NaHCO$_3$ solution (10 mL) and Na$_2$S$_2$O$_3$ solution (5 mL). The aqueous solution was extracted with EtOAc (2×20 mL) and the combined organic phase was dried over anhydrous Na$_2$SO$_4$. After filtration, the filtrate was concentrated in vacuo to give the crude product, which was purified by column chromatography on silica gel (eluting with 80% EtOAc in petroleum ether) to give (S)-3-((R)-7-bromo-4-methyl-3-oxo-2,3,4,10-tetrahydro-9-oxa-1,2,4a-triaza-phenanthren-6-ylamino)-pyrrolidine-1-carboxylic acid tert-butyl ester (0.5 g, 85%) as a yellow solid. $^1$H NMR (400 MHz, CDCl$_3$): δ 8.26 (s, 1H), 7.14 (s, 1H), 6.19 (s, 1H), 4.72 (q, J=6.4 Hz, 1H), 4.47-4.55 (m, 2H), 4.15-4.21 (m, 1H), 3.99 (m, 1H), 3.78 (m, 1H), 3.45 (m, 1H), 3.25 (m, 1H), 2.16-2.29 (m, 1H), 1.93 (m, 1H), 1.46-1.51 (m, 12H). SFC (Table 1, Method 39) R$_t$=9.23 min.

Step F. (S)-3-[(R)-7-((E)-2-Ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester

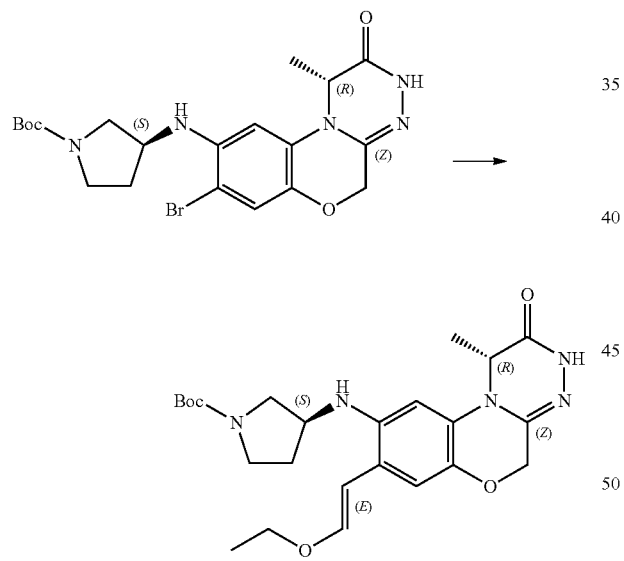

To a mixture of (S)-3-((R)-7-bromo-4-methyl-3-oxo-2,3,4,10-tetrahydro-9-oxa-1,2,4a-triaza-phenanthren-6-ylamino)-pyrrolidine-1-carboxylic acid tert-butyl ester (0.6 g, 1.249 mmol), PdCl$_2$(dppf)-CH$_2$Cl$_2$ adduct (0.051 g, 0.060 mmol) and K$_2$CO$_3$ (0.259 g, 1.87 mmol) in dioxane (24 mL) and water (4 mL) was added (E)-2-(2-ethoxyvinyl)-4,4,5,5-tetramethyl-1,3,2-dioxaborolane (0.124 g, 0.62 mmol) and the reaction mixture was stirred at 100° C. for 3 h. The reaction mixture was cooled to ambient temperature and concentrated in vacuo to give the crude product, which was purified by column chromatography on silica gel (eluting with 50% EtOAc in petroleum ether) to give (S)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (0.3 g, 50%) as a light yellow solid. $^1$H NMR (400 MHz, CDCl$_3$): δ 8.16 (s, 1H), 6.73 (s, 1H), 6.61 (d, J=12.4 Hz, 1H), 6.07 (s, 1H), 5.56 (d, J=12.4 Hz, 1H), 5.23 (s, 1H), 4.65 (m, 1H), 4.37-4.52 (m, 2H), 3.77-3.96 (m, 3H), 3.64 (m, 1H), 3.35 (m, 2H), 3.08-3.31 (m, 1H), 2.06-2.22 (m, 1H), 1.82 (m, 1H), 1.42 (m, 12H), 1.28 (t, J=7.2 Hz, 3H). LC/MS (Table 1, Method 2) R$_t$=1.097 min.; MS m/z: 472 [M+H]$^+$. SFC (Table 1, Method 37) R$_t$=1.919 min.

Step G. (R)-1-Methyl-10-(S)-pyrrolidin-3-yl-3,5-dihydro-10H-6-oxa-3,4,10,11b-tetraaza-cyclopenta[b]phenanthren-2-one hydrochloric acid (Example #151-1, Diastereomer 1)

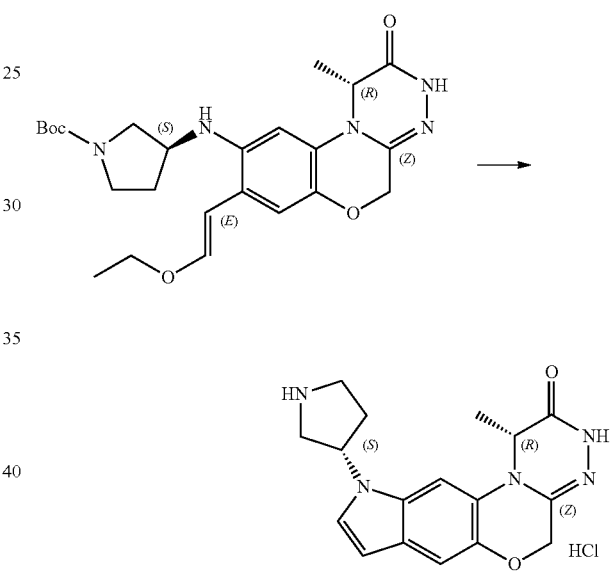

A mixture of (S)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (0.1 g, 0.212 mmol) in TFA (1 mL) was stirred at ambient temperature for 0.5 h. The reaction mixture was concentrated in vacuo to give the crude product, which was purified by prep-HPLC (Table 3, Method 27) to give (R)-1-methyl-10-(S)-pyrrolidin-3-yl-3,5-dihydro-10H-6-oxa-3,4,10,11b-tetraaza-cyclopenta[b]phenanthren-2-one hydrochloric acid (Example #151-1, Diastereomer 1, 0.029 g, 42%) as a brown solid. $^1$H NMR (400 MHz, DMSO-d$_6$): δ 10.74 (s, 1H) 9.41-10.00 (m, 2H) 7.63 (d, J=2.4 Hz, 1H), 7.45 (s, 1H), 7.14 (s, 1H), 6.40 (d, J=2.4 Hz, 1H), 5.41 (m, 1H), 4.98 (q, J=6.4 Hz, 1H), 4.47-4.60 (m, 2H), 3.20-3.52 (m, 4H), 2.40-2.47 (m, 1H), 2.25 (m, 1H), 1.33 (d, J=6.4 Hz, 3H). LCMS (Table 1, Method 4) R$_t$=1.273 min.; MS m/z: 326 [M+H]$^+$. SFC (Table 1, Method 38) R$_t$=5.618 min.

TABLE 19

The following analog was prepared from 6-amino-4-methyl-2,10-dihydro-9-oxa-1,2,4a-triaza-phenanthren-3-one (Preparation #2, Step E) and tert-butyl 3-oxopiperidine-1-carboxylate using the similar procedure detailed in Example #151, Steps A-D without the chiral separation in Step A

| Structure | Example # | Reagent | R, min (method) | m/z ESI+ (M + H)+ |
|---|---|---|---|---|
| 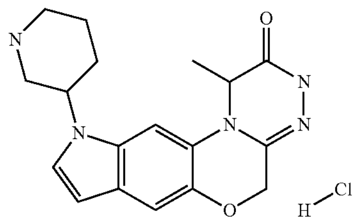 | 152 | | 1.3 (Table 1, Method 4) | 340 |

Example #153

(R)-1-Methyl-10-(R)-pyrrolidin-3-yl-3,5,9,10-tetrahydro-8H-6-oxa-3,4,10,11b-tetraaza-cyclopenta[b]phenanthren-2-one hydrochloric acid Example #154

(R)-1-Methyl-10-(S)-pyrrolidin-3-yl-3,5,9,10-tetrahydro-8H-6-oxa-3,4,10,11b-tetraaza-cyclopenta[b]phenanthren-2-one hydrochloric acid

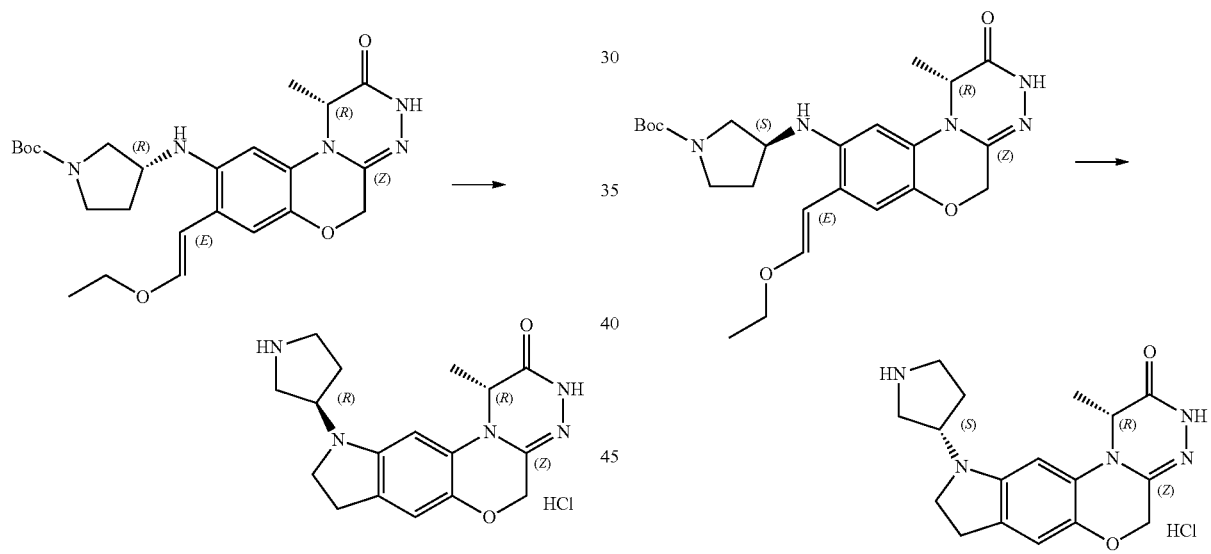

A mixture of (R)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (Example #151, Step C, 0.1 g, 0.212 mmol) in TFA (1 mL) was stirred at ambient temperature for 0.5 h. Triethylsilane (3 mL) was added and the reaction mixture was stirred overnight. The reaction mixture was concentrated in vacuo to give the crude product, which was purified by prep-HPLC (Table 3, Method 27) to give (R)-1-methyl-10-(R)-pyrrolidin-3-yl-3,5,9,10-tetrahydro-8H-6-oxa-3,4,10,11b-tetraaza-cyclopenta[b]phenanthren-2-one hydrochloric acid (0.032 g, 46%) as a red solid. $^1$H NMR (400 MHz, DMSO-$d_6$): δ 10.70 (s, 1H), 9.20 (s, 2H), 6.74 (s, 1H), 6.51 (s, 1H), 4.87 (q, J=6.4 Hz, 1H), 4.40-4.49 (m, 3H), 3.22-3.48 (m, 4H), 3.00-3.19 (m, 2H), 2.73-2.88 (m, 2H), 2.08-2.16 (m, 1H), 1.86-1.99 (m, 1H), 1.24 (d, J=6.4 Hz, 3H). LCMS (Table 1, Method 4) $R_t$=1.260 min.; MS m/z: 328 [M+H]$^+$. SFC (Table 1, Method 40) $R_t$=4.42 min.

A mixture of (S)-3-[(R)-7-((E)-2-ethoxy-vinyl)-4-methyl-3-oxo-2,3,4,10-tetrahydro-9-oxa-1,2,4a-triaza-phenanthren-6-ylamino]-pyrrolidine-1-carboxylic acid tert-butyl ester (Example #151, Step F, 0.1 g, 0.212 mmol) in TFA (1 mL) was stirred at ambient temperature for 0.5 h. Triethylsilane (3 mL) was added and the reaction mixture was stirred overnight. The reaction mixture was concentrated in vacuo to give the crude product, which was purified by prep-HPLC (Table 3, Method 27) to give (R)-1-methyl-10-(S)-pyrrolidin-3-yl-3,5,9,10-tetrahydro-8H-6-oxa-3,4,10,11b-tetraaza-cyclopenta[b]phenanthren-2-one hydrochloric acid (0.022 g, 31%) as a red solid. $^1$H NMR (400 MHz, DMSO-$d_6$): δ 10.70 (s, 1H), 9.44 (s, 2H), 6.74 (s, 1H), 6.53 (s, 1H), 4.87 (q, J=6.4 Hz, 1H), 4.45 (m, 3H), 3.48 (m, 4H), 3.00-3.19 (m, 2H), 2.73-2.88 (m, 2H), 2.14 (m, 1H), 1.96 (m, 1H), 1.24 (d, J=6.4 Hz, 3H). LCMS (Table 1, Method 4) $R_t$=1.219 min.; MS m/z: 328 [M+H]$^+$. SFC (Table 1, Method 40) $R_t$=9.55 min.

Example #155

(R)-10-(1-Acetyl-3-methyl-azetidin-3-yl)-1-methyl-3,5-dihydro-10H-6-oxa-3,4,10,11b-tetraaza-cyclopenta[b]phenanthren-2-one hydrochloric acid

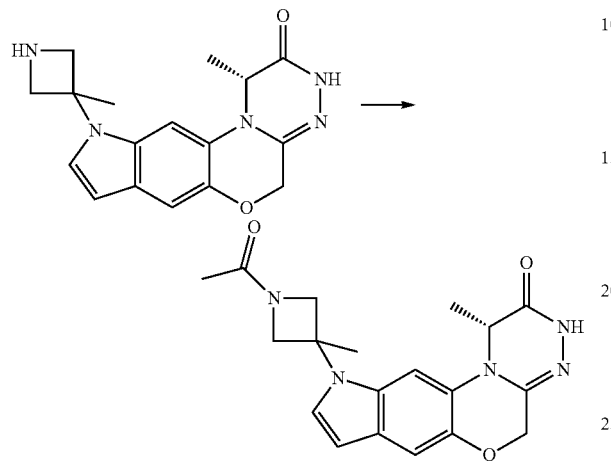

To a mixture of (R)-1-methyl-10-(3-methyl-azetidin-3-yl)-3,5-dihydro-10H-6-oxa-3,4,10,11b-tetraaza-cyclopenta[b]phenanthren-2-one hydrochloric acid (Example #148, 0.4 g, 1.2 mmol) in DCM (15 mL) was added acetyl chloride (0.42 g, 5.35 mmol) and TEA (0.37 g, 3.69 mmol) at 0° C. The reaction mixture was stirred at ambient temperature for 1 h. The mixture was concentrated in vacuo and the residue was purified by prep-HPLC (Table 3, Method 29) to give (R)-10-(1-acetyl-3-methyl-azetidin-3-yl)-1-methyl-3,5-dihydro-10H-6-oxa-3,4,10,11b-tetraaza-cyclopenta[b]phenanthren-2-one (0.146 g, 11%) as a pale yellow solid. $^1$H NMR (400 MHz, methanol-$d_4$): δ 7.27 (s, 1H), 7.21 (s, 1H), 6.87 (d, J=10.8 Hz, 1H), 6.45 (s, 1H), 5.04 (m, 1H), 4.90 (m, 1H), 4.61 (m, 4H), 4.34 (m, 1H), 2.04 (m, 3H), 1.79 (m, 3H), 1.44 (m, 3H). LC/MS (Table 1, Method 4) $R_t$=1.836 min.; MS m/z: 368 [M+H]+.

Example #156

(R)-8-Ethyl-1-methyl-10-(3-methyl-azetidin-3-yl)-3,5-dihydro-10H-6-oxa-3,4,10,11b-tetraaza-cyclopenta[b]phenanthren-2-one hydrochloride

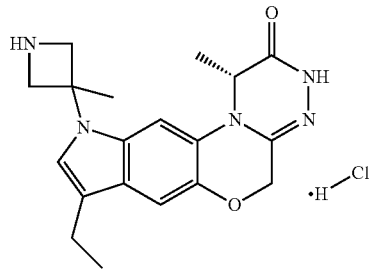

Step A. 3-((R)-8-Iodo-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester

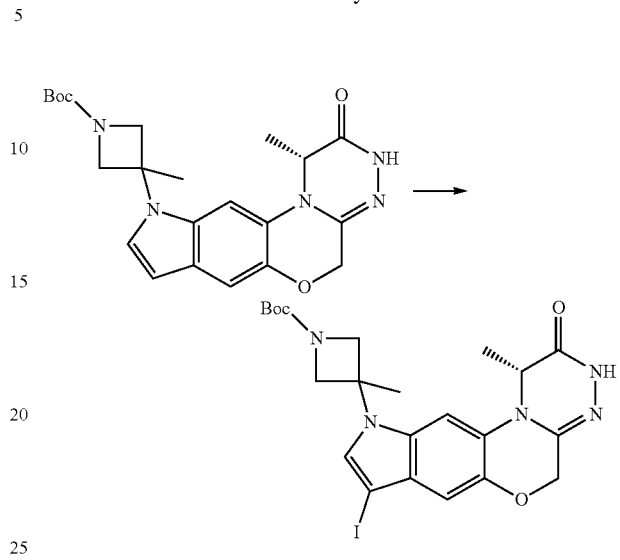

To a solution of 3-methyl-3-((R)-1-methyl-2-oxo-1,2,3,5-tetrahydro-6-oxa-3,4,10,11b-tetraaza-cyclopenta[b]phenanthren-10-yl)-azetidine-1-carboxylic acid tert-butyl ester (Example #148, Step J, 1 g, 2.35 mmol) in THF (20 mL) was added 1-iodopyrrolidine-2,5-dione (0.582 g, 2.59 mmol) in portions at −5-0° C. The reaction mixture was stirred at 0° C. for 3 h. Saturated aqueous sodium sulphite solution (5 mL) was added to quench the reaction and the solvent was removed in vacuo. The residue was purified by column chromatography on silica gel (eluting with 10%~100% EtOAc in petroleum ether) to give 3-((R)-8-iodo-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester (0.4 g, 30%) as a yellow solid. $^1$H NMR (400 MHz, methanol-$d_4$): δ 7.39 (s, 1H), 6.97 (s, 1H), 6.89 (s, 1H), 4.97 (m, 1H), 4.53 (d, J=8.5 Hz, 2H), 4.59 (m, 2H), 4.54 (m, 2H), 4.29 (m, 2H), 1.81 (s, 3H), 1.51-1.48 (m, 12H). LC/MS (Table 1, Method 2) $R_t$=1.279 min.; MS m/z: 552 [M+H]$^+$.

Step B. 3-Methyl-3-((R)-1-methyl-2-oxo-8-vinyl-1,2,3,5-tetrahydro-6-oxa-3,4,10,11b-tetraaza-cyclopenta[b]phenanthren-10-yl)-azetidine-1-carboxylic acid tert-butyl ester

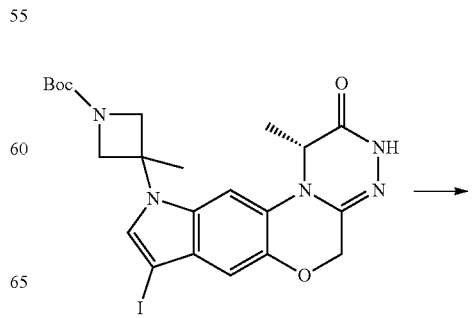

-continued

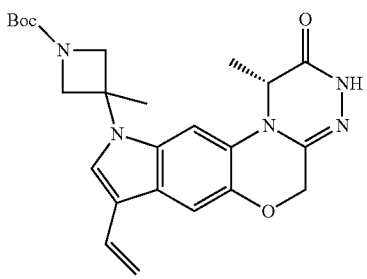

A mixture of 3-((R)-8-iodo-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester (0.3 g, 0.544 mmol), 4,4,5,5-tetramethyl-2-vinyl-1,3,2-dioxaborolane (0.838 g, 5.44 mmol), K$_2$CO$_3$ (0.15 g, 1.088 mmol) and Pd(dppf)Cl$_2$·CH$_2$Cl$_2$ (0.044 g, 0.054 mmol) in dioxane (6 mL) and water (1 mL) was heated at 68° C. for 14 h. The reaction mixture was cooled to ambient temperature and the solvent was removed in vacuo. The residue was purified by column chromatography on silica gel (eluting with 10%~100% EtOAc in petroleum ether) to give 3-methyl-3-((R)-1-methyl-2-oxo-8-vinyl-1,2,3,5-tetrahydro-6-oxa-3,4,10,11b-tetraaza-cyclopenta[b]phenanthren-10-yl)-azetidine-1-carboxylic acid tert-butyl ester (0.22 g, 90%) as yellow gum, which was used directly in the next step. LC/MS (Table 1, Method 25) R$_f$=0.892 min.; MS m/z: 452 [M+H]$^+$.

Step C. 3-((R)-8-Ethyl-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester

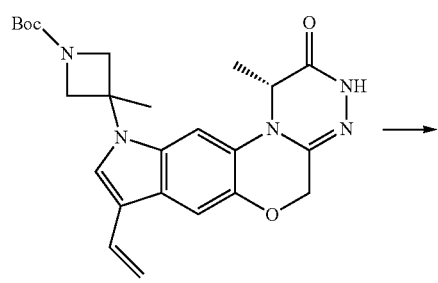

A mixture of 3-methyl-3-((R)-1-methyl-2-oxo-8-vinyl-1,2,3,5-tetrahydro-6-oxa-3,4,10,11 b-tetraaza-cyclopenta[b]phenanthren-10-yl)-azetidine-1-carboxylic acid tert-butyl ester (0.08 g, 0.177 mmol) and 10% Pd/C (0.002 g, 0.018 mmol) in methanol (2 mL) was stirred under an atmosphere of H$_2$ at 20° C. for 2.5 h. The mixture was filtered and the filtrate was evaporated in vacuo. The residue was purified by prep-HPLC (Table 3, Method 32) to give 3-((R)-8-ethyl-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester (0.04 g, 49%) as a gum. $^1$H NMR (400 MHz, methanol-d$_4$): δ 7.18 (s, 1H), 7.00 (s, 1H), 6.81 (s, 1H), 4.98 (m, 1H), 4.61-4.47 (m, 4H), 4.27 (m, 2H), 2.70 (q, J=7.6 Hz, 2H), 1.77 (s, 3H), 1.50-1.47 (m, 12H), 1.32 (m, J=7.6 Hz, 3H). LC/MS (Table 1, Method 25) R$_f$=0.896 min.; MS m/z: 454 [M+H]$^+$.

Step D. (R)-8-Ethyl-1-methyl-10-(3-methyl-azetidin-3-yl)-3,5-dihydro-10H-6-oxa-3,4,10,11b-tetraaza-cyclopenta[b]phenanthren-2-one hydrochloride

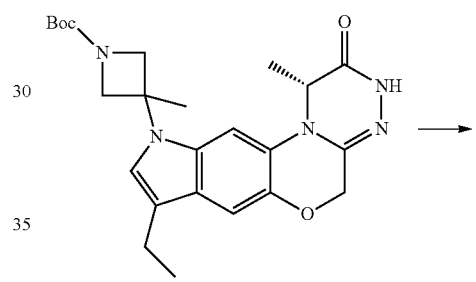

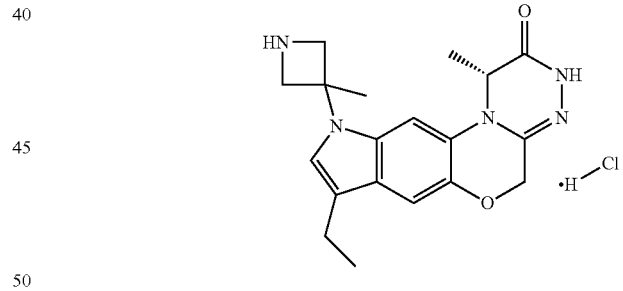

A solution of 3-((R)-8-ethyl-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester (0.04 g, 0.088 mmol) in HCl (4M in EtOAc, 3 mL) was stirred at −5-0° C. for 2 h. The solvent was removed in vacuo to give (R)-8-ethyl-1-methyl-10-(3-methyl-azetidin-3-yl)-3,5-dihydro-10H-6-oxa-3,4,10,11b-tetraaza-cyclopenta[b]phenanthren-2-one hydrochloride (0.0122 g, 39%) as a yellow solid. $^1$H NMR (400 MHz, methanol-d$_4$): δ 7.22 (s, 1H), 7.06 (s, 1H), 6.78 (s, 1H), 4.95 (m, 1H), 4.75 (m, 2H), 4.63-4.50 (m, 4H), 2.72 (q, J=7.6 Hz, 2H), 1.85 (s, 3H), 1.46 (d, J=6.8 Hz, 3H), 1.33 (t, J=7.6 Hz, 3H). LC/MS (Table 1, Method 4) R$_f$=1.591 min.; MS m/z: 354 [M+H]$^+$.

TABLE 20

The following analog was prepared from 3-((R)-8-iodo-1-methyl-2-oxo-1,2,3,5-tetrahydro-6-oxa-3,4,10,11b-tetraaza-cyclopenta[b]phenanthren-10-yl)-3-methyl-azetidine-1-carboxylic acid tert-butyl ester (Example #156, Step A) and methylboronic acid using the procedure detailed in Example #156, Steps B & D.

| Structure | Example # | Reagent | $R_t$ min (method) | m/z ESI+ $(M + H)^+$ |
|---|---|---|---|---|
| 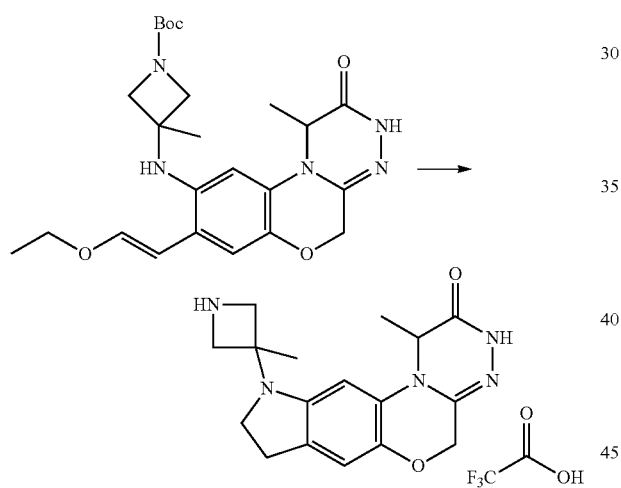 | 157 | /B(OH)₂ | 1.502 (Table 1, Method 4) | 340 |

Example #158

1-Methyl-10-(3-methyl-azetidin-3-yl)-3,5,9,10-tetrahydro-8H-6-oxa-3,4,10,11b-tetraaza-cyclopenta[b]phenanthren-2-one 2,2,2-trifluoroacetate

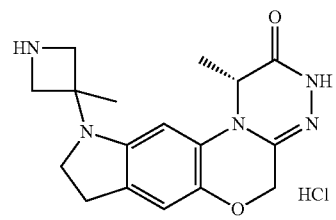 [SMILES: C[C@@H]1C(=O)NN=C2COc3cc4c(cc3N21)N(C1(C)CNC1)CC4 ; Cl]

A mixture of 3-[7-((E)-2-ethoxy-vinyl)-4-methyl-3-oxo-2,3,4,10-tetrahydro-9-oxa-1,2,4a-triaza-phenanthren-6-ylamino]-3-methyl-azetidine-1-carboxylic acid tert-butyl ester (prepared from tert-butyl 3-((8-bromo-1-methyl-2-oxo-1,2,3,5-tetrahydrobenzo[5,6][1,4]oxazino[3,4-c][1,2,4]triazin-9-yl)amino)-3-methylazetidine-1-carboxylate (Preparation #18) using the similar procedure detailed in Example #148, Step H) 0.65 g, 1.378 mmol) in TFA (4 mL) was stirred at ambient temperature for 20 min. Triethylsilane (4.8 g, 41.4 mmol) was added and the reaction mixture was stirred for 24 h. The solvent was removed in vacuo to give 1-methyl-10-(3-methylazetidin-3-yl)-5,8,9,10-tetrahydro-1H-[1,2,4]triazino[4',3':4,5][1,4]oxazino[2,3-f]indol-2(3H)-one 2,2,2-trifluoroacetate (0.65 g, crude). Prep-HPLC (Table 3, Method 29) purification of 20 mg of crude product gave 1-methyl-10-(3-methyl-azetidin-3-yl)-3,5,9,10-tetrahydro-8H-6-oxa-3,4,10,11b-tetraaza-cyclopenta[b]phenanthren-2-one 2,2,2-trifluoroacetate (0.011 g). ¹H NMR (400 MHz, DMSO-d₆): δ 10.69 (s, 1H), 9.15 (s, 1H), 8.91 (brs, 1H), 6.80 (s, 1H), 5.95 (s, 1H), 4.98 (m, 1H), 4.45 (s, 2H), 4.11 (m, 4H), 3.25 (m, 1H), 2.84 (m, 2H), 1.40 (s, 3H), 1.20 (m, 3H). LC/MS (Table 1, Method 4) $R_t$=0.799 min; MS m/z: 328 [M+H]⁺.

Example #159

1-Methyl-10-(3-methyl-azetidin-3-yl)-3,5,9,10-tetrahydro-8H-6-oxa-3,4,10,11b-tetraaza-cyclopenta[b]phenanthren-2-one hydrochloride Step A. 3-Methyl-3-(1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester

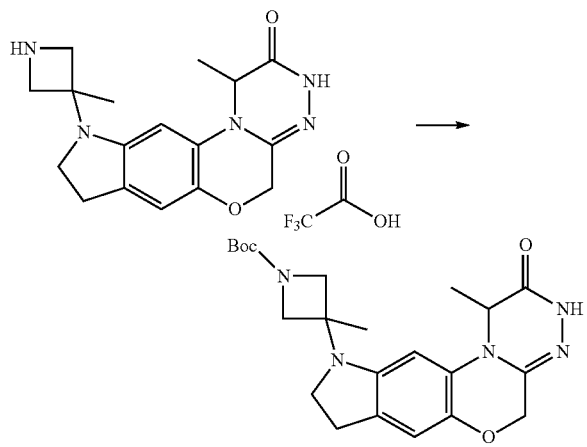

To a solution of 1-methyl-10-(3-methyl-azetidin-3-yl)-3,5,9,10-tetrahydro-8H-6-oxa-3,4,10,11b-tetraaza-cyclopenta[b]phenanthren-2-one 2,2,2-trifluoroacetate (Example #158, 0.65 g, crude, 1.985 mmol) in DCM (15 mL) was added TEA (0.603 g, 5.96 mmol), DMAP (0.024 g, 0.199 mmol) and BOC₂O (0.867 g, 3.97 mmol). The resultant mixture was stirred at ambient temperature for 3 h. Water (2×10 mL) was added and the reaction mixture was extracted with EtOAc (2×40 mL). The combined organic phase was washed with brine (20 mL) and dried over anhydrous Na₂SO₄. After filtration, the filtrate was dried in vacuo and the residue was purified by column chromatography on silica gel (eluting with 10%-50% EtOAc in petroleum ether) to give racemic 3-methyl-3-(1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester (0.43 g, 1.006 mmol). LC/MS (Table 1, Method 25) $R_t$=0.823 min; MS m/z: 428 [M+1]⁺.

Step B. 3-Methyl-3-((R)-1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester

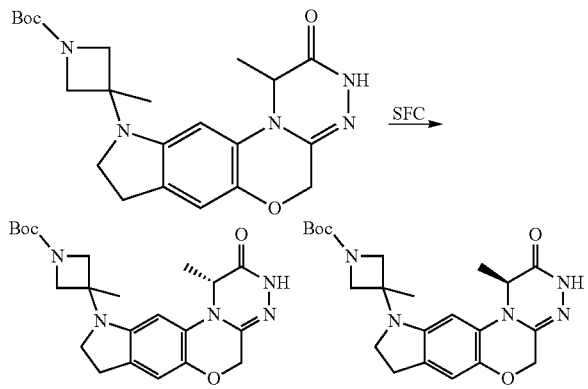

Racemic 3-methyl-3-(1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester (0.1 g, 0.234 mmol) was separated by chiral SFC (Table 2, Method 21) to give 3-methyl-3-((S)-1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester (0.04 g, 0.094 mmol) (enantiomer 1, SFC (Table 1, Method 36) $R_t$=7.081 min) and 3-methyl-3-((R)-1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester (0.04 g, 0.094 mmol) (enantiomer 2, SFC (Table 1, Method 36) $R_t$=7.550 min)

Step C. (R)-1-Methyl-10-(3-methyl-azetidin-3-yl)-3,5,9,10-tetrahydro-8H-6-oxa-3,4,10,11b-tetraaza-cyclopenta[b]phenanthren-2-one hydrochloride

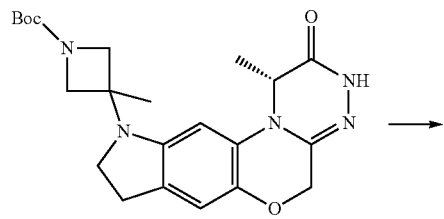

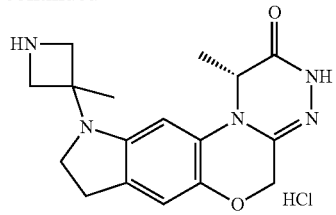

A mixture of 3-methyl-3-((R)-1-methyl-2-oxo-1,2,3,5,8,9-hexahydro-6-oxa-3,4,10,11b-tetraaza-cyclopenta[b]phenanthren-10-yl)-azetidine-1-carboxylic acid tert-butyl ester (enantiomer 2, 0.04 g, 0.094 mmol) in HCl (4M in EtOAc, 5 mL) was stirred at ambient temperature for 20 min. The solvent was removed in vacuo to give (R)-1-methyl-10-(3-methyl-azetidin-3-yl)-3,5,9,10-tetrahydro-8H-6-oxa-3,4,10,11b-tetraaza-cyclopenta[b]phenanthren-2-one hydrochloride (0.026 g, 0.079 mmol, 85%). ¹H NMR (400 MHz, DMSO-d₆): δ 10.68 (s, 1H), 6.78 (s, 1H), 5.80 (s, 1H), 4.98 (m, 1H), 4.45 (s, 2H), 4.11 (m, 4H), 3.30-3.20 (m, 2H), 2.74 (m, 2H), 1.39 (s, 3H), 1.20 (d, J=6.4 Hz, 3H). LC/MS (Table 1, Method 41) $R_t$=2.422 min; MS m/z: 328 [M+H]⁺. SFC (Table 1, Method 37) $R_t$=10.675 min.

Example #160

(R)-10-(1,3-Dimethyl-azetidin-3-yl)-1-methyl-3,5-dihydro-10H-6-oxa-3,4,10,11b-tetraaza-cyclopenta[b]phenanthren-2-one hydrochloride

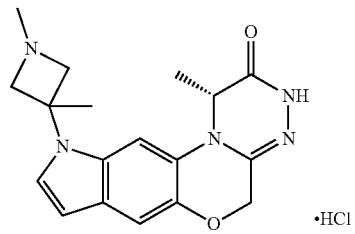 [SMILES: C[C@@H]1C(=O)NN=C2COc3cc4ccn(C5(C)CN(C)C5)c4cc3N21 ; Cl]

Step A. (R)-7-Bromo-4-methyl-6-(3-methyl-azetidin-3-ylamino)-2,10-dihydro-9-oxa-1,2,4a-triaza-phenanthren-3-one

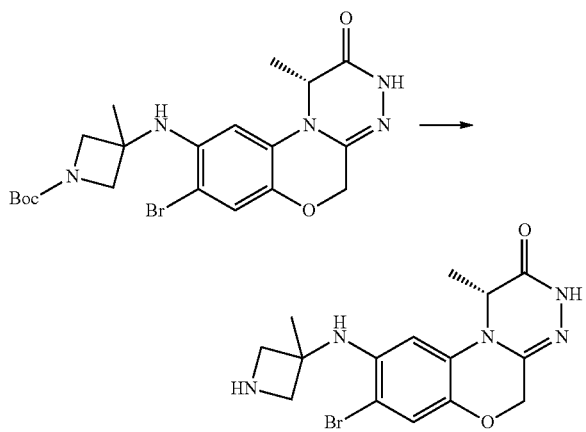

A solution of 3-((R)-7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester (Example #148, Step G, 5 g, 10.4 mmol) in TFA (4 mL) and DCM (24 mL) was stirred at ambient temperature for 3 h. The solvent was removed in vacuo to give (R)-7-bromo-4-methyl-6-(3-methyl-azetidin-3-ylamino)-2,10-dihydro-9-oxa-1,2,4a-triaza-phenanthren-3-one (4 g, 100%). $^1$H NMR (400 MHz, DMSO-d$_6$) δ 10.77 (s, 1H), 7.19 (s, 1H), 5.83 (s, 1H), 5.55 (s, 1H), 4.91 (q, J=6.4 Hz, 1H), 4.51 (s, 2H), 4.05 (m, 4H), 1.55 (s, 3H), 1.25 (d, J=6.4 Hz, 3H). LC/MS (Table 1, Method 6) R$_t$=0.656 min.; MS m/z: 380 [M+H]$^+$ and 382 [M+H+2]$^+$.

Step B. (R)-7-Bromo-6-(1,3-dimethyl-azetidin-3-ylamino)-4-methyl-2,10-dihydro-9-oxa-1,2,4a-triaza-phenanthren-3-one

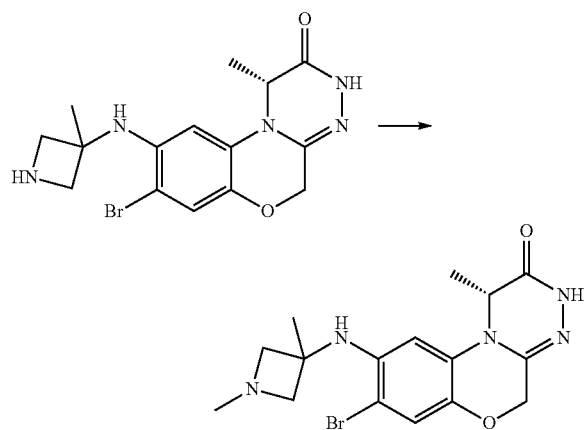

A mixture of (R)-7-bromo-4-methyl-6-(3-methyl-azetidin-3-ylamino)-2,10-dihydro-9-oxa-1,2,4a-triaza-phenanthren-3-one (4.0 g, 10.4 mmol) and polyformaldehyde (0.78 g, 26 mmol) in MeOH (10 mL) was stirred at ambient temperature for 10 min followed by the addition of AcOH (0.5 mL). The mixture was stirred at ambient temperature for 30 min before the addition of sodium cyanoborohydride (1.4 g, 22.8 mmol). The mixture was stirred at 40° C. overnight. The mixture was cooled to ambient temperature and concentrated in vacuo to give the residue, which was purified by chromatography on silica gel (eluting with 1% methanol in dichloromethane) to give (R)-7-bromo-6-(1,3-dimethyl-azetidin-3-ylamino)-4-methyl-2,10-dihydro-9-oxa-1,2,4a-triaza-phenanthren-3-one (2.8 g, 62%). $^1$H NMR (400 MHz, CDCl$_3$) δ=8.77 (s, 1H), 7.14 (s, 1H), 6.01 (s, 1H), 4.63 (q, J=6.8 Hz, 1H), 4.56 (d, J=12.8 Hz, 2H), 4.46 (s, 1H), 3.87 (m, 2H), 3.46 (m, 2H), 2.57 (s, 3H), 1.65 (s, 3H), 1.55 (d, J=6.8 Hz, 3H). LC/MS (Table 1, Method 25) R$_t$=0.659 min.; MS m/z: 394 [M+H]$^+$ and 396 [M+H+2]$^+$.

Step C. (R)-6-(1,3-Dimethyl-azetidin-3-ylamino)-7-((E)-2-ethoxy-vinyl)-4-methyl-2,10-dihydro-9-oxa-1,2,4a-triaza-phenanthren-3-one

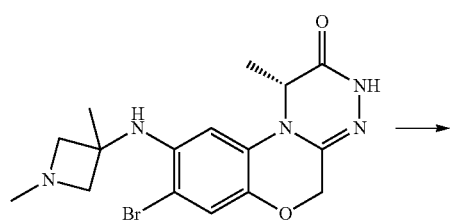

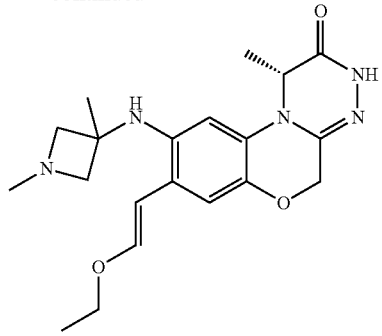

To a solution of (R)-7-bromo-6-(1,3-dimethyl-azetidin-3-ylamino)-4-methyl-2,10-dihydro-9-oxa-1,2,4a-triaza-phenanthren-3-one (1.2 g, 3.04 mmol) and (E)-2-(2-ethoxyvinyl)-4,4,5,5-tetramethyl-1,3,2-dioxaborolane (0.66 g, 3.35 mmol) in a mixture of dioxane (12 mL) and water (2 mL) was added PdCl$_2$(dppf)-CH$_2$Cl$_2$ adduct (0.25 g, 0.30 mmol) and K$_2$CO$_3$ (0.842 g, 6.09 mmol). The mixture was stirred at 100° C. for 3 h. The mixture was cooled to ambient temperature and the solvent was removed in vacuo to give the residue product, which was purified by chromatography on silica gel (eluting with 10% MeOH in dichloromethane) to give (R)-6-(1,3-dimethyl-azetidin-3-ylamino)-7-((E)-2-ethoxy-vinyl)-4-methyl-2,10-dihydro-9-oxa-1,2,4a-triaza-phenanthren-3-one (0.8 g, 68%) $^1$H NMR (400 MHz, CDCl$_3$) δ=8.20 (s, 1H), 6.80 (s, 1H), 6.71 (d, J=12.4 Hz, 1H), 5.90 (s, 1H), 5.64 (d, J=12.4 Hz, 1H), 4.63-4.46 (m, 3H), 3.91 (q, J=6.8 Hz, 2H), 3.53 (m, 2H), 3.27 (m, 2H), 2.43 (s, 3H), 1.61 (s, 3H), 1.50 (d, J=6.8 Hz, 3H), 1.35 (t, J=6.8 Hz, 3H). LC/MS (Table 1, Method 2) R$_t$=0.889 min; MS m/z: 386 [M+H]$^+$.

Step D. (R)-10-(1,3-Dimethyl-azetidin-3-yl)-1-methyl-3,5-dihydro-10H-6-oxa-3,4,10,11b-tetraaza-cyclopenta[b]phenanthren-2-one hydrochloride

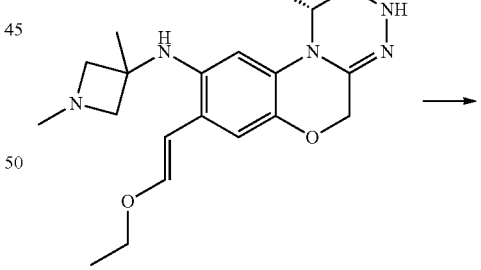

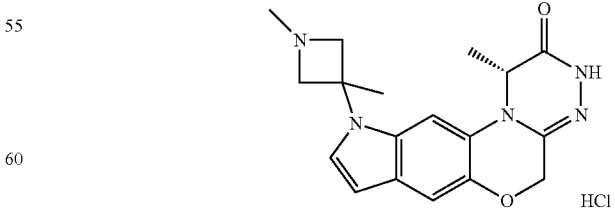

A solution of (R)-6-(1,3-dimethyl-azetidin-3-ylamino)-7-((E)-2-ethoxy-vinyl)-4-methyl-2,10-dihydro-9-oxa-1,2,4a-triaza-phenanthren-3-one (0.8 g, 2.07 mmol) in TFA (25 mL) was stirred at ambient temperature for 2 h. The solvent was removed in vacuo to give the residue, which was purified by pre-HPLC (Table 3, Method 30) to give (R)-10-(1,3-dimethyl-azetidin-3-yl)-1-methyl-3,5-dihydro-10H-6-oxa-3,4,10,11b-tetraaza-cyclopenta[b]phenanthren-2-one hydrochloride (0.31 g, 44%) as a pale yellow powder. $^1$H NMR (400 MHz, DMSO-d$_6$) δ=10.44 (brs, 1H), 7.42-7.19 (m, 2H), 6.89 (s, 1H), 6.43 (s, 1H), 5.11 (m, 1H), 4.80 (m, 1H), 4.55 (m, 5H), 2.87 (s, 3H), 1.86 (s, 3H), 1.35 (d, J=6.4 Hz, 3H). LC/MS (Table 1, Method 4) R$_t$=1.287 min; MS m/z: 340 [M+H]$^+$).

TABLE 21

The following analogs were prepared from 10-azetidin-3-yl-1-methyl-3,5-dihydro-10H-6-oxa-3,4,10,11b-tetraaza-cyclopenta[b]phenanthren-2-one trifluoroacetic acid (Example #103, Step B) using the procedure detailed in Example #134, Step A.

| Structure | Example # | R$_t$ min (method) | m/z ESI+ (M + H)$^+$ |
|---|---|---|---|
| 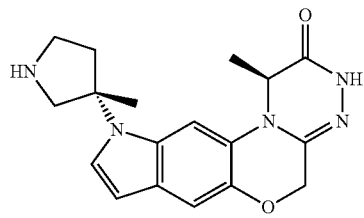 [SMILES: C[C@H]1C(=O)NN=C2COc3cc4ccn([C@@]5(C)CCNC5)c4cc3N21] | 161 | 1.223 (Table 1, Method 4) | 326 |

Example #162

(S)-1-Methyl-10-((S)-3-methyl-pyrrolidin-3-yl)-3,5-dihydro-10H-6-oxa-3,4,10,11b-tetraaza-cyclopenta[b]phenanthren-2-one

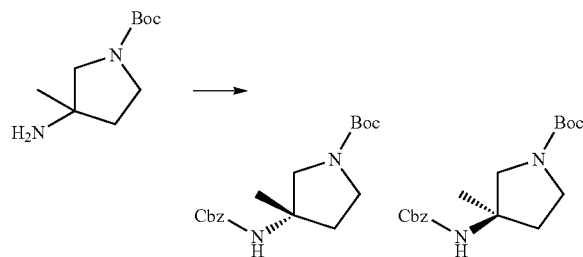

Step A. (S)-3-Benzyloxycarbonylamino-3-methyl-pyrrolidine-1-carboxylic acid tert-butyl ester and (R)-3-benzyloxycarbonylamino-3-methyl-pyrrolidine-1-carboxylic acid tert-butyl ester To a mixture of 3-amino-3-methyl-pyrrolidine-1-carboxylic acid tert-butyl ester (5.0 g, 25 mmol) and potassium carbonate (3.8 g, 27 mmol) in THF (25 mL) and water (25 mL) was added benzyl carbonochloridate (4.6 g, 27 mmol) at 0° C. and the reaction mixture was stirred at ambient temperature overnight. The reaction mixture was diluted with water (25 mL) and extracted with EtOAc (3×15 mL). The combined organic phase was washed with brine (25 mL), dried over sodium sulfate and filtered. The filtrate was concentrated in vacuo and the residue was purified by column chromatography on silica gel (eluting with 4% EtOAc in petroleum) to give 3-benzyloxycarbonylamino-3-methyl-pyrrolidine-1-carboxylic acid tert-butyl ester (5.5 g, 70%). $^1$H NMR (400 MHz, CDCl$_3$) δ 7.35 (s, 5H), 5.14-5.02 (m, 2H), 4.88-4.79 (m, 1H), 3.63-3.23 (m, 4H), 2.25 (m, 1H), 1.88-1.77 (m, 1H), 1.45 (s, 12H).

The racemic compound was separated by SFC (Table 2, Method 25) to give two isomers, (S)-3-benzyloxycarbonylamino-3-methyl-pyrrolidine-1-carboxylic acid tert-butyl ester (enantiomer 1, SFC (Table 1, Method 51) R$_t$=3.693 min, 2.4 g, 29%) and (R)-3-benzyloxycarbonylamino-3-methyl-pyrrolidine-1-carboxylic acid tert-butyl ester (enantiomer 2, SFC (Table 1, Method 51) R$_t$=4.162 min, 2.3 g, 28%).

Step B.
(S)-3-Amino-3-methyl-pyrrolidine-1-carboxylic acid tert-butyl ester

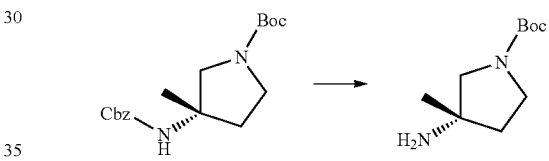

A mixture of (S)-3-benzyloxycarbonylamino-3-methyl-pyrrolidine-1-carboxylic acid tert-butyl ester (enantiomer 1, SFC (Table 1, Method 51) R$_t$=3.693 min, 1.7 g, 5.08 mmol) and Pd/C (10%, 0.2 g, 0.19 mmol) in MeOH (10 mL) was stirred at ambient temperature under an atmosphere of H$_2$ (1 atm) for 2 h. The reaction mixture was filtered and the filtrate was concentrated in vacuo to give (S)-3-amino-3-methyl-pyrrolidine-1-carboxylic acid tert-butyl ester (0.12 g, 67%). $^1$H NMR (400 MHz, CDCl$_3$) δ 3.62-3.06 (m, 4H), 1.88-1.70 (m, 2H), 1.48 (s, 9H), 1.34-1.26 (s, 3H).

Step C. (S)-3-Methyl-3-[4-methyl-3-oxo-2-(2-trimethylsilanyl-ethoxymethyl)-2,3,4,10-tetrahydro-9-oxa-1,2,4a-triaza-phenanthren-6-ylamino]-pyrrolidine-1-carboxylic acid tert-butyl ester

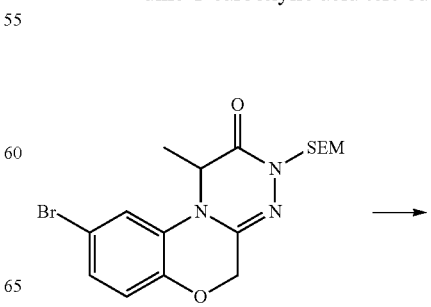

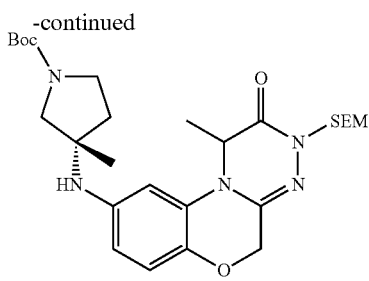

To a solution of 6-bromo-4-methyl-2-(2-trimethylsilanyl-ethoxymethyl)-2,10-dihydro-9-oxa-1,2,4a-triaza-phenanthren-3-one ((Preparation #1, Step E, 2.184 g, 5.12 mmol) and (S)-3-amino-3-methyl-pyrrolidine-1-carboxylic acid tert-butyl ester (0.977 g, 4.88 mmol) in toluene (5 mL) was added Pd(OAc)$_2$ (0.110 g, 0.488 mmol) and dicyclohexyl(2',4',6'-triisopropyl-[1,1'-biphenyl]-2-yl)phosphine (0.464 g, 0.976 mmol) followed by cesium carbonate (3.18 g, 9.76 mmol) and the reaction mixture was heated at reflux overnight. The reaction mixture was cooled to ambient temperature and concentrated in vacuo. The residue was purified by column chromatography on silica gel (eluting with 50% EtOAc in petroleum ether) to give (S)-3-methyl-3-[4-methyl-3-oxo-2-(2-trimethylsilanyl-ethoxymethyl)-2,3,4,10-tetrahydro-9-oxa-1,2,4a-triaza-phenanthren-6-ylamino]pyrrolidine-1-carboxylic acid tert-butyl ester (1 g, 38%). $^1$H NMR (400 MHz, CDCl$_3$) δ 6.85 (m, 1H), 6.34-6.28 (m, 2H), 5.11 (m, 2H), 4.70-4.52 (m, 3H), 3.68 (m, 2H), 3.70-3.35 (m, 4H), 2.20 (m, 1H), 1.88 (m, 1H), 1.46 (m., 12H), 1.05 (m, 2H), 0.03 (s, 9H).

Step D. (S)-3-Methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester

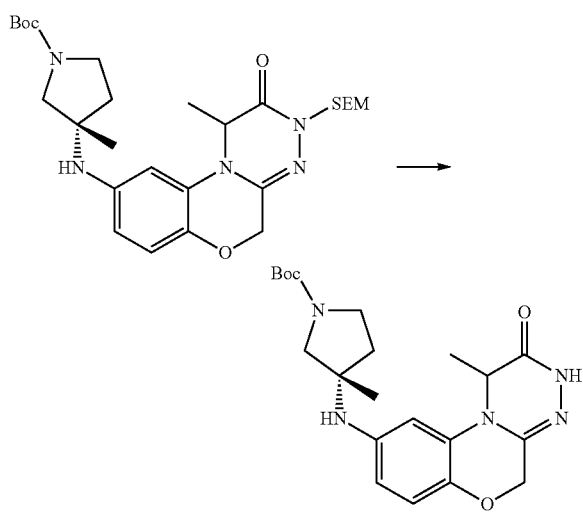

A mixture of (S)-3-methyl-3-[4-methyl-3-oxo-2-(2-trimethylsilanyl-ethoxymethyl)-2,3,4,10-tetrahydro-9-oxa-1,2,4a-triaza-phenanthren-6-ylamino]-pyrrolidine-1-carboxylic acid tert-butyl ester (1.1 g, 2.016 mmol) in a solution of TBAF in THF (1 M, 20 mL, 20 mmoL) was stirred at 80° C. overnight. The reaction mixture was cooled to ambient temperature and diluted with water (25 mL). The aqueous solution was extracted with EtOAc (3×25 mL). The combined organic phase was washed with brine (10 mL), dried over sodium sulfate and filtered. The filtrate was concentrate in vacuo to give the residue, which was purified by column chromatography on silica gel (eluting with 10% EtOAc in petroleum) to give (S)-3-methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester (0.45 g, 54%). $^1$H NMR (400 MHz, CDCl$_3$) δ 8.19-8.05 (m, 1H), 6.94-6.77 (m, 1H), 6.53-6.23 (m, 2H), 4.74-4.46 (m, 3H), 3.62-3.30 (m, 4H), 2.32-2.17 (m, 1H), 2.00-1.86 (m, 1H), 1.59-1.44 (m, 15H).

Step E. (S)-3-((R)-7-Bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester and (S)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester

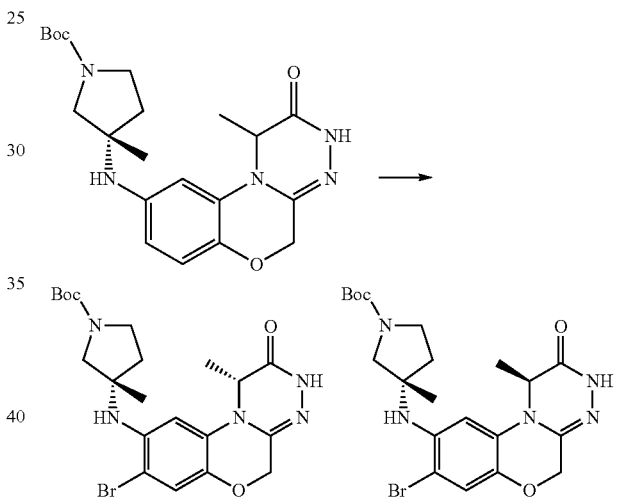

To a solution of (S)-3-methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester (0.800 g, 1.925 mmol) in DCM (10 mL) and MeOH (3 mL) was added Bu$_4$NBr$_3$ (0.928 g, 1.925 mmol) and the reaction mixture was stirred at ambient temperature for 0.5 h. The mixture was diluted with EtOAc (30 mL) and washed with brine (30 mL). The solvent was removed in vacuo and the residue was purified by column chromatography on silica gel (eluting with 5%~20% EtOAc in petroleum ether) to give (S)-3-(7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (0.501 g, 53%). $^1$H-NMR (400 MHz, CDCl$_3$) δ 8.12-7.99 (m, 1H), 7.13 (s, 1H), 6.42-6.26 (m, 1H), 4.73-4.58 (m, 1H), 4.58-4.43 (m, 2H), 3.60-3.36 (m, 4H), 2.35-2.10 (m, 1H), 2.01-1.88 (m, 1H), 1.54-1.47 (m, 6H), 1.45 (s, 9H). LC/MS (Table 1, Method 25) R$_t$=0.877 min; MS m/z: 494 [M+H]$^+$ & 496 [M+H+2]$^+$.

The above compound was separated by Chiral SFC (Table 2, Method 25) to give two isomers.

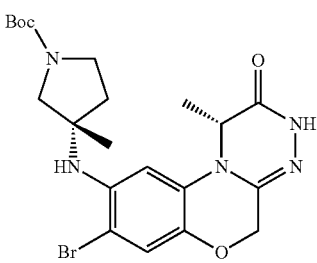 [SMILES: C[C@@H]1C(=O)NN=C2COc3cc(Br)c(N[C@@]4(C)CCN(C(=O)OC(C)(C)C)C4)cc3N21]

(S)-3-((R)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer B, SFC (Table 1, Method 52) $R_t$=3.282 min, 0.180 g, 32%). LC/MS (Table 1, Method 25) $R_t$=0.844 min; MS m/z: 516 [M+Na]$^+$& 518 [M+Na+2]$^+$

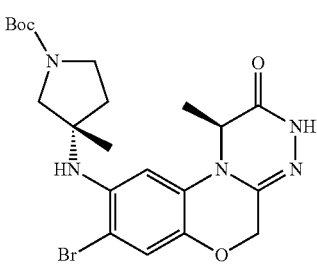 [SMILES: C[C@H]1C(=O)NN=C2COc3cc(Br)c(N[C@@]4(C)CCN(C(=O)OC(C)(C)C)C4)cc3N21]

(S)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer A, SFC (Table 1, Method 52) $R_t$=2.880 min, 0.300 g, 54%). LC/MS (Table 1, Method 25) $R_t$=0.852 min; MS m/z: 516 [M+Na]$^+$& 518 [M+Na+2]$^+$ Step F. (S)-3-[(S)-7-((E)-2-Ethoxy-vinyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester

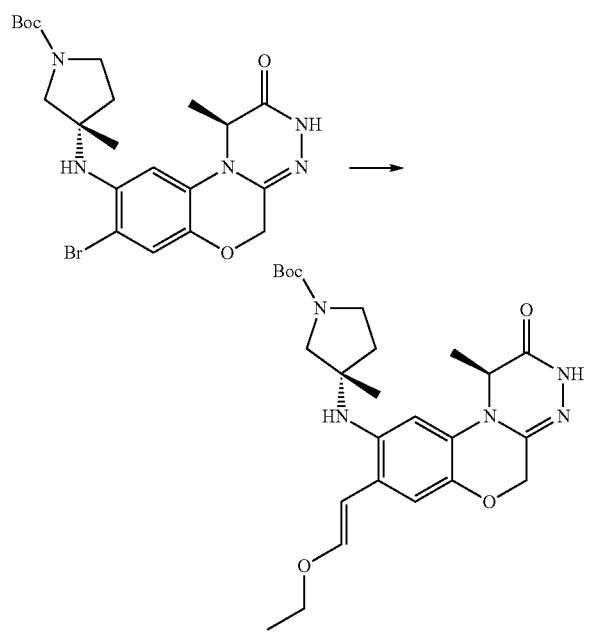

A mixture of (S)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer A, SFC (Table 1, Method 52) $R_t$=2.880 min, 0.030 g, 0.061 mmol), $K_2CO_3$ (0.017 g, 0.121 mmol), (E)-2-(2-ethoxyvinyl)-4,4,5,5-tetramethyl-1,3,2-dioxaborolane (0.018 g, 0.091 mmol) and $PdCl_2(dppf)\cdot CH_2Cl_2$ adduct (4.96 mg, 6.07 µmol) in dioxane (2 mL) and water (0.3 mL) was stirred at 90° C. for 14 h. The reaction mixture was cooled to ambient temperature and concentrated in vacuo. The residue was purified by column chromatography on silica gel (eluting with 3%~20% EtOAc in petroleum ether) to give (S)-3-[(S)-7-((E)-2-ethoxy-vinyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester (10 mg, 34%) as a pale solid. LC/MS (Table 1, Method 25) $R_t$=0.826 min; MS m/z: 508 [M+Na]$^+$.

Step G. (S)-1-Methyl-104(S)-3-methyl-pyrrolidin-3-yl)-3,5-dihydro-10H-6-oxa-3,4,10,11b-tetraaza-cyclopenta[b]phenanthren-2-one

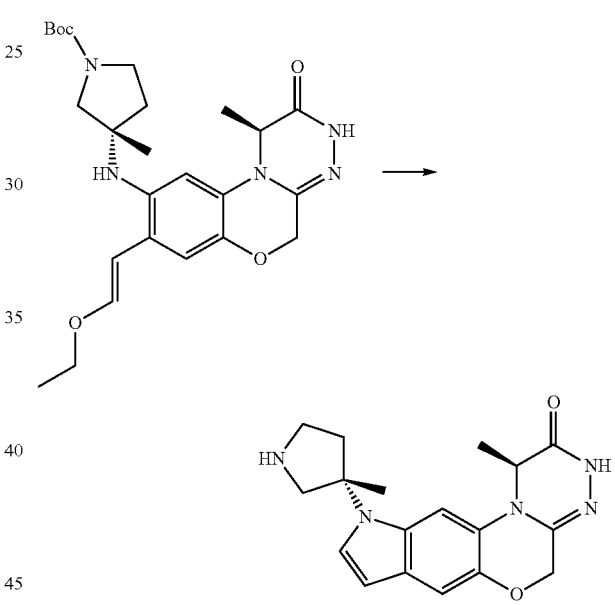

To a solution of (S)-3-[(S)-7-((E)-2-ethoxy-vinyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester (0.115 g, 0.273 mmol) in DCM (2 mL) was added TFA (1 mL) and the reaction mixture was stirred at ambient temperature for 1 h. The solvent was removed in vacuo and the residue was purified by prep-TLC (eluting with 15% MeOH in DCM) to give (S)-1-methyl-10-((S)-3-methyl-pyrrolidin-3-yl)-3,5-dihydro-10H-6-oxa-3,4,10,11b-tetraaza-cyclopenta[b]phenanthren-2-one (0.020 g, 25%, SFC (Table 1, Method 53) $R_t$=1.81 min) as a white solid. $^1$H-NMR (400 MHz, methanol-$d_4$) δ 7.41 (d, J=3.2 Hz, 1H), 7.25 (s, 1H), 7.22 (s, 1H), 6.49 (d, J=3.2 Hz, 1H), 5.11 (q J=6.8 Hz, 1H), 4.62-4.54 (d, J=13.6 Hz, 2H), 4.16-4.09 (m, 1H), 3.88-3.82 (m, 1H), 3.67-3.47 (m, 2H), 3.10-2.97 (m, 1H), 2.71-2.59 (m, 1H), 1.78 (s, 3H), 1.49 (d, J=6.8 Hz, 3H). LC/MS (Table 1, Method 5) $R_t$=1.916 min; MS m/z: 340 [M+1]$^+$.

Example #163

(R)-1-Methyl-10-((S)-3-methyl-pyrrolidin-3-yl)-3,5-dihydro-10H-6-oxa-3,4,10,11b-tetraaza-cyclopenta[b]phenanthren-2-one

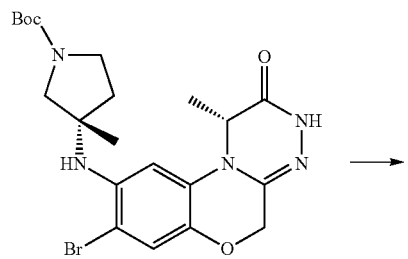

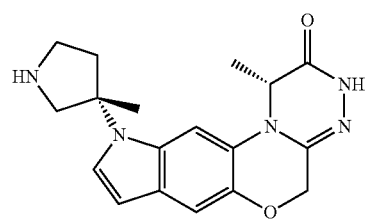

Using a similar procedure as described in Example #162, Step F-G, (R)-1-methyl-10-((S)-3-methyl-pyrrolidin-3-yl)-3,5-dihydro-10H-6-oxa-3,4,10,11b-tetraaza-cyclopenta[b]phenanthren-2-one (SFC (Table 1, Method 53) $R_t$=2.14 min, 0.01 g, 12%) was prepared from (S)-3-((R)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer B, SFC (Table 1, Method 52) $R_t$=3.282 min, 0.180 g). $^1$H NMR (400 MHz, DMSO-$d_6$) δ 10.75-10.70 (s, 1H), 7.45 (s, 1H), 7.28 (s, 1H), 7.20 (s, 1H), 6.42 (s, 1H), 4.59-4.51 (m, 3H), 3.82-3.78 (m, 2H), 1.66-1.65 (s, 3H), 1.32-1.30 (s, 3H). LC/MS (Table 1, Method 4) $R_t$=1.199 min; MS m/z: 340 [M+1]$^+$, 0.01 g, 12%).

Example #164

(R)-1-Methyl-10-((R)-3-methyl-pyrrolidin-3-yl)-3,5-dihydro-10H-6-oxa-3,4,10,11b-tetraaza-cyclopenta[b]phenanthren-2-one

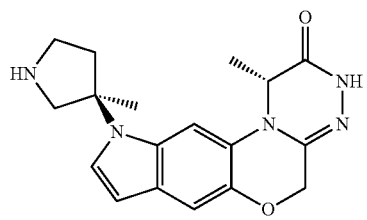 [SMILES: C[C@@H]1C(=O)NN=C2COc3cc4ccn([C@]5(C)CCNC5)c4cc3N21]

Step A. (R)-3-(7-Bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester

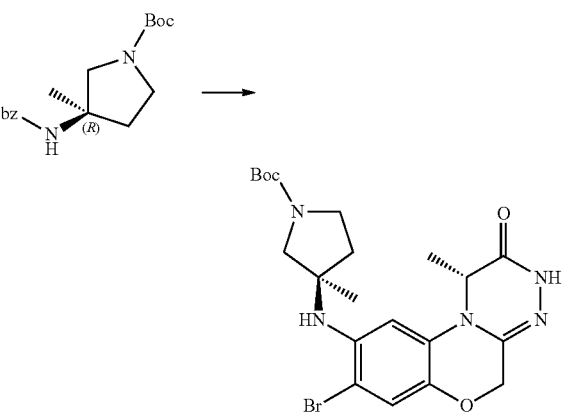

Using a similar procedure as described in Example #162, Step B-E, (R)-3-(7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (1.8 g, 12%) was prepared from (R)-3-benzyloxycarbonylamino-3-methyl-pyrrolidine-1-carboxylic acid tert-butyl ester (enantiomer 2, SFC (Table 1, Method 51) $R_t$=4.162 min, 10 g).

Step B. (R)-3-((R)-7-Bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester and (R)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester

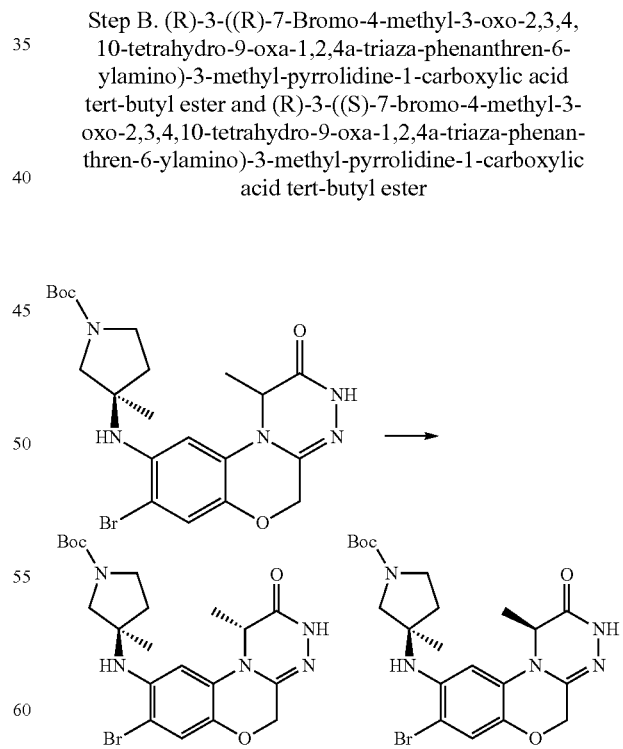

(R)-3-(7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester was separated by SFC (Table 2, Method 25) to give two isomers.

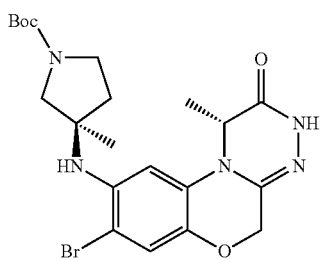 [SMILES: C[C@@H]1C(=O)NN=C2COc3cc(Br)c(N[C@]4(C)CCN(C(=O)OC(C)(C)C)C4)cc3N21]

(R)-3-((R)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer C, SFC (Table 1, Method 54) $R_t$=1.534 min, 0.9 g, 49%). LC/MS (Table 1, Method 25) $R_t$=0.871 min; MS m/z: 438 [M+H−56]$^+$.

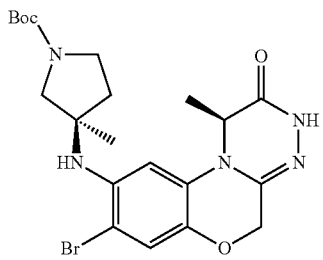 [SMILES: C[C@H]1C(=O)NN=C2COc3cc(Br)c(N[C@]4(C)CCN(C(=O)OC(C)(C)C)C4)cc3N21]

(R)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer D, SFC (Table 1, Method 54), $R_t$=1.752 min, 0.9 g, 49%) LC/MS (Table 1, Method 25) $R_t$=0.869 min; MS m/z: 438 [M+H−56]$^+$.

Step C. (R)-1-Methyl-10-((R)-3-methyl-pyrrolidin-3-yl)-3,5-dihydro-10H-6-oxa-3,4,10,11b-tetraaza-cyclopenta[b]phenanthren-2-one

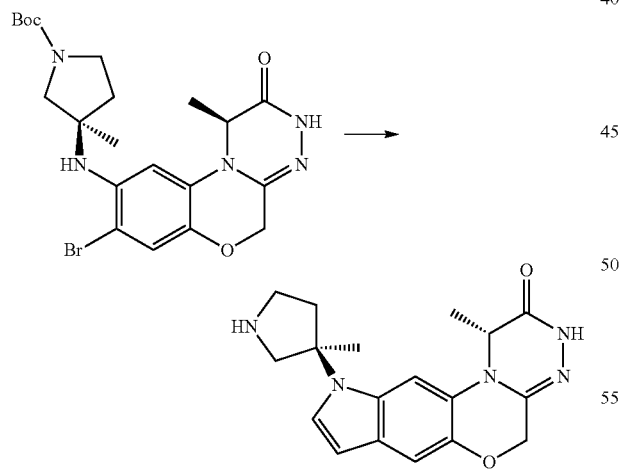

Using a similar procedure as described in Example #162, Step F-G, (R)-1-methyl-10-((R)-3-methyl-pyrrolidin-3-yl)-3,5-dihydro-10H-6-oxa-3,4,10,11b-tetraaza-cyclopenta[b]phenanthren-2-one (SFC (Table 1, Method 52) $R_t$=4.593 min 0.015 g, 5%) was prepared from (R)-3-((R)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (isomer C, SFC (Table 1, Method 54), $R_t$=1.752 min, 0.45 g, 0.9 mmol). $^1$H NMR (400 MHz, DMSO-d$_6$) δ 10.71 (brs, 1H), 7.34 (s, 1H), 7.29 (s, 1H), 7.16 (s, 1H), 6.31 (s, 1H), 5.09 (q, J=6.4 Hz, 1H), 4.54 (d, J=14.8 Hz, 2H), 3.11 (m, 4H), 2.45 (m, 2H), 1.57 (s, 3H), 1.32 (d, J=6.4 Hz, 3H). LC/MS (Table 1, Method 4) $R_t$=1.363 min; MS (ESI): m/z 340 [M+1]$^+$.

Example #165

(S)-1-Methyl-10-((R)-3-methyl-pyrrolidin-3-yl)-3,5-dihydro-10H-6-oxa-3,4,10,11b-tetraaza-cyclopenta[b]phenanthren-2-one

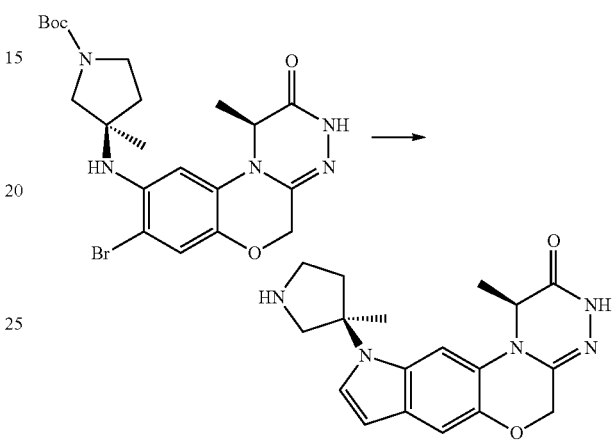

Using a similar procedure as described in Example #162, Step F-G, (S)-1-Methyl-10-((R)-3-methyl-pyrrolidin-3-yl)-3,5-dihydro-10H-6-oxa-3,4,10,11b-tetraaza-cyclopenta[b]phenanthren-2-one (SFC (Table 1, Method 54) $R_t$=4.016 min, 0.019 g, 6%) was prepared from (R)-3-((S)-7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (Example #164, Step B, isomer D, SFC (Table 1, Method 54), $R_t$=1.752 min, 0.45 g, 0.9 mmol). $^1$H NMR (400 MHz, methanol-d$_4$) δ 7.37 (s, 1H), 7.23 (s, 1H), 7.19 (s, 1H), 6.46 (s, 1H), 5.05 (q, J=6.4 Hz, 1H), 4.58 (m, 2H), 4.04 (d, J=12.0 Hz, 1H), 3.79 (d, J=12.0 Hz, 1H), 3.59-3.43 (m, 2H), 2.98 (m, 1H), 2.68 (m, 1H), 1.76 (s, 3H), 1.49 (d, J=6.8 Hz, 3H). LC/MS (Table 1, Method 4) $R_t$=1.290 min; MS (ESI): m/z 340 [M+H]$^+$.

Example #166

6-[(1,3-Dimethyl-azetidin-3-yl)-ethyl-amino]-7-(2-fluoro-phenyl)-4-methyl-2,10-dihydro-9-oxa-1,2,4a-triaza-phenanthren-3-one hydrochloride acid

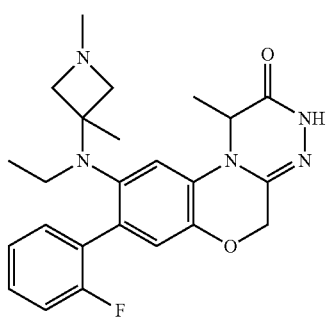 [SMILES: CCN(c1cc2c(cc1-c1ccccc1F)OCC1=NNC(=O)C(C)N12)C1(C)CN(C)C1]

319

Step A. 3-[7-(2-Fluoro-phenyl)-4-methyl-3-oxo-2,3,4,10-tetrahydro-9-oxa-1,2,4a-triaza-phenanthren-6-ylamino]-3-methyl-azetidine-1-carboxylic acid tert-butyl estercarboxylate

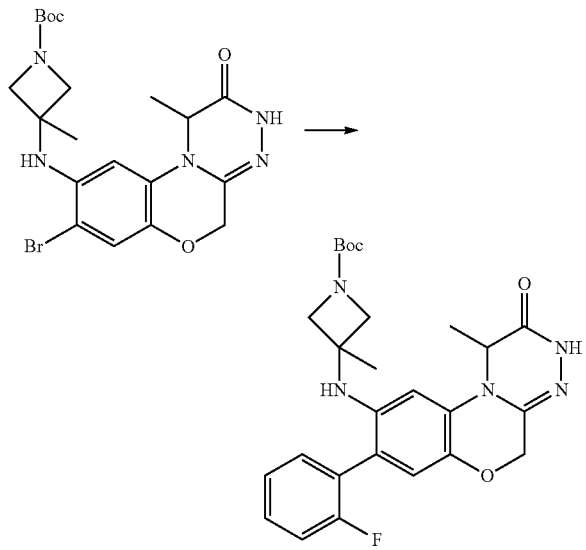

A mixture of 3-(7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester (Preparation #18, 0.300 g, 0.625 mmol), (2-fluorophenyl)boronic acid (0.105 g, 0.749 mmol), $K_2CO_3$ (0.173 g, 1.249 mmol) and Pd(dppf)Cl$_2$.DCM (0.102 g, 0.125 mmol) in dioxane (12 mL) and water (2 mL) was stirred at 80° C. overnight. The reaction mixture was cooled to ambient temperature and filtered. The filtrate was concentrated in vacuo and the residue was purified by column chromatography on silica gel (eluting with 5-40% EtOAc in petroleum ether) to give 3-[7-(2-fluoro-phenyl)-4-methyl-3-oxo-2,3,4,10-tetrahydro-9-oxa-1,2,4a-triaza-phenanthren-6-ylamino]-3-methyl-azetidine-1-carboxylic acid tert-butyl estercarboxylate as pale-white solid (0.27 g, 87%). $^1$H-NMR (CDCl$_3$, 400 MHz): δ 8.12 (s, 1H), 7.43-7.35 (m, 1H), 7.34-7.28 (m, 1H), 7.26-7.21 (m, 1H), 7.18 (t, J=9.0 Hz, 1H), 6.83 (s, 1H), 4.67 (q, J=6.6 Hz, 1H), 4.62-4.51 (m, 2H), 3.96-3.67 (m, 4H), 1.59 (brs., 3H), 1.56 (d, J=6.8 Hz, 3H), 1.45 (s, 9H).

Step B. 7-(2-Fluoro-phenyl)-4-methyl-6-(3-methyl-azetidin-3-ylamino)-2,10-dihydro-9-oxa-1,2,4a-triaza-phenanthren-3-one

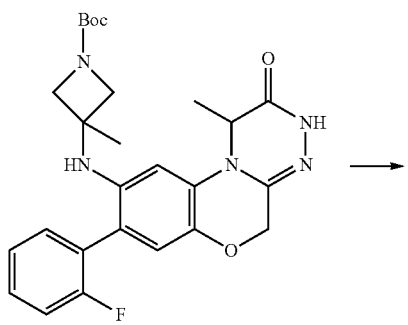

320

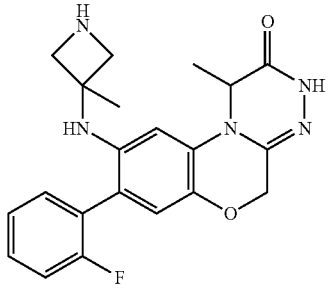

A solution of 3-[7-(2-fluoro-phenyl)-4-methyl-3-oxo-2,3,4,10-tetrahydro-9-oxa-1,2,4a-triaza-phenanthren-6-ylamino]-3-methyl-azetidine-1-carboxylic acid tert-butyl estercarboxylate (0.27 g, 0.545 mmol) in TFA (1 mL) and DCM (4 mL) was stirred at ambient temperature for 2 h. The solvent was removed in vacuo and the residue was dissolved in MeOH (10 mL). Then, aqueous solution of ammonium (5 mL, 25%) was added and the mixture was concentrated in vacuo to give the crude 7-(2-fluoro-phenyl)-4-methyl-6-(3-methyl-azetidin-3-ylamino)-2,10-dihydro-9-oxa-1,2,4a-triaza-phenanthren-3-one (0.4 g), which was used in the next step directly. LC/MS (Table 1, Method 4) R$_t$=1.570 min.; MS m/z: 396 [M+H]$^+$.

Step C. 6-(1,3-Dimethyl-azetidin-3-ylamino)-7-(2-fluoro-phenyl)-4-methyl-2,10-dihydro-9-oxa-1,2,4a-triaza-phenanthren-3-one

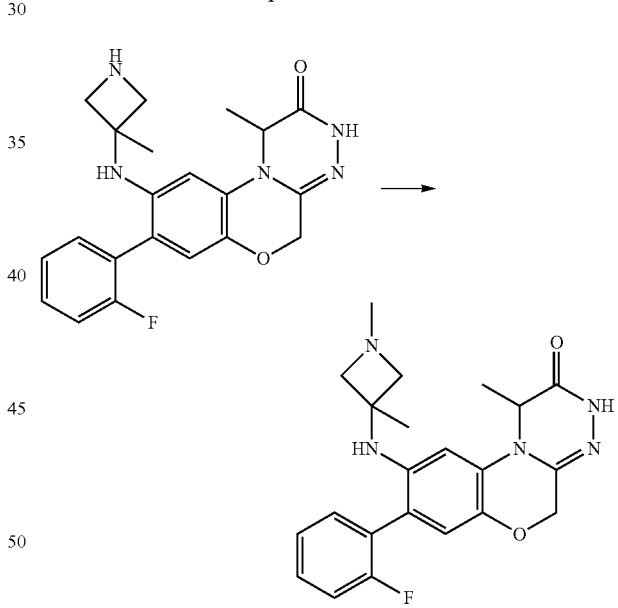

To a solution of 7-(2-fluoro-phenyl)-4-methyl-6-(3-methyl-azetidin-3-ylamino)-2,10-dihydro-9-oxa-1,2,4a-triaza-phenanthren-3-one (0.216 g, 0.545 mmol) in MeOH (10 mL) and acetic acid (1 mL) was added paraformaldehyde (0.05 g, 1.635 mmol) followed by NaBH$_3$CN (0.068 g, 1.090 mmol). The mixture was stirred at ambient temperature for 30 min. Water (10 mL) was added and the reaction mixture was extracted with EtOAc (30 mL×3). The combined organic phase was washed with brine (10 mL), dried over anhydrous Na$_2$SO$_4$, filtered and evaporated in vacuo to give the residue, which was purified by chromatography on silica gel (eluting with 50% EtOAc in petroleum ether to 10% methanol in EtOAc) to give 6-(1,3-dimethyl-azetidin-3-ylamino)-7-(2-fluoro-phenyl)-4-methyl-2,10-dihydro-9-oxa-1,2,4a-triaza-phenanthren-3-one (0.150 g, 67%). $^1$H NMR (CDCl$_3$, 400

MHz): δ 7.37 (m, 2H), 7.24 (m, 2H), 6.78 (s, 1H), 6.02 (s, 1H), 4.78 (m, 1H), 4.55 (m, 2H), 3.90 (m, 2H), 3.80 (m, 2H), 2.75 (s, 3H), 1.59 (s, 3H), 1.48 (d, J=6.8 Hz, 3H). LC/MS (Table 1, Method 25) $R_t$=0.715 min.; MS m/z: 410 [M+H]$^+$.

Step D. 6-[(1,3-Dimethyl-azetidin-3-yl)-ethyl-amino]-7-(2-fluoro-phenyl)-4-methyl-2,10-dihydro-9-oxa-1,2,4a-triaza-phenanthren-3-one hydrochloride acid

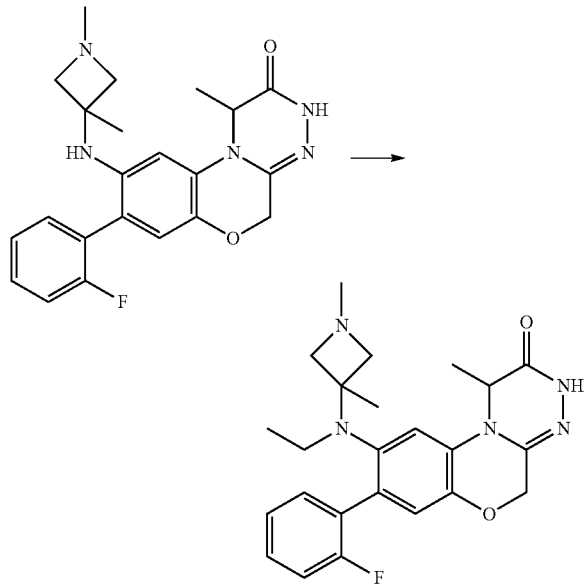

To a solution of 6-(1,3-dimethyl-azetidin-3-ylamino)-7-(2-fluoro-phenyl)-4-methyl-2,10-dihydro-9-oxa-1,2,4a-triaza-phenanthren-3-one (0.140 g, 0.342 mmol) in MeOH (5 mL) and acetic acid (0.5 mL) was added acetaldehyde (4 mL, 40%) followed by 4 A molecular sieve (500 mg) and anhydrous magnesium sulfate (500 mg). After stirring at ambient temperature for 1 h, NaBH$_3$CN (0.043 g, 0.684 mmol) was added and the mixture was stirred at this temperature for about 60 h, then at 50° C. for 6 h. The reaction mixture was cooled to ambient temperature and filtered. The filter cake was washed with EtOAc (5×30 mL). The filtrate was washed with brine (10 mL), dried over anhydrous Na$_2$SO$_4$, filtered and evaporated in vacuo to give the residue, which was purified by pre-HPLC (Table 3, Method 31) to give 6-[(1,3-dimethyl-azetidin-3-yl)-ethyl-amino]-7-(2-fluoro-phenyl)-4-methyl-2,10-dihydro-9-oxa-1,2,4a-triaza-phenanthren-3-one hydrochloride acid (0.032 g, 21% mmol) as a yellow solid. $^1$H NMR (400 MHz, CD$_3$OD) δ 7.48-7.39 (m, 2H), 7.34-7.23 (m, 2H), 6.99 (s, 1H), 6.94 (s, 1H), 4.94-4.91 (m, 1H), 4.72-4.61 (m, 2H), 4.01 (d, J=8.8 Hz, 1H), 3.93 (d, J=9.5 Hz, 1H), 3.79 (d, J=9.5 Hz, 1H), 3.69 (d, J=9.8 Hz, 1H), 2.97 (t, J=6.3 Hz, 2H), 2.67 (s, 3H), 1.57 (s, 3H), 1.51 (d, J=6.0 Hz, 3H), 0.90 (t, J=6.7 Hz, 3H). LC/MS (Table 1, Method 5) $R_t$=2.378 min.; MS m/z: 438 [M+H]$^+$.

TABLE 22

The following analogs were prepared from 7-bromo-6-[(1,3-dimethyl-azetidin-3-yl)-methyl-amino]-4-methyl-2,10-dihydro-9-oxa-1,2,4a-triaza-phenanthren-3-one (Preparation #16) using the procedure detailed in Example #166, Step A.

| Structure | Example # | Boronate | $R_t$ min (method) | m/z ESI+ (M + H)$^+$ |
|---|---|---|---|---|
| 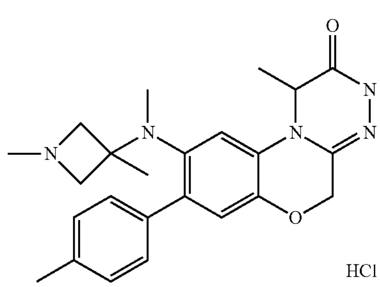 [SMILES: Cc1ccc(-c2cc3c(cc2N(C)C2(C)CN(C)C2)N2C(=NNC(=O)C2C)CO3)cc1 ; Cl] | 167 |  | 2.437 (Table 1, Method 4) | 420 |
| 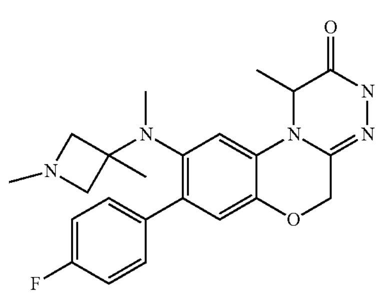 [SMILES: CC1C(=O)NN=C2COc3cc(-c4ccc(F)cc4)c(N(C)C4(C)CN(C)C4)cc3N21] | 168 |  | 1.969 (Table 1, Method 4) | 424 |

TABLE 22-continued

The following analogs were prepared from 7-bromo-6-[(1,3-dimethyl-azetidin-3-yl)-methyl-amino]-4-methyl-2,10-dihydro-9-oxa-1,2,4a-triaza-phenanthren-3-one (Preparation #16) using the procedure detailed in Example #166, Step A.

| Structure | Example # | Boronate | $R_t$ min (method) | m/z ESI+ (M + H)+ |
|---|---|---|---|---|
| 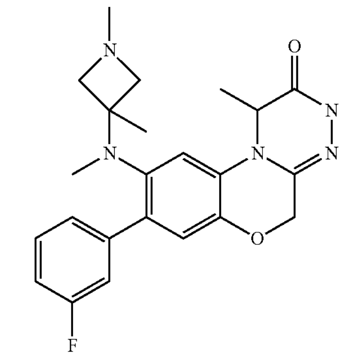 [SMILES: CC1C(=O)NN=C2COc3cc(-c4cccc(F)c4)c(N(C)C4(C)CN(C)C4)cc3N21] | 169 | 3-fluorophenylboronic acid | 1.887 (Table 1, Method 4) | 424 |
| 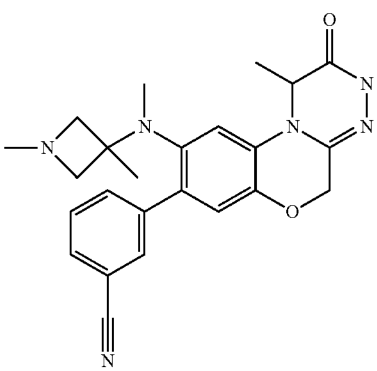 [SMILES: CC1C(=O)NN=C2COc3cc(-c4cccc(C#N)c4)c(N(C)C4(C)CN(C)C4)cc3N21] | 170 | 3-cyanophenylboronic acid | 1.765 (Table 1, Method 4) | 431 |
| 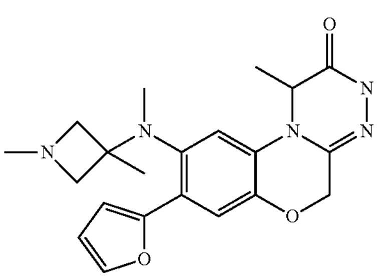 [SMILES: CC1C(=O)NN=C2COc3cc(-c4ccco4)c(N(C)C4(C)CN(C)C4)cc3N21] | 171 | 2-furanylboronic acid | 2.142 (Table 1, Method 4) | 396 |
| 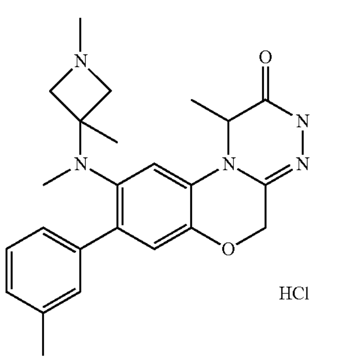 [SMILES: Cc1cccc(-c2cc3c(cc2N(C)C2(C)CN(C)C2)N2C(=NNC(=O)C2C)CO3)c1 ; Cl] | 172 | 3-methylphenylboronic acid | 2.545 (Table 1, Method 4) | 420 |

TABLE 22-continued

The following analogs were prepared from 7-bromo-6-[(1,3-dimethyl-azetidin-3-yl)-methyl-amino]-4-methyl-2,10-dihydro-9-oxa-1,2,4a-triaza-phenanthren-3-one (Preparation #16) using the procedure detailed in Example #166, Step A.

| Structure | Example # | Boronate | $R_t$ min (method) | m/z ESI+ (M + H)+ |
|---|---|---|---|---|
| 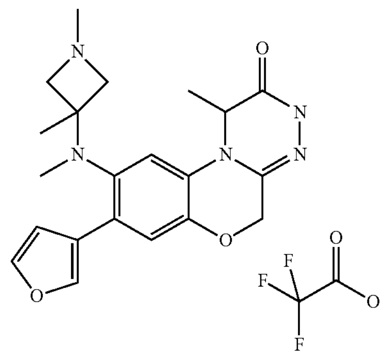 | 173 | 3-furyl B(OH)$_2$ | 1.653 (Table 1, Method 4) | 396 |
| 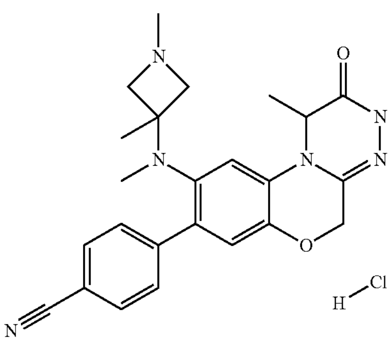 [SMILES: CC1C(=O)NN=C2COc3cc(-c4ccc(C#N)cc4)c(N(C)C4(C)CN(C)C4)cc3N21 ; Cl] | 174 | 4-cyanophenyl B(OH)$_2$ | 2.489 (Table 1, Method 4) | 431 |

TABLE 23

The following analogs were prepared from (R)-7-bromo-6-[(1,3-dimethyl-azetidin-3-yl)-methyl-amino]-4-methyl-2,10-dihydro-9-oxa-1,2,4a-triaza-phenanthren-3-one (Preparation #15, Step C) using the procedure detailed in Example #166, Step A.

| Structure | Example # | Boronate | Chiral Purification step | $R_t$ min (method) | m/z ESI+ (M + H)+ |
|---|---|---|---|---|---|
| 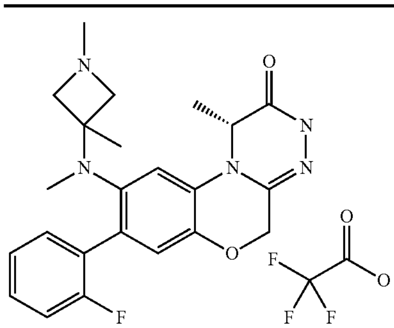 | 175 | 2-fluorophenyl B(OH)$_2$ | SFC of Ndiphenylone—Br prior to Suzuki coupling | 1.774 (Table 1, Method 4) | 424 |

TABLE 23-continued

The following analogs were prepared from (R)-7-bromo-6-[(1,3-dimethyl-azetidin-3-yl)-methyl-amino]-4-methyl-2,10-dihydro-9-oxa-1,2,4a-triaza-phenanthren-3-one (Preparation #15, Step C) using the procedure detailed in Example #166, Step A.

| Structure | Example # | Boronate | Chiral Purification step | R$_t$ min (method) | m/z ESI+ (M + H)$^+$ |
|---|---|---|---|---|---|
| 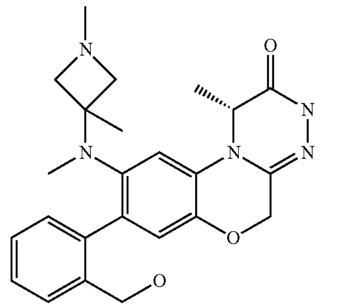 [SMILES: C[C@@H]1C(=O)NN=C2COc3cc(-c4ccccc4CO)c(N(C)C4(C)CN(C)C4)cc3N21] | 176 | 2-hydroxymethylphenylboronic acid | SFC at final step | 1.583 (Table 1, Method 4) | 436 |
| 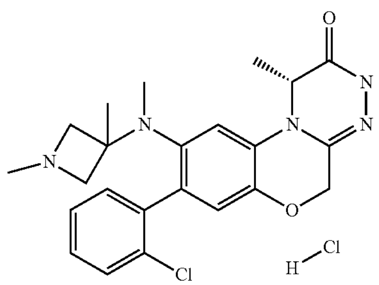 | 177 | 2-chlorophenylboronic acid | SFC at final step | 2.573 (Table 1, Method 4) | 440 |
| 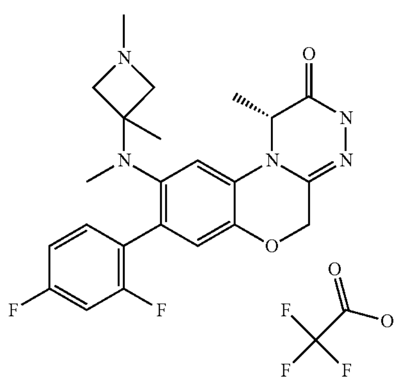 | 178 | 2,4-difluorophenylboronic acid | SFC of Ndiphenylone—Br prior to Suzuki coupling | 1.968 (Table 1, Method 4) | 442 |
| 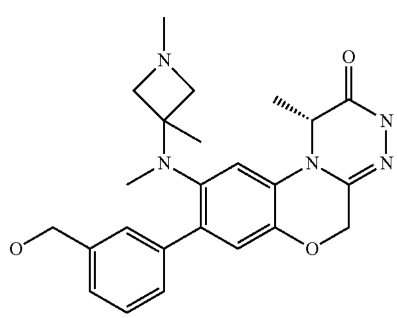 [SMILES: C[C@@H]1C(=O)NN=C2COc3cc(-c4cccc(CO)c4)c(N(C)C4(C)CN(C)C4)cc3N21] | 179 | 3-hydroxymethylphenylboronic acid | SFC at final step | 1.642 (Table 1, Method 4) | 436 |

TABLE 23-continued

The following analogs were prepared from (R)-7-bromo-6-[(1,3-dimethyl-azetidin-3-yl)-methyl-amino]-4-methyl-2,10-dihydro-9-oxa-1,2,4a-triaza-phenanthren-3-one (Preparation #15, Step C) using the procedure detailed in Example #166, Step A.

| Structure | Example # | Boronate | Chiral Purification step | R$_t$ min (method) | m/z ESI+ (M + H)+ |
|---|---|---|---|---|---|
| 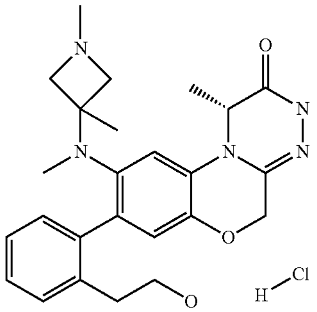 [SMILES: C[C@@H]1C(=O)NN=C2COc3cc(-c4ccccc4CCO)c(N(C)C4(C)CN(C)C4)cc3N21 ; Cl] | 180 | | Not required | 1.388 (Table 1, Method 4) | 450 |
| 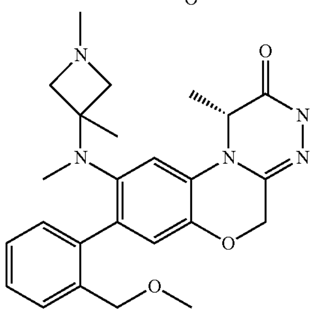 | 181 | | Not required | 2.42 (Table 1, Method 4) | 450 |
| 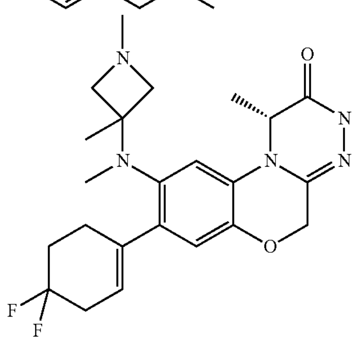 | 182 | | SFC at final step | 1.667 (Table 1, Method 4) | 446 |

Example #183

(R)-6-[(1-Acetyl-3-methyl-azetidin-3-yl)-methyl-amino]-7-(2-fluoro-phenyl)-4-methyl-2,10-dihydro-9-oxa-1,2,4a-triaza-phenanthren-3-one Step A. 3-{[(R)-7-(2-Fluoro-phenyl)-4-methyl-3-oxo-2,3,4,10-tetrahydro-9-oxa-1,2,4a-triaza-phenanthren-6-yl]-methyl-amino}-3-methyl-azetidine-1-carboxylic acid tert-butyl ester

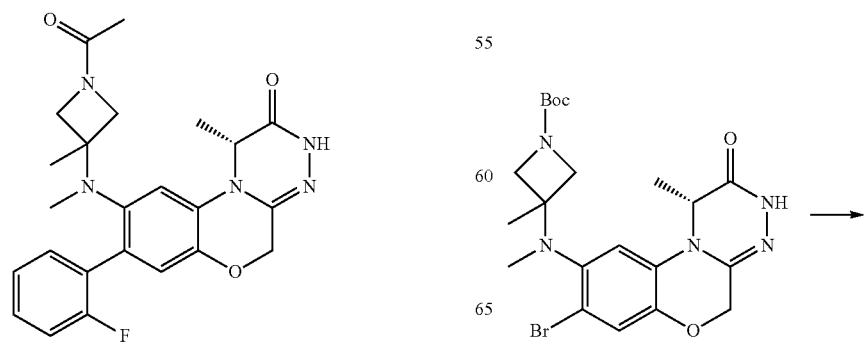

-continued

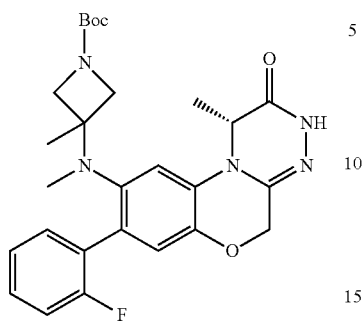

A degassed solution of potassium carbonate (0.432 g, 3.13 mmol), PdCl$_2$(dppf)-CH$_2$Cl$_2$ adduct (0.255 g, 0.313 mmol), 3-[((R)-7-bromo-4-methyl-3-oxo-2,3,4,10-tetrahydro-9-oxa-1,2,4a-triaza-phenanthren-6-yl)-methyl-amino]-3-methyl-azetidine-1-carboxylic acid tert-butyl ester (prepared from 3-((R)-7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester (Example #148, Step G) using the similar procedure detailed in Example #102, Step A), 0.618 g, 1.25 mmol) and (2-fluorophenyl)boronic acid (0.262 g, 1.875 mmol) in 1,4-dioxane (15 mL) and water (3 mL) were heated at 90° C. for 4 h. The reaction mixture was cooled to rt and concentrated in vacuo. The residue was purified by column chromatography on silica gel (eluting with 25% EtOAc in petroleum ether) to afford 3-{[(R)-7-(2-fluoro-phenyl)-4-methyl-3-oxo-2,3,4,10-tetrahydro-9-oxa-1,2,4a-triaza-phenanthren-6-yl]-methyl-amino}-3-methyl-azetidine-1-carboxylic acid ten-butyl ester (0.540 g, 85%). $^1$H NMR (CDCl$_3$, 400 MHz): δ 8.14 (s, 1H), 7.35-7.26 (m, 2H), 7.19-7.10 (m, 2H), 6.94 (s, 1H), 6.54 (s, 1H), 4.71-4.56 (m, 3H), 3.86-3.78 (m, 2H), 3.48 (m, 2H), 2.41 (s, 3H). 1.54 (d, J=6.8 Hz, 3H), 1.42 (s, 9H), 1.26 (s, 3H). LC/MS (Table 1, Method 25) R$_t$=0.913 min., MS m/z: 510 [M+H]$^+$ Step B. (R)-7-(2-Fluoro-phenyl)-4-methyl-6-[methyl-(3-methyl-azetidin-3-yl)-amino]-2,10-dihydro-9-oxa-1,2,4a-triaza-phenanthren-3-one hydrochloride acid

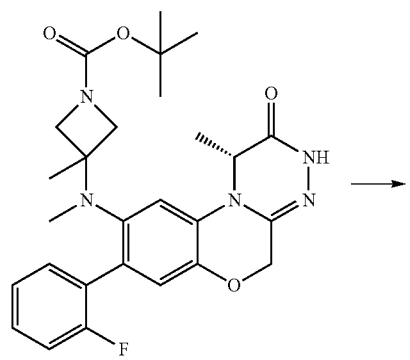

To a solution of 3-{[(R)-7-(2-fluoro-phenyl)-4-methyl-3-oxo-2,3,4,10-tetrahydro-9-oxa-1,2,4a-triaza-phenanthren-6-yl]-methyl-amino}-3-methyl-azetidine-1-carboxylic acid tert-butyl ester (0.250 g, 0.491 mmol) in EtOAc (2 mL) was added HCl (4M in EtOAc, 3 mL). The reaction mixture was stirred at ambient temperature for 30 min and then concentrated in vacuo to give (R)-7-(2-fluoro-phenyl)-4-methyl-6-[methyl-(3-methyl-azetidin-3-yl)-amino]-2,10-dihydro-9-oxa-1,2,4a-triaza-phenanthren-3-one hydrochloride acid which was used directly in the next step without further purification. LC/MS (Table 1, Method 25), R$_t$=0.722 min., MS m/z: 410 [M+H]$^+$ Step C. (R)-6-[(1-Acetyl-3-methyl-azetidin-3-yl)-methyl-amino]-7-(2-fluoro-phenyl)-4-methyl-2,10-dihydro-9-oxa-1,2,4a-triaza-phenanthren-3-one

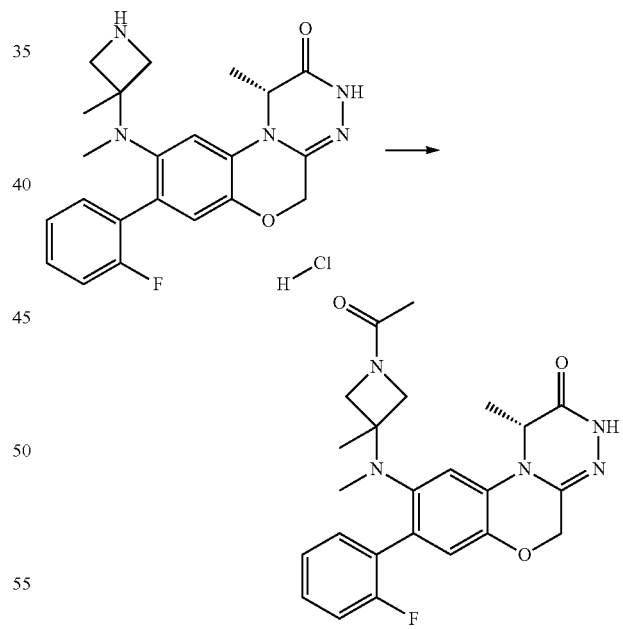

(R)-7-(2-fluoro-phenyl)-4-methyl-6-[methyl-(3-methyl-azetidin-3-yl)-amino]-2,10-dihydro-9-oxa-1,2,4a-triaza-phenanthren-3-one hydrochloride acid (0.125 g, 0.30 mmol) was dissolved in DCM (1 mL) and DIPEA (98 µl, 0.561 mmol) was added. The reaction mixture was stirred at room temperature for 6 min then acetyl chloride (59.8 µl, 0.841 mmol) was added. The reaction mixture was stirred at rt for 10 min and concentrated in vacuo. The residue was purified by basic prep-HPLC (Table 3, Method 32) to give (R)-6-[(1- acetyl-3-methyl-azetidin-3-yl)-methyl-amino]-7-(2-fluoro-phenyl)-4-methyl-2,10-dihydro-9-oxa-1,2,4a-triaza-phenanthren-3-one (0.024 g, 18%). $^1$H NMR (CD$_3$OD, 400 MHz) δ 7.36-7.33 (m, 2H), 7.25-7.22 (m, 1H), 7.17-7.14 (m, 1H), 6.95-6.92 (m, 2H), 4.80 (m, 1H), 4.68-4.62 (m, 2H), 4.09-4.05 (m, 1H), 3.85-3.73 (m, 2H), 3.55-3.50 (m, 1H), 2.58 (m, 3H), 1.79 (s, 3H), 1.50 (m, 3H), 1.44 (m, 3H). LC/MS (Table 1, Method 4), R$_t$=2.300 min., MS m/z: 452 [M+H]$^+$.

TABLE 24

The following analogs were prepared from (R)-7-(2-fluoro-phenyl)-4-methyl-6-[methyl-(3-methyl-azetidin-3-yl)-amino]-2,10-dihydro-9-oxa-1,2,4a-triaza-phenanthren-3-one hydrochloride acid (Example #183, Step B) using the procedure detailed in Example #183, Step C.

| Structure | Example # | Acid Chloride | R$_t$ min (method) | m/z ESI+ (M + H)$^+$ |
|---|---|---|---|---|
| 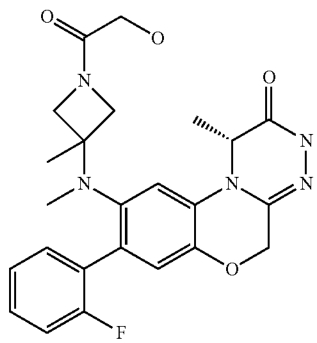 [SMILES: C[C@@H]1C(=O)NN=C2COc3cc(-c4ccccc4F)c(N(C)C4(C)CN(C(=O)CO)C4)cc3N21] | 184 | | 2.196 (Table 1, Method 4) | 468 |
| 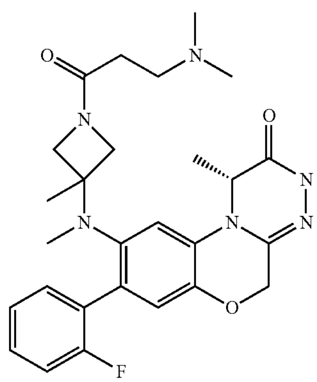 [SMILES: C[C@@H]1C(=O)NN=C2COc3cc(-c4ccccc4F)c(N(C)C4(C)CN(C(=O)CCN(C)C)C4)cc3N21] | 185 | | 2.543 (Table 1, Method 4) | 509 |
| 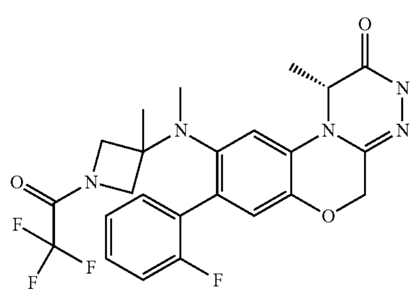 [SMILES: C[C@@H]1C(=O)NN=C2COc3cc(-c4ccccc4F)c(N(C)C4(C)CN(C(=O)C(F)(F)F)C4)cc3N21] | 186 | | 2.719 (Table 1, Method 4) | 506 |
| 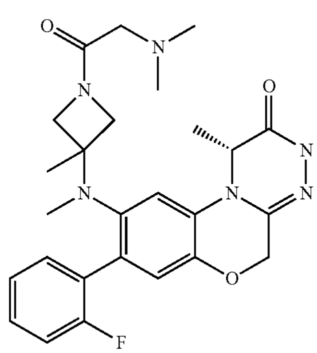 [SMILES: C[C@@H]1C(=O)NN=C2COc3cc(-c4ccccc4F)c(N(C)C4(C)CN(C(=O)CN(C)C)C4)cc3N21] | 187 | | 2.515 (Table 1, Method 4) | 495 |

TABLE 25a

The following analogs were prepared from (R)-7-(2-fluoro-phenyl)-4-methyl-6-[methyl-(3-methyl-azetidin-3-yl)-amino]-2,10-dihydro-9-oxa-1,2,4a-triaza-phenanthren-3-one hydrochloride acid (Example #183, Step B) using the procedure detailed in Example #139.

| Structure | Example # | Reagent | $R_t$ min (method) | m/z ESI+ $(M + H)^+$ |
|---|---|---|---|---|
| 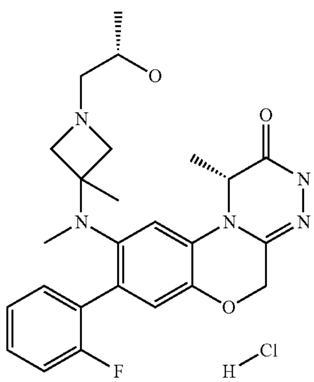 | 188 | | 1.653 (Table 1, Method 4) | 468 |
| 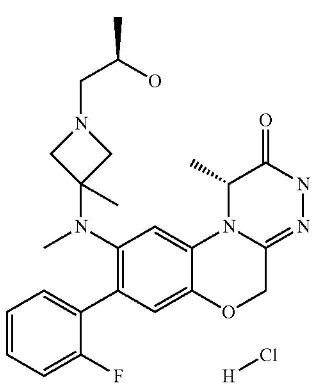 | 189 | | 1.68 (Table 1, Method 4) | 468 |
| 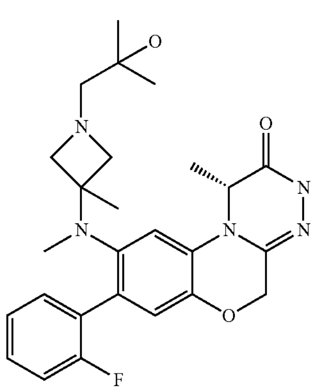 [SMILES: C[C@@H]1C(=O)NN=C2COc3cc(-c4ccccc4F)c(N(C)C4(C)CN(CC(C)(C)O)C4)cc3N21] | 190 | | 1.911 (Table 1, Method 4) | 482 |

TABLE 25

The following analogs were prepared from (R)-7-(2-fluoro-phenyl)-4-methyl-6-[methyl-(3-methyl-azetidin-3-yl)-amino]-2,10-dihydro-9-oxa-1,2,4a-triaza-phenanthren-3-one hydrochloride acid (Example #183, Step B) using the procedure detailed in Example #138. In cases where a TBS group was present, the TBS group was also removed under the reaction conditions.

| Structure | Example # | Reagent | $R_t$ min (method) | m/z ESI+ (M + H)+ |
|---|---|---|---|---|
| 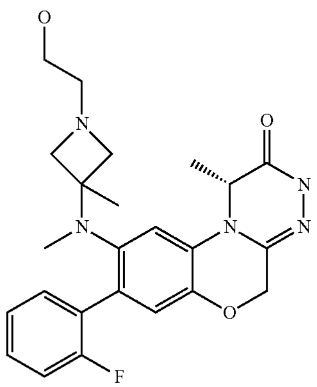 [SMILES: C[C@@H]1C(=O)NN=C2COc3cc(-c4ccccc4F)c(N(C)C4(C)CN(CCO)C4)cc3N21] | 191 | TBSO-CH2-CHO | 1.816 (Table 1, Method 4) | 454 |
| 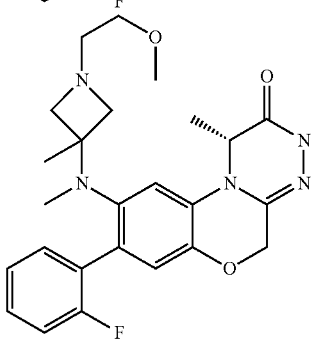 | 192 | MeO-CH2-CHO | 2.504 (Table 1, Method 4) | 468 |
| 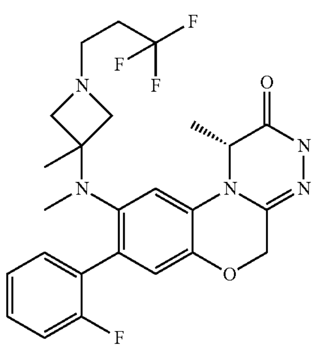 [SMILES: C[C@@H]1C(=O)NN=C2COc3cc(-c4ccccc4F)c(N(C)C4(C)CN(CCC(F)(F)F)C4)cc3N21] | 193 | F3C-CH2-CHO | 2.065 (Table 1, Method 4) | 506 |
| 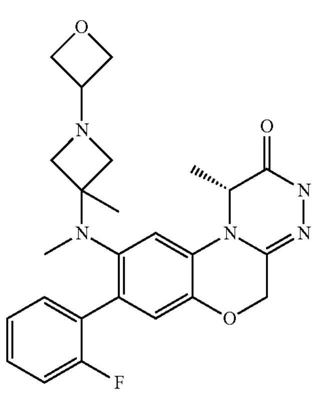 [SMILES: C[C@@H]1C(=O)NN=C2COc3cc(-c4ccccc4F)c(N(C)C4(C)CN(C5COC5)C4)cc3N21] | 194 | oxetan-3-one | 1.595 (Table 1, Method 4) | 466 |

TABLE 25b

The following analogs were prepared from (R)-7-(2-hydroxymethyl-phenyl)-4-methyl-6-[methyl-(3-methyl-azetidin-3-yl)-amino]-2,10-dihydro-9-oxa-1,2,4a-triaza-phenanthren-3-one hydrochloride acid (prepared from 3-[((R)-7-bromo-4-methyl-3-oxo-2,3,4,10-tetrahydro-9-oxa-1,2,4a-triaza-phenanthren-6-yl)-methyl-amino]-3-methyl-azetidine-1-carboxylic acid tert-butyl ester) and (2-(hydroxymethyl)phenyl)boronic acid using the similar procedure detailed in Example #183, Steps A-B) using the procedure detailed in Example #138, Step A. In cases where a TBS group was present, the TBS group was also removed under the reaction conditions.

| Structure | Example # | Reagent | R$_t$ min (method) | m/z ESI+ (M + H)$^+$ |
|---|---|---|---|---|
| 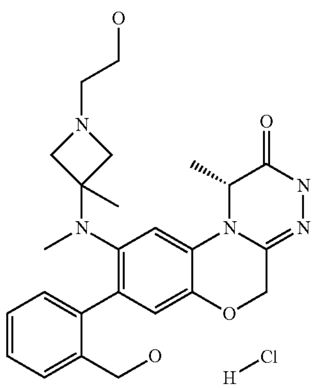 | 195 | TBSO-CHO | 1.515 (Table 1, Method 4) | 466 |

TABLE 25c

The following analog was prepared from 4-methyl-6-[methyl-(3-methyl-azetidin-3-yl)-amino]-7-phenyl-2,10-dihydro-9-oxa-1,2,4a-triaza-phenanthren-3-one hydrochloride acid (prepared from 3-[(7-bromo-4-methyl-3-oxo-2,3,4,10-tetrahydro-9-oxa-1,2,4a-triaza-phenanthren-6-yl)-methyl-amino]-3-methyl-azetidine-1-carboxylic acid tert-butyl ester) and phenylboronic acid using the similar procedure detailed in Example #183, Steps A-B) using the procedure detailed in Example #138, Step A.

| Structure | Example # | Reagent | R$_t$ min (method) | m/z ESI+ (M + H)$^+$ |
|---|---|---|---|---|
| 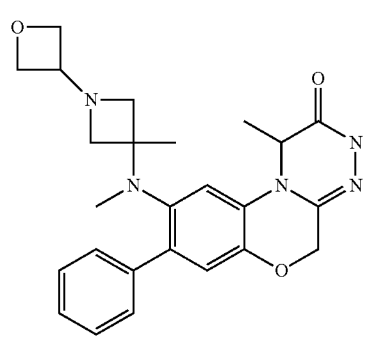 [SMILES: CC1C(=O)NN=C2COc3cc(-c4ccccc4)c(N(C)C4(C)CN(C5COC5)C4)cc3N21] | 196 | oxetan-3-one | 1.72 (Table 1, Method 4) | 448 |

Example #198

(S)-6-[((S)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-1, Enantiomer 1) & (S)-6-[((R)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-2, Enantiomer 2) & (R)-6-[((S)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-3, Enantiomer 3) & (R)-6-[((R)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-4, Enantiomer 4)

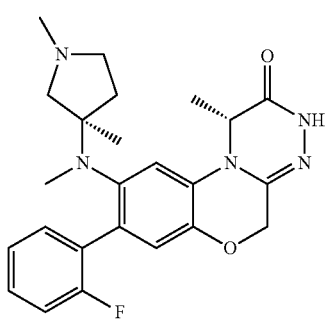

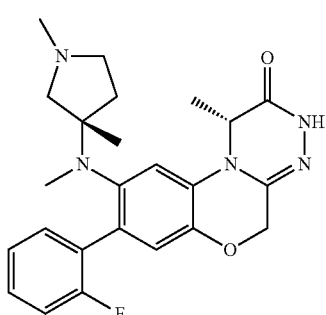

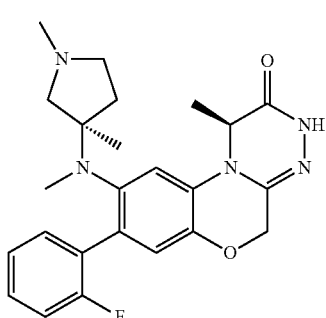

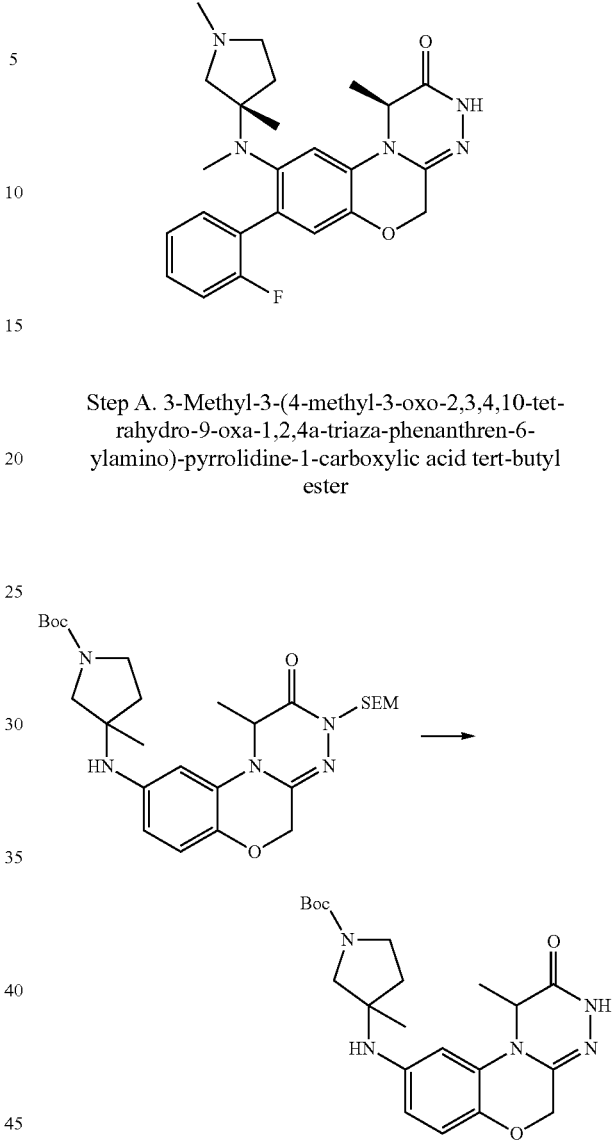

Step A. 3-Methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester A mixture of 3-methyl-3-[4-methyl-3-oxo-2-(2-trimethylsilanyl-ethoxymethyl)-2,3,4,10-tetrahydro-9-oxa-1,2,4a-triaza-phenanthren-6-ylamino]-pyrrolidine-1-carboxylic acid tert-butyl ester (prepared using a similar procedure as detailed in Example #162, Step C from 3-amino-3-methyl-pyrrolidine-1-carboxylic acid tert-butyl ester, 1.1 g, 2.016 mmol) in a solution of TBAF in THF (1 M, 20 mL, 20 mmoL) was stirred at 80° C. for 16 h. The reaction mixture was cooled to ambient temperature and diluted with water (25 mL). The aqueous solution was extracted with EtOAc (3×25 mL) and the combined organic phase was washed with brine (10 mL), dried over sodium sulfate and filtered. The filtrate was concentrated in vacuo and the residue was purified by column chromatography on silica gel (eluting with 10% EtOAc in petroleum) to give 3-methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester (0.45 g, 54%). LC/MS (Table 1, Method 2) $R_f$=0.890 min; MS m/z: 438 [M+Na]$^+$.

Step B. 3-(7-Bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester

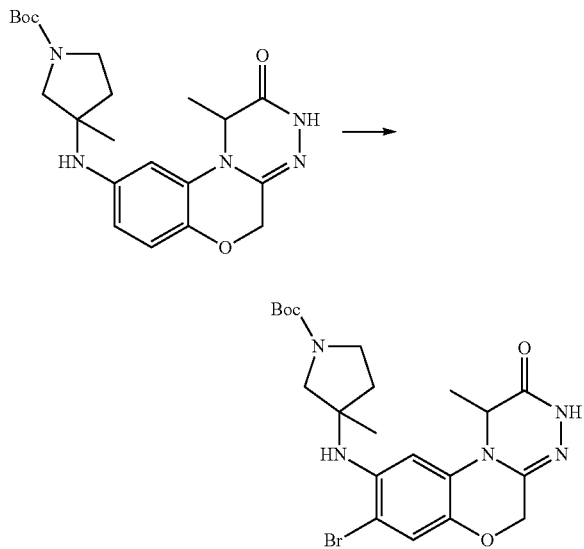

To a solution of 3-methyl-3-(4-methyl-3-oxo-2,3,4,10-tetrahydro-9-oxa-1,2,4a-triaza-phenanthren-6-ylamino)-pyrrolidine-1-carboxylic acid tert-butyl ester (0.240 g, 0.578 mmol) in DCM (3 mL) and MeOH (1 mL) was added Bu$_4$NBr$_3$ (0.279 g, 0.578 mmol) and the reaction mixture was stirred at ambient temperature for 2 h. The solvent was removed in vacuo and the residue was purified by column chromatography on silica gel (eluting with 2%~10% EtOAc in petroleum ether) to give 3-(7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (0.265 g, 93%). $^1$H-NMR (400 MHz, CDCl$_3$) δ 8.11-8.03 (brs, 1H), 7.13 (s, 1H), 6.43-6.36 (m, 1H), 4.73-4.62 (m, 1H), 4.61-4.45 (m, 2H), 3.65-3.40 (m, 4H), 2.35-2.19 (m, 1H), 2.04-1.91 (m, 1H), 1.57-1.54 (m, 3H), 1.53-1.51 (m, 3H), 1.49 (s, 9H).

Step C. 3-[7-(2-Fluoro-phenyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester

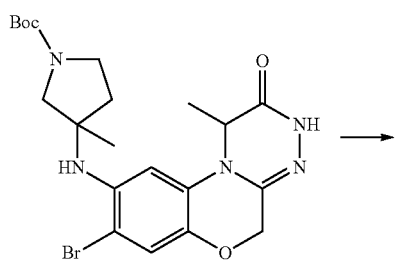

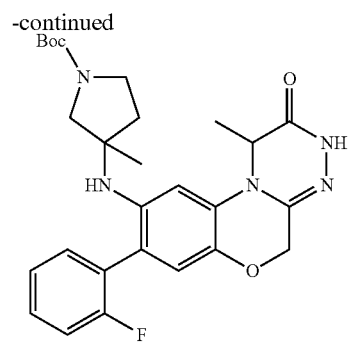

A mixture of 3-(7-bromo-4-methyl-3-oxo-2,3,4,10-tetrahydro-9-oxa-1,2,4a-triaza-phenanthren-6-ylamino)-3-methyl-pyrrolidine-1-carboxylic acid tert-butyl ester (0.230 g, 0.465 mmol), K$_2$CO$_3$ (0.129 g, 0.930 mmol), (2-fluorophenyl)boronic acid (0.098 g, 0.698 mmol) and PdCl$_2$(dppf)-CH$_2$Cl$_2$ adduct (0.038 g, 0.047 mmol) in dioxane (4 mL) and water (0.66 mL) was heated at 90° C. for 14 h. The reaction mixture was cooled to ambient temperature and concentrated in vacuo. The residue was purified by prep-TLC (eluting with 10% EtOAc in petroleum ether) to give 3-[7-(2-fluoro-phenyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester (0.220 g, 93%) as a pale solid. $^1$H-NMR (400 MHz, CDCl$_3$) δ 8.09-8.00 (brs, 1H), 7.41-7.31 (m, 1H), 7.24-7.19 (m, 2H), 7.19-7.08 (m, 1H), 6.73 (s, 1H), 6.46 (s, 1H), 4.79-4.66 (m, 1H), 4.64-4.47 (m, 1H), 3.55-3.08 (m, 4H), 2.16-1.93 (m, 2H), 1.58-1.55 (m, 3H), 1.50-1.37 (m, 12H). LC/MS (Table 1, Method 25) R$_t$=0.895 min; MS m/z: 510 [M+1]$^+$.

Step D. 7-(2-Fluoro-phenyl)-4-methyl-6-(3-methyl-pyrrolidin-3-ylamino)-2,10-dihydro-9-oxa-1,2,4a-triaza-phenanthren-3-one hydrochloride acid

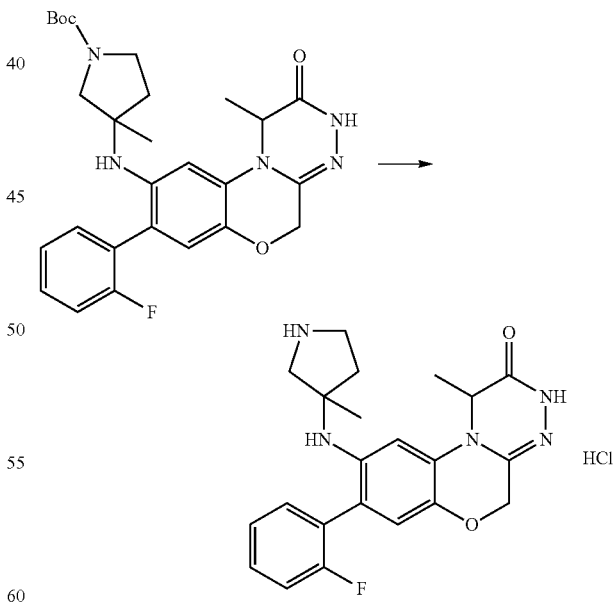

A mixture of 3-[7-(2-fluoro-phenyl)-4-methyl-3-oxo-2,3,4,10-tetrahydro-9-oxa-1,2,4a-triaza-phenanthren-6-ylamino]-3-methyl-pyrrolidine-1-carboxylic acid tert-butyl ester (0.008 g, 0.017 mmol) in HCl (4 M in EtOAc, 2 mL) was stirred at ambient temperature for 1 h. The solvent was removed in vacuo to give 7-(2-fluoro-phenyl)-4-methyl-6-(3-methyl-pyrrolidin-3-ylamino)-2,10-dihydro-9-oxa-1,2,4a- triaza-phenanthren-3-one hydrochloride acid (0.007 g, 87%) as a white solid. $^1$H NMR (400 MHz, methanol-d$_4$) δ 7.53-7.42 (m, 1H), 7.41-7.34 (m, 1H), 7.34-7.29 (m, 1H), 7.29-7.22 (m, 1H), 6.89 (s, 1H), 6.70-6.64 (m, 1H), 4.97-4.93 (m, 1H), 4.64-4.57 (s, 2H), 3.60-3.45 (m, 1H), 3.38-3.34 (m, 2H), 3.18-3.07 (m, 1H), 2.20-2.06 (m, 1H), 2.04-1.92 (m, 1H), 1.56-1.47 (m, 3H), 1.39 (m, 3H). LC/MS (Table 1, Method 5) R$_t$=2.272 min; MS m/z: 410 [M+H]$^+$.

Step E. (S)-6-[((S)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-1, Enantiomer 1), (S)-6-[((R)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-2, Enantiomer 2), (R)-6-[((S)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-3, Enantiomer 3), and (R)-6-[((R)-1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-4, Enantiomer 4)

Chiral SFC (Table 2, Method 24) separation gave the following four isomers.

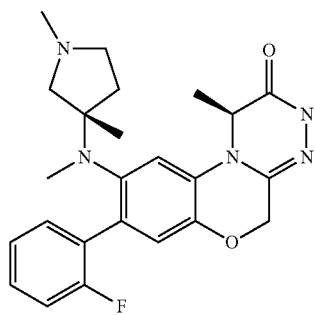 [SMILES: C[C@H]1C(=O)NN=C2COc3cc(-c4ccccc4F)c(N(C)[C@@]4(C)CCN(C)C4)cc3N21]

(S)-6-[((S)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-1, Enantiomer 1, SFC (Table 1, Method 50) R$_t$=14.061 min, 0.021 g, 20%). $^1$H NMR (400 MHz, methanol-d$_4$) δ=7.40-7.28 (m, 2H), 7.25-7.18 (m, 1H), 7.17-7.10 (m, 2H), 6.95 (s, 1H), 4.86-4.83 (m, 1H), 4.67-4.62 (m, 2H), 2.75-2.68 (m, 1H),

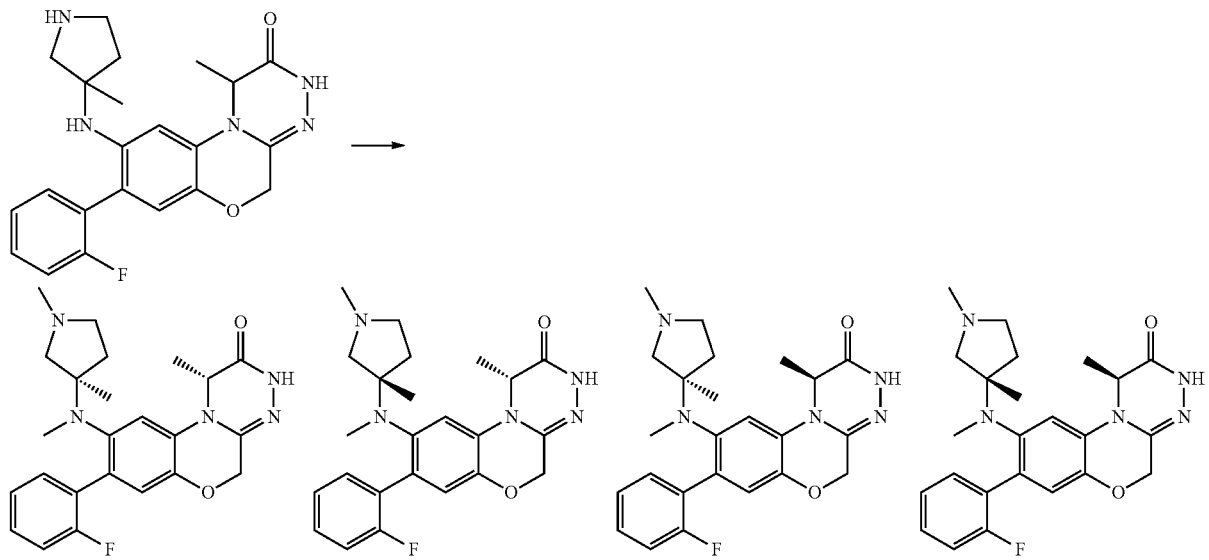

A mixture of 7-(2-fluoro-phenyl)-4-methyl-6-(3-methyl-pyrrolidin-3-ylamino)-2,10-dihydro-9-oxa-1,2,4a-triaza-phenanthren-3-one (0.201 g, 0.491 mmol) and paraformaldehyde (0.088 mg, 2.95 mmol) in MeOH (5 mL) and AcOH (0.5 mL) was stirred at ambient temperature for 3 h. Then, NaBH$_3$CN (0.185 mg, 2.95 mmol) was added and the reaction mixture was stirred for 4 h. The reaction mixture was evaporated in vacuo and the residue was purified by prep-TLC (eluting with 10% MeOH in DCM) to give 6-[(1,3-dimethyl-pyrrolidin-3-yl)-methyl-amino]-7-(2-fluoro-phenyl)-4-methyl-2,10-dihydro-9-oxa-1,2,4a-triaza-phenanthren-3-one (0.106 g, 49%) as a pale solid. $^1$H NMR (400 MHz, methanol-d$_4$) δ 7.49-7.32 (m, 2H), 7.32-7.26 (m, 1H), 7.25-7.17 (m, 1H), 7.17-7.11 (m, 1H), 7.02-6.95 (m, 1H), 4.98-4.94 (m, 1H), 4.73-4.59 (m, 2H), 3.91-3.54 (m, 2H), 3.14-2.88 (m, 2H), 2.85-2.76 (m, 4H), 2.71-2.65 (m, 2H), 2.29-2.04 (m, 1H), 1.76-1.57 (m, 1H), 1.55-1.48 (m, 3H), 1.41-1.28 (m, 3H). LC/MS (Table 1, Method 5) R$_t$=2.358 min; MS m/z: 438 [M+1]$^+$.

2.66 (s, 3H), 2.62-2.53 (m, 1H), 2.52-2.42 (m, 1H), 2.27 (s, 3H), 2.18-1.97 (m, 2H), 1.54-1.48 (m, 3H), 1.27 (s, 3H). LC/MS (Table 1, Method 5) R$_t$=2.369 min; MS m/z: 438 [M+1]$^+$.

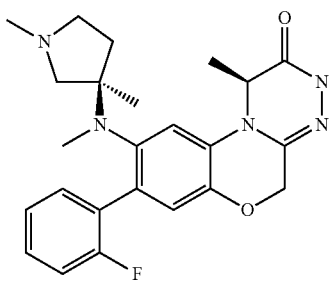 [SMILES: C[C@H]1C(=O)NN=C2COc3cc(-c4ccccc4F)c(N(C)[C@]4(C)CCN(C)C4)cc3N21]

(S)-6-[((R)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-2, Enantiomer 2, 2, SFC (Table 1, Method 50) R$_t$=12.988 min, 0.015 g, 15%). $^1$H NMR (400 MHz, methanol-d$_4$) δ 7.39-7.28 (m, 2H), 7.24-7.18 (m, 1H), 7.17 (m, 2H), 6.95 (s, 1H), 4.87-4.84 (m, 1H), 4.68-4.59 (m, 2H), 2.65 (s, 4H), 2.58-2.44 (m, 2H), 2.24 (s, 3H), 2.12-1.87 (m, 2H), 1.55-1.48 (m, 3H), 1.47-1.37 (m, 1H), 1.27 (s, 3H). LC/MS (Table 1, Method 5) R$_t$=2.378 min; MS m/z: 438 [M+1]$^+$.

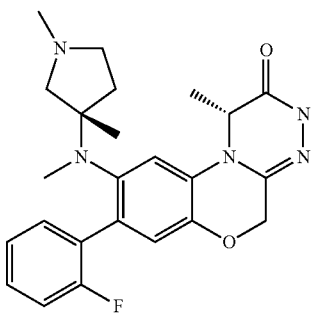 [SMILES: C[C@@H]1C(=O)NN=C2COc3cc(-c4ccccc4F)c(N(C)[C@@]4(C)CCN(C)C4)cc3N21]

(R)-6-[((S)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-3, Enantiomer 3, SFC (Table 1, Method 50) R$_t$=11.766 min, 0.020 g, 20%). $^1$H NMR (400 MHz, methanol-d$_4$) δ 7.40-7.28 (m, 2H), 7.24-7.18 (m, 1H), 7.17-7.09 (m, 2H), 6.96 (s, 1H), 4.86-4.84 (m, 1H), 4.67-4.60 (m, 2H), 2.73-2.58 (m, 4H), 2.55-2.43 (m, 2H), 2.29-2.18 (m, 3H), 2.14-1.85 (m, 2H), 1.56-1.47 (m, 3H), 1.46-1.35 (m, 1H), 1.30-1.22 (m, 3H). LC/MS (Table 1, Method 5) R$_t$=2.379 min; MS m/z: 438 [M+1]$^+$.

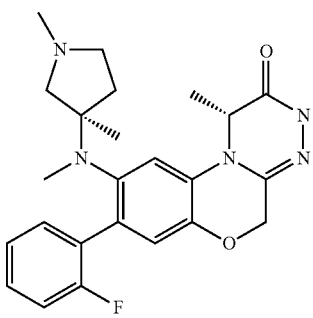 [SMILES: C[C@@H]1C(=O)NN=C2COc3cc(-c4ccccc4F)c(N(C)[C@]4(C)CCN(C)C4)cc3N21]

(R)-6-[((R)-1,3-Dimethyl-pyrrolidin-3-yl)-methyl-amino]-7-(2-fluoro-phenyl)-4-methyl-2,10-dihydro-9-oxa-1,2,4a-triaza-phenanthren-3-one (Example #198-4, Enantiomer 4, SFC (Table 1, Method 50) R$_t$=10.960 min, 0.021 g, 21%). $^1$H NMR (400 MHz, methanol-d$_4$) δ 7.48-7.33 (m, 2H), 7.32-7.25 (m, 1H), 7.24-7.10 (m, 2H), 6.97 (s, 1H), 4.66 (m, 3H), 3.29-2.96 (m, 2H), 2.80 (s, 3H), 2.75-2.61 (m, 3H), 2.43-1.91 (m, 1H), 1.82-1.57 (m, 1H), 1.57-1.46 (m, 3H), 1.36-1.31 (m, 3H). LC/MS (Table 1, Method 5) R$_t$=2.375 min; MS m/z: 438 [M+1]$^+$.

Example #199

(R)-6-((3R,4R)-1,3-Dimethyl-piperidin-4-yl)-7-(2-fluoro-phenyl)-4-methyl-2,10-dihydro-9-oxa-1,2,4a-triaza-phenanthren-3-one hydrochloride acid

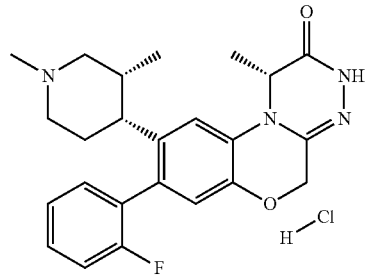

Step A. 3-Methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester

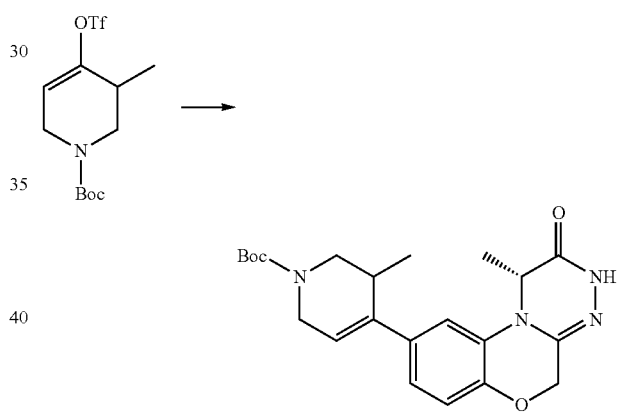

To a mixture of 3-methyl-4-trifluoromethanesulfonyloxy-3,6-dihydro-2H-pyridine-1-carboxylic acid tert-butyl ester (Preparation #13, 5.07 g, 14.69 mmol), (R)-4-methyl-6-(4,4,5,5-tetramethyl-[1,3,2]dioxaborolan-2-yl)-2,10-dihydro-9-oxa-1,2,4a-triaza-phenanthren-3-one (Preparation #11, Step E, 2.8 g, 8.16 mmol) and K$_3$PO$_4$ (3.46 g, 16.32 mmol) in DMF (60 mL) and water (10 mL) was added Pd(Ph$_3$P)$_4$ (3.77 g, 3.26 mmol). The reaction mixture was stirred at 80° C. overnight then cooled to ambient temperature and concentrated in vacuo. The residue was purified by column chromatography on silica gel (eluting with 3-50% EtOAc in petroleum ether) to give 3-methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (3.5 g) as a yellow liquid. Further purification by prep-HPLC (Table 3, Method 33) ave 3-methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (1.5 g, 44%) as a white solid. $^1$H NMR (CDCl$_3$, 400 MHz): δ 8.03 (brs, 1H), 7.02-6.93 (m, 2H), 6.87 (s, 1H), 5.81 (brs, 1H), 4.77 (q, J=6.8 Hz, 1H), 4.66-4.53 (d, J=13.2 Hz, 2H), 4.47-4.18 (m, 1H), 3.95-3.77 (m, 2H), 3.32 (d, J=13.2 Hz, 1H), 2.79 (brs, 1H), 1.53 (m, 3H), 1.51 (s, 9H), 1.02 (d, J=6.8 Hz, 3H). LC/MS (Table 1, Method 44) R$_t$=3.339 min.; MS m/z: 414 [M+H]$^+$.

Step B. (R)-3-Methyl-4-((R)-4-methyl-3-oxo-2,3,4, 10-tetrahydro-9-oxa-1,2,4a-triaza-phenanthren-6-yl)-3,6-dihydro-2H-pyridine-1-carboxylic acid tert-butyl ester & (S)-3-methyl-4-((R)-4-methyl-3-oxo-2,3,4, 10-tetrahydro-9-oxa-1,2,4a-triaza-phenanthren-6-yl)-3,6-dihydro-2H-pyridine-1-carboxylic acid tert-butyl ester

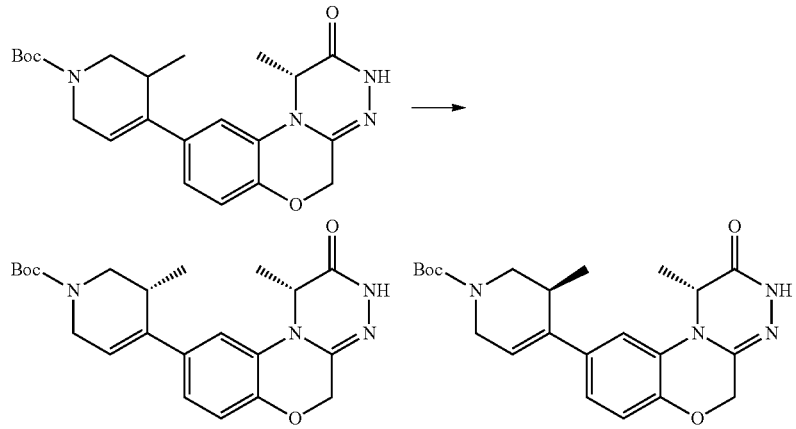

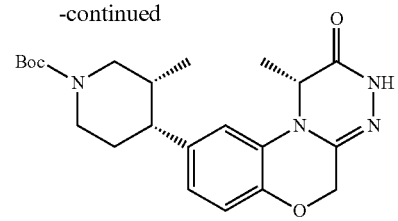

3-Methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (1.5 g, 3.64 mmol) was separated by chiral SFC (Table 2, Method 22) to give two isomers: (R)-3-methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (isomer 1, SFC (Table 1, Method 42), R$_t$=8.561 min., 0.57 g, 38%) & (S)-3-methyl-4-((R)-4-methyl-3-oxo-2,3,4,10-tetrahydro-9-oxa-1, 2,4a-triaza-phenanthren-6-yl)-3,6-dihydro-2H-pyridine-1-carboxylic acid tert-butyl ester (isomer 2, SFC (Table 1, Method 42), R$_t$=6.856 min., 0.57 g, 38%) as white solids.

isomer 1: $^1$H NMR (CDCl$_3$, 400 MHz): δ 8.03 (brs, 1H), 6.99-6.94 (m, 2H), 6.86 (s, 1H), 5.81 (d, J=15.6 Hz, 1H), 4.77 (q, J=6.6 Hz, 1H), 4.67-4.53 (m, 2H), 3.85 (dd, J=3.3, 13.1 Hz, 2H), 3.31 (dd, J=3.9, 12.9 Hz, 1H), 2.79 (brs, 1H), 1.55 (d, J=6.8 Hz, 3H), 1.51 (s, 9H), 1.02 (d, J=6.8 Hz, 3H). LC/MS (Table 1, Method 25), R$_t$=0.869 min.; MS m/z: 413 [M+H]$^+$.

isomer 2: $^1$H NMR (CDCl$_3$, 400 MHz): δ 8.08 (brs, 1H), 7.01-6.93 (m, 2H), 6.87 (s, 1H), 5.82 (brs, 1H), 4.77 (q, J=6.6 Hz, 1H), 4.60 (q, J=13.1 Hz, 2H), 4.47-4.13 (m, 1H), 3.85 (dd, J=3.0, 12.8 Hz, 2H), 3.32 (dd, J=3.4, 12.9 Hz, 1H), 2.78 (brs, 1H), 1.55-1.51 (m, 3H), 1.51 (s, 9H), 1.02 (d, J=6.8 Hz, 3H). LC/MS (Table 1, Method 25), R$_t$=0.869 min.; MS m/z: 413 [M+H]$^+$.

Step C. (3R,4R)-3-Methyl-4-((R)-4-methyl-3-oxo-2, 3,4,10-tetrahydro-9-oxa-1,2,4a-triaza-phenanthren-6-yl)-piperidine-1-carboxylic acid tert-butyl ester

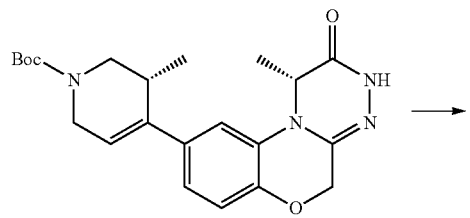

A mixture of (R)-3-methyl-4-((R)-4-methyl-3-oxo-2,3,4, 10-tetrahydro-9-oxa-1,2,4a-triaza-phenanthren-6-yl)-3,6-dihydro-2H-pyridine-1-carboxylic acid tert-butyl ester (isomer 1, SFC (Table 1, Method 42), R$_t$=8.561 min., 0.55 g, 1.333 mmol) and Pd/C (10%, 0.142 g) in MeOH (20 mL) was stirred under an atmosphere of H$_2$ (1 atm) at ambient temperature for 3 h. The reaction mixture was filtered and the filtrate was concentrated in vacuo to give (3R,4R)-3-methyl-4-((R)-4-methyl-3-oxo-2,3,4,10-tetrahydro-9-oxa-1,2,4a-triaza-phenanthren-6-yl)-piperidine-1-carboxylic acid tert-butyl ester (0.54 g, 98%) as a colorless solid. $^1$H NMR (CDCl$_3$, 400 MHz) δ 8.35 (s, 1H), 6.97 (d, J=8.4 Hz, 1H), 6.79 (d, J=8.4 Hz, 1H), 6.71 (s, 1H), 4.77 (q, J=6.8 Hz, 1H), 4.65-4.52 (d, J=13.2 Hz, 2H), 4.48-3.98 (m, 2H), 3.18-2.73 (m, 3H), 2.13-1.92 (m, 2H), 1.61 (brs, 1H), 1.55-1.48 (m, 13H), 0.76-0.67 (d, J=5.6 Hz, 3H). LC/MS (Table 1, Method 25), R$_t$=0.869 min.; MS m/z: 415 [M+H]$^+$. SFC (Table 1, Method 45), R$_t$=4.910 min.

Step D. (3R,4R)-4-((R)-7-Bromo-4-methyl-3-oxo-2, 3,4,10-tetrahydro-9-oxa-1,2,4a-triaza-phenanthren-6-yl)-3-methyl-piperidine-1-carboxylic acid tert-butyl ester

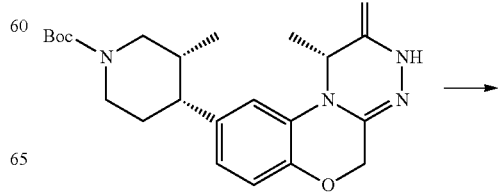

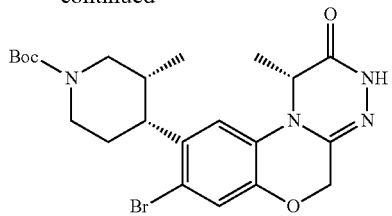

To a mixture of (3R,4R)-3-methyl-4-((R)-4-methyl-3-oxo-2,3,4,10-tetrahydro-9-oxa-1,2,4a-triaza-phenanthren-6-yl)-piperidine-1-carboxylic acid tert-butyl ester (0.2 g, 0.483 mmol) in DCM (20 mL) and MeOH (10 mL) was added tetra-N-butylammonium tribromide (0.233 g, 0.483 mmol) and the reaction mixture was stirred at ambient temperature for 30 min. Saturated aqueous $Na_2S_2O_3$ (6 mL) was added to quench the reaction and the mixture was extracted with DCM (4×10 mL). The combined organic phase was washed with brine (30 mL), dried over $Na_2SO_4$ and concentrated in vacuo. The residue was purified by prep-TLC (eluting with 50% EtOAc in petroleum ether) to give (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (0.12 g, 50%) as a colorless solid. $^1$H NMR (MeOD, 400 MHz) δ 7.23 (s, 1H), 6.84 (s, 1H), 4.87-4.81 (m, 1H), 4.64-4.54 (m, 2H), 4.32 (d, J=12.8 Hz, 1H), 4.05 (d, J=13.2 Hz, 1H), 3.20-2.75 (m, 3H), 2.37-2.17 (m, 3H), 1.48 (s, 9H), 1.44-1.38 (m, 4H), 0.73 (d, J=6.8 Hz, 3H). LC/MS (Table 1, Method 25), $R_t$=0.934 min.; MS m/z: 495 [M+H+2]$^+$ & 493 [M+H]$^+$. SFC (Table 1, Method 46), $R_t$=6.79 min.

Step E. (3R,4R)-4-[(R)-7-(2-Fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester

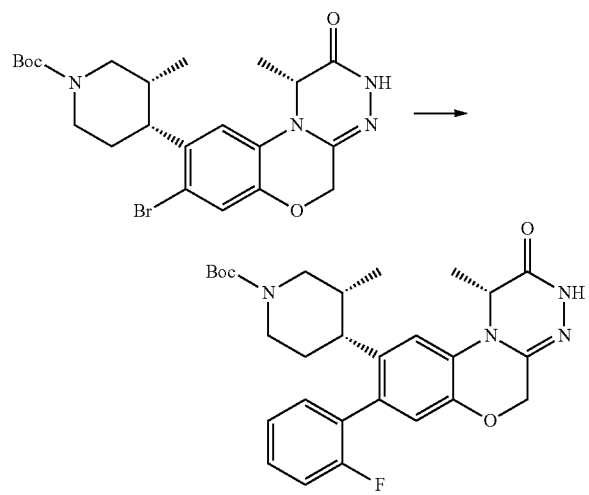

To a mixture of (2-fluorophenyl)boronic acid (0.051 g, 0.365 mmol), (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (0.12 g, 0.243 mmol) and $K_2CO_3$ (0.067 g, 0.486 mmol) in dioxane (12 mL) and water (2 mL) was added $PdCl_2$(dppf)-$CH_2Cl_2$ adduct (0.020 g, 0.024 mmol) and the reaction mixture was stirred at 90° C. overnight. The reaction mixture was cooled to ambient temperature, concentrated in vacuo and the residue was purified by column chromatography on silica gel (eluting with 3-30% EtOAc in petroleum ether) to give (3R,4R)-4-[(R)-7-(2-fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.076 g, 61%) as a colorless solid. $^1$H NMR (CDCl$_3$, 400 MHz) δ 8.34 (brs, 1H), 7.44-7.32 (m, 1H), 7.24-7.11 (m, 3H), 6.85 (s, 1H), 6.73 (brs, 1H), 4.80 (brs, 1H), 4.70-4.53 (m, 2H), 4.43-4.17 (m, 1H), 3.90-3.60 (m, 1H), 2.89 (brs, 1H), 2.60 (brs, 2H), 1.56 (d, J=6.8 Hz, 3H), 1.46 (m, 10H), 0.72 (m, 3H). LC/MS (Table 1, Method 25), $R_t$=0.948 min.; MS m/z: 509 [M+H]$^+$ & 453 [M+H–56]$^+$. SFC (Table 1, Method 46), $R_t$=6.21 min.

Step F. (R)-7-(2-Fluoro-phenyl)-4-methyl-6-((3R,4R)-3-methyl-piperidin-4-yl)-2,10-dihydro-9-oxa-1,2,4a-triaza-phenanthren-3-one hydrochloride acid

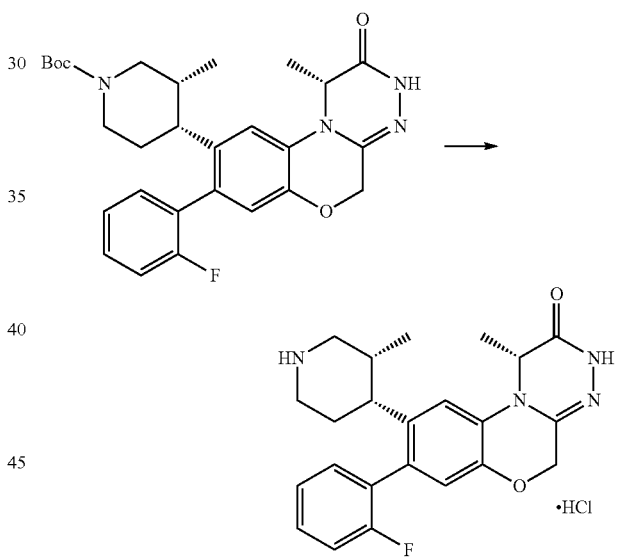

A mixture of (3R,4R)-4-[(R)-7-(2-fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.076 g, 0.149 mmol) in HCl (4M in EtOAc, 15 mL) was stirred at 20° C. for 1 h. The reaction mixture was concentrated in vacuo to give (R)-7-(2-fluoro-phenyl)-4-methyl-6-((3R,4R)-3-methyl-piperidin-4-yl)-2,10-dihydro-9-oxa-1,2,4a-triaza-phenanthren-3-one hydrochloride acid (0.065 g, 98%). $^1$H NMR (MeOD, 400 MHz) δ 7.50-7.41 (m, 1H), 7.32-7.19 (m, 3H), 6.91 (brs, 1H), 6.86 (s, 1H), 4.80 (m, 1H), 4.70-4.59 (m, 2H), 3.48 (m, 1H), 3.15-2.98 (m, 2H), 2.82 (m, 1H), 2.43 (m, 1H), 1.88 (m, 2H), 1.50 (d, J=6.4 Hz, 3H), 0.91 (brs, 3H). LC/MS (Table 1, Method 4) $R_t$=1.534 min.; MS m/z: 409 [M+H]$^+$. SFC (Table 1, Method 43), $R_t$=1.341 min.

Step G. (R)-6-(3R,4R)-1,3-Dimethyl-piperidin-4-yl)-7-(2-fluoro-phenyl)-4-methyl-2,10-dihydro-9-oxa-1,2,4a-triaza-phenanthren-3-one hydrochloride acid

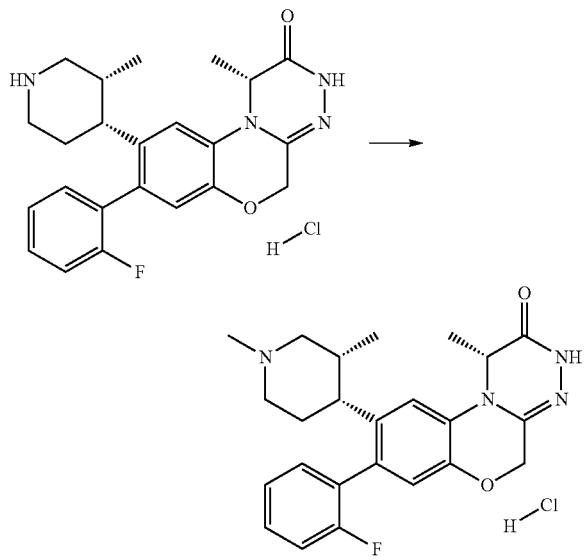

A mixture of (R)-7-(2-fluoro-phenyl)-4-methyl-6-((3R,4R)-3-methyl-piperidin-4-yl)-2,10-dihydro-9-oxa-1,2,4a-triaza-phenanthren-3-one hydrochloride acid (3.05 g, 6.88 mmol) and paraformaldehyde (2.066 g, 68.8 mmol) in MeOH (60 mL) and AcOH (6 mL) was stirred at 80° C. for 16 h. Then, sodium cyanotrihydroborate (0.865 g, 13.76 mmol) was added and the reaction mixture was stirred at ambient temperature for 0.5 h. The reaction mixture was concentrated in vacuo and the residue was purified by column chromatography on basified silica gel (eluting with 10% MeOH in DCM) to give (R)-6-((3R,4R)-1,3-dimethyl-piperidin-4-yl)-7-(2-fluoro-phenyl)-4-methyl-2,10-dihydro-9-oxa-1,2,4a-triaza-phenanthren-3-one (1.15 g, 40%) as a white solid. The white solid was stirred in HCl/EtOAc (4 M, 50 mL) for 30 min and the reaction mixture was concentrated in vacuo to give (R)-6-((3R,4R)-1,3-dimethyl-piperidin-4-yl)-7-(2-fluoro-phenyl)-4-methyl-2,10-dihydro-9-oxa-1,2,4a-triaza-phenanthren-3-one hydrochloride acid (1.215 g, 39%) as a white solid. $^1$H NMR (400 MHz, MeOD) δ 7.44 (m, 1H), 7.32-7.16 (m, 3H), 6.90 (m, 1H), 6.84 (s, 1H), 4.68-4.57 (d, J=13.2 Hz, 2H), 3.57 (m, 1H), 3.25 (m, 1H), 3.05 (m, 2H), 2.86 (m, 1H), 2.79 (s, 3H), 2.50 (m, 1H), 1.91 (m, 2H), 1.48 (d, J=6.8 Hz, 3H), 0.91 (m, 3H). LC/MS (Table 1, Method 5) R$_t$=2.275 min.; MS m/z: 423 [M+H]$^+$. SFC (Table 1, Method 47), R$_t$=1.145 min.

TABLE 26a

The following analogs were prepared from (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (Example #199, Step D) using the procedure detailed in Example #199, Steps E-G.

| Structure | Example # | Boronate | R$_t$ min (method) | m/z ESI+ (M + H)$^+$ |
|---|---|---|---|---|
| 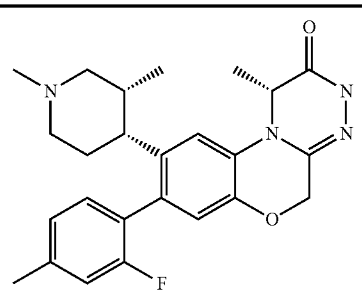 | 200 |  | 1.871 (Table 1, Method 4) | 437 |
| 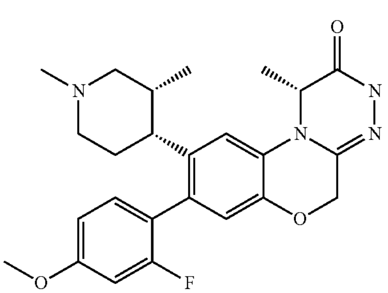 [SMILES: COc1ccc(-c2cc3c(cc2[C@@H]2CCN(C)C[C@@H]2C)N2C(=NNC(=O)[C@H]2C)CO3)c(F)c1] | 201 |  | 1.728 (Table 1, Method 4) | 453 |

TABLE 26

The following analogs were prepared from (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (Example #199, Step D) using the procedure detailed in Example #76, Steps A-C.

| Structure | Example # | Boronate | R, min (method) | m/z ESI+ (M + H)+ |
|---|---|---|---|---|
| (structure shown) | 202 | (structure shown) | 1.577 (Table 1, Method 4) | 357 |

Example #203

(R)-6-((3S,4S)-1,3-Dimethyl-piperidin-4-yl)-7-(2-fluoro-phenyl)-4-methyl-2,10-dihydro-9-oxa-1,2,4a-triaza-phenanthren-3-one hydrochloride acid

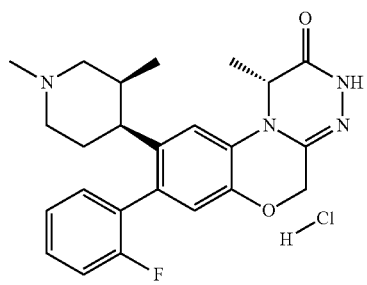

Step A. (3S,4S)-3-Methyl-4-((R)-4-methyl-3-oxo-2,3,4,10-tetrahydro-9-oxa-1,2,4a-triaza-phenanthren-6-yl)-piperidine-1-carboxylic acid tert-butyl ester

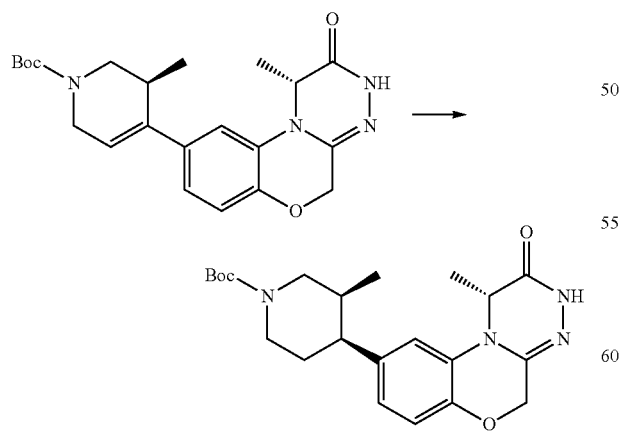

A mixture of (S)-3-methyl-4-((R)-4-methyl-3-oxo-2,3,4,10-tetrahydro-9-oxa-1,2,4a-triaza-phenanthren-6-yl)-3,6-dihydro-2H-pyridine-1-carboxylic acid tert-butyl ester (Example #199, Step B, isomer 2, SFC (Table 1, Method 42), $R_f$=6.856 min., 0.55 g, 1.333 mmol) and 10% Pd/C (0.142 g) in MeOH (20 mL) was stirred at rt for 3 h. The reaction mixture was filtered and the filtrate was concentrated in vacuo to give (3S,4S)-3-methyl-4-((R)-4-methyl-3-oxo-2,3,4,10-tetrahydro-9-oxa-1,2,4a-triaza-phenanthren-6-yl)-piperidine-1-carboxylic acid tert-butyl ester (0.55 g, 100%) as a white solid. $^1$H NMR (400 MHz, CDCl$_3$) δ 8.40 (brs, 1H), 6.98-6.91 (d, J=8.0 Hz, 1H), 6.75-6.70 (d, J=8.0 Hz, 1H), 6.70-6.65 (s, 1H), 4.76-4.70 (q, J=6.8 Hz, 1H), 4.64-4.52 (d, J=13.2 Hz, 2H), 4.47-4.18 (m, 1H), 4.10-3.96 (m, 1H), 3.18-2.66 (m, 3H), 2.10-1.90 (m, 2H), 1.62-1.55 (m, 1H), 1.53-1.45 (m, 12H), 0.70 (d, J=6.8 Hz, 3H). LC/MS (Table 1, Method 25) $R_t$=0.864 min.; MS m/z: 415 [M+H]$^+$ & 359 [M+H−56]$^+$. SFC (Table 1, Method 45), $R_t$=4.693 min.

Step B. (3S,4S)-4-((R)-7-Bromo-4-methyl-3-oxo-2,3,4,10-tetrahydro-9-oxa-1,2,4a-triaza-phenanthren-6-yl)-3-methyl-piperidine-1-carboxylic acid tert-butyl ester

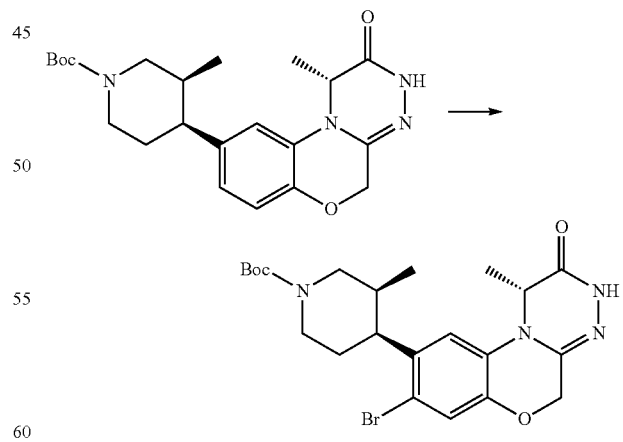

To a mixture of (3S,4S)-3-methyl-4-((R)-4-methyl-3-oxo-2,3,4,10-tetrahydro-9-oxa-1,2,4a-triaza-phenanthren-6-yl)-piperidine-1-carboxylic acid tert-butyl ester (0.1 g, 0.241 mmol) in DCM (10 mL) and MeOH (5 mL) was added tetra-N-butylammonium tribromide (0.116 g, 0.241 mmol) and the reaction mixture was stirred at rt for 0.5 h. The reaction mixture was purified by prep-TLC (eluting with 50% EtOAc in petroleum ether) to give (3S,4S)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (0.045 g, 37%) as a white solid. $^1$H NMR (400 MHz, CDCl$_3$) δ 7.22 (s, 1H), 6.81-6.55 (m, 1H), 4.96-4.70 (m, 1H), 4.66-4.54 (m, 2H), 4.46-3.95 (m, 2H), 3.28 (m, 1H), 3.19-2.71 (m, 2H), 2.34-1.93 (m, 2H), 1.54-1.41 (m, 13H), 0.81-0.67 (m, 3H). LC/MS (Table 1, Method 25) R$_t$=0.977 min.; MS m/z: 493 [M+H]$^+$ & 495 [M+H+2]$^+$. SFC (Table 1, Method 46), R$_t$=8.05 min.

Step C. (3S,4S)-4-[(R)-7-(2-Fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester

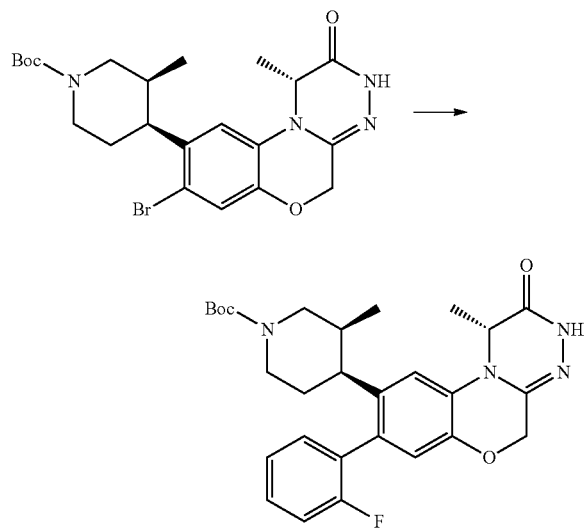

To a mixture of (2-fluorophenyl)boronic acid (0.019 g, 0.137 mmol), (3S,4S)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (0.045 g, 0.091 mmol) and K$_2$CO$_3$ (0.025 g, 0.182 mmol) in dioxane (12 mL) and water (2 mL) was added PdCl$_2$(dppf)-CH$_2$Cl$_2$ adduct (7.45 mg, 9.12 μmol) and the reaction mixture was heated at 90° C. overnight. The reaction mixture was cooled to ambient temperature and concentrated in vacuo. The residue was purified by prep-TLC (eluting with 55% EtOAc in petroleum ether) to give (3S,4S)-4-[(R)-7-(2-fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.036 g, 78%) as a white solid. $^1$H NMR (400 MHz, MeOD) δ 7.48-7.37 (m, 1H), 7.29-7.14 (m, 3H), 6.91 (s, 1H), 6.81 (s, 1H), 4.93 (m, 1H), 4.63-4.58 (m, 2H), 4.23 (m, 1H), 3.81 (m, 1H), 3.03-2.86 (m, 1H), 2.79-2.42 (m, 3H), 2.34-2.11 (m, 2H), 1.50-1.41 (m, 14H), 0.75 (m, 3H). LC/MS (Table 1, Method 4) R$_t$=2.830 min.; MS m/z: 531 [M+Na]$^+$ & 453 [M+H−56]$^+$. SFC (Table 1, Method 46), R$_t$=6.84 min.

Step D. (R)-7-(2-Fluoro-phenyl)-4-methyl-6-((3S,4S)-3-methyl-piperidin-4-yl)-2,10-dihydro-9-oxa-1,2,4a-triaza-phenanthren-3-one hydrochloride acid

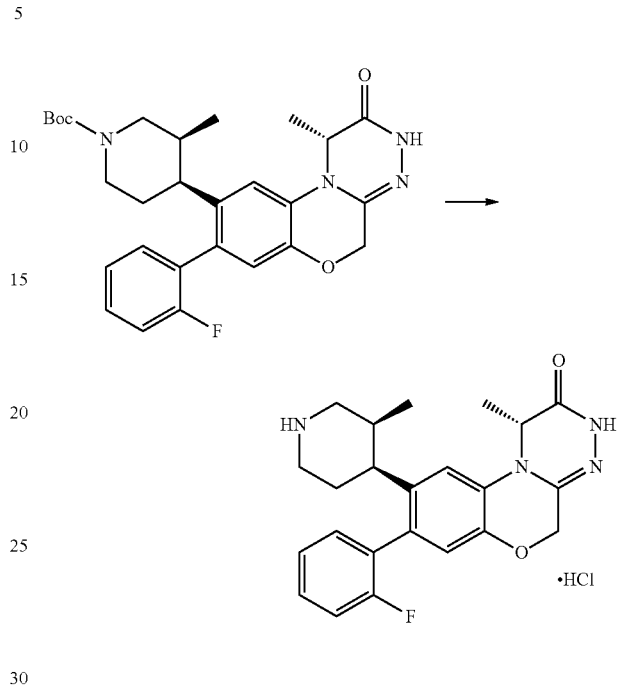

A mixture of (3S,4S)-4-[(R)-7-(2-fluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.035 g, 0.069 mmol) in HCl (4 M in EtOAc, 10 mL) was stirred at 20° C. for 2 h. The reaction mixture was concentrated in vacuo to give (R)-7-(2-fluoro-phenyl)-4-methyl-6-((3S,4S)-3-methyl-piperidin-4-yl)-2,10-dihydro-9-oxa-1,2,4a-triaza-phenanthren-3-one hydrochloride acid as a colorless solid (0.015 g, 53%). $^1$H NMR (400 MHz, MeOD) δ 7.52-7.41 (m, 1H), 7.35-7.18 (m, 3H), 6.93 (s, 1H), 6.86 (s, 1H), 4.90 (m, 1H), 4.65 (s, 2H), 3.47 (m, 1H), 3.22-2.94 (m, 4H), 2.84 (d, J=9.8 Hz, 1H), 2.55-2.27 (m, 2H), 2.00-1.80 (m, 3H), 1.51 (d, J=6.4 Hz, 3H), 1.00-0.80 (m, 3H). SFC (Table 1, Method 43), R$_t$=3.789 min., LC/MS (Table 1, Method 4) R$_t$=1.748 min.; MS m/z: 409 [M+H]$^+$.

Step E. (R)-6-((3S,4S)-1,3-Dimethyl-piperidin-4-yl)-7-(2-fluoro-phenyl)-4-methyl-2,10-dihydro-9-oxa-1,2,4a-triaza-phenanthren-3-one hydrochloride acid

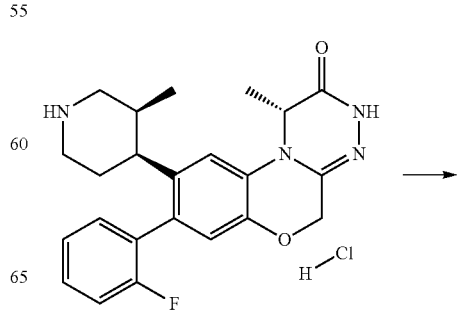

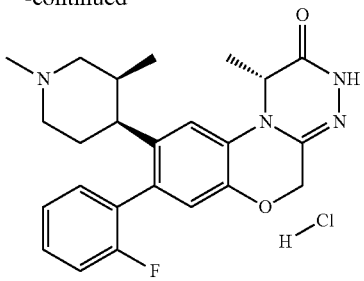

A mixture of (R)-7-(2-fluoro-phenyl)-4-methyl-6-((3S,4S)-3-methyl-piperidin-4-yl)-2,10-dihydro-9-oxa-1,2,4a-triaza-phenanthren-3-one hydrochloride acid (3.0 g, 6.74 mmol) and paraformaldehyde (0.506 g, 16.86 mmol) in MeOH (100 mL) and AcOH (10 mL) was stirred at ambient temperature for 2 h. Then, sodium cyanotrihydroborate (0.847 g, 13.49 mmol) was added and the reaction mixture was stirred at ambient temperature for 0.5 h. The reaction mixture was concentrated in vacuo and the residue was purified by column chromatography on basified silica gel (eluting with 10% MeOH in EA) to give (R)-6-((3S,4S)-1,3-dimethyl-piperidin-4-yl)-7-(2-fluoro-phenyl)-4-methyl-2,10-dihydro-9-oxa-1,2,4a-triaza-phenanthren-3-one (2.0 g, 65%) as a white solid. The white solid was stirred in HCl/EtOAc (4 M, 15 mL) for 30 min and the reaction mixture was concentrated in vacuo to give (R)-6-((3S,4S)-1,3-dimethyl-piperidin-4-yl)-7-(2-fluoro-phenyl)-4-methyl-2,10-dihydro-9-oxa-1,2,4a-triaza-phenanthren-3-one hydrochloride acid (1.65 g, 53%) as a white solid. $^1$H NMR (400 MHz, methanol-d$_4$) δ 7.49-7.40 (m, 1H), 7.33-7.17 (m, 3H), 6.91 (s, 1H), 6.85 (s, 1H), 4.99-4.93 (m, 1H), 4.70-4.65 (m, 2H), 3.60-3.50 (m, 1H), 3.25-3.00 (m, 3H), 2.90-2.85 (m, 1H), 2.80 (s, 3H), 2.55-2.45 (m, 1H), 2.01-1.84 (m, 2H), 1.49 (d, J=6.4 Hz, 3H), 1.00-0.90 (m, 3H). LC/MS (Table 1, Method 4) R$_t$=1.654 min.; MS m/z: 423 [M+H]$^+$. SFC (Table 1, Method 48), R$_t$=3.206 min.

TABLE 27

The following analogs were prepared from (3S,4S)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (Example #203 (Step B) using the procedure detailed in Example #203, Steps C-D (Ex. #204) and Steps C-E (Ex. #205).

| Structure | Example # | Boronate | R$_t$ min (method) | m/z ESI+ (M + H)$^+$ |
|---|---|---|---|---|
| 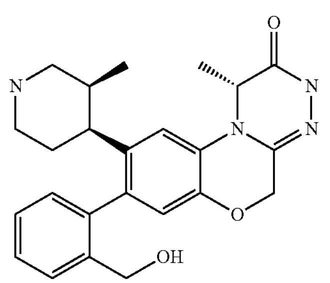 [SMILES: C[C@@H]1CNCC[C@@H]1c1cc2c(cc1-c1ccccc1CO)OCC1=NNC(=O)[C@@H](C)N12] | 204 | | 2.004 & 2.135 (Table 1, Method 5) | 421 |
| 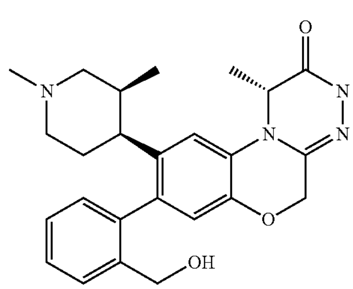 [SMILES: C[C@@H]1CN(C)CC[C@@H]1c1cc2c(cc1-c1ccccc1CO)OCC1=NNC(=O)[C@@H](C)N12] | 205 | | 1.427 & 1.553 (Table 1, Method 4) | 435 |

TABLE 28a

The following analog was prepared from (R)-7-(2-fluoro-phenyl)-4-methyl-6-((3R,4R)-3-methyl-piperidin-4-yl)-2,10-dihydro-9-oxa-1,2,4a-triaza-phenanthren-3-one hydrochloride acid (Example #199, Step F) using the procedure detailed in Example #138. The TBS group was also removed under the reaction conditions.

| Structure | Example # | Piperidine | Aldehyde | $R_t$ min (method) | m/z ESI+ $(M + H)^+$ |
|---|---|---|---|---|---|
| (structure) | 206 | (structure) | (structure) OTBS / CHO | 2.035 (Table 1, Method 44) | 453 |

TABLE 28

The following analog was prepared from (R)-7-(2-fluoro-phenyl)-4-methyl-6-((3S,4S)-3-methyl-piperidin-4-yl)-2,10-dihydro-9-oxa-1,2,4a-triaza-phenanthren-3-one hydrochloride acid (Example #203, Step D) using the procedure detailed in Example #138. The TBS group was also removed under the reaction conditions.

| Structure | Example # | Piperidine | Aldehyde | $R_t$ min (method) | m/z ESI+ $(M + H)^+$ |
|---|---|---|---|---|---|
| (structure) | 207 | (structure) | (structure) OTBS / CHO | 1.683 (Table 1, Method 4) | 453 |

TABLE 29a

The following analog was prepared from 4-((R)-7-bromo-4-methyl-3-oxo-2,3,4,10-tetrahydro-9-oxa-1,2,4a-triaza-phenanthren-6-yl)-piperidine-1-carboxylic acid tert-butyl ester (Preparation #8, Step B) using the procedure detailed in Example #199, Steps E-F and Example #76, Step B.

| Structure | Example # | Boronate | $R_t$ min (method) | m/z ESI+ $(M + H)^+$ |
|---|---|---|---|---|
| (structure) | 208 | (structure) | 1.585 (Table 1, Method 4) | 343 |

TABLE 29

The following analogs were prepared from 4-((R)-7-bromo-4-methyl-3-oxo-2,3,4,10-tetrahydro-9-oxa-1,2,4a-triaza-phenanthren-6-yl)-piperidine-1-carboxylic acid tert-butyl ester (Preparation #8, Step B) using the procedure detailed in Example #199, Steps E-F.

| Structure | Example # | Boronate | $R_t$ min (method) | m/z ESI+ $(M + H)^+$ |
|---|---|---|---|---|
| 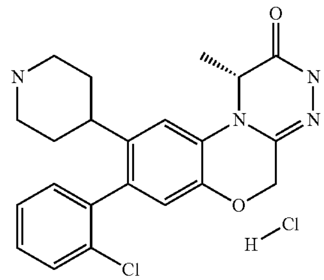 | 210 | | 1.884 (Table 1, Method 4) | 411 |
| 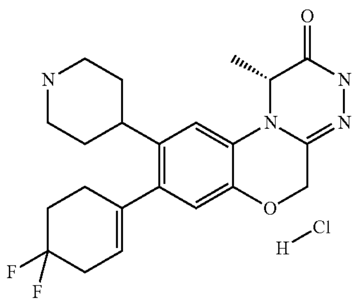 | 211 | | 1.846 (Table 1, Method 4) | 417 |

Example #212

(R)-7-(2-Fluoro-phenyl)-4-methyl-6-(1-methyl-piperidin-4-yl)-2,10-dihydro-9-oxa-1,2,4a-triaza-phenanthren-3-one

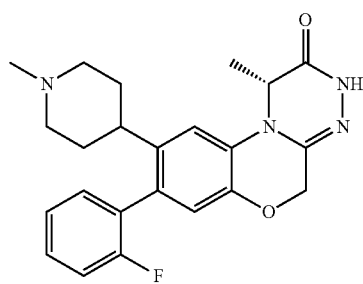 [SMILES: C[C@@H]1C(=O)NN=C2COc3cc(-c4ccccc4F)c(C4CCN(C)CC4)cc3N21]

Step A. (R)-7-(2-Fluoro-phenyl)-4-methyl-2,10-dihydro-9-oxa-1,2,4a-triaza-phenanthren-3-one

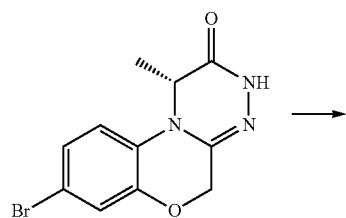

-continued

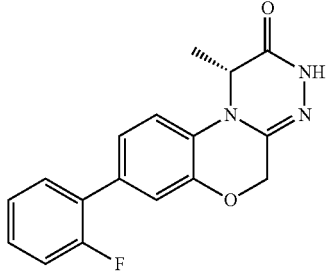

A mixture of (R)-7-bromo-4-methyl-2,10-dihydro-9-oxa-1,2,4a-triaza-phenanthren-3-one (Preparation #10, Step E, 5.0 g, 16.88 mmol), (2-fluorophenyl)boronic acid (3.54 g, 25.32 mmol), $K_2CO_3$ (4.67 g, 33.78 mmol) and 1,1'-bis(diphenylphosphino)ferrocene-palladium(II)dichloride dichloromethane complex (2.76 g, 3.37 mmol) in dioxane (60 mL) and water (10 mL) was stirred at 90° C. for 2 h. The reaction mixture was cooled to ambient temperature and the solvent was removed in vacuo. The residue was purified by column chromatography on silica gel (eluting with 10-50% EtOAc in petroleum ether) to give (R)-7-(2-fluoro-phenyl)-4-methyl-2,10-dihydro-9-oxa-1,2,4a-triaza-phenanthren-3-one (2.5 g, 46%) as a red solid. $^1$H NMR (400 MHz, DMSO-$d_6$) δ 10.81 (s, 1H), 7.51 (m, 1H), 7.43-7.13 (m, 6H), 4.83 (q, J=6.4 Hz, 1H), 4.69-4.60 (d, J=13.2 Hz, 2H), 1.33 (d, J=6.4 Hz, 3H).

Step B. (R)-6-Bromo-7-(2-fluoro-phenyl)-4-methyl-2,10-dihydro-9-oxa-1,2,4a-triaza-phenanthren-3-one

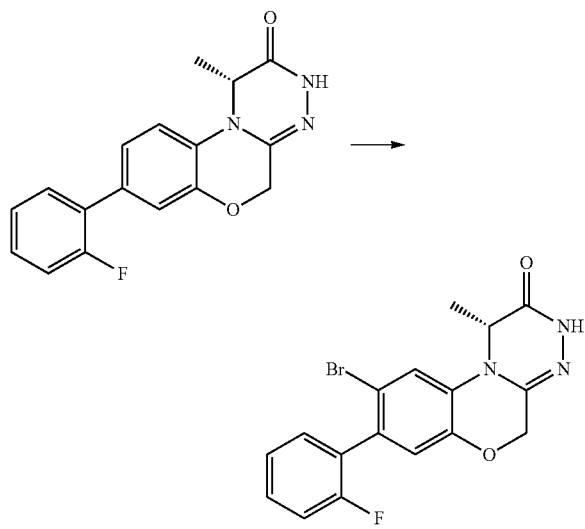

To a solution of (R)-7-(2-fluoro-phenyl)-4-methyl-2,10-dihydro-9-oxa-1,2,4a-triaza-phenanthren-3-one (2.4 g, 7.71 mmol) in TFA (20 mL) was added NBS (1.37 g, 7.71 mmol) in portions. The reaction mixture was stirred at ambient temperature for 3 h then concentrated in vacuo. The residue was purified by column chromatography on silica gel (eluting with 10-50% EtOAc in petroleum ether) to give (R)-6-bromo-7-(2-fluoro-phenyl)-4-methyl-2,10-dihydro-9-oxa-1,2,4a-triaza-phenanthren-3-one (2.2 g, 73%) as a colorless solid. $^1$H NMR (400 MHz, CDCl$_3$) δ 8.23 (brs, 1H), 7.45-7.36 (m, 1H), 7.30-7.11 (m, 5H), 6.99 (s, 1H), 4.74-4.69 (m, 1H), 4.69-4.55 (m, 2H), 1.58 (d, J=6.8 Hz, 3H).

Step C

4-[(R)-7-(2-Fluoro-phenyl)-4-methyl-3-oxo-2,3,4,10-tetrahydro-9-oxa-1,2,4a-triaza-phenanthren-6-yl]-3,6-dihydro-2H-pyridine-1-carboxylic acid tert-butyl ester

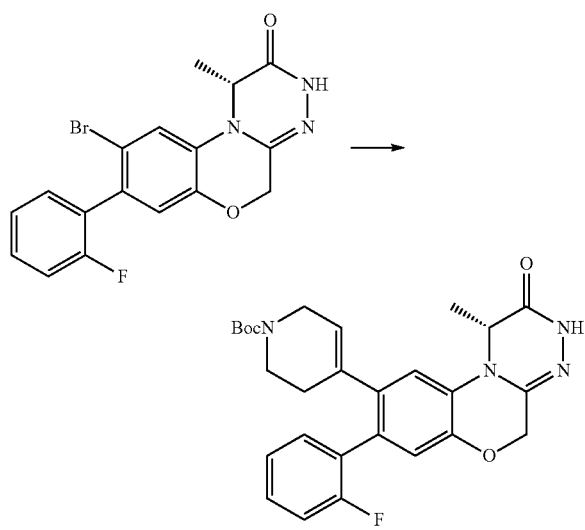

A mixture of (R)-6-bromo-7-(2-fluoro-phenyl)-4-methyl-2,10-dihydro-9-oxa-1,2,4a-triaza-phenanthren-3-one (2.0 g, 5.13 mmol), tert-butyl 4-(4,4,5,5-tetramethyl-1,3,2-dioxaborolan-2-yl)-5,6-dihydropyridine-1(2H)-carboxylate (2.38 g, 7.69 mmol), 1,1'-bis(diphenylphosphino)ferrocene-palladium(II)dichloride dichloromethane complex (0.84 g, 1.03 mmol) and K$_2$CO$_3$ (1.42 g, 10.25 mmol) in dioxane (21 mL) and water (7 mL) was heated at 90° C. overnight. The mixture was cooled to ambient temperature and concentrated in vacuo. The residue was purified by column chromatography on silica gel (eluting with 10-50% EtOAc in petroleum ether) to give 4-[(R)-7-(2-fluoro-phenyl)-4-methyl-3-oxo-2,3,4,10-tetrahydro-9-oxa-1,2,4a-triaza-phenanthren-6-yl]-3,6-dihydro-2H-pyridine-1-carboxylic acid tert-butyl ester (1.6 g, 61%) as a yellow solid. $^1$H-NMR (400 MHz, CDCl$_3$) δ 8.64 (brs, 1H), 7.36-7.20 (m, 3H), 7.19-7.05 (m, 2H), 6.99 (s, 1H), 6.81 (s, 1H), 5.49 (brs, 1H), 4.79 (q, J=6.4 Hz, 1H), 4.72-4.57 (m, 2H), 3.88 (brs, 2H), 3.35 (m, 2H), 2.06 (brs, 2H), 1.60-1.57 (m, 3H), 1.47 (s, 9H).

Step D. 4-[(R)-7-(2-fluoro-phenyl)-4-methyl-3-oxo-2,3,4,10-tetrahydro-9-oxa-1,2,4a-triaza-phenanthren-6-yl]-piperidine-1-carboxylic acid tert-butyl ester

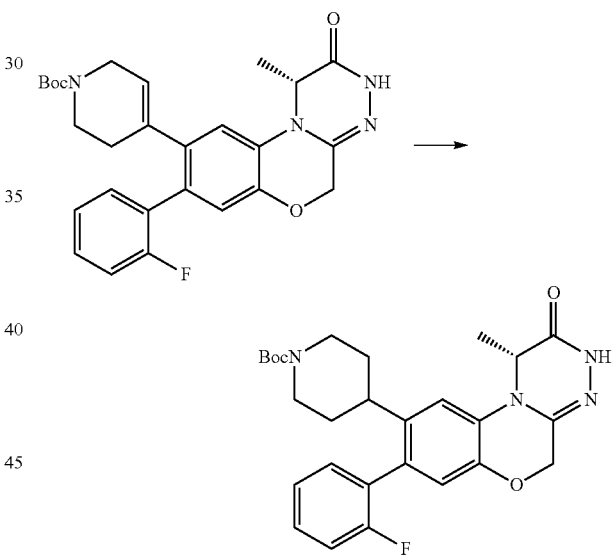

To a suspension of Pd/C (10%, 0.324 g, 3.05 mmol) in MeOH (30 mL) was added 4-[(R)-7-(2-fluoro-phenyl)-4-methyl-3-oxo-2,3,4,10-tetrahydro-9-oxa-1,2,4a-triaza-phenanthren-6-yl]-3,6-dihydro-2H-pyridine-1-carboxylic acid tert-butyl ester (1.5 g, 3.05 mmol) and the reaction mixture was stirred at 50° C. under H$_2$ (50 psi) overnight. The reaction mixture was cooled to ambient temperature, filtered and the filtrate was concentrated in vacuo to give 4-[(R)-7-(2-fluoro-phenyl)-4-methyl-3-oxo-2,3,4,10-tetrahydro-9-oxa-1,2,4a-triaza-phenanthren-6-yl]-piperidine-1-carboxylic acid tert-butyl ester (1.2 g, 80%) as a yellow solid. $^1$H NMR (400 MHz, methanol-d$_4$) δ 7.49-7.38 (m, 1H), 7.31-7.16 (m, 3H), 7.09 (s, 1H), 6.82 (s, 1H), 5.00-4.94 (m, 1H), 4.68-4.57 (m, 2H), 4.24-4.07 (m, 2H), 2.58 (m, 3H), 1.76 (m, 2H), 1.67-1.56 (m, 2H), 1.50-1.46 (m, 12H).

367

Step E. (R)-7-(2-fluoro-phenyl)-4-methyl-6-piperidin-4-yl-2,10-dihydro-9-oxa-1,2,4a-triaza-phenanthren-3-one hydrochloride acid

368

Step F. (R)-7-(2-Fluoro-phenyl)-4-methyl-6-(1-methyl-piperidin-4-yl)-2,10-dihydro-9-oxa-1,2,4a-triaza-phenanthren-3-one

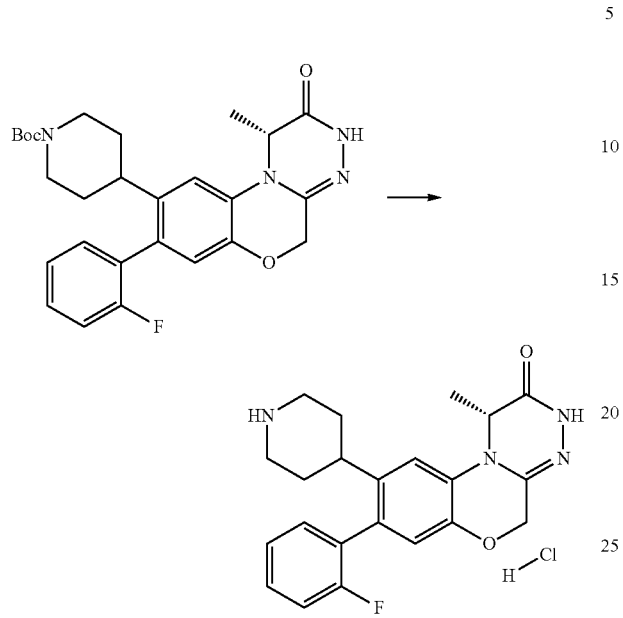

To HCl (1 M in EtOAc, 10 mL) was added 4-[(R)-7-(2-fluoro-phenyl)-4-methyl-3-oxo-2,3,4,10-tetrahydro-9-oxa-1,2,4a-triaza-phenanthren-6-yl]-piperidine-1-carboxylic acid tert-butyl ester (1 g, 2.20 mmol) and the reaction mixture was stirred at ambient temperature for 1 h. The solvent was removed in vacuo to give (R)-7-(2-fluoro-phenyl)-4-methyl-6-piperidin-4-yl-2,10-dihydro-9-oxa-1,2,4a-triaza-phenanthren-3-one hydrochloride (0.65 g, 81%) as a yellow solid. $^1$H NMR (400 MHz, methanol-$d_4$) δ 7.51-7.41 (m, 1H), 7.32-7.27 (m, 2H), 7.23 (t, J=9.0 Hz, 1H), 7.03 (s, 1H), 6.87 (s, 1H), 5.01-4.95 (m, 1H), 4.70-4.60 (m, 2H), 3.50-3.38 (m, 2H), 3.01-2.69 (m, 3H), 2.05 (m, 2H), 1.90 (m, 2H), 1.52 (m, 3H). LCMS (Table 1, Method 5) $R_t$=2.351 min; MS m/z: 395[M+H]$^+$.

To a solution of MeOH (10 mL) and acetic acid (1 mL) was added (R)-7-(2-fluoro-phenyl)-4-methyl-6-piperidin-4-yl-2,10-dihydro-9-oxa-1,2,4a-triaza-phenanthren-3-one hydrochloride acid (0.300, 0.761 mmol) and paraformaldehyde (0.228 g, 7.61 mmol) and the reaction mixture was stirred at rt for 4 h. Then NaCNBH$_3$ (0.096 g, 1.52 mmol) was added and the reaction mixture was stirred for 30 min. The solvent was removed in vacuo and the residue was purified by prep-TLC (eluting with 10% MeOH in DCM) to give (R)-7-(2-fluoro-phenyl)-4-methyl-6-(1-methyl-piperidin-4-yl)-2,10-dihydro-9-oxa-1,2,4a-triaza-phenanthren-3-one (0.160 g, 51%) as a white solid. $^1$H NMR (400 MHz, methanol-$d_4$) δ 7.50-7.41 (m, 1H), 7.32-7.26 (m, 2H), 7.25-7.19 (m, 1H), 7.09 (s, 1H), 6.86 (s, 1H), 5.02-4.93 (m, 1H), 4.70-4.59 (m, 2H), 3.63-3.46 (m, 2H), 3.04-2.89 (m, 2H), 2.84 (s, 3H), 2.76 (m, 1H), 2.28-2.01 (m, 3H), 1.96-1.83 (m, 1H), 1.52 (d, J=6.4 Hz, 3H). LCMS (Table 1, Method 4) Rt=1.617 min; MS m/z: 409 [M+H]$^+$.

TABLE 30

The following analog was prepared from (R)-4-methyl-7-(4,4,5,5-tetramethyl-[1,3,2]dioxaborolan-2-yl)-2,10-dihydro-9-oxa-1,2,4a-triaza-phenanthren-3-one (Preparation #10, Step F), using the procedure detailed in Example #212, Steps A-E.

| Structure | Example # | Halogen | $R_t$ min (method) | m/z ESI+ (M + H)$^+$ |
|---|---|---|---|---|
| 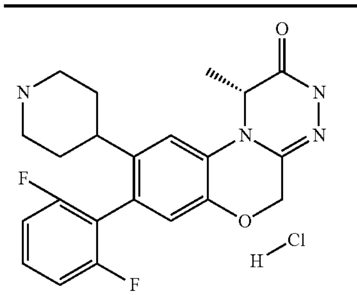 | 213 | F | 2.415 (Table 1, Method 4) | 413 |

TABLE 31

The following analogs were prepared from (R)-6-bromo-7-(2-fluoro-phenyl)-4-methyl-2,10-dihydro-9-oxa-1,2,4a-triaza-phenanthren-3-one (Example #212, Step B), using the procedure detailed in Example #212, Steps C-E and routine SFC separation.

| Structure | Example # | OTf | R$_t$ min (method) | m/z ESI+ (M + H)+ |
|---|---|---|---|---|
| 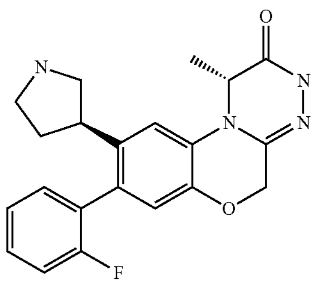 [SMILES: C[C@@H]1C(=O)NN=C2COc3cc(-c4ccccc4F)c([C@H]4CCNC4)cc3N21] | 214 | | 2.374 (Table 1, Method 4) | 381 |
| 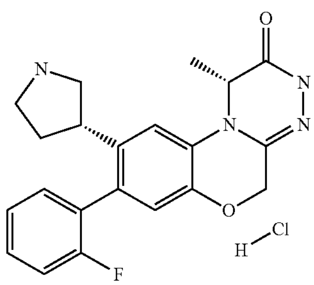 | 215 | | 2.331 (Table 1, Method 4) | 381 |
| 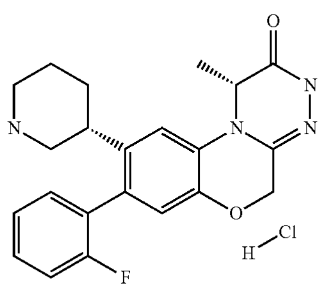 | 216 | | 1.613 (Table 1, Method 4) | 395 |
| 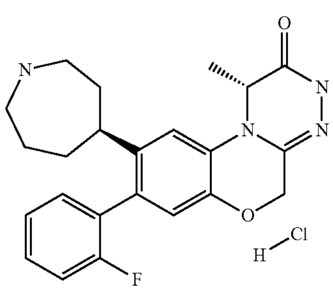 | 217 | | 1.678 (Table 1, Method 4) | 409 |
| 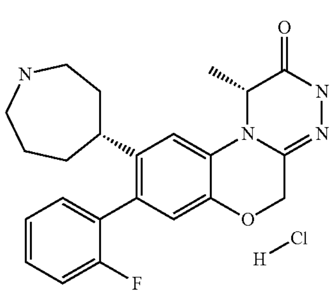 | 218 | | 1.67 (Table 1, Method 4) | 409 |

TABLE 32

The following analogs were prepared from corresponding secondary amine as shown using the procedure detailed in Example #212, Step F.

| Structure | Example # | Secondary amine | R$_t$ min (method) | m/z ESI+ (M + H)+ |
|---|---|---|---|---|
| | 219 | | Example #208 | 1.56 (Table 1, Method 4) | 357 |
| | 220 | | Example #214 | 2.334 (Table 1, Method 4) | 395 |
| | 221 | | Example #215 | 2.362 (Table 1, Method 4) | 395 |

Example #222

(R)-7-(2-Fluoro-phenyl)-4-methyl-6-piperazin-1-yl-2,10-dihydro-9-oxa-1,2,4a-triaza-phenanthren-3-one

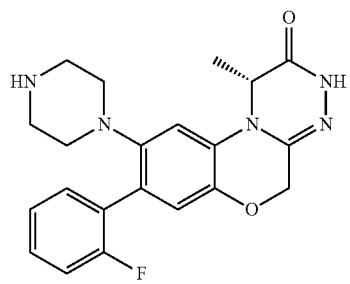 [SMILES: C[C@@H]1C(=O)NN=C2COc3cc(-c4ccccc4F)c(N4CCNCC4)cc3N21]

Step A. 4-[4-Methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester

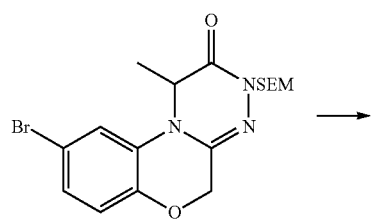

→

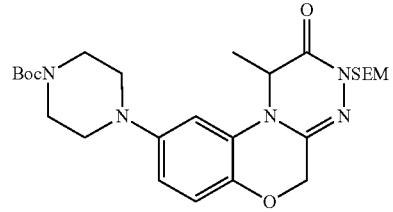

To a mixture of 6-bromo-4-methyl-2-(2-trimethylsilanyl-ethoxymethyl)-2,10-dihydro-9-oxa-1,2,4a-triaza-phenanthren-3-one (Preparation #1, Step E, 0.5 g, 1.173 mmol), tert-butyl piperazine-1-carboxylate (0.655 g, 3.52 mmol) and sodium 2-methylpropan-2-olate (0.225 g, 2.345 mmol) in toluene (50 mL) was added dicyclohexyl(2',4',6'-triisopropyl-[1,1'-biphenyl]-2-yl)phosphine (0.224 g, 0.469 mmol) and diacetoxypalladium (0.026 g, 0.117 mmol) and the reaction mixture was heated at reflux overnight. The reaction mixture was cooled to ambient temperature and concentrated in vacuo. The residue was purified by column chromatography on silica gel (eluting with 3-20% EtOAc in petroleum ether) to give 4-[4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.210 g, 33%). $^1$H NMR (400 MHz, CDCl$_3$) δ 6.92 (d, J=8.8 Hz, 1H), 6.56 (dd, J=2.6, 8.7 Hz, 1H), 6.50 (d, J=2.5 Hz, 1H), 5.18-5.05 (m, 2H), 4.73 (q, J=6.6 Hz, 1H), 4.65-4.52 (m, 2H), 3.67 (t, J=8.4 Hz, 2H), 3.63-3.57 (m, 4H), 3.04 (d, J=4.0 Hz, 4H), 1.58 (s, 5H), 1.51-1.46 (m, 12H), 1.03-0.94 (m, 2H), 0.02 (s, 9H).

Step B. 4-[7-Bromo-4-methyl-3-oxo-2-(2-trimethyl-silanyl-ethoxymethyl)-2,3,4,10-tetrahydro-9-oxa-1,2,4a-triaza-phenanthren-6-yl]-piperazine-1-carboxylic acid tert-butyl ester

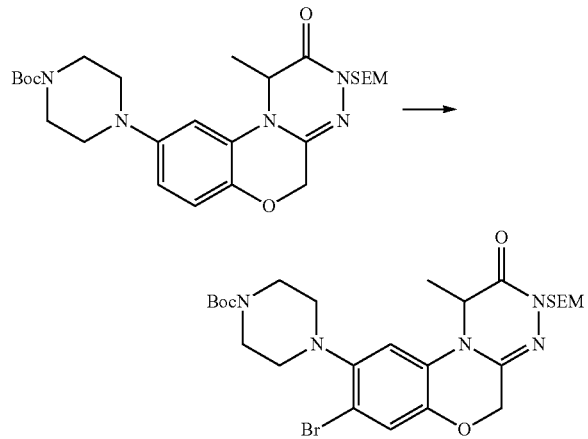

To a mixture of 4-[4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.23 g, 0.433 mmol) in DCM (8 mL) and MeOH (4 mL) was added tetra-N-butylammonium tribromide (0.219 g, 0.454 mmol) and the reaction mixture was stirred at rt for 30 min. The reaction mixture was concentrated in vacuo and the residue was purified by column chromatography on silica gel (eluting with 3-15% EtOAc in petroleum ether) to give 4-[7-bromo-4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.22 g, 83%) as a white solid. $^1$H NMR (400 MHz, CDCl$_3$) δ 7.24 (s, 1H), 6.56 (s, 1H), 5.15-5.06 (m, 2H), 4.72-4.66 (m, 1H), 4.66-4.54 (d, J=13.2 Hz, 2H), 3.65 (m, 6H), 2.92 (m, 4H), 1.57 (s, 6H), 1.50 (s, 9H), 1.47 (d, J=6.8 Hz, 3H), 0.03-0.00 (m, 9H).

Step C. 4-[7-(2-Fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester

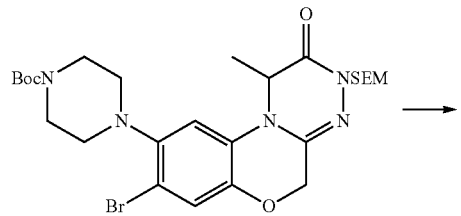

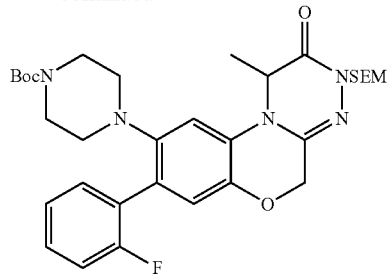

To a mixture of 4-[7-bromo-4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.31 g, 0.508 mmol), (2-fluorophenyl)boronic acid (0.107 g, 0.762 mmol), potassium carbonate (0.140 g, 1.015 mmol) in dioxane (12 mL) and water (2 mL) was added PdCl$_2$(dppf)-CH$_2$Cl$_2$ adduct (0.041 g, 0.051 mmol) and the reaction mixture was heated at 90° C. overnight. The reaction mixture was cooled to ambient temperature and concentrated in vacuo. The residue was purified by column chromatography on silica gel (eluting with 3-15% EtOAc in petroleum ether) to give 4-[7-(2-fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.22 g, 69%) as a white solid. $^1$H NMR (400 MHz, CDCl$_3$) δ 7.40 (m, 1H), 7.32 (m, 1H), 7.21-7.09 (m, 2H), 6.95 (s, 1H), 6.61 (s, 1H), 5.19-5.07 (m, 1H), 4.76 (q, J=6.8 Hz, 1H), 4.72-4.57 (d, J=13.2 Hz, 2H), 3.71-3.64 (m, 2H), 3.25 (m, 4H), 2.71 (t, J=4.8 Hz, 4H), 1.52 (d, J=6.8 Hz, 3H), 1.44 (s, 9H), 1.04-0.93 (m, 2H), 0.05-0.02 (m, 9H)

Step D. 4-[7-(2-Fluoro-phenyl)-4-methyl-3-oxo-2,3,4,10-tetrahydro-9-oxa-1,2,4a-triaza-phenanthren-6-yl]-piperazine-1-carboxylic acid tert-butyl ester

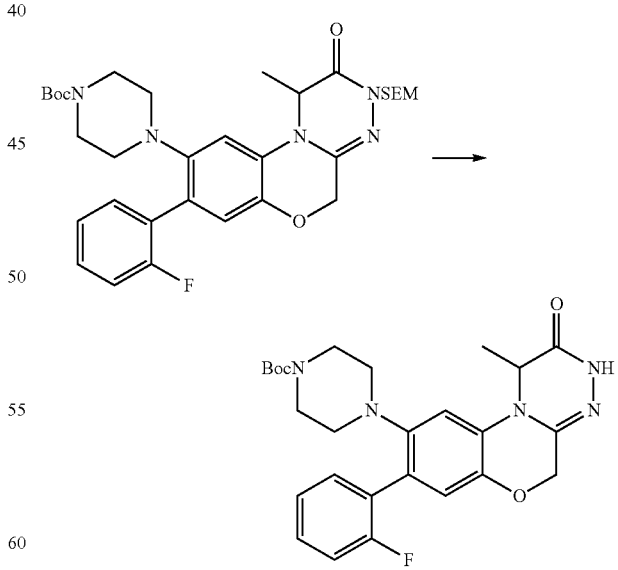

4-[7-(2-Fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (0.2 g, 0.320 mmol) was dissolved in tetrabutylammonium fluoride (1M in THF, 20 mL, 20.00 mmol) and the reaction mixture was heated at 80° C. overnight. The reaction mixture was cooled to ambient temperature, quenched by the addition of water (20 mL) and extracted with EtOAc (3×15 mL). The combined organic phase was washed with brine (2×30 mL) and concentrated in vacuo. The residue was purified by column chromatography on silica gel (eluting with 7-50% EtOAc in petroleum ether) to give 4-[7-(2-fluoro-phenyl)-4-methyl-3-oxo-2,3,4,10-tetrahydro-9-oxa-1,2,4a-triaza-phenanthren-6-yl]-piperazine-1-carboxylic acid tert-butyl ester (0.086 g, 54%) as a colorless solid. $^1$H NMR (400 MHz, CDCl$_3$) δ 8.07 (brs, 1H), 7.40 (m, 1H), 7.36-7.29 (m, 1H), 7.22-7.09 (m, 2H), 6.96 (s, 1H), 6.62 (s, 1H), 4.75 (q, J=6.8 Hz, 1H), 4.60 (d, J=13.2 Hz, 2H), 3.26 (brs, 4H), 2.72 (brs, 4H), 1.57 (s, 3H), 1.45 (s, 9H).

Step E. 7-(2-Fluoro-phenyl)-4-methyl-6-piperazin-1-yl-2,10-dihydro-9-oxa-1,2,4a-triaza-phenanthren-3-one hydrochloride

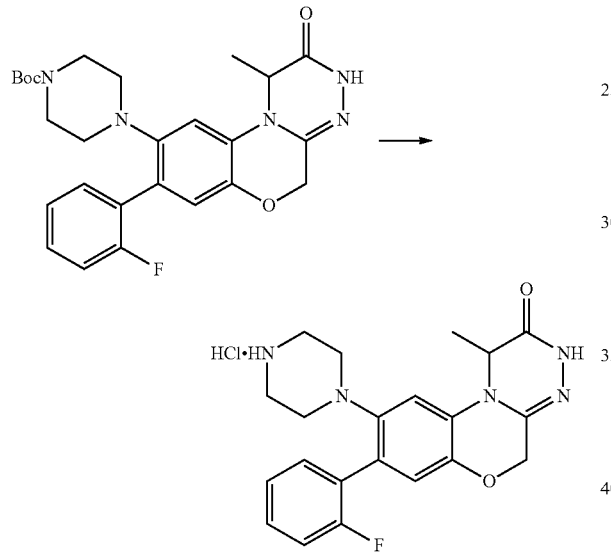

A mixture of 4-[7-(2-fluoro-phenyl)-4-methyl-3-oxo-2,3,4,10-tetrahydro-9-oxa-1,2,4a-triaza-phenanthren-6-yl]-piperazine-1-carboxylic acid tert-butyl ester (0.076 g, 0.153 mmol) in HCl (4M in EtOAc, 30 mL) was stirred at rt for 2 h. The reaction mixture was concentrated in vacuo to give 7-(2-fluoro-phenyl)-4-methyl-6-piperazin-1-yl-2,10-dihydro-9-oxa-1,2,4a-triaza-phenanthren-3-one hydrochloride (0.065 g, 96%) as a white solid. $^1$H NMR (400 MHz, MeOD) δ 7.45-7.34 (m, 2H), 7.29-7.14 (m, 2H), 6.92 (s, 2H), 4.89 (q, J=6.8 Hz, 1H), 4.65-4.56 (d, J=13.2 Hz, 2H), 3.03 (m, 8H), 1.48 (d, J=6.8 Hz, 3H).

Step F. (R)-7-(2-Fluoro-phenyl)-4-methyl-6-piperazin-1-yl-2,10-dihydro-9-oxa-1,2,4a-triaza-phenanthren-3-one

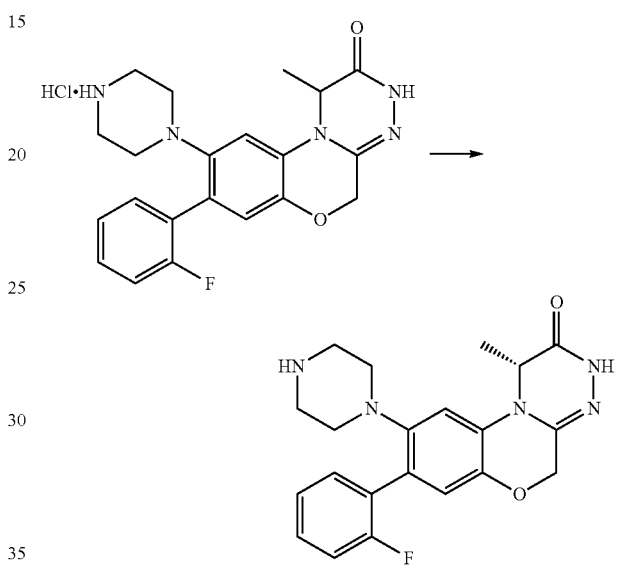

7-(2-Fluoro-phenyl)-4-methyl-6-piperazin-1-yl-2,10-dihydro-9-oxa-1,2,4a-triaza-phenanthren-3-one hydrochloride was purified by SFC (Table 2, Method 23) to give (R)-7-(2-fluoro-phenyl)-4-methyl-6-piperazin-1-yl-2,10-dihydro-9-oxa-1,2,4a-triaza-phenanthren-3-one (0.023 g, 0.058 mmol). $^1$H NMR (400 MHz, methanol-d$_4$) δ 7.48-7.33 (m, 2H), 7.28-7.13 (m, 2H), 6.95-6.85 (m, 2H), 4.66-4.56 (m, 3H), 2.92-2.76 (m, 8H), 1.51 (d, J=6.8 Hz, 3H). LC/MS (Table 1, Method 4) R$_t$=1.692 min.; MS m/z: 396 [M+H]$^+$. SFC (Table 1, Method 43) R$_t$=3.975 min.,

TABLE L

The following analogs were prepared from 6-bromo-4-methyl-2-(2-trimethylsilanyl-ethoxymethyl)-2,10-dihydro-9-oxa-1,2,4a-triaza-phenanthren-3-one (Preparation #1, Step E) using the procedure detailed in Example #222, Steps A-F and routine SFC separation.

| Structure | Example # | Piperazine | R$_t$ min (method) | m/z ESI+ (M + H)$^+$ |
|---|---|---|---|---|
| 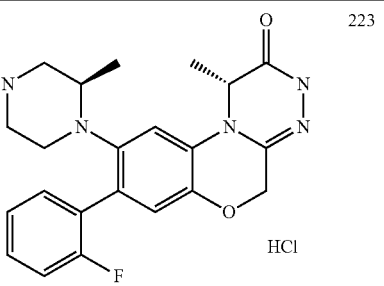 | 223 | 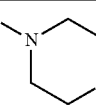 | 1.667 (Table 1, Method 4) | 410 |

TABLE L-continued

The following analogs were prepared from 6-bromo-4-methyl-2-(2-trimethylsilanyl-ethoxymethyl)-2,10-dihydro-9-oxa-1,2,4a-triaza-phenanthren-3-one (Preparation #1, Step E) using the procedure detailed in Example #222, Steps A-F and routine SFC separation.

| Structure | Example # | Piperazine | $R_t$ min (method) | m/z ESI+ $(M + H)^+$ |
|---|---|---|---|---|
| 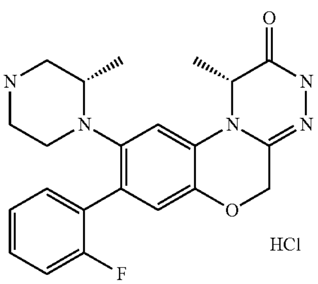 [SMILES: C[C@@H]1C(=O)NN=C2COc3cc(-c4ccccc4F)c(N4CCNC[C@@H]4C)cc3N21 ; Cl] | 224 | | 2.336 (Table 1, Method 5) | 410 |
| 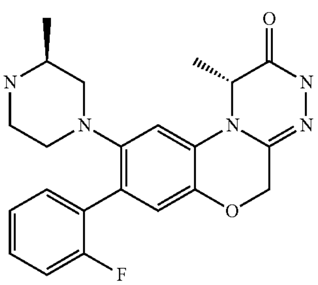 [SMILES: C[C@@H]1C(=O)NN=C2COc3cc(-c4ccccc4F)c(N4CCN[C@@H](C)C4)cc3N21] | 225 | | 1.691 (Table 1, Method 4) | 410 |
| 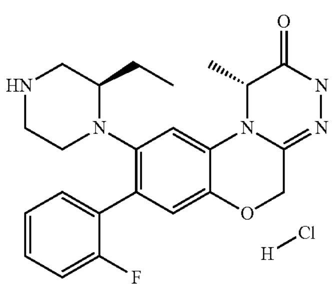 | 226 | | 1.789 (Table 1, Method 4) | 424 |
| 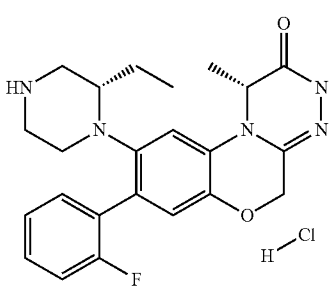 | 227 | | 1.803 (Table 1, Method 4) | 424 |
| 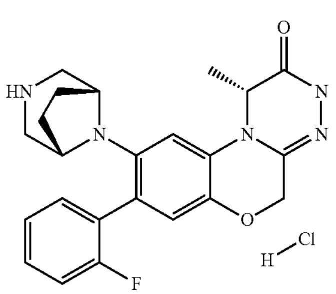 | 228 | | 2.273 (Table 1, Method 5) | 422 |

TABLE L-continued

The following analogs were prepared from 6-bromo-4-methyl-2-(2-trimethylsilanyl-ethoxymethyl)-2,10-dihydro-9-oxa-1,2,4a-triaza-phenanthren-3-one (Preparation #1, Step E) using the procedure detailed in Example #222, Steps A-F and routine SFC separation.

| Structure | Example # | Piperazine | R$_t$ min (method) | m/z ESI+ (M + H)$^+$ |
|---|---|---|---|---|
| 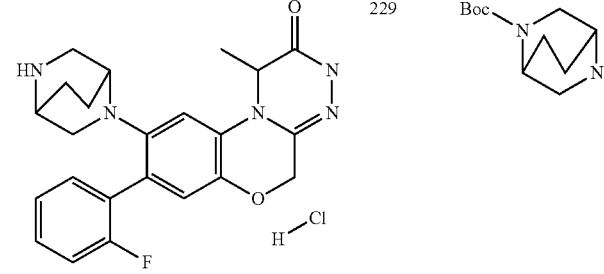 | 229 |  | 1.707 (Table 1, Method 4) | 422 |

TABLE 33

The following analogs were prepared from the corresponding piperazine using the procedure detailed in Example #212, Step F.

| Structure | Ex # | Piperazine | R$_t$ min (method) | m/z ESI+ (M + H)$^+$ |
|---|---|---|---|---|
| 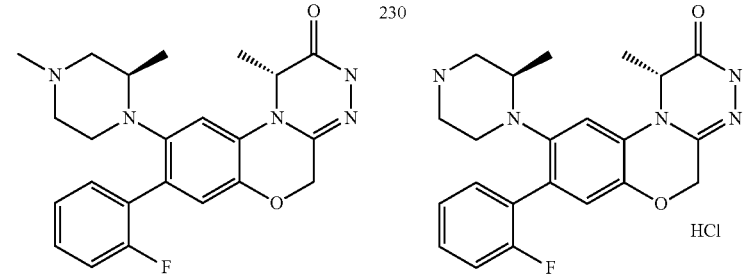 | 230 |  | Example #223 1.655 (Table 1, Method 4) | 424 |
| 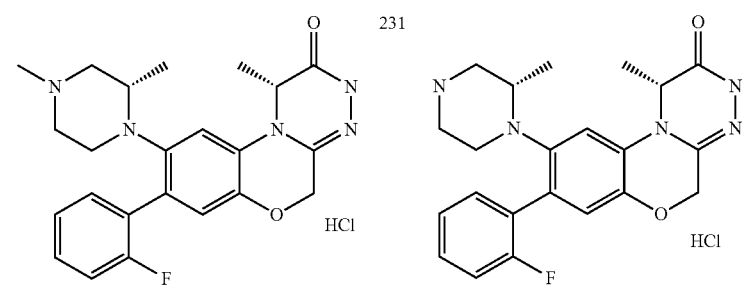 | 231 | 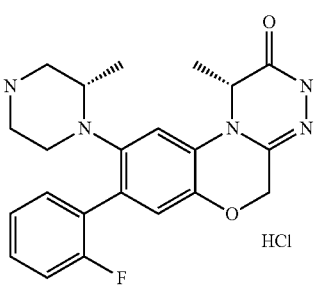 [SMILES: C[C@@H]1C(=O)NN=C2COc3cc(-c4ccccc4F)c(N4CCNC[C@@H]4C)cc3N21 ; Cl] | Example #224 2.196 (Table 1, Method 4) | 468 |
| 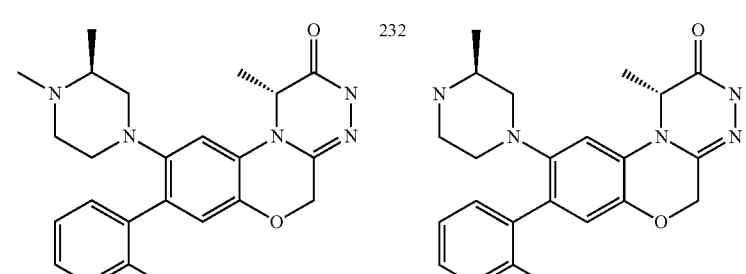 | 232 |  | Example #225 1.672 (Table 1, Method 4) | 424 |

TABLE 33-continued

The following analogs were prepared from the corresponding piperazine using the procedure detailed in Example #212, Step F.

| Structure | Ex # | Piperazine | R<sub>t</sub> min (method) | m/z ESI+ (M + H)+ |
|---|---|---|---|---|
| | 233 | | Example #226 | 1.712 (Table 1, Method 4) | 438 |
| | 234 | | Example #227 | 1.802 (Table 1, Method 4) | 438 |
| | 235 | | Example #228 | 2.292 (Table 1, Method 5) | 436 |
| | 236 | | Example #229 | 1.716 (Table 1, Method 4) | 436 |

Example #237

(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one

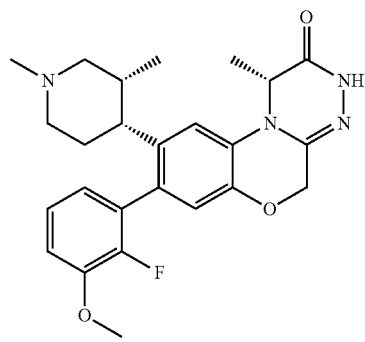 [SMILES: COc1cccc(-c2cc3c(cc2[C@@H]2CCN(C)C[C@@H]2C)N2C(=NNC(=O)[C@H]2C)CO3)c1F]

Step A. (R)-7-Bromo-4-methyl-6-((3R,4R)-3-methyl-piperidin-4-yl)-2,10-dihydro-9-oxa-1,2,4a-triaza-phenanthren-3-one hydrochloride

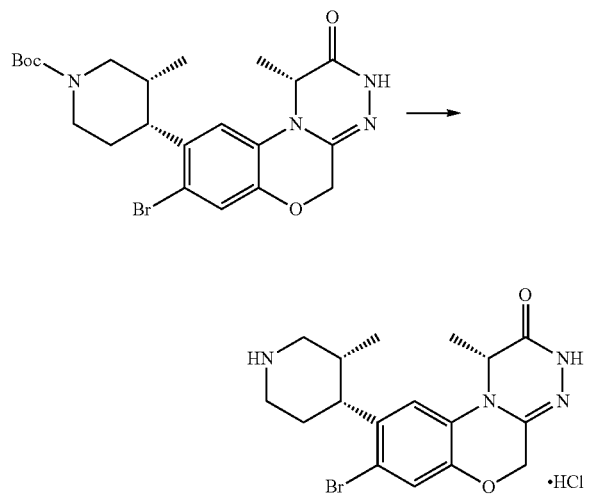 [SMILES: C[C@@H]1C(=O)NN=C2COc3cc(Br)c([C@@H]4CCN(C(=O)OC(C)(C)C)C[C@@H]4C)cc3N21 ; C[C@@H]1C(=O)NN=C2COc3cc(Br)c([C@@H]4CCNC[C@@H]4C)cc3N21 ; Cl]

A solution of (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (Example #199, Step D, 3 g, 6.08 mmol) in HCl (4M in EtOAc, 10 mL) was stirred at ambient temperature for 1 h. The organic solvent was removed in vacuo to give crude (R)-7-bromo-4-methyl-6-((3R,4R)-3-methyl-piperidin-4-yl)-2,10-dihydro-9-oxa-1,2,4a-triaza-phenanthren-3-one hydrochloride (2.2 g, 82%) as a white solid, which was used directly in the next step. LC/MS (Table 1, Method 25) $R_t$=0.720 min.; MS m/z: 393 [M+H]$^+$ & 395 [M+H+2]$^+$.

Step B. (R)-7-Bromo-6-((3R,4R)-1,3-dimethyl-piperidin-4-yl)-4-methyl-2,10-dihydro-9-oxa-1,2,4a-triaza-phenanthren-3-one

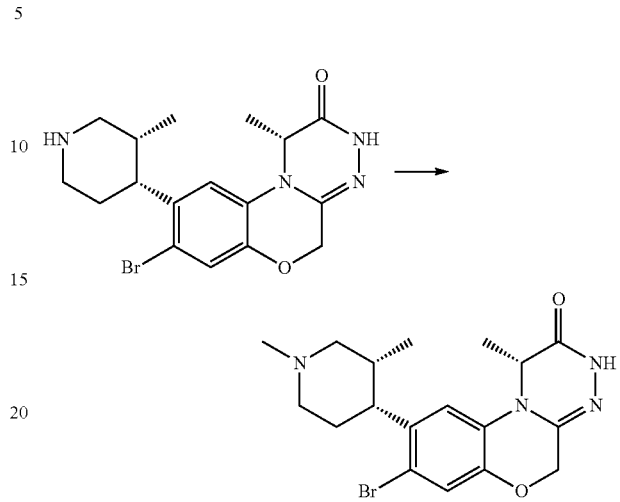

To a solution of (R)-7-bromo-4-methyl-6-((3R,4R)-3-methyl-piperidin-4-yl)-2,10-dihydro-9-oxa-1,2,4a-triaza-phenanthren-3-one (2.2 g, 5.59 mmol) in AcOH (10 mL) and MeOH (100 mL) was added paraformaldehyde (0.839 g, 28.0 mmol). The reaction mixture was stirred at ambient temperature for 1 h. NaBH$_3$CN (0.557 g, 14.0 mmol) was added and the resulting mixture was stirred at ambient temperature overnight. Aqueous saturated NaHCO$_3$ solution (30 mL) was added and the reaction mixture was extracted with EtOAc (3×50 mL). The combined organic phase was dried over anhydrous sodium sulfate, filtered and concentrated in vacuo. The residue was purified by a reverse-phase preparatory HPLC (Table 3, Method 35) to give (R)-7-bromo-6-((3R,4R)-1,3-dimethyl-piperidin-4-yl)-4-methyl-2,10-dihydro-9-oxa-1,2,4a-triaza-phenanthren-3-one (1.8 g, 79%). $^1$H NMR (400 MHz, CD$_3$OD) δ 7.22 (s, 1H), 6.86 (s, 1H), 4.87-4.91 (m, 1H), 4.58 (d, J=13.2 Hz, 2H), 3.15 (m, 1H), 3.04 (m, 1H), 2.84 (m, 1H), 2.23-2.39 (m, 6H), 2.07-2.18 (m, 1H), 1.55 (m, 1H), 1.43 (d, J=6.5 Hz, 3H), 0.83 (d, J=7.0 Hz, 3H). LC/MS (Table 1, Method 25) $R_t$=0.681 min.; MS m/z: 407 [M+H]$^+$ & 409 [M+H+2]$^+$.

Step C.

(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one

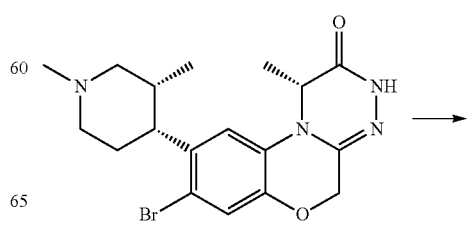

-continued

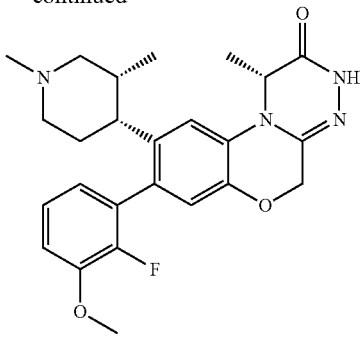

A mixture of (R)-7-bromo-6-((3R,4R)-1,3-dimethyl-piperidin-4-yl)-4-methyl-2,10-dihydro-9-oxa-1,2,4a-triaza-phenanthren-3-one (0.050 g, 0.123 mmol), (2-fluoro-3-methoxyphenyl)boronic acid (0.025 g, 0.147 mmol), $K_2CO_3$ (0.034 g, 0.246 mmol) and $PdCl_2(dppf)\text{-}CH_2Cl_2$ adduct (0.020 g, 0.025 mmol) in dioxane (3 mL) and water (0.5 mL) was stirred at 90° C. overnight. The reaction mixture was cooled to ambient temperature and concentrated in vacuo. The residue was purified by preparative TLC (eluting with 17% MeOH in EtOAc) to give (R)-6-((3R,4R)-1,3-dimethyl-piperidin-4-yl)-7-(2-fluoro-3-methoxy-phenyl)-4-methyl-2,10-dihydro-9-oxa-1,2,4a-triaza-phenanthren-3-one (0.0248 g, 45%) as a solid. $^1$H NMR (400 MHz, $CD_3OD$): δ 7.14 (m, 2H), 6.96-6.90 (m, 1H), 6.81-6.72 (m, 2H), 4.95-4.91 (m, 1H), 4.60 (d, J=13.2 Hz, 2H), 3.90 (s, 3H), 3.13 (m, 1H), 3.00-2.74 (m, 2H), 2.34 (m, 3H), 2.19 (m, 2H), 2.14 (m, 1H), 1.67 (m, 2H), 1.48 (m, 3H), 0.89-0.79 (m, 3H). LC/MS (Table 1, Method 4) $R_t$=2.075 min.; MS m/z: 453 $[M+H]^+$. SFC (Table 2, Method 27), $R_t$=3.239 min.

TABLE 33a

The following analogs were prepared from (R)-7-bromo-6-((3R,4R)-1,3-dimethyl-piperidin-4-yl)-4-methyl-2,10-dihydro-9-oxa-1,2,4a-triaza-phenanthren-3-one (Example #237, Step B) using the similar procedure detailed in Example #237, Step C.

| Structure | Ex # | Boronic acid or boronic ester | $R_t$ min (method) | m/z ESI+ $(M + H)^+$ |
|---|---|---|---|---|
| 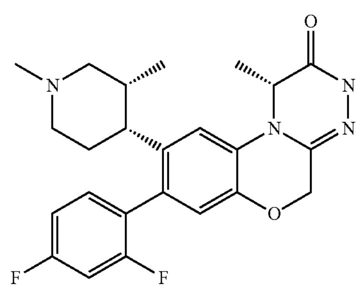 [SMILES: C[C@@H]1C(=O)NN=C2COc3cc(-c4ccc(F)cc4F)c([C@@H]4CCN(C)C[C@@H]4C)cc3N21] | 238 |  | 1.771 (Table 1, Method 4) | 441 |
| 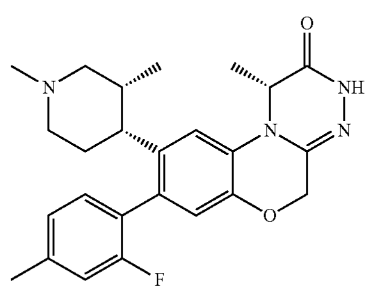 [SMILES: Cc1ccc(-c2cc3c(cc2[C@@H]2CCN(C)C[C@@H]2C)N2C(=NNC(=O)[C@H]2C)CO3)c(F)c1] | 239 |  | 1.871 (Table 1, Method 4) | 437 |
| 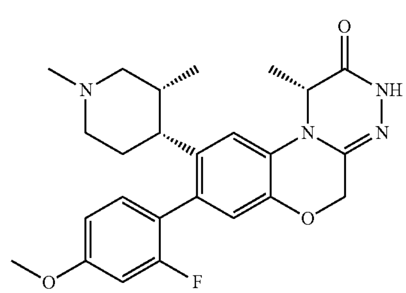 [SMILES: COc1ccc(-c2cc3c(cc2[C@@H]2CCN(C)C[C@@H]2C)N2C(=NNC(=O)[C@H]2C)CO3)c(F)c1] | 240 |  | 1.728 (Table 1, Method 4) | 453 |

TABLE 33a-continued

The following analogs were prepared from (R)-7-bromo-6-((3R,4R)-1,3-dimethyl-piperidin-4-yl)-4-methyl-2,10-dihydro-9-oxa-1,2,4a-triaza-phenanthren-3-one (Example #237, Step B) using the similar procedure detailed in Example #237, Step C.

| Structure | Ex # | Boronic acid or boronic ester | $R_t$ min (method) | m/z ESI+ $(M + H)^+$ |
|---|---|---|---|---|
| 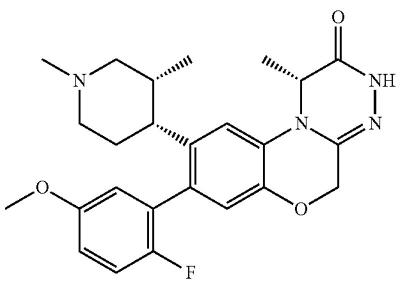 [SMILES: COc1ccc(F)c(-c2cc3c(cc2[C@@H]2CCN(C)C[C@@H]2C)N2C(=NNC(=O)[C@H]2C)CO3)c1] | 241 |  | 2.121 (Table 1, Method 4) | 453 |
| 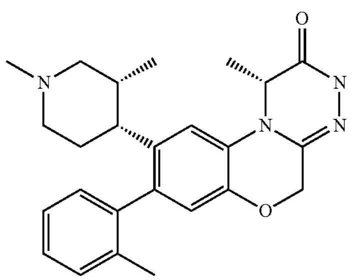 [SMILES: Cc1ccccc1-c1cc2c(cc1[C@@H]1CCN(C)C[C@@H]1C)N1C(=NNC(=O)[C@H]1C)CO2] | 242 |  | 1.788 (Table 1, Method 4) | 419 |
| 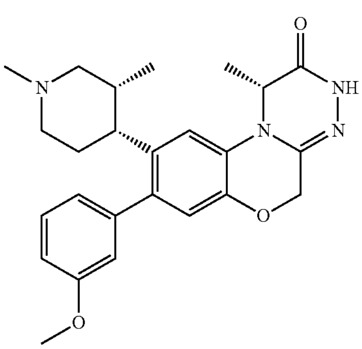 [SMILES: COc1cccc(-c2cc3c(cc2[C@@H]2CCN(C)C[C@@H]2C)N2C(=NNC(=O)[C@H]2C)CO3)c1] | 243 |  | 1.383 (Table 1, Method 4) | 435 |
| 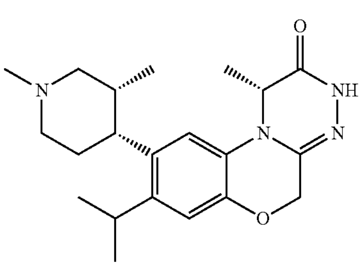 [SMILES: CC(C)c1cc2c(cc1[C@@H]1CCN(C)C[C@@H]1C)N1C(=NNC(=O)[C@H]1C)CO2] | 244 | plus additional hydrogenation step as described in Ex. 82, Step C) | 1.937 (Table 1, Method 4) | 371 |

Example #245

(R)-7-(2,6-Difluoro-phenyl)-6-(3R,4R)-1,3-dimethyl-piperidin-4-yl)-4-methyl-2,10-dihydro-9-oxa-1,2,4a-triaza-phenanthren-3-one

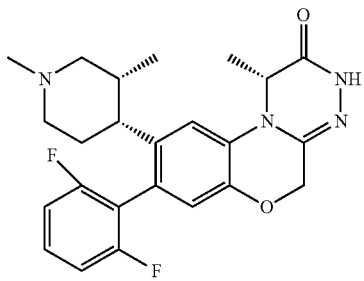 [SMILES: C[C@@H]1C(=O)NN=C2COc3cc(-c4c(F)cccc4F)c([C@@H]4CCN(C)C[C@@H]4C)cc3N21]

Step A. (3R,4R)-3-Methyl-4-[(R)-4-methyl-3-oxo-7-(4,4,5,5-tetramethyl-[1,3,2]dioxaborolan-2-yl)-2,3,4,10-tetrahydro-9-oxa-1,2,4a-triaza-phenanthren-6-yl]-piperidine-1-carboxylic acid tert-butyl ester

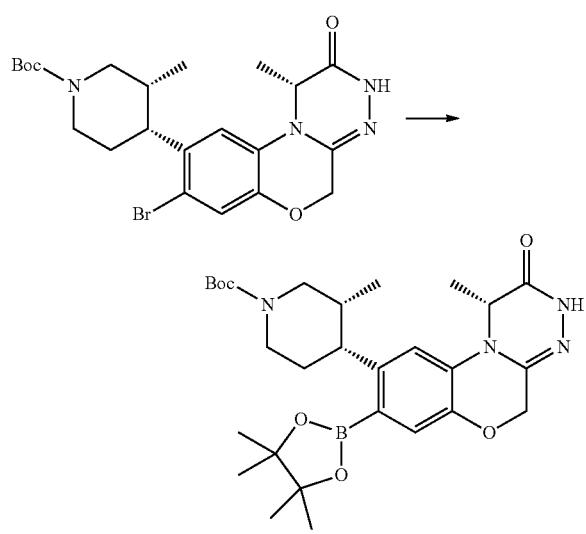

A mixture of (3R,4R)-4-((R)-7-bromo-4-methyl-3-oxo-2,3,4,10-tetrahydro-9-oxa-1,2,4a-triaza-phenanthren-6-yl)-3-methyl-piperidine-1-carboxylic acid tert-butyl ester (Example #199, Step D, 0.150 g, 0.304 mmol), 4,4,5,5,4',4',5',5'-octamethyl-[2,2]bi[[1,3,2]dioxaborolanyl] (0.232 g, 0.912 mmol), PdCl$_2$(dppf) (0.044 g, 0.061 mmol) and KOAc (0.090 g, 0.912 mmol) in EtOH (5 mL) was heated at 90° C. for 16 h. The reaction mixture was cooled to ambient temperature and the solvent was removed in vacuo. The residue was purified by prep-TLC (eluting with 50% EtOAc in petroleum ether) to give (3R,4R)-3-methyl-4-[(R)-4-methyl-3-oxo-7-(4,4,5,5-tetramethyl-[1,3,2]dioxaborolan-2-yl)-2,3,4,10-tetrahydro-9-oxa-1,2,4a-triaza-phenanthren-6-yl]-piperidine-1-carboxylic acid tert-butyl ester (0.090 g, 55%). LC/MS (Table 1, Method 25) R$_t$=0.967 min; MS m/z: 563 [M+23]$^+$.

Step B. (3R,4R)-4-[(R)-7-(2,6-Difluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester

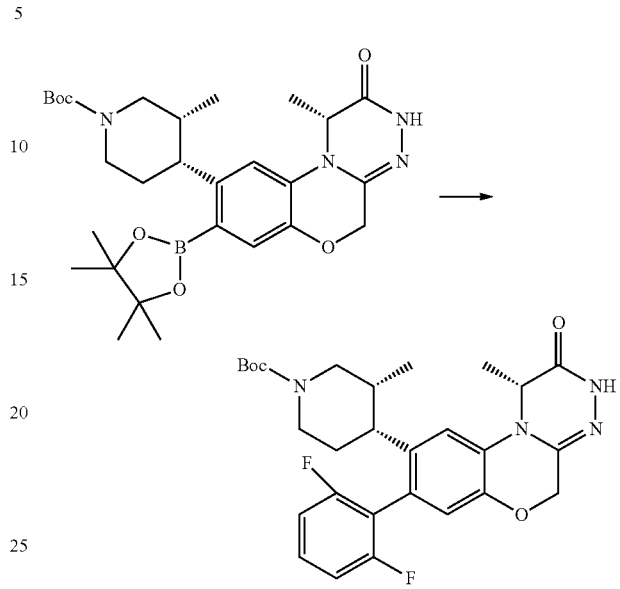

To a mixture of (3R,4R)-3-methyl-4-[(R)-4-methyl-3-oxo-7-(4,4,5,5-tetramethyl-[1,3,2]dioxaborolan-2-yl)-2,3,4,10-tetrahydro-9-oxa-1,2,4a-triaza-phenanthren-6-yl]-piperidine-1-carboxylic acid (0.028 g, 0.052 mmol), 2-bromo-1,3-difluoro-benzene (0.015 g, 0.078 mmol) and sodium carbonate (0.018 g, 0.130 mmol) in 1,4-dioxane (3.0 mL) and water (0.5 mL) was added PdCl$_2$(dppf)-CH$_2$Cl$_2$ adduct (0.008 g, 0.010 mmol) and the reaction mixture was stirred at 90° C. overnight. The reaction mixture was cooled to ambient temperature and filtered. The filtrate was partitioned between EtOAc (20 mL) and water (20 mL). The organic portion was separated and the aqueous layer was extracted with EtOAc (3×50 mL). The combined organic phase was dried over anhydrous sodium sulfate, filtered and concentrated in vacuo. The residue was purified by preparative HPLC (Table 3, Method 36) to give (3R,4R)-4-[(R)-7-(2,6-difluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.005 g, 18%) as a white solid. $^1$H NMR (400 MHz, CD$_3$OD) δ 7.41-7.51 (m, 1H), 7.08 (m, 2H), 6.95 (s, 1H), 6.82 (s, 1H), 4.57-4.65 (m, 5H), 4.25 (m, 1H), 3.83 (m, 1H), 2.80 (m, 1H), 2.43-2.74 (m, 2H), 2.15-2.30 (m, 1H), 1.40-1.51 (m, 12H), 1.29 (s, 3H). LC/MS (Table 1, Method 25) R$_t$=0.930 min; MS (ESI): m/z 527 [M+H]$^+$.

Step C. (R)-7-(2,6-Difluoro-phenyl)-4-methyl-6-((3R,4R)-3-methyl-piperidin-4-yl)-2,10-dihydro-9-oxa-1,2,4a-triaza-phenanthren-3-one hydrochloride

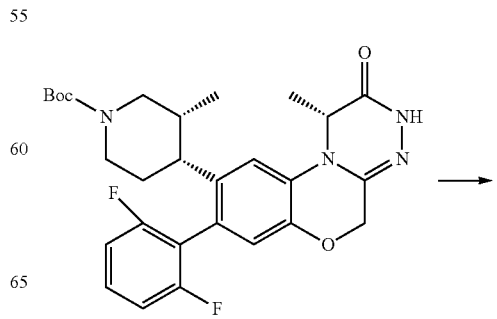

-continued

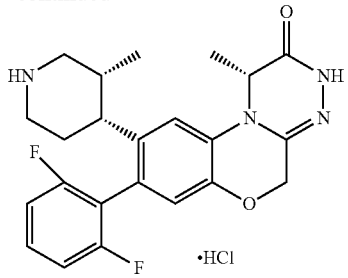

A solution of (3R,4R)-4-[(R)-7-(2,6-difluoro-phenyl)-4-methyl-3-oxo-2,3,4,10-tetrahydro-9-oxa-1,2,4a-triaza-phenanthren-6-yl]-3-methyl-piperidine-1-carboxylic acid tert-butyl ester (0.005 g, 0.01 mmol) in HCl (4M in EtOAc, 1 mL) was stirred at ambient temperature for 1 h. The solvent was removed in vacuo to give crude (R)-7-(2,6-difluoro-phenyl)-4-methyl-6-((3R,4R)-3-methyl-piperidin-4-yl)-2,10-dihydro-9-oxa-1,2,4a-triaza-phenanthren-3-one hydrochloride (0.005 g, 100%), which was used directly in the next step without purification. LC/MS (Table 1, Method 25) $R_t$=0.717 min.; MS m/z: 427 [M+H]$^+$.

Step D. (R)-7-(2,6-Difluoro-phenyl)-6-((3R,4R)-1,3-dimethyl-piperidin-4-yl)-4-methyl-2,10-dihydro-9-oxa-1,2,4a-triaza-phenanthren-3-one

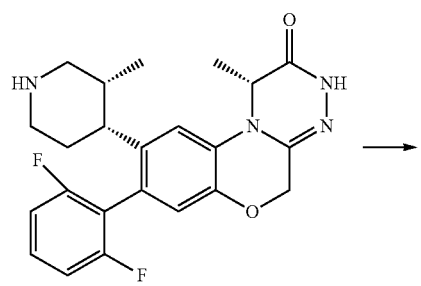

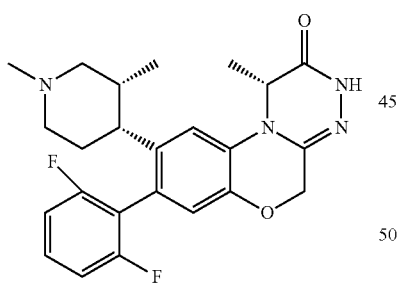

To a mixture of (R)-7-(2,6-difluoro-phenyl)-4-methyl-6-((3R,4R)-3-methyl-piperidin-4-yl)-2,10-dihydro-9-oxa-1,2,4a-triaza-phenanthren-3-one (0.005 g, 0.012 mmol) in AcOH (0.2 mL) and MeOH (2 mL) was added paraformaldehyde (0.004 g, 0.117 mmol) and the reaction mixture was stirred at ambient temperature for 1 h. NaBH$_3$CN (0.002 g, 0.029 mmol) was added and the reaction mixture was stirred at ambient temperature overnight. Aqueous saturated NaHCO$_3$ solution (30 mL) was added and the reaction mixture was extracted with EtOAc (3×50 mL). The combined organic phase was dried over anhydrous sodium sulfate, filtered and evaporated in vacuo. The residue was purified by preparative TLC (eluting with 20% MeOH in EtOAc) to give (R)-7-(2,6-difluoro-phenyl)-6-((3R,4R)-1,3-dimethyl-piperidin-4-yl)-4-methyl-2,10-dihydro-9-oxa-1,2,4a-triaza-phenanthren-3-one (0.0041 g, 79%). $^1$H NMR (400 MHz, CD$_3$OD): 7.47-7.54 (m, 1H), 7.13 (t, J=7.91 Hz, 2H), 6.96 (s, 1H), 6.89 (s, 1H), 4.94-4.96 (m, 1H), 4.67 (m, 2H), 3.58 (m, 1H), 2.89-3.11 (m, 3H), 2.82 (s, 3H), 2.44-2.60 (m, 2H), 2.26-2.42 (m, 1H), 1.94 (m, 2H), 1.51 (d, J=6.4 Hz, 3H), 0.94 (d, J=7.4 Hz, 3H). LC/MS (Table 1, Method 4) $R_t$=1.656 min.; MS m/z: 441 [M+H]$^+$. SFC (Table 2, Method 28), $R_t$=4.708 min.

Example #246

(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one

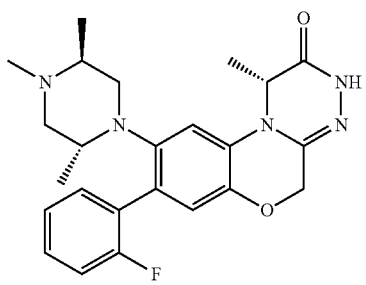 [SMILES: C[C@@H]1CN(C)[C@@H](C)CN1c1cc2c(cc1-c1ccccc1F)OCC1=NNC(=O)[C@@H](C)N12]

Step A. (2S,5R)-2,5-Dimethyl-4-[4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester

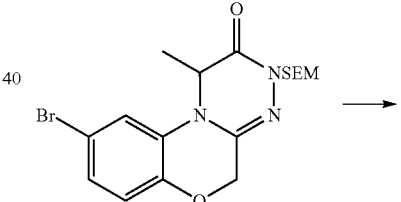

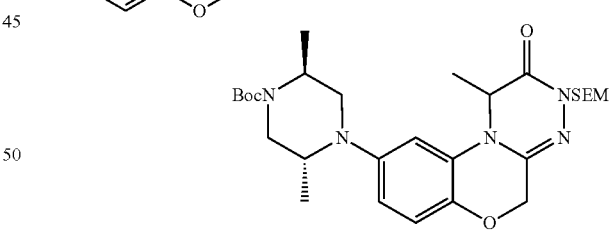

A mixture of (2S,5R)-2,5-dimethyl-piperazine-1-carboxylic acid tert-butyl ester (1.5 g, 7.00 mmol), 6-bromo-4-methyl-2-(2-trimethylsilanyl-ethoxymethyl)-2,10-dihydro-9-oxa-1,2,4a-triaza-phenanthren-3-one (Preparation #1, Step E, 1.990 g, 4.67 mmol), Pd(OAc)$_2$ (0.210 g, 0.933 mmol), 2-(dicyclohexylphosphino)-2',4',6'-triisoproplylbiphenyl (0.667 g, 1.400 mmol) and t-BuONa (0.897 g, 9.33 mmol) in toluene (120 mL) was heated at 100° C. for 3 h. The reaction mixture was cooled to ambient temperature and concentrated in vacuo. The residue was purified by column chromatography on silica gel (eluting with 0-50% EtOAc in petroleum ether) to give (2S,5R)-2,5-dimethyl-4-[4-methyl-3-oxo-2-(2-trimethylsilanyl-ethoxymethyl)-2,3,4,10-tetrahydro-9-oxa- 1,2,4a-triaza-phenanthren-6-yl]-piperazine-1-carboxylic acid tert-butyl ester (0.5 g, 19%) as a solid. LC/MS (Table 1, Method 25) $R_f$=1.072 min.; MS m/z: 560 [M+H]$^+$.

Step B. (2S,5R)-4-[7-Bromo-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester

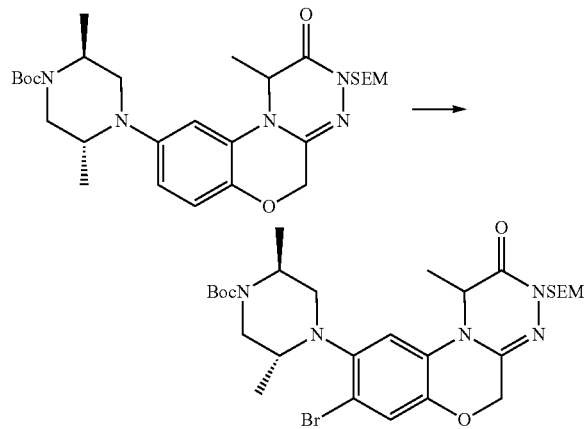

To a solution of (2S,5R)-2,5-dimethyl-4-[4-methyl-3-oxo-2-(2-trimethylsilanyl-ethoxymethyl)-2,3,4,10-tetrahydro-9-oxa-1,2,4a-triaza-phenanthren-6-yl]-piperazine-1-carboxylic acid tert-butyl ester (1.39 g, 2.483 mmol) in DCM (10 mL) and MeOH (10 mL) was added a solution of n-Bu$_4$NBr$_3$ (1.197 g, 2.483 mmol) in DCM (10 mL) drop-wise and the reaction mixture was stirred at ambient temperature for 1 h. Aqueous saturated Na$_2$S$_2$O$_3$ solution (10 mL) was added followed by addition of aqueous NaHCO$_3$ solution to adjust the pH to 8. The reaction mixture was extracted with EtOAc (3×30 mL) and the combined organic phase was washed with brine (3×30 mL) and dried over anhydrous Na$_2$SO$_4$. The mixture was concentrated in vacuo and the residue was purified by column chromatography on silica gel (eluting with 0-20% EtOAc in petroleum ether) to give (2S,5R)-4-[7-bromo-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester (0.422 g, 27%) as a solid. LC/MS (Table 1, Method 25) $R_f$=1.159 min.; MS m/z: 638 [M+H]$^+$ & 640 [M+H+2]$^+$.

Step C. (2S,5R)-4-[7-(2-Fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester

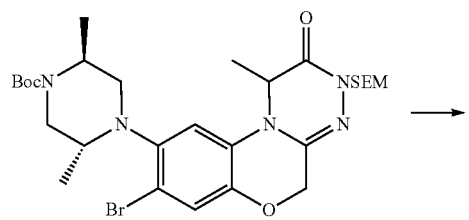

-continued

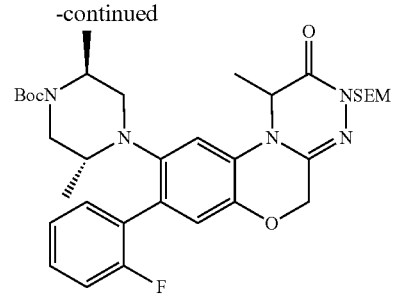

A mixture of (2S,5R)-4-[7-bromo-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester (0.4 g, 0.626 mmol), 2-fluorophenylboronic acid (0.105 g, 0.752 mmol), K$_2$CO$_3$ (0.173 g, 1.253 mmol) and PdCl$_2$(dppf)-CH$_2$Cl$_2$ adduct (0.101 g, 0.125 mmol) in dioxane (8 mL) and water (2 mL) was stirred at 90° C. for 2.5 h. The reaction mixture was cooled to ambient temperature and concentrated in vacuo. The residue was purified by column chromatography on silica gel (eluting with 0-20% EtOAc in petroleum ether) to give (2S,5R)-4-[7-(2-fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester (0.250 g, 61%) as a solid. LC/MS (Table 1, Method 25) $R_f$=1.143 min.; MS m/z: 654 [M+H]$^+$.

Step D. (2S,5R)-4-[7-(2-Fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester

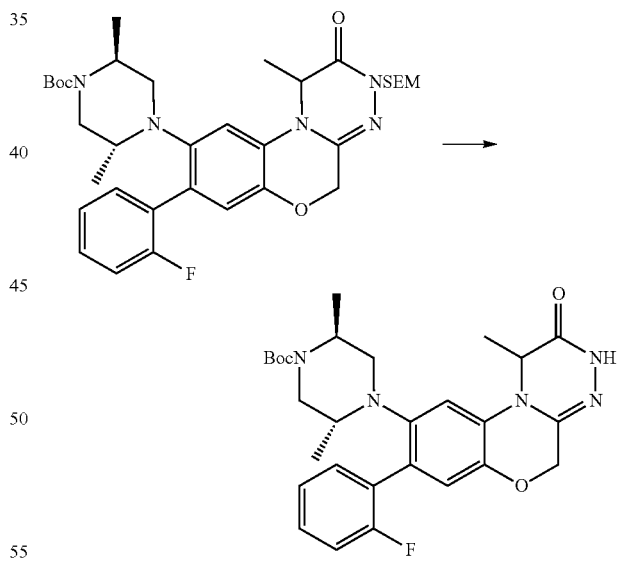

(2S,5R)-4-[7-(2-Fluoro-phenyl)-4-methyl-3-oxo-2-(2-trimethylsilanyl-ethoxymethyl)-2,3,4,10-tetrahydro-9-oxa-1,2,4a-triaza-phenanthren-6-yl]-2,5-dimethyl-piperazine-1-carboxylic acid tert-butyl ester (0.2 g, 0.306 mmol) was dissolved in tetrabutylammonium fluoride (1M in THF, 3.06 mL, 3.06 mmol) and the reaction mixture was heated at 80° C. overnight. The reaction mixture was cooled to ambient temperature and water (10 mL) was added. The reaction mixture was extracted with EtOAc (3×10 mL). The combined organic phase was washed with brine (3×10 mL) and concentrated in vacuo. The residue was purified by column chromatography on silica gel (eluting with 0-40% EtOAc in petroleum ether)

to give (2S,5R)-4-[7-(2-fluoro-phenyl)-4-methyl-3-oxo-2,3, 4,10-tetrahydro-9-oxa-1,2,4a-triaza-phenanthren-6-yl]-2,5-dimethyl-piperazine-1-carboxylic acid tert-butyl ester (0.112 g, 70%) as a solid. LC/MS (Table 1, Method 25) R$_t$=0.959 min.; MS m/z: 524 [M+H]$^+$. $^1$H NMR (400 MHz, CDCl$_3$): δ 8.15-8.08 (m, 1H), 7.42 (m, 1H), 7.35-7.29 (m, 1H), 7.22-7.10 (m, 2H), 6.95-6.91 (m, 1H), 6.52-6.46 (m, 1H), 4.76-4.72 (m, 1H), 4.65-4.54 (m, 2H), 4.35 (m, 1H), 3.45 (m, 1H), 3.33 (m, 1H), 2.85 (m, 1H), 2.69 (m, 1H), 2.60 (m, 1H), 1.52 (m, 3H), 1.49-1.32 (m, 9H), 1.24 (m, 3H), 0.81 (m, 3H).

Step E. (2S,5R)-4-[(R)-7-(2-Fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester & (2S,5R)-4-[(S)-7-(2-fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester

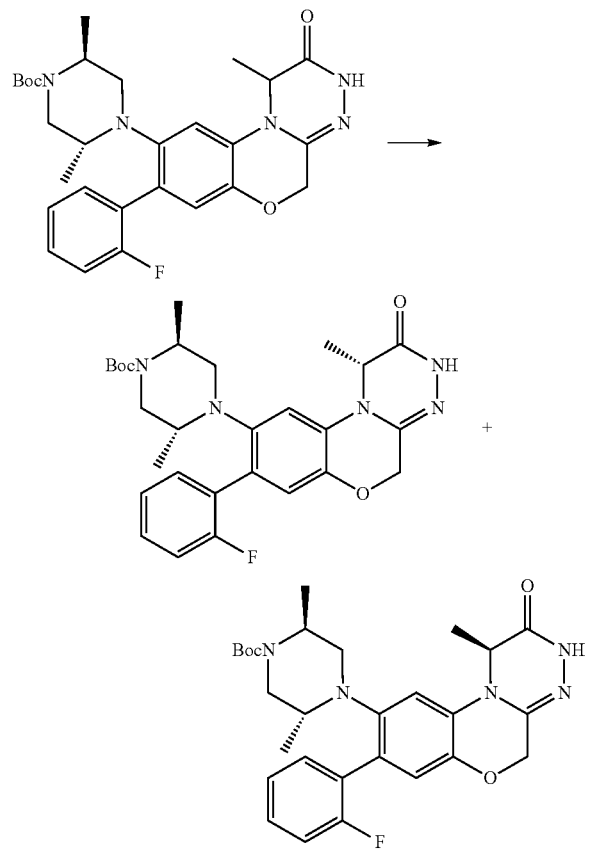

(2S,5R)-4-[7-(2-Fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester (0.142 g, 0.271 mmol) was separated by chiral SFC (Table 2, Method 29) to give two isomers: (2S,5R)-4-[(S)-7-(2-fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester (isomer 1, SFC (Table 1, Method 55), R$_t$=2.248 min., 0.050 g, 35%, LC/MS (Table 1, Method 25) R$_t$=0.946 min.; MS m/z: 524 [M+H]$^+$) and (2S,5R)-4-[(R)-7-(2-fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester (isomer 2, SFC (Table 1, Method 55), R$_t$=5.643 min., 0.054 g, 38%, LC/MS (Table 1, Method 25) R$_t$=0.944 min.; MS m/z: 424 [M−100+H]$^+$).

Step F. (R)-6-((2R,5S)-2,5-Dimethyl-piperazin-1-yl)-7-(2-fluoro-phenyl)-4-methyl-2,10-dihydro-9-oxa-1,2,4a-triaza-phenanthren-3-one hydrochloride

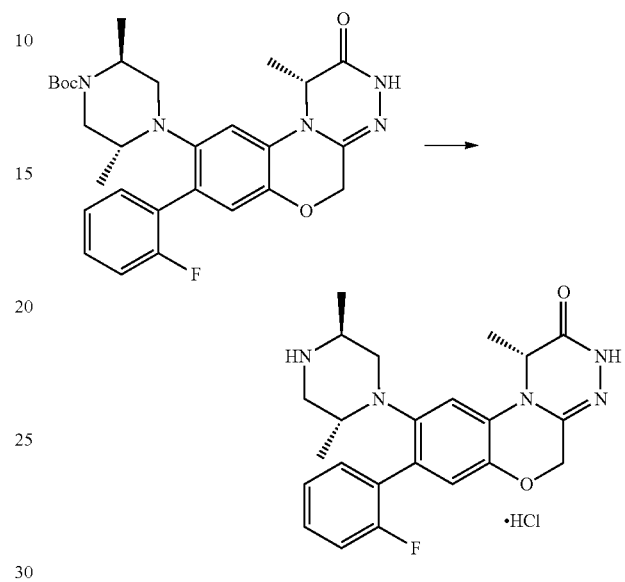

A solution of (2S,5R)-4-[(R)-7-(2-fluoro-phenyl)-4-methyl-3-oxo-2,3,4,10-tetrahydro-9-oxa-1,2,4a-triaza-phenanthren-6-yl]-2,5-dimethyl-piperazine-1-carboxylic acid tert-butyl ester (isomer 2, SFC (Table 1, Method 55), R$_t$=5.643 min., 0.05 g, 0.095 mmol) in HCl (4 M in EtOAc, 2 mL) was stirred at ambient temperature for 1 h. The solvent was concentrated in vacuo to give (R)-6-((2R,5S)-2,5-dimethyl-piperazin-1-yl)-7-(2-fluoro-phenyl)-4-methyl-2,10-dihydro-9-oxa-1,2,4a-triaza-phenanthren-3-one hydrochloride (0.040 g, 99%) as a white solid. $^1$H NMR (CD$_3$OD, 400 MHz) δ 7.27-7.40 (m, 1H), 7.22-7.26 (m, 2H), 7.15-7.22 (m, 1H), 7.05 (s, 1H), 6.96 (s, 1H), 4.90-4.91 (m, 1H), 4.59-4.70 (m, 2H), 3.09-3.25 (m, 3H), 3.03 (m, 1H), 2.78-2.87 (m, 1H), 2.49 (m, 1H), 1.49 (d, J=6.5 Hz, 3H), 1.24 (d, J=6.5 Hz, 3H), 0.76 (d, J=6.3 Hz, 3H). LC/MS (Table 1, Method 4) R$_t$=1.739 min.; MS m/z: 424 [M+H]$^+$. SFC (Table 1, Method 55), R$_t$=6.795 min.

Step G. (R)-7-(2-Fluoro-phenyl)-4-methyl-6-((2R, 5S)-2,4,5-trimethyl-piperazin-1-yl)-2,10-dihydro-9-oxa-1,2,4a-triaza-phenanthren-3-one

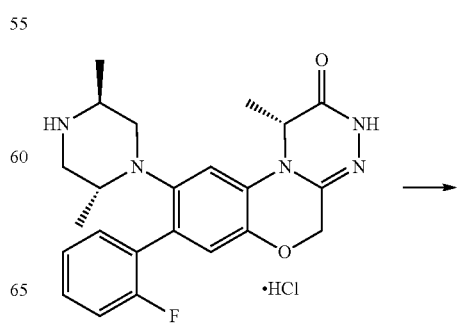

-continued

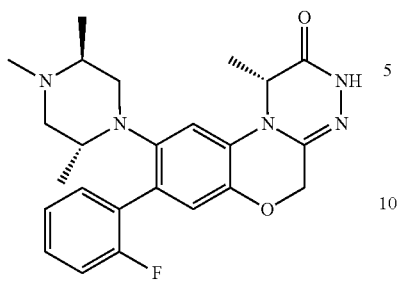

To a solution of (R)-6-((2R,5S)-2,5-dimethyl-piperazin-1-yl)-7-(2-fluoro-phenyl)-4-methyl-2,10-dihydro-9-oxa-1,2,4a-triaza-phenanthren-3-one hydrochloride (0.040 g, 0.094 mmol) in AcOH (1 mL) and MeOH (10 mL) was added paraformaldehyde (0.028 g, 0.945 mmol) and the reaction mixture was stirred at ambient temperature for 1 h. NaBH$_3$CN (0.015 g, 0.236 mmol) was added and the reaction mixture was stirred at ambient temperature overnight. Aqueous saturated NaHCO$_3$ solution (10 mL) was added and the reaction mixture was extracted with EtOAc (3×20 mL). The combined organic phase was dried over anhydrous sodium sulfate, filtered and concentrated in vacuo. The residue was purified by preparative TLC (eluting with 20% MeOH in EtOAc) to give (R)-7-(2-fluoro-phenyl)-4-methyl-6-((2R,5S)-2,4,5-trimethyl-piperazin-1-yl)-2,10-dihydro-9-oxa-1,2,4a-triaza-phenanthren-3-one (0.011 g, 60%). $^1$H NMR (400 MHz, CD$_3$OD): δ 7.33-7.41 (m, 1H), 7.18-7.29 (m, 2H), 7.14 (m, 1H), 7.06 (s, 1H), 6.93 (s, 1H), 4.58-4.69 (m, 3H), 3.18 (m, 2H), 2.96 (m, 1H), 2.71 (m, 2H), 2.59 (m, 3H), 2.27 (m, 1H), 1.48 (d, J=6.5 Hz, 3H), 1.15 (d, J=4.8 Hz, 3H), 0.75 (d, J=6.0 Hz, 3H). LC/MS (Table 1, Method 4) R$_t$=1.708 min.; MS m/z: 439 [M+H]$^+$. SFC (Table 1, Method 56), R$_t$=2.337 min.

Preparation #1. 6-Bromo-4-methyl-2-(2-trimethylsilanyl-ethoxymethyl)-2,10-dihydro-9-oxa-1,2,4a-triaza-phenanthren-3-one

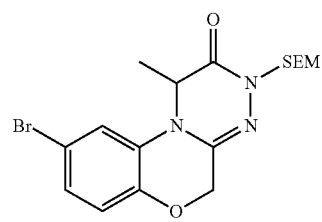 [SMILES: CC1C(=O)N(COCC[Si](C)(C)C)N=C2COc3ccc(Br)cc3N21]

Step A. 6-Bromo-4H-benzo[1,4]oxazin-3-one

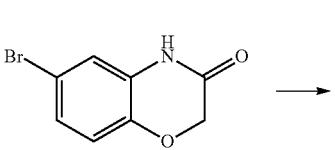

To a solution of 2-amino-4-bromophenol (25 g, 133.0 mmol), NaHCO$_3$ (22.4 g, 266.0 mmol) in 4-methylpentan-2-one (50 mL) and water (50 mL) at 0° C. was added 2-chloroacetyl chloride (10.0 mL, 200.0 mmol) dropwise. The reaction mixture was stirred at 80° C. for 24 h then cooled to ambient temperature and filtered. The filtrate was washed with water (3×10 mL) and dried over anhydrous Na$_2$SO$_4$. After filtration, the organic phase was evaporated to give 6-bromo-4H-benzo[1,4]oxazin-3-one as a white solid (27 g, 89%). $^1$H NMR (CDCl$_3$, 400 MHz): δ 8.49 (brs, 1H), 7.08 (dd, J=8.4 Hz, J=2.0 Hz, 1H), 6.93 (d, J=2.0 Hz, 1H), 6.87 (d, J=8.4 Hz, 1H), 4.61 (s, 2H).

Step B. 2-(6-Bromo-3-oxo-2,3-dihydro-benzo[1,4]oxazin-4-yl)-propionic acid ethyl ester TABLE 33b The following analog was prepared from 6-bromo-4-methyl-2-(2-trimethylsilanyl-ethoxymethyl)-2,10-dihydro-9-oxa-1,2,4a-triaza-phenanthren-3-one (Preparation #1, Step E) using the similar procedure detailed in Example #246, Steps A-G.

| Structure | Example # | Piperazine (Step A) | R$_t$ min (method) | m/z ESI+ (M + H)$^+$ |
|---|---|---|---|---|
| (structure shown) | 247 | (Boc-piperazine structure) | 1.777 (Table 1, Method 4) | 438 |

-continued

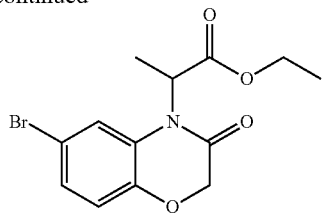

To a suspension of 6-bromo-4H-benzo[1,4]oxazin-3-one (27 g, 118.4 mmol) and K₂CO₃ (49.1 g, 355.2 mmol) in acetone (200 mL) was added 2-bromo-propionic acid ethyl ester (32.1 g, 177.6 mmol) and the reaction mixture was heated at 70° C. for 5 h. The reaction mixture was cooled to ambient temperature and the solvent was removed in vacuo and the residue was dissolved in DCM (50 mL). The organic phase was washed with water (3×20 mL), dried over anhydrous Na₂SO₄. After filtration, the filtrate was evaporated to dryness and the residue was purified by chromatography on silica gel (eluting with 5% EtOAc in petroleum ether) to give 2-(6-bromo-3-oxo-2,3-dihydro-benzo[1,4]oxazin-4-yl)-propionic acid ethyl ester as a colorless liquid (32.5 g, 100 mmol, 84%). ¹H NMR (CDCl₃, 400 MHz): δ 7.09 (dd, J=8 Hz, J=2 Hz, 1H), 6.94 (d, J=2.0 Hz, 1H), 6.90 (d, J=8.4 Hz, 1H), 5.28 (q, J=14.8 Hz, 1H), 5.21 (q, J=5.4 Hz, 1H), 4.55 (d, J=15.2 Hz, 2H), 4.17 (m, 1H), 1.63 (d, J=1.2 Hz, 3H), 1.22 (t, J=1.2 Hz, 3H).

Step C. 2-(6-Bromo-3-thioxo-2,3-dihydro-benzo[1,4]oxazin-4-yl)-propionic acid ethyl ester

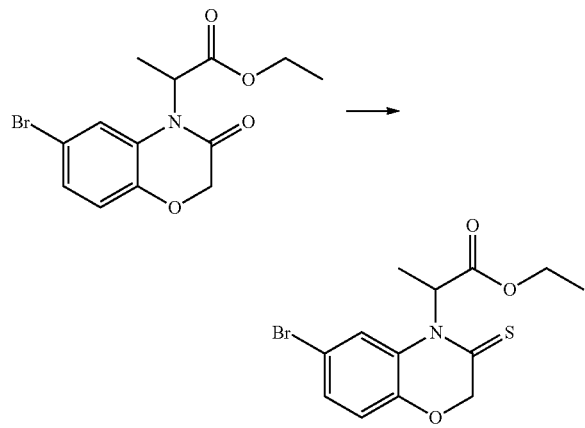

A solution of 2-(6-bromo-3-oxo-2,3-dihydro-benzo[1,4] oxazin-4-yl)-propionic acid ethyl ester (32.5 g, 100 mmol) and Lawesson reagent (80.1 g, 200 mmol) in toluene (200 mL) was heated at 120° C. for 3 h then cooled at ambient temperature. The solvent was removed in vacuo to give the crude product, which was purified by chromatography on silica gel (eluting with 1% EtOAc in petroleum ether) to give 2-(6-bromo-3-thioxo-2,3-dihydro-benzo[1,4]oxazin-4-yl)-propionic acid ethyl ester (28 g, 81.4 mmol, 82%) as a yellow liquid. ¹H NMR (CDCl₃, 400 MHz): δ 7.18 (dd, J=8.8 Hz, J=2.0 Hz, 1H), 7.01 (d, J=2.0 Hz, 1H), 6.91 (s, J=8.8 Hz, 1H), 6.54 (s, 1H), 4.90 (q, J=15.2 Hz, 2H), 4.22 (m, 2H), 1.68 (d, J=7.2 Hz, 3H), 1.16 (t, J=7.2 Hz, 3H).

Step D. 6-Bromo-4-methyl-2,10-dihydro-9-oxa-1,2,4a-triaza-phenanthren-3-one

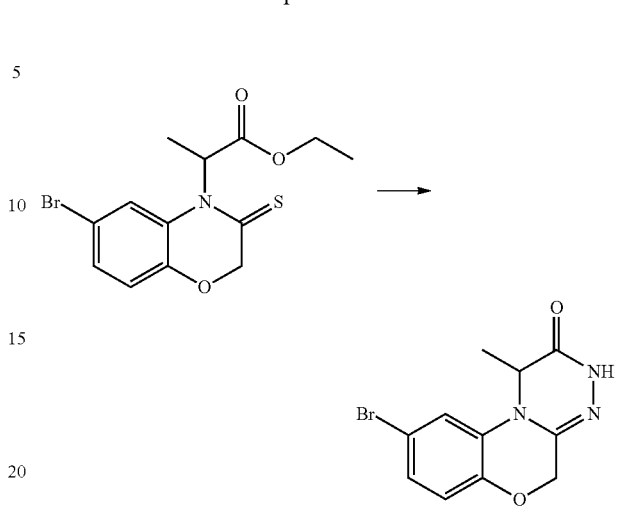

To a solution of 2-(6-bromo-3-thioxo-2,3-dihydro-benzo [1,4]oxazin-4-yl)-propionic acid ethyl ester (28 g, 81.4 mmol) in EtOH (100 mL) was added hydrazine hydrate (98%, 13.1 g, 162.8 mmol). The reaction mixture was stirred at ambient temperature overnight. The precipitate was collected by filtration and washed with cold EtOH (3×10 mL) to give 6-bromo-4-methyl-2,10-dihydro-9-oxa-1,2,4a-triaza-phenanthren-3-one as a yellow solid (22.0 g, 74.3 mmol, 92%). ¹H NMR (DMSO-d₆, 400 MHz): δ 10.83 (s, 1H), 7.41 (d, J=2.0 Hz, 1H), 7.11 (d, J=2.0 Hz, J=8.4 Hz, 1H), 6.94 (d, J=8.4 Hz, 1H), 4.82 (q, J=6.8 Hz, 1H), 4.62 (d, J=13.2 Hz, 2H), 1.28 (d, J=6.8 Hz, 3H).

Step E. 6-Bromo-4-methyl-2-(2-trimethylsilanyl-ethoxymethyl)-2,10-dihydro-9-oxa-1,2,4a-triaza-phenanthren-3-one

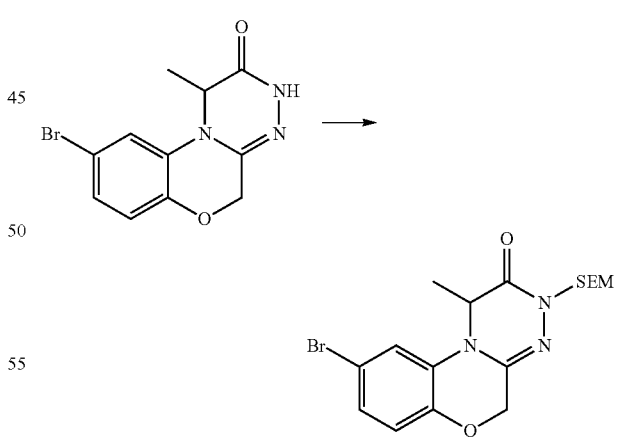

A solution of 6-bromo-4-methyl-2,10-dihydro-9-oxa-1,2,4a-triaza-phenanthren-3-one (4.0 g, 13.5 mmol) in anhydrous DMF (20 mL) was stirred at 0° C. Sodium hydride (60% in mineral oil, 0.8 g, 20.3 mmol) was added portion-wise and the reaction mixture was stirred at 0° C. for 0.5 h. (2-(Chloromethoxy)ethyl)trimethylsilane (3.4 g, 20.3 mmol) was added to the solution dropwise and the reaction mixture was stirred at 25° C. for 3 h. The reaction mixture was diluted with water (100 mL) and extracted with EtOAc (3×30 mL). The combined organic layer was concentrated in vacuo, washed with brine (3×30 mL), dried over anhydrous Na₂SO₄, filtered and concentrated to give the crude product, which was purified by chromatography on silica gel (eluting with 1% EtOAc in petroleum ether) to give 6-bromo-4-methyl-2-(2-trimethylsilanyl-ethoxymethyl)-2,10-dihydro-9-oxa-1,2,4a-triazaphenanthren-3-one (4 g, 70%) as a yellow solid. $^1$H NMR (CDCl₃, 400 MHz): δ 7.08 (dd, J=8.4 Hz, J=2.0 Hz, 1H), 7.01 (d, J=2.0 Hz, 1H), 6.86 (d, J=8.4 Hz, 1H), 5.08 (d, J=10.0 Hz, 2H), 4.67 (m, 1H), 4.6 (d, J=12.8 Hz, 2H), 3.65 (t, J=8.4 Hz, 2H), 1.47 (d, J=6.8 Hz, 3H), 0.95 (t, J=8.4 Hz, 2H), 0.00 (s, 9H).

Preparation #2. 6-Amino-7-bromo-4-methyl-2,10-dihydro-9-oxa-1,2,4a-triaza-phenanthren-3-one

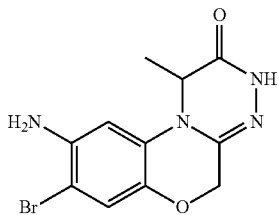 [SMILES: CC1C(=O)NN=C2COc3cc(Br)c(N)cc3N21]

Step A. 6-Nitro-2H-benzo[b][1,4]oxazin-3(4H)-one

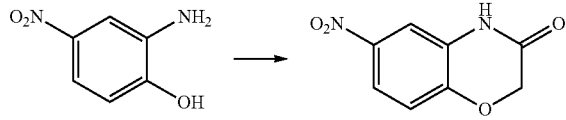 [SMILES: Nc1cc([N+](=O)[O-])ccc1O ; O=C1COc2ccc([N+](=O)[O-])cc2N1]

To a solution of 2-amino-4-nitrophenol (114.0 g, 740 mmol), K₂CO₃ (306.2 g, 2220 mmol) and tetrabutyl ammonium bromide (23.8 g, 74 mmol) in MeCN (1.50 L) at 0° C. was added 2-chloroacetyl chloride (83.6 mL, 1110 mmol) dropwise. The reaction mixture was heated at 80° C. for 1 h. The mixture was cooled to ambient temperature and concentrated in vacuo. The residue was dissolved in water (500 mL) and extracted with EtOAc (3×150 mL). The combined organic phase was dried over anhydrous Na₂SO₄ and filtered. The filtrate was evaporated in vacuo to give 6-nitro-2H-benzo[1,4]oxazin-3-one as a white solid (135.0 g, 94%). $^1$H NMR (DMSO-d₆, 400 MHz): δ 7.83 (dd, J=2.8 Hz, J=9.2 Hz, 1H), 7.75 (d, J=2.8 Hz, 1H), 7.15 (d, J=9.2 Hz, 1H), 4.78 (s, 2H). The amide proton was not observed in DMSO-d₆.

Step B. 2-(6-Nitro-3-oxo-2,3-dihydro-benzo[1,4]oxazin-4-yl)-propionic acid ethyl ester

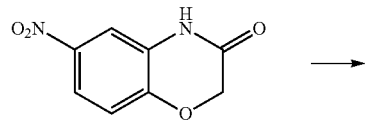

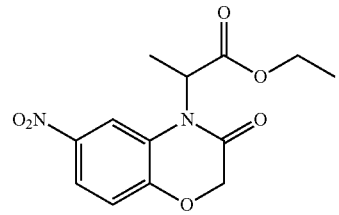

A suspension of 6-nitro-4H-benzo[1,4]oxazin-3-one (135.0 g, 700 mmol) and K₂CO₃ (289.8 g, 2100 mmol) in DMF (1.5 L) was stirred at 70° C. for 0.5 h and then 2-bromopropionic acid ethyl ester (136.3 mL, 1050 mmol) was added to the mixture. The reaction mixture was heated at 80° C. for 2 h then cooled to ambient temperature. The solvent was removed in vacuo and the residue was dissolved in water (600 mL) and extracted with EtOAc (3×200 mL). The combined organic layer was concentrated, washed with brine (3×30 mL), dried over anhydrous Na₂SO₄, filtered and concentrated in vacuo to give the crude product, which was purified by chromatography on silica gel (eluting with 20% EtOAc in petroleum ether) to give 2-(6-nitro-3-oxo-2,3-dihydro-benzo[1,4]oxazin-4-yl)-propionic acid ethyl ester as a brown liquid (185.0 g, 90%). $^1$H NMR (CDCl₃, 400 MHz): δ 7.90 (dd, J=2.4 Hz, J=9.2 Hz, 1H), 7.72 (d, J=2.4 Hz, 1H), 7.06 (d, J=9.2 Hz, 1H), 5.27 (q, J=7.2 Hz, 1H), 4.67 (d, J=15.2 Hz, 2H), 4.18 (m, 2H), 1.62 (d, J=7.2 Hz, 3H), 1.18 (t, J=7.2 Hz, 3H).

Step C. 2-(6-Nitro-3-thioxo-2,3-dihydro-benzo[1,4]oxazin-4-yl)-propionic acid ethyl ester

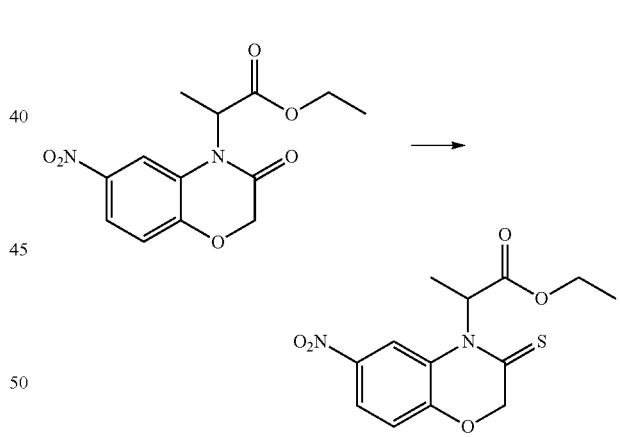

A solution of 2-(6-nitro-3-oxo-2,3-dihydro-benzo[1,4]oxazin-4-yl)-propionic acid ethyl ester (185.0 g, 630 mmol) and Lawesson's reagent (279.4 g, 690 mmol) in toluene (1.5 L) was heated to 120° C. for 3 h. The reaction mixture was cooled to ambient temperature and the solvent was removed in vacuo to give the crude product which was purified by chromatography on silica gel (eluting with 5% EtOAc in petroleum ether) to give 2-(6-nitro-3-thioxo-2,3-dihydro-benzo[1,4]oxazin-4-yl)-propionic acid ethyl ester (133.0 g, 72%) as a yellow liquid. $^1$H NMR (CDCl₃, 400 MHz): δ 8.02 (dd, J=2.4 Hz, J=8.8 Hz, 1H), 7.85 (d, J=2.4 Hz, 1H), 7.15 (d, J=8.8 Hz, 1H), 6.70 (m, 1H), 5.07 (d, J=15.2 Hz, 2H), 4.28 (q, J=7.2 Hz, 2H), 1.75 (d, J=7.6 Hz, 3H), 1.24 (t, J=7.2 Hz, 3H).

Step D. 4-Methyl-6-nitro-2,10-dihydro-9-oxa-1,2,4a-triaza-phenanthren-3-one

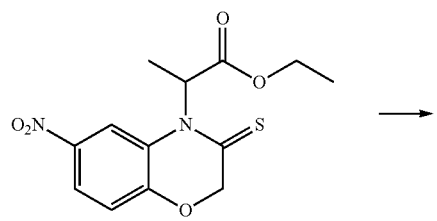

To a solution of 2-(6-nitro-3-thioxo-2,3-dihydro-benzo[1,4]oxazin-4-yl)-propionic acid ethyl ester (133.0 g, 450 mmol) in EtOH (1.5 L) was added hydrazine hydrate (45.0 g, 900 mmol, 98%) and the mixture was heated to 80° C. and stirred for 3 h. The reaction mixture was cooled to ambient temperature and filtered. The filtrate was washed with cold EtOH (3×50 mL) to give 4-methyl-6-nitro-2,10-dihydro-9-oxa-1,2,4a-triaza-phenanthren-3-one as a yellow solid (80.0 g, 68%). $^1$H NMR (DMSO-$d_6$, 400 MHz): δ 10.91 (s, 1H), 7.98 (d, J=2.8 Hz, 1H), 7.86 (dd, J=2.8 Hz, J=8.8 Hz, 1H), 7.23 (d, J=8.8 Hz, 1H), 4.99 (q, J=6.4 Hz, 1H), 4.78 (d, J=12.8 Hz, 2H), 1.36 (d, =6.8 Hz, 3H).

Step E. 6-Amino-4-methyl-2,10-dihydro-9-oxa-1,2,4a-triaza-phenanthren-3-one

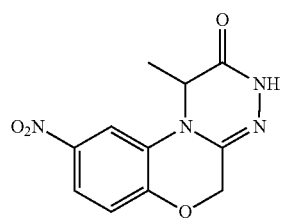

To a solution of 4-methyl-6-nitro-2,10-dihydro-9-oxa-1,2,4a-triaza-phenanthren-3-one (10 g, 38.2 mmol) and ammonium chloride (20.5 g, 382.0 mmol) in MeOH (200 mL) was added zinc powder (24.8 g, 382.0 mol) and the resulting mixture was stirred for 24 h at 25° C. The reaction mixture was filtered and the filtrate was washed with methanol (5×30 mL). The filtrate was combined and concentrated in vacuo and the residue was purified by chromatography on silica gel (eluting with 10% MeOH in DCM) to give 6-amino-4-methyl-2,10-dihydro-9-oxa-1,2,4a-triaza-phenanthren-3-one (6.8 g, 77%) as a yellow solid. $^1$H NMR (DMSO-$d_6$, 400 MHz): δ 10.72 (s, 1H), 6.67 (d, J=8.4 Hz, 1H), 6.42 (d, J=2.4 Hz, 1H), 6.15 (q, J=8.4 Hz, J=2.4 Hz, 1H), 4.82 (brs, 2H), 4.52 (q, J=6.4 Hz, 1H), 4.43 (d, J=12.8 Hz, 2H), 1.30 (d, =6.4 Hz, 3H).

Step F. 6-Amino-7-bromo-4-methyl-2,10-dihydro-9-oxa-1,2,4a-triaza-phenanthren-3-one

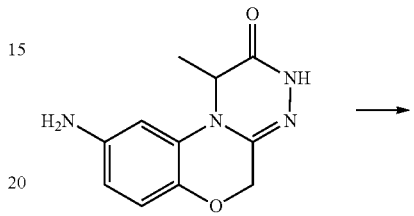

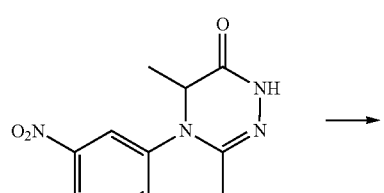

To a solution of 6-amino-4-methyl-2,10-dihydro-9-oxa-1,2,4a-triaza-phenanthren-3-one (5.0 g, 21.5 mmol) in MeOH (20 mL) and DCM (40 mL) was added tetrabutylammonium tribromide (10.9 g, 22.6 mmol) portionwise and the resulting reaction mixture was stirred for 0.5 h at 25° C. The reaction was quenched by addition of saturated aqueous sodium thiosulphate (10 mL). The mixture was neutralized by the addition of saturated aqueous NaHCO$_3$, diluted with water (100 mL) and extracted with DCM (3×50 mL). The combined organic layer was concentrated, washed with brine (3×30 mL), dried over anhydrous Na$_2$SO$_4$, filtered and concentrated to give the crude product, which was purified by column chromatography on silica gel (eluting with 5% MeOH in DCM) to give 6-amino-7-bromo-4-methyl-2,10-dihydro-9-oxa-1,2,4a-triaza-phenanthren-3-one (3.0 g, 46%) as a brown solid. $^1$H NMR (DMSO-$d_6$, 400 MHz): δ 10.78 (s, 1H), 7.02 (s, 1H), 6.68 (s, 1H), 4.98 (brs, 2H), 4.50 (m, 3H), 1.31 (d, J=6.8 Hz, 3H).

Preparation #3.
1-Benzhydryl-3-methyl-azetidin-3-ylamine hydrochloride salt

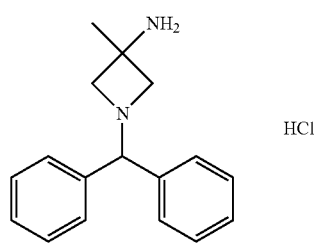 [SMILES: CC1(N)CN(C(c2ccccc2)c2ccccc2)C1 ; Cl]

Step A. 1-Benzhydryl-3-methyl-azetidin-3-ol

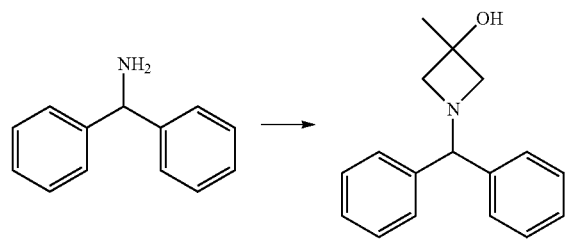 [SMILES: NC(c1ccccc1)c1ccccc1 ; CC1(O)CN(C(c2ccccc2)c2ccccc2)C1]

Diphenylmethanamine (68.8 mL, 375 mmol) was added dropwise into a solution of 2-(chloromethyl)-2-methyloxirane (40 g, 375 mmol) in methanol (160 mL) and the reaction was stirred at rt for 72 h and then at reflux for 20 h. The reaction was cooled to ambient temperature, evaporated in vacuo and suspended in acetone (200 mL). The solid was collected by filtration to give 1-benzhydryl-3-methyl-azetidin-3-ol (60 g, 63%) as a white solid. $^1$H NMR (DMSO-$d_6$, 400 MHz): δ7.61 (m, 4H), 7.31 (m, 6H), 6.43 (m, 1H), 6.00 (m, 1H), 3.80-4.00 (m, 4H), 1.45 (m, 3H).

Step B. Methanesulfonic acid 1-benzhydryl-3-methyl-azetidin-3-yl ester and 1-benzhydryl-3-chloro-3-methyl-azetidine

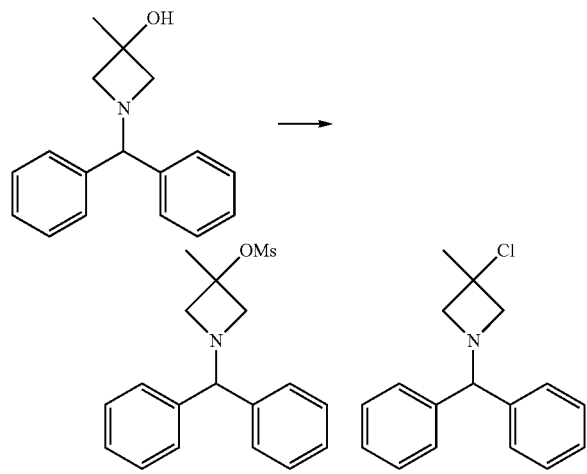

To a mixture of TEA (30 g, 296 mmol) and 1-benzhydryl-3-methyl-azetidin-3-ol (30 g, 118 mmol) in DCM (300 mL) at 0° C. was added a solution of methanesulfonyl chloride (20.49 g, 179 mmol) in DCM (15 mL) keeping the internal temperature below 5° C. The mixture was stirred at ambient temperature for 20 h and quenched by addition of water (50 mL). The organic phase was separated, dried over anhydrous $Na_2SO_4$ and evaporated in vacuo. The residue was purified by column chromatography on silica gel (eluting with 0% EtOAc to 50% EtOAc in petroleum ether) to give 1-benzhydryl-3-chloro-3-methyl-azetidine (7 g, 22%): $^1$H NMR (CDCl$_3$, 400 MHz): δ7.42-7.45 (m, 4H), 7.27-7.31 (m, 4H), 7.18-7.23 (m, 2H), 4.48 (s, 1H), 3.38-3.44 (m, 4H), 1.87 (s, 3H) and methanesulfonic acid 1-benzhydryl-3-methyl-azetidin-3-yl ester (16 g, 41%). $^1$H NMR (CDCl$_3$, 400 MHz): δ7.40-7.37 (m, 4H), 7.20-7.28 (m, 4H), 7.16-7.20 (m, 2H), 4.42 (s, 1H), 3.33 (s, 4H), 3.02 (s, 3H), 1.90 (s, 3H).

Step C. 1-Benzhydryl-3-methyl-azetidin-3-ylamine

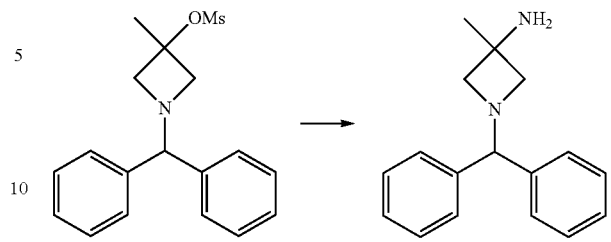

To a solution of methanesulfonic acid 1-benzhydryl-3-methyl-azetidin-3-yl ester (12 g, 36.3 mmol) in DCM (100 mL) was added a saturated solution of ammonia in MeOH (200 mL) and the mixture was stirred for 3 h. The solvent was removed in vacuo and the residue was purified by column chromatography on silica gel (eluting with 0-100% EtOAc in petroleum ether) to give 1-benzhydryl-3-methyl-azetidin-3-ylamine (5.31 g, 58%), which was used directly in step F. Alternatively, 1-benzhydryl-3-methyl-azetidin-3-ylamine can be prepared via steps D and E. TLC (eluting with 20% EtOAc/heptane) $R_f$=0.2.

Step D. 3-Azido-1-benzhydryl-3-methyl-azetidine

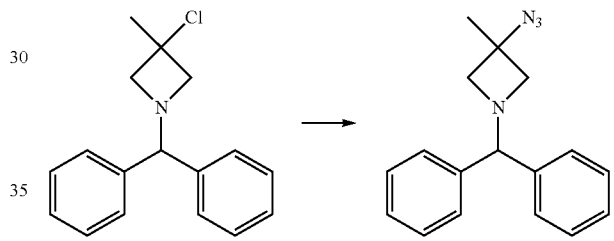

A mixture of 1-benzhydryl-3-chloro-3-methyl-azetidine (2 g, 7.39 mmol) and NaN$_3$ (0.8 g, 12.31 mmol) was dissolved in DMF (30 mL) and the mixture was stirred at 100° C. overnight. The mixture was cooled to ambient temperature and partitioned between water (150 mL) and DCM (50 mL). The organic phase was washed with brine (3×30 mL), dried over anhydrous Na$_2$SO$_4$ and concentrated in vacuo to give 3-azido-1-benzhydryl-3-methyl-azetidine as a yellow oil (2.1 g, 100%), which was used directly in the next step. LC/MS (Table 1, Method 2) $R_t$=0.915 min; MS m/z: 279 [M+H]$^+$

Step E. 1-Benzhydryl-3-methyl-azetidin-3-ylamine

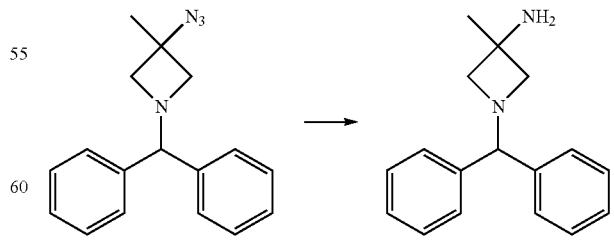

A solution of triphenylphosphine (3.97 g, 15.14 mmol) and 3-azido-1-benzhydryl-3-methyl-azetidine (2.1 g, 7.57 mmol) in THF (20 mL) and water (2 mL) was stirred for 48 h. The solvent was removed in vacuo and a solution of hydrochloric acid (1M, 100 mL) was added to the residue. The aqueous solution was washed with DCM (50 mL) and the aqueous solution was basified to pH 8 with a solution of sodium hydroxide in water (1M). Then, the aqueous solution was extracted with EtOAc (3×50 mL). The combined organic phase was concentrated in vacuo and the residue was purified by column chromatography on silica gel (eluting with 10-100% EtOAc in petroleum ether) to give crude 1-benzhydryl-3-methyl-azetidin-3-ylamine (1.6 g, 6.37 mmol, 84%). $^1$H NMR (CDCl$_3$, 400 MHz): δ7.40-7.33 (m, 4H), 7.21-7.25 (m, 4H), 7.12-7.18 (m, 2H), 4.22-4.30 (m, 1H), 3.10-3.20 (m, 2H), 2.80-2.92 (m, 2H), 1.41-1.47 (m, 3H). The two NH$_2$ protons were not observed in CDCl$_3$.

Step F.
(1-Benzhydryl-3-methyl-azetidin-3-yl)-carbamic acid tert-butyl ester

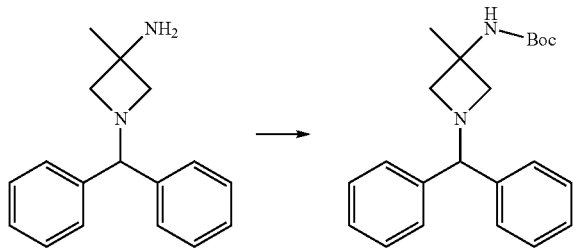 [SMILES: CC1(N)CN(C(c2ccccc2)c2ccccc2)C1 ; CC1(NC(=O)OC(C)(C)C)CN(C(c2ccccc2)c2ccccc2)C1]

Di-tert-butyl dicarbonate (2.076 g, 9.51 mmol) was added slowly into a solution of 1-benzhydryl-3-methyl-azetidin-3-ylamine (1.6 g, 6.34 mmol) and TEA (1.283 g, 12.68 mmol) in DCM (40 mL) and the mixture was stirred at rt overnight. The reaction mixture was concentrated in vacuo and the residue was purified by column chromatography on silica gel (eluting with 0-10% EtOAc in petroleum ether) to give (1-benzhydryl-3-methyl-azetidin-3-yl)-carbamic acid tert-butyl ester (1.0 g, 45%). $^1$H NMR (CDCl$_3$, 400 MHz): δ 7.42-7.44 (m, 4H), 7.28-7.30 (m, 4H), 7.17-7.21 (m, 2H), 4.711 (m, 1H), 4.46 (s, 1H), 3.18 (m, 4H), 1.61 (s, 3H), 1.45 (s, 9H).

Step G. 1-Benzhydryl-3-methyl-azetidin-3-ylamine hydrochloride salt

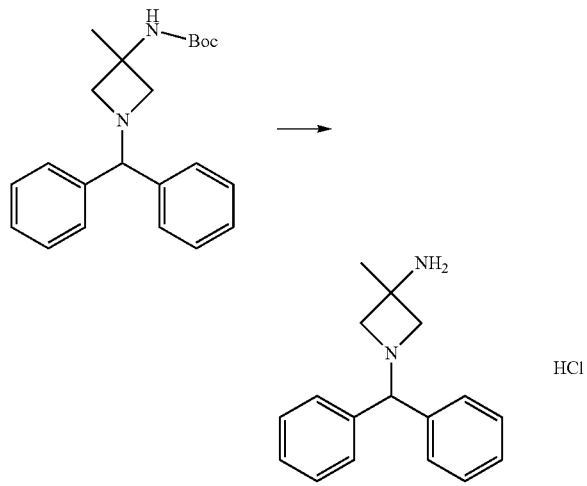

To a solution of HCl in EtOAc (4M, 10 mL, 40 mmol) was added (1-benzhydryl-3-methyl-azetidin-3-yl)-carbamic acid tert-butyl ester (0.750 g, 2.128 mmol) and the mixture was stirred for 2 h. The mixture was concentrated to give 1-benzhydryl-3-methyl-azetidin-3-ylamine hydrochloride salt as solid (0.600 g, 2.077 mmol, 98%). $^1$H NMR (CDCl$_3$, 400 MHz): δ 9.04 (m, 3H), 7.46-7.67 (m, 4H), 7.21-7.42 (m, 6H), 4.35 (m, 2H), 3.89 (m, 2H), 1.52-1.65 (m, 3H).

Preparation #4. 3-(1-Trifluoromethanesulfonyloxy-vinyl)-azetidine-1-carboxylic acid tert-butyl ester Step A. 3-(Methoxy-methyl-carbamoyl)-azetidine-1-carboxylic acid tert-butyl ester

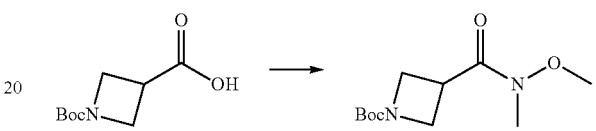

To a solution of azetidine-1,3-dicarboxylic acid mono-tert-butyl ester (Alfa, 5.0 g, 24.9 mmol) in THF (80 mL) was added DIEA (9.55 mL, 54.7 mmol) and HATU (11.34 g, 29.8 mol) and the reaction mixture was stirred at ambient temperature for 1.5 h. N,O-dimethylhydroxylamine (1.82 g, 29.8 mmol) was added and the reaction mixture was stirred at ambient temperature overnight. The reaction mixture was diluted with aqueous NH$_4$Cl (100 mL). The aqueous layer was extracted with EtOAc (3×100 mL). The combined organic layers were washed with water (20 mL) and brine (20 mL), dried over Na$_2$SO$_4$, filtered and evaporated in vacuo. The residue was purified by column chromatography on silica gel (eluting with 15% EtOAc in petroleum ether) to give 3-(methoxy-methyl-carbamoyl)-azetidine-1-carboxylic acid tert-butyl ester (6.0 g, 99.0%). $^1$H NMR (DMSO-d$_6$, 400 MHz): δ 4.02 (m, 4H), 3.71 (m, 1H), 3.63 (s, 3H), 3.11 (s, 3H), 1.38 (s, 9H).

Step B. 3-Acetyl-azetidine-1-carboxylic acid tert-butyl ester

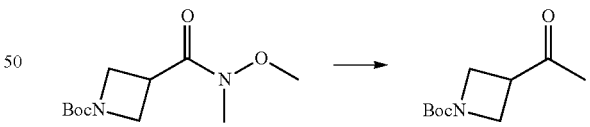

To a solution of 3-(methoxy-methyl-carbamoyl)-azetidine-1-carboxylic acid tert-butyl ester (6.0 g, 24.56 mmol) in THF (15 mL) at −78° C. was added a solution of methymagnesium bromide (3M in toluene, 12.3 mL, 36.9 mmol). The reaction mixture was stirred at −78° C. for 1 h. The reaction mixture was warmed to ambient temperature gradually and stirred for 1 h. The reaction was quenched by the addition of aqueous KHSO$_4$ solution (20 mL). The aqueous layer was extracted with EtOAc (3×20 mL). The combined organic layers were washed with water (20 mL) and brine (20 mL), dried over Na$_2$SO$_4$, filtered and concentrated in vacuo. The residue was purified by column chromatography on silica gel (eluting with 10% EtOAc in petroleum ether) to give 3-acetylazetidine-1-carboxylic acid tert-butyl ester (3.2 g, 65.4%). ¹H NMR (DMSO-d₆, 400 MHz): δ 3.88 (m, 4H), 3.53 (m, 1H), 2.08 (s, 3H), 1.34 (s, 9H).

Step C. 3-(1-Trifluoromethanesulfonyloxy-vinyl)-azetidine-1-carboxylic acid tert-butyl ester

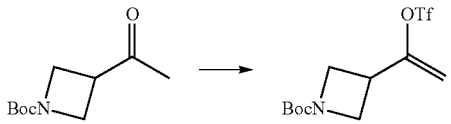 [SMILES: CC(=O)C1CN(C(=O)OC(C)(C)C)C1 ; C=C(OS(=O)(=O)C(F)(F)F)C1CN(C(=O)OC(C)(C)C)C1]

To a −78° C. solution of 3-acetyl-azetidine-1-carboxylic acid tert-butyl ester (0.1 g, 0.5 mmol) in THF (10 mL) was added a solution of LiHMDS (1M, 1.0 mL, 1.0 mmol). The reaction mixture was warmed to ambient temperature gradually and stirred for 4 h. The reaction mixture was cooled to −78° C. and a solution of 1,1,1-trifluoro-N-phenyl-N-(trifluoromethylsulfonyl)methanesulfonamide (0.36 g, 1.0 mmol) in THF (5 mL) was added. The reaction mixture was warmed to ambient temperature gradually and stirred overnight. The reaction was quenched by the addition of aqueous NH₄Cl solution (20 mL). The aqueous layer was extracted with EtOAc (3×20 mL). The combined organic layers were washed with brine (20 mL), dried over Na₂SO₄, filtered and evaporated in vacuo. The residue was purified by column chromatography on silica gel (eluting with 10% EtOAc in petroleum ether) to give 3-(1-trifluoromethanesulfonyloxy-vinyl)-azetidine-1-carboxylic acid tert-butyl ester (0.092 g, 55.3%). ¹H NMR (DMSO-d₆, 400 MHz): δ 5.56 (d, J=4.8 Hz, 1H), 5.36 (d, J=4.8 Hz, 1H), 4.05 (m, 2H), 3.79 (m, 2H), 3.56 (m, 1H), 1.35 (s, 9H).

Preparation #5. 2-(6-Bromo-3-oxo-7-trifluoromethyl-2,3-dihydro-benzo[1,4]oxazin-4-yl)-propionic acid ethyl ester Step A.
1-(2-Fluoro-4-hydroxy-5-nitro-phenyl)-ethanone

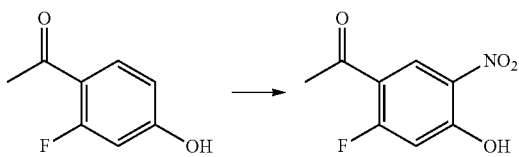

To a mixture of 1-(2-fluoro-4-hydroxy-phenyl)-ethanone (Alfa, 5 g, 32.5 mmol) in concentrated sulfuric acid (50 mL) at −5° C. was added KNO₃ (3.29 g, 32.6 mmol) and the reaction mixture was stirred for 3 h. The reaction mixture was poured into ice water (500 mL) carefully and the aqueous solution was extracted with EtOAc (3×150 mL). The combined organic phase was washed with brine (100 mL), dried over anhydrous Na₂SO₄ and filtered. The filtrate was evaporated in vacuo and the residue was purified by column chromatography on silica gel (eluting with 2-10% EtOAc in petroleum ether) to give 1-(2-fluoro-4-hydroxy-5-nitro-phenyl)-ethanone as yellow solid (4.59 g, 71%). ¹H NMR (CDCl₃, 400 MHz): δ 10.95 (s, 1H), 8.79 (d, J=7.2 Hz, 1H), 6.92 (d, J=11.2 Hz, 1H), 2.63 (d, J=5.2 Hz, 3H).

Step B.
1-(5-Amino-2-fluoro-4-hydroxy-phenyl)-ethanone

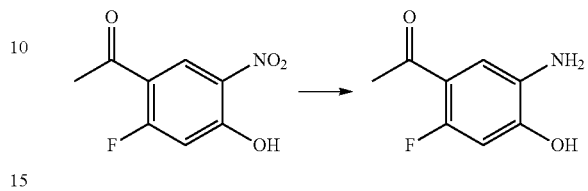

To a solution of 1-(2-fluoro-4-hydroxy-5-nitro-phenyl)-ethanone (3 g, 15.7 mmol) in EtOH (30 mL) and THF (6 mL) was added 10% Pd/C (1.5 g, 1.4 mmol) and the reaction mixture was stirred at ambient temperature under an atmosphere of H₂ for 2 h. The reaction mixture was filtered and the filtrate was evaporated in vacuo to give 1-(5-amino-2-fluoro-4-hydroxy-phenyl)-ethanone as black solid (2.5 g, 94%), which was used in the next step directly without further purification. ¹H NMR (DMSO-d₆, 400 MHz): δ 7.01 (d, J=8.0 Hz, 1H), 6.48 (d, J=12.4 Hz, 1H), 2.39 (d, J=4.8 Hz, 3H).

Step C.
6-Acetyl-7-fluoro-4H-benzo[1,4]oxazin-3-one

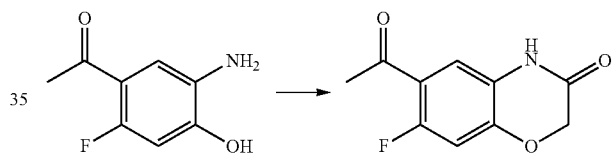

To a mixture of 1-(5-amino-2-fluoro-4-hydroxy-phenyl)-ethanone (13.2 g, 78 mmol), NaHCO₃ (19.67 g, 234 mmol) in water (90 mL), and 4-methyl-2-pentanone (90 mL) at 0° C. was added 2-chloroacetyl chloride (13.22 g, 8.8 mL, 117 mmol) dropwise. After addition, the reaction mixture was stirred at ambient temperature for 0.5 h and then at 80° C. for 18 h. The mixture was cooled to ambient temperature and filtered to give 6-acetyl-7-fluoro-4H-benzo[1,4]oxazin-3-one as gray solid (12 g, 74%), which was used in next step directly without further purification. ¹H NMR (DMSO-d₆, 400 MHz): δ 10.90 (s 1H), 7.35 (d, J=7.6 Hz, 1H), 7.02 (d, J=11.6 Hz, 1H), 4.71 (s, 2H), 2.47 (d, J=4.8 Hz, 3H).

Preparation #6. 6-Bromo-4,7-dimethyl-2-(2-trimethylsilanyl-ethoxymethyl)-2,10-dihydro-9-oxa-1,2,4a-triaza-phenanthren-3-one Step A. 7-Methyl-4H-benzo[1,4]oxazin-3-one

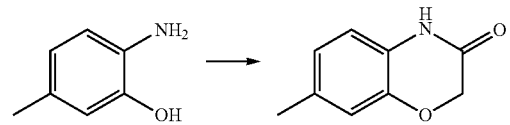

To a mixture of 2-amino-5-methyl-phenol (Alfa, 15.0 g, 122 mmol), K₂CO₃ (50.5 g, 365 mmol) and Bu₄NBr (3.94 g, 12.18 mmol) in acetonitrile (400 mL) at 0° C. was added 2-chloroacetyl chloride (15.1 g, 10.0 mL, 134 mmol) dropwise. After addition, the mixture was heated at reflux for 2.5 h. The reaction mixture was cooled to ambient temperature and evaporated in vacuo. Water was added (500 mL) and the aqueous solution was extracted with EtOAc (3×150 mL). The combined organic phase was washed with brine (100 mL), dried over anhydrous Na$_2$SO$_4$, filtered and concentrated in vacuo. The residue was purified by column chromatography on silica gel (eluting with 25% EtOAc in petroleum ether) to give 7-methyl-4H-benzo[1,4]oxazin-3-one as a brown solid (14.1 g, 71%). $^1$H NMR (DMSO-d$_6$, 400 MHz): δ 10.58 (s, 1H), 6.76 (m, 3H), 4.52 (s, 2H), 2.21 (s, 3H).

Step B. 2-(7-Methyl-3-oxo-2,3-dihydro-benzo[1,4]oxazin-4-yl)-propionic acid ethyl ester

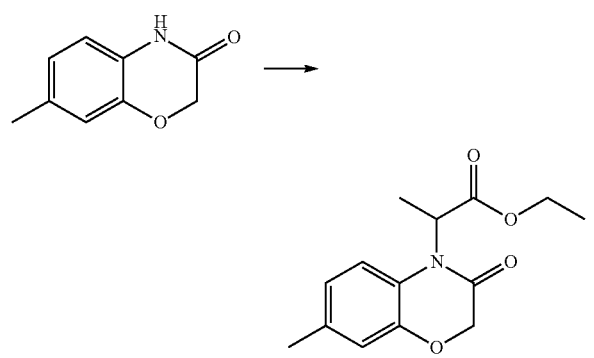

To a mixture of 7-methyl-4H-benzo[1,4]oxazin-3-one (14.1 g, 86 mmol) and Cs$_2$CO$_3$ (70.4 g, 216 mmol) in DMF (500 mL) was added ethyl 2-bromopropanoate (31.3 g, 173 mmol) at ambient temperature and the reaction mixture was heated to 70° C. for 3 h. The reaction mixture was cooled to ambient temperature and the DMF was removed in vacuo. Water (500 mL) was added to the residue and the aqueous solution was extracted with EtOAc (3×150 mL). The combined organic phase was washed with brine (100 mL) and dried over anhydrous Na$_2$SO$_4$, filtered and concentrated in vacuo. The residue was purified by column chromatography on silica gel (eluting with 10% EtOAc in petroleum ether) to give 2-(7-methyl-3-oxo-2,3-dihydro-benzo[1,4]oxazin-4-yl)-propionic acid ethyl ester as brown solid (22.2 g, 98%). TLC (eluting with 20% EtOAc/heptane) R$_f$=0.3.

Step C. 2-(6-Bromo-7-methyl-3-oxo-2,3-dihydro-benzo[1,4]oxazin-4-yl)-propionic acid ethyl ester

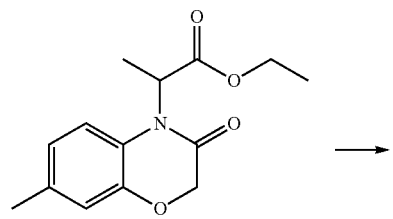

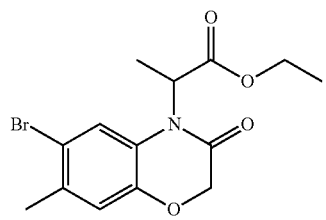

To a solution of 2-(7-methyl-3-oxo-2,3-dihydro-benzo[1,4]oxazin-4-yl)-propionic acid ethyl ester (21.0 g, 80 mmol) in DCM (250 mL) was added 1-bromopyrrolidine-2,5-dione (15.6 g, 88 mmol) and the reaction mixture was stirred at ambient temperature for 3 h. The reaction mixture was quenched by addition of a saturated solution of thiosulfate in water (50 mL). The organic phase was separated and the aqueous portion was extracted with DCM (3×20 mL). The combined organic phase was washed with brine (100 mL), dried over anhydrous Na$_2$SO$_4$, filtered and concentrated in vacuo. The residue was purified by column chromatography on silica gel (eluting with 20% EtOAc in petroleum ether) to give -(6-bromo-7-methyl-3-oxo-2,3-dihydro-benzo[1,4]oxazin-4-yl)-propionic acid ethyl ester as solid (23.1 g, 85%). LC/MS (Table 1, Method 3) R$_f$=1.259 min.; MS m/z: 342/344 [M+H]$^+$.

Step D. 2-(6-Bromo-7-methyl-3-thioxo-2,3-dihydro-benzo[1,4]oxazin-4-yl)-propionic acid ethyl ester

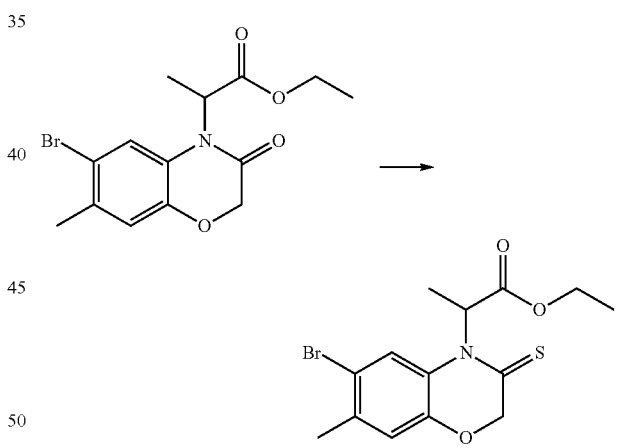

To a solution of 2-(6-bromo-7-methyl-3-oxo-2,3-dihydro-benzo[1,4]oxazin-4-yl)-propionic acid ethyl ester (23.6 g, 69 mmol) in toluene (300 mL) was added Lawesson's reagent (30.7 g, 76 mmol) and the reaction mixture was heated at reflux for 4 h. The reaction mixture was cooled to ambient temperature water (300 mL) was added. The organic phase was separated and the aqueous portion was extracted with EtOAc (3×100 mL). The combined organic phase was washed with brine (100 mL), dried over anhydrous Na$_2$SO$_4$, filtered and concentrated in vacuo. The residue was purified by column chromatography on silica gel (eluting with 5% EtOAc in petroleum ether) to give 2-(6-bromo-7-methyl-3-thioxo-2,3-dihydro-benzo[1,4]oxazin-4-yl)-propionic acid ethyl ester as solid (20.0 g, 81%). $^1$H NMR (DMSO-d$_6$, 400

MHz): δ 7.41 (s, 1H), 7.16 (s, 1H), 6.03 (m, 1H), 4.90 (s, 2H), 4.14 (m, 2H), 2.29 (s, 3H), 1.61 (d, J=6.8 Hz, 3H), 1.08 (t, J=7.2 Hz, 3H).

Step E. 6-Bromo-4,7-dimethyl-2,10-dihydro-9-oxa-1,2,4a-triaza-phenanthren-3-one

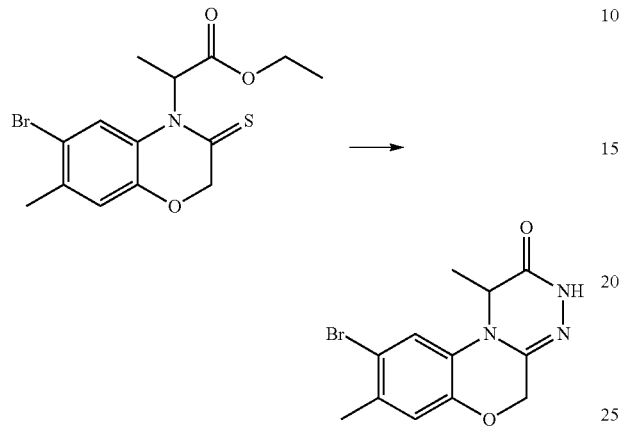

To a solution of 2-(6-bromo-7-methyl-3-thioxo-2,3-dihydro-benzo[1,4]oxazin-4-yl)-propionic acid ethyl ester (0.192 g, 0.536 mmol) in EtOH (3 mL) was added anhydrous hydrazine hydrate (0.107 g, 2.144 mmol) and the mixture was heated at reflux for 4 h. The reaction mixture was cooled to ambient temperature and evaporated in vacuo. The residue was purified by column chromatography on silica gel (eluting with 25% EtOAc in petroleum ether) to give 6-bromo-4,7-dimethyl-2,10-dihydro-9-oxa-1,2,4a-triaza-phenanthren-3-one as white solid (0.15 g, 90%). $^1$H NMR (DMSO-d$_6$, 400 MHz): δ 10.80 (s, 1H), 7.46 (s, 1H), 7.02 (s, 1H), 4.86 (q, J=6.8 Hz, 1H), 4.60 (dd, J=12.8 Hz, 2H), 2.26 (s, 3H), 1.27 (d, J=6.8 Hz, 3H).

Step F. 6-Bromo-4,7-dimethyl-2-(2-trimethylsilanyl-ethoxymethyl)-2,10-dihydro-9-oxa-1,2,4a-triaza-phenanthren-3-one

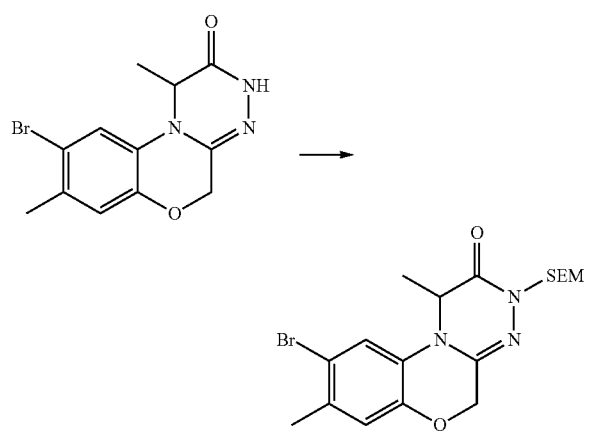

To a suspension of NaH (60%, 0.387 g, 9.67 mmol) in DMF (15 mL) was added 6-bromo-4,7-dimethyl-2,10-dihydro-9-oxa-1,2,4a-triaza-phenanthren-3-one (2.0 g, 6.45 mmol) in portions and the reaction mixture was stirred at 0° C. for 0.5 h. (2-(Chloromethoxy)ethyl)trimethylsilane (1.613 g, 9.67 mmol) was added and the reaction mixture was warmed to ambient temperature and stirred for 2 h. Water (100 mL) was added and the aqueous solution was extracted with EtOAc (3×50 mL). The combined organic phase was washed with brine (100 mL) and dried over anhydrous Na$_2$SO$_4$, filtered and concentrated in vacuo. The residue was purified by column chromatography on silica gel (eluting with 30% EtOAc in petroleum ether) to give 6-bromo-4,7-dimethyl-2-(2-trimethylsilanyl-ethoxymethyl)-2,10-dihydro-9-oxa-1,2,4a-triaza-phenanthren-3-one as solid (2.24 g, 79%). $^1$H NMR (DMSO-d$_6$, 400 MHz): δ 7.52 (s, 1H), 7.12 (s, 1H), 5.01 (m, 2H), 4.95 (m, 1H), 4.68 (s, 2H), 3.60 (m, 2H), 2.28 (s, 3H), 1.32 (m, 3H), 0.89 (m, 2H), 0.00 (s, 9H).

Preparation #7. 6-Bromo-7-fluoro-4-methyl-2,10-dihydro-9-oxa-1,2,4a-triaza-phenanthren-3-one Step A. 4-Bromo-5-fluoro-2-nitrophenol

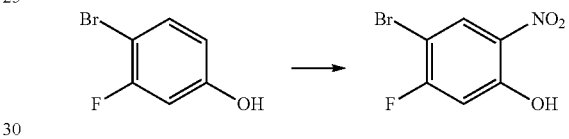

To a 0° C. mixture of 4-bromo-3-fluorophenol (70.0 g, 366 mmol) in DCM (500 mL) was added HNO$_3$ (23.0 g, 366 mmol) carefully and the reaction mixture was stirred 30 min. The reaction mixture was poured into water (1 L) and extracted with DCM (3×500 mL). The combined organic portion was washed with brine (300 mL) and dried over anhydrous Na$_2$SO$_4$, filtered and concentrated in vacuo. The residue was crystallized from EtOH to give 4-bromo-5-fluoro-2-nitrophenol (42.0 g, 49%). $^1$H NMR (DMSO-d$_6$, 400 MHz): δ 11.72 (brs, 1H), δ 8.30 (d, J=7.2 Hz, 1H), 7.09 (d, J=10.0 Hz, 1H).

Step B. 2-Amino-4-bromo-5-fluorophenol

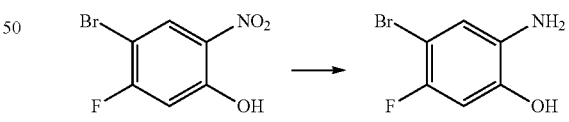

To a solution of 4-bromo-5-fluoro-2-nitrophenol (40.0 g, 169 mmol) in MeOH (250 mL) and THF (250 mL) was added zinc powder (91.0 g, 1700 mmol) and ammonium chloride (111.0 g, 1700 mmol) and the reaction mixture was stirred at ambient temperature overnight. The reaction mixture was filtered and the filtrate was concentrated in vacuo. The residue was washed with cold water to give 2-amino-4-bromo-5-fluorophenol (38.0 g, crude) which was used in the next step directly without further purification. $^1$H NMR (DMSO-d$_6$, 400 MHz): δ 9.82 (br s, 1H), δ 6.76 (d, J=7.2 Hz, 1H), 6.60 (d, J=10.0 Hz, 1H), 4.65 (br s, 2H).

Step C.
6-Bromo-7-fluoro-4H-benzo[1,4]oxazin-3-one

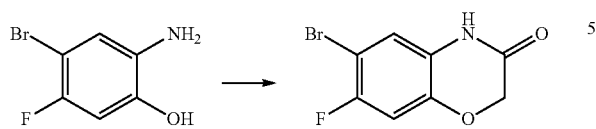

To a 0° C. mixture of 2-amino-4-bromo-5-fluorophenol (38.0 g, crude from previous step) and K₂CO₃ (76.0 g, 553 mmol) in DMF (100 mL) was added 2-chloroacetyl chloride (23.0 g, 15.3 mL, 203 mmol) drop-wise. The reaction mixture was heated at 80° C. overnight then cooled to ambient temperature and poured into water (300 mL). The precipitate was collected by filtration, washed with water and dried to give 6-bromo-7-fluoro-4H-benzo[1,4]oxazin-3-one (41.0 g, 90%). $^1$H NMR (DMSO-$d_6$, 400 MHz): δ 7.13 (m, 2H), 4.62 (s, 2H). The amide proton was not observed.

Step D. 2-(6-Bromo-7-fluoro-3-oxo-2,3-dihydro-benzo[1,4]oxazin-4-yl)-propionic acid ethyl ester

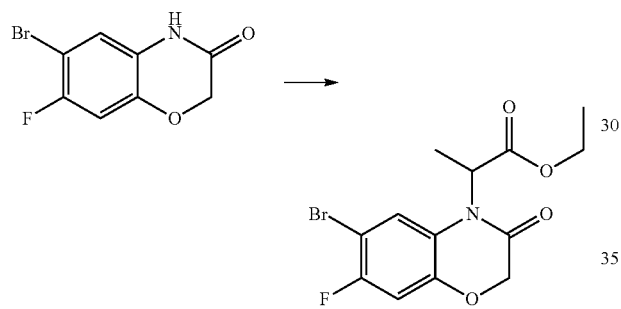

To a mixture of 6-bromo-7-fluoro-4H-benzo[1,4]oxazin-3-one (41.0 g, 167 mmol) and K₂CO₃ (23.0 g, 167 mmol) in acetone (300 mL) was added ethyl 2-bromopropanoate (75.0 g, 53.8 mL, 417 mmol) drop-wise at ambient temperature and the mixture was heated at reflux overnight. The mixture was cooled to ambient temperature and filtered. The filtrate was evaporated in vacuo and the residue was purified by column chromatography on silica gel (eluting with 10% EtOAc in petroleum ether) to give 2-(6-bromo-7-fluoro-3-oxo-2,3-dihydro-benzo[1,4]oxazin-4-yl)-propionic acid ethyl ester (43.0 g, 75%). $^1$H NMR (CDCl₃, 400 MHz): δ 6.97 (d, J=6.4 Hz, 1H), 6.85 (d, J=8.4 Hz, 1H), 5.25 (q, J=7.2 Hz, 1H), 4.59 (dd, J=15.2 Hz, 2H), 4.27 (m, 2H), 1.63 (d, J=7.2 Hz, 3H), 1.23 (t, J=7.2 Hz, 3H).

Step E. 2-(6-Bromo-7-fluoro-3-thioxo-2,3-dihydro-benzo[1,4]oxazin-4-yl)-propionic acid ethyl ester

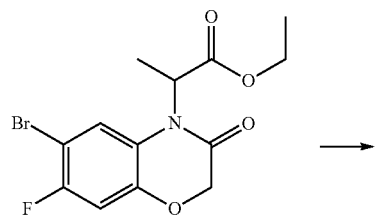

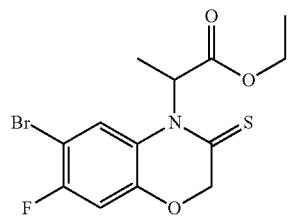

To a mixture of 2-(6-bromo-7-fluoro-3-oxo-2,3-dihydro-benzo[1,4]oxazin-4-yl)-propionic acid ethyl ester (43.0 g, 124 mmol) in toluene (300 mL) was added Lawesson's reagent (50.6 g, 124 mmol) and the mixture was heated at reflux overnight. The reaction mixture was cooled to ambient temperature and the solvent was removed in vacuo The residue was purified by chromatography on silica gel (eluting with 5% EtOAc in petroleum ether) to give 2-(6-bromo-7-fluoro-3-thioxo-2,3-dihydro-benzo[1,4]oxazin-4-yl)-propionic acid ethyl ester (36.0 g, 80%). $^1$H NMR (CDCl₃, 400 MHz): δ 7.09 (d, J=6.4 Hz, 1H), 6.88 (d, J=8.4 Hz, 1H), 6.62 (brs, 1H), 4.96 (dd, J=15.2 Hz, 2H), 4.23 (m, 2H), 1.72 (d, J=7.2 Hz, 3H), 1.21 (t, J=7.2 Hz, 3H).

Step F. 6-Bromo-7-fluoro-4-methyl-2,10-dihydro-9-oxa-1,2,4a-triaza-phenanthren-3-one

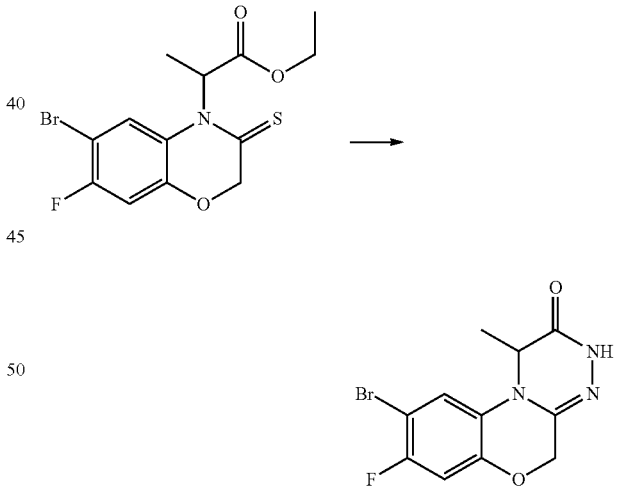

To a mixture of 2-(6-bromo-7-fluoro-3-thioxo-2,3-dihydro-benzo[1,4]oxazin-4-yl)-propionic acid ethyl ester (33.0 g, 91 mmol) in EtOH (100 mL) was added hydrizine hydrate (19.0 g, 364 mmol) and the reaction mixture was heated at reflux for 3 h. The mixture was cooled to ambient temperature. The precipitate was collected by filtration and washed with cold EtOH to give 6-bromo-7-fluoro-4-methyl-2,10-dihydro-9-oxa-1,2,4a-triaza-phenanthren-3-one (24.0 g, 84%). $^1$H NMR (DMSO-$d_6$, 400 MHz): δ 10.81 (brs, 1H), 7.59 (d, J=6.8 Hz, 1H), 7.17 (d, J=9.2 Hz, 1H), 4.87 (q, J=6.8 Hz, 1H), 4.66 (m, 2H), 1.28 (d, J=6.8 Hz, 3H).

Preparation #8. 4-((R)-7-Bromo-4-methyl-3-oxo-2,3,4,10-tetrahydro-9-oxa-1,2,4a-triaza-phenanthren-6-yl)-piperidine-1-carboxylic acid tert-butyl ester

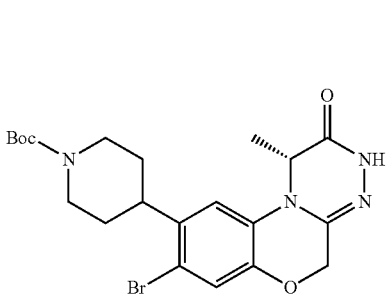

Step A. 4-((R)-4-Methyl-3-oxo-2,3,4,10-tetrahydro-9-oxa-1,2,4a-triaza-phenanthren-6-yl)-piperidine-1-carboxylic acid tert-butyl ester

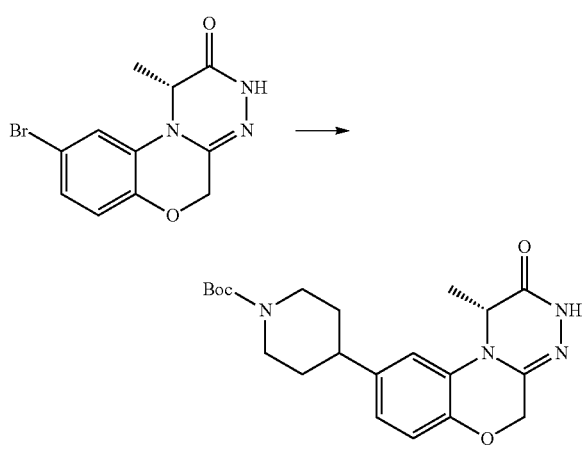

Using a similar procedure as described in Example #71, Step A-B, 4-((R)-4-methyl-3-oxo-2,3,4,10-tetrahydro-9-oxa-1,2,4a-triaza-phenanthren-6-yl)-piperidine-1-carboxylic acid tert-butyl ester was prepared from (R)-6-bromo-4-methyl-2,10-dihydro-9-oxa-1,2,4a-triaza-phenanthren-3-one (Preparation #11, Step D). LC/MS (Table 1, Method 3) Rt=1.428 min; MS m/z: 401 [M+H]$^+$.

Step B. 4-((R)-7-Bromo-4-methyl-3-oxo-2,3,4,10-tetrahydro-9-oxa-1,2,4a-triaza-phenanthren-6-yl)-piperidine-1-carboxylic acid tert-butyl ester

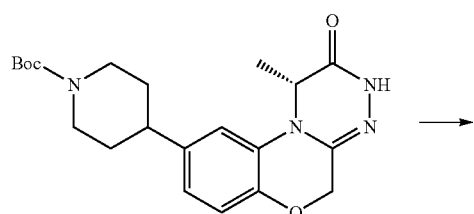

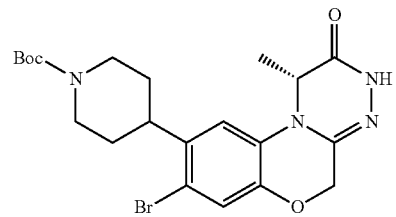 [SMILES: C[C@@H]1C(=O)NN=C2COc3cc(Br)c(C4CCN(C(=O)OC(C)(C)C)CC4)cc3N21]

To a solution of 4-((R)-4-methyl-3-oxo-2,3,4,10-tetrahydro-9-oxa-1,2,4a-triaza-phenanthren-6-yl)-piperidine-1-carboxylic acid tert-butyl ester (2.0 g, 4.99 mmol) in DCM (20 mL) and MeOH (10 mL) was added tetra-N-butylammonium tribromide (2.65 g, 5.49 mmol). The reaction mixture was stirred at ambient temperature for 2 h. Additional tetra-N-butylammonium tribromide (0.5 g, 1 mmol) was added and the reaction mixture was stirred overnight. Aqueous saturated Na$_2$S$_2$O$_3$ solution (10 mL) and NaHCO$_3$ (10 mL) were added. The organic phase was separated and the aqueous solution was extracted with EtOAcEtOAc (3×20 mL). The organic phase was combined and concentrated in vacuo. The residue was purified by column chromatography on silica gel (eluting with 25%~50% EtOAc in petroleum ether) to give 4-((R)-7-bromo-4-methyl-3-oxo-2,3,4,10-tetrahydro-9-oxa-1,2,4a-triaza-phenanthren-6-yl)-piperidine-1-carboxylic acid tert-butyl ester (1.4 g, 58%) as a solid. $^1$H NMR (400 MHz, CDCl$_3$) δ ppm 8.24 (brs, 1H), 7.21 (s, 1H), 6.74 (s, 1H), 4.75 (m, 1H), 4.63-4.49 (d, J=13.2 Hz, 2H), 4.28 (m, 2H), 3.15-3.02 (m, 1H), 2.92-2.76 (m, 2H), 1.86-1.78 (m, 2H), 1.64-1.54 (m, 2H), 1.51-1.48 (m, 12H).

Preparation #9. (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one hydrochloride acid

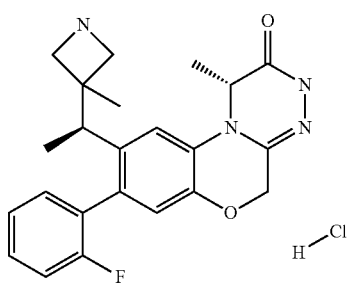 [SMILES: C[C@@H]1C(=O)NN=C2COc3cc(-c4ccccc4F)c([C@@H](C)C4(C)CNC4)cc3N21 ; Cl]

Using a similar procedure as described in Example #133, Steps E and G, (R)-7-(2-fluoro-phenyl)-4-methyl-6-[(R)-1-(3-methyl-azetidin-3-yl)-ethyl]-2,10-dihydro-9-oxa-1,2,4a-triaza-phenanthren-3-one hydrochloride acid was prepared from 3-[(S)-1-((R)-7-bromo-4-methyl-3-oxo-2,3,4,10-tetrahydro-9-oxa-1,2,4a-triaza-phenanthren-6-yl)-ethyl]-3-methyl-azetidine-1-carboxylic acid tert-butyl ester (Example #133, Step D) and (2-fluorophenyl)boronic acid. LC/MS (Table 1, Method 25) R$_t$=0.750 min; MS m/z: 409 [M+H]$^+$.

Preparation #10. (R)-4-methyl-7-(4,4,5,5-tetramethyl-[1,3,2]dioxaborolan-2-yl)-2,10-dihydro-9-oxa-1,2,4a-triaza-phenanthren-3-one

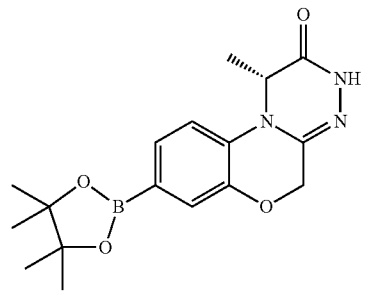 [SMILES: C[C@@H]1C(=O)NN=C2COc3cc(B4OC(C)(C)C(C)(C)O4)ccc3N21]

Step A. 7-Bromo-4H-benzo[1,4]oxazin-3-one

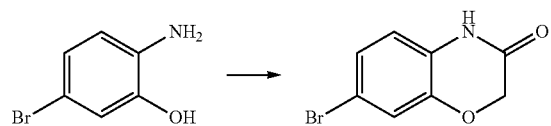 [SMILES: Nc1ccc(Br)cc1O ; O=C1COc2cc(Br)ccc2N1]

To a mixture of 2-amino-5-bromophenol (51.3 g, 273 mmol) and NaHCO₃ (68.8 g, 819 mmol) in water (200 mL) and DME (200 mL) was added 2-chloroacetyl chloride (46.2 g, 409 mmol) at 0° C. and the reaction mixture was stirred at 15° C. for 0.5 h then heated at 80° C. for 18 h. The reaction mixture was cooled to ambient temperature. The precipitate was collected by suction, washed with water and dried in vacuo to give 7-bromo-4H-benzo[1,4]oxazin-3-one (59.7 g, 96%) as a brown solid. $^1$H NMR (400 MHz, DMSO-d$_6$) δ 10.83 (br s, 1H), 7.17 (s, 1H), 7.12 (d, J=8.4 Hz, 1H), 6.83 (d, J=8.4 Hz, 1H), 4.59 (s, 2H).

Step B.
(S)-2-Trifluoromethanesulfonyloxy-propionic acid ethyl ester

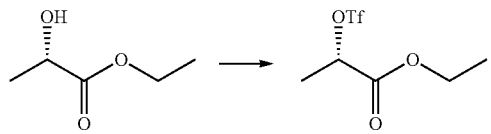

To a solution of (S)-ethyl lactate (80 g, 677 mmol) in DCM (800 mL) was added trifluoromethansulfonicanhydride (210 g, 745 mmol) at 0° C. drop-wise. The solution was stirred for 15 min at 0° C. and then pyridine (58.9 g, 745 mmol) was added drop-wise. The suspension was stirred for another 15 min at 0° C. followed by the removal of the solvent in vacuo. To the residue was added water (800 mL) and the aqueous solution was extracted with petroleum ether (3×800 mL). The combined organic layer was washed with brine (2×1500 mL), dried over Na₂SO₄, filtered and concentrated in vacuo to give (S)-2-trifluoromethanesulfonyloxy-propionic acid ethyl ester (150 g, 89%) as a brown liquid, which was used in the next step directly without further purification. $^1$H NMR (400 MHz, CDCl₃) δ 5.14-5.28 (m, 1H) 4.21-4.35 (m, 1H) 1.63-1.73 (m, 3H) 1.25-1.37 (m, 3H)

Step C. (R)-2-(7-Bromo-3-oxo-2,3-dihydro-benzo[1,4]oxazin-4-yl)-propionic acid ethyl ester

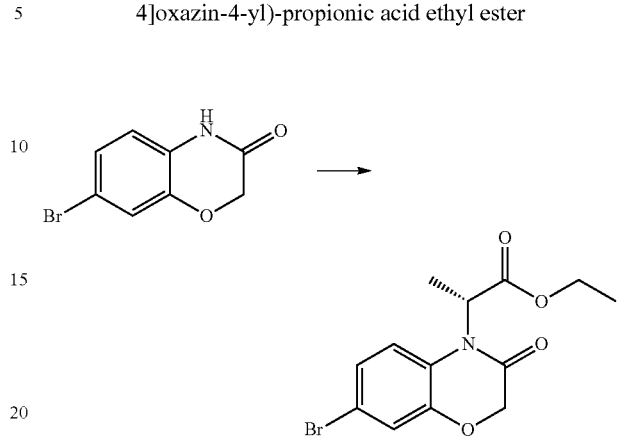

To a mixture of 7-bromo-4H-benzo[1,4]oxazin-3-one (59.7 g, 263 mmol) in THF (700 mL) was added KHMDS solution (1M in THF, 263 mL, 263 mmol) drop-wise at 0° C. and the reaction mixture was stirred for 30 min. give (S)-2-trifluoromethanesulfonyloxy-propionic acid ethyl ester (132 g, 526 mmol) was added at 0° C. and the reaction mixture was allowed to warm to ambient temperature and stirred for 2 h. The reaction mixture was quenched with water (1000 mL). The organic phase was separated and the aqueous solution was extracted with EtOAc (4×500 mL). The combined organic phase was washed with brine (1 L), dried over anhydrous Na₂SO₄ and concentrated in vacuo. The residue was purified by chromatography on silica gel (eluting with 5~15% EtOAc in petroleum ether) to give (R)-2-(7-bromo-3-oxo-2,3-dihydro-benzo[1,4]oxazin-4-yl)-propionic acid ethyl ester (80 g, 93%) as a brown liquid. $^1$H NMR (400 MHz, CDCl₃) δ 7.20 (s, 1H), 7.13 (d, J=8.8 Hz, 1H), 6.69 (d, J=8.7 Hz, 1H), 5.36 (q, J=7.2 Hz, 1H), 4.68-4.58 (m, 2H), 4.24-4.16 (m, 2H), 1.62 (d, J=7.2 Hz, 3H), 1.21 (t, J=7.2 Hz, 3H). SFC (Table 1, Method 29) R$_t$=4.346 min.; [α]$_D^{20}$=26.92 (C=0.002 g/mL in methanol).

Step D. (R)-2-(7-Bromo-3-thioxo-2,3-dihydro-benzo[1,4]oxazin-4-yl)-propionic acid ethyl ester

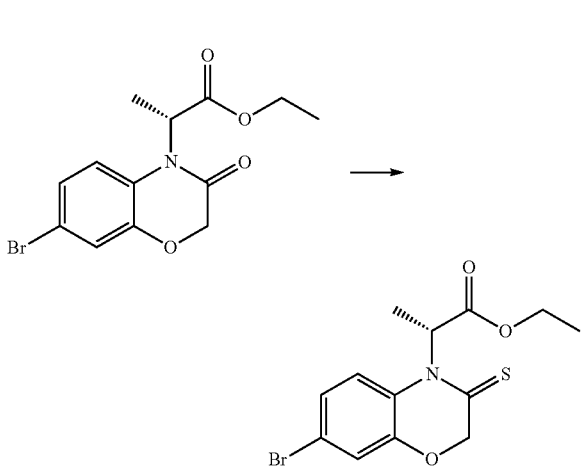

421

A solution of (R)-2-(7-bromo-3-oxo-2,3-dihydro-benzo[1,4]oxazin-4-yl)-propionic acid ethyl ester (80 g, 244 mmol) and Lawesson's reagent (59.1 g, 146 mmol) in toluene (900 mL) was heated at reflux for 3 h then cooled to ambient temperature. The solvent was removed in vacuo and the residue was purified by chromatography on silica gel (eluting with 5-10% EtOAc in petroleum ether) to give (R)-2-(7-bromo-3-thioxo-2,3-dihydro-benzo[1,4]oxazin-4-yl)-propionic acid ethyl ester (60 g, 71%) as a yellow liquid. $^1$H NMR (400 MHz, CDCl$_3$): δ 7.20 (s, 1H), 7.12 (d, J=8.8 Hz, 1H), 6.77 (d, J=8.8 Hz, 1H), 6.70 (m, 1H), 4.99-4.88 (m, 2H), 4.23-4.15 (m, 2H), 1.57 (d, J=7.2 Hz, 3H), 1.16 (t, J=7.2 Hz, 3H). SFC (Table 1, Method 30) R$_t$=2.902 min.; [α]$_D^{20}$=20.79 (C=0.002 g/mL in methanol).

Step E. (R)-7-Bromo-4-methyl-2,10-dihydro-9-oxa-1,2,4a-triaza-phenanthren-3-one

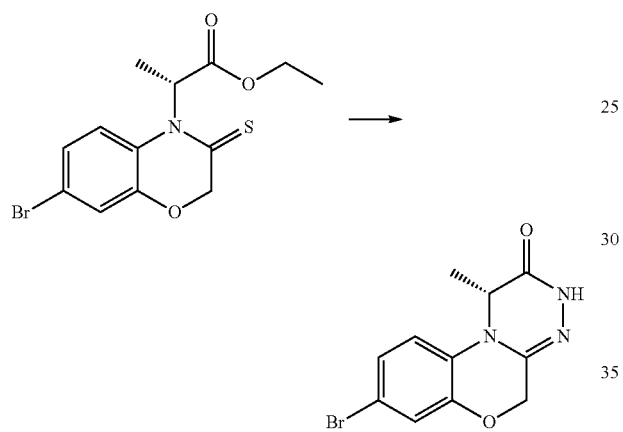

To a mixture of (R)-2-(7-bromo-3-thioxo-2,3-dihydro-benzo[1,4]oxazin-4-yl)-propionic acid ethyl ester (60 g, 174 mmol) in EtOH (800 mL) was added hydrazine hydrate (98%, 17.4 g, 349 mmol) and the reaction mixture was stirred at ambient temperature overnight. The precipitate was collected by filtration and washed with cold EtOH (3×80 mL) to give (R)-7-bromo-4-methyl-2,10-dihydro-9-oxa-1,2,4a-triaza-phenanthren-3-one (32.5 g, 59%) as a white solid. $^1$H NMR (400 MHz, DMSO-d$_6$) δ 10.82 (s, 1H), 7.23 (s, 1H), 7.21 (s, 2H), 4.78 (q, J=6.8 Hz, 1H), 4.68-4.60 (m, 2H), 1.29 (d, J=6.8 Hz, 3H). SFC (Table 1, Method 31) R$_t$=6.114 min.; [α]$_D^{20}$=−342.08 (C=0.002 g/mL in methanol).

Step F. (R)-4-Methyl-7-(4,4,5,5-tetramethyl-[1,3,2]dioxaborolan-2-yl)-2,10-dihydro-9-oxa-1,2,4a-triaza-phenanthren-3-one

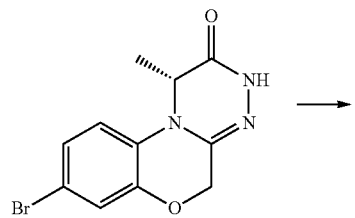

422
-continued

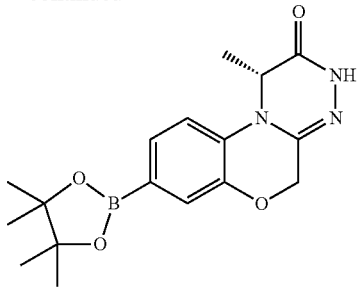

A mixture of (R)-7-bromo-4-methyl-2,10-dihydro-9-oxa-1,2,4a-triaza-phenanthren-3-one (10.0 g, 33.8 mmol), 4,4,4',4',5,5,5',5'-octamethyl-2,2'-bi(1,3,2-dioxaborolane) (10.29 g, 40.5 mmol), PdCl$_2$(dppf) (2.471 g, 3.38 mmol) and potassium acetate (6.63 g, 67.5 mmol) in dioxane (200 mL) was stirred at 90° C. overnight. The reaction mixture was cooled to ambient temperature and concentrated in vacuo. The residue was purified by column chromatography on silica gel (eluting with 6% EtOAc in petroleum ether) to give (R)-4-methyl-7-(4,4,5,5-tetramethyl-[1,3,2]dioxaborolan-2-yl)-2,10-dihydro-9-oxa-1,2,4a-triaza-phenanthren-3-one (11.23 g, 97%) as a solid. $^1$H NMR (CDCl$_3$, 400 MHz): δ 8.24 (brs, 1H), 7.52 (d, J=8.0 Hz, 1H), 7.46 (s, 1H), 6.94 (d, J=8.0 Hz, 1H), 4.78 (q, J=6.8 Hz, 1H), 4.67-4.52 (m, 2H), 1.53 (d, J=6.8 Hz, 3H), 1.42-1.29 (s, 12H). LC/MS (Table 1, Method 25) R$_t$=0.822 min.; MS m/z: 344 [M+H]$^+$.

Preparation #11. (R)-4-Methyl-6-(4,4,5,5-tetramethyl-[1,3,2]dioxaborolan-2-yl)-2,10-dihydro-9-oxa-1,2,4a-triaza-phenanthren-3-one

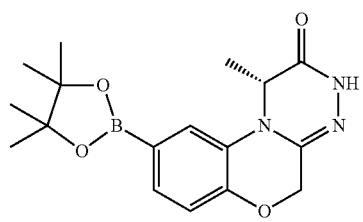 [SMILES: C[C@@H]1C(=O)NN=C2COc3ccc(B4OC(C)(C)C(C)(C)O4)cc3N21]

Step A. 6-Bromo-4H-benzo[1,4]oxazin-3-one

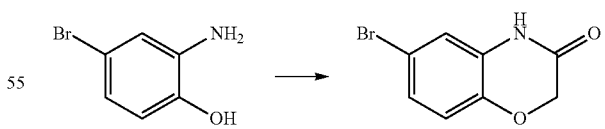

To a mixture of 2-amino-4-bromophenol (50 g, 266 mmol) and NaHCO$_3$ (67.0 g, 798 mmol) in water (200 mL) and DME (200 mL) was added 2-chloroacetyl chloride (45.1 g, 399 mmol) at 0° C. The mixture was stirred at 15° C. for 0.5 h and then stirred at 80° C. overnight. The mixture was cooled to ambient temperature and quenched with water (400 mL). The precipitate was collected by suction filtration, washed with water (200 mL) and petroleum ether (300 mL) in turn, and dried to give 6-bromo-4H-benzo[1,4]oxazin-3-one (59 g, 97%) as a gray solid. $^1$H NMR (DMSO-$d_6$, 400 MHz): δ 7.07 (d, J=8.4 Hz, 1H), 7.02 (s, 1H), 6.90 (d, J=8.4 Hz, 1H), 4.59 (s, 2H).

Step B. (R)-2-(6-Bromo-3-oxo-2,3-dihydro-benzo[1,4]oxazin-4-yl)-propionic acid ethyl ester

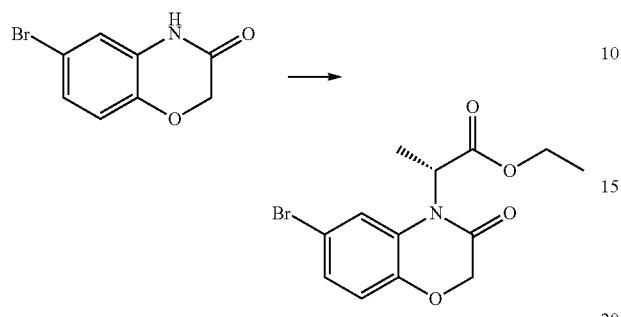

To a mixture of 6-bromo-4H-benzo[1,4]oxazin-3-one (59 g, 259 mmol) in anhydrous THF (800 mL) was added KHMDS solution (1M in THF, 259 mL, 259 mmol) dropwise at 0° C. and the reaction mixture was stirred for 30 min. (S)-2-trifluoromethanesulfonyloxy-propionic acid ethyl ester (Preparation #10, Step B, 117 g, 466 mmol) was added. The reaction mixture was warmed to ambient temperature and stirred for 2 h. The reaction mixture was quenched by the addition of water (1000 mL). The organic phase was separated and the aqueous solution was extracted with EtOAc (4×500 mL). The combined organic phase was washed with brine (1 L), dried over $Na_2SO_4$ and concentrated in vacuo. The residue was purified by column chromatography on silica gel (eluting with 5-10% EtOAc in petroleum ether) to give (R)-2-(6-bromo-3-oxo-2,3-dihydro-benzo[1,4]oxazin-4-yl)-propionic acid ethyl ester (82.4 g, 97%) as a brown liquid. $^1$H NMR (400 MHz, $CDCl_3$) δ 7.12 (d, J=8.8 Hz, 1H), 6.97 (s, 1H), 6.92 (d, J=8.8 Hz, 1H), 5.23 (q, J=6.8 Hz, 2H), 4.67-4.58 (d, J=14.8 Hz, 2H), 4.26-4.20 (m, 2H), 1.60 (d, J=6.8 Hz, 3H), 1.23 (t, J=7.6 Hz, 3H). SFC (Table 1, Method 29) $R_t$=4.146 min.; $[α]^D_{20}$=31.45 (C=0.002 g/mL in methanol).

Step C. (R)-2-(6-Bromo-3-thioxo-2,3-dihydro-benzo[1,4]oxazin-4-yl)-propionic acid ethyl ester

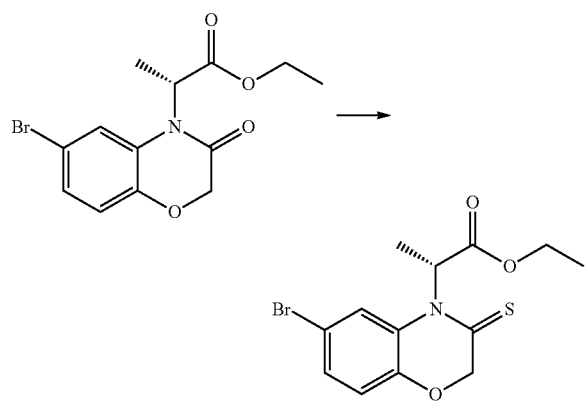

A solution of (R)-2-(6-bromo-3-oxo-2,3-dihydro-benzo[1,4]oxazin-4-yl)-propionic acid ethyl ester (82.4 g, 252 mmol) and Lawesson's reagent (61.1 g, 151 mmol) in toluene (900 mL) was heated at reflux for 3 h and then cooled to ambient temperature. The solvent was removed in vacuo and the residue was purified by chromatography on silica gel (eluting with 5-10% EtOAc in petroleum ether) to give (R)-2-(6-bromo-3-thioxo-2,3-dihydro-benzo[1,4]oxazin-4-yl)-propionic acid ethyl ester (75.2 g, 87%) as a yellow solid. $^1$H NMR (400 MHz, $CDCl_3$): δ 7.19 (d, J=8.8 Hz, 1H), 7.04 (s, 1H), 6.93 (d, J=8.8 Hz, 1H), 6.57 (m, 2H), 4.96-4.87 (m, 2H), 4.29-4.16 (m, 2H), 1.71 (d, J=6.8 Hz, 3H), 1.18 (t, J=6.8 Hz, 3H). SFC (Table 1, Method 29) $R_t$=3.529 min.; $[α]^D_{20}$=19.25 (C=0.002 g/mL in methanol).

Step D. (R)-6-Bromo-4-methyl-2,10-dihydro-9-oxa-1,2,4a-triaza-phenanthren-3-one

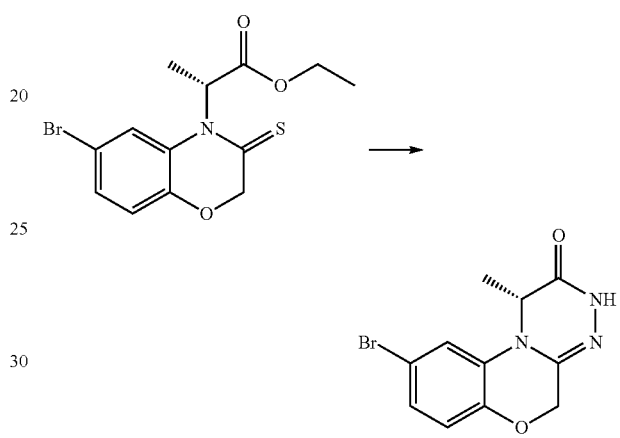

To a mixture of (R)-2-(6-bromo-3-thioxo-2,3-dihydro-benzo[1,4]oxazin-4-yl)-propionic acid ethyl ester (75.2 g, 219 mmol) in EtOH (800 mL) was added hydrazine hydrate (98%, 21.9 g, 438 mmol) and the mixture was stirred at ambient temperature overnight. The precipitate was collected by filtration and washed with cold EtOH (3×80 mL) to give 6-bromo-4-methyl-2,10-dihydro-9-oxa-1,2,4a-triaza-phenanthren-3-one (6 g, 9%) as a yellow solid. The filtrate was concentrated to give 70 g of crude product, which was purified by chromatography on silica gel (eluting with 10-25% EtOAc in petroleum ether) to give a second batch of (R)-6-bromo-4-methyl-2,10-dihydro-9-oxa-1,2,4a-triaza-phenanthren-3-one (45.9 g, 71%) as a yellow solid. $^1$H NMR (400 MHz, $CDCl_3$): δ 8.53 (brs, 1H), 7.10 (d, J=8.4 Hz, 1H), 7.03 (s, 1H), 6.89 (d, J=8.4 Hz, 1H), 4.69-4.52 (m, 3H), 1.52 (d, J=6.8 Hz, 3H). SFC (Table 1, Method 32) $R_t$=6.075 min.; $[α]_D^{20}$=−314.92 (C=0.002 g/mL in methanol).

Step E. (R)-4-Methyl-6-(4,4,5,5-tetramethyl-[1,3,2]dioxaborolan-2-yl)-2,10-dihydro-9-oxa-1,2,4a-triaza-phenanthren-3-one

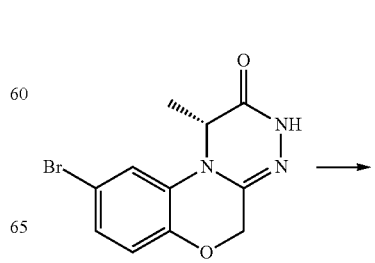

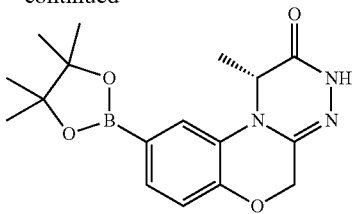

To a mixture of PdCl$_2$(dppf) (4.94 g, 6.75 mmol) and 4,4,4',4',5,5,5',5'-octamethyl-2,2'-bi(1,3,2-dioxaborolane) (20.58 g, 81 mmol), (R)-6-bromo-4-methyl-2,10-dihydro-9-oxa-1,2,4a-triaza-phenanthren-3-one (20 g, 67.5 mmol) in dioxane (200 mL) was added potassium acetate (13.26 g, 135 mmol) and the reaction mixture was stirred at 90° C. for 4 h. The reaction mixture was cooled to ambient temperature and concentrated in vacuo. The residue was purified by column chromatography on silica gel (eluting with 50-100% EtOAc in petroleum ether, then eluting with 1-10% MeOH in EtOAc) to give (R)-4-methyl-6-(4,4,5,5-tetramethyl-[1,3,2]dioxaborolan-2-yl)-2,10-dihydro-9-oxa-1,2,4a-triaza-phenanthren-3-one (23 g, 99%) as a brown solid. SFC (Table 1, Method 4), R$_t$=6.51 min. $^1$H NMR (400 MHz, methanol-d$_4$) δ 7.44-7.36 (m, 2H), 7.05-6.95 (m, 1H), 4.85-4.75 (m, 1H), 4.65-4.55 (d, J=1.28 Hz, 2H), 1.45 (d, J=6.8 Hz, 3H), 1.35 (s, 12H). LC/MS (Table 1, Method 25) R$_t$=0.823 min.; MS m/z: 344 [M+H]$^+$.

Preparation #12. 4-(2-Bromo-3,4-dichloro-phenyl)-piperazine-1-carboxylic acid tert-butyl ester

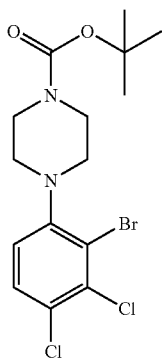 [SMILES: CC(C)(C)OC(=O)N1CCN(c2ccc(Cl)c(Cl)c2Br)CC1]

Step A.
4-(3,4-Dichloro-phenyl)-piperazine-1-carboxylic acid tert-butyl ester

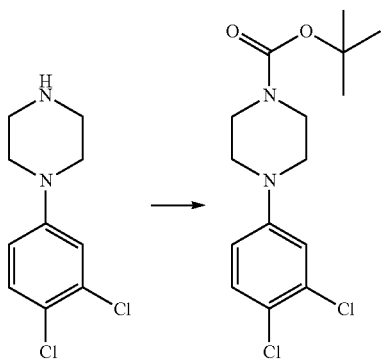 [SMILES: Clc1ccc(N2CCNCC2)cc1Cl ; CC(C)(C)OC(=O)N1CCN(c2ccc(Cl)c(Cl)c2)CC1]

To a solution of 1-(3,4-dichlorophenyl)piperazine (4.62 g, 20 mmol) in DCM (50 mL) was added drop-wise Boc$_2$O (4.88 mL, 21.00 mmol) and the mixture was stirred at ambient temperature for 30 min. The mixture was concentrated in vacuo to give crude 4-(3,4-dichloro-phenyl)-piperazine-1-carboxylic acid tert-butyl ester (6.7 g, 100%), which was used in the next step directly without further purification. $^1$H NMR (CDCl$_3$, 400 MHz) δ 7.30 (d, J=9.2 Hz, 1H), 6.97 (d, J=2.8, 1H), 6.76 (dd, J=9.2, 2.8 Hz, 1H), 3.58 (t, J=5.2 Hz, 4H), 3.13 (t, J=5.2 Hz, 4H), 1.50 (s, 9H). TLC (eluting with 10% EtOAc in petroleum ether), R$_f$=0.4.

Step B. 4-(2-Bromo-4,5-dichloro-phenyl)-piperazine-1-carboxylic acid tert-butyl ester and 4-(2-bromo-3,4-dichloro-phenyl)-piperazine-1-carboxylic acid tert-butyl ester

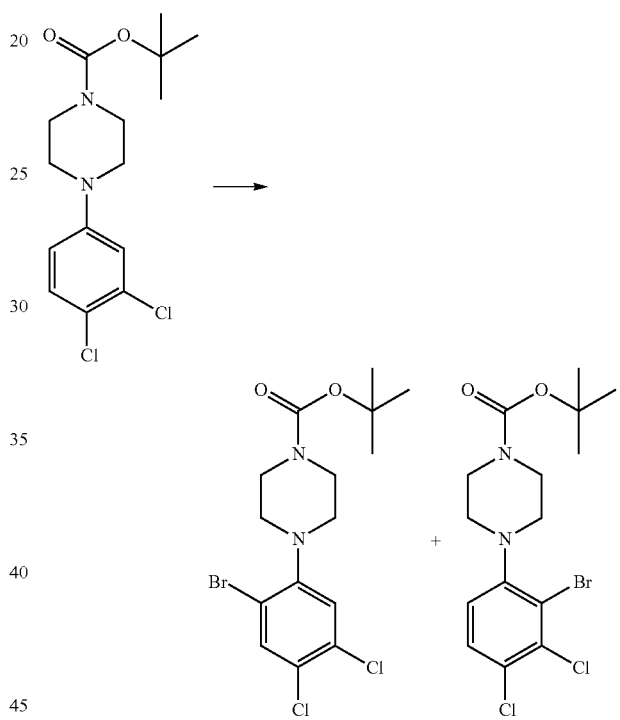

To a solution of 4-(3,4-dichloro-phenyl)-piperazine-1-carboxylic acid tert-butyl ester (3.31 g, 10 mmol) in DCM (150 mL) was added tetrabutylamnonium tribromide (7.23 g, 15.00 mmol) portion-wise. Powdered sodium tert-butoxide (0.961 g, 10.00 mmol) was added slowly and the mixture was stirred at ambient temperature for 1 h. After filtration, the filtrate was concentrated in vacuo and the residue was purified by column chromatography on silica gel (eluting with 3% EtOAc in petroleum ether) to give two isomers, 4-(2-bromo-4,5-dichloro-phenyl)-piperazine-1-carboxylic acid tert-butyl ester (0.55 g, 13%) and 4-(2-bromo-3,4-dichloro-phenyl)-piperazine-1-carboxylic acid tert-butyl ester (0.11 g, 2%). 4-(2-Bromo-4,5-dichloro-phenyl)-piperazine-1-carboxylic acid tert-butyl ester: $^1$H NMR (CDCl$_3$, 400 MHz) δ 7.65 (s, 1H), 7.05 (s, 1H), 3.60 (t, J=4.4 Hz, 4H), 2.94 (t, J=4.4 Hz, 4H), 1.48 (s, 9H). 4-(2-Bromo-3,4-dichloro-phenyl)-piperazine-1-carboxylic acid tert-butyl ester: $^1$H NMR (CDCl$_3$ 400 MHz) δ 7.39 (d, J=8.8 Hz, 1H), 6.89 (d, J=8.8 Hz, 1H), 3.61 (br s, 4H), 2.95 (br s, 4H), 1.49 (s, 9H). TLC (petroleum ether:EtOAc=10:1), R$_f$=0.5.

Preparation #13: 3-Methyl-4-trifluoromethanesulfonyloxy-3,6-dihydro-2H-pyridine-1-carboxylic acid tert-butyl ester

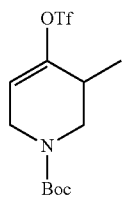

To a mixture of 3-methyl-4-oxo-piperidine-1-carboxylic acid tert-butyl ester (0.4 g, 1.876 mmol) in THF (5 mL) was added KHMDS (1M in THF, 2.81 mL, 2.81 mmol) dropwise at −78° C. and the reaction mixture was stirred for 30 min then allowed to warm to ambient temperature and stirred for 3 h. The reaction mixture was cooled at −78° C. and a solution of N-(5-chloropyridin-2-yl)-1,1,1-trifluoro-N-((trifluoromethyl)sulfonyl)methanesulfonamide (0.884 g, 2.251 mmol) in THF (5 mL) was added dropwise. The reaction mixture was allowed to warm to rt and stirred overnight. Saturated aqueous NH$_4$Cl (20 mL) was added and the reaction mixture was extracted with EtOAc (3×10 mL). The combined organic layer was washed with brine (20 mL), dried over Na$_2$SO$_4$ and concentrated in vacuo. The residue was purified by column chromatography on silica gel (eluting with 1-15% EtOAc in petroleum ether) to give 3-methyl-4-trifluoromethanesulfonyloxy-3,6-dihydro-2H-pyridine-1-carboxylic acid tert-butyl ester (0.31 g, 47%) as a colorless oil. $^1$H NMR (CDCl$_3$, 400 MHz): δ 5.73 (brs, 1H), 4.24-3.89 (m, 2H), 3.76-3.31 (m, 2H), 2.63 (brs, 1H), 1.48 (s, 9H), 1.16 (d, J=7.0 Hz, 3H)

Preparation #14. Methanesulfonic acid 1-benzhydryl-3-methyl-azetidin-3-yl ester

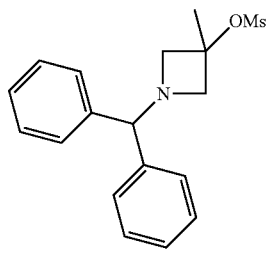 [SMILES: CC1(OS(C)(=O)=O)CN(C(c2ccccc2)c2ccccc2)C1]

Step A. 1-Benzhydryl-3-methyl-azetidin-3-ol

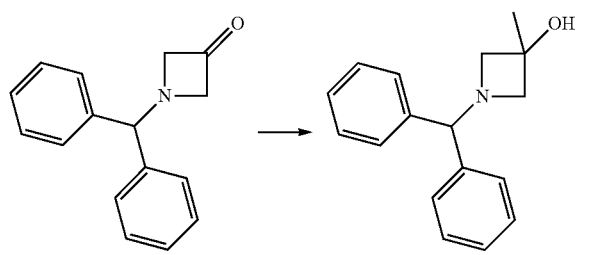 [SMILES: O=C1CN(C(c2ccccc2)c2ccccc2)C1 ; CC1(O)CN(C(c2ccccc2)c2ccccc2)C1]

To a solution of methylmagnesium bromide (263 mL, 790 mmol) in anhydrous THF (800 mL) was added a solution of 1-benzhydrylazetidin-3-one (75 g, 316 mmol) in THF (300 mL) rapidly with vigorous stirring at 0° C. The reaction mixture was stirred for 10 min, then allowed to warm to 25° C. and stirred for 2 h. The reaction mixture was quenched by the addition of saturated aqueous ammonium chloride (1 L), diluted with water (1 L) and extracted with EtOAc (3×1 L). The combined organic phase was washed with brine (0.5 L), dried over anhydrous Na$_2$SO$_4$ and filtered. The filtrate was evaporated in vacuo and the residue was purified by column chromatography on silica gel (eluting with 10-20% EtOAc in petroleum ether) to give 1-benzhydryl-3-methylazetidin-3-ol (65 g, 81%) as a white solid. $^1$H NMR (CDCl$_3$, 400 MHz): δ 7.42 (m, 4H), 7.31 (m, 4H), 7.22 (m, 2H), 4.36 (s, 1H), 3.20 (m, 2H), 2.99 (m, 2H), 1.53 (s, 3H).

Step B. Methanesulfonic acid 1-benzhydryl-3-methyl-azetidin-3-yl ester

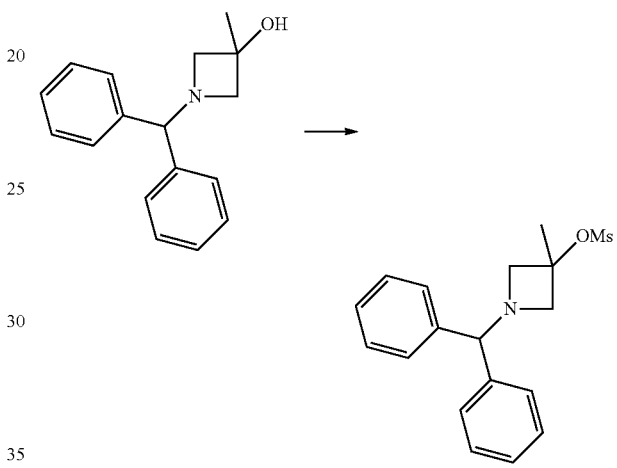

To a 0° C. solution of 1-benzhydryl-3-methylazetidin-3-ol (70 g, 276 mmol) and TEA (53.1 g, 525 mmol) in DCM (700 mL) was added drop-wise methanesulfonyl chloride (57 g, 497 mmol). The reaction mixture was stirred for 2 h then filtered and the filter cake was washed with DCM (3×50 mL). The filtrate was washed with water (3×100 mL), dried over anhydrous Na$_2$SO$_4$ and filtered. The filtrate was concentrated in vacuo to give methanesulfonic acid 1-benzhydryl-3-methyl-azetidin-3-yl ester (90 g, 98%) as a brown solid, which was used in the next step without further purification. $^1$H NMR (CDCl$_3$, 400 MHz): δ 7.44 (m, 4H), 7.33 (m, 4H), 7.26 (m, 2H), 4.55 (brs, 1H), 3.46 (m, 4H), 3.07 (s, 3H), 1.94 (s, 3H).

Preparation #15. (R)-7-Bromo-6-[(1,3-dimethyl-azetidin-3-yl)-methyl-amino]-4-methyl-2,10-dihydro-9-oxa-1,2,4a-triaza-phenanthren-3-one

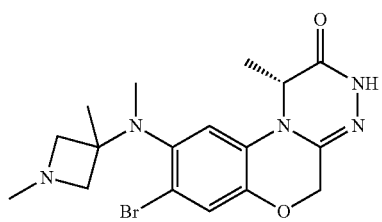 [SMILES: C[C@@H]1C(=O)NN=C2COc3cc(Br)c(N(C)C4(C)CN(C)C4)cc3N21]

Step A. (R)-4-methyl-6-(3-methyl-azetidin-3-ylamino)-2,10-dihydro-9-oxa-1,2,4a-triaza-phenanthren-3-one

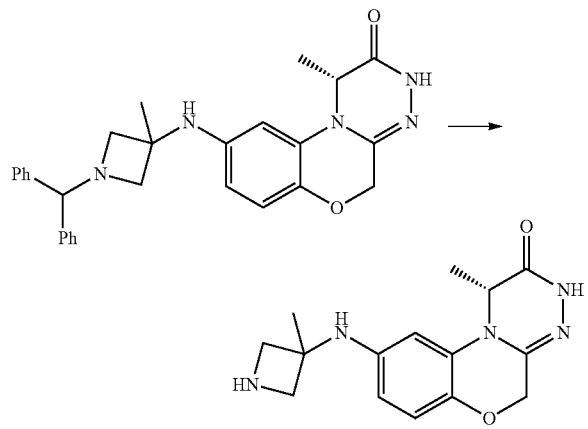

A suspension of (R)-6-(1-benzhydryl-3-methyl-azetidin-3-ylamino)-4-methyl-2,10-dihydro-9-oxa-1,2,4a-triaza-phenanthren-3-one (Example #148, Step E, 20 g, 42.8 mmol) and PdOH$_2$/C (10%, 10 g, 71.2 mmol) in MeOH (400 mL) and HCl (2 mL) was stirred at 50° C. under H$_2$ (50 psi) for 48 h. The reaction mixture was cooled to ambient temperature and filtered, washed with hot MeOH (3×100 mL). The combined filtrate was concentrated in vacuo to give (R)-4-methyl-6-(3-methyl-azetidin-3-ylamino)-2,10-dihydro-9-oxa-1,2,4a-triaza-phenanthren-3-one (18 g, 99%), which was used directly. LC/MS (Table 1, Method 25) R$_f$=0.525 min.; MS m/z: 302 [M+H]$^+$.

Step B. (R)-6-[(1,3-Dimethyl-azetidin-3-yl)-methyl-amino]-4-methyl-2,10-dihydro-9-oxa-1,2,4a-triaza-phenanthren-3-one

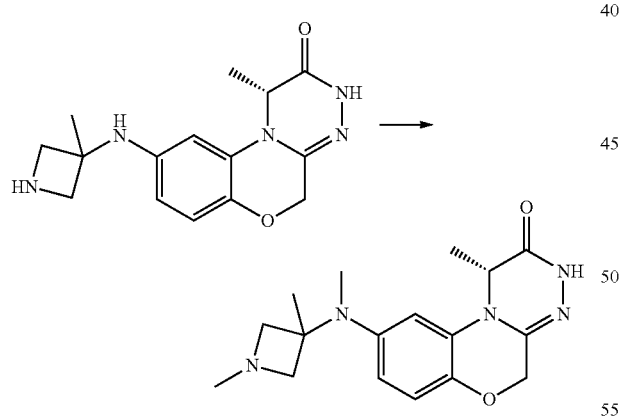

A mixture of (R)-4-methyl-6-(3-methyl-azetidin-3-ylamino)-2,10-dihydro-9-oxa-1,2,4a-triaza-phenanthren-3-one (9 g, 21.21 mmol) and paraformaldehyde (3.82 g, 127 mmol) in MeOH/AcOH (300 mL/30 mL) was stirred at ambient temperature for 0.5 h. Sodium cyanotrihydroborate (4.0 g, 63.6 mmol) was added and the reaction mixture was stirred at ambient temperature for 16 h. The reaction mixture was concentrated in vacuo and the residue was purified by column chromatography on basified silica gel (eluting with 10% MeOH in DCM) to give (R)-6-[(1,3-dimethyl-azetidin-3-yl)-methyl-amino]-4-methyl-2,10-dihydro-9-oxa-1,2,4a-triaza-phenanthren-3-one (6 g, 86%). LC/MS (Table 1, Method 3) R$_f$=0.967 min.; MS m/z: 330 [M+H]$^+$.

Step C. (R)-7-bromo-6-[(1,3-dimethyl-azetidin-3-yl)-methyl-amino]-4-methyl-2,10-dihydro-9-oxa-1,2,4a-triaza-phenanthren-3-one

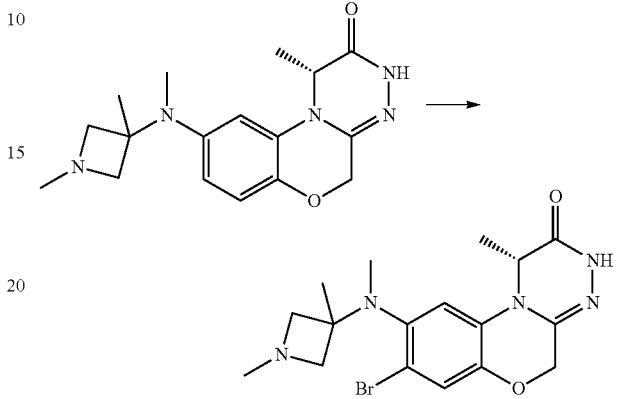

To a mixture of (R)-6-[(1,3-dimethyl-azetidin-3-yl)-methyl-amino]-4-methyl-2,10-dihydro-9-oxa-1,2,4a-triaza-phenanthren-3-one (3 g, 9.11 mmol) in DCM (40 mL) and MeOH (20 mL) was added tetra-n-butylammonium tribromide (6.59 g, 13.66 mmol) in portions and the reaction mixture was stirred at 20° C. for 16 h. Saturated aqueous Na$_2$S$_2$O$_3$ (10 mL) was added and saturated aqueous sodium bicarbonate (5 mL) was added to neutralize the mixture. The organic phase was separated, dried over anhydrous Na$_2$SO$_4$ and concentrated in vacuo. The residue was purified by column chromatography on basified silica gel (eluting with 10% MeOH in DCM) to give (R)-7-bromo-6-[(1,3-dimethyl-azetidin-3-yl)-methyl-amino]-4-methyl-2,10-dihydro-9-oxa-1,2,4a-triaza-phenanthren-3-one (3 g, 81%) as a brown solid. LC/MS (Table 1, Method 3), R$_f$=1.060 min.; MS m/z: 410 [M+H+2]$^+$ & 408 [M+H]$^+$. SFC (Table 1, Method 49), R$_f$=5.174 min.

Preparation #16: 7-Bromo-6-[(1,3-dimethyl-azetidin-3-yl)-methyl-amino]-4-methyl-2,10-dihydro-9-oxa-1,2,4a-triaza-phenanthren-3-one

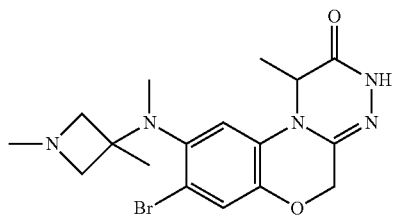 [SMILES: CC1C(=O)NN=C2COc3cc(Br)c(N(C)C4(C)CN(C)C4)cc3N21]

Using a similar procedure as described in Preparation #15, Step A-C, 7-bromo-6-[(1,3-dimethyl-azetidin-3-yl)-methyl-amino]-4-methyl-2,10-dihydro-9-oxa-1,2,4a-triaza-phenanthren-3-one was prepared from 6-(1-benzhydryl-3-methyl-azetidin-3-ylamino)-4-methyl-2,10-dihydro-9-oxa-1,2,4a-triaza-phenanthren-3-one (Example #79, Step A). LC/MS (Table 1, Method 3), R$_f$=1.060 min.; MS m/z: 410 [M+H+2]$^+$ & 408 [M+H]$^+$.

Preparation #17: Methanesulfonic acid 1-benzhydryl-3-ethyl-azetidin-3-yl ester

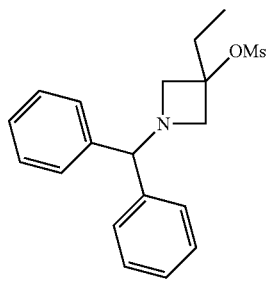 [SMILES: CCC1(OS(C)(=O)=O)CN(C(c2ccccc2)c2ccccc2)C1]

Using a similar procedure as described in Preparation #14, Step A-B, methanesulfonic acid 1-benzhydryl-3-ethyl-azetidin-3-yl ester was prepared from 1-benzhydryl-azetidin-3-one and ethylmagnesium bromide. $^1$H NMR (CDCl$_3$, 400 MHz): δ 7.42 (m, 4H) 7.27 (m, 4H), 7.20 (m, 2H), 4.45 (s, 1H), 3.36 (m, 4H), 3.05 (s, 3H), 2.20 (q, J=7.40 Hz, 2H), 1.08 (t, J=7.40 Hz, 3H).

Preparation #18. 3-(7-Bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester

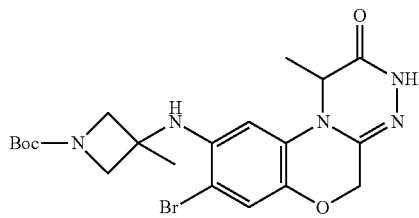

Using a similar procedure as described in Example #148, Step F-G, 3-(7-bromo-4-methyl-3-oxo-2,3,4,10-tetrahydro-9-oxa-1,2,4a-triaza-phenanthren-6-ylamino)-3-methyl-azetidine-1-carboxylic acid tert-butyl ester was prepared from 6-(1-benzhydryl-3-methyl-azetidin-3-ylamino)-4-methyl-2,10-dihydro-9-oxa-1,2,4a-triaza-phenanthren-3-one (Example #79, Step A). LC/MS (Table 1, Method 25) R$_t$=0.867 min; MS m/z: 482 [M+H+2]$^+$ & 480 [M+H]$^+$.

Preparation #19: 4-Methyl-7-(4,4,5,5-tetramethyl-[1,3,2]dioxaborolan-2-yl)-2,10-dihydro-9-oxa-1,2,4a-triaza-phenanthren-3-one

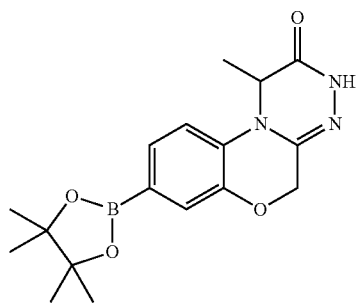 [SMILES: CC1C(=O)NN=C2COc3cc(B4OC(C)(C)C(C)(C)O4)ccc3N21]

Using a similar procedure as described in Preparation #10, Step C-F, 4-methyl-7-(4,4,5,5-tetramethyl-[1,3,2]dioxaborolan-2-yl)-2,10-dihydro-9-oxa-1,2,4a-triaza-phenanthren-3-one was prepared from 7-bromo-4H-benzo[1,4]oxazin-3-one (Preparation #10, Step A). LC/MS (Table 1, Method 25) R$_t$=0.822 min.; MS m/z: 344 [M+H]$^+$.

Preparation #20. 3-Methyl-3-(1-trifluoromethanesulfonyloxy-vinyl)-azetidine-1-carboxylic acid tert-butyl ester

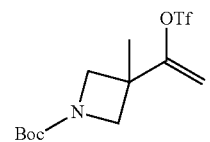 [SMILES: C=C(OS(=O)(=O)C(F)(F)F)C1(C)CN(C(=O)OC(C)(C)C)C1]

Using a similar procedure as described in Preparation #4, Step A-C, 3-methyl-3-(1-trifluoromethanesulfonyloxy-vinyl)-azetidine-1-carboxylic acid tert-butyl ester was prepared from 3-methyl-azetidine-1,3-dicarboxylic acid mono-tert-butyl ester. $^1$H-NMR (400 MHz, CDCl$_3$) δ 5.30 (d, J=4.8 Hz, 1H), 5.09 (d, J=4.8 Hz, 1H), 4.06 (d, J=8.4 Hz, 2H), 3.69 (d, J=8.8 Hz, 2H), 1.55 (s, 3H), 1.45 (s, 9H).

Preparation #21. 3-(1-Iodo-vinyl)-3-methyl-azetidine-1-carboxylic acid tert-butyl ester

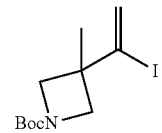

Step A. 3-(1-Hydrazono-ethyl)-3-methyl-azetidine-1-carboxylic acid tert-butyl ester

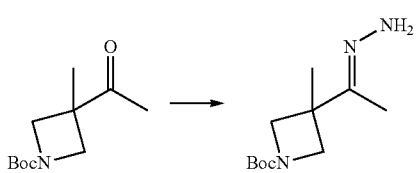 [SMILES: CC(=O)C1(C)CN(C(=O)OC(C)(C)C)C1 ; C/C(=N\N)C1(C)CN(C(=O)OC(C)(C)C)C1]

To a solution of 3-acetyl-3-methyl-azetidine-1-carboxylic acid tert-butyl ester (prepared from 1-(tert-butoxycarbonyl)-3-methylazetidine-3-carboxylic acid using the similar procedure detailed in Preparation #4, Steps A-B, 0.10 g, 0.47 mmol) and triethylamine (0.5 mL, 3.8 mmol) in EtOH (2 mL) was added aqueous hydrazine hydrate (85%, 0.117 g, 2.34 mmol) and the solution was heated at reflux for 4 h. The reaction mixture was cooled to ambient temperature and poured into water. The mixture was extracted with DCM (3×15 mL) and the combined organic phase was washed with brine (10 mL) and concentrated in vacuo to give 3-(1-hydrazono-ethyl)-3-methyl-azetidine-1-carboxylic acid tert-butyl ester (0.076 g, 71%), which was used directly in the next step without further purification. TLC: R$_f$=0.15 (eluting with 50% EtOAc in petroleum ether).

Step B. 3-(1-Iodo-vinyl)-3-methyl-azetidine-1-carboxylic acid tert-butyl ester

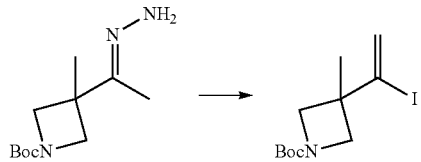 [SMILES: C/C(=N\N)C1(C)CN(C(=O)OC(C)(C)C)C1 ; C=C(I)C1(C)CN(C(=O)OC(C)(C)C)C1]

To a solution of 3-(1-hydrazono-ethyl)-3-methyl-azetidine-1-carboxylic acid tert-butyl ester (0.076 g, 0.33 mmol) and triethylamine (0.169 g, 1.67 mmol) in THF (3 mL) was added dropwise a solution of iodine (0.127 g, 0.50 mmol) in THF (1 mL). The reaction mixture was stirred for 1 h at ambient temperature then concentrated in vacuo. The residue was dissolved in DCM (10 mL) and washed with aqueous $Na_2S_2O_3$ (5%, 2 mL). The organic phase was separated and concentrated in vacuo. The residue was purified by silica gel chromatography (eluting with 20% EtOAc in petroleum ether) to give 3-(1-iodo-vinyl)-3-methyl-azetidine-1-carboxylic acid tert-butyl ester (0.060 g, 55%), which was unstable and used without further purification. TLC: $R_f$=0.30 (eluting with 10% EtOAc in petroleum ether).

TABLE 34

PKCθ & PKCα enzyme data at 100 μM ATP (generated using in vitro enzyme assays described above) and cell data (generated using T-blasts CD3/CD28-induced IL-2 assay described above)

| Example # | PKCθ enzyme $IC_{50}$ | PKCα enzyme $IC_{50}$ | CD3/CD28-stimulated IL2 in T-blasts $EC_{50}$ |
|---|---|---|---|
| 1-1 | A | C | A |
| 1-2 | B | C | C |
| 2 | A | B | A |
| 3 | A | C | A |
| 4 | A | C | A |
| 5 | A | C | A |
| 6 | A | C | A |
| 7 | A | C | A |
| 8 | A | C | A |
| 9 | A | C | A |
| 10 | A | C | A |
| 11 | B | C | A |
| 12 | A | C | A |
| 13 | A | C | A |
| 14 | B | C | A |
| 15 | A | C | A |
| 16 | B | C | A |
| 17 | A | C | A |
| 18 | A | C | A |
| 19 | B | C | A |
| 20 | A | C | A |
| 21 | B | C | A |
| 22 | A | C | A |
| 23 | A | C | A |
| 24 | B | C | A |
| 25 | A | C | A |
| 26 | B | C | A |
| 27 | A | C | A |
| 28 | A | C | A |
| 29 | A | C | A |
| 30 | A | C | B |
| 31 | A | C | B |
| 32 | A | C | B |
| 33 | A | C | B |
| 34 | A | C | B |
| 35 | A | C | A |
| 36 | A | C | A |
| 37 | A | C | A |
| 38 | A | C | B |
| 39 | A | C | B |
| 40 | B | C | B |
| 41 | B | C | B |
| 42 | A | C | A |
| 43 | A | C | A |
| 44 | A | C | A |
| 45 | A | C | A |
| 46 | A | C | A |
| 47 | A | C | A |
| 48 | A | C | A |
| 49 | A | C | A |
| 50 | A | C | A |
| 51 | A | C | B |
| 52 | A | C | B |
| 53-1 | B | C | B |
| 53-2 | A | C | A |
| 54-1 | A | C | B |
| 54-2 | B | C | C |
| 55 | B | C | C |
| 56-1 | B | C | C |
| 56-2 | A | C | A |
| 57-1 | A | C | A |
| 57-2 | B | C | C |
| 58 | A | C | A |
| 59 | A | C | B |
| 60 | A | C | B |
| 61 | A | C | B |
| 62 | A | C | B |
| 63 | A | C | A |
| 64-1 | A | C | A |
| 64-2 | B | C | C |
| 65 | A | C | A |
| 66 | A | C | A |
| 67 | A | C | A |
| 68 | B | C | B |
| 69 | A | C | A |
| 70 | A | C | B |
| 71 | A | C | A |
| 72 | B | C | C |
| 73 | B | C | C |
| 74 | A | C | B |
| 75 | A | C | B |
| 76 | B | C | B |
| 77 | A | C | B |
| 78 | A | C | A |
| 79 | B | C | C |
| 80 | A | C | A |
| 81 | A | C | B |
| 82 | A | B | A |
| 83 | A | C | A |
| 84 | A | C | A |
| 85 | A | C | B |
| 86 | A | C | A |
| 87 | A | C | B |
| 88 | A | A | A |
| 89 | A | C | B |
| 90 | A | A | A |
| 91 | A | B | A |
| 92 | A | B | A |
| 93 | A | C | C |
| 94 | A | B | A |
| 95 | A | B | A |
| 96 | A | C | A |
| 97 | A | C | A |
| 98 | C | C | |
| 99 | A | C | B |
| 100-1 | A | C | A |
| 100-2 | A | B | B |
| 101-1 | A | C | B |

TABLE 34-continued

PKCθ & PKCα enzyme data at 100 μM ATP (generated using in vitro enzyme assays described above) and cell data (generated using T-blasts CD3/CD28-induced IL-2 assay described above)

| Example # | PKCθ enzyme $IC_{50}$ | PKCα enzyme $IC_{50}$ | CD3/CD28-stimulated IL2 in T-blasts $EC_{50}$ |
|---|---|---|---|
| 101-2 | A | C | B |
| 102 | A | B | B |
| 103 | A | C | B |
| 104-1 | A | A | A |
| 104-2 | A | B | A |
| 105 | A | C | B |
| 106 | A | C | B |
| 107 | A | A | A |
| 108 | A | B | A |
| 109-1 | A | C | A |
| 109-2 | A | C | A |
| 110 | B | C | B |
| 111 | A | C | B |
| 112 | C | C | C |
| 113 | A | C | A |
| 114 | A | C | A |
| 115 | A | C | A |
| 116 | A | C | B |
| 117 | A | C | B |
| 118 | B | C |   |
| 119 | A | C | A |
| 120 | A | C | B |
| 121-1 | A | C | B |
| 121-2 | B | C | C |
| 122 | A | C | C |
| 123 | B | C | C |
| 124 | A | C | A |
| 125 | A | C | B |
| 126 | A | C | B |
| 127 | A | C | B |
| 128 | A | C | B |
| 129 | A | C | B |
| 130 | B | C | B |
| 131 | A | C | B |
| 132 | A | C | B |
| 133 | B | C | B |
| 134 | A | C | B |
| 135 | A | B | A |
| 136 | A | C | B |
| 137 | A | C | B |
| 138 | A | B | B |
| 139 | A | A | A |
| 140 | A | B | A |
| 141 | A | B | A |
| 142 | A | C | B |
| 143 | A | B | A |
| 144 | A | C | B |
| 145 | A | C | B |
| 146 | A | A | A |
| 147-1 | A | B | A |
| 147-2 | C | C |   |
| 148 | A | B | A |
| 149 | A | C | A |
| 150 | A | C | B |
| 151-1 | A | B | A |
| 151-2 | A | C | B |
| 152 | A | C | B |
| 153 | B | C | C |
| 154 | A | C | B |
| 155 | A | C | B |
| 156 | A | C | B |
| 157 | A | B | A |
| 158 | A | C | A |
| 159 | A | C | A |
| 160 | A | B | A |
| 161 | A | C | B |
| 162 | A | B | A |
| 163 | A | A | A |
| 164 | A | C | B |
| 165 | B | C |   |
| 166 | A | A | A |
| 167 | A | B | A |
| 168 | A | B | A |
| 169 | A | B | A |
| 170 | A | C | A |
| 171 | A | C | A |
| 172 | A | B | A |
| 173 | A | C | B |
| 174 | A | C | B |
| 175 | A | A | A |
| 176 | A | B | A |
| 177 | A | B | A |
| 178 | A | B | A |
| 179 | A | B | A |
| 180 | A | C | A |
| 181 | A | C | B |
| 182 | A | C | B |
| 183 | A | C | B |
| 184 | A | C | B |
| 185 | A | B | A |
| 186 | B | C | B |
| 187 | A | C | B |
| 188 | A | A | A |
| 189 | A | B | A |
| 190 | A | B | A |
| 191 | A | B | A |
| 192 | A | B | A |
| 193 | A | C | B |
| 194 | A | B | B |
| 195 | A | C | A |
| 196 | A | C | C |
| 198-1 | A | C | C |
| 198-2 | A | C | C |
| 198-3 | A | B | A |
| 198-4 | A | B | A |
| 199 | A | B | A |
| 200 | A | A | A |
| 201 | A | A | A |
| 202 | A | C | A |
| 203 | A | B | A |
| 204 | A | C | B |
| 205 | A | B | A |
| 206 | A | C | A |
| 207 | A | C | B |
| 208 | A | C | A |
| 210 | A | C | A |
| 213 | A | C | A |
| 211 | A | C | B |
| 212 | A | C | A |
| 214 | A | C | A |
| 215 | A | C | A |
| 216 | A | C | B |
| 217 | A | C | B |
| 218 | A | C | B |
| 219 | A | C | A |
| 220 | A | C | A |
| 221 | A | C | A |
| 222 | A | C | B |
| 223 | A | B | A |
| 224 | A | B | A |
| 225 | A | B | A |
| 226 | A | B | B |
| 227 | A | C | B |
| 228 | A | B | B |
| 229 | B | C |   |
| 230 | A | B | A |
| 231 | A | B | A |
| 232 | A | B | A |
| 233 | A | B | A |
| 234 | A | C | B |
| 235 | A | B | B |
| 236 | A | C | C |

TABLE 34-continued

PKCθ & PKCα enzyme data at 100 μM ATP (generated using in vitro enzyme assays described above) and cell data (generated using T-blasts CD3/CD28-induced IL-2 assay described above)

| Example # | PKCθ enzyme IC$_{50}$ | PKCα enzyme IC$_{50}$ | CD3/CD28-stimulated IL2 in T-blasts EC$_{50}$ |
|---|---|---|---|
| 237 | A |   | A |
| 238 | A | A | A |
| 239 | A | A | A |
| 240 | A | A | A |
| 241 | A |   | A |
| 242 | A | B | A |
| 243 | A | B | A |
| 244 | A | B | A |
| 245 | A | B | A |
| 246 | A | B | A |
| 247 | A | A | A |

Key:
A <0.25 μM
B 0.25-<1 μM
C 1-10 μM

What is claimed:
1. A compound of Formula (I):

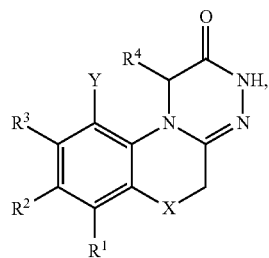

Formula (I)

or a pharmaceutically acceptable salt, a stereoisomer, or a tautomer thereof, wherein
  $R^1$ is —H, deuterium, —CF$_3$, halo, (C$_1$-C$_3$)alkyl optionally substituted with 1-3 groups selected from halo, hydroxy, or —(C$_1$-C$_3$)alkoxy, or (C$_3$-C$_6$)cycloalkyl optionally substituted with 1-3 groups selected from halo, hydroxy, —(C$_1$-C$_3$)alkyl, or —(C$_1$-C$_3$)alkoxy;
  $R^2$ is —H, deuterium, halo, —CF$_3$, —CHF$_2$, —CH$_2$F, —C(H)(CH$_3$)CF$_3$, cyano, —NR$^a$R$^b$, —OR$^c$, (C$_1$-C$_6$) alkyl optionally substituted with one or more halo, optionally substituted (C$_3$-C$_6$)cycloalkyl, optionally substituted (C$_5$-C$_7$)cycloalkenyl, optionally substituted bridged (C$_3$-C$_8$)cycloalkyl, (C$_1$-C$_3$)alkoxy optionally substituted with aryl, optionally substituted aryl, optionally substituted 5-10 membered heteroaryl, aryloxy, 5-10 membered bridged carbocyclyl or heterocyclyl, or optionally substituted 4-10 membered heterocyclyl;
  wherein in $R^2$, (C$_3$-C$_6$)cycloalkyl, (C$_5$-C$_7$)cycloalkenyl, bridged (C$_3$-C$_8$)cycloalkyl, aryl, 5-10 membered heteroaryl, and 4-10 membered heterocyclyl are each independently optionally substituted with one or more groups selected from halo, —CF$_3$, cyano, —(C$_1$-C$_4$)alkyl, -hydroxy(C$_1$-C$_4$)alkyl, -halo(C$_1$-C$_3$) alkyl, -halo(C$_1$-C$_3$)alkoxy, —S(O)(C$_1$-C$_3$)alkyl, —S(O)$_2$(C$_1$-C$_3$)alkyl, —NR$^a$R$^b$, —(C$_1$-C$_3$)alkoxy, —(C$_1$-C$_4$)alkoxy(C$_1$-C$_3$)alkyl or piperazinyl;
  $R^3$ is —H, deuterium, halo, —CF$_3$, —CH$_2$F, —CHF$_2$, —NR$^a$R$^b$, —OR$^c$, —SR$^c$, —SCH$_3$, —S(O)R$^c$, —S(O)$_2$R$^c$, —S(O)CH$_3$, (C$_1$-C$_3$)alkyl optionally substituted with one or more halo or —OH, heterocyclic spirocyclyl optionally substituted with 1-3 groups selected from halo, —CH$_3$, or —OH, 5-10 membered bridged heterocyclyl, optionally substituted 4-10 membered heterocyclyl, or —C(R$^d$)(R$^e$)-optionally substituted 4-10 membered heterocyclyl, wherein the 4-10 membered heterocyclyl is optionally substituted with 1-3 groups selected from —H, halo, —CF$_3$, —OH, —(C$_1$-C$_3$)alkyl, -hydroxy(C$_1$-C$_4$)alkyl, -halo(C$_1$-C$_3$)alkyl, amino(C$_1$-C$_3$)alkyl, —(C$_1$-C$_4$)alkoxy(C$_1$-C$_3$)alkyl, —C(O)(C$_1$-C$_3$)alkyl, —C(O)halo(C$_1$-C$_3$)alkyl, —C(O)hydroxy(C$_1$-C$_4$) alkyl, —C(O)—(C$_1$-C$_3$)alkylene-N(CH$_3$)$_2$, —(C$_1$-C$_3$)aralkyl, oxetanyl, —CH$_2$-oxetanyl, tetrahydropyranyl, —CH$_2$-tetrahydropyranyl, or —NR$^a$R$^b$;
  wherein each substitutable nitrogen atom in the heterocyclyl and heteroaryl is optionally substituted with —(C$_1$-C$_3$)alkyl, -hydroxy(C$_2$-C$_4$)alkyl, -halo(C$_1$-C$_3$) alkyl, —(C$_2$-C$_4$)alkoxy(C$_1$-C$_3$)alkyl, —C(O)(C$_1$-C$_3$) alkyl, —C(O)halo(C$_1$-C$_3$)alkyl, —C(O)hydroxy(C$_1$-C$_4$)alkyl, —C(O)(C$_1$-C$_3$)alkyleneN(CH$_3$)$_2$, optionally substituted azetidinyl, oxetanyl, optionally substituted piperidinyl, optionally substituted pyrrolidinyl, —CH$_2$-oxetanyl, -tetrahydropyranyl, —CH$_2$-tetrahydropyranyl, or —(C$_1$-C$_3$)aralkyl, wherein the azetidinyl, pyrrolidinyl, and piperidinyl are each independently optionally substituted with —(C$_1$-C$_3$) alkyl or —C(O)(C$_1$-C$_3$)alkyl; and
  wherein each substitutable carbon atom in the heterocyclyl and heteroaryl is optionally substituted with one or more substituents independently selected from deuterium, halo, —(C$_1$-C$_4$)alkyl, -hydroxy(C$_1$-C$_4$) alkyl, -halo(C$_1$-C$_4$)alkyl, —(C$_1$-C$_4$)alkoxy(C$_1$-C$_4$) alkyl, —C(O)(C$_1$-C$_3$)alkyl, —C(O)halo(C$_1$-C$_3$) alkyl, —C(O)hydroxy, —C(O)(C$_1$-C$_3$)alkylene-N (CH$_3$)$_2$, oxetanyl, —(C$_1$-C$_3$)alkyl-oxetanyl, -tetrahydropyranyl, —(C$_1$-C$_3$)alkyl-tetrahydropyranyl, or —(C$_1$-C$_3$)aralkyl;
  $R^4$ is —CF$_3$, —CHF$_2$, —CH$_2$F, or (C$_1$-C$_6$)alkyl optionally substituted with 1-3 groups selected from halo, hydroxy, or —(C$_1$-C$_3$)alkoxy;
  $R^a$ is independently —H or (C$_1$-C$_3$)alkyl;
  $R^b$ is independently —H, —(C$_1$-C$_3$)alkyl, phenyl optionally substituted with hydroxy —(C$_1$-C$_3$)alkyl or 4-10 membered heterocyclyl, 4-10 membered heterocyclyl, aralkyl, 4-8 membered bridged heterocyclyl, or —C(O)-optionally substituted 4-10 membered heterocyclyl, wherein the 4-10 membered heterocyclyl is optionally substituted with 1-3 groups independently selected from: halo, —(C$_1$-C$_3$)alkyl, -hydroxy(C$_1$-C$_4$)alkyl, -halo(C$_1$-C$_3$)alkyl, —(C$_1$-C$_4$) alkoxy(C$_1$-C$_3$)alkyl, —(C$_1$-C$_3$)alkoxy, -halo(C$_1$-C$_3$) alkoxy, —C(O)(C$_1$-C$_3$)alkyl, —C(O)halo(C$_1$-C$_3$) alkyl, —C(O)hydroxy(C$_1$-C$_4$)alkyl, —C(O)(C$_1$-C$_3$) alkyleneN(CH$_3$)$_2$, —(C$_1$-C$_3$)aralkyl, oxetanyl, —CH$_2$-oxetanyl, tetrahydropyranyl, or —CH$_2$-tetrahydropyranyl; and
  $R^c$ is independently —H, —CH$_2$-optionally substituted phenyl, optionally substituted phenyl, or 4-10 membered heterocyclyl optionally substituted with one or more (C$_1$-C$_3$)alkyl; wherein each phenyl is independently optionally substituted with —(C$_1$-C$_3$)alkyl;
  $R^d$ and $R^e$, together with the carbon atom to which they are attached, form cyclopropyl, oxetanyl, or cyclobutyl, and wherein the cyclopropyl, oxetanyl, and cyclobutyl are each independently optionally substituted with 1 or 2 groups selected from halo, —CH$_3$, or —OH or 4-10 membered heterocyclyl, or, R$^d$ and R$^e$ are independently —H or —(C$_1$-C$_3$)alkyl;
  X is O; and
  Y is —H, deuterium, or —F;
  provided that $R^1$, $R^2$, $R^3$ and Y are not all —H.

2. The compound of claim 1, wherein:

$R^2$ is —H; halo; —$CF_3$; cyano; —$NR^aR^b$; —$OR^c$; optionally substituted ($C_1$-$C_6$)alkyl; optionally substituted ($C_3$-$C_6$)cycloalkyl; optionally substituted ($C_5$-$C_7$)cycloalkenyl; optionally substituted bridged ($C_3$-$C_8$)cycloalkyl; optionally substituted ($C_1$-$C_3$)alkoxy; optionally substituted aryl; optionally substituted 5-10 membered heteroaryl; optionally substituted 5-10 membered bridged carbocyclyl; or optionally substituted 4-10 membered heterocyclyl;

wherein ($C_1$-$C_3$)alkoxy is optionally substituted with aryl;

wherein ($C_1$-$C_6$)alkyl is optionally substituted with one or more halo; and, wherein in $R^2$, ($C_3$-$C_6$)cycloalkyl, ($C_5$-$C_7$)cycloalkenyl, bridged ($C_3$-$C_8$)cycloalkyl, aryl, 5-10 membered heteroaryl, and 4-10 membered heterocyclyl are each independently optionally substituted with one or more groups selected from halo, —$CF_3$, cyano, —($C_1$-$C_4$)alkyl, -hydroxy($C_1$-$C_4$)alkyl, -halo($C_1$-$C_3$)alkyl, -halo($C_1$-$C_3$)alkoxy, —S(O)($C_1$-$C_3$)alkyl, —$S(O)_2$($C_1$-$C_3$)alkyl, —$NR^aR^b$, —($C_1$-$C_3$)alkoxy, —($C_1$-$C_4$)alkoxy($C_1$-$C_3$)alkyl or piperazinyl.

3. The compound of claim 2, wherein:

$R^3$ is —$CF_3$; —$CH_2F$; —$CHF_2$; —F; —$NR^aR^b$; —$OR^c$; optionally substituted ($C_1$-$C_3$)alkyl; —$CH_2$-(4-10 membered)heterocyclyl; —CH(($C_1$-$C_3$)alkyl)-(4-10 membered)heterocyclyl; —C(($C_1$-$C_3$)alkyl)$_2$-(4-10 membered)heterocyclyl; optionally substituted heterocyclic spirocyclyl; optionally substituted 4-10 membered heterocyclyl; or —$C(R^d)(R^e)$-(4-10 membered)heterocyclyl;

wherein the ($C_1$-$C_3$)alkyl is optionally substituted with one or more halo or —OH;

wherein the heterocyclic spirocyclyl is optionally substituted with 1-3 groups selected from halo, —$CH_3$, or —OH;

wherein the 4-10 membered heterocyclyl is optionally substituted with 1-3 groups selected from —H, halo, —$CF_3$, —OH, —($C_1$-$C_3$)alkyl, -hydroxy($C_1$-$C_4$)alkyl, -halo($C_1$-$C_3$)alkyl, amino($C_1$-$C_3$)alkyl, —($C_1$-$C_4$)alkoxy($C_1$-$C_3$)alkyl, —C(O)($C_1$-$C_3$)alkyl, —C(O)halo($C_1$-$C_3$)alkyl, —C(O)hydroxy($C_1$-$C_4$)alkyl, —C(O)—($C_1$-$C_3$)alkylene-N($CH_3$)$_2$, —($C_1$-$C_3$)aralkyl, oxetanyl, —$CH_2$-oxetanyl, tetrahydropyranyl, —$CH_2$-tetrahydropyranyl, or —$NR^aR^b$; and, wherein —$C(R^d)(R^e)$ forms cyclopropyl, oxetanyl, or cyclobutyl, and wherein the cyclopropyl, oxetanyl, and cyclobutyl are each independently optionally substituted with 1 or 2 groups selected from halo, —$CH_3$, or —OH.

4. The compound of claim 3, wherein:

$R^2$ is —H; halo; —$CF_3$; cyano; —$NR^aR^b$; —$OR^c$; optionally substituted ($C_3$-$C_6$)cycloalkyl; optionally substituted ($C_5$-$C_6$)cycloalkenyl, optionally substituted furanyl; optionally substituted benzothiazolyl; optionally substituted tetrahydropyranyl; optionally substituted piperidinyl; optionally substituted 1,4-diazabicyclo[2.2.1]heptanyl, optionally substituted bicyclo[1.1.1]pentyl, optionally substituted bicyclo[2.1.0]pentyl, optionally substituted pyrrolidinyl; optionally substituted pyridinyl; optionally substituted phenyl, optionally substituted naphthyl; or —($C_1$-$C_6$)alkyl optionally substituted with one or more halo, wherein the —($C_3$-$C_6$)cycloalkyl, —($C_5$-$C_6$)cycloalkenyl, furanyl, benzothiazolyl, tetrahydropyranyl, piperidinyl, 1,4-diazabicyclo[2.2.1]heptanyl, bicyclo[1.1.1]pentyl, bicyclo[2.1.0]pentyl, pyrrolidinyl, pyridinyl, phenyl, and naphthyl are each optionally substituted with 1-3 groups independently selected from halo, —$CF_3$, cyano, —($C_1$-$C_4$)alkyl, -hydroxy($C_1$-$C_4$)alkyl, -halo($C_1$-$C_3$)alkyl, -halo($C_1$-$C_3$)alkoxy, —($C_1$-$C_3$)alkoxy, —S(O)($C_1$-$C_3$)alkyl, —$S(O)_2$($C_1$-$C_3$)alkyl, —$NR^aR^b$, —($C_1$-$C_4$)alkoxy($C_1$-$C_3$)alkyl or piperazinyl.

5. The compound of claim 4, wherein:

$R^3$ is —$NR^aR^b$, —$OR^c$, —$CH_2$-(4-10 membered)heterocyclyl, —CH(($C_1$-$C_3$)alkyl)-(4-10 membered)heterocyclyl, —C(($C_1$-$C_3$)alkyl)$_2$-(4-10 membered)heterocyclyl, or 4-10 membered heterocyclyl;

wherein each 4-10 membered heterocyclyl is independently selected from the group consisting of azetidinyl, oxetanyl, tetrahydrofuranyl, pyrrolidinyl, imidazolidinyl, pyrazolidinyl, tetrahydropyranyl, piperidinyl, piperazinyl, morpholinyl, 1,4-dioxanyl, 1,3-dioxanyl, azepanyl, octahydroindolizinyl, octahydropyrrolo[1,2-a]pyrazinyl; and, wherein each 4-10 membered heterocyclyl is optionally substituted with 1-3 groups independently selected from —$CF_3$, —($C_1$-$C_3$)aralkyl, —($C_1$-$C_3$)alkyl, halo($C_1$-$C_3$)alkyl, hydroxy($C_1$-$C_3$)alkyl, or amino($C_1$-$C_3$)alkyl.

6. The compound of claim 5, wherein:

$R^1$ is —H, deuterium, halo, —$CF_3$, —($C_1$-$C_3$)alkyl, or —($C_3$-$C_6$)cycloalkyl, wherein —($C_1$-$C_3$)alkyl is optionally substituted with 1-3 groups selected from halo, hydroxy, or —($C_1$-$C_3$)alkoxy; and wherein —($C_3$-$C_6$)cycloalkyl is optionally substituted with 1-3 groups selected from halo, hydroxy, —($C_1$-$C_3$)alkyl, or —($C_1$-$C_3$)alkoxy;

$R^4$ is —$CF_3$, —$CHF_2$, —$CH_2F$, or —($C_1$-$C_6$)alkyl optionally substituted with 1-3 groups selected from halo, hydroxy, or —($C_1$-$C_3$)alkoxy;

$R^a$ is independently —H or —($C_1$-$C_3$)alkyl;

$R^b$ is independently —H, phenyl optionally substituted with hydroxy or —($C_1$-$C_3$)alkyl, or 4-10 membered heterocyclyl; wherein the 4-10 membered heterocyclyl is optionally substituted with 1-3 groups independently selected from: halo, —($C_1$-$C_3$)alkyl, -hydroxy($C_1$-$C_4$)alkyl, -halo($C_1$-$C_3$)alkyl, —($C_1$-$C_4$)alkoxy($C_1$-$C_3$)alkyl, —($C_1$-$C_3$)alkoxy, -halo($C_1$-$C_3$)alkoxy, —C(O)($C_1$-$C_3$)alkyl, —C(O)halo($C_1$-$C_3$)alkyl, —C(O)hydroxy($C_1$-$C_4$)alkyl, —C(O)($C_1$-$C_3$)alkyleneN($CH_3$)$_2$, —($C_1$-$C_3$)aralkyl, oxetanyl, —$CH_2$-oxetanyl, tetrahydropyranyl, or —$CH_2$-tetrahydropyranyl; and, $R^c$ is independently —$CH_2$-optionally substituted phenyl, optionally substituted phenyl, or 4-10 membered heterocyclyl optionally substituted with one or more ($C_1$-$C_3$)alkyl; wherein each phenyl is independently optionally substituted with —($C_1$-$C_3$)alkyl.

7. The compound of claim 3, having the Formula (II):

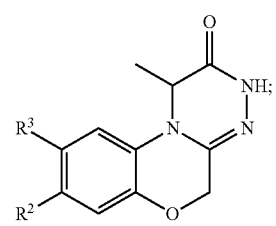

(II)

or a pharmaceutically acceptable salt, a stereoisomer, or a tautomer thereof.

8. The compound of claim 7, wherein $R^3$ is represented by structural formula (i):

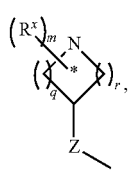

(i)

wherein:
m is 1, 2, 3, or 4;
q is 1, 2, or 3;
r is 1 or 2; and,
Z is absent, $NR^7$, O, or $C(H)R^7$; wherein $R^7$ is —H or —($C_1$-$C_3$)alkyl;
when Z is $NR^7$ or $C(H)R^7$, each $R^x$ is independently —H, halo, —($C_1$-$C_3$)alkyl, -hydroxy($C_1$-$C_4$)alkyl, -halo($C_1$-$C_3$)alkyl, —($C_1$-$C_4$)alkoxy($C_1$-$C_3$)alkyl, —C(O)($C_1$-$C_3$)alkyl, —C(O)halo($C_1$-$C_3$)alkyl, —C(O)hydroxy($C_1$-$C_4$)alkyl, —C(O)($C_1$-$C_3$)alkylene-N(CH$_3$)$_2$, —($C_1$-$C_3$)aralkyl, oxetanyl, —CH$_2$-oxetanyl, tetrahydropyranyl, or —CH$_2$-tetrahydropyranyl;
when Z is O, each $R^x$ is independently H or —($C_1$-$C_3$)alkyl; and,
when Z is absent, each $R^x$ is independently H, —CF$_3$, —($C_1$-$C_3$)alkyl, -hydroxy($C_1$-$C_4$)alkyl, or —($C_1$-$C_3$)aralkyl; or
when Z is absent, two $R^x$, together with the atoms to which they are attached, form a ring fused to the heterocyclic ring to form an optionally substituted bicyclic ring.

9. The compound of claim 8, wherein the compound is of Formula (III) or Formula (IV):

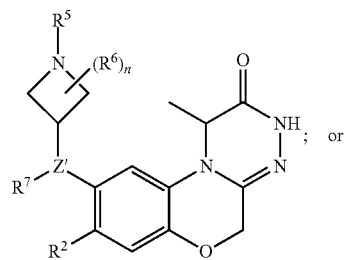

(III)

or

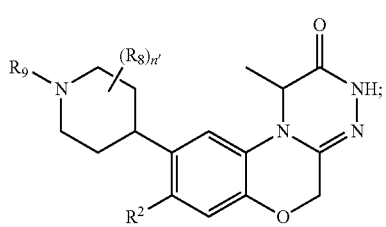

(IV)

or a pharmaceutically acceptable salt, a stereoisomer, or a tautomer thereof, wherein:
$R^5$, $R^6$, $R^8$ and $R^9$ are each independently an $R^x$; wherein $R^5$ and $R^9$ are independently —H, —($C_1$-$C_3$)alkyl, -hydroxy($C_2$-$C_4$)alkyl, -halo($C_1$-$C_3$)alkyl, —($C_2$-$C_4$)alkoxy($C_1$-$C_3$)alkyl, —C(O)($C_1$-$C_3$)alkyl, —C(O)halo($C_1$-$C_3$)alkyl, —C(O)hydroxy($C_1$-$C_4$)alkyl, —C(O)($C_1$-$C_3$)alkyleneN(CH$_3$)$_2$, —($C_1$-$C_3$)aralkyl, oxetanyl, —CH$_2$-oxetanyl, tetrahydropyranyl, or —CH$_2$-tetrahydropyranyl;
$R^6$ is independently —H or —($C_1$-$C_3$)alkyl;
$R^8$ is —H, —CF$_3$, —($C_1$-$C_3$)alkyl or ($C_1$-$C_3$)aralkyl; or
two $R^8$, together with the atoms to which they are attached, form a ring fused to a piperidine ring to form an optionally substituted bicyclic ring;
$R^7$ is —H or —($C_1$-$C_3$)alkyl;
n is 0, 1, 2, or 3;
n' is 0, 1, 2, or 3; and
Z' is N or CH, or Z' is O and $R^7$ is absent.

10. The compound of claim 9, wherein the compound is of Formula (IV), Formula (V), or Formula (VI):

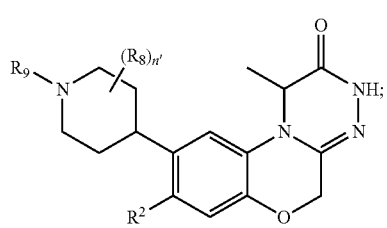

(IV)

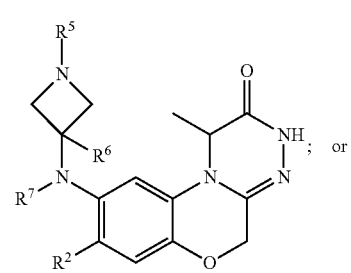

(V)

or

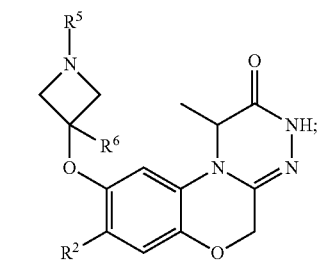

(VI)

wherein $R^8$ is —H, —CF$_3$, —CH$_3$, or —CH$_2$-aryl.

11. The compound of claim 10, wherein $R^5$ and $R^7$ are each independently —H or —($C_1$-$C_3$)alkyl; $R^6$ is —($C_1$-$C_3$)alkyl; and $R^8$ is —H, —CH$_3$, or —CH$_2$-aryl.

12. The compound of claim 7, wherein $R^3$ is represented by structural formula (ii):

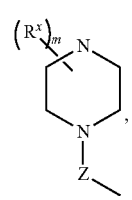

(ii)

wherein:
m is 1, 2, 3, or 4;
Z is absent or —CH$_2$-optionally substituted with —($C_1$-$C_3$)alkyl; and each substitutable ring atom of $R^3$ is optionally substituted by $R^x$, and each $R^x$ is independently —H, halo, —$CF_3$, —($C_1$-$C_3$)alkyl, -hydroxy($C_1$-$C_4$)alkyl, -halo ($C_1$-$C_3$)alkyl, —($C_1$-$C_4$)alkoxy($C_1$-$C_3$)alkyl, —C(O)($C_1$-$C_3$)alkyl, —C(O)halo($C_1$-$C_3$)alkyl, —C(O)hydroxy($C_1$-$C_4$)alkyl, —C(O)—($C_1$-$C_3$)alkylene-N($CH_3$)$_2$, —($C_1$-$C_3$)aralkyl, oxetanyl, —$CH_2$-oxetanyl, tetrahydropyranyl, or —$CH_2$-tetrahydropyranyl; or when Z is absent, two $R^x$, together with the atoms to which they are attached, form a ring fused to the heterocyclic ring to form an optionally substituted bicyclic ring.

13. The compound of claim 8 or 12, wherein the compound is of Formula (IV-1), Formula (IV-2), Formula (IV-3), or Formula (IV-4):

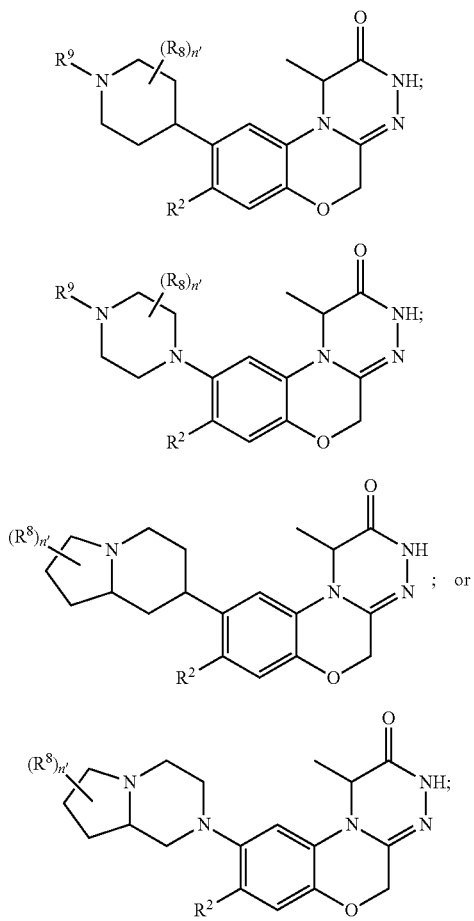

or a pharmaceutically acceptable salt, a stereoisomer, or a tautomer thereof, wherein:
$R^8$ and $R^9$ are each independently an $R^x$;
n' is 0, 1, 2 or 3;
$R^8$ is —$CF_3$, —($C_1$-$C_3$)alkyl or —$CH_2$-aryl; and
$R^9$ is independently —H, —($C_1$-$C_3$)alkyl, -hydroxy($C_2$-$C_4$)alkyl, -halo($C_1$-$C_3$)alkyl, —($C_2$-$C_4$)alkoxy($C_1$-$C_3$)alkyl, —C(O)($C_1$-$C_3$)alkyl, —C(O)halo($C_1$-$C_3$)alkyl, —C(O)hydroxy($C_1$-$C_4$)alkyl, —C(O)($C_1$-$C_3$)alkylene-N($CH_3$)$_2$, —($C_1$-$C_3$)aralkyl, oxetanyl, —$CH_2$-oxetanyl, tetrahydropyranyl, or —$CH_2$-tetrahydropyranyl.

14. The compound of claim 13, wherein $R^2$ is selected from —H; halo; —$CF_3$; —$CH_3$; ethyl; isopropyl; —$CH(CH_3)CF_3$; furanyl; cyclopentyl; cyclopropyl; bicyclo[1.1.1]pentyl, bicyclo[2.1.0]pentyl, benzothiazolyl; optionally substituted cyclohexenyl; optionally substituted naphthyl; optionally substituted tetrahydropyranyl, optionally substituted pyridinyl; or optionally substituted phenyl;
wherein the cyclohexenyl is optionally substituted with halo;
wherein the naphthyl is optionally substituted with one or more groups selected from halo, —($C_1$-$C_3$)alkyl, or —($C_1$-$C_3$)alkoxy; and,
wherein the phenyl is optionally substituted with one or more groups independently selected from halo, —$CF_3$, —$CH_3$, —CN, —($C_1$-$C_4$)alkyl, —($C_1$-$C_3$)alkoxy, -halo($C_1$-$C_3$)alkoxy, —($C_1$-$C_4$)alkoxy($C_1$-$C_3$)alkyl, -halo($C_1$-$C_3$)alkyl, —N(($C_1$-$C_3$)alkyl)$_2$, —S(O)$CH_3$, and —S(O)$_2$$CH_3$.

15. The compound of claim 1, wherein:
$R^1$ is —H or —F;
$R^2$ is —H, —Br, —F, —$CF_3$, —$NR^aR^b$, —$CH_3$, ethyl, isopropyl, isobutyl, —C(H)($CH_3$)$CF_3$, cyclopropyl, cyclopentyl, cyclohexyl, methoxy, optionally substituted naphthyl, optionally substituted phenyl, optionally substituted tetrahydropyranyl, benzothiazolyl, optionally substituted pyridinyl, or phenoxy;
$R^3$ is —$NR^aR^b$, —$OR^c$, —$CH_2$-azetidinyl, 3,7-diazaspiro[3.5]nonanyl, optionally substituted piperidinyl, optionally substituted piperazinyl, or optionally substituted pyrrolidinyl;
$R^4$ is —$CH_3$;
$R^a$ is —H or —$CH_3$;
$R^b$ is —H, phenyl, optionally substituted azetidinyl, azabicyclo[3.2.1]octanyl, or optionally substituted piperidinyl;
$R^c$ is —H, or optionally substituted azetidinyl; and
X is O.

16. The compound of claim 1, wherein the compound is selected from:
6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
(R)-6-(1-Cyclobutyl-ethylamino)-4,7-dimethyl-2,10-dihydro-9-oxa-1,2,4a-triaza-phenanthren-3-one;
6-(Azetidin-3-ylamino)-4-(R)-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(R)-6-(Azetidin-3-ylamino)-4-methyl-7-o-tolyl-2,10-dihydro-9-oxa-1,2,4a-triaza-phenanthren-3-one;
(R)-6-(Azetidin-3-ylamino)-7-(3-fluoro-phenyl)-4-methyl-2,10-dihydro-9-oxa-1,2,4a-triaza-phenanthren-3-one;
(R)-6-(Azetidin-3-ylamino)-7-(4-chloro-phenyl)-4-methyl-2,10-dihydro-9-oxa-1,2,4a-triaza-phenanthren-3-one;

(R)-6-(Azetidin-3-ylamino)-7-(2,4-dichloro-phenyl)-4-methyl-2,10-dihydro-9-oxa-1,2,4a-triaza-phenanthren-3-one;
(R)-6-(Azetidin-3-ylamino)-7-(4-fluoro-phenyl)-4-methyl-2,10-dihydro-9-oxa-1,2,4a-triaza-phenanthren-3-one;
(R)-6-(Azetidin-3-ylamino)-4-methyl-7-naphthalen-1-yl-2,10-dihydro-9-oxa-1,2,4a-triaza-phenanthren-3-one;
(R)-6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(azetidin-3-ylamino)-4(R)-methyl-7-trifluoromethyl-2,10-dihydro-9-oxa-1,2,4a-triaza-phenanthren-3-one;
6-(Azetidin-3-ylamino)-4(R),7-dimethyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-(azetidin-3-ylamino)-7-fluoro-4(R)-methyl-2,10-dihydro-9-oxa-1,2,4a-triaza-phenanthren-3-one;
6-(Azetidin-3-ylamino)-7-isopropyl-4(R)-methyl-2,10-dihydro-9-oxa-1,2,4a-triaza-phenanthren-3-one;
6-(Azetidin-3-ylamino)-7-cyclopropyl-4(R)-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
6-Azetidin-3-ylmethyl-4-methyl-2,10-dihydro-9-oxa-1,2,4a-triaza-phenanthren-3-one;
4-Methyl-6-(3-methyl-azetidin-3-ylamino)-7-phenyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4-Methyl-6-(3-methyl-azetidin-3-ylamino)-7-trifluoromethyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-yloxy)-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(2-Benzyl-piperidin-4-yl)-4-methyl-2,10-dihydro-9-oxa-1,2,4a-triaza-phenanthren-3-one;

6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4-methyl-7-o-tolyl-2,10-dihydro-9-oxa-1,2,4a-triaza-phenanthren-3-one;
6-[(1,3-Dimethyl-azetidin-3-yl)-methyl-amino]-7-(2-fluoro-phenyl)-4-methyl-2,10-dihydro-9-oxa-1,2,4a-triaza-phenanthren-3-one;
4-Methyl-6-[methyl-(3-methyl-azetidin-3-yl)-amino]-7-phenyl-2,10-dihydro-9-oxa-1,2,4a-triaza-phenanthren-3-one;
6-[(1-Isopropyl-3-methyl-azetidin-3-yl)-methyl-amino]-4-methyl-7-phenyl-2,10-dihydro-9-oxa-1,2,4a-triaza-phenanthren-3-one;
6-[(1-Ethyl-3-methyl-azetidin-3-yl)-methyl-amino]-4-methyl-7-phenyl-2,10-dihydro-9-oxa-1,2,4a-triaza-phenanthren-3-one;
(R)-6-(Azetidin-3-yloxy)-7-isopropyl-4-methyl-2,10-dihydro-9-oxa-1,2,4a-triaza-phenanthren-3-one;
4,7-Dimethyl-6-(3-methyl-azetidin-3-ylamino)-2,10-dihydro-9-oxa-1,2,4a-triaza-phenanthren-3-one;
6-Azetidin-3-ylmethyl-4-methyl-7-trifluoromethyl-2,10-dihydro-9-oxa-1,2,4a-triaza-phenanthren-3-one;
(R)-4-Methyl-6-(3-methyl-azetidin-3-ylamino)-7-trifluoromethyl-2,10-dihydro-9-oxa-1,2,4a-triaza-phenanthren-3-one;
(R)-6-(1,3-dimethyl-azetidin-3-ylamino)-4-methyl-7-trifluoromethyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
6-[(1,3-dimethyl-azetidin-2-yl)-methyl-amino]-4(S)-methyl-7-phenyl-2,10-dihydro-9-oxa-1,2,4a-triaza-phenanthren-3-one;
6-(1,3-Dimethyl-azetidin-3-ylamino)-4-methyl-7-phenyl-2,10-dihydro-9-oxa-1,2,4a-triaza-phenanthren-3-one;
(R)-6-((2S,4S)-2-Benzyl-piperidin-4-yl)-4-methyl-2,10-dihydro-9-oxa-1,2,4a-triaza-phenanthren-3-one;
(R)-6-((2S,4R)-2-benzyl-piperidin-4-yl)-4-methyl-2,10-dihydro-9-oxa-1,2,4a-triaza-phenanthren-3-one;
(R)-6-(Azetidin-3-ylamino)-4-methyl-7-(2,2,2-trifluoro-1-methyl-ethyl)-2,10-dihydro-9-oxa-1,2,4a-triaza-phenanthren-3-one;
6-(3-Isopropyl-azetidin-3-ylamino)-4-methyl-2,10-dihydro-9-oxa-1,2,4a-triaza-phenanthren-3-one;
6-(2-Benzyl-piperidin-4-yl)-4-methyl-7-trifluoromethyl-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(1-Isopropyl-3-methyl-azetidin-3-ylamino)-4-methyl-7-(tetrahydro-pyran-4-yl)-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
(R)-6-(Azetidin-3-ylamino)-4-methyl-7-((R)-2,2,2-trifluoro-1-methyl-ethyl)-2,10-dihydro-9-oxa-1,2,4a-triaza-phenanthren-3-one;
(R)-6-(Azetidin-3-ylamino)-4-methyl-7-((S)-2,2,2-trifluoro-1-methyl-ethyl)-2,10-dihydro-9-oxa-1,2,4a-triaza-phenanthren-3-one;
4-Methyl-6-(3-methyl-azetidin-3-ylamino)-7-(2,2,2-trifluoro-1-methyl-ethyl)-2,10-dihydro-9-oxa-1,2,4a-triaza-phenanthren-3-one;
6-(Azetidin-3-yloxy)-4,7-dimethyl-2,10-dihydro-9-oxa-1,2,4a-triaza-phenanthren-3-one;
7-Fluoro-4-methyl-6-piperidin-4-yl-2,10-dihydro-9-oxa-1,2,4a-triaza-phenanthren-3-one;
4-Methyl-6-(3-methyl-piperidin-4-yl)-2,10-dihydro-9-oxa-1,2,4a-triaza-phenanthren-3-one;
6-(3,3-Dimethyl-piperidin-4-yl)-4-methyl-2,10-dihydro-9-oxa-1,2,4a-triaza-phenanthren-3-one;
6-[(1-Benzyl-3-methyl-azetidin-3-yl)-methyl-amino]-4-methyl-7-phenyl-2,10-dihydro-9-oxa-1,2,4a-triaza-phenanthren-3-one;
4-Methyl-6-{methyl-[3-methyl-1-(tetrahydro-pyran-4-yl)-azetidin-3-yl]-amino}-7-phenyl-2,10-dihydro-9-oxa-1,2,4a-triaza-phenanthren-3-one;
4-Methyl-6-{methyl-[3-methyl-1-(tetrahydro-pyran-4-ylmethyl)-azetidin-3-yl]-amino}-7-phenyl-2,10-dihydro-9-oxa-1,2,4a-triaza-phenanthren-3-one;
(S)-4-methyl-6-(3-methyl-azetidin-3-ylamino)-7-trifluoromethyl-2,10-dihydro-9-oxa-1,2,4a-triaza-phenanthren-3-one;
(S)-6-(1,3-Dimethyl-azetidin-3-ylamino)-4-methyl-7-trifluoromethyl-2,10-dihydro-9-oxa-1,2,4a-triaza-phenanthren-3-one;
(R)-4-Methyl-6-[methyl-(3-methyl-azetidin-3-yl)-amino]-7-trifluoromethyl-2,10-dihydro-9-oxa-1,2,4a-triaza-phenanthren-3-one;
6-(Azetidin-3-ylamino)-4-methyl-7-phenoxy-2,10-dihydro-9-oxa-1,2,4a-triaza-phenanthren-3-one;

4-Methyl-6-(3-methyl-azetidin-3-yloxy)-7-trifluoromethyl-2,10-dihydro-9-oxa-1,2,4a-triaza-phenanthren-3-one;
(R)-6-((S)-1-Azetidin-3-yl-ethyl)-4-methyl-2,10-dihydro-9-oxa-1,2,4a-triaza-phenanthren-3-one;
(R)-6-((R)-1-Azetidin-3-yl-ethyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
4-Methyl-6-(2-methyl-azetidin-3-ylamino)-2,10-dihydro-9-oxa-1,2,4a-triaza-phenanthren-3-one;
4-Methyl-6-piperidin-4-yl-7-trifluoromethyl-2,10-dihydro-9-oxa-1,2,4a-triaza-phenanthren-3-one;
(R)-7-Isopropyl-4-methyl-6-(3-methyl-azetidin-3-yloxy)-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
(R)-6-(Azetidin-3-yloxy)-7-fluoro-4-methyl-2,10-dihydro-9-oxa-1,2,4a-triaza-phenanthren-3-one;
4,7-Dimethyl-6-(1-methyl-azetidin-3-ylamino)-2,10-dihydro-9-oxa-1,2,4a-triaza-phenanthren-3-one;
6-(Azetidin-3-ylamino)-7-benzyloxy-4-methyl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
4-Methyl-6-[1-(3-methyl-azetidin-3-yl)-ethyl]-2,10-dihydro-9-oxa-1,2,4a-triaza-phenanthren-3-one;
6-(azetidin-3-ylamino)-4-(S)-methyl-7-phenyl-2,10-dihydro-9-oxa-1,2,4a-triaza-phenanthren-3-one;
6-(Azetidin-3-ylamino)-4(S)-methyl-7-trifluoromethyl-2,10-dihydro-9-oxa-1,2,4a-triaza-phenanthren-3-one;
6-(azetidin-3-ylamino)-4(S),7-dimethyl-2,10-dihydro-9-oxa-1,2,4a-triaza-phenanthren-3-one;
6-(Azetidin-3-ylamino)-7-fluoro-4(S)-methyl-2,10-dihydro-9-oxa-1,2,4a-triaza-phenanthren-3-one;
6-(azetidin-3-ylamino)-7-isopropyl-4(S)-methyl-2,10-dihydro-9-oxa-1,2,4a-triaza-phenanthren-3-one;
6-(azetidin-3-ylamino)-7-cyclopropyl-4(S)-methyl-2,10-dihydro-9-oxa-1,2,4a-triaza-phenanthren-3-one;
(S)-7-isopropyl-4-methyl-6-(3-methyl-azetidin-3-yloxy)-2,10-dihydro-9-oxa-1,2,4a-triaza-phenanthren-3-one;
3-((R)-7-Fluoro-4-methyl-3-oxo-2,3,4,10-tetrahydro-9-oxa-1,2,4a-triaza-phenanthren-6-ylamino)-azetidine-1-carboxylic acid 1-acetoxy-ethyl;
(S)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(S)-6-(Azetidin-3-ylamino)-4-methyl-7-o-tolyl-2,10-dihydro-9-oxa-1,2,4a-triaza-phenanthren-3-one;
(S)-6-(Azetidin-3-ylamino)-7-cyclopropyl-4-methyl-2,10-dihydro-9-oxa-1,2,4a-triaza-phenanthren-3-one;
(S)-6-(Azetidin-3-ylamino)-7-(3-fluoro-phenyl)-4-methyl-2,10-dihydro-9-oxa-1,2,4a-triaza-phenanthren-3-one;
(S)-6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
(S)-6-(Azetidin-3-ylamino)-7-(4-fluoro-phenyl)-4-methyl-2,10-dihydro-9-oxa-1,2,4a-triaza-phenanthren-3-one;
(S)-6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
(S)-6-(Azetidin-3-ylamino)-4-methyl-7-phenyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-isopropyl-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-isopropyl-4-methyl-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
(S)-6-(Azetidin-3-ylamino)-4-methyl-7-trifluoromethyl-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
(S)-6-(Azetidin-3-ylamino)-4-methyl-7-(4-trifluoromethoxy-phenyl)-2,10-dihydro-9-oxa-1,2,4a-triaza-phenanthren-3-one;
(S)-6-(Azetidin-3-ylamino)-4,7-dimethyl-2,10-dihydro-9-oxa-1,2,4a-triaza-phenanthren-3-one;

(S)-6-(Azetidin-3-ylamino)-7-fluoro-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
10-Methyl-6-(3-methyl-azetidin-3-ylamino)-7-phenyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-4-methyl-7-trifluoromethyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
(1R,3S)-3-Amino-cyclopentanecarboxylic acid ((R)-4-methyl-3-oxo-2,3,4,10-tetrahydro-9-oxa-1,2,4a-triaza-phenanthren-6-yl)-amide;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
(1R,3S)-3-Amino-cyclopentanecarboxylic acid ((S)-4-methyl-3-oxo-2,3,4,10-tetrahydro-9-oxa-1,2,4a-triaza-phenanthren-6-yl)-amide;
6-(Azetidin-3-ylamino)-2,10-dihydro-9-oxa-1,2,4a-triaza-phenanthrene-3,4-dione;
6-Azetidin-3-ylmethyl-4-methyl-2,10-dihydro-9-oxa-1,2,4a-triaza-phenanthren-3-one;
(S)-6-(Azetidin-3-yloxy)-7-fluoro-4-methyl-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-4,7-dimethyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
4-Methyl-6-(3-methyl-azetidin-3-ylamino)-2,10-dihydro-9-oxa-1,2,4a-triaza-phenanthren-3-one;
4,7-Dimethyl-6-(1-methyl-azetidin-3-ylamino)-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-[(1S,5R)-(8-Aza-bicyclo[3.2.1]oct-3-yl)amino]-7-fluoro-4-methyl-2,10-dihydro-9-oxa-1,2,4a-triaza-phenanthren-3-one;
6-(Azetidin-3-yl-benzyl-amino)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;
7-Fluoro-4-methyl-6-piperidin-4-yl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
(3S,4S)-3-Methyl-piperidine-4-carboxylic acid (4-methyl-3-oxo-2,3,4,10-tetrahydro-9-oxa-1,2,4a-triaza-phenanthren-6-yl)-amide;

7-Fluoro-4-methyl-6-(1-methyl-azetidin-3-ylamino)-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(Azetidin-3-ylamino)-7-cyclohexyl-4-methyl-2,10-dihydro-9-oxa-1,2,4a-triaza-phenanthren-3-one;
6-(Azetidin-3-ylamino)-7-(6-cyclopropylmethoxy-pyridin-3-yl)-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
(R)-6-(Azetidin-3-ylamino)-4-methyl-7-trifluoromethyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-chloro-4-methyl-2,10-dihydro-9-oxa-1,2,4a-triaza-phenanthren-3-one;
4,7-Dimethyl-6-(1,2,3,6-tetrahydro-pyridin-4-yl)-2,10-dihydro-9-oxa-1,2,4a-triaza-phenanthren-3-one;
6-(Azetidin-3-ylamino)-4-methyl-7-(tetrahydro-pyran-4-yl)-2,10-dihydro-9-oxa-1,2,4a-triaza-phenanthren-3-one;
4-Methyl-6-(1-methyl-azetidin-3-ylamino)-2,10-dihydro-9-oxa-1,2,4a-triaza-phenanthren-3-one;
(R)-6-(Azetidin-3-ylamino)-7-isopropyl-4-methyl-2,10-dihydro-9-oxa-1,2,4a-triaza-phenanthren-3-one;
6-(Azetidin-3-yl-methyl-amino)-7-fluoro-4-methyl-2,10-dihydro-9-oxa-1,2,4a-triaza-phenanthren-3-one;
6-(Azetidin-3-ylamino)-7-methoxy-4-methyl-2,10-dihydro-9-oxa-1,2,4a-triaza-phenanthren-3-one;
4-Methyl-6-(1-methyl-piperidin-4-yl)-2,10-dihydro-9-oxa-1,2,4a-triaza-phenanthren-3-one;
4-Methyl-6-pyrrolidin-3-yl-2,10-dihydro-9-oxa-1,2,4a-triaza-phenanthren-3-one;
6-(Azetidin-3-yl-cyclopropyl-amino)-2,10-dihydro-9-oxa-1,2,4a-triaza-phenanthren-3-one;
(1R,8S)-8-(2,6-difluorophenyl)-9-((3R,4R)-1,3-dimethylpiperidin-4-yl)-1-methyl-3,5-dihydrobenzo[5,6][1,4]oxazino[3,4-c][1,2,4]triazin-2(1H)-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-6-(3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(S)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-7-(3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-7-(2,6-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((2R,5S)-2,5-Dimethyl-piperazin-1-yl)-7-(2-fluoro-phenyl)-4-methyl-2,10-dihydro-9-oxa-1,2,4a-triaza-phenanthren-3-one hydrochloride;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one; or
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one.

17. A pharmaceutical composition comprising a compound of claim 1 and a pharmaceutically acceptable carrier or diluent.

18. The pharmaceutical composition according to claim 17 wherein the compound is:
6-[(1,3-Dimethyl-azetidin-3-yl)-methyl-amino]-4-methyl-7-phenyl-2,10-dihydro-9-oxa-1,2,4a-triaza-phenanthren-3-one;
6-[(1,3-Dimethyl-azetidin-3-yl)-methyl-amino]-4(R)-methyl-7-phenyl-2,10-dihydro-9-oxa-1,2,4a-triaza-phenanthren-3-one;
(R)-6-(1-Cyclobutyl-ethylamino)-4,7-dimethyl-2,10-dihydro-9-oxa-1,2,4a-triaza-phenanthren-3-one;
6-(Azetidin-3-ylamino)-4-(R)-methyl-7-phenyl-2,10-dihydro-9-oxa-1,2,4a-triaza-phenanthren-3-one;

6-(Azetidin-3-yloxy)-7-isopropyl-4-methyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(R)-6-(Azetidin-3-ylamino)-4-methyl-7-o-tolyl-2,10-dihydro-9-oxa-1,2,4a-triaza-phenanthren-3-one;
(R)-6-(Azetidin-3-ylamino)-7-(3-fluoro-phenyl)-4-methyl-2,10-dihydro-9-oxa-1,2,4a-triaza-phenanthren-3-one;
(R)-6-(Azetidin-3-ylamino)-7-(4-chloro-phenyl)-4-methyl-2,10-dihydro-9-oxa-1,2,4a-triaza-phenanthren-3-one;
(R)-6-(Azetidin-3-ylamino)-7-(2,4-dichloro-phenyl)-4-methyl-2,10-dihydro-9-oxa-1,2,4a-triaza-phenanthren-3-one;
(R)-6-(Azetidin-3-ylamino)-7-(4-fluoro-phenyl)-4-methyl-2,10-dihydro-9-oxa-1,2,4a-triaza-phenanthren-3-one;
(R)-6-(Azetidin-3-ylamino)-4-methyl-7-naphthalen-1-yl-2,10-dihydro-9-oxa-1,2,4a-triaza-phenanthren-3-one;
(R)-6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
6-(Azetidin-3-ylamino)-7-(3-chloro-phenyl)-4-methyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(azetidin-3-ylamino)-4(R)-methyl-7-trifluoromethyl-2,10-dihydro-9-oxa-1,2,4a-triaza-phenanthren-3-one;
6-(Azetidin-3-ylamino)-4(R),7-dimethyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-(azetidin-3-ylamino)-7-fluoro-4(R)-methyl-2,10-dihydro-9-oxa-1,2,4a-triaza-phenanthren-3-one;
6-(Azetidin-3-ylamino)-7-isopropyl-4(R)-methyl-2,10-dihydro-9-oxa-1,2,4a-triaza-phenanthren-3-one;
6-(Azetidin-3-ylamino)-7-cyclopropyl-4(R)-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
6-Azetidin-3-ylmethyl-4-methyl-2,10-dihydro-9-oxa-1,2,4a-triaza-phenanthren-3-one;

4-Methyl-6-(3-methyl-azetidin-3-ylamino)-7-phenyl-2,10-dihydro-9-oxa-1,2,4a-triaza-phenanthren-3-one;

7-Fluoro-4-methyl-6-(3-methyl-azetidin-3-yloxy)-2,10-dihydro-9-oxa-1,2,4a-triaza-phenanthren-3-one;

4-Methyl-6-(3-methyl-azetidin-3-ylamino)-7-trifluoromethyl-2,10-dihydro-9-oxa-1,2,4a-triaza-phenanthren-3-one;

6-(Azetidin-3-yloxy)-7-isopropyl-4-methyl-2,10-dihydro-9-oxa-1,2,4a-triaza-phenanthren-3-one;

4,7-Dimethyl-6-(3-methyl-azetidin-3-yloxy)-2,10-dihydro-9-oxa-1,2,4a-triaza-phenanthren-3-one;

7-Fluoro-4-methyl-6-(3-methyl-azetidin-3-ylamino)-2,10-dihydro-9-oxa-1,2,4a-triaza-phenanthren-3-one;

6-(Azetidin-3-ylamino)-7-bromo-4-methyl-2,10-dihydro-9-oxa-1,2,4a-triaza-phenanthren-3-one;

6-(2-Benzyl-piperidin-4-yl)-4-methyl-2,10-dihydro-9-oxa-1,2,4a-triaza-phenanthren-3-one;

6-[(1,3-Dimethyl-azetidin-3-yl)-methyl-amino]-4-methyl-7-phenyl-2,10-dihydro-9-oxa-1,2,4a-triaza-phenanthren-3-one;

6-[(1,3-Dimethyl-azetidin-3-yl)-methyl-amino]-4-methyl-7-o-tolyl-2,10-dihydro-9-oxa-1,2,4a-triaza-phenanthren-3-one;

6-[(1,3-Dimethyl-azetidin-3-yl)-methyl-amino]-7-(2-fluoro-phenyl)-4-methyl-2,10-dihydro-9-oxa-1,2,4a-triaza-phenanthren-3-one;

4-Methyl-6-[methyl-(3-methyl-azetidin-3-yl)-amino]-7-phenyl-2,10-dihydro-9-oxa-1,2,4a-triaza-phenanthren-3-one;

6-[(1-Isopropyl-3-methyl-azetidin-3-yl)-methyl-amino]-4-methyl-7-phenyl-2,10-dihydro-9-oxa-1,2,4a-triaza-phenanthren-3-one;

6-[(1-Ethyl-3-methyl-azetidin-3-yl)-methyl-amino]-4-methyl-7-phenyl-2,10-dihydro-9-oxa-1,2,4a-triaza-phenanthren-3-one;

(R)-6-(Azetidin-3-yloxy)-7-isopropyl-4-methyl-2,10-dihydro-9-oxa-1,2,4a-triaza-phenanthren-3-one;

4,7-Dimethyl-6-(3-methyl-azetidin-3-ylamino)-2,10-dihydro-9-oxa-1,2,4a-triaza-phenanthren-3-one;

6-Azetidin-3-ylmethyl-4-methyl-7-trifluoromethyl-2,10-dihydro-9-oxa-1,2,4a-triaza-phenanthren-3-one;

(R)-4-Methyl-6-(3-methyl-azetidin-3-ylamino)-7-trifluoromethyl-2,10-dihydro-9-oxa-1,2,4a-triaza-phenanthren-3-one;

(R)-6-(1,3-dimethyl-azetidin-3-ylamino)-4-methyl-7-trifluoromethyl-2,10-dihydro-9-oxa-1,2,4a-triaza-phenanthren-3-one;

6-[(1,3-Dimethyl-azetidin-3-yl)-methyl-amino]-4(R)-methyl-7-phenyl-2,10-dihydro-9-oxa-1,2,4a-triaza-phenanthren-3-one;

6-[(1,3-dimethyl-azetidin-3-yl)-methyl-amino]-4(S)-methyl-7-phenyl-2,10-dihydro-9-oxa-1,2,4a-triaza-phenanthren-3-one;

6-(1,3-Dimethyl-azetidin-3-ylamino)-4-methyl-7-phenyl-2,10-dihydro-9-oxa-1,2,4a-triaza-phenanthren-3-one;

(R)-6-((2S,4S)-2-Benzyl-piperidin-4-yl)-4-methyl-2,10-dihydro-9-oxa-1,2,4a-triaza-phenanthren-3-one;

(R)-6-((2S,4R)-2-benzyl-piperidin-4-yl)-4-methyl-2,10-dihydro-9-oxa-1,2,4a-triaza-phenanthren-3-one;

(R)-6-(Azetidin-3-ylamino)-4-methyl-7-(2,2,2-trifluoro-1-methyl-ethyl)-2,10-dihydro-9-oxa-1,2,4a-triaza-phenanthren-3-one;

6-(3-Isopropyl-azetidin-3-ylamino)-4-methyl-2,10-dihydro-9-oxa-1,2,4a-triaza-phenanthren-3-one;

6-(2-Benzyl-piperidin-4-yl)-4-methyl-7-trifluoromethyl-2,10-dihydro-9-oxa-1,2,4a-triaza-phenanthren-3-one;

4-Methyl-7-phenyl-6-piperidin-4-yl-2,10-dihydro-9-oxa-1,2,4a-triaza-phenanthren-3-one;

6-(1-Isopropyl-3-methyl-azetidin-3-ylamino)-4-methyl-7-(tetrahydro-pyran-4-yl)-2,10-dihydro-9-oxa-1,2,4a-triaza-phenanthren-3-one;

6-(Azetidin-3-ylamino)-7-(4-methoxy-phenyl)-4-methyl-2,10-dihydro-9-oxa-1,2,4a-triaza-phenanthren-3-one;

6-(Azetidin-3-ylamino)-7-(2-fluoro-5-methyl-phenyl)-4-methyl-2,10-dihydro-9-oxa-1,2,4a-triaza-phenanthren-3-one;

6-(Azetidin-3-ylamino)-7-(4-fluoro-3-methyl-phenyl)-4-methyl-2,10-dihydro-9-oxa-1,2,4a-triaza-phenanthren-3-one;

6-(Azetidin-3-ylamino)-7-(3-fluoro-5-methyl-phenyl)-4-methyl-2,10-dihydro-9-oxa-1,2,4a-triaza-phenanthren-3-one;

6-(Azetidin-3-ylamino)-7-(2-methoxy-phenyl)-4-methyl-2,10-dihydro-9-oxa-1,2,4a-triaza-phenanthren-3-one;

6-(Azetidin-3-ylamino)-7-(6-methoxy-naphthalen-2-yl)-4-methyl-2,10-dihydro-9-oxa-1,2,4a-triaza-phenanthren-3-one;

6-(Azetidin-3-ylamino)-4-methyl-7-naphthalen-2-yl-2,10-dihydro-9-oxa-1,2,4a-triaza-phenanthren-3-one;

6-(Azetidin-3-ylamino)-7-benzothiazol-5-yl-4-methyl-2,10-dihydro-9-oxa-1,2,4a-triaza-phenanthren-3-one;

6-(Azetidin-3-ylamino)-7-benzothiazol-6-yl-4-methyl-2,10-dihydro-9-oxa-1,2,4a-triaza-phenanthren-3-one;

3-[6-(Azetidin-3-ylamino)-4-methyl-3-oxo-2,3,4,10-tetrahydro-9-oxa-1,2,4a-triaza-phenanthren-7-yl]-benzonitrile;

6-(Azetidin-3-ylamino)-7-(3-tert-butoxymethyl-phenyl)-4-methyl-2,10-dihydro-9-oxa-1,2,4a-triaza-phenanthren-3-one;

4-[6-(Azetidin-3-ylamino)-4-methyl-3-oxo-2,3,4,10-tetrahydro-9-oxa-1,2,4a-triaza-phenanthren-7-yl]-benzonitrile;

6-(Azetidin-3-ylamino)-4-methyl-7-naphthalen-1-yl-2,10-dihydro-9-oxa-1,2,4a-triaza-phenanthren-3-one;

6-(Azetidin-3-ylamino)-7-fluoro-4-methyl-2,10-dihydro-9-oxa-1,2,4a-triaza-phenanthren-3-one;

6-(Azetidin-3-ylamino)-7-isobutyl-4-methyl-2,10-dihydro-9-oxa-1,2,4a-triaza-phenanthren-3-one;

6-(Azetidin-3-ylamino)-7-ethyl-4-methyl-2,10-dihydro-9-oxa-1,2,4a-triaza-phenanthren-3-one;

6-(Azetidin-3-ylamino)-7-cyclopentyl-4-methyl-2,10-dihydro-9-oxa-1,2,4a-triaza-phenanthren-3-one;

(R)-6-(Azetidin-3-ylamino)-4-methyl-7-((R)-2,2,2-trifluoro-1-methyl-ethyl)-2,10-dihydro-9-oxa-1,2,4a-triaza-phenanthren-3-one;

(R)-6-(Azetidin-3-ylamino)-4-methyl-7-((S)-2,2,2-trifluoro-1-methyl-ethyl)-2,10-dihydro-9-oxa-1,2,4a-triaza-phenanthren-3-one;

4-Methyl-6-(3-methyl-azetidin-3-ylamino)-7-(2,2,2-trifluoro-1-methyl-ethyl)-2,10-dihydro-9-oxa-1,2,4a-triaza-phenanthren-3-one;

6-(Azetidin-3-yloxy)-4,7-dimethyl-2,10-dihydro-9-oxa-1,2,4a-triaza-phenanthren-3-one;

7-Fluoro-4-methyl-6-piperidin-4-yl-2,10-dihydro-9-oxa-1,2,4a-triaza-phenanthren-3-one;

4-Methyl-6-(3-methyl-piperidin-4-yl)-2,10-dihydro-9-oxa-1,2,4a-triaza-phenanthren-3-one;

6-(3,3-Dimethyl-piperidin-4-yl)-4-methyl-2,10-dihydro-9-oxa-1,2,4a-triaza-phenanthren-3-one;

6-[(1-Benzyl-3-methyl-azetidin-3-yl)-methyl-amino]-4-methyl-7-phenyl-2,10-dihydro-9-oxa-1,2,4a-triaza-phenanthren-3-one;

4-Methyl-6-{methyl-[3-methyl-1-(tetrahydro-pyran-4-yl)-azetidin-3-yl]-amino}-7-phenyl-2,10-dihydro-9-oxa-1,2,4a-triaza-phenanthren-3-one;
4-Methyl-6-{methyl-[3-methyl-1-(tetrahydro-pyran-4-yl-methyl)-azetidin-3-yl]-amino}-7-phenyl-2,10-dihydro-9-oxa-1,2,4a-triaza-phenanthren-3-one;
(S)-4-methyl-6-(3-methyl-azetidin-3-ylamino)-7-trifluoromethyl-2,10-dihydro-9-oxa-1,2,4a-triaza-phenanthren-3-one;
(S)-6-(1,3-Dimethyl-azetidin-3-ylamino)-4-methyl-7-trifluoromethyl-2,10-dihydro-9-oxa-1,2,4a-triaza-phenanthren-3-one;
(R)-4-Methyl-6-[methyl-(3-methyl-azetidin-3-yl)-amino]-7-trifluoromethyl-2,10-dihydro-9-oxa-1,2,4a-triaza-phenanthren-3-one;
6-(Azetidin-3-ylamino)-4-methyl-7-phenoxy-2,10-dihydro-9-oxa-1,2,4a-triaza-phenanthren-3-one;
4-Methyl-6-(3-methyl-azetidin-3-yloxy)-7-trifluoromethyl-2,10-dihydro-9-oxa-1,2,4a-triaza-phenanthren-3-one;
(R)-6-((S)-1-Azetidin-3-yl-ethyl)-4-methyl-2,10-dihydro-9-oxa-1,2,4a-triaza-phenanthren-3-one;
(R)-6-((R)-1-Azetidin-3-yl-ethyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
4-Methyl-6-(2-methyl-azetidin-3-ylamino)-2,10-dihydro-9-oxa-1,2,4a-triaza-phenanthren-3-one;
4-Methyl-6-piperidin-4-yl-7-trifluoromethyl-2,10-dihydro-9-oxa-1,2,4a-triaza-phenanthren-3-one;
(R)-7-Isopropyl-4-methyl-6-(3-methyl-azetidin-3-yloxy)-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
(R)-6-(Azetidin-3-yloxy)-7-fluoro-4-methyl-2,10-dihydro-9-oxa-1,2,4a-triaza-phenanthren-3-one;
4,7-Dimethyl-6-(1-methyl-azetidin-3-ylamino)-2,10-dihydro-9-oxa-1,2,4a-triaza-phenanthren-3-one;
6-(Azetidin-3-ylamino)-7-benzyloxy-4-methyl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
4-Methyl-6-[1-(3-methyl-azetidin-3-yl)-ethyl]-2,10-dihydro-9-oxa-1,2,4a-triaza-phenanthren-3-one;
6-(azetidin-3-ylamino)-4-(S)-methyl-7-phenyl-2,10-dihydro-9-oxa-1,2,4a-triaza-phenanthren-3-one;
6-(Azetidin-3-ylamino)-4(S)-methyl-7-trifluoromethyl-2,10-dihydro-9-oxa-1,2,4a-triaza-phenanthren-3-one;
6-(azetidin-3-ylamino)-4(S),7-dimethyl-2,10-dihydro-9-oxa-1,2,4a-triaza-phenanthren-3-one;
6-(Azetidin-3-ylamino)-7-fluoro-4(S)-methyl-2,10-dihydro-9-oxa-1,2,4a-triaza-phenanthren-3-one;
6-(azetidin-3-ylamino)-7-isopropyl-4(S)-methyl-2,10-dihydro-9-oxa-1,2,4a-triaza-phenanthren-3-one;
6-(azetidin-3-ylamino)-7-cyclopropyl-4(S)-methyl-2,10-dihydro-9-oxa-1,2,4a-triaza-phenanthren-3-one;
(S)-7-isopropyl-4-methyl-6-(3-methyl-azetidin-3-yloxy)-2,10-dihydro-9-oxa-1,2,4a-triaza-phenanthren-3-one;
3-((R)-7-Fluoro-4-methyl-3-oxo-2,3,4,10-tetrahydro-9-oxa-1,2,4a-triaza-phenanthren-6-ylamino)-azetidine-1-carboxylic acid 1-acetoxy-ethyl;
(S)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(2-fluoro-phenyl)-4-methyl-2,10-dihydro-9-oxa-1,2,4a-triaza-phenanthren-3-one;
(R)-6-(Azetidin-3-ylamino)-7-(2,4-difluoro-phenyl)-4-methyl-2,10-dihydro-9-oxa-1,2,4a-triaza-phenanthren-3-one;
(S)-6-(Azetidin-3-ylamino)-4-methyl-7-o-tolyl-2,10-dihydro-9-oxa-1,2,4a-triaza-phenanthren-3-one;
(S)-6-(Azetidin-3-ylamino)-7-cyclopropyl-4-methyl-2,10-dihydro-9-oxa-1,2,4a-triaza-phenanthren-3-one;
(S)-6-(Azetidin-3-ylamino)-7-(3-fluoro-phenyl)-4-methyl-2,10-dihydro-9-oxa-1,2,4a-triaza-phenanthren-3-one;
(S)-6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-(2,4-dichloro-phenyl)-4-methyl-2,10-dihydro-9-oxa-1,2,4a-triaza-phenanthren-3-one;
6-(Azetidin-3-ylamino)-7-(2,4-dichloro-phenyl)-4-methyl-2,10-dihydro-9-oxa-1,2,4a-triaza-phenanthren-3-one;
(S)-6-(Azetidin-3-ylamino)-7-(4-fluoro-phenyl)-4-methyl-2,10-dihydro-9-oxa-1,2,4a-triaza-phenanthren-3-one;
(S)-6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-7-(2-fluoro-4-methyl-phenyl)-4-methyl-2,10-dihydro-9-oxa-1,2,4a-triaza-phenanthren-3-one;
6-(Azetidin-3-ylamino)-7-(4-fluoro-2-methyl-phenyl)-4-methyl-2,10-dihydro-9-oxa-1,2,4a-triaza-phenanthren-3-one;
6-(Azetidin-3-ylamino)-7-(2-chloro-phenyl)-4-methyl-2,10-dihydro-9-oxa-1,2,4a-triaza-phenanthren-3-one;
(S)-6-(Azetidin-3-ylamino)-4-methyl-7-phenyl-2,10-dihydro-9-oxa-1,2,4a-triaza-phenanthren-3-one;
6-(Azetidin-3-ylamino)-7-(4-chloro-phenyl)-4-methyl-2,10-dihydro-9-oxa-1,2,4a-triaza-phenanthren-3-one;
(S)-6-(Azetidin-3-ylamino)-7-isopropyl-4-methyl-2,10-dihydro-9-oxa-1,2,4a-triaza-phenanthren-3-one;
6-(Azetidin-3-ylamino)-7-(3-fluoro-phenyl)-4-methyl-2,10-dihydro-9-oxa-1,2,4a-triaza-phenanthren-3-one;
6-(Azetidin-3-ylamino)-7-(2,4-difluoro-phenyl)-4-methyl-2,10-dihydro-9-oxa-1,2,4a-triaza-phenanthren-3-one;
6-(Azetidin-3-ylamino)-4-methyl-7-o-tolyl-2,10-dihydro-9-oxa-1,2,4a-triaza-phenanthren-3-one;
6-(Azetidin-3-ylamino)-4-methyl-7-(4-trifluoromethyl-phenyl)-2,10-dihydro-9-oxa-1,2,4a-triaza-phenanthren-3-one;
6-(Azetidin-3-ylamino)-7-bromo-4-methyl-2,10-dihydro-9-oxa-1,2,4a-triaza-phenanthren-3-one;
6-(Azetidin-3-ylamino)-7-cyclopropyl-4-methyl-2,10-dihydro-9-oxa-1,2,4a-triaza-phenanthren-3-one;
6-(Azetidin-3-ylamino)-7-isopropyl-4-methyl-2,10-dihydro-9-oxa-1,2,4a-triaza-phenanthren-3-one;
6-(Azetidin-3-ylamino)-7-(5-fluoro-2-methyl-phenyl)-4-methyl-2,10-dihydro-9-oxa-1,2,4a-triaza-phenanthren-3-one;
6-(Azetidin-3-ylamino)-4-methyl-7-(3-trifluoromethoxy-phenyl)-2,10-dihydro-9-oxa-1,2,4a-triaza-phenanthren-3-one;
S)-6-(Azetidin-3-ylamino)-4-methyl-7-trifluoromethyl-2,10-dihydro-9-oxa-1,2,4a-triaza-phenanthren-3-one;

6-(Azetidin-3-ylamino)-7-(3-chloro-phenyl)-4-methyl-2,10-dihydro-9-oxa-1,2,4a-triaza-phenanthren-3-one;
6-(Azetidin-3-yloxy)-7-cyclopropyl-4-methyl-2,10-dihydro-9-oxa-1,2,4a-triaza-phenanthren-3-one;
6-(Azetidin-3-yloxy)-4-methyl-7-phenyl-2,10-dihydro-9-oxa-1,2,4a-triaza-phenanthren-3-one;
6-(Azetidin-3-ylamino)-7-(3-fluoro-4-methyl-phenyl)-4-methyl-2,10-dihydro-9-oxa-1,2,4a-triaza-phenanthren-3-one;
(S)-6-(Azetidin-3-ylamino)-4-methyl-7-(4-trifluoromethoxy-phenyl)-2,10-dihydro-9-oxa-1,2,4a-triaza-phenanthren-3-one;
(S)-6-(Azetidin-3-ylamino)-4,7-dimethyl-2,10-dihydro-9-oxa-1,2,4a-triaza-phenanthren-3-one;
(S)-6-(Azetidin-3-ylamino)-7-fluoro-4-methyl-2,10-dihydro-9-oxa-1,2,4a-triaza-phenanthren-3-one;
6-(Azetidin-3-ylamino)-7-(4-dimethylamino-phenyl)-4-methyl-2,10-dihydro-9-oxa-1,2,4a-triaza-phenanthren-3-one;
6-(Azetidin-3-ylamino)-7-(3-methoxy-phenyl)-4-methyl-2,10-dihydro-9-oxa-1,2,4a-triaza-phenanthren-3-one;
6-(Azetidin-3-ylamino)-7-(4-fluoro-phenyl)-4-methyl-2,10-dihydro-9-oxa-1,2,4a-triaza-phenanthren-3-one;
6-(Azetidin-3-yloxy)-7-isopropyl-4-methyl-2,10-dihydro-9-oxa-1,2,4a-triaza-phenanthren-3-one;
6-(Azetidin-3-ylamino)-4-methyl-7-(4-trifluoromethoxy-phenyl)-2,10-dihydro-9-oxa-1,2,4a-triaza-phenanthren-3-one;
6-(Azetidin-3-ylamino)-4-methyl-7-m-tolyl-2,10-dihydro-9-oxa-1,2,4a-triaza-phenanthren-3-one;
10-Methyl-6-(3-methyl-azetidin-3-ylamino)-7-phenyl-2,10-dihydro-9-oxa-1,2,4a-triaza-phenanthren-3-one;
6-(Azetidin-3-ylamino)-7-(3,4-difluoro-phenyl)-4-methyl-2,10-dihydro-9-oxa-1,2,4a-triaza-phenanthren-3-one;
6-(Azetidin-3-ylamino)-4-methyl-7-(3-trifluoromethyl-phenyl)-2,10-dihydro-9-oxa-1,2,4a-triaza-phenanthren-3-one;
6-(Azetidin-3-ylamino)-4-methyl-7-trifluoromethyl-2,10-dihydro-9-oxa-1,2,4a-triaza-phenanthren-3-one;
7-Fluoro-4-methyl-6-(3-methyl-azetidin-3-yloxy)-2,10-dihydro-9-oxa-1,2,4a-triaza-phenanthren-3-one;
4,7-Dimethyl-6-piperidin-4-yl-2,10-dihydro-9-oxa-1,2,4a-triaza-phenanthren-3-one;
4-Methyl-6-(3-methyl-azetidin-3-yloxy)-2,10-dihydro-9-oxa-1,2,4a-triaza-phenanthren-3-one;
6-(1,3-Dimethyl-azetidin-3-ylamino)-4-methyl-7-trifluoromethyl-2,10-dihydro-9-oxa-1,2,4a-triaza-phenanthren-3-one;
4-Methyl-6-piperidin-4-yl-2,10-dihydro-9-oxa-1,2,4a-triaza-phenanthren-3-one;
6-(Azetidin-3-ylamino)-7-(3,4-dichloro-phenyl)-4-methyl-2,10-dihydro-9-oxa-1,2,4a-triaza-phenanthren-3-one;
6-(Azetidin-3-ylamino)-7-(4-tert-butyl-phenyl)-4-methyl-2,10-dihydro-9-oxa-1,2,4a-triaza-phenanthren-3-one;
6-(Azetidin-3-ylamino)-4-methyl-7-(2-trifluoromethoxy-phenyl)-2,10-dihydro-9-oxa-1,2,4a-triaza-phenanthren-3-one;
6-(Azetidin-3-ylamino)-4-methyl-7-(2-trifluoromethyl-phenyl)-2,10-dihydro-9-oxa-1,2,4a-triaza-phenanthren-3-one;
(1R,3S)-3-Amino-cyclopentanecarboxylic acid ((R)-4-methyl-3-oxo-2,3,4,10-tetrahydro-9-oxa-1,2,4a-triaza-phenanthren-6-yl)-amide;
7-Isopropyl-4-methyl-6-piperidin-4-yl-2,10-dihydro-9-oxa-1,2,4a-triaza-phenanthren-3-one;
7-Cyclopropyl-4-methyl-6-piperidin-4-yl-2,10-dihydro-9-oxa-1,2,4a-triaza-phenanthren-3-one;
(1R,3S)-3-Amino-cyclopentanecarboxylic acid ((S)-4-methyl-3-oxo-2,3,4,10-tetrahydro-9-oxa-1,2,4a-triaza-phenanthren-6-yl)-amide;
6-(Azetidin-3-ylamino)-2,10-dihydro-9-oxa-1,2,4a-triaza-phenanthrene-3,4-dione;
6-Azetidin-3-ylmethyl-4-methyl-2,10-dihydro-9-oxa-1,2,4a-triaza-phenanthren-3-one;
(S)-6-(Azetidin-3-yloxy)-7-fluoro-4-methyl-2,10-dihydro-9-oxa-1,2,4a-triaza-phenanthren-3-one;
6-(Azetidin-3-ylamino)-4-methyl-7-p-tolyl-2,10-dihydro-9-oxa-1,2,4a-triaza-phenanthren-3-one;
7-Fluoro-4-methyl-6-(3-methyl-azetidin-3-ylamino)-2,10-dihydro-9-oxa-1,2,4a-triaza-phenanthren-3-one;
6-(Azetidin-3-ylamino)-4-methyl-7-phenyl-2,10-dihydro-9-oxa-1,2,4a-triaza-phenanthren-3-one;
6-(Azetidin-3-ylamino)-7-(4-methoxy-phenyl)-4-methyl-2,10-dihydro-9-oxa-1,2,4a-triaza-phenanthren-3-one;
6-(Azetidin-3-ylamino)-7-isobutyl-4-methyl-2,10-dihydro-9-oxa-1,2,4a-triaza-phenanthren-3-one;
6-(Azetidin-3-ylamino)-7-cyclopentyl-4-methyl-2,10-dihydro-9-oxa-1,2,4a-triaza-phenanthren-3-one;
6-(Azetidin-3-ylamino)-7-ethyl-4-methyl-2,10-dihydro-9-oxa-1,2,4a-triaza-phenanthren-3-one;
6-(Azetidin-3-ylamino)-7-(2-fluoro-5-methyl-phenyl)-4-methyl-2,10-dihydro-9-oxa-1,2,4a-triaza-phenanthren-3-one;
6-(Azetidin-3-ylamino)-7-(4-fluoro-3-methyl-phenyl)-4-methyl-2,10-dihydro-9-oxa-1,2,4a-triaza-phenanthren-3-one;
6-(Azetidin-3-ylamino)-7-fluoro-4-methyl-2,10-dihydro-9-oxa-1,2,4a-triaza-phenanthren-3-one;
6-(Azetidin-3-ylamino)-4-methyl-7-naphthalen-1-yl-2,10-dihydro-9-oxa-1,2,4a-triaza-phenanthren-3-one;
6-(Azetidin-3-ylamino)-4-methyl-7-phenylamino-2,10-dihydro-9-oxa-1,2,4a-triaza-phenanthren-3-one;
6-(Azetidin-3-ylamino)-7-(3-fluoro-5-methyl-phenyl)-4-methyl-2,10-dihydro-9-oxa-1,2,4a-triaza-phenanthren-3-one;
6-(Azetidin-3-ylamino)-7,8-difluoro-4-methyl-2,10-dihydro-9-oxa-1,2,4a-triaza-phenanthren-3-one;
6-(Azetidin-3-ylamino)-4,7-dimethyl-2,10-dihydro-9-oxa-1,2,4a-triaza-phenanthren-3-one;
6-(Azetidin-3-yloxy)-4,7-dimethyl-2,10-dihydro-9-oxa-1,2,4a-triaza-phenanthren-3-one;
6-(Azetidin-3-ylamino)-7-(2-methoxy-phenyl)-4-methyl-2,10-dihydro-9-oxa-1,2,4a-triaza-phenanthren-3-one;
6-(Azetidin-3-yloxy)-7-fluoro-4-methyl-2,10-dihydro-9-oxa-1,2,4a-triaza-phenanthren-3-one;
4-Methyl-6-(3-methyl-azetidin-3-ylamino)-2,10-dihydro-9-oxa-1,2,4a-triaza-phenanthren-3-one;
4,7-Dimethyl-6-(1-methyl-azetidin-3-ylamino)-2,10-dihydro-9-oxa-1,2,4a-triaza-phenanthren-3-one;
6-(2-Aminomethyl-pyrrolidin-1-yl)-4-methyl-2,10-dihydro-9-oxa-1,2,4a-triaza-phenanthren-3-one;
6-(Azetidin-3-yl-methyl-amino)-4,7-dimethyl-2,10-dihydro-9-oxa-1,2,4a-triaza-phenanthren-3-one;
6-[(1S,5R)-(8-Aza-bicyclo[3.2.1]oct-3-yl)amino]-7-fluoro-4-methyl-2,10-dihydro-9-oxa-1,2,4a-triaza-phenanthren-3-one;
6-(Azetidin-3-yl-benzyl-amino)-4-methyl-2,10-dihydro-9-oxa-1,2,4a-triaza-phenanthren-3-one;
6-(Azetidin-3-ylamino)-7-(6-methoxy-naphthalen-2-yl)-4-methyl-2,10-dihydro-9-oxa-1,2,4a-triaza-phenanthren-3-one;
6-(Azetidin-3-ylamino)-4-methyl-7-naphthalen-2-yl-2,10-dihydro-9-oxa-1,2,4a-triaza-phenanthren-3-one;
6-(Azetidin-3-ylamino)-7-benzothiazol-5-yl-4-methyl-2,10-dihydro-9-oxa-1,2,4a-triaza-phenanthren-3-one;
6-(Azetidin-3-ylamino)-7-benzothiazol-6-yl-4-methyl-2,10-dihydro-9-oxa-1,2,4a-triaza-phenanthren-3-one;

7-Fluoro-4-methyl-6-piperidin-4-yl-2,10-dihydro-9-oxa-1,2,4a-triaza-phenanthren-3-one;
6-(1,7-Diaza-spiro[3.5]non-1-yl)-4,7-dimethyl-2,10-dihydro-9-oxa-1,2,4a-triaza-phenanthren-3-one;
(3S,4S)-3-Methyl-piperidine-4-carboxylic acid (4-methyl-3-oxo-2,3,4,10-tetrahydro-9-oxa-1,2,4a-triaza-phenanthren-6-yl)-amide;
7-Fluoro-4-methyl-6-(1-methyl-azetidin-3-ylamino)-2,10-dihydro-9-oxa-1,2,4a-triaza-phenanthren-3-one;
4-Methyl-7-phenyl-6-piperidin-4-yl-2,10-dihydro-9-oxa-1,2,4a-triaza-phenanthren-3-one;
6-(Azetidin-3-ylamino)-7-cyclohexyl-4-methyl-2,10-dihydro-9-oxa-1,2,4a-triaza-phenanthren-3-one;
6-(Azetidin-3-ylamino)-7-(6-cyclopropylmethoxy-pyridin-3-yl)-4-methyl-2,10-dihydro-9-oxa-1,2,4a-triaza-phenanthren-3-one;
3-[6-(Azetidin-3-ylamino)-4-methyl-3-oxo-2,3,4,10-tetrahydro-9-oxa-1,2,4a-triaza-phenanthren-7-yl]-benzonitrile;
(R)-6-(Azetidin-3-ylamino)-4-methyl-7-trifluoromethyl-2,10-dihydro-9-oxa-1,2,4a-triaza-phenanthren-3-one;
(R)-6-(Azetidin-3-ylamino)-7-(2-fluoro-phenyl)-4-methyl-2,10-dihydro-9-oxa-1,2,4a-triaza-phenanthren-3-one;
6-(Azetidin-3-ylamino)-7-(3-tert-butoxymethyl-phenyl)-4-methyl-2,10-dihydro-9-oxa-1,2,4a-triaza-phenanthren-3-one;
4-[6-(Azetidin-3-ylamino)-4-methyl-3-oxo-2,3,4,10-tetrahydro-9-oxa-1,2,4a-triaza-phenanthren-7-yl]-benzonitrile;
6-(Azetidin-3-ylamino)-7-chloro-4-methyl-2,10-dihydro-9-oxa-1,2,4a-triaza-phenanthren-3-one;
4,7-Dimethyl-6-(1,2,3,6-tetrahydro-pyridin-4-yl)-2,10-dihydro-9-oxa-1,2,4a-triaza-phenanthren-3-one;
6-(Azetidin-3-ylamino)-4-methyl-7-(tetrahydro-pyran-4-yl)-2,10-dihydro-9-oxa-1,2,4a-triaza-phenanthren-3-one;
4-Methyl-6-(1-methyl-azetidin-3-ylamino)-2,10-dihydro-9-oxa-1,2,4a-triaza-phenanthren-3-one;
(R)-6-(Azetidin-3-ylamino)-7-isopropyl-4-methyl-2,10-dihydro-9-oxa-1,2,4a-triaza-phenanthren-3-one;
6-(Azetidin-3-yl-methyl-amino)-7-fluoro-4-methyl-2,10-dihydro-9-oxa-1,2,4a-triaza-phenanthren-3-one;
6-(Azetidin-3-ylamino)-7-methoxy-4-methyl-2,10-dihydro-9-oxa-1,2,4a-triaza-phenanthren-3-one;
4-Methyl-6-(1-methyl-piperidin-4-yl)-2,10-dihydro-9-oxa-1,2,4a-triaza-phenanthren-3-one;
4-Methyl-6-pyrrolidin-3-yl-2,10-dihydro-9-oxa-1,2,4a-triaza-phenanthren-3-one;
6-(Azetidin-3-yl-cyclopropyl-amino)-2,10-dihydro-9-oxa-1,2,4a-triaza-phenanthren-3-one;
(1R,8S)-8-(2,6-difluorophenyl)-9-((3R,4R)-1,3-dimethylpiperidin-4-yl)-1-methyl-3,5-dihydrobenzo[5,6][1,4]oxazino[3,4-c][1,2,4]triazin-2(1H)-one;
R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-6-(3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(S)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one;
(R)-6-((3R,4R)-1,3-Dimethyl-piperidin-4-yl)-7-(3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-3-methoxy-phenyl)-4-methyl-2,10-dihydro-9-oxa-1,2,4a-triaza-phenanthren-3-one;
(R)-7-(2,4-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methyl-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-4-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-7-(2-fluoro-5-methoxy-phenyl)-4-methyl-2,10-dihydro-9-oxa-1,2,4a-triaza-phenanthren-3-one;
(R)-6-((3R,4R)-1,3-Dimethyl-piperidin-4-yl)-4-methyl-7-o-tolyl-2,10-dihydro-9-oxa-1,2,4a-triaza-phenanthren-3-one;
(R)-6-((3R,4R)-1,3-Dimethyl-piperidin-4-yl)-7-isopropyl-4-methyl-2,10-dihydro-9-oxa-1,2,4a-triaza-phenanthren-3-one;
(R)-7-(2,6-Difluoro-phenyl)-6-((3R,4R)-1,3-dimethyl-piperidin-4-yl)-4-methyl-2,10-dihydro-9-oxa-1,2,4a-triaza-phenanthren-3-one;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one;
(R)-6-((2R,5S)-2,5-Dimethyl-piperazin-1-yl)-7-(2-fluoro-phenyl)-4-methyl-2,10-dihydro-9-oxa-1,2,4a-triaza-phenanthren-3-one hydrochloride;
(R)-7-(2-Fluoro-phenyl)-4-methyl-6-((2R,5S)-2,4,5-trimethyl-piperazin-1-yl)-2,10-dihydro-9-oxa-1,2,4a-triaza-phenanthren-3-one; or, (R)-7-(2-Fluoro-phenyl)-4-methyl-6-((2S,5S)-2,4,5-trimethyl-piperazin-1-yl)-2,10-dihydro-9-oxa-1,2,4a-triaza-phenanthren-3-one.

19. A method of treating rheumatoid arthritis in a mammal, comprising administering to said mammal a therapeutically effective amount of a compound of claim 1.

* * * * *